United States Patent
Hays et al.

(10) Patent No.: US 9,145,410 B2
(45) Date of Patent: *Sep. 29, 2015

(54) PYRAZOLOPYRIDINES AND ANALOGS THEREOF

(75) Inventors: David S. Hays, Woodbury, MN (US); Michael E. Danielson, St. Paul, MN (US); John F. Gerster, Woodbury, MN (US); Shri Niwas, Maple Grove, MN (US); Ryan B. Prince, St. Paul, MN (US); Tushar A. Kshirsagar, Woodbury, MN (US); Philip D. Heppner, Forest Lake, MN (US); William H. Moser, Edina, MN (US); Joan T. Moseman, Lake Elmo, MN (US); Matthew R. Radmer, Robbinsdale, MN (US); Maureen A. Kavanagh, Stanchfield, MN (US); Sarah A. Strong, Louisville, CO (US); Jason D. Bonk, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 477 days.

This patent is subject to a terminal disclaimer.

(21) Appl. No.: 13/359,213

(22) Filed: Jan. 26, 2012

(65) Prior Publication Data

US 2012/0121651 A1 May 17, 2012

Related U.S. Application Data

(63) Continuation of application No. 11/887,496, filed as application No. PCT/US2006/011953 on Mar. 31, 2006, now abandoned, which is a continuation-in-part of application No. 11/097,715, which is a continuation-in-part of application No. PCT/US2004/032480, filed on Oct. 1, 2004, now Pat. No. 7,544,697.

(60) Provisional application No. 60/508,352, filed on Oct. 3, 2003, provisional application No. 60/554,680, filed on Mar. 19, 2004, provisional application No. 60/603,303, filed on Aug. 20, 2004.

(51) Int. Cl.
*C07D 471/04* (2006.01)
*C07D 471/14* (2006.01)
*C07D 401/14* (2006.01)
*C07D 495/14* (2006.01)

(52) U.S. Cl.
CPC ............ *C07D 471/04* (2013.01); *C07D 401/14* (2013.01); *C07D 471/14* (2013.01); *C07D 495/14* (2013.01)

(58) Field of Classification Search
CPC .. C07D 471/04; C07D 471/14; C07D 401/14; C07D 495/14
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,826,986 A | 5/1989 | Huser et al. |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |

(Continued)

FOREIGN PATENT DOCUMENTS

| EP | 0 394 026 | 10/1990 |
|---|---|---|
| EP | 1 104 764 | 6/2001 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner* — Samira Jean-Louis

(57) ABSTRACT

Pyrazolopyridin-4-amines, pyrazoloquinolin-4-amines, pyrazolonaphthyridin-4-amines, 6,7,8,9-tetrahydropyrazoloquinolin-4-amines, and prodrugs thereof, pharmaceutical compositions containing the compounds, intermediates, methods of making, and methods of use of these compounds as immunomodulators, for inducing or inhibiting cytokine biosynthesis in animals and in the treatment of diseases including viral and neoplastic diseases, are disclosed.

17 Claims, No Drawings

(56) References Cited

U.S. PATENT DOCUMENTS

| | | |
|---|---|---|
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,939,526 B2 | 5/2011 | Radmer et al. |
| 7,943,609 B2 | 5/2011 | Griesgraber et al. |
| 7,968,562 B2 | 6/2011 | Skwierczynski et al. |
| 7,968,563 B2 | 6/2011 | Kshirsager et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 | 10/2011 | Griesgraber et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |

(56) References Cited

U.S. PATENT DOCUMENTS

| | | |
|---|---|---|
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 02/36592 | 5/2002 |
| WO | WO 2004/041285 | 5/2004 |
| WO | WO 2005/003064 | 1/2005 |
| WO | WO 2005/018555 | 3/2005 |
| WO | WO 2005/020999 | 3/2005 |
| WO | WO 2006/028451 | 3/2006 |
| WO | WO 2006063072 | 6/2006 |
| WO | WO 2006/121528 | 11/2006 |
| WO | WO 2007/030775 | 3/2007 |

OTHER PUBLICATIONS

Brennan et al., "Automated Bioassay of Interferons in Micro-test Plated.", *Biotechniques*, Jun./Jul. 78, 1983.

Testerman et al., "Cytokine Induction by the Immunomodulators Imiquimod and S-27609,", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Developmental of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNFα Suppressors: Synthesis and Structure-Activity Relationship of 1-, 2- and 4-substituted 1H-imidazo[4,5-c]pyridines.", *Bioorganic & Medicinal Chemistry*, 11, pp. 2541-2550 (2003).

Szabo, et al., British Journal of Pharmacology, Suppression of Macrophage Inflammatory Protein (MIP)-1α Production and Collagen-Induced Arthritis by Adenosine Receptor Agonists, vol. 125, pp. 379-387, (1998).

Roy, OSAR & Combinatorial Science, OSAR of Adenosine Receptor Antagonists II: Exploring Physicochemical Requirements for Selective Binding of 2-Arylpyrazolo[3,4-c]quinoline Derivatives with Adenosine $A_1$ and $A_3$ Receptor Subtypes, vol. 22, pp. 614-6210 (2003).

Adams et al., "Carbolines, Part VII, Anisidines, Convenient Tools to Synthesize Hydroxy-β-Carbolines", *J. Herterocyclic Chem.*, 32, pp. 1171-1175 (1995).

Colotta, et al., J. Med. Chem. 2000, 43, Synthesis and Structure-Activity Relationships of a New Set of 2-Arylpyrazolo[3,4-c]quinoline Derivatives as Adenosine Receptor Antagonists, pp. 3118-3124.

Kourafalos, V. N., et al., "The Synthesis of 4-Deazaformycin A" *Journal of Organic Chemistry*, vol. 68, No. 16, (2003) pp. 6466-6469.

Dicken et al., Reactions at High Pressures. [3+2] Dipolar cycloaddition of nitrones with vinyl ethers. J Org Chem. 1982;47:2047-2051.

Eriks et al., Histamine H2-receptor agonists. Synthesis, in vitro pharmacology, and qualitative structure-activity relationships of substituted 4- and 5-(aminoethyl)thiazoles. J Med Chem. Aug. 21, 1992;35(17):3239-46.

(56) References Cited

OTHER PUBLICATIONS

Huppatz, Systemic fungicides. The synthesis of certain pyrazole analogues of carboxin. Aust J Chem. 1983;36:135-47.

Iwashita et al., Sytheses of isoretronecanol and lupinine. J Org Chem. 1982; 47:230-233.

Jacobs, The Synthesis of Acetylenes. *Organic Reactions*. New York: Wiley & Sons, Inc., 1949. vol 5. 1-77.

Kloetzel et al., Reactions of nitroparaffins. I. Synthesis and reduction of some γ-nitrokenes. J Am Chem Soc. 1947;69:2271-2275.

Kourafalos et al., Synthesis of 7-aminopyrazolo[3,4-c]pyridine as a probe for the preparation of compounds of pharmacological interest. Heterocycles. 2002;57(12):2335-2343.

L. Claisen, *Berichte*, 42, pp. 59-69 (1909).

L. Claisen, *Berichte*, 59, pp. 601-607 (1909).

Liu et al., Synthesis of halogen-substituted 3-deazaadenosine and 3-deazaguanosine analogues as potential antitumor/antiviral agents. Nucleosides, Nucleotides, Nucleic Acids. Dec. 2001;20(12):1975-2000.

Moraczewski et al., Using Hydrogen Bonding to Control Carbamate C—N Rotamer Equilibria. J. Org. Chem. Oct. 16, 1998;63(21):7258-7262.

Muller et al., An improved one-pot procedure for the synthesis of alkynes from aldehydes. Synlett. 1996;6:521-522.

Nagarajan et al., Condenses heterotricycles: synthesis of pyrazolo[3,4-c]quinoline derivatives. Indian Journal of Chemistry. 1992;31B:316-321.

Ohana et al., Differential effect of adenosine on tumor and normal cell growth: focus on the A3 adenosine receptor. J Cell Physiol. Jan. 2001;186(1):19-23. Review.

Pawlas et al., Novel anionic annelation tactics for construction of fused heteraromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. J. Org Chem. Jun. 15, 2001;66(12):4214-9.

Peschke et al., Synthesis and in vitro characterization of new growth hormone secretagogues derived from ipamorelin with dipeptidomimetic N-terminals. Eur. J Med Chem. 1999;34:363-380.

Ritter et al., A new reaction of nitriles; amides from alkenes and mononitriles. J Am Chem Soc. Dec. 1948;70(12):4045-8.

Rocca et al., Connection between metalation and cross-coupling strategies. A new convergent route to azacarbazoles. Tetrahedron, 1993;49(I):49-64.

Kunal, et. Al., QSAR of adenosine receptor antagonists II: exploring physiochemical requirements for selective binding of 2-arlypyrazolo[3,4-c]quinoline derivatives with adenosine $A_1$ and $A_3$ receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Scheuer et al., Application of the Ritter reaction to mesityl oxide and chalcone. J Am Chem Soc. 1957;22:674-676.

Sonohashira et al., A convenient synthesis of acetylenes: catalytic substitutions of acetylenic hydrogen with bromoalkenes, Iodoarenes, and bromopyridines. Tetrahedron Letts. 1975;50:4467-4470.

Spivey et al., Configurationally stable biaryl analogues of 4-(dimethylamino)pyridine: A novel class of chiral nucleophilic catalysts. J Org Chem. 1999;64:9430-9443.

Thesing et al., *Chem. Ber.*, 92, pp. 1748-1755 (1959).

Thiruvikraman et al., Synthesis and reactions of pyrazolo-[3,4-c]quinoline derivatives. Indian Journal of Chemistry, 1987;26B:695-696.

PYRAZOLOPYRIDINES AND ANALOGS THEREOF

CROSS REFERENCE TO RELATED APPLICATIONS

This application is a continuation of U.S. application Ser. No. 11/887,496, filed Mar. 31, 2006 now abandoned, which is a national stage filing under 35 U.S.C. 371 of International Patent Application No. PCT/US2006/011953, which is a continuation-in-part of U.S. application Ser. No. 11/097,715, filed on Apr. 1, 2005, now U.S. Pat. No. 7,544,697, which is a continuation-in-part of International Patent Application No. PCT/US04/32480, with an international filing date of Oct. 1, 2004, which claims the benefit under 35 U.S.C. 119(e) of U.S. Provisional Application Ser. Nos. 60/508,352, filed Oct. 3, 2003, 60/554,680, filed Mar. 19, 2004, and 60/603,303, filed Aug. 20, 2004, all of which are incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY OF THE INVENTION

A new class of compounds useful for modulating cytokine biosynthesis has now been found. In one aspect, the present invention provides such compounds, which are of the Formulas I and Ia:

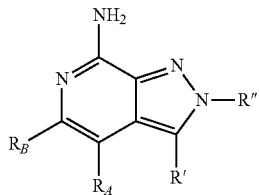

I

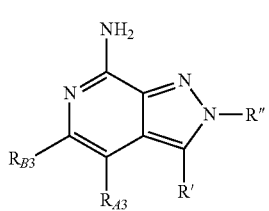

Ia and more specifically the following compounds of the Formulas II, III, IV, V, VI, VII, VIII, IX, and LXXX:

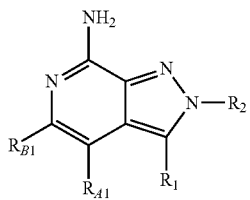

II

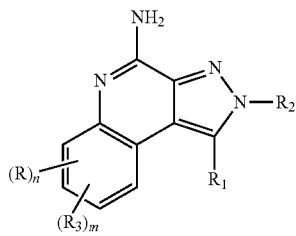

III

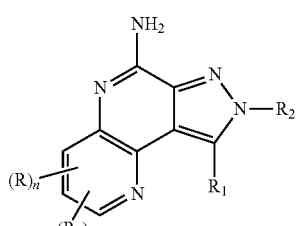

IV

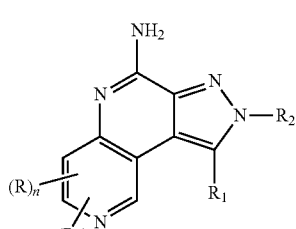

V

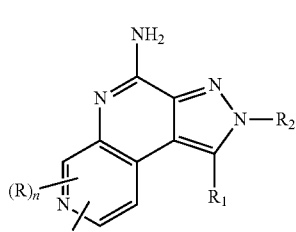

VI

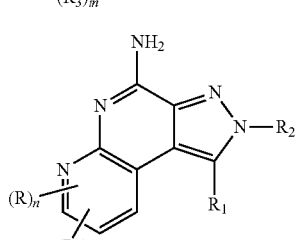

VII

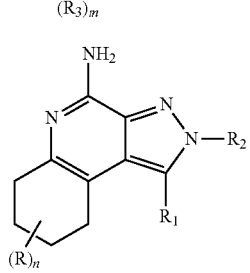

VIII

-continued

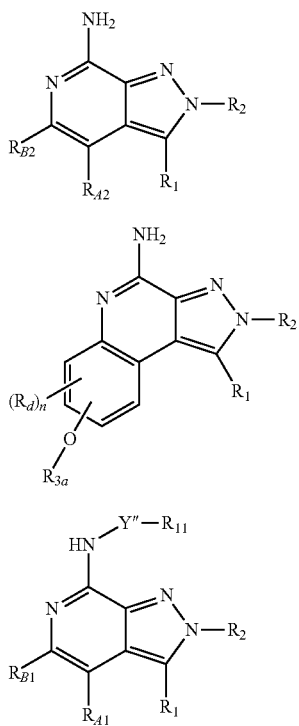

wherein $R_A$, $R_B$, R', R", $R_{A1}$, $R_{B1}$, $R_1$, $R_2$, $R_3$, $R_{3a}$, R, $R_d$, $R_{A2}$, $R_{B2}$, $R_{A3}$, $R_{B3}$, $R_{11}$, Y", n, and m are as defined below; and pharmaceutically acceptable salts thereof.

The compounds of Formulas I, Ia, II, II-1, III, IV, V, VI, VII, VIII, IX, and LXXX are useful as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human peripheral blood mononuclear cells (PBMC) in a culture with the compound(s) at a concentration range of 30 to 0.014 µM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 µM and analyzing for tumor necrosis factor (α) in the culture supernatant. The ability to modulate cytokine biosynthesis, for example, induce the biosynthesis of one or more cytokines, makes the compounds useful for treating various conditions such as viral diseases and neoplastic diseases, that are responsive to such changes in the immune response.

In another aspect, the present invention provides pharmaceutical compositions that contain the immune response modifier compounds, and methods of modulating (e.g., inducing or inhibiting) cytokine biosynthesis in an animal, treating a viral disease in an animal, and treating a neoplastic disease in an animal, by administering an effective amount of one or more compounds of the Formulas I, Ia, II, II-1, III, IV, V, VI, VII, VIII, IX, and/or LXXX and/or pharmaceutically acceptable salts thereof to the animal.

In another aspect, the invention provides methods of synthesizing compounds of the Formulas I, Ia, II, II-1, III, IV, V, VI, VII, VIII, IX, and LXXX and intermediates useful in the synthesis of these compounds.

In another aspect, the invention provides prodrugs of compounds of the invention as well as pharmaceutical compositions containing the prodrugs.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

In one aspect, the present invention provides compounds of the formula (I):

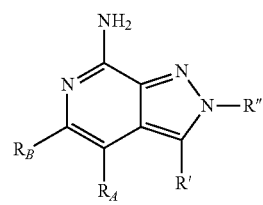

wherein:

$R_A$ and $R_B$ are each independently selected from the group consisting of
  hydrogen,
  halogen,
  alkyl,
  alkenyl,
  alkoxy,
  alkylthio, and
  —N($R_9$)$_2$;

or when taken together, $R_A$ and $R_B$ form a fused aryl ring or heteroaryl ring containing one heteroatom selected from the group consisting of N and S wherein the aryl or heteroaryl ring is unsubstituted or substituted by one or more R''' groups;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
  halogen,
  hydroxy,
  alkyl,
  alkenyl,
  haloalkyl,
  alkoxy,
  alkylthio, and
  —N($R_9$)$_2$;

R' and R" are independently selected from the group consisting of hydrogen and non-interfering substitutents;

R′″ is a non-interfering substituent; and $R_9$ is selected from the group consisting of hydrogen and alkyl;

with the proviso that at least one of $R_A$, $R_B$, R′, or R″ is other than hydrogen; and with the further proviso that when $R_A$ and $R_B$ form a benzene ring unsubstituted or substituted with chloro, and R′ is hydrogen, then R″ is other than phenyl or phenyl substituted with methyl, methoxy, chloro, or fluoro; or a pharmaceutically acceptable salt thereof.

In one embodiment, the present invention provides compounds of the formula (II):

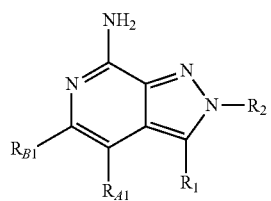

II wherein:

$R_{A1}$ and $R_{B1}$ are each independently selected from the group consisting of:
hydrogen,
halogen,
alkyl,
alkenyl,
alkoxy,
alkylthio, and
—N($R_9$)$_2$;

or when taken together, $R_{A1}$ and $R_{B1}$ form a fused aryl ring or heteroaryl ring containing one heteroatom selected from the group consisting of N and S wherein the aryl or heteroaryl ring is unsubstituted or substituted by one or more R groups, or substituted by one $R_3$ group, or substituted by one $R_3$ group and one R group;

or when taken together, $R_{A1}$ and $R_{B1}$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of:
—$R_4$,
—X—$R_4$,
—X—Y—$R_4$, and
—X—$R_5$;

$R_3$ is selected from the group consisting of:
—Z—$R_4$,
—Z—X—$R_4$,
—Z—X—Y—$R_4$, —Z—X—Y—X—Y—$R_4$, and
—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

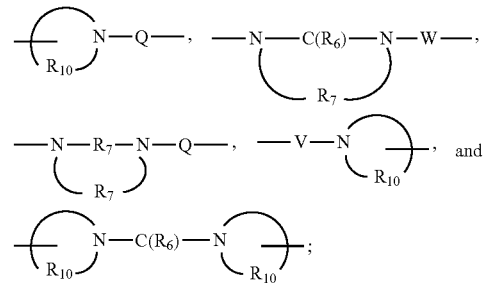

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

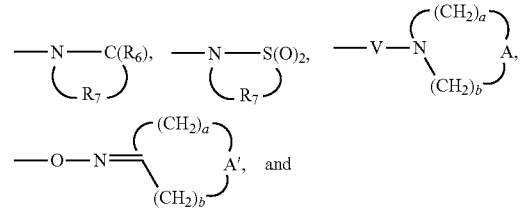

-continued

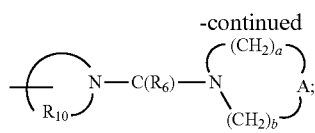

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that at least one of $R_{A1}$, $R_{B1}$, $R_1$, or $R_2$ is other than hydrogen; and with the further proviso that when $R_{A1}$ and $R_{B1}$ form a fused benzene ring unsubstituted or substituted with chloro, and $R_1$ is hydrogen, then $R_2$ is other than phenyl or phenyl substituted with methyl, methoxy, chloro, or fluoro;
or a pharmaceutically acceptable salt thereof. For certain embodiments of Formula II, the above group from which Y is selected further includes —C(=N—O—R$_8$)—NH—.

In another embodiment, the present invention provides compounds of the formula (III):

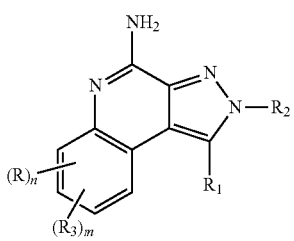

III wherein:
R is selected from the group consisting of:
halogen,
hydroxy,
alkyl,
alkenyl,
haloalkyl,
alkoxy,
alkylthio, and
—N(R$_9$)$_2$;
$R_1$ is selected from the group consisting of:
—R$_4$,
—X—R$_4$,
—X—Y—X—Y—R$_4$, and
—X—R$_5$;
$R_2$ is selected from the group consisting of:
—R$_4$,
—X—R$_4$,
—X—Y—R$_4$, and
—X—R$_5$;
$R_3$ is selected from the group consisting of:
—Z—R$_4$,
—Z—X—R$_4$,
—Z—X—Y—R$_4$,
—Z—X—Y—X—Y—R$_4$, and
Z—X—R$_5$;
n is 0 to 4;
m is 0 or 1; with the proviso that when m is 1, then n is 0 or 1;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$-,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

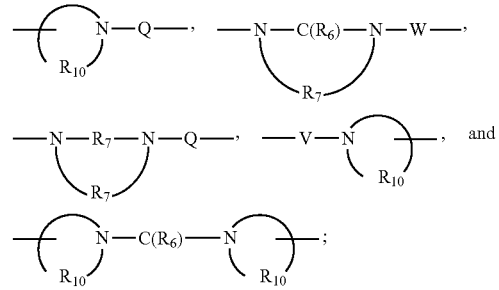

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of $$-N(R_7)-C(R_6)-, \quad -N(R_7)-S(O)_2-, \quad -V-N\begin{pmatrix}(CH_2)_a\\(CH_2)_b\end{pmatrix}A,$$

$$-O-N=\begin{pmatrix}(CH_2)_a\\(CH_2)_b\end{pmatrix}A', \text{ and}$$

$$-N(R_{10})-C(R_6)-N\begin{pmatrix}(CH_2)_a\\(CH_2)_b\end{pmatrix}A;$$

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, and —N(R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7; with the proviso that when $R_1$ is hydrogen, m is 0, and R is chloro, then $R_2$ is other than phenyl or phenyl substituted with methyl, methoxy, chloro, or fluoro;

or a pharmaceutically acceptable salt thereof. For certain embodiments of Formula III, the above group from which Y is selected further includes —C(=N—O—R$_8$)—NH—.

In other embodiments, the present invention provides compounds of the formulas (IV, V, VI, and VII):

IV

V

VI

VII wherein:
R is selected from the group consisting of:
halogen,
hydroxy,
alkyl,
alkenyl,
haloalkyl,
alkoxy,
alkylthio, and
—N(R$_9$)$_2$;
$R_1$ is selected from the group consisting of:
—R$_4$,
—X—R$_4$,
—X—Y—R$_4$,
—X—Y—X—Y—R$_4$, and
—X—R$_5$;
$R_2$ is selected from the group consisting of:
—R$_4$,
—X—R$_4$,
—X—Y—R$_4$, and
—X—R$_5$;
$R_3$ is selected from the group consisting of:
—Z—R$_4$,
—Z—X—R$_4$,
—Z—X—Y—X—Y—R$_4$, and
—Z—X—R$_5$;
n is 0 or 1;
m is 0 or 1;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$-,
—S(O)$_2$—N(R$_3$)—,
—C(R$_6$)—,
—C(R$_6$)—O—,
—O—C(R$_6$)—,
—O—C(O)—O—,
—N(R$_8$)-Q-,
—C(R$_6$)—N(R$_3$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

[structures with N—Q, N—C(R$_6$)—N—W, N—R$_7$—N—Q, V—N, and N—C(R$_6$)—N ring systems with R$_7$, R$_{10}$ labels]

Z is a bond or —O—;

R$_4$ is selected from the group consisting of hydrogen, alkyl, alkenyl, alkynyl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

[structures: —N—C(R$_6$) with R$_7$, —N—S(O)$_2$ with R$_7$, —V—N ring with (CH$_2$)$_a$/(CH$_2$)$_b$/A, —O—N= ring with (CH$_2$)$_a$/(CH$_2$)$_b$/A', and N—C(R$_6$)—N ring with R$_{10}$, (CH$_2$)$_a$/(CH$_2$)$_b$/A;]

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;

R$_9$ is selected from the group consisting of hydrogen and alkyl;
R$_{10}$ is C$_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof. For certain embodiments of Formulas IV, V, VI, and VII, the above group from which Y is selected further includes —C(=N—O—R$_8$)—NH—. For certain of these embodiments, the compound or salt is selected from the group consisting of the formulas (IV and VII):

[Structure IV: tricyclic pyrazolo-naphthyridine with NH$_2$, N—R$_2$, R$_1$, (R)$_n$, (R$_3$)$_m$]

IV

[Structure VII: tricyclic pyrazolo-naphthyridine isomer with NH$_2$, N—R$_2$, R$_1$, (R)$_n$, (R$_3$)$_m$]

VII or a pharmaceutically acceptable salt thereof.

In another embodiment, the present invention provides compounds of the formula (VIII):

[Structure VIII: tetrahydro tricyclic compound with NH$_2$, N—R$_2$, R$_1$, (R)$_n$]

VIII wherein:
R is selected from the group consisting of:
halogen,
hydroxy,
alkyl,
alkenyl, haloalkyl,
alkoxy,
alkylthio, and
—N(R$_9$)$_2$;
R$_1$ is selected from the group consisting of:
—R$_4$,
—X—R$_4$,
—X—Y—R$_4$,
—X—Y—X—Y—R$_4$, and
—X—R$_5$;
R$_2$ is selected from the group consisting of:
—R$_4$,
—X—R$_4$,
—X—Y—R$_4$, and
—X—R$_5$;
n is 0 to 4;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$-,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

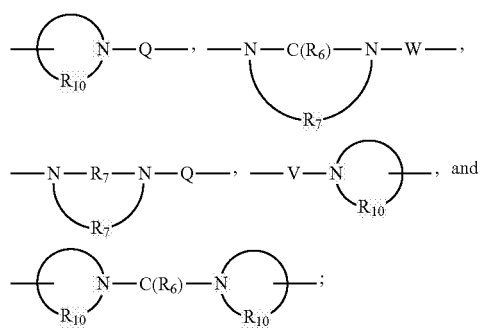

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_5$ is selected from the group consisting of

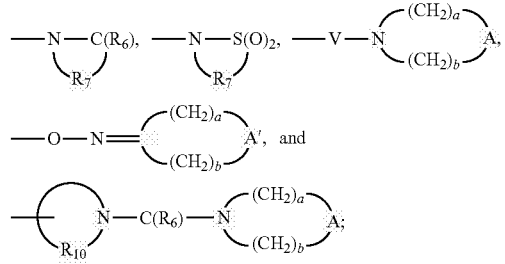

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$-, and —N(R$_4$)—;
N is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof. For certain embodiments of Formula VIII, the above group from which Y is selected further includes —C(=N—O—R$_8$)—NH—.

In another embodiment, the present invention provides compounds of the formula (IX):

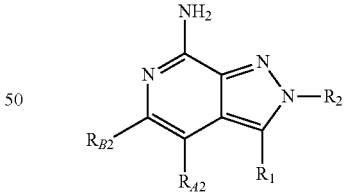

wherein:
R$_{A2}$ and R$_{B2}$ are each independently selected from the group consisting of:
hydrogen,
halogen,
alkyl,
alkenyl,
alkoxy,
alkylthio, and
—N(R$_9$)$_2$;
R$_1$ is selected from the group consisting of:
—R$_4$,
—X—R$_4$, —X—Y—R$_4$,
—X—Y—X—Y—R$_4$, and
—X—R$_5$;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$-,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N=C(R$_4$)—,
—C(=N—O—R$_8$)—,
—CH(—N(—O—R$_8$)-Q-R$_4$)—,

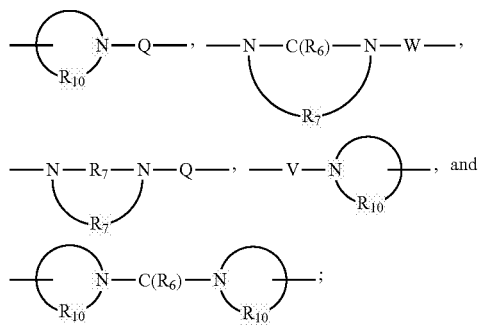

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, allylamino, dialkylamino, (dialkylamino)alkyleneoxy, and in the case of alkyl, alkenyl, alkynyl, and heterocyclyl, oxo;

R$_5$ is selected from the group consisting of

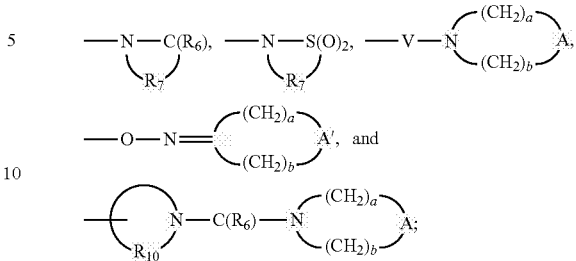

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that at least one of R$_{A2}$, R$_{B2}$, R$_1$, or R$_2$ is other than hydrogen;
or a pharmaceutically acceptable salt thereof. For certain embodiments of Formula IX, the above group from which Y is selected further includes —C(=N—O—R$_8$)—NH—.

In another embodiment, the present invention provides compounds of the formula (Ia):

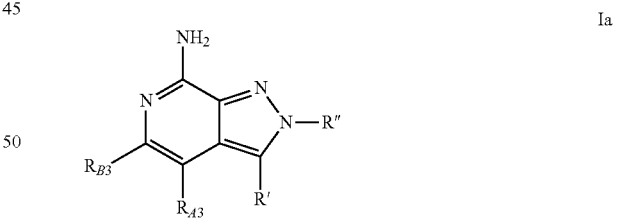

wherein:
R$_{A3}$ and R$_{B3}$ are each independently selected from the group consisting of:
hydrogen,
halogen,
alkyl,
alkenyl,
alkoxy,
alkylthio, and
—N(R$_9$)$_2$;
or when taken together, R$_{A3}$ and R$_{B3}$ form a fused aryl ring or heteroaryl ring containing one heteroatom or 5 to 7 membered saturated ring optionally containing one heteroatom wherein the heteroatom is selected from the group consisting of N and S and wherein the aryl, heteroaryl, or 5 to 7 membered saturated ring optionally containing one heteroatom is unsubstituted or substituted by one or more non-interfering substituents;

R and R" are independently selected from the group consisting of hydrogen and non-interfering substitutents; and $R_9$ is selected from the group consisting of hydrogen and alkyl;

with the proviso that at least one of $R_{A3}$, $R_{B3}$, R', or R" is other than hydrogen; and with the further proviso that when $R_{A3}$ and $R_{B3}$ form a benzene ring unsubstituted or substituted with chloro, and R' is hydrogen, then R" is other than phenyl or phenyl substituted with methyl, methoxy, chloro, or fluoro; or a pharmaceutically acceptable salt thereof.

In another embodiment, the present invention provides compounds of the following formula (LXXX):

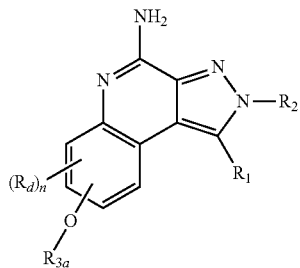

LXXX wherein:
$R_d$ is selected from the group consisting of:
halogen,
alkyl,
alkenyl,
trifluoromethyl, and
dialkylamino;
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_{3a}$ is selected from the group consisting of:
—Y'—$R_4$,

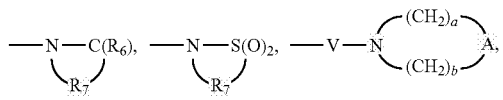

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—$S(O)_{0-2}$—,
—$S(O)_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—C(=N—O—$R_8$)—,
—C(=N—O—$R_8$)—NH—,
—CH(—N(—O—$R_8$)-Q-$R_4$)—,

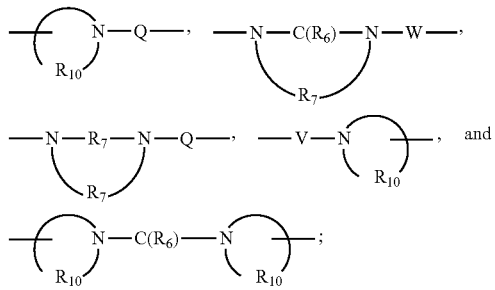

Y' is selected from the group consisting of —$S(O)_2$—, —$S(O)_2$—N($R_8$)—, —C($R_6$)—, —C($R_6$)—O—, and —C($R_6$)—N($R_8$)—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

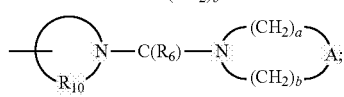

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;
or a pharmaceutically acceptable salt thereof. For certain embodiments, when Y' is —S(O)$_2$— then R$_4$ is other than haloalkyl. For certain of these embodiments, when Y' is —S(O)$_2$— then R$_4$ is other than trifluoromethyl.

Compounds of Formula LXXX are not only useful for modulating cytokine biosynthesis, but certain of these compounds are useful, for example, as prodrugs and/or intermediates in the preparation of compounds of Formulas I, Ia, II, III, and VIII.

In another embodiment, the present invention provides compounds of the formula (II-1):

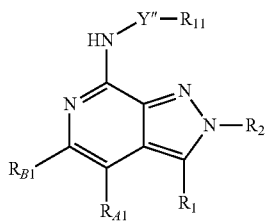

II-1 wherein:
Y" is selected from the group consisting of —C(O)—, —C(O)—O—, and —C(=NR$_9$)—;
$R_{11}$ is alkyl that is unsubstituted or substituted by one or more substituents selected from the group consisting of halogen, hydroxy, nitro, cyano, carboxy, $C_{1-4}$ alkoxy, aryl, heteroaryl, arylC$_{1-4}$ alkylenyl, heteroarylC$_{1-4}$ alkylenyl, haloC$_{1-4}$ alkyl, haloC$_{1-4}$ alkoxy, —O—C(O)—CH$_3$, —CO$_2$CH$_3$, —CONH$_2$, —O—CH$_2$—CONH$_2$, —NH$_2$, and —SO$_2$—NH$_2$;
$R_{A1}$ and $R_{B1}$ are each independently selected from the group consisting of:
hydrogen,
halogen,
alkyl,
alkenyl,
alkoxy,
alkylthio and
—N(R$_9$)$_2$;
or when taken together, $R_{A1}$ and $R_{B1}$ form a fused aryl ring or heteroaryl ring containing one heteroatom selected from the group consisting of N and S wherein the aryl or heteroaryl ring is unsubstituted or substituted by one or more R groups, or substituted by one R$_3$ group, or substituted by one R$_3$ group and one R group;
or when taken together, $R_{A1}$ and $R_{B1}$ form a fused 5 to 7 membered saturated ring, optionally containing one heteroatom selected from the group consisting of N and S, and unsubstituted or substituted by one or more R groups;
R is selected from the group consisting of:
halogen,
hydroxy,
alkyl,
alkenyl,
haloalkyl,
alkoxy,
alkylthio, and
—N(R$_9$)$_2$;
$R_1$ is selected from the group consisting of:
—R$_4$,
—X—R$_4$,
—X—Y—R$_4$,
—X—Y—X—Y—R$_4$, and
—X—R$_5$;
$R_2$ is selected from the group consisting of:
—R$_4$,
—X—R$_4$,
—X—Y—R$_4$, and
—X—R$_5$;
$R_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$-,
—S(O)$_2$—N(R$_8$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—C(=N—O—R$_8$)—NH—,
—CH(—N(—O—R$_8$)-Q-R$_4$)—,

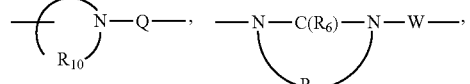

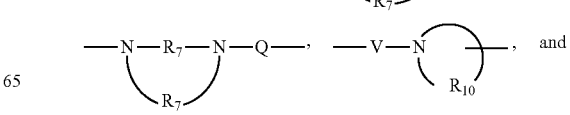

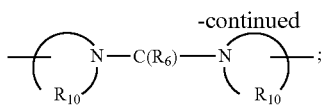

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

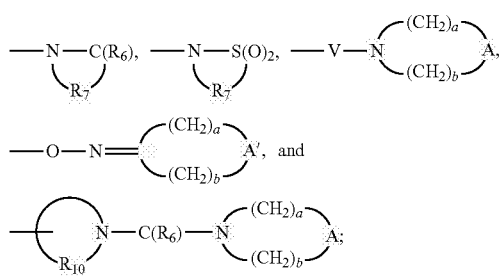

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that at least one of R$_{A1}$, R$_{B1}$, R$_1$, or R$_2$ is other than hydrogen; and with the further proviso that when R$_{A1}$ and R$_{B1}$ form a fused benzene ring unsubstituted or substituted with chloro, and R$_1$ is hydrogen, then R$_2$ is other than phenyl or phenyl substituted with methyl, methoxy, chloro, or fluoro;
or a pharmaceutically acceptable salt thereof. For certain embodiments, Y" is selected from the group consisting of —C(O)— and —C(O)—O—, and R$_{11}$ is C$_{1-6}$ alkyl.

Compounds and salts of Formula II-1 are useful as prodrugs for compounds and salts of Formulas I, Ia, II, III, IV, V, VI, VII, VIII, and IX. For certain embodiments, the compounds or salts of Formula II-1 are 2H-pyrazolo[3,4-c]quinolines of the Formula II-2:

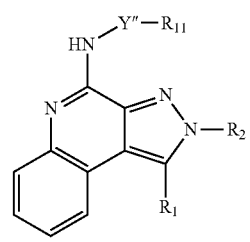

or pharmaceutically acceptable salts thereof, which are examples of prodrugs for compounds or salts of Formula III. For certain embodiments, the compound or salt of Formula II-1 or any one of its above embodiments is selected from the group consisting of:
N-(1-isobutyl-2-methyl-2H-pyrazolo[3,4-c]quinolin-4-yl)acetamide;
ethyl 1-isobutyl-2-methyl-2H-pyrazolo[3,4-c]quinolin-4-ylcarbamate; and
ethyl 2-methyl-1-{2-[(methylsulfonyl)amino]ethyl}-6,7,8,9-tetrahydro-2H-pyrazolo[3,4-c]quinolin-4-ylcarbamate;
or a pharmaceutically acceptable salt thereof.

Herein, "non-interfering" means that the ability of the compound or salt, which contains a non-interfering substituent, to modulate (e.g., induce or inhibit) the biosynthesis of one or more cytokines is not destroyed by the non-interfering substitutent. Illustrative non-interfering R' groups include those described herein for R$_1$. Illustrative non-interfering R" groups include those described herein for R$_2$. Illustrative non-interfering substituents (e.g., R''') for a substituted, fused aryl or heteroaryl ring, formed when R$_A$ and R$_B$ (in Formula I) or R$_{A3}$ and R$_{B3}$ (in Formula Ia) are taken together, include those described herein for R and R$_3$. Illustrative non-interfering substituents for a substituted, fused 5 to 7 membered saturated ring optionally containing one heteroatom, formed when R$_A$ and R$_B$ (in Formula I) or R$_{A3}$ and R$_{B3}$ (in Formula Ia) are taken together, include those described herein for R.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems.

Examples of aryl groups include phenyl, naphthyl, biphenyl, fluorenyl and indenyl.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

The terms "arylene," "heteroarylene," and "heterocyclylene" are the divalent forms of the "aryl," "heteroaryl," and "heterocyclyl" groups defined above. The terms, "arylenyl", "heteroarylenyl", and "heterocyclylenyl" are used when "arylene," "heteroarylene," and "heterocyclylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno. In certain embodiments, the fused aryl ring is benzo.

The term "fused heteroaryl ring" includes the fused forms of 5 or 6 membered aromatic rings that contain one heteroatom selected from S and N. In certain embodiments, the fused heteroaryl ring is pyrido or thieno. In certain embodiments, the fused heteroaryl ring is pyrido. In certain of these embodiments, the pyrido ring is

wherein the highlighted bond indicates the position where the ring is fused.

The term "fused 5 to 7 membered saturated ring" includes rings which are fully saturated except for the bond where the ring is fused. In certain embodiments, the ring is a cyclohexene ring. In certain embodiments wherein one heteroatom (N or S) is present, the ring is tetrahydropyrido or dihydrothieno. In certain embodiments, the ring is tetrahydropyrido. In certain of these embodiments, the ring is

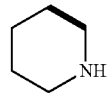

wherein the highlighted bond indicates the position where the ring is fused.

When a group (or substituent or variable) is present more than once in any formula described herein, each group (or substituent or variable) is independently selected, whether explicitly stated or not. For example, for the formula —N($R_8$)—C($R_6$)—N($R_8$)— each $R_8$ group is independently selected. In another example, when an $R_2$ and an $R_3$ group both contain an $R_4$ group, each $R_4$ group is independently selected. In a further example, when more than one Y group is present (i.e., $R_2$ and $R_3$ both contain a Y group) and each Y group contains one or more $R_8$ groups, then each Y group is independently selected, and each $R_8$ group is independently selected.

The invention is inclusive of the compounds described herein and salts thereof, in any of their pharmaceutically acceptable forms, including isomers (e.g., diastereomers and enantiomers), solvates, polymorphs, prodrugs, and the like. In particular, if a compound is optically active, the invention specifically includes each of the compound's enantiomers as well as racemic mixtures of the enantiomers. It should be understood that the term "compound" or the term "compounds" includes any or all of such forms, whether explicitly stated or not (although at times, "salts" are explicitly stated).

The term "prodrug" means a compound that is transformed in vivo to yield a compound of the invention or a pharmaceutically acceptable salt, hydrate or solvate of the compound. The transformation may occur by various mechanisms, such as through hydrolysis, for example, in the blood. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyolacton-4-yl, di-N,N—$C_{1-2}$alkylamino$C_{2-3}$ alkyl (such as β-dimethylaminoethyl), carbamoyl-$C_{1-2}$ alkyl, N,N-di$C_{1-2}$alkylcarbamoyl-$C_{1-2}$ alkyl and piperidino-, pyrrolidino-, or morpholino$C_{2-3}$ alkyl.

If a compound of the present invention contains an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O—$C_{1-6}$ alkyl)$_2$ or glycosyl (the radical resulting from the removal of a hydroxyl group of the hemiacetal form of a carbohydrate).

A prodrug can also be formed by replacement of a hydrogen atom in the 4-amino group or in another amino group in a compound of the present invention with a group such as R''''-carbonyl, R''''—O-carbonyl, N(R'''')(R'''')-carbonyl where R'''' and R''''' are each independently $C_{1-10}$ alkyl, $C_{3-7}$ cycloalkyl, benzyl, or R''''-carbonyl is a natural α-aminoacyl or natural α-aminoacyl-natural α-aminoacyl, —C(OH)C(O)OY''' wherein Y''' is H, $C_{1-6}$ alkyl or benzyl, —C(OY$_0$)Y$_1$ wherein Y$_0$ is $C_{1-4}$ alkyl and Y$_1$ is $C_{1-6}$ alkyl, carboxy$C_{1-6}$ alkyl, amino$C_{1-4}$ alkyl or mono-N— or di-N,N—$C_{1-6}$ alkylaminoalkyl, —C(Y$_2$)Y$_3$ wherein Y$_2$ is H or methyl and Y$_3$ is non-N— or di-N,N—$C_{1-6}$ alkylamino, morpholino, piperidin-1-yl or pyrrolidin-1-yl.

Compounds and intermediates of the present invention may exist in different tautomeric forms, and all such forms are embraced within the scope of the invention. The term "tautomer" or "tautomeric form" refers to structural isomers of different energies which are interconvertible via a low energy barrier. For example proton tautomers (protrotropic tautomers) include interconversions via migration of a proton, such as keto-enol and imine-enamine isomerizations. In another example, when compounds of the present invention have a hydrogen atom at the 2-position, proton migration between the 1- and 3-positions may occur.

The compounds of the present invention may exist in unsolvated as well as solvated forms with pharmaceutically acceptable solvents such as water, ethanol, and the like. The present invention embraces both solvated and unsolvated forms.

In some embodiments, compounds of the invention (for example, compounds of Formulas Ia and I-IX, including embodiments thereof described herein) induce the biosynthesis of one or more cytokines, for example, IFN-α and/or TNF-α.

In some embodiments, compounds of the invention (for example, compounds of Formulas Ia and I-IX, including embodiments thereof described herein) inhibit the biosynthesis of one or more cytokines, for example, TNF-α.

For any of the compounds presented herein, each one of the following variables (e.g., R, R', R'', R''', R$_1$, R$_2$, R$_3$, n, m, A, X, Y, Z, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, each of R, R', R'', and R''' is independently a non-interfering substituent. For certain embodiments, each R' and R'' is independently selected from the group consisting of hydrogen and non-interfering substituents.

In some embodiments of Formula I, R$_A$ and R$_B$ are each independently selected from the group consisting of hydrogen, halogen, alkyl, alkenyl, alkoxy, alkylthio, and —N(R$_9$)$_2$; or when taken together, R$_A$ and R$_B$ form a fused aryl ring or heteroaryl ring containing one heteroatom selected from the group consisting of N and S wherein the aryl or heteroaryl ring is unsubstituted or substituted by one or more non-interfering substituents; or when taken together, R$_A$ and R$_B$ form a fused 5 to 7 membered saturated ring, optionally containing one heteroatom selected from the group consisting of N and S, and unsubstituted or substituted by one or more substituents selected from the group consisting of halogen, hydroxy, alkyl, alkenyl, haloalkyl, alkoxy, alkylthio, and —N(R$_9$)$_2$.

In some embodiments of Formula I, R$_A$ and R$_B$ are each independently selected from the group consisting of hydrogen, halogen, alkyl, alkenyl, alkoxy, alkylthio, and —N(R$_9$)$_2$; or when taken together, R$_A$ and R$_B$ form a fused aryl ring or heteroaryl ring containing one heteroatom selected from the group consisting of N and S wherein the aryl or heteroaryl ring is unsubstituted or substituted by one or more R''' groups; or when taken together, R$_A$ and R$_B$ form a fused 5 to 7 membered saturated ring, optionally containing one heteroatom selected from the group consisting of N and S, and unsubstituted or substituted by one or more R groups; wherein each R is independently selected from the group consisting of halogen, hydroxy, alkyl, alkenyl, haloalkyl, alkoxy, alkylthio, and —N(R$_9$)$_2$.

In some embodiments of Formula I, R$_A$ and R$_B$ are each independently selected from the group consisting of hydrogen, halogen, alkyl, alkenyl, alkoxy, alkylthio, and —N(R$_9$)$_2$.

In some embodiments of Formula I, R$_A$ and R$_B$ form a fused aryl or heteroaryl ring.

In some embodiments of Formula I, R$_A$ and R$_B$ form a fused aryl ring.

In some embodiments of Formula I, R$_A$ and R$_B$ form a fused heteroaryl ring.

In some embodiments of Formula I, R$_A$ and R$_B$ form a fused 5 to 7 membered saturated ring.

In some embodiments of Formula I, R$_A$ and R$_B$ form a fused 5 to 7 membered saturated ring containing one heteroatom selected from the group consisting of N and S. In certain embodiments the heteroatom is N.

In some embodiments of Formula II, R$_{A1}$ and R$_{B1}$ are each independently selected from the group consisting of hydrogen, halogen, alkyl, alkenyl, alkoxy, alkylthio and —N(R$_9$)$_2$; or when taken together, R$_{A1}$ and R$_{B1}$ form a fused aryl ring or heteroaryl ring containing one heteroatom selected from the group consisting of N and S wherein the aryl or heteroaryl ring is unsubstituted or substituted by one or more R groups, or substituted by one R$_3$ group, or substituted by one R$_3$ group and one R group; or when taken together, R$_{A1}$ and R$_{B1}$ form a fused 5 to 7 membered saturated ring, optionally containing one heteroatom selected from the group consisting of N and S, and unsubstituted or substituted by one or more R groups; wherein R is selected from the group consisting of halogen, hydroxy, alkyl, alkenyl, haloalkyl, alkoxy, alkylthio, and —N(R$_9$)$_2$; and R$_3$ is selected from the group consisting of —Z—R$_4$, —Z—X—R$_4$, —Z—X—Y—R$_4$, —Z—X—Y—X—Y—R$_4$, and —Z—X—R$_5$.

In some embodiments of Formula II, R$_{A1}$ and R$_{B1}$ form a fused aryl ring.

In some embodiments of Formula II, R$_{A1}$ and R$_{B1}$ form a fused benzene ring which is unsubstituted.

In some embodiments of Formula II, $R_{A1}$ and $R_{B1}$ form a fused heteroaryl ring.

In some embodiments of Formula II, $R_{A1}$ and $R_{B1}$ form a fused pyridine ring which is unsubstituted.

In some embodiments of Formula II, $R_{A1}$ and $R_{B1}$ form a fused 5 to 7 membered saturated ring, optionally containing one heteroatom selected from the group consisting of N and S, wherein the ring is unsubstituted.

In some embodiments of Formula II, $R_{A1}$ and $R_{B1}$ form a fused 5 to 7 membered saturated ring.

In some embodiments of Formula II, $R_{A1}$ and $R_{B1}$ form a fused 5 to 7 membered saturated ring containing one heteroatom selected from the group consisting of N and S. In certain embodiments the heteroatom is N.

In some embodiments of Formula IX, $R_{A2}$ and $R_{B2}$ are each independently selected from the group consisting of hydrogen, halogen, alkyl, alkenyl, alkoxy, alkylthio, and —N(R$_9$)$_2$. In certain of these embodiments, $R_{A2}$ and $R_{B2}$ are each independently alkyl. In certain of these embodiments, $R_{A2}$ and $R_{B2}$ are each methyl.

In some embodiments of Formula Ia, $R_{A3}$ and $R_{B3}$ are each independently selected from the group consisting of hydrogen, halogen, alkyl, alkenyl, alkoxy, alkylthio, and —N(R$_9$)$_2$; or when taken together, $R_{A3}$ and $R_{B3}$ form a fused aryl ring or heteroaryl ring containing one heteroatom or a 5 to 7 membered saturated ring containing one heteroatom wherein the heteroatom is selected from the group consisting of N and S and wherein the aryl, heteroaryl, or 5 to 7 membered saturated ring is unsubstituted or substituted by one or more non-interfering substituents.

In some embodiments (e.g., of Formulas I through VIII), $R_d$ is selected from the group consisting of halogen, hydroxy, alkyl, alkenyl, haloalkyl, alkoxy, alkylthio, and —N(R$_9$)$_2$.

In some embodiments (e.g., of Formulas I through VIII and particularly Formula III), R is selected from the group consisting of hydroxy and methoxy. In certain of these embodiments (e.g., of Formula III), m is 0. In certain of these embodiments, m is 0 and n is 1.

In some embodiments (e.g., of Formula LXXX), $R_d$ is selected from the group consisting of halogen, alkyl, alkenyl, trifluoromethyl, and dialkylamino In some embodiments of Formulas I and Ia, R' is selected from the group consisting of —R$_4$, —X—R$_4$, —X—Y—R$_4$, —X—Y—X—Y—R$_4$, and —X—R$_5$; wherein:

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of —O—, —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N═C(R$_4$)—, —C(═N—O—R$_8$)—, —CH(—N(—O—R$_8$)-Q-R$_4$)—,

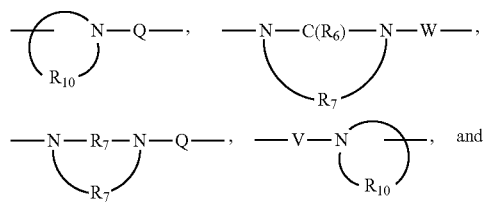

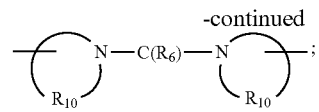

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

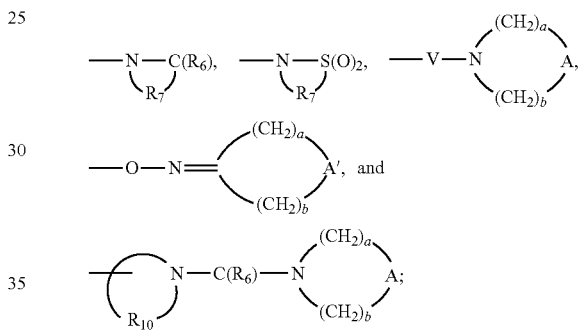

$R_6$ is selected from the group consisting of ═O and ═S;
$R_7$ is C$_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is C$_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7. In certain of these embodiments, the above group from which Y is selected also includes —C(═N—O—R$_8$)—NH—. In certain of these embodiments of Formulas I and Ia, Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

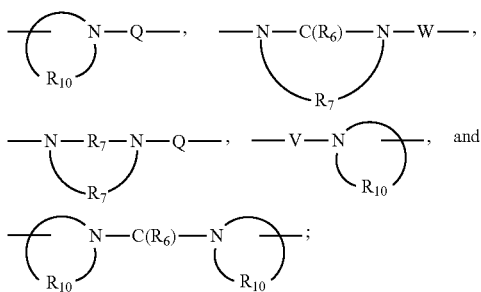

$R_5$ is selected from the group consisting of

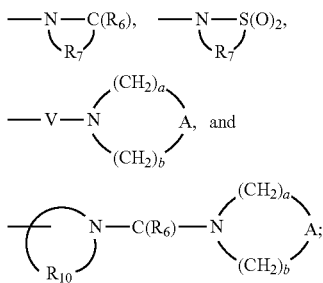

and $R_8$ is selected from the group consisting of hydrogen, alkyl, alkoxyalkylenyl, hydroxyalkylenyl, and arylalkylenyl. In certain of these embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

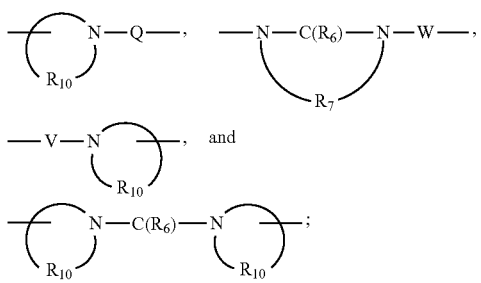

$R_5$ is selected from the group consisting of

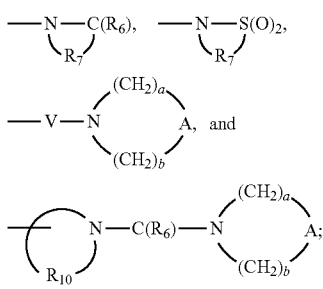

$R_8$ is selected from the group consisting of hydrogen, alkyl, alkoxyalkylenyl, and arylalkylenyl; and Q is selected from the group consisting of a bond, —C(R$_6$)—, —C(R$_6$)—C(R$_6$)—, —S(O)$_2$—, —C(R$_6$)—N(R$_3$)—W—, —S(O)$_2$—N(R$_8$)—, —C(R$_6$)—O—, and —C(R$_6$)—N(OR$_9$)—.

In some embodiments of Formulas I and Ia, R' is selected from the group consisting of —R$_4$, —X—R$_4$, —X—Y—X$^1$—Y$^1$—R$_4$, and —X—R$_5$; wherein:

X is alkylene that is optionally interrupted or terminated by heterocyclylene and optionally interrupted by one —O— group;

Y is selected from the group consisting of —O—, —S(O)$_2$—, —S(O)$_2$—N(R$_8$)—, —C(O)—, —C(O)—O—, —O—C(O)—, —N(R$_8$)-Q-, —C(O)—N(R$_8$)—,

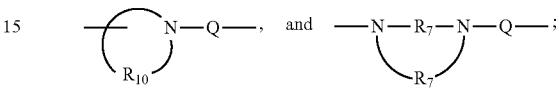

$X^1$ is selected from the group consisting of alkylene and arylene;

$Y^1$ is selected from the group consisting of —S—, —C(O)—, —C(O)—O—, —C(O)—N(R$_8$)—, —S(O)$_2$—N(R$_8$)—, and —N(R$_8$)—C(O)—;

$R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo;

$R_5$ is selected from the group consisting of:

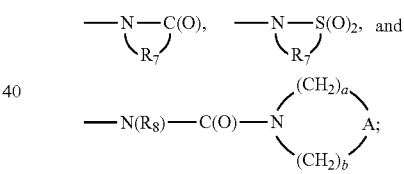

$R_6$ is selected from the group consisting of =O and =S;

$R_7$ is C$_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_{10}$ is C$_{3-8}$ alkylene;

A is selected from the group consisting of —O—, —C(O)—, and —N(R$_4$)—;

Q is selected from the group consisting of a bond, —C(R$_6$)—, —S(O)$_2$—, —C(R$_6$)—N(R$_8$)—W—, —S(O)$_2$—N(R$_8$)—, —C(O)—O—, and —C(O)—S—;

W is selected from the group consisting of a bond and —C(O)—; and a and b are independently integers from 1 to 6 with the proviso that a+b is ≤7.

In certain of these embodiments of Formulas I and Ia, X is alkylene that is optionally interrupted or terminated by heterocyclylene; Y is selected from the group consisting of —S(O)$_2$—, —C(O)—, —C(O)—O—, —O—C(O)—, —N(R$_8$)-Q-, —C(O)—N(R$_8$)—,

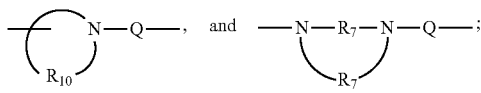

$R_4$ is selected from the group consisting of hydrogen, alkyl, aryl, heterocyclyl, heteroaryl, heteroarylalkylenyl, alkynyl, and arylalkenylenyl, wherein the alkyl, aryl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo; and $R_8$ is selected from the group consisting of hydrogen, alkyl, alkoxyalkylenyl, hydroxyalkylenyl, and arylalkylenyl.

In some embodiments of Formulas I and Ia, R' is selected from the group consisting of alkyl, arylalkylenyl, heterocyclylalkylenyl wherein heterocyclyl is unsubstituted or substituted with one or two oxo groups, aryloxyalkylenyl, hydroxyalkylenyl, aminoalkylenyl, haloalkylenyl, alkylsulfonylalkylenyl, —X—Y—$R_4$, and —X—$R_5$; wherein X is alkylene; Y is —N($R_8$)—C(O)—, —N($R_8$)—S(O)$_2$—, —N($R_8$)—C(O)—N($R_8$)—, —N($R_8$)—C(S)—N($R_8$)—, —N($R_8$)—S(O)$_2$—N($R_8$)—, or

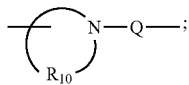

$R_4$ is alkyl, aryl, or heteroaryl; and $R_5$ is

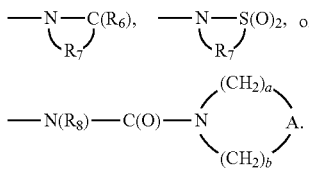

In some embodiments of Formulas I and Ia, R' is selected from the group consisting of $C_{1-5}$ alkyl, $C_{2-5}$ alkynyl, aryl$C_{1-4}$alkylenyl, cycloalkyl$C_{1-4}$alkylenyl, $C_{1-4}$ alkyl-S(O)$_2$—$C_{1-4}$alkylenyl, aryl-S(O)$_2$—$C_{1-4}$ alkylenyl, $C_{1-4}$ alkyl-S(O)$_2$—$C_{1-4}$ alkylenyl-O—$C_{1-4}$ alkylenyl, $C_{1-4}$ alkyl-S(O)$_2$—NH—$C_{1-4}$ alkylenyl, hydroxy$C_{1-4}$alkylenyl, halo$C_{1-4}$ alkylenyl, amino$C_{1-4}$alkylenyl, $C_{1-4}$ alkyl-C(O)—O—$C_{1-4}$ alkylenyl, $C_{1-6}$ alkyl-C(O)—NH—$C_{1-4}$ alkylenyl, aryl-C(O)—NH—$C_{1-4}$ alkylenyl wherein aryl is unsubstituted or substituted with one or two halogen groups, heteroaryl-C(O)—NH—$C_{1-4}$ alkylenyl, di($C_{1-4}$ alkyl)amino-S(O)$_2$—NH—$C_{1-4}$ alkylenyl, aryl-S(O)$_2$—NH—$C_{1-4}$alkylenyl, aryl-NH—C(O)—NH—$C_{1-4}$ alkylenyl, heteroaryl-NH—C(S)—NH—$C_{1-4}$ alkylenyl, di($C_{1-4}$alkyl)amino-C(O)—NH—$C_{1-4}$alkylenyl, $C_{1-4}$ alkylamino-C(O)—NH—$C_{1-4}$ alkylenyl, di($C_{1-4}$ alkyl)amino-S(O)$_2$—$C_{1-4}$ alkylenyl, $C_{1-4}$ alkylamino-S(O)$_2$—$C_{1-4}$ alkylenyl, amino-S(O)$_2$—$C_{1-4}$ alkylenyl, heteroaryl$C_{1-4}$alkylenyl wherein heteroaryl is unsubstituted or substituted by a substituent selected from the group consisting of aryl, heteroaryl, and alkyl, and heterocyclyl$C_{1-4}$ alkylenyl wherein heterocyclyl is unsubstituted or substituted by one or two substituents selected from the group consisting of heteroaryl and oxo. In some embodiments of Formulas I and Ia, the above group from which R' is selected also includes hydrogen, $C_{1-4}$ alkyl-S(O)$_2$—$C_{1-4}$ alkylenyl-NH—$C_{1-4}$ alkylenyl, cyano$C_{1-4}$alkylenyl, hydroxyimino $C_{2-5}$alkylenyl, $C_{1-4}$ alkoxyimino$C_{2-5}$alkylenyl, amino(hydroxyimino)$C_{2-5}$alkylenyl, NH$_2$—C(O)—$C_{1-4}$alkylenyl, $C_{1-4}$ alkyl-C(O)—$C_{1-4}$ alkylenyl, $C_{1-6}$ alkyl-O—C(O)—NH—$C_{1-4}$alkylenyl, heterocyclyl-C(O)—NH—$C_{1-4}$ alkylenyl; and wherein heteroaryl is unsubstituted or substituted by a substituent selected from the group consisting of aryl, arylalkylenyl, heteroaryl, and alkyl; and wherein heterocyclyl is unsubstituted or substituted by one or two substituents selected from the group consisting of arylalkylenyl, heteroaryl, and oxo.

In some embodiments of Formulas I and Ia, R' is selected from the group consisting of methyl, ethyl, propyl, 2-methylpropyl, 2,2-dimethylpropyl, butyl, pent-4-ynyl, 2-phenylethyl, 2-hydroxy-2-methylpropyl, 4-hydroxybutyl, 2-amino-2-methylpropyl, 2-aminoethyl, 4-aminobutyl, 2-methanesulfonylethyl, 2-(propylsulfonyl)ethyl, 4-(methylsulfonyl)butyl, 3-(phenylsulfonyl)propyl, 2-methyl-2-[2-(methylsulfonyl)ethoxy]propyl, 4-acetoxybutyl, 4-methanesulfonylaminobutyl, 2-methyl-2-[(methylsulfonyl)amino]propyl, 2-(2-propanesulfonylamino)ethyl, 2-(benzenesulfonylamino)ethyl, 2-(dimethylaminosulfonylamino)ethyl, 4-(aminosulfonyl)butyl, 4-[(methylamino)sulfonyl]butyl, 4-[(dimethylamino)sulfonyl]butyl, 2-[(cyclohexylcarbonyl)amino]-2-methylpropyl, 2-[(cyclopropylcarbonyl)amino]-2-methylpropyl, 2-(isobutyrylamino)-2-methylpropyl, 2-methyl-2-(propionylamino)propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-(isobutyrylamino)ethyl, 2-{[(isopropylamino)carbonyl]amino-2-methylpropyl, 2-{[(isopropylamino)carbonyl]amino}ethyl, 4-[(morpholin-4-ylcarbonyl)amino]butyl, 4-(4-pyridin-2-ylpiperazin-1-yl)butyl, 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, 4-(3-methyl-1-oxa-2,4-diazaspiro[4.4]non-2-en-4-yl)butyl, 2-{[(pyridin-3-ylamino)carbonothioyl]amino}ethyl, 2-{[(dimethylamino)carbonyl]amino}ethyl, and 2-{[(phenylamino)carbonyl]amino}ethyl. In some embodiments of Formulas I and Ia, the above group from which R' is selected also includes hydrogen, hydroxymethyl, 2-cyano-2-methylpropyl, 3-amino-2,2-dimethyl-3-oxopropyl, 2,2-dimethyl-4-oxopentyl, 2-methyl-2-(methylsulfonyl)propyl, 2-methyl-2-{[2-(methylsulfonyl)ethyl]amino}propyl, 2-[(methylsulfonyl)amino]ethyl, 3-[(methylsulfonyl)amino]propyl, 2-[(cyclopropylcarbonyl)amino]ethyl, 2-(acetylamino)ethyl, 2-(propionylamino)ethyl, 2-[(4-fluorobenzoyl)amino]ethyl, 2-{[(ethylamino)carbonyl]amino}ethyl, 2-[(morpholin-4-ylcarbonyl)amino]ethyl, 2-[(ethoxycarbonyl)amino]ethyl, 2-(1,1-dioxidoisothiazolidin-2-yl)ethyl, 3-(1H-pyrrol-3-yl)propyl, 3-(1-benzyl-1H-pyrrol-3-yl)propyl, 3-(1-benzyl-2,5-dihydro-1H-pyrrol-3-yl)propyl, 3-(5-butylisoxazol-3-yl)propyl, 3-(5-phenylisoxazol-3-yl)propyl, 3-(5-pyridin-3-ylisoxazol-3-yl)propyl, 2-({[(3,4-difluorophenyl)amino]carbonyl}amino)ethyl, 2-({[(4-fluorophenyl)amino]carbonyl}amino)ethyl, 4-(hydroxyimino)butyl, 4-(methoxyimino)butyl, and 5-amino-5-(hydroxyimino)pentyl.

In some embodiments of Formulas I and Ia, R' is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 4-[(morpholin-4-ylcarbonyl)amino]butyl, 2-(benzoylamino)ethyl, and 4-methanesulfonylaminobutyl. In some embodiments of Formulas I and Ia, the above group from which R' is selected also includes 3-amino-2,2-dimethyl-3-oxopropyl and 2,2-dimethyl-4-oxopentyl.

In some embodiments of Formulas I and Ia, R'' is selected from the group consisting of —$R_4$, —X—$R_4$, —X—Y—$R_4$, and —X—$R_5$; wherein:

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of —O—, —S(O)$_{0\text{-}2}$-, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —C(=N—O—$R_8$)—, —CH(—N(—O—$R_8$)-Q-$R_4$)—,

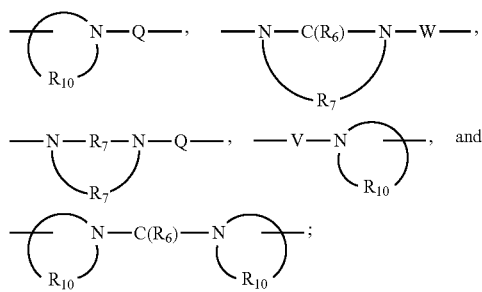

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

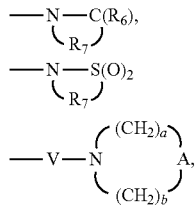

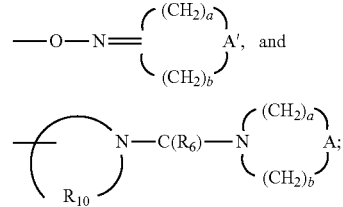

$R_6$ is selected from the group consisting of =O and =S;
$R_7$ is $C_{2\text{-}7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3\text{-}8}$ alkylene;
A is selected from the group consisting of —O—, —C(O)—, —S(O)$_{0\text{-}2}$-, and —N($R_4$)—;
A' is selected from the group consisting of —O—, —S(O)$_{0\text{-}2}$-, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≤7. In certain of these embodiments, the above group from which Y is selected also includes —C(=N—O—$R_8$)—NH—. In certain of these embodiments of Formulas I and Ia, Y is selected from the group consisting of —S(O)$_{0\text{-}2}$-, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—,

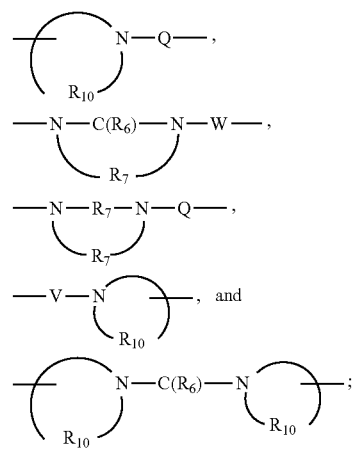

and
$R_5$ is selected from the group consisting of

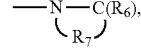

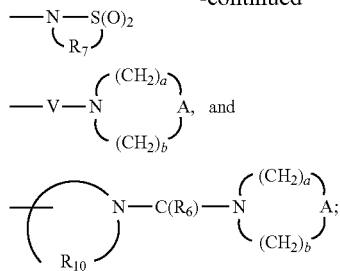

and R_8 is selected from the group consisting of hydrogen, alkyl, alkoxyalkylenyl, hydroxyalkylenyl, and arylalkylenyl. In certain of these embodiments of Formulas I and Ia, Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

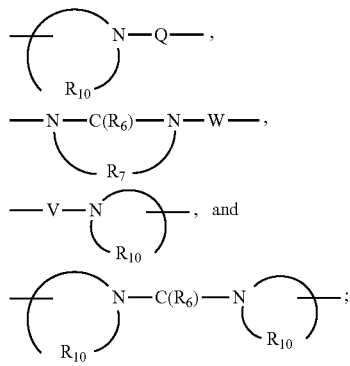

R$_5$ is selected from the group consisting of

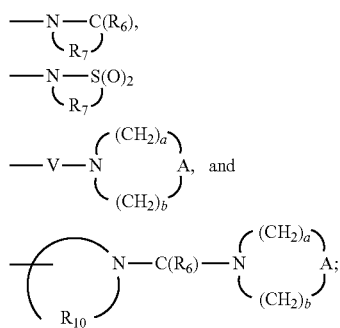

R$_8$ is selected from the group consisting of hydrogen, alkyl, alkoxyalkylenyl, and arylalkylenyl; and Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In some embodiments of Formulas I and Ia, R" is selected from the group consisting of —R$_4$, —X—R$_4$, and —X—Y—R$_4$; wherein:

X is alkylene that is optionally terminated by arylene or heterocyclylene;

Y is selected from the group consisting of —S(O)$_2$—, —C(O)—, —C(O)—O—, —N(R$_8$)-Q-, —C(O)—N(R$_8$)—, and

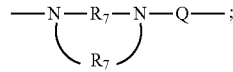

R$_4$ is selected from the group consisting of hydrogen, alkyl, aryl, arylalkylenyl, aryloxyalkylenyl, heterocyclyl, and heteroaryl, wherein the alkyl, aryl, aryloxyalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, cyano, aryl, aryloxy, heteroaryl, heterocyclyl, and in the case of heterocyclyl, oxo;

R$_6$ is selected from the group consisting of =O and =S;

R$_7$ is C$_{2-7}$ alkylene;

R$_8$ is in selected from the group consisting of hydrogen, alkyl, alkoxyalkylenyl, hydroxyalkylenyl, and arylalkylenyl; and Q is selected from the group consisting of a bond, —C(O)—, —S(O)$_2$—, —C(R$_6$)—NR$_8$)—, and —S(O)$_2$—N(R$_8$)—.

In some embodiments of Formulas I and Ia, R" is selected from the group consisting of hydrogen, alkyl, arylalkylenyl, alkoxyalkylenyl, and hydroxyalkylenyl. In certain embodiments, R' is selected from the group consisting of hydrogen, alkyl, arylalkylenyl, and alkoxyalkylenyl. In certain embodiments, R" is selected from the group consisting of hydrogen, alkyl, and alkoxyalkylenyl.

In some embodiments of Formulas I and Ia, R" is selected from the group consisting of hydrogen, C$_{1-5}$ alkyl, C$_{1-4}$alkoxyC$_{1-4}$alkylenyl, hydroxyC$_{1-4}$alkylenyl, and arylC$_{1-4}$ alkylenyl wherein aryl is unsubstituted or substituted by one or more substituents selected from the group consisting of chloro, fluoro, methoxy, methyl, cyano, and methoxycarbonyl. In certain embodiments, R" is selected from the group consisting of hydrogen, C$_{1-5}$ alkyl, C$_{1-4}$ alkoxyC$_{1-4}$ alkylenyl, and arylC$_{1-4}$ alkylenyl wherein aryl is unsubstituted or substituted by one or more substituents selected from the group consisting of chloro, fluoro, methoxy, methyl, cyano, and methoxycarbonyl. In certain embodiments, R" is selected from the group consisting of hydrogen, C$_{1-4}$ alkyl, and C$_{1-4}$ alkoxyC$_{1-4}$ alkylenyl.

In some embodiments of Formulas I and Ia, R" is selected from the group consisting of hydrogen, methyl, ethyl, propyl, butyl, 2-methoxyethyl, 2-hydroxyethyl, and benzyl. In certain embodiments, R" is selected from the group consisting of hydrogen, methyl, ethyl, propyl, butyl, 2-methoxyethyl, and benzyl. In certain embodiments, R" is selected from the group consisting of hydrogen, methyl, ethyl, propyl, butyl, and benzyl. In certain embodiments, R" is selected from the group consisting of methyl, ethyl, propyl, and butyl. In certain embodiments, R" is selected from the group consisting of methyl, ethyl, propyl, butyl, 2-methoxyethyl, and 2-hydroxyethyl.

In some embodiments of Formula I, one or more R'" groups are present. In certain of these embodiments, R'" is one or more R groups, or one R group and one R$_3$ group, or one R$_3$ group.

In some embodiments (e.g., of Formulas II through IX and LXXX), R$_1$ is selected from the group consisting of —R$_4$, —X—R$_4$, —X—Y—R$_4$, —X—Y—X—Y—R$_4$, and —X—R$_5$; wherein:

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of —O—, —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—,

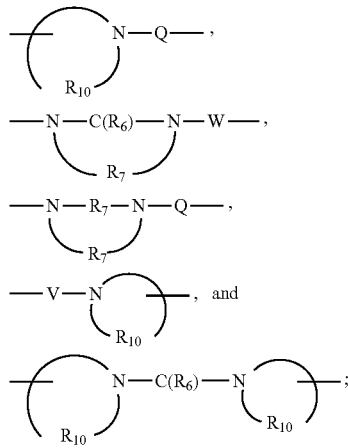

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

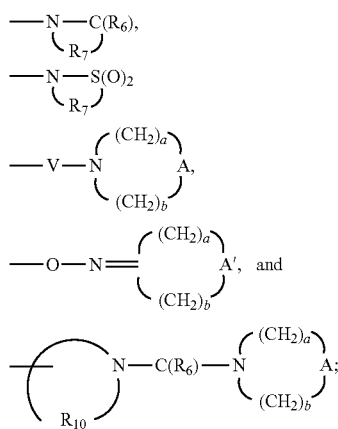

R$_6$ is selected from the group consisting of =O and =S;
R$_7$ is C$_{2-7}$ alkylene;

R$_8$ is selected from the group consisting of hydrogen, alkyl, alkoxyalkylenyl, hydroxyalkylenyl, arylalkylenyl, and heteroarylalkylenyl;

R$_9$ is selected from the group consisting of hydrogen and alkyl;

R$_{10}$ is C$_{3-8}$ alkylene;

A is selected from the group consisting of —O—, —C(O)—, —S(O)$_{0-2}$-, and —N(R$_4$)—;

A' is selected from the group consisting of —O—, —S(O)$_{0-2}$-, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7. In certain of these embodiments, the above group from which Y is selected also includes —C(=N—O—R$_8$)—NH—. In certain of these embodiments (e.g., of Formulas II through IX and LXXX), Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

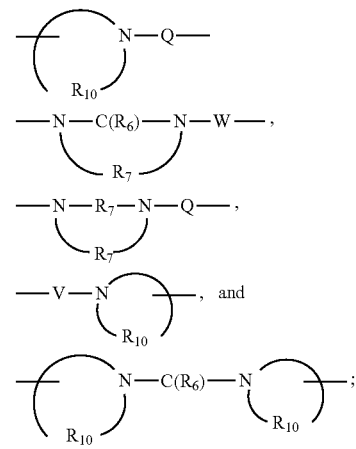

R$_5$ is selected from the group consisting of

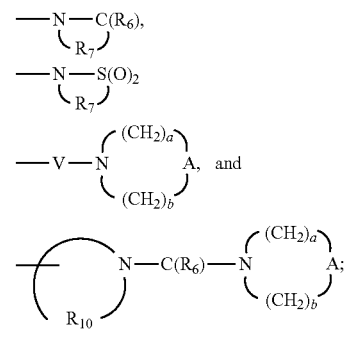

and R$_8$ is selected from the group consisting of hydrogen, alkyl, alkoxyalkylenyl, hydroxyalkylenyl, and arylalkylenyl. In certain of these embodiments, Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

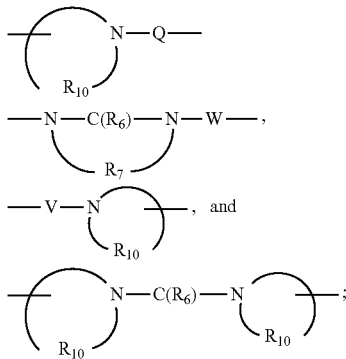

R$_5$ is selected from the group consisting of

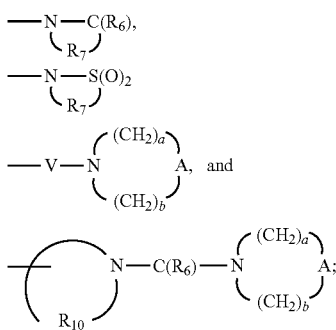

R$_8$ is selected from the group consisting of hydrogen, alkyl, alkoxyalkylenyl, and arylalkylenyl; and Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In some embodiments (e.g., of Formulas II through IX and LXXX), R$_1$ is selected from the group consisting of —R$_4$, —X—R$_4$, —X—Y—R$_4$, —X—Y—X$^1$—Y$^1$—R$_4$, and —X—R$_5$; wherein:

X is alkylene that is optionally interrupted or terminated by heterocyclylene and optionally interrupted by one —O— group;

Y is selected from the group consisting of —O—, —S(O)$_2$—, —S(O)$_2$—N(R$_8$)—, —C(O)—, —C(O)—O—, —O—C(O)—, —N(R$_8$)-Q-, —C(O)—N(R$_8$)—,

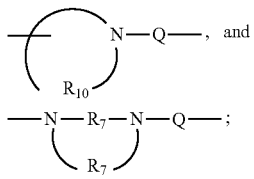

X$^1$ is selected from the group consisting of alkylene and arylene;

Y$^1$ is selected from the group consisting of —S—, —C(O)—, —C(O)—O—, —C(O)—N(R$_8$)—, —S(O)$_2$—N(R$_8$)—, and —N(R$_8$)—C(O)—;

R$_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo;

R$_5$ is selected from the group consisting of

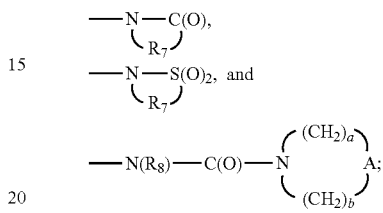

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_{10}$ is C$_{3-8}$ alkylene;
A is selected from the group consisting of —O—, —C(O)—, and —N(R$_4$)—;
Q is selected from the group consisting of a bond, —C(R$_6$)—, —S(O)$_2$—, —C(R$_6$)—N(R$_8$)—W—, —S(O)$_2$—N(R$_3$)—, —C(O)—O—, and —C(O)—S—;
W is selected from the group consisting of a bond and —C(O)—; and
a and b are independently integers from 1 to 6 with the proviso that a+b is ≤7.

In certain of these embodiments, X is alkylene that is optionally interrupted or terminated by heterocyclylene; Y is selected from the group consisting of —S(O)$_2$—, —C(O)—, —C(O)—O—, —O—C(O)—, —N(R$_8$)-Q-, —C(O)—N(R$_8$)—,

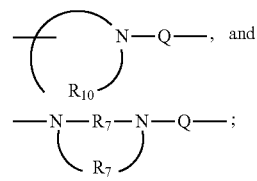

R$_4$ is selected from the group consisting of hydrogen, alkyl, aryl, heterocyclyl, heteroaryl, heteroarylalkylenyl, alkynyl, and arylalkenylenyl, wherein the alkyl, aryl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo; and R$_8$ is selected from the group consisting of hydrogen, alkyl, alkoxyalkylenyl, hydroxyalkylenyl, and arylalkylenyl.

In some embodiments (e.g., of Formulas II through IX and LXXX), R$_1$ is selected from the group consisting of alkyl, arylalkylenyl, heterocyclylalkylenyl wherein heterocyclyl is unsubstituted or substituted with one or two oxo groups, aryloxyalkylenyl, hydroxyalkylenyl, aminoalkylenyl, haloalkylenyl, alkylsulfonylalkylenyl, —X—Y—R$_4$, and —X—R$_5$; wherein X is alkylene; Y is —N(R$_8$)—C(O)—, —N(R$_8$)—S(O)$_2$—, —N(R$_8$)—C(O)—N(R$_8$)—, —N(R$_8$)—C(S)—N(R$_8$)—, —N(R$_8$)—S(O)$_2$—N(R$_8$)—, or

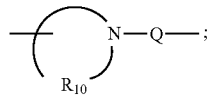

R$_4$ is alkyl, aryl, or heteroaryl; and R$_5$ is

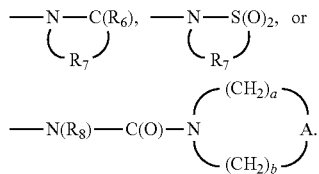

In some embodiments (e.g., of Formulas II through IX and LXXX), R$_1$ is selected from the group consisting of alkyl, arylalkylenyl, aryloxyalkylenyl, hydroxyalkyl, alkylsulfonylalkylenyl, —X—Y—R$_4$, and —X—R$_5$; wherein X is alkylene; Y is —N(R$_8$)—C(O)—, —N(R$_8$)—S(O)$_2$—, —N(R$_8$)—C(O)—N(R$_8$)—, or

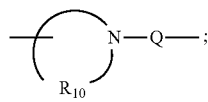

R$_4$ is alkyl, aryl, or heteroaryl; and R$_5$ is

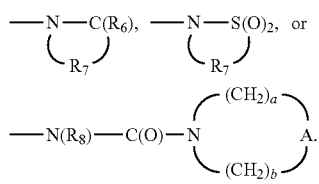

In some embodiments (e.g., of Formulas II through IX and LXXX), R$_1$ is —R$_4$.

In some embodiments (e.g., of Formulas II through IX and LXXX), R$_1$ is —X—R$_4$.

In some embodiments (e.g., of Formulas II through IX and LXXX), R$_1$ is —X—Y—R$_4$.

In some embodiments (e.g., of Formulas II through IX and LXXX), R$_1$ is —X—Y—X—Y—R$_5$.

In some embodiments (e.g., of Formulas II through IX and LXXX), R$_1$ is —X—Y—X$^1$—Y$^1$—R$_4$.

In some embodiments (e.g., of Formulas II through IX and LXXX), R$_1$ is —X—R$_5$.

In some embodiments (e.g., of Formulas II through IX and LXXX), R$_1$ is selected from the group consisting of C$_{1-5}$ alkyl, C$_{2-5}$ alkynyl, arylC$_{1-4}$ alkylenyl, cycloalkylC$_{1-4}$ alkylenyl, C$_{1-4}$ alkyl-S(O)$_2$—C$_{1-4}$ alkylenyl, aryl-S(O)$_2$—C$_{1-4}$ alkylenyl, C$_{1-4}$ alkyl-S(O)$_2$—C$_{1-4}$ alkylenyl-O—C$_{1-4}$ alkylenyl, C$_{1-4}$ alkyl-S(O)$_2$—NH—C$_{1-4}$ alkylenyl, hydroxy C$_{1-4}$alkylenyl, haloC$_{1-4}$ alkylenyl, aminoC$_{1-4}$alkylenyl, C$_{1-4}$ alkyl-C(O)—O—C$_{1-4}$ alkylenyl, C$_{1-6}$ alkyl-C(O)—NH—C$_{1-4}$ alkylenyl, aryl-C(O)—NH—C$_{1-4}$ alkylenyl wherein aryl is unsubstituted or substituted with one or two halogen groups, heteroaryl-C(O)—NH—C$_{1-4}$ alkylenyl, di(C$_{1-4}$alkyl)amino-S(O)$_2$—NH—C$_{1-4}$ alkylenyl, aryl-S(O)$_2$—NH—C$_{1-4}$ alkylenyl, aryl-NH—C(O)—NH—C$_{1-4}$ alkylenyl, heteroaryl-NH—C(S)—NH—C$_{1-4}$ alkylenyl, di(C$_{1-4}$alkyl)amino-C(O)—NH—C$_{1-4}$ alkylenyl, C$_{1-4}$ alkylamino-C(O)—NH—C$_{1-4}$ alkylenyl, di(C$_{1-4}$ alkyl)amino-S(O)$_2$—C$_{1-4}$alkylenyl, C$_{1-4}$ alkylamino-S(O)$_2$—C$_{1-4}$ alkylenyl, amino-S(O)$_2$—C$_{1-4}$ alkylenyl, heteroarylC$_{1-4}$ alkylenyl wherein heteroaryl is unsubstituted or substituted by a substituent selected from the group consisting of aryl, heteroaryl, and alkyl, and heterocyclylC$_{1-4}$alkylenyl wherein heterocyclyl is unsubstituted or substituted by one or two substituents selected from the group consisting of heteroaryl and oxo. In some embodiments (e.g., of Formulas II through IX and LXXX), the above group from which R$_1$ is selected also includes hydrogen, C$_{1-4}$ alkyl-S(O)$_2$—C$_{1-4}$ alkylenyl-NH—C$_{1-4}$ alkylenyl, cyanoC$_{1-4}$alkylenyl, hydroxyiminoC$_{2-5}$ alkylenyl, C$_{1-4}$ alkoxyiminoC$_{2-5}$ alkylenyl, amino(hydroxyimino)C$_{2-5}$ alkylenyl, NH$_2$—C(O)—C$_{1-4}$alkylenyl, C$_{1-4}$ alkyl-C(O)—C$_{1-4}$ alkylenyl, C$_{1-6}$ alkyl-O—C(O)—NH—C$_{1-4}$ alkylenyl, heterocyclyl-C(O)—NH—C$_{1-4}$ alkylenyl; and wherein heteroaryl is unsubstituted or substituted by a substituent selected from the group consisting of aryl, arylalkylenyl, heteroaryl, and alkyl; and wherein heterocyclyl is unsubstituted or substituted by one or two substituents selected from the group consisting of arylalkylenyl, heteroaryl, alkylcarbonyl, alkylsulfonyl, alkylaminocarbonyl, and oxo.

In some embodiments (e.g., of Formulas II through IX and LXXX), R$_1$ is selected from the group consisting of C$_{1-5}$ alkyl, arylC$_{1-4}$alkylenyl, cycloalkylC$_{1-4}$alkylenyl, C$_{1-4}$ alkyl-S(O)$_2$—C$_{1-4}$ alkylenyl, C$_{1-4}$ alkyl-S(O)$_2$—NH—C$_{1-4}$ alkylenyl, hydroxyC$_{1-4}$ alkylenyl, haloC$_{1-4}$ alkylenyl, amino C$_{1-4}$alkylenyl, C$_{1-6}$ alkyl-C(O)—NH—C$_{1-4}$ alkylenyl, aryl-C(O)—NH—C$_{1-4}$ alkylenyl, heteroaryl-C(O)—NH—C$_{1-4}$ alkylenyl, di(C$_{1-4}$ alkylamino-S(O)$_2$—NH—C$_{1-4}$ alkylenyl, aryl-S(O)$_2$—NH—C$_{1-4}$ alkylenyl, aryl-NH—C(O)—NH—C$_{1-4}$ alkylenyl, heteroaryl-NH—C(S)—NH—C$_{1-4}$ alkylenyl, di(C$_{1-4}$ alkyl)amino-C(O)—NH—C$_{1-4}$ alkylenyl, C$_{1-4}$ alkylamino-C(O)—NH—C$_{1-4}$ alkylenyl, heteroarylC$_{1-4}$ alkylenyl wherein heteroaryl is unsubstituted or substituted by a substituent selected from the group consisting of aryl, heteroaryl, and alkyl, and heterocyclylC$_{1-4}$ alkylenyl wherein heterocyclyl is unsubstituted or substituted by one or two substituents selected from the group consisting of heteroaryl and oxo.

In some embodiments (e.g., of Formulas II through IX and LXXX), R$_1$ is selected from the group consisting of C$_{1-4}$ alkyl, C$_{1-4}$ alkyl-S(O)$_2$—C$_{1-4}$ alkylenyl, C$_{1-4}$ alkyl-S(O)$_2$—NH—C$_{1-4}$ alkylenyl, hydroxyC$_{1-4}$ alkylenyl, aminoC$_{1-4}$ alkylenyl, C$_{1-6}$ alkyl-C(O)—NH—C$_{1-4}$ alkylenyl, aryl-C(O)—NH—C$_{1-4}$ alkylenyl, heteroaryl-C(O)—NH—C$_{1-4}$ alkylenyl, di(C$_{1-4}$ alkyl)amino-S(O)$_2$—NH—C$_{1-4}$ alkylenyl, aryl-S(O)$_2$—NH—C$_{1-4}$ alkylenyl, aryl-NH—C(O)—NH—C$_{1-4}$ alkylenyl, heteroaryl-NH—C(S)—NH—C$_{1-4}$ alkylenyl, and di(C$_{1-4}$ alkyl)amino-C(O)—NH—C$_{1-4}$ alkylenyl, and heterocyclylC$_{1-4}$alkylenyl wherein heterocyclyl is unsubstituted or substituted with one or two oxo groups.

In some embodiments (e.g., of Formulas II through IX and LXXX), R$_1$ is selected from the group consisting of methyl, ethyl, propyl, 2-methylpropyl, 2,2-dimethylpropyl, butyl, pent-4-ynyl, 2-phenylethyl, 2-hydroxy-2-methylpropyl, 4-hydroxybutyl, 2-amino-2-methylpropyl, 2-aminoethyl, 4-aminobutyl, 2-methanesulfonylethyl, 2-(propylsulfonyl)

ethyl, 4-(methylsulfonyl)butyl, 3-(phenylsulfonyl)propyl, 2-methyl-2-[2-(methylsulfonyl)ethoxy]propyl, 4-acetoxybutyl, 4-methanesulfonylaminobutyl, 2-methyl-2-[(methylsulfonyl)aminopropyl, 2-(2-propanesulfonylamino)ethyl, 2-(benzenesulfonylamino)ethyl, 2-(dimethylaminosulfonylamino)ethyl, 4-(aminosulfonyl)butyl, 4-[(methylamino)sulfonyl]butyl, 4-[(dimethylamino)sulfonyl]butyl, 2-[(cyclohexylcarbonyl)amino]-2-methylpropyl, 2-[(cyclopropylcarbonyl)amino]-2-methylpropyl, 2-(isobutyrylamino)-2-methylpropyl, 2-methyl-2-(propionylamino) propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-(isobutyrylamino) ethyl, 2-{[(isopropylamino)carbonyl]amino}-2-methylpropyl, 2-{[(isopropylamino)carbonyl]amino}ethyl, 4-[(morpholin-4-ylcarbonyl)amino]butyl, 4-(4-pyridin-2-ylpiperazin-1-yl)butyl, 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, 4-(3-methyl-1-oxa-2,4-diazaspiro[4.4]non-2-en-4-yl)butyl, 2-{[(pyridin-3-ylamino)carbonothioyl]amino}ethyl, 2-{[(dimethylamino) carbonyl]amino}ethyl, and 2-[(phenylamino)carbonyl] amino}ethyl. In some embodiments (e.g., of Formulas II through IX and LXXX), the above group from which $R_1$ is selected also includes hydrogen, hydroxymethyl, aminomethyl, 2-cyano-2-methylpropyl, 3-amino-2,2-dimethyl-3-oxopropyl, 2,2-dimethyl-4-oxopentyl, 2-methyl-2-(methylsulfonyl)propyl, 2-methyl-2-{[2-(methylsulfonyl)ethyl] amino}propyl, 2-[(methylsulfonyl)amino]ethyl, 3-[(methylsulfonyl)amino]propyl, 2-[(cyclopropylcarbonyl) amino]ethyl, 2-(acetylamino)ethyl, 2-(propionylamino) ethyl, 2-[(4-fluorobenzoyl)amino]ethyl, 2-{[(ethylamino) carbonyl]amino}ethyl, piperidin-4-ylmethyl, (1-benzylpiperidin-4-yl)methyl, (1-acetylpiperidin-4-yl)methyl, 1-[(propylamino)carbonyl]piperidin-4-yl}methyl, [1-(methylsulfonyl)piperidin-4-yl]methyl, 2-[(morpholin-4-yl-carbonyl)amino]ethyl, 2-[(ethoxycarbonyl)amino]ethyl, 2-(1,1-dioxidoisothiazolidin-2-yl)ethyl, 3-(1H-pyrrol-3-yl) propyl, 3-(1-benzyl-1H-pyrrol-3-yl)propyl, 3-(1-benzyl-2,5-dihydro-1H-pyrrol-3-yl)propyl, 3-(5-butylisoxazol-3-yl) propyl, 3-(5-phenylisoxazol-3-yl)propyl, 3-(5-pyridin-3-ylisoxazol-3-yl)propyl, 2-({[(3,4-difluorophenyl)amino] carbonyl}amino)ethyl, 2-({[(4-fluorophenyl)amino] carbonyl}amino)ethyl, 4-(hydroxyimino)butyl, 4-(methoxyimino)butyl, and 5-amino-5-(hydroxyimino)pentyl.

In some embodiments (e.g., of Formula VIII), $R_1$ is selected from the group consisting of methyl, ethyl, propyl, 2-methylpropyl, 2,2-dimethylpropyl, butyl, pent-4-ynyl, 2-cyclohexylethyl, 2-hydroxy-2-methylpropyl, 4-hydroxybutyl, 2-amino-2-methylpropyl, 2-aminoethyl, 4-aminobutyl, 2-methanesulfonylethyl, 2-(propylsulfonyl)ethyl, 4-(methylsulfonyl)butyl, 3-(phenylsulfonyl)propyl, 2-methyl-2-[2-(methylsulfonyl)ethoxy]propyl, 4-acetoxybutyl, 4-methanesulfonylaminobutyl, 2-methyl-2-[(methylsulfonyl)aminopropyl, 2-(2-propanesulfonylamino)ethyl, 2-(benzenesulfonylamino)ethyl, 2-(dimethylaminosulfonylamino) ethyl, 4-(aminosulfonyl)butyl, 4-[(methylamino)sulfonyl] butyl, 4-[(dimethylamino)sulfonyl]butyl, 2-[(cyclohexylcarbonyl)amino]-2-methylpropyl, 2-[(cyclopropylcarbonyl)amino]-2-methylpropyl, 2-(isobutyrylamino)-2-methylpropyl, 2-methyl-2-(propionylamino)propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-(isobutyrylamino) ethyl, 2-{[(isopropylamino)carbonyl]amino}-2-methylpropyl, 2-{[(isopropylamino)carbonyl]amino}ethyl, 4-[(morpholin-4-ylcarbonyl)amino]butyl, 4-(4-pyridin-2-ylpiperazin-1-yl)butyl, 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, 4-(3-methyl-1-oxa-2,4-diazaspiro[4.4]non-2-en-4-yl)butyl, 2-{[(pyridin-3-ylamino)carbonothioyl]amino}ethyl, 2-[(dimethylamino) carbonyl]amino}ethyl, and 2-{[(phenylamino)carbonyl] amino}ethyl.

In some embodiments (e.g., of Formulas II through IX and LXXX), $R_1$ is selected from the group consisting of methyl, ethyl, 2-methylpropyl, 2,2-dimethylpropyl, 2-phenylethyl, 2-hydroxy-2-methylpropyl, 4-hydroxybutyl, 2-amino-2-methylpropyl, 2-aminoethyl, 2-methanesulfonylethyl, 2-(propylsulfonyl)ethyl, 4-methanesulfonylaminobutyl, 2-methyl-2-[(methylsulfonyl)aminopropyl, 2-(2-propanesulfonylamino)ethyl, 2-(benzenesulfonylamino) ethyl, 2-(dimethylaminosulfonylamino)ethyl, 2-[(cyclohexylcarbonyl)amino]-2-methylpropyl, 2-(isobutyrylamino)-2-methylpropyl, 2-methyl-2-[(pyridin-3-ylcarbonyl)amino]propyl, 2-(acetylamino)-2-methylpropyl, 2-(benzoylamino)ethyl, 2-(benzoylamino)-2-methylpropyl, 2-[(pyridin-3-ylcarbonyl)amino]ethyl, 2-(isobutyrylamino) ethyl, 2-{[(isopropylamino)carbonyl]amino}-2-methylpropyl, 2-{[(isopropylamino)carbonyl]amino}ethyl, 4-(4-pyridin-2-ylpiperazin-1-yl)butyl, 3-(3-pyridin-3-ylisoxazol-5-yl)propyl, 2-{[(pyridin-3-ylamino)carbonothioyl] amino}ethyl, 2-{[(dimethylamino)carbonyl]amino}ethyl, and 2-{[(phenylamino)carbonyl]amino}ethyl.

In some embodiments (e.g., of Formulas II through IX and LXXX), $R_1$ is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl) amino]propyl, 2-[(cyclohexylcarbonyl)amino]-2-methylpropyl, 2-{[(isopropylamino)carbonyl]amino}ethyl, 4-[(morpholin-4-ylcarbonyl)amino]butyl, 2-(benzoylamino)ethyl, and 4-methanesulfonylaminobutyl. In some embodiments (e.g., of Formulas II through IX and LXXX), the above group from which $R_1$ is selected also includes 3-amino-2,2-dimethyl-3-oxopropyl and 2,2-dimethyl-4-oxopentyl.

In some embodiments (e.g., of Formulas II through IX and LXXX), $R_1$ is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl) amino]propyl, 2-[(cyclohexylcarbonyl)amino]-2-methylpropyl, 2-{[(isopropylamino)carbonyl]amino}ethyl, 2-(benzoylamino)ethyl, and 4-methanesulfonylaminobutyl.

In some embodiments (e.g., of Formulas II through IX and LXXX), $R_1$ is selected from the group consisting of methyl, 2-cyclohexylethyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 2-(benzoylamino)ethyl, 4-methanesulfonylaminobutyl, and 2-methylpropyl.

In some embodiments (e.g., of Formulas II through IX and LXXX), $R_1$ is selected from the group consisting of methyl, ethyl, propyl, butyl, 2-methylpropyl, 2-methanesulfonylethyl, and 4-methanesulfonylaminobutyl.

In some embodiments (e.g., of Formulas II through IX and LXXX), $R_1$ is selected from the group consisting of 2-methylpropyl, 2,2-dimethylpropyl, ethyl, and 4-[(morpholin-4-ylcarbonyl)amino]butyl.

In some embodiments (e.g., of Formulas II through IX and LXXX), $R_1$ is selected from the group consisting of 2-methylpropyl, 2,2-dimethylpropyl, and ethyl.

In some embodiments (e.g., of Formulas II through IX and LXXX), $R_1$ is selected from the group consisting of methyl and 2-methylpropyl.

In some embodiments (e.g., of Formulas II through IX and LXXX), $R_1$ is 2-methylpropyl.

In some embodiments, $R_1$ is $C_{1-4}$ alkyl. In certain embodiments, $R_1$ is straight chain $C_{1-4}$ alkyl. In certain embodiments, $R_1$ is branched $C_{1-4}$ alkyl.

In some embodiments, $R_1$ is selected from the group consisting of methyl, ethyl, propyl, 2-methylpropyl, 2,2-dimethylpropyl, and butyl.

In some embodiments, $R_1$ is selected from the group consisting of pent-4-ynyl and 2-phenylethyl. In certain embodiments, $R_1$ is 2-phenylethyl.

In some embodiments, $R_1$ is selected from the group consisting of 2-hydroxy-2-methylpropyl and 2-amino-2-methylpropyl. In certain embodiments, $R_1$ is 2-hydroxy-2-methylpropyl. In certain embodiments, $R_1$ is 2-amino-2-methylpropyl.

In some embodiments, $R_1$ is selected from the group consisting of 4-hydroxybutyl, 2-aminoethyl, 4-aminobutyl, 4-chlorobutyl, and 4-acetoxybutyl.

In some embodiments, $R_1$ is $C_{1-4}$ alkyl-$S(O)_2$—$C_{1-4}$ alkylenyl.

In some embodiments, $R_1$ is phenyl-$S(O)_2$—$C_{1-4}$ alkylenyl.

In some embodiments, $R_1$ is selected from the group consisting of 2-methanesulfonylethyl, 2-(propylsulfonyl)ethyl, 4-(methylsulfonyl)butyl, and 3-(phenylsulfonyl)propyl.

In some embodiments, $R_1$ is $C_{1-4}$ alkyl-$S(O)_2$—$C_{1-4}$ alkyleneoxy$C_{1-4}$ alkylenyl.

In some embodiments, $R_1$ is 2-methyl-2-[2-(methylsulfonyl)ethoxy]propyl.

In some embodiments, $R_1$ is $C_{1-4}$ alkyl-$S(O)_2$—NH—$C_{1-4}$ alkylenyl.

In some embodiments, $R_1$ is aryl-$S(O)_2$—NH—$C_{1-4}$ alkylenyl.

In some embodiments, $R_1$ is di$C_{1-4}$ alkyl-N—$S(O)_2$—NH—$C_{1-4}$ alkylenyl.

In some embodiments, $R_1$ is selected from the group consisting of 4-methanesulfonylaminobutyl, 2-(benzenesulfonylamino)ethyl, 2-(2-propanesulfonylamino)ethyl, and 2-(dimethylaminosulfonylamino)ethyl. In certain embodiments, $R_1$ is 4-methanesulfonylaminobutyl.

In some embodiments, $R_1$ is $NH_2$—C(O)-alkylenyl.

In some embodiments, $R_1$ is 3-amino-2,2-dimethyl-3-oxopropyl.

In some embodiments, $R_1$ is alkyl-C(O)-alkylenyl.

In some embodiments, $R_1$ is 2,2-dimethyl-4-oxopentyl.

In some embodiments, $R_1$ is hydrogen.

In some embodiments, $R_1$ is $C_{1-4}$ alkyl-C(O)—NH—$C_{1-4}$ alkylenyl.

In some embodiments, $R_1$ is aryl-C(O)—NH—$C_{1-4}$ alkylenyl.

In some embodiments, $R_1$ is heteroaryl-C(O)—NH—$C_{1-4}$ alkylenyl.

In some embodiments, $R_1$ is selected from the group consisting of 2-(benzoylamino)ethyl, 2-[(pyridin-3-ylcarbonyl)amino]ethyl, and 2-(isobutyrylamino)ethyl.

In some embodiments, $R_1$ is $C_{1-6}$ alkyl-NH—C(O)—NH—$C_{1-4}$ alkylenyl.

In some embodiments, $R_1$ is $N(C_{1-4}$ alkyl$)_2$-C(O)—NH—$C_{1-4}$ alkylenyl.

In some embodiments, $R_1$ is aryl-NH—C(O)—NH—$C_{1-4}$ alkylenyl.

In some embodiments, $R_1$ is heteroaryl-NH—$C(R_6)$—NH—$C_{1-4}$ alkylenyl.

In some embodiments, $R_1$ is heterocyclyl-C(O)—NH—$C_{1-4}$ alkylenyl.

In some embodiments, $R_1$ is selected from the group consisting of 4-[(morpholin-4-ylcarbonyl)amino]butyl, 2-{[(isopropylamino)carbonyl]amino}ethyl, 2-{[(pyridin-3-ylamino)carbonothioyl]amino}ethyl, 2-{[(pyridin-3-ylamino)carbonyl]amino}ethyl, 2-{[(dimethylamino)carbonyl]amino}ethyl, and 2-{[(phenylamino)carbonyl]amino}ethyl.

In some embodiments, $R_1$ is 2-methyl-2-[(methylsulfonyl)aminopropyl.

In some embodiments, $R_1$ is selected from the group consisting of 2-[(cyclohexylcarbonyl)amino]-2-methylpropyl, 2-[(cyclopropylcarbonyl)amino]-2-methylpropyl, 2-(isobutylylamino)-2-methylpropyl, 2-methyl-2-(propionylamino)propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)-2-methylpropyl, 2-[(4-fluorobenzoyl)amino]-2-methylpropyl, and 2-[(3,4-difluorobenzoyl)amino]-2-methylpropyl.

In some embodiments, $R_1$ is 2-{[(isopropylamino)carbonyl]amino}-2-methylpropyl.

In some embodiments, $R_1$ is selected from the group consisting of 4-(aminosulfonyl)butyl, 4-[(methylamino)sulfonyl]butyl, and 4-[(dimethylamino)sulfonyl]butyl.

In some embodiments, $R_1$ is heteroaryl$C_{1-4}$alkylenyl wherein heteroaryl is unsubstituted or substituted by a substituent selected from the group consisting of aryl, heteroaryl, and alkyl.

In some embodiments, $R_1$ is selected from the group consisting of 3-(3-methylisoxazol-5-yl)propyl, 3-(3-isopropylisoxazol-5-yl)propyl, 3-(3-phenylisoxazol-5-yl)propyl, 3-(3-pyridin-3-ylisoxazol-5-yl)propyl, 4-(3,5,5-trimethyl-1,2,4-oxadiazol-4(5H)-yl)butyl, and 4-(3-methyl-1-oxa-2,4-diazaspiro[4.4]non-2-en-4-yl)butyl In some embodiments, $R_1$ is 4-(4-pyridin-2-ylpiperazin-1-yl)butyl.

Each of the embodiments for $R_1$ described above can be combined with one or more embodiments for $R_2$ described below. Each of the resulting combinations is an embodiment.

In some embodiments (e.g., of Formulas II through IX and LXXX), $R_2$ is selected from the group consisting of —$R_4$, —X—$R_4$, —X—Y—$R_4$, and —X—$R_5$; wherein:

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of —O—, —$S(O)_{0-2}$-, —$S(O)_2$—$N(R_8)$—, —$C(R_6)$—O—, —O—C$(R_6)$—, —O—C(O)—O—, —$N(R_8)$-Q-, —$C(R_6)$—N$(R_8)$—, —O—C$(R_6)$—N$(R_8)$—, —$C(R_6)$—N(O$R_9$)—, —O—N$(R_8)$-Q-, —O—N=C$(R_4)$—, —C(=N—O—$R_8$)—, —CH(—N(—O—$R_8$)-Q-$R_4$)—,

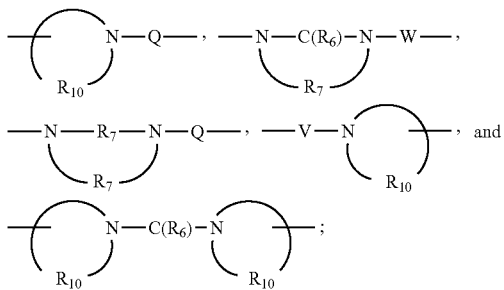

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

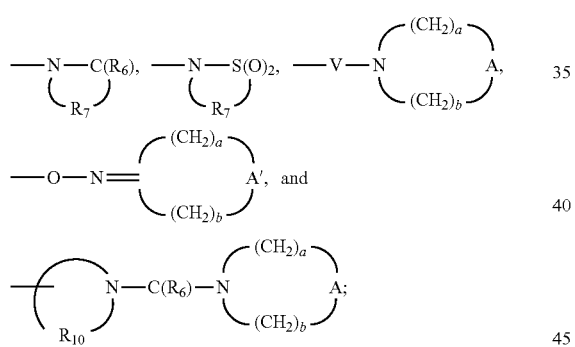

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and a and b are independently integers from 1 to 6 with the proviso that a+b is ≤7. In certain of these embodiments, the above group from which Y is selected also includes —C(=N—O—R$_8$)—NH—. In certain of these embodiments (e.g., of Formulas II through IX and LXXX), Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_3$)-Q-, —C(R$_6$)—N(R$_8$)—, —O—C(R$_6$)—N(R$_8$)—, —C(R$_6$)—N(OR$_9$)—,

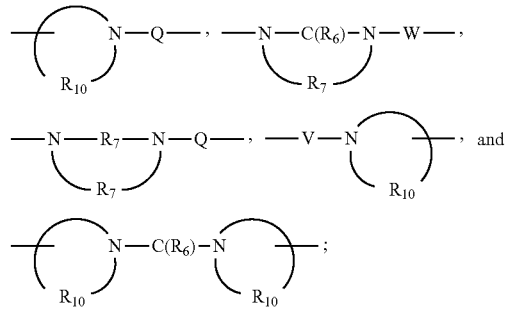

$R_5$ is selected from the group consisting of

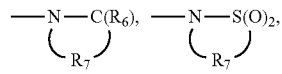
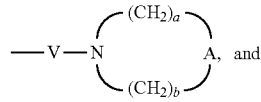

and $R_8$ is selected from the group consisting of hydrogen, alkyl, alkoxyalkylenyl, hydroxyalkylenyl, and arylalkylenyl. In certain of these embodiments (e.g., of Formulas II through IX and LXXX), Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

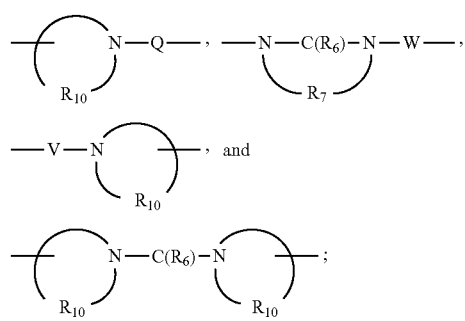

$R_5$ is selected from the group consisting of

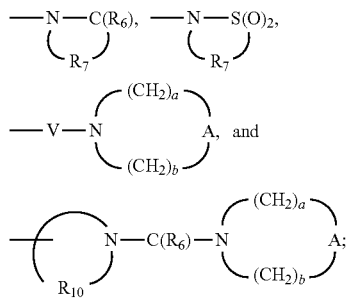

$R_8$ is selected from the group consisting of hydrogen, alkyl, alkoxyalkylenyl, and arylalkylenyl; and Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—.

In some embodiments (e.g., of Formulas II through IX and LXXX), $R_2$ is selected from the group consisting of —$R_4$, —X—$R_4$, and —X—Y—$R_4$; wherein:

X is alkylene that is optionally terminated by arylene or heterocyclylene;

Y is selected from the group consisting of —S(O)$_2$—, —C(O)—, —C(O)—O—, —N($R_8$)-Q-, —C(O)—N($R_8$)—, and

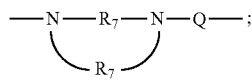

$R_4$ is selected from the group consisting of hydrogen, alkyl, aryl, arylalkylenyl, aryloxyalkylenyl, heterocyclyl, and heteroaryl, wherein the alkyl, aryl, aryloxyalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, cyano, aryl, aryloxy, heteroaryl, heterocyclyl, and in the case of heterocyclyl, oxo;

$R_6$ is selected from the group consisting of =O and =S;

$R_7$ is $C_{2-7}$ alkylene;

$R_8$ is in selected from the group consisting of hydrogen, alkyl, alkoxyalkylenyl, hydroxyalkylenyl, and arylalkylenyl; and Q is selected from the group consisting of a bond, —C(O)—, —S(O)$_2$—, —C($R_6$)—N($R_8$)—, and —S(O)$_2$—N($R_8$)—.

In some embodiments (e.g., of Formulas II through IX and LXXX), $R_2$ is —$R_4$.

In some embodiments (e.g., of Formulas II through IX and LXXX), $R_2$ is —X—$R_4$.

In some embodiments (e.g., of Formulas II through IX and LXXX), $R_2$ is —X—Y—$R_4$.

In some embodiments (e.g., of Formulas II through IX and LXXX), $R_2$ is selected from the group consisting of hydrogen, alkyl, arylalkylenyl, alkoxyalkylenyl, and hydroxyalkylenyl. In certain embodiments, $R_2$ is selected from the group consisting of hydrogen, alkyl, arylalkylenyl, and alkoxyalkylenyl. In certain embodiments, $R_2$ is selected from the group consisting of hydrogen, alkyl, and alkoxyalkylenyl.

In some embodiments (e.g., of Formulas II through IX and LXXX), $R_2$ is selected from the group consisting of hydrogen, $C_{1-5}$ alkyl, $C_{1-4}$ alkoxy$C_{1-4}$ alkylenyl, hydroxy$C_{1-4}$alkylenyl, and aryl$C_{1-4}$alkylenyl wherein aryl is unsubstituted or substituted by one or more substituents selected from the group consisting of chloro, fluoro, methoxy, methyl, cyano, and methoxycarbonyl.

In some embodiments, $R_2$ is selected from the group consisting of hydrogen, $C_{1-5}$ alkyl, $C_{1-4}$ alkoxy$C_{1-4}$alkylenyl, and aryl$C_{1-4}$ alkylenyl wherein aryl is unsubstituted or substituted by one or more substituents selected from the group consisting of chloro, fluoro, methoxy, methyl, cyano, and methoxycarbonyl.

In some embodiments, $R_2$ is selected from the group consisting of hydrogen, $C_{1-4}$ alkyl, and $C_{1-4}$ alkoxy$C_{1-4}$ alkylenyl.

In some embodiments (e.g., of Formulas II through IX and LXXX), $R_2$ is selected from the group consisting of hydrogen, methyl, ethyl, propyl, butyl, 2-methoxyethyl, 2-hydroxyethyl, and benzyl.

In some embodiments (e.g., of Formulas II through IX and LXXX), $R_2$ is selected from the group consisting of hydrogen, methyl, ethyl, propyl, butyl, 2-methoxyethyl, and benzyl.

In some embodiments (e.g., of Formulas II through IX and LXXX), $R_2$ is selected from the group consisting of hydrogen, methyl, ethyl, propyl, butyl, and benzyl.

In some embodiments (e.g., of Formulas II through IX and LXXX), $R_2$ is selected from the group consisting of methyl, ethyl, propyl, butyl, and benzyl.

In some embodiments (e.g., of Formulas II through IX and LXXX), $R_2$ is selected from the group consisting of methyl, ethyl, propyl, and butyl.

In some embodiments (e.g., of Formulas II through IX and LXXX), $R_2$ is selected from the group consisting of methyl, ethyl, propyl, butyl, 2-methoxyethyl, and 2-hydroxyethyl.

In some embodiments (e.g., of Formulas II through IX and LXXX), $R_2$ is methyl.

In some embodiments (e.g., of Formulas II through IX and LXXX), $R_1$ is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 4-[(morpholin-4-ylcarbonyl)amino]butyl, 2-(benzoylamino)ethyl, and 4-methanesulfonylaminobutyl; and $R_2$ is selected from the group consisting of hydrogen, methyl, ethyl, propyl, butyl, 2-methoxyethyl, 2-hydroxyethyl, and benzyl. In some embodiments (e.g., of Formulas II through IX and LXXX), the above group from which $R_1$ is selected also includes 3-amino-2,2-dimethyl-3-oxopropyl and 2,2-dimethyl-4-oxopentyl. In certain of these embodiments, m and n are 0.

In some embodiments (e.g., of Formulas II through IX and LXXX), $R_1$ is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 2-(benzoylamino)ethyl, and 4-methanesulfonylaminobutyl; and $R_2$ is selected from the group consisting of hydrogen, methyl, ethyl, propyl, butyl, 2-methoxyethyl, and benzyl. In certain of these embodiments, m and n are 0.

In some embodiments (e.g., of Formulas II through IX and LXXX), $R_1$ is selected from the group consisting of 2-methylpropyl, 2,2-dimethylpropyl, ethyl, and 4-[(morpholin-4-ylcarbonyl)amino]butyl; and $R_2$ is selected from the group consisting of methyl, ethyl, propyl, butyl, and benzyl. In certain of these embodiments m and n are 0. In certain of these embodiments, $R_1$ is selected from the group consisting of 2-methylpropyl, 2,2-dimethylpropyl, and ethyl.

In some embodiments (e.g., of Formulas II through IX and LXXX), $R_1$ is 2-hydroxy-2-methylpropyl, and $R_2$ is selected from the group consisting of methyl, ethyl, propyl, butyl, 2-methoxyethyl, and 2-hydroxyethyl. For certain of these embodiments, $R_1$ is 2-hydroxy-2-methylpropyl, and $R_2$ is ethyl.

In some embodiments (e.g., of Formulas III through VII), $R_1$ is selected from the group consisting of methyl, ethyl, propyl, butyl, 2-methylpropyl, 2-methanesulfonylethyl, and 4-methanesulfonylaminobutyl; and $R_2$ is selected from the group consisting of hydrogen, methyl, ethyl, propyl, butyl, and benzyl. In certain of these embodiments, m and n are 0.

In some embodiments (e.g., of Formulas III through VII), $R_1$ is 2-methylpropyl; and $R_2$ is selected from the group consisting of methyl, ethyl, propyl, and butyl. In certain of these embodiments, m and n are 0.

In some embodiments of Formula VIII, $R_1$ is selected from the group consisting of methyl, ethyl, propyl, butyl, 2-methylpropyl, 2,2-dimethylpropyl, 2-cyclohexylethyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 4-[(morpholin-4-ylcarbonyl)amino]butyl, 2-(benzoylamino)ethyl, and 4-methanesulfonylaminobutyl; and $R_2$ is selected from the group consisting of hydrogen, methyl, ethyl, propyl, butyl, 2-methoxyethyl, and 2-hydroxyethyl. In certain of these embodiments, n is 0.

In some embodiments of Formula VIII, $R_1$ is selected from the group consisting of methyl, 2-cyclohexylethyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 2-(benzoylamino)ethyl, 4-methanesulfonylaminobutyl, and 2-methylpropyl; and $R_2$ is selected from the group consisting of methyl, ethyl, propyl, and butyl. In certain of these embodiments, n is 0.

In some embodiments of Formula VIII, $R_1$ is selected from the group consisting of methyl and 2-methylpropyl; $R_2$ is methyl. In certain of these embodiments, n is 0.

In some embodiments of Formula IX, $R_1$ is selected from the group consisting of methyl and 2-methylpropyl; and $R_2$ is methyl. In certain of these embodiments, $R_{A2}$ and $R_{B2}$ are each methyl.

In some embodiments (e.g., of Formulas II through VII), $R_3$ is selected from the group consisting of —Z—$R_4$, —Z—X—$R_4$, —Z—X—Y—$R_4$, —Z—X—Y—X—Y—$R_4$, and —Z—X—$R_5$ wherein:

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of —O—, —S(O)$_{0-2}$-, —S(O)$_2$—N($R_8$)—, —C($R_6$)—O—, —O—C($R_6$)—, —O—C(O)—O—, —N($R_8$)-Q-, —C($R_6$)—N($R_3$)—, —O—C($R_6$)—N($R_8$)—, —C($R_6$)—N(O$R_9$)—, —O—N($R_8$)-Q-, —O—N=C($R_4$)—, —C(=N—O—$R_8$)—, —CH(—N(—O—$R_8$)-Q-$R_4$)—,

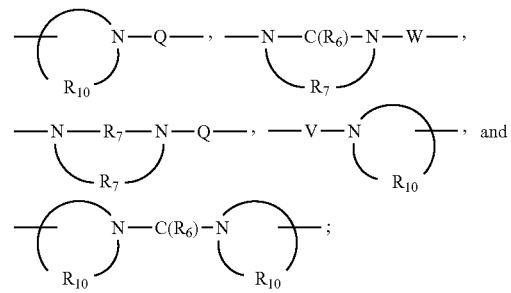

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

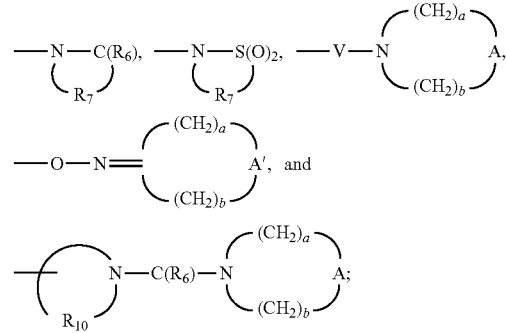

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$-, and —N($R_4$)—;

A' is selected from the group consisting of —O—, —S(O)$_{0-2}$-, —N(-Q-$R_4$)—, and —CH$_2$—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≤7. In certain of these embodiments, the above group from which Y is selected also includes —C(=N—O—R$_8$)—NH—. In certain of these embodiments (e.g., of Formulas II through VII), Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

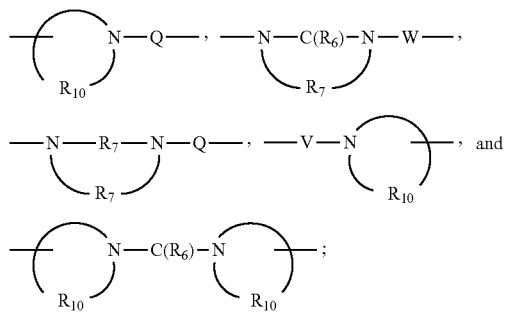

R$_5$ is selected from the group consisting of

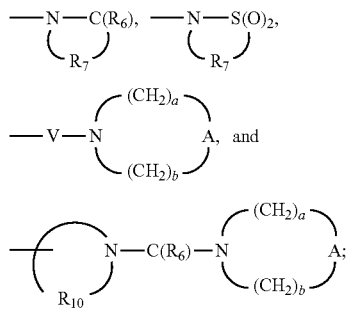

and R$_8$ is selected from the group consisting of hydrogen, alkyl, alkoxyalkylenyl, hydroxyalkylenyl, and arylalkylenyl. In certain of these embodiments (e.g., of Formulas II through VII), Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_3$)—, —C(R$_6$)—N(OR$_9$)—,

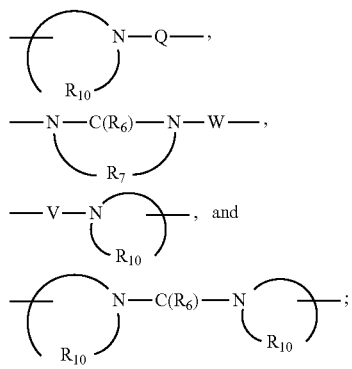

R$_5$ is selected from the group consisting of

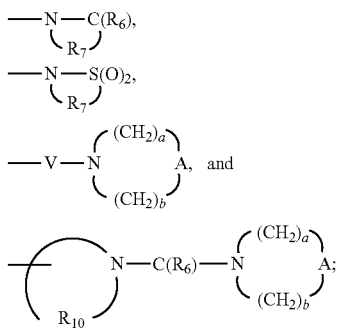

R$_8$ is selected from the group consisting of hydrogen, alkyl, alkoxyalkylenyl, and arylalkylenyl; and Q is selected from the group consisting of a bond, —C(R$_6$)—, —C(R$_6$)—C(R$_6$)—, —S(O)$_2$—, —C(R$_6$)—N(R$_3$)—W—, —S(O)$_2$—N(R$_3$)—, —C(R$_6$)—O—, and —C(R$_6$)—N(OR$_9$)—.

In some embodiments (e.g., of Formulas II through VII), R$_3$ is at the 7-position of the pyrazoloquinoline or pyrazolonaphthyridine.

In some embodiments (e.g., of Formulas II through VII), R$_3$ is selected from the group consisting of alkylsulfonylalkyleneoxy, alkylsulfonylaminoalkyleneoxy, alkylcarbonylaminoalkyleneoxy, aryl, arylalkyleneoxy, heteroaryl, heteroarylalkyleneoxy, heterocyclyl, and heterocyclylalkyleneoxy; wherein aryl and heteroaryl are unsubstituted or substituted by one or more substituents selected from the group consisting of alkyl, alkoxy, hydroxyalkyl, halogen, heterocyclylcarbonyl, and dialkylaminocarbonyl; and wherein heterocyclyl is unsubstituted or substituted by one or more substituents selected from the group consisting of alkylsulfonyl, alkylcarbonyl, and oxo.

In some embodiments (e.g., of Formulas II through VII), R$_3$ is selected from the group consisting of aryl, arylalkyleneoxy, heteroarylalkyleneoxy, and heteroaryl, wherein aryl, arylalkyleneoxy, and heteroaryl are unsubstituted or substituted with one or more substituents selected from the group consisting of alkyl, hydroxyalkyl, and halogen, m is 1, and n is 0.

In some embodiments (e.g., of Formulas II through VII), R$_3$ is selected from the group consisting of aryl, arylalkyleneoxy, and heteroaryl, wherein aryl, arylalkyleneoxy, and heteroaryl are unsubstituted or substituted with one or more substituents selected from the group consisting of alkyl and halogen.

In some embodiments (e.g., of Formulas II through VII), R$_3$ is selected from the group consisting of phenyl, benzyloxy, 3-furyl, pyridin-3-yl, 5-(hydroxymethyl)pyridin-3-yl, 6-chloropyridin-3-yl, 6-fluoropyridin-3-yl, 6-methylpyridin-3-yl, 3-quinolin-3-yl, thiazol-4-ylmethoxy, p-toluoyl, (4-chlorobenzyl)oxy, and (4-methylbenzyl)oxy.

In some embodiments (e.g., of Formulas II through VII), R$_3$ is selected from the group consisting of phenyl, benzyloxy, 3-furyl, pyridin-3-yl, p-toluoyl, (4-chlorobenzyl)oxy, and (4-methylbenzyl)oxy.

In some embodiments (e.g., of Formulas II through VII), R$_3$ is selected from the group consisting of benzyloxy, (4-chlorobenzyl)oxy, (4-methylbenzyl)oxy, thiazol-4-ylmethoxy, phenyl, p-toluoyl, 2-ethoxyphenyl, 3-(morpholine-4-carbonyl)phenyl, 3-(N,N-dimethylaminocarbonyl)phenyl, 3-furyl, pyridin-3-yl, pyridin-4-yl, 6-chloropyridin-3-yl, 6-fluoropyridin-3-yl, 6-methylpyridin-3-yl, 5-(hydroxymethyl)pyridin-3-yl, and quinolin-3-yl.

In some embodiments (e.g., of Formulas II through VII), $R_3$ is pyridin-3-yl, pyridin-4-yl, 6-fluoropyridin-3-yl, 5-(hydroxymethyl)pyridin-3-yl, quinolin-3-yl, 2-ethoxyphenyl, or 3-(morpholine-4-carbonyl)phenyl.

In some embodiments (e.g., of Formulas II through VII), $R_3$ is 2-oxo-1,3-oxazolidin-3-yl.

In some embodiments (e.g., of Formulas II through VII), $R_3$ is 1,3-thiazol-4-ylmethoxy, (1-methyl-1H-imidazol-2-yl)methoxy, or pyridin-3-ylmethoxy.

In some embodiments (e.g., of Formulas II through VII), $R_3$ is 2-pyrrolidin-1-ylethoxy, 2-(2-oxopyrrolidin-1-yl)ethoxy, 2-(1,1-dioxidoisothiazolidin-2-yl)ethoxy, 2-morpholin-4-ylethoxy, 3-pyrrolidin-1-ylpropoxy, 3-(2-oxopyrrolidin-1-yl)propoxy, 3-(1,1-dioxidoisothiazolidin-2-yl)propoxy, 3-morpholin-4-ylpropoxy, 2-morpholin-4-yl-2-oxoethoxy, and

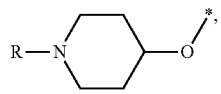

wherein R is alkylsulfonyl or alkylcarbonyl.

In some embodiments (e.g., of Formulas II through VII), $R_3$ is alkyl-S(O)$_2$—NH—(CH$_2$)$_{2-3}$-O—, alkyl-S(O)$_2$-(C$_{1-12}$)$_{2-3}$-O—, or alkyl-C(O)—NH—(CH$_2$)$_{2-3}$-O—.

In some embodiments (e.g., of Formulas II through VII), $R_1$ is 2-hydroxy-2-methylpropyl, $R_2$ is 2-hydroxyethyl, and $R_3$ is phenyl which is substituted by one or two substituents independently selected from chloro and fluoro.

In some embodiments, including any one of the above embodiments which particularly defines $R_3$, $R_3$ is at the 7-position of the pyrazoloquinoline or pyrazolonaphthyridine. In certain of these embodiments, m is 1, and n is 0.

In some embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. In certain of these embodiments, $R_4$ is alkyl, aryl, or heteroaryl.

In some embodiments, $R_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo.

In some embodiments, $R_4$ is selected from the group consisting of hydrogen, alkyl, aryl, heterocyclyl, heteroaryl, heteroarylalkylenyl, alkynyl, and arylalkenylenyl, wherein the alkyl, aryl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo.

In some embodiments, $R_4$ is selected from the group consisting of hydrogen, alkyl, aryl, arylalkylenyl, aryloxyalkylenyl, heterocyclyl, and heteroaryl, wherein the alkyl, aryl, aryloxyalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, cyano, aryl, aryloxy, heteroaryl, heterocyclyl, and in the case of heterocyclyl, oxo.

In some embodiments, $R_4$ is alkyl, aryl, or heteroaryl. In certain embodiments, $R_4$ is alkyl. In certain embodiments, $R_4$ is aryl. In certain embodiments, $R_4$ is heteroaryl.

In some embodiments, $R_5$ is selected from the group consisting of

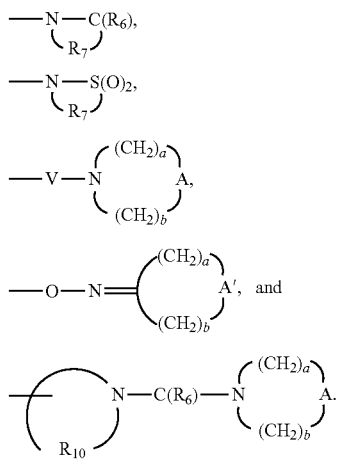

In some embodiments, $R_5$ is selected from the group consisting of

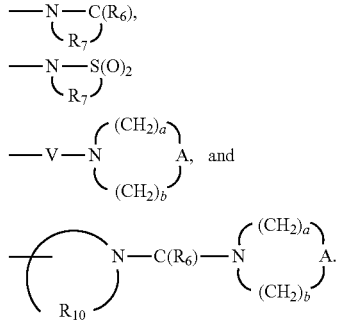

In some embodiments, $R_5$ is selected from the group consisting of

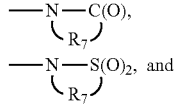

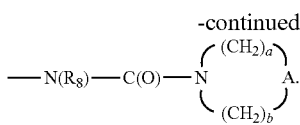

In some embodiments, $R_6$ is selected from the group consisting of =O and =S. In certain embodiments, $R_6$ is =O. In certain embodiments, $R_6$ is =S.

In some embodiments, $R_7$ is $C_{2-7}$ alkylene. In certain embodiments, $R_7$ is $C_{3-4}$ alkylene.

In some embodiments, $R_8$ is selected from the group consisting of hydrogen, alkyl, alkoxyalkylenyl, hydroxyalkylenyl, arylalkylenyl, and heteroarylalkylenyl. In certain embodiments, $R_8$ is selected from the group consisting of hydrogen, alkyl, alkoxyalkylenyl, hydroxyalkylenyl, and arylalkylenyl. In certain embodiments, is selected from the group consisting of hydrogen, alkyl, alkoxyalkylenyl, and arylalkylenyl. In certain embodiments, $R_8$ is hydrogen, alkyl, or hydroxyalkylenyl. In certain embodiments, $R_8$ is hydrogen. In certain embodiments, $R_8$ is alkyl.

In some embodiments, $R_9$ is selected from the group consisting of hydrogen and alkyl. In certain embodiments, $R_9$ is alkyl. In certain embodiments, $R_9$ is hydrogen.

In some embodiments, $R_{10}$ is $C_{3-8}$ alkylene. In certain embodiments, $R_{10}$ is $C_{4-5}$ alkylene.

In some embodiments, A is selected from the group consisting of —O—, —C(O)—, —S(O)$_{0-2}$-, and —N(R$_4$)—. In certain embodiments, A is selected from the group consisting of —O—, —C(O)—, and —N(R$_4$)—. In certain embodiments, A is —O—.

In some embodiments, A' is selected from the group consisting of —O—, —S(O)$_{0-2}$-, —N(-Q-R$_4$)—, and —CH$_2$-.

In some embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—. In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—. In certain embodiments, Q is selected from the group consisting of a bond, —C(R$_6$)—, —S(O)$_2$—, —C(R$_6$)—N(R$_8$)—W—, —S(O)$_2$—N(R$_8$)—, —C(O)—O—, and —C(O)—S—. In certain embodiments, Q is selected from the group consisting of a bond, —C(O)—, —S(O)$_2$—, —C(R$_6$)—N(R$_8$)—, and —S(O)$_2$—N(R$_8$)—. In certain embodiments, Q is selected from the group consisting of a bond, —C(R$_6$)—, —S(O)$_2$—, and —C(R$_6$)—N(R$_8$)—W—. In certain embodiments, Q is selected from the group consisting of a bond, —C(O)—, —S(O)$_2$—, and —C(O)—N(R$_8$)—.

In some embodiments, V is selected from the group consisting of —C(R$_6$)—, —O—C(R$_6$)—, —N(R$_8$)—C(R$_6$)—, and —S(O)$_2$—. In certain embodiments, V is —C(R$_6$)—. In certain embodiments, V is —N(R$_8$)—C(R$_6$)—.

In some embodiments, W is selected from the group consisting of a bond, —C(O)—, and —S(O)$_2$—. In certain embodiments, W is selected from the group consisting of a bond and —C(O)—. In certain embodiments, W is a bond.

In some embodiments, X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

In some embodiments, X is alkylene that is optionally interrupted or terminated by heterocyclylene and optionally interrupted by one —O— group.

In some embodiments, X is alkylene that is optionally terminated by arylene or heterocyclylene.

In some embodiments, X is alkylene that is optionally interrupted or terminated by heterocyclylene.

In some embodiments, X is alkylene. In certain embodiments, X is $C_{1-4}$alkylene.

In some embodiments, $X^1$ is selected from the group consisting of alkylene and arylene. In certain embodiments, $X^1$ is alkylene. In certain embodiments, $X^1$ is $C_{1-4}$ alkylene. In certain embodiments, $X^1$ is arylene.

In some embodiments, Y is selected from the group consisting of —O—, —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

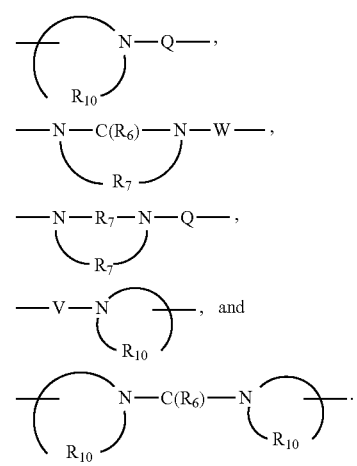

In some embodiments, the above group from which Y is selected also includes —C(=N—O—R$_8$)—NH—.

In some embodiments, Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

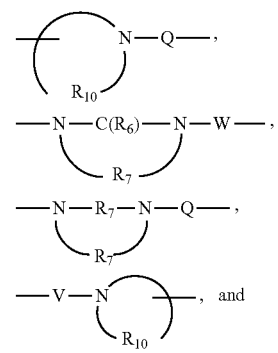

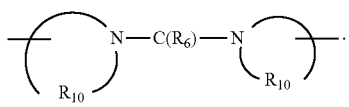

In some embodiments, Y is selected from the group consisting of —S(O)$_{0-2}$-, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

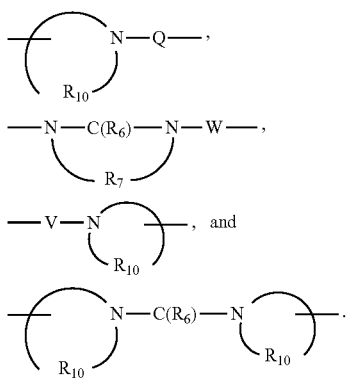

In some embodiments, Y is selected from the group consisting of —S(O)$_2$—, —S(O)$_2$—N(R$_8$)—, —C(O)—, —C(O)—O—, —O—C(O)—, —N(R$_8$)-Q-, —C(O)—N(R$_8$)—,

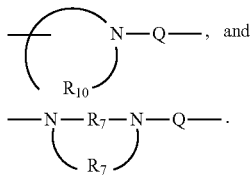

In some embodiments, Y is selected from the group consisting of —S(O)$_2$—, —C(O)—, —C(O)—O—, —N(R$_8$)-Q-, —C(O)—N(R$_8$)—, and

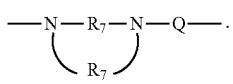

In some embodiments, Y is —N(R$_8$)—C(O)—, —N(R$_8$)—S(O)$_2$—, —N(R$_8$)—C(O)—N(R$_8$)—, —N(R$_8$)—C(S)—N(R$_8$)—, —N(R$_8$)—S(O)$_2$—N(R$_8$)—, or

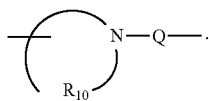

In some embodiments, Y is —N(R$_8$)—C(O)—, —N(R$_8$)—S(O)$_2$—, —N(R$_8$)—C(O)—N(R$_8$)—, or

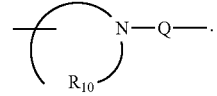

In some embodiments, Y is —N(R$_8$)—C(O)—, —N(R$_8$)—S(O)$_2$—, —S(O)$_2$—N(R$_8$)—, or —N(R$_8$)—C(O)—N(R$_8$)—. In certain embodiments, Y is —N(R$_8$)—C(O)—. In certain embodiments, Y is —N(R$_8$)—S(O)$_2$—. In certain embodiments, Y is —S(O)$_2$—N(R$_8$)—. In certain embodiments, Y is —N(R$_8$)—C(O)—N(R$_8$)—.

In some embodiments, Y$^1$ is selected from the group consisting of —S—, —C(O)—, —C(O)—O—, —C(O)—N(R$_8$)—, —S(O)$_2$—N(R$_8$)—, and —N(R$_8$)—C(O)—. In some embodiments, Y$^1$ is selected from the group consisting of —S—, —C(O)—, and —C(O)—O—.

In some embodiments, Z is a bond or —O—. In certain embodiments, Z is a bond. In certain embodiments, Z is —O—.

In some embodiments, a and b are independently integers from 1 to 6 with the proviso that a+b is ≤7. In some embodiments, a and b are each the integer 2.

In some embodiments (e.g., of Formulas III-VII), n is 0, or m is 0.

In some embodiments (e.g., of Formulas III-VII), m and n are 0.

In some embodiments (e.g., of Formulas III-VII), m is 0, and n is 1.

In some embodiments (e.g., of Formulas III-VII), m is 1, and n is 0.

In some embodiments (e.g., of Formula VIII), n is 0.

For certain embodiments, the compound of Formula III is selected from the group consisting of 7-(benzyloxy)-2-ethyl-2H-pyrazolo[3,4-c]quinolin-4-amine and 4-amino-2-ethyl-2H-pyrazolo[3,4-c]quinolin-7-ol; or a pharmaceutically acceptable salt thereof.

For certain embodiments, the compound of Formula III is selected from the group consisting of 3-(4-amino-2-propyl-2H-pyrazolo[3,4-c]quinolin-1-yl)-2,2-dimethylpropanamide and 3-[4-amino-2-(2-methoxyethyl)-2H-pyrazolo[3,4-c]quinolin-1-yl]-2,2-dimethylpropanamide; or a pharmaceutically acceptable salt thereof.

For certain embodiments, the compound of Formula III is 5-(4-Amino-2-propyl-2H-pyrazolo[3,4-c]quinolin-1-yl)-N-hydroxypentanamidine; or a pharmaceutically acceptable salt thereof.

For certain embodiments, there is provided compound of the Formula IIIa:

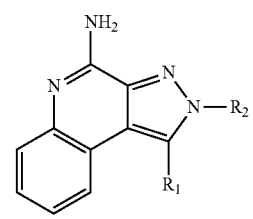

IIIa wherein R$_1$ is selected from the group consisting of aminomethyl, piperidin-4-ylmethyl, (1-benzylpiperidin-4-yl)methyl, (1-acetylpiperidin-4-yl)methyl, {1-[(propylamino)carbonyl]piperidin-4-yl)}methyl, [1-(methylsulfonyl)piperidin-4-yl]methyl, 2-(1,1-dioxidoisothiazolidin-2-yl)ethyl, 2-({[(4- fluorophenyl)amino]carbonyl}amino)ethyl, hydroxymethyl, 2-methyl-2-(methylsulfonyl)propyl, 2-methyl-2-{[2-(methylsulfonyl)ethyl]amino}propyl, 3-[(methylsulfonyl)amino] propyl, 2-cyano-2-methylpropyl, 3-(5-butylisoxazol-3-yl) propyl, 3-(5-phenylisoxazol-3-yl)propyl, 3-(5-pyridin-3-ylisoxazol-3-yl)propyl, 4-(hydroxyimino)butyl, 4-(methoxyimino)butyl, 5-amino-5-(hydroxyimino)pentyl, 3-(1H-pyrrol-3-yl)propyl, 3-(1-benzyl-1H-pyrrol-3-yl)propyl, and 3-(1-benzyl-2,5-dihydro-1H-pyrrol-3-yl)propyl; and $R_2$ is selected from the group consisting of hydrogen, methyl, ethyl, n-propyl, n-butyl, and benzyl. For certain of these embodiments, there is included the proviso that when $R_2$ is hydrogen, n-butyl, benzyl, 2-methoxyethyl, or 2-hydroxyethyl then $R_1$ can be further selected from the group consisting of 2-[(4-fluorobenzoyl)amino]ethyl, 2-[(cyclopropylcarbonyl)amino]ethyl, 2-(acetylamino)ethyl, 2-(propionylamino)ethyl, 2-[(methylsulfonyl)amino]ethyl, 2-{[(ethylamino)carbonyl]amino}ethyl, 2-({[(3,4-difluorophenyl) amino]carbonyl}amino)ethyl, 2-{[(isopropylamino) carbonyl]amino}ethyl, 2-[(ethoxycarbonyl)amino]ethyl, and 2-[(morpholin-4-ylcarbonyl)amino]ethyl. For certain of these embodiments, there is included the further proviso that when $R_2$ is methyl or ethyl then $R_1$ can also be 2-[(4-fluorobenzoyl)amino]ethyl; and/or when $R_2$ is methyl or n-propyl then $R_1$ can also be 2-[(morpholin-4-ylcarbonyl)amino]ethyl; or a pharmaceutically acceptable salt thereof.

For certain embodiments, the compound or salt of Formula IIIa is selected from the group consisting of:
1-[2-(1,1-dioxidoisothiazolidin-2-yl)ethyl]-2-propyl-2H-pyrazolo[3,4-c]quinolin-4-amine;
(4-amino-2-ethyl-2H-pyrazolo[3,4-c]quinolin-1-yl)methanol;
3-(4-amino-2-propyl-2H-pyrazolo[3,4-c]quinolin-1-yl)-2,2-dimethylpropanenitrile;
3-[4-amino-2-(2-methoxyethyl)-2H-pyrazolo[3,4-c]quinolin-1-yl]-2,2-dimethylpropanenitrile;
N-[2-(4-amino-2-propyl-2H-pyrazolo[3,4-c]quinolin-1-yl) ethyl]-N-(4-fluorophenyl)urea;
1-[3-(5-phenylisoxazol-3-yl)propyl]-2-propyl-2H-pyrazolo [3,4-c]quinolin-4-amine;
1-[3-(5-butylisoxazol-3-yl)propyl]-2-propyl-2H-pyrazolo[3, 4-c]quinolin-4-amine; and
2-propyl-1-[3-(5-pyridin-3-ylisoxazol-3-yl)propyl]-2H-pyrazolo[3,4-c]quinolin-4-amine;
or a pharmaceutically acceptable salt thereof.

In some embodiments, the present invention provides a pharmaceutical composition comprising a therapeutically effective amount of a compound or salt of any one of Formulas I, Ia, II, III, IV, V, VI, VII, VIII, IX, LXXX, II-1, or any one of the above embodiments in combination with a pharmaceutically acceptable carrier.

In some embodiments, the present invention provides a method of inducing cytokine biosynthesis in an animal comprising administering an effective amount of a compound or salt of any one of Formulas I, Ia, II, III, IV, V, VI, VII, VIII, IX, LXXX, II1, or any one of the above embodiments or administering any one of the above pharmaceutical compositions to the animal.

In some embodiments, the present invention provides a method of treating a viral disease in an animal in need thereof comprising administering a therapeutically effective amount of a compound or salt of any one of Formulas I, Ia, II, III, IV, V, VI, VII, VIII, IX, LXXX, II-1, or any one of the above embodiments or administering any one of the above pharmaceutical compositions to the animal.

In some embodiments, the present invention provides a method of treating a neoplastic disease in an animal in need thereof comprising administering a therapeutically effective amount of a compound or salt of any one of Formulas I, Ia, II, III, IV, V, VI, VII, VIII, IX, LXXX, II-1, or any one of the above embodiments or administering any one of the above pharmaceutical compositions to the animal.

Preparation of Compounds

Compounds of the invention can be prepared according to Reaction Scheme I, where R, $R_1$, $R_2$, and n are defined as above. Ketoesters of Formula X in Reaction Scheme I and their sodium salts are known and can be prepared from a variety of ketones using conventional methods, such as the Claisen condensation, Claisen, L., *Berichte,* 42, 59 (1909).

Numerous functionalized ketones useful as Claisen condensation starting materials are commercially available; others can be prepared by known methods. For example, tert-butyl 1,1-dimethyl-3-oxobutylcarbamate, also called (1,1-dimethyl-3-oxobutyl)carbamic acid tert-butyl ester, has been reported, Peschke, B. et al, *Eur. J. Med. Chem.,* 34, pp. 363-380, (1999). In another example, 4-(propylthio)butan-2-one can be prepared by combining 1-propanethiol and 4-chloro-2-butanone at ambient temperature in the presence of sodium hydride in a suitable solvent such as tetrahydrofuran (THF) and isolating the product using conventional methods. In a third example, a Michael addition can be carried out with phenyl vinyl sulfone and a carbanion generated from methyl acetoacetate and sodium methoxide. The resulting Michael adduct can be decarboxylated under acidic conditions, for example hydrochloric acid in methanol, to provide 5-(phenylsulfonyl)pentan-2-one.

In step (1) of Reaction Scheme I, a sodium salt of a compound of Formula X reacts with a hydrazine of Formula $R_2NHNH_2$ to provide a pyrazole carboxylate of Formula XI. The reaction is conveniently carried out by slowly adding the hydrazine to a solution of the salt of a compound of Formula X in a suitable solvent such as acetic acid. The reaction can be carried out at ambient temperature, and the product can be isolated using conventional methods.

If step (1) is carried out using hydrazine, the resulting pyrazole carboxylate of Formula XI where $R_2$ is hydrogen can be alkylated using known synthetic methods, Auwers, K. v., Hollman, H., *Berichte,* 59, 606 (1926), to provide a pyrazole carboxylate of Formula XI where $R_2$ is defined as above. The alkylation is conveniently carried out by treating a solution of the pyrazole carboxylate of Formula XI, where $R_2$ is hydrogen, with a base such as sodium ethoxide followed by an alkylating agent of Formula $R_2$—Halide. The reaction is run in a suitable solvent such as ethanol and can be carried out at an elevated temperature, for example, the reflux temperature of the solvent, or at ambient temperature. Numerous reagents of Formula $R_2$-Halide are commercially available; others can be prepared using known synthetic methods. The pyrazole carboxylate of Formula XI can be isolated from the reaction and separated from its isomer using conventional methods.

In step (2) of Reaction Scheme I, the ester group of a pyrazole carboxylate of Formula XI is converted to an amide. The amination is conveniently carried out by adding ammonium hydroxide to the pyrazole carboxylate of Formula XI in a suitable solvent such as methanol and heating at an elevated temperature such as 100° C. The reaction can be carried out in a pressure vessel. The resulting pyrazole carboxamide of Formula XII can be isolated using conventional methods.

Alternatively, step (2) can be carried out by first hydrolyzing a pyrazole carboxylate of Formula XI to a carboxylic acid and then converting the carboxylic acid to an amide. The ester hydrolysis can be carried out under basic conditions by combining a pyrazole carboxylate of Formula XI with lithium hydroxide or sodium hydroxide in water and in a suitable solvent such as methanol or ethanol. The reaction can be carried out at ambient temperature, and the carboxylic acid product can be isolated using conventional methods. The conversion of the carboxylic acid to a pyrazole carboxamide of Formula XII can be carried out by first treating the carboxylic acid with oxalyl chloride at ambient temperature in a suitable solvent such as dichloromethane to generate an acid chloride, which can then be treated with ammonium hydroxide at a sub-ambient temperature such as 0° C. Alternatively, the conversion of the carboxylic acid to a pyrazole carboxamide of Formula XII can be carried out under coupling conditions by adding 1-hydroxybenzotriazole and 1-(3-dimethylaminopropyl)-3-ethylcarbodiimide hydrochloride to a solution of the carboxylic acid in a suitable solvent such as N,N-dimethylformamide (DMF) at ambient temperature and then adding concentrated ammonium hydroxide. The product can be isolated using conventional methods.

In step (3) of Reaction Scheme I, a pyrazole carboxamide of Formula XII is dehydrated to a pyrazole carbonitrile of Formula XIII. Suitable dehydrating agents include thionyl chloride, trifluoroacetic anhydride, and phosphorous oxychloride. The reaction is conveniently carried out by treating the pyrazole carboxamide of Formula XII with phosphorous oxychloride and heating the reaction at an elevated temperature such as 90° C. The reaction can also be carried out by combining the pyrazole carboxamide of Formula XII with trifluoroacetic anhydride in the presence of a base such as triethylamine and in a suitable solvent such as dichloromethane. The reaction can be carried out at ambient temperature or at a sub-ambient temperature such as 0° C. The product can be isolated using conventional methods.

In step (4) of Reaction Scheme I, a pyrazole carbonitrile of Formula XIII is brominated to provide a bromo-substituted pyrazole carbonitrile of Formula XIV. The bromination is conveniently carried out by adding bromine to a solution of the pyrazole carbonitrile of Formula XIII and potassium acetate in acetic acid. The reaction can be carried out at ambient temperature, and the product can be isolated using conventional methods.

In step (5) of Reaction Scheme I, a bromo-substituted pyrazole carbonitrile of Formula XIV undergoes a transition-metal catalyzed cross coupling reaction with a reagent of Formula XV to form a pyrazole-substituted aniline of Formula XVI. Reagents of Formula XV, where M is, for example, —B(OH)$_2$, —B(O-alkyl)$_2$, —Sn(alkyl)$_3$, and —Zn-Halide, are known to undergo coupling reactions. Several reagents of Formula XV are commercially available; others can be prepared using known synthetic methods. For example, tert-butoxycarbonyl (Boc)-protected anilines undergo directed ortho metalation in the presence of butyllithium reagents. The resulting organolithium intermediate reacts with electrophiles such as B(O-alkyl)$_3$ and ClSn(alkyl)$_3$ to provide compounds of Formula XV, where M is —B(O-alkyl)$_2$ or —B(OH)$_2$ and —Sn(alkyl)$_3$, respectively, after removal of the Boc protecting group.

In step (5), a Suzuki coupling reaction is conveniently carried out by heating a mixture of the bromo-substituted pyrazole carbonitrile of Formula XIV, palladium (II) acetate, triphenylphosphine, and a boron reagent of Formula XV, where M is —B(OH)$_2$ or —B(O-alkyl)$_2$, in the presence of a base such as sodium carbonate. The reaction is carried out in a suitable solvent or solvent mixture such as n-propanol:water and can be heated at an elevated temperature such as 100° C. The product can be isolated using conventional methods.

In step (6) of Reaction Scheme I, the amine and nitrile functionalities of a pyrazole-substituted aniline of Formula XVI react under acidic conditions to form a pyrazolo[3,4-c]quinoline of Formula XVII, a subgenus of Formulas I, II, III, and Ia. The intramolecular addition is conveniently carried out by stirring acetyl chloride in ethanol and adding the resulting acidic solution to the pyrazole-substituted aniline of Formula XVI. The reaction is then heated at reflux to provide the pyrazolo[3,4-c]quinoline of Formula XVII. The product or pharmaceutically acceptable salt thereof can be isolated using conventional methods.

Alternatively, in steps (5) and (6) of Reaction Scheme I, a bromo-substituted pyrazole carbonitrile of Formula XIV undergoes a Suzuki coupling with a reagent of Formula XLII.

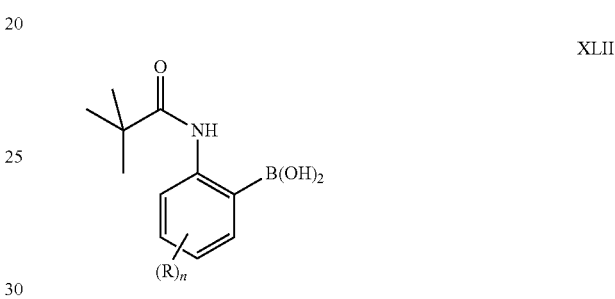

XLII

Some compounds of Formula XLII are known or can be prepared by known synthetic methods; see, Rocca, P. et al, *Tetrahedron*, 49, pp. 49-64 (1993). The Suzuki coupling reaction can be carried out according to the method described above. The resulting pivaloylamino-substituted compound undergoes a base-promoted intramolecular cyclization in step (6) of Reaction Scheme I and subsequent cleavage of the pivaloyl group to provide a pyrazolo[3,4-c]quinoline of Formula XVII. The reaction is conveniently carried out by heating the pivaloylamino-substituted coupling product with potassium tert-butoxide in a suitable solvent such as ethanol at an elevated temperature such as the reflux temperature of the solvent. The product or pharmaceutically acceptable salt thereof can be isolated using conventional methods.

For some embodiments, compounds in Reaction Scheme I can be further elaborated using conventional synthetic methods. For example, R$_1$ can be a 2-[(tert-butoxycarbonyl)amino]-2-methylpropyl group if tert-butyl 1,1-dimethyl-3-oxobutylcarbamate is used as the starting ketone to make the ketoester of Formula X. The tert-butoxycarbonyl group is removed under the acidic cyclization conditions described in step (6) to provide a 2-amino-2-methylpropyl group, which can be converted to an amide, a sulfonamide, a sulfamide, or a urea using the methods described below in step (11) of Reaction Scheme VII.

In another example, an olefin-containing R$_1$ group may be oxidized to an epoxide by conventional methods. The oxidation is conveniently carried out prior to step (4) of Reaction Scheme I by adding 3-chloroperoxybenzoic acid to a solution of a pyrazole carbonitrile of Formula XIII, which contains an olefin substituent, in a suitable solvent such as dichloromethane. The reaction may be carried out at ambient temperature, and the product can be isolated by conventional methods. The epoxide can be opened during the bromination in step (4) by combining the compound of Formula XIII, which contains an epoxide substituent, with two equivalents of bromine in acetic acid at ambient temperature to provide a compound of Formula XIV substituted at $R_1$ with a vicinal bromohydrin. The bromohydrin may then be reduced under free radical conditions to provide a compound of Formula XIV substituted with a hydroxyalkyl group. The reduction may be carried out by adding tributyltin hydride and azobisisobutyronitrile at ambient temperature to a bromohydrin-substituted compound of Formula XIV in a suitable solvent such as toluene. The product may be isolated by conventional methods and then subjected to steps (5) and (6) of Reaction Scheme I. Using these methods an $R_1$ 2-methylpropenyl group can be converted into a 2-hydroxy-2-methylpropyl group.

A hydroxy group introduced at the $R_1$ position according to the above method can be treated with sodium hydride to form an alkoxide, which is reacted with a vinyl sulfone of Formula $CH_2$=CH—S(O)$_2$—$R_4$ to provide a compound in which $R_1$ is —X—Y—$R_4$, wherein Y is —SO$_2$—. The reaction can be carried out by adding catalytic sodium hydride dispersed in mineral oil to a solution of a compound of Formula XIV, wherein $R_1$ has hydroxy group, and a vinyl sulfone in a suitable solvent such DMF or tetrahydrofuran. The reaction can be run at ambient temperature. The product or a pharmaceutically acceptable salt thereof can be isolated by conventional methods and then subjected to steps (5) and (6) of Reaction Scheme I. Many vinyl sulfones are commercially available or can be prepared using known synthetic methods. These methods can be used to provide a compound of Formula XVII, wherein $R_1$ is a 2-methyl-2-[2-(methylsulfonyl)ethoxy]propyl group.

In another example, $R_1$ can be —X—Y—$R_4$, wherein Y is —S—. The thioether group may be oxidized to a sulfone prior to step (2) of Reaction Scheme I to provide a compound where $R_1$ is —X—Y—$R_4$ and Y is —SO$_2$—. The oxidation is conveniently carried out by adding 3-chloroperoxybenzoic acid to a solution of a pyrazole carboxylate of Formula XI in a suitable solvent such as dichloromethane or chloroform. The product may be isolated by conventional methods and then subjected to steps (2) through (6) of Reaction Scheme I.

Reaction Scheme I

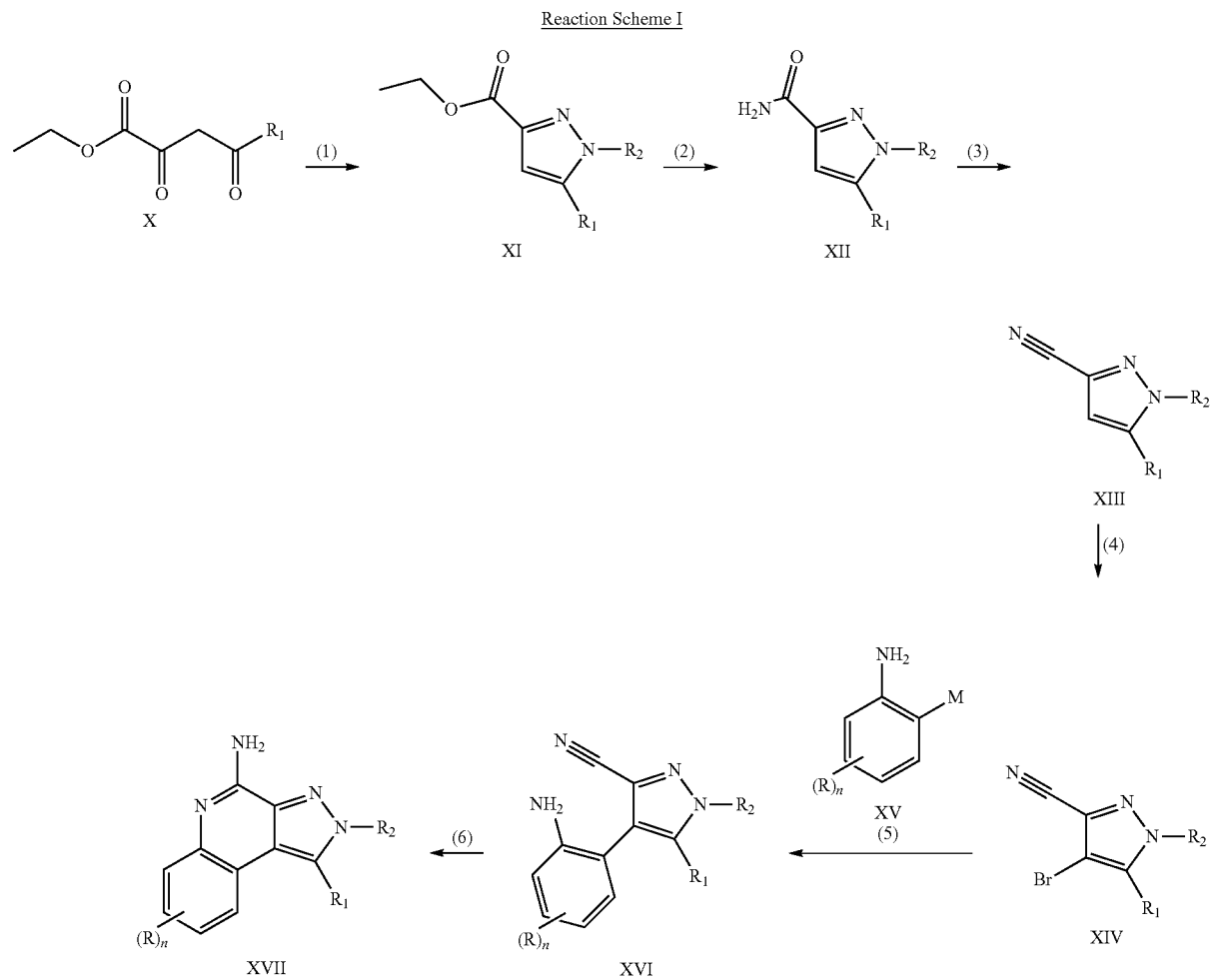

Pyrazolo[3,4-c]naphthyridines of the invention can be prepared according to Reaction Scheme II, where R, $R_1$, $R_2$, and n are as defined above. In step (1) of Reaction Scheme II, a bromo-substituted pyrazole carbonitrile of Formula XIV undergoes a transition-metal catalyzed cross coupling reaction with a reagent of Formula XVIII or a positional isomer thereof, where M is as defined above, to form a pyrazole-substituted aminopyridine of Formula XIX. Reagents of Formula XVIII and its isomers can be prepared using known methods, for example, by directed ortho metalation of Boc-protected aminopyridines and subsequent electrophilic substitution. Alternatively, for some isomers, halogen-lithium exchange and subsequent electrophilic substitution can be used. For example, halogen-lithium exchange can be carried out on a 2-bromopyridine that has a protected amino group in the 3-position; subsequent electrophilic substitution with tributyltin chloride and deprotection of the amino group provides 3-amino-2-tri-n-butylstannylpyridine, a useful reagent for step (1) of Reaction Scheme II. The coupling reaction in step (1) of Reaction Scheme II can be carried out as described for step (5) of Reaction Scheme I.

In step (2) of Reaction Scheme II, the amine and nitrile functionalities of a pyrazole-substituted aminopyridine of Formula XIX react under acidic conditions to form a pyrazolo [3,4-c]naphthyridine of Formula XX, a subgenus of Formulas I, II, VI, and Ia, or an isomer thereof. Step (2) of Reaction Scheme II can be carried out as described for step (6) of Reaction Scheme I, and the product can be isolated by conventional methods.

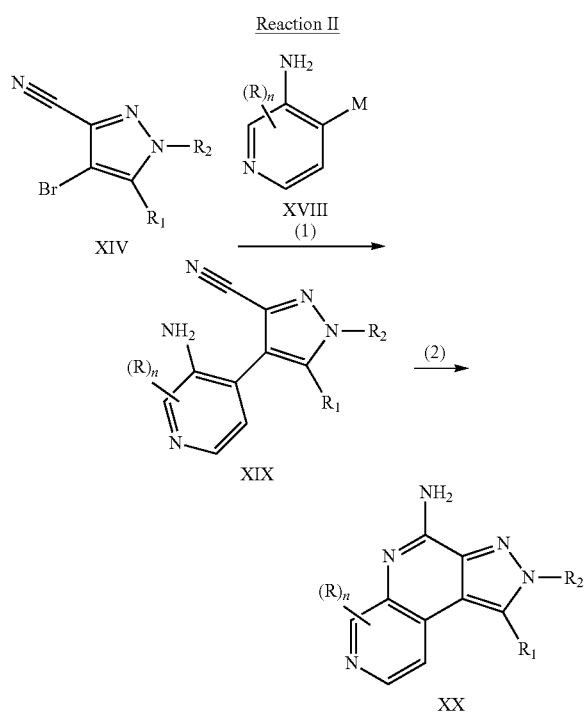

Reaction II

Compounds of the invention can also be prepared according to Reaction Scheme III, where n is defined as above and $R_a$, $R_{1a}$, and $R_{2a}$ are subsets of R, $R_1$, and $R_2$ as defined above that do not include those substituents which one skilled in the art would recognize as being susceptible to oxidation in step (5). These susceptible substituents include —S— or heteroaryl groups.

Acetals of Formula XXI are reported in the literature and can be prepared using known synthetic methods, Royals, E. E., Robinson, A. G. III, J. Am. Chem. Soc., 78, 4161 (1956). For example, a ketone of Formula $CH_3C(O)R_{1a}$ can be condensed with ethyl diethoxyacetate under Claisen condensation conditions to provide an acetal of Formula XXI. The reaction is conveniently carried out by adding sodium tert-butoxide to a solution of ethyl diethoxyacetate and the ketone of Formula $CH_3C(O)R_{1a}$ in ethanol and heating the reaction at reflux. Numerous ketones of Formula $CH_3C(O)R_{1a}$ are commercially available. Others can be readily prepared using known synthetic methods. Amido ketones can be prepared according to the literature procedure, Ritter, J. J. and Minieri, P. P., J. Am. Chem. Soc., 70, 4045, (1948) by adding a nitrile of Formula $R_4$—CN to an α,β-unsaturated ketone under acidic conditions.

In step (1) of Reaction Scheme III, an acetal of Formula XXI is reacted with a hydrazine of Formula $R_{2a}$—NH—$NH_2$ to provide a pyrazole of Formula XXII. The reaction is conveniently carried out by slowly adding the hydrazine to a solution of an acetal of Formula XXI in a suitable solvent such as ethanol. The reaction can be run at ambient temperature, and the product can be isolated using conventional methods.

In step (2) of Reaction Scheme III, the acetal in the pyrazole of Formula XXII is converted to an aldehyde under acidic conditions. The reaction is conveniently carried out by treating the acetal-substituted pyrazole of Formula XXII with hydrochloric acid in a suitable solvent such as tetrahydrofuran. The reaction can be carried out at ambient temperature to provide an aldehyde-substituted pyrazole of Formula XXIII. The product can be isolated using conventional methods.

In step (3) of Reaction Scheme III, a pyrazole of Formula XXIII is brominated provide a bromo-substituted pyrazole of Formula XXIV. The reaction can be carried out as described in step (4) of Reaction Scheme I.

In step (4) of Reaction Scheme III, a bromo-substituted pyrazole of Formula XXIV undergoes a transition-metal catalyzed cross coupling reaction with a reagent of Formula XV, where M is defined as above. The reaction is conveniently carried out using the Suzuki reaction conditions described in step (5) of Reaction Scheme I. Under these reaction conditions, intramolecular condensation of the amine with the aldehyde group takes place to form a pyrazolo[3,4-c]quinoline of Formula XXV. The product can be isolated using conventional methods.

In step (5) of Reaction Scheme III, a pyrazolo[3,4-c]quinoline of Formula XXV is oxidized to provide a pyrazolo[3,4-c]quinoline-5N-oxide of Formula XXVI using a conventional oxidizing agent capable of forming N-oxides. The reaction is conveniently carried out by adding 3-chloroperoxybenzoic acid to a solution of a compound of Formula XXV in a solvent such as dichloromethane or chloroform. The reaction can be carried out at ambient temperature, and the product can be isolated using conventional methods.

In step (6) of Reaction Scheme III, a pyrazolo[3,4-c]quinoline-5N-oxide of Formula XXVI is aminated to provide a pyrazolo[3,4-c]quinolin-4-amine of Formula XVIIa, a subgenus of Formulas I, II, III, and Ia. Step (6) can be carried out by the activation of an N-oxide of Formula XXVI by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXVI in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Alternatively step (6) can be carried out by the reaction of a pyrazolo[3,4-c]quinoline-5N-oxide of Formula XXVI with trichloroacetyl isocyanate followed by base-promoted hydrolysis of the resulting intermediate to provide a pyrazolo[3,4-c]quinolin-4-amine of Formula XVIIa. The reaction is conveniently carried out in two steps by (i) adding trichloroacetyl isocyanate to a solution of the N-oxide of Formula XXVI in a solvent such as dichloromethane and stirring at ambient temperature to provide an isolable amide intermediate. In step (ii), a solution of the intermediate in methanol is treated with a base such as sodium methoxide at ambient temperature. The product or pharmaceutically acceptable salt thereof can be isolated using conventional methods.

Pyrazolo[3,4-c]naphthyridines of the invention can be prepared according to Reaction Scheme IV, where $R_a$, $R_{1a}$, $R_{2a}$, and n are as defined above. In step (1) of Reaction Scheme IV, a bromo-substituted pyrazole of Formula XXIV undergoes a transition-metal catalyzed cross coupling reaction with a reagent of Formula XVIII, where M is defined as above, or one of its isomers. Step (1) of Reaction Scheme IV can be carried out as described for step (5) of Reaction Scheme I, and under these reaction conditions an intramolecular addition can take place to provide the pyrazolo[3,4-c]naphthyridine of Formula XXVII.

In step (2) of Reaction Scheme IV, a pyrazolo[3,4-c]naphthyridine of Formula XXVII is oxidized to a pyrazolo[3,4-c]naphthyridine-5N-oxide of Formula XXVIII, which is aminated in step (3) to provide a pyrazolo[3,4-c]naphthyridin-4-amine of Formula XXa, a subgenus of Formulas I, II, VI, and Ia, or an isomer thereof. Steps (2) and (3) of Reaction Scheme IV can be carried out as described for steps (5) and (6), respectively, of Reaction Scheme III.

Reaction Scheme III

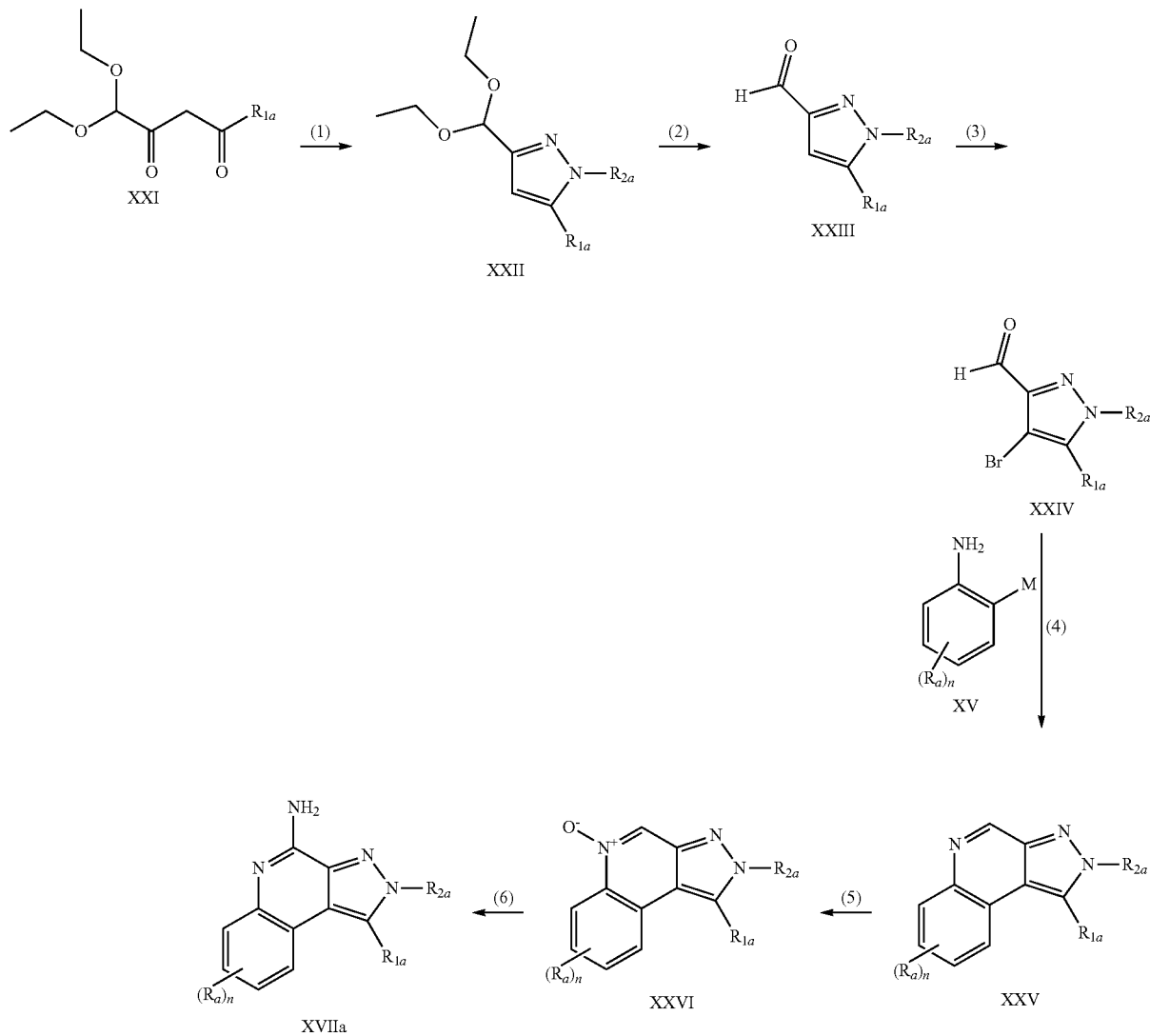

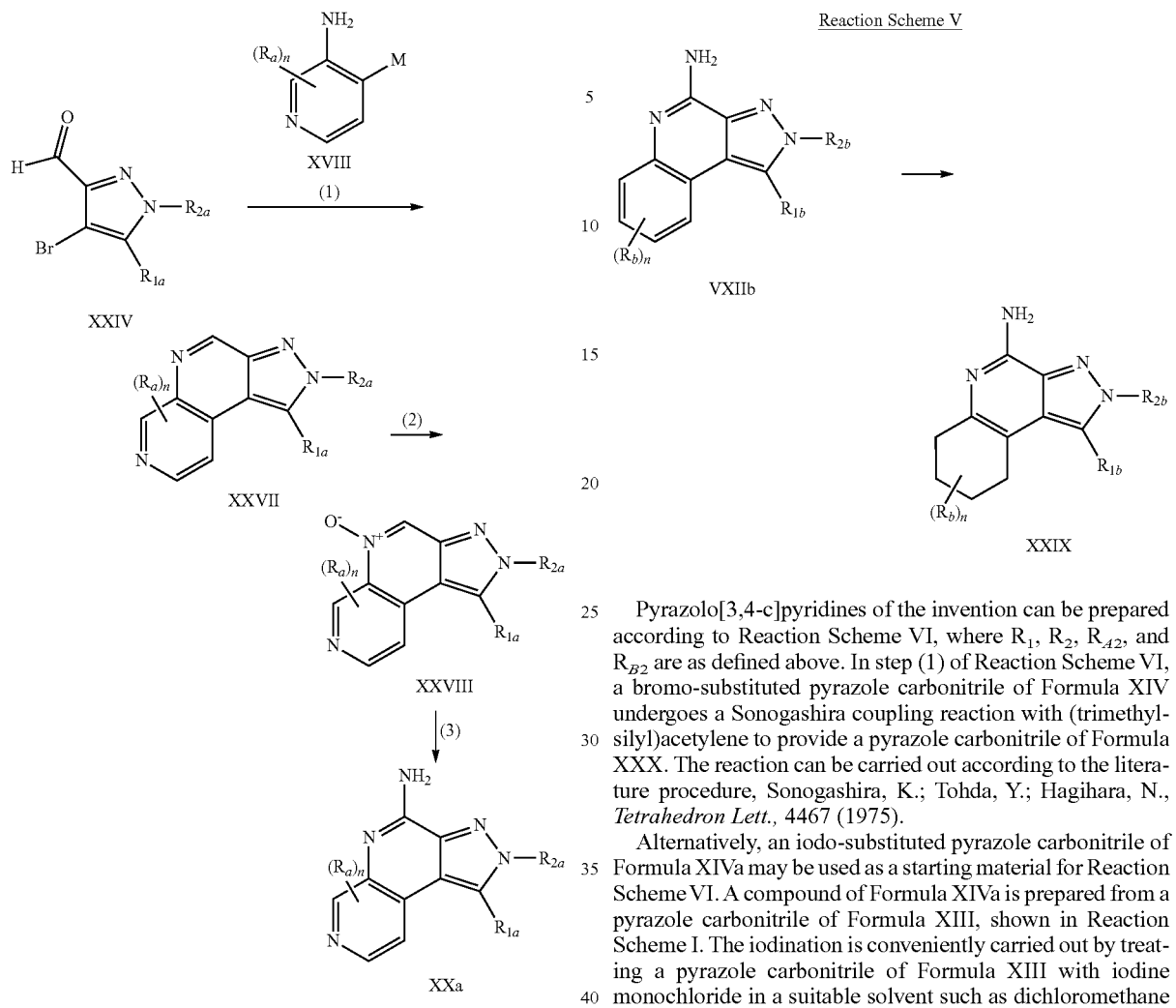

Tetrahydroquinolines of the invention may be prepared according to Reaction Scheme V, where n is as defined above and $R_b$, $R_{1b}$, and $R_{2b}$ are subsets of R, $R_1$, and $R_2$ as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents. However, a compound of Formula XVII bearing an aryl substituent at $R_1$, for example, may be used as a substrate in the reaction to provide a compound of Formula XXIX where the aryl group is reduced. In this manner, a phenylethyl group at $R_1$ may be converted to a cyclohexylethyl group.

As shown in Reaction Scheme V, a pyrazolo[3,4-c]quinolin-4-amine of Formula XVIIb can be reduced to a 6,7,8,9-tetrahydro-2H-pyrazolo[3,4-c]quinolin-4-amine of Formula XXIX, a subgenus of Formulas I, II, VIII, and Ia. The reaction may be carried out under heterogeneous hydrogenation conditions by adding platinum (IV) oxide to a solution or suspension of the compound of Formula XVIIb in a suitable solvent such as trifluoroacetic acid and placing the reaction under hydrogen pressure. The product or pharmaceutically acceptable salt thereof can be isolated by conventional methods.

Pyrazolo[3,4-c]pyridines of the invention can be prepared according to Reaction Scheme VI, where $R_1$, $R_2$, $R_{A2}$, and $R_{B2}$ are as defined above. In step (1) of Reaction Scheme VI, a bromo-substituted pyrazole carbonitrile of Formula XIV undergoes a Sonogashira coupling reaction with (trimethylsilyl)acetylene to provide a pyrazole carbonitrile of Formula XXX. The reaction can be carried out according to the literature procedure, Sonogashira, K.; Tohda, Y.; Hagihara, N., *Tetrahedron Lett.*, 4467 (1975).

Alternatively, an iodo-substituted pyrazole carbonitrile of Formula XIVa may be used as a starting material for Reaction Scheme VI. A compound of Formula XIVa is prepared from a pyrazole carbonitrile of Formula XIII, shown in Reaction Scheme I. The iodination is conveniently carried out by treating a pyrazole carbonitrile of Formula XIII with iodine monochloride in a suitable solvent such as dichloromethane in the presence of a base such as potassium carbonate. The reaction can be carried out at ambient temperature, and the product can be isolated by conventional methods.

In step (2) of Reaction Scheme VI, the trimethylsilyl group of the pyrazole of Formula XXX is removed to provide the pyrazole of Formula XXXI. Potassium carbonate in methanol or tetrabutylammonium fluoride in tetrahydrofuran can be used to carry out the transformation.

In step (3) of Reaction Scheme VI, the acetylene of the pyrazole of Formula XXXI is alkylated using conventional synthetic methods, Jacobs, T. L. in *Organic Reactions*, 5, 1, (1949), to provide a pyrazole of Formula XXXII. The reaction can be carried out by deprotonation of the compound of Formula XXXI with a base and reaction of the resulting carbanion with an electrophile of Formula $R_{B2}$-Halide, for example, iodomethane. Step (3) can be omitted when $R_{B2}$ is hydrogen.

For some embodiments, steps (1) through (3) of Reaction Scheme VI may be replaced with one step from a compound of Formula XIVa using a Sonogashira coupling reaction. The coupling is conveniently carried out by combining an alkyne of Formula $R_{B2}$-C≡H, copper(I) iodide, dichlorobis(triphenylphosphine)palladium(II), and triethylamine in a suitable solvent such as acetonitrile and then heating at an elevated temperature, such as the reflux temperature of the solvent. The product of Formula XXXII can be isolated using conventional methods.

In step (4) of Reaction Scheme VI, a pyrazole of Formula XXXII reacts with ammonia to provide a pyrazolo[3,4-c]pyridin-4-amine of Formula XXXIII, a subgenus of Formulas I, II, IX, and Ia. The reaction can be carried out by adding a solution of ammonia in methanol to the pyrazole of Formula XXXII and heating at an elevated temperature, such as 150° C. The reaction may be carried out in a pressure vessel. The product or pharmaceutically acceptable salt thereof can be isolated by conventional methods.

Steps (5) and (6) may be carried out to provide a compound of Formula IX in which $R_{A2}$ is other than hydrogen. In step (5) of Reaction Scheme VI, a pyrazolo[3,4-c]pyridin-4-amine of Formula XXXIII is brominated under conventional bromination conditions to provide a bromo-substituted pyrazolo[3,4-c]pyridin-4-amine of Formula XXXIV, a subgenus of Formulas I, II, IX, and Ia. The reaction can be carried out as described in step (4) of Reaction Scheme I.

In step (6) of Reaction Scheme VI, a bromo-substituted pyrazolo[3,4-c]pyridin-4-amine of Formula XXXIV undergoes a transition metal catalyzed coupling reaction with a reagent of Formula $R_{A2}$-M, where $R_{A2}$ is alkenyl, alkoxy, and —N($R_9$)$_2$ to provide a pyrazolo[3,4-c]pyridin-4-amine of Formula IX. Reagents of Formula $R_{A2}$-M, where M is, for example, —B(OH)$_2$, —B(O-alkyl)$_2$, —Sn(alkyl)$_3$, and —Zn-Halide, are known to undergo coupling reactions. The transformation can be carried out by first protecting the amino group of the compound of Formula XXXIV, treating the protected compound with a reagent of Formula $R_{A2}$-M in the presence of a transition metal catalyst using conditions described in step (5) of Reaction Scheme I, and deprotecting the amine to provide the pyrazolo[3,4-c]pyridin-4-amine of Formula IX. Alternatively, step (6) can be carried out by coupling a compound of Formula XXXIV with an alkyne under Sonogashira conditions as described in step (1) of this reaction scheme. The resulting alkyne can be reduced under conventional hydrogenation conditions to provide a compound of Formula IX, where $R_{A2}$ is alkenyl or alkyl. Step (6) may also be carried out by (i) protecting the amino group of the compound of Formula XXXIV, for example, with a Boc group; (ii) performing a lithium-halogen exchange; (iii) treating with an electrophile of the Formula $R_{A2}$-Halide, for example iodomethane; and (iv) deprotecting the amine to provide a compound of Formula IX. The product or pharmaceutically acceptable salt thereof can be isolated by conventional methods.

Reaction Scheme VI

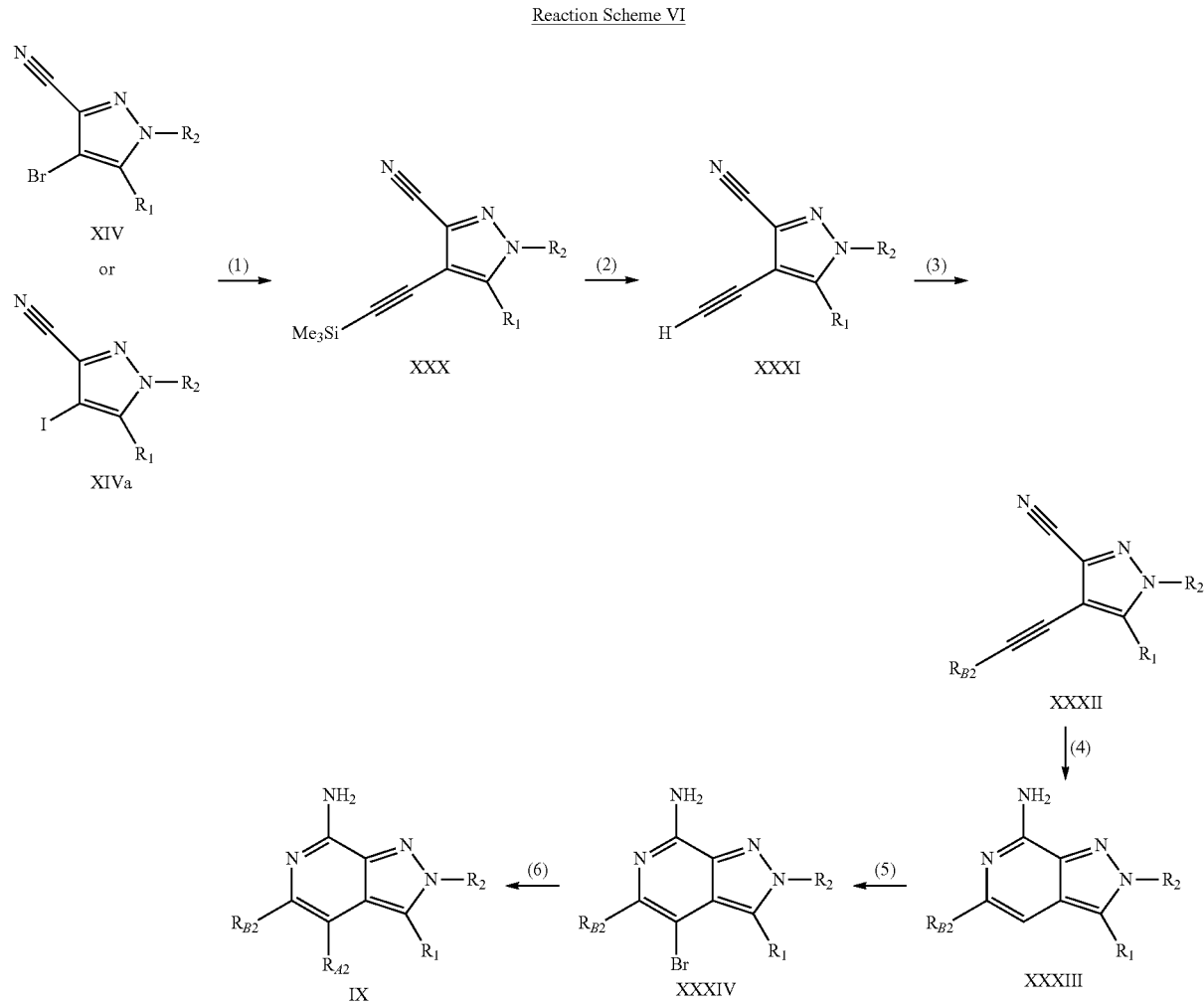

For some embodiments, compounds of the invention are prepared according to Reaction Scheme VII, wherein R, $R_2$, $R_4$, $R_8$, Q, M, and n are as defined above. In step (1) of Reaction Scheme VII, 4-phthalimido-2-butanone, which is obtained from the literature procedure, Eriks et al, *J. Med. Chem.*, 35, 3239-3246, (1992), undergoes a Claisen condensation with diethyl oxalate under conventional conditions to yield a compound of Formula XXXV.

In step (2) of Reaction Scheme VII, a compound of Formula XXXV reacts with a hydrazine of Formula $R_2NHNH_2$ to provide a pyrazole carboxylate of Formula XXXVI. The reaction is conveniently carried out as described in Step (1) of Reaction Scheme I.

In steps (3) and (4) of Reaction Scheme VII, a pyrazole carboxylate of Formula XXXVI is converted to a pyrazole carboxamide. In step (3) the pyrazole carboxylate of Formula XXXVI is first hydrolyzed under acidic conditions to provide a carboxylic acid of Formula XXXVII. The reaction is conveniently carried out by heating a mixture of the carboxylate of Formula XXXVI in a mixture of hydrochloric acid and acetic acid at an elevated temperature, such as 100-120° C. The product can be isolated by conventional methods. In step (4), a carboxylic acid of Formula XXXVII is then converted to its acid chloride. The reaction is conveniently carried out by heating (115° C.) the carboxylic acid of Formula XXXVII with thionyl chloride in a suitable solvent such as toluene. The acid chloride can be isolated by conventional methods before converting it to a pyrazole carboxamide of Formula XXXVIII. The conversion to the amide is conveniently carried out by adding concentrated ammonium hydroxide to a solution of the acid chloride in a suitable solvent such as dichloromethane. The reaction can be carried out at ambient temperature, and the product can be isolated using conventional methods.

In step (5) of Reaction Scheme VII, a pyrazole carboxamide of Formula XXXVIII is dehydrated to a pyrazole carbonitrile of Formula XXXIX. Suitable dehydrating agents include thionyl chloride, trifluoroacetic anhydride, and phosphorous oxychloride. The reaction is conveniently carried out by treating a pyrazole carboxamide of Formula XXXVIII with excess thionyl chloride in a suitable solvent such as toluene. The reaction can be run at elevated temperature, for example, at the reflux temperature of the solvent, and the product can be isolated using conventional methods.

In step (6) of Reaction Scheme VII, a pyrazole carbonitrile of Formula XXXIX is brominated according to the method described in step (4) of Reaction Scheme I to provide a bromo-substituted pyrazole carbonitrile of Formula XL.

In step (7) of Reaction Scheme VII, the phthalimide protecting group of the pyrazole of Formula XL is removed to reveal an amine, which is then protected by a tert-butoxycarbonyl (Boc) group. The deprotection is conveniently carried out by treating the compound of Formula XL with hydrazine in a suitable solvent such as ethanol. The reaction can be run at an elevated temperature, such as the reflux temperature of the solvent, and the amine can be isolated using conventional methods. The Boc protection is then conveniently carried out by treating the amine with di-tert-butyl Bicarbonate in a suitable solvent such as 1-methyl-2-pyrrolidinone (NMP). The reaction can be carried out at ambient temperature, and the product of Formula XLI can be isolated by conventional methods.

In steps (8) and (9a) of Reaction Scheme VII, a bromo-substituted pyrazole carbonitrile of Formula XLI undergoes a transition-metal catalyzed cross coupling reaction with a reagent of Formula XV to form a pyrazole-substituted aniline of Formula XLIII, which undergoes intramolecular cyclization and removal of the Boc group under acidic conditions in step (9a) to provide a pyrazolo[3,4-c]quinoline of Formula XLV, a subgenus of Formulas I, II, III, and Ia. Steps (8) and (9a) of Reaction Scheme VII can be carried out as described in steps (5) and (6) of Reaction Scheme I.

Alternatively, in step (8) of Reaction Scheme VII, a bromo-substituted pyrazole carbonitrile of Formula XLI undergoes a Suzuki coupling with a reagent of Formula XLII.

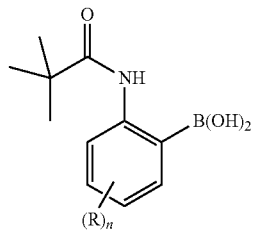

XLII

The resulting pivaloylamino-substituted compound undergoes a base-promoted intramolecular cyclization in step (9) of Reaction Scheme VII and subsequent cleavage of the pivaloyl group to provide a pyrazolo[3,4-c]quinoline of Formula XLIV, a subgenus of Formulas I, II, III, and Ia. The reaction with XLII and the base-promoted cyclization are carried out as described in steps (5) and (6) of Reaction Scheme I. The product or pharmaceutically acceptable salt thereof can be isolated using conventional methods.

In step (10) of Reaction Scheme VII, the Boc protecting group on a pyrazolo[3,4-c]quinoline of Formula XLIV is removed to provide an aminoethyl pyrazolo[3,4-c]quinoline of Formula XLV, a subgenus of Formulas I, II, III, and Ia. The deprotection is conveniently carried out under acidic conditions by adding hydrogen chloride in ethanol to a pyrazolo[3,4-c]quinoline of Formula XLIV in a suitable solvent such as ethanol. The reaction can be run at ambient temperature, and the product or pharmaceutically acceptable salt thereof can be isolated using conventional methods.

In step (11) of Reaction Scheme VII, an aminoethyl-2H-pyrazolo[3,4-c]quinoline of Formula XLV or pharmaceutically acceptable salt thereof is converted to an amide, sulfonamide, sulfamide, or urea of Formula XLVI using conventional methods. Formula XLVI represents a subgenus of Formula I, II, III, and Ia. In step (11), an aminoethyl 2H-pyrazolo[3,4-c]quinoline of Formula XLV can react with an acid chloride of Formula $R_4C(O)Cl$ to provide a compound of Formula XLVI in which -Q- is —C(O)—. In addition, an aminoethyl-2H-pyrazolo[3,4-c]quinoline of Formula XLV can react with sulfonyl chloride of Formula $R_4S(O)_2Cl$ or a sulfonic anhydride of Formula $(R_4S(O)_2)_2O$ to provide a compound of Formula XLVI in which -Q- is —S(O)$_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the aminoethyl-2H-pyrazolo[3,4-c]quinoline of Formula XLV in a suitable solvent such as chloroform, dichloromethane, or DMF. Optionally a base such as triethylamine or N,N-diisopropylethylamine can be added. The reaction can be carried out at ambient temperature or a sub-ambient temperature such as 0° C. The product or pharmaceutically acceptable salt thereof can be isolated using conventional methods.

Ureas of Formula XLVI, where -Q- is —C(O)—N(R$_8$)— and R$_8$ is as defined above, can be prepared by reacting an aminoethyl-2H-pyrazolo[3,4-c]quinoline of Formula XLV or pharmaceutically acceptable salt thereof with isocyanates of Formula $R_4N\!\!=\!\!C\!\!=\!\!O$ or with carbamoyl chlorides of Formula $R_4N\!\!-\!\!(R_8)\!\!-\!\!C(O)Cl$. Numerous isocyanates of Formula $R_4N\!\!=\!\!C\!\!=\!\!O$ and carbamoyl chlorides of Formula $R_4N\!\!-\!\!(R_8)\!\!-\!\!C(O)Cl$ are commercially available; others can be readily prepared using known synthetic methods. The reaction can be conveniently carried out by adding the isocyanate of Formula $R_4N\!\!=\!\!C\!\!=\!\!O$ or carbamoyl chloride of Formula $R_4N\!\!-\!\!(R_8)\!\!-\!\!C(O)Cl$ to a solution of the aminoethyl-2H-pyrazolo[3,4-c]quinoline of Formula XLV in a suitable solvent such as DMF or chloroform. Optionally a base such as triethylamine or N,N-diisopropylethylamine can be added. The reaction can be carried out at ambient temperature or a sub-ambient temperature such as 0° C. Alternatively, a compound of Formula XLV can be treated with an isocyanate of Formula $R_4(CO)N\!\!=\!\!C\!\!=\!\!O$, a thioisocyanate of Formula $R_4N\!\!=\!\!C\!\!=\!\!S$, or a sulfonyl isocyanate of Formula $R_4S(O)_2N\!\!=\!\!C\!\!=\!\!O$ to provide a compound of Formula XLVI, where -Q- is $-C(O)-N(R_8)-(CO)-$, $-C(S)-N(R_8)-$, or $-C(O)-N(R_8)-S(O)_2-$, respectively. The product or pharmaceutically acceptable salt thereof can be isolated using conventional methods.

Sulfamides of Formula XLVI, where -Q- is $-S(O)_2-N(R_8)-$, can be prepared by reacting a compound or salt of Formula XLV with sulfuryl chloride to generate a sulfamoyl chloride in situ, and then reacting the sulfamoyl chloride with an amine of formula $HN(R_8)R_4$. Alternatively, sulfamides of Formula XLVI can be prepared by reacting a compound of Formula XLV with a sulfamoyl chloride of formula $R_4(R_8)N\!\!-\!\!S(O)_2Cl$. The product or a pharmaceutically acceptable salt thereof can be isolated using conventional methods. Many amines of Formula $HN(R_8)R_4$ and some sulfamoyl chlorides of formula $R_4(R_8)N\!\!-\!\!S(O)_2Cl$ are commercially available; others can be prepared using known synthetic methods. The product or pharmaceutically acceptable salt thereof can be isolated using conventional methods.

Reaction Scheme VII

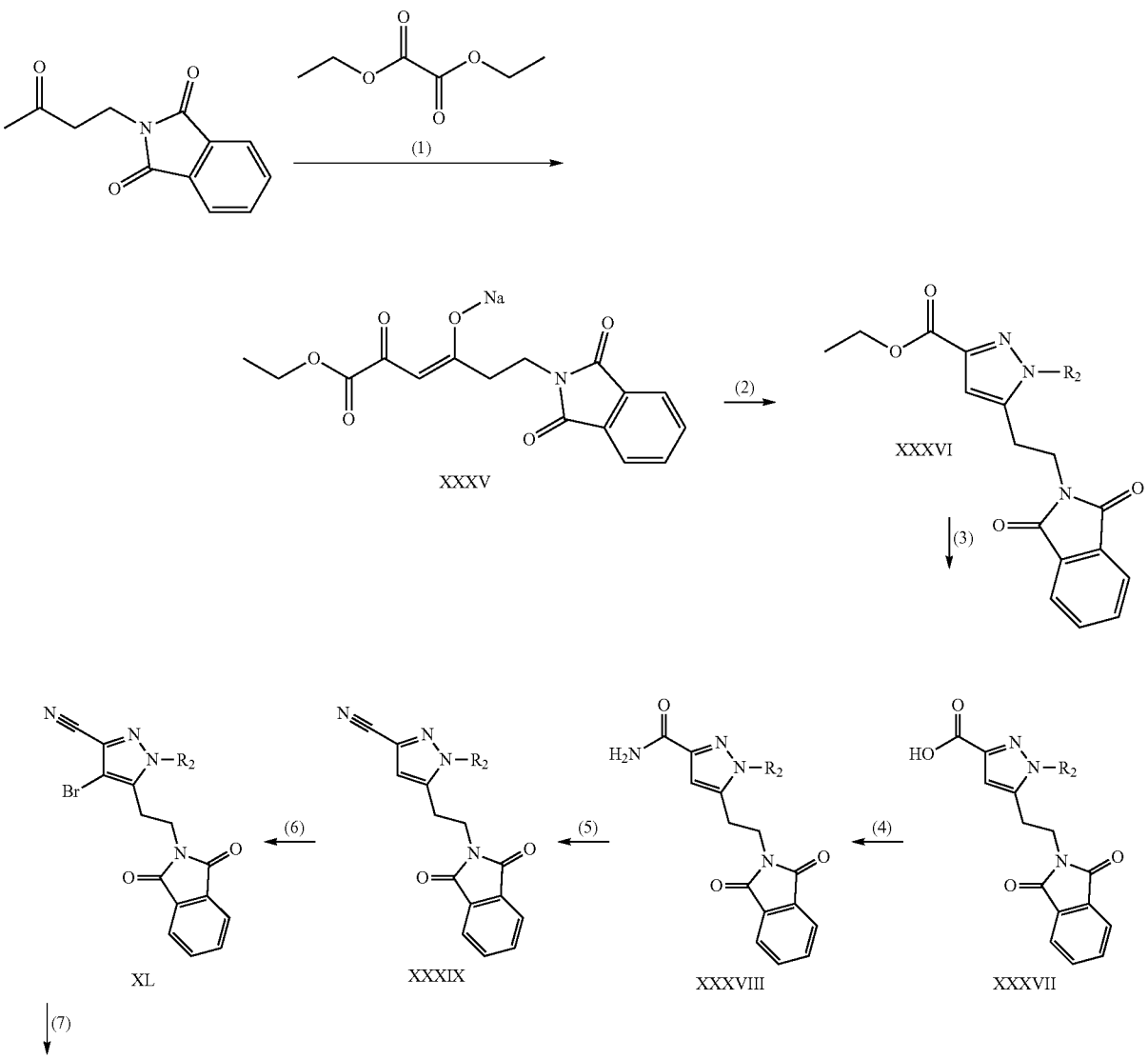

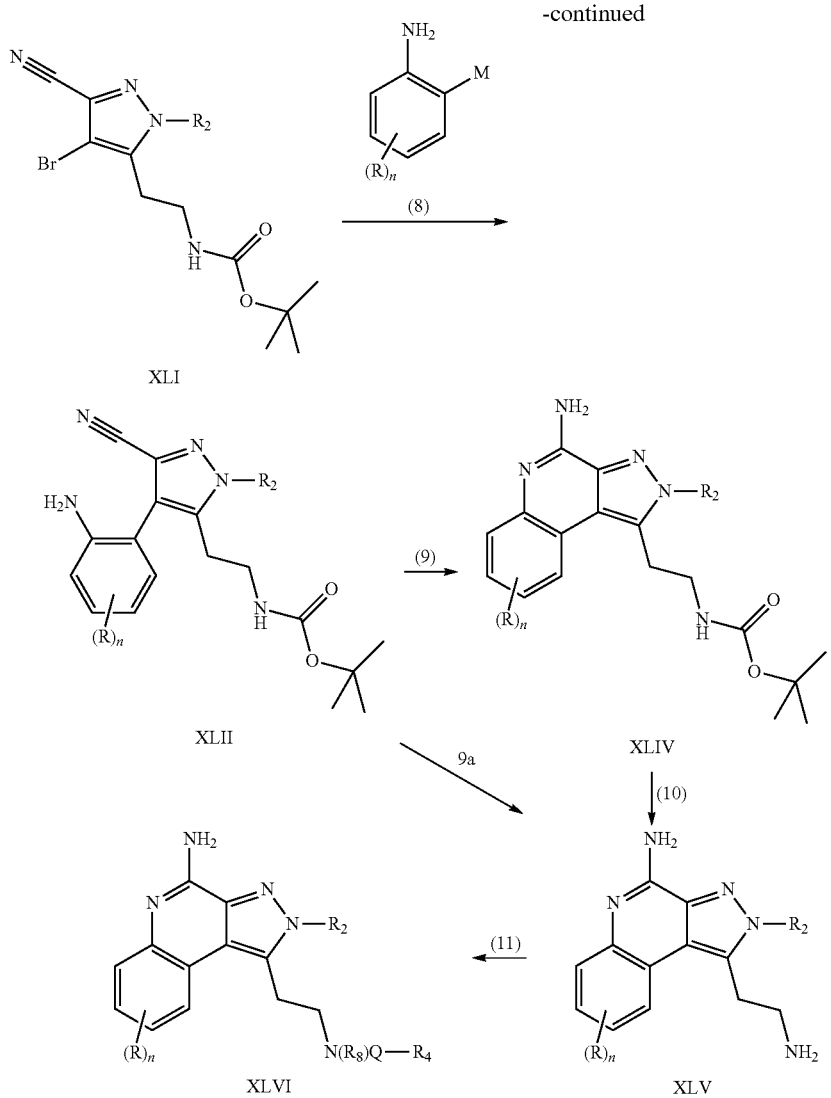

For some embodiments, compounds of the invention are prepared according to Reaction Scheme VIII; wherein R, $R_2$, $R_4$, $R_8$, Q, M, Y, and n are as defined above; $X_a$ is alkylene optionally interrupted with one or more —O— groups, wherein there are at least three atoms in the linking chain; and $R_{4a}$ is heterocyclyl that is unsubstituted or substituted as defined in $R_4$ above, wherein the heterocyclyl is attached at a nitrogen atom. In step (1) of Reaction Scheme VIII, a chloro-substituted ketoester of Formula XLVII reacts with a hydrazine of Formula $R_2NHNH_2$ to provide a pyrazole carboxylate of Formula XLVIII. Compounds of Formula XLVII are readily prepared by reacting diethyl oxalate with ketones of Formula $CH_3$—C(O)—$X_a$—Cl under Claisen condensation conditions. Some ketones of Formula $CH_3$—C(O)—$X_a$—Cl are commercially available; others can be prepared by known synthetic methods. The reaction in step (1) is conveniently carried out as described in step (1) of Reaction Scheme I.

In step (2) of Reaction Scheme VIII, a chloro-substituted pyrazole carboxylate of Formula XLVIII is converted to an acetate-substituted pyrazole carboxylate of Formula XLIX. The reaction is conveniently carried out by treating a chloro-substituted pyrazole carboxylate of Formula XLVIII with potassium acetate and sodium iodide in a suitable solvent such as DMF. The reaction can be carried out at an elevated temperature such as 90° C., and the product can be isolated using conventional methods.

In step (3) of Reaction Scheme VIII, the ester group of a pyrazole carboxylate of Formula XLIX is converted to an amide according to the reaction conditions described in step (2) of Reaction Scheme I. Under the reaction conditions, the acetate group of the compound of Formula XLIX is converted to a hydroxyl group to provide a compound of Formula L, which can be isolated using conventional methods.

In step (4) of Reaction Scheme VIII, a pyrazole carboxamide of Formula L is dehydrated to a pyrazole carbonitrile according to the reaction conditions described in step (3) of Reaction Scheme I. Under these reaction conditions, the hydroxyl group of the compound of Formula L is converted to a chloro group to provide a compound of Formula LI, which can be isolated using conventional methods.

In steps (5) and (6) of Reaction Scheme VIII, a pyrazole carbonitrile of Formula LI is first brominated to provide a pyrazole carbonitrile of Formula LII, which then undergoes a transition-metal catalyzed cross coupling reaction to provide a pyrazole-substituted aniline of Formula LIII. Steps (5) and (6) of Reaction Scheme VIII are conveniently carried out as described in steps (4) and (5) of Reaction Scheme I.

In step (7) of Reaction Scheme VIII, the amine and nitrile functionalities of a pyrazole-substituted aniline of Formula LIII react under acidic conditions to form a pyrazolo[3,4-c]quinoline of Formula LIV, which is a subgenus of Formulas I, II, III, and Ia. The intramolecular addition is conveniently carried out by heating at reflux a pyrazole-substituted aniline of Formula LIII in the presence of hydrogen chloride in a suitable solvent such as ethanol. The reaction may also be carried out as described in step (6) of Reaction Scheme I. The product or pharmaceutically acceptable salt thereof can be isolated by conventional methods.

In step (8) or (8a) of Reaction Scheme VIII, a chloro-substituted pyrazolo[3,4-c]quinoline of Formula LIV reacts with a nucleophile to provide a pyrazolo[3,4-c]quinoline of Formula LV or LVa, subgenera of Formulas I, II, III, and Ia. For example, a compound of Formula LIV can react with methanesulfonamide to provide a compound of Formula LV, wherein —Y—$R_4$ is —NH—S(O)$_2$—CH$_3$. The reaction is conveniently carried out by combining sodium hydride and methanesulfonamide in a suitable solvent such as DMF and then adding a compound of Formula LIV and sodium iodide. The reaction can be carried out at an elevated temperature such as 80-90° C. The product or pharmaceutically acceptable salt thereof can be isolated by conventional methods.

Also, in step (8) of Reaction Scheme VIII, the chloro group on a pyrazolo[3,4-c]quinoline of Formula LIV can be displaced by a thiol under basic conditions to provide a compound of Formula LV where —Y— is —S—. The reaction is conveniently carried out by adding a thiol to a solution of a pyrazolo[3,4-c]quinoline of Formula LIV in the presence of a base such as potassium tert-butoxide in a suitable solvent such as DMF. The product or pharmaceutically acceptable salt thereof can be isolated by conventional methods. A compound of Formula LV where —Y— is —S— can then be oxidized to a compound of Formula LV where —Y— is —S(O)$_2$— using conventional oxidizing agents. The reaction is conveniently carried out by adding peracetic acid to the compound of Formula LV where —Y— is —S— in a suitable solvent. The conversion of a compound of Formula LIV to a compound of Formula LV where —Y— is —S(O)$_2$— can conveniently be carried out in one pot without isolating the thioether from the reaction mixture. The product or pharmaceutically acceptable salt thereof can be isolated by conventional methods.

Alternatively, the chloro group of a pyrazolo[3,4-c]quinoline of Formula LIV can displaced with potassium thioacetate. The reaction is conveniently carried out at ambient temperature by adding potassium thioacetate to a solution of a pyrazolo[3,4-c]quinoline of Formula LIV in a suitable solvent such as DMF. The thioacetate group can then be cleaved under basic conditions at ambient temperature by adding a solution of sodium methoxide in methanol to provide a compound of Formula LV wherein —Y—$R_4$ is —SH. A thiol-substituted pyrazolo[3,4-c]quinoline of Formula LV can then be oxidized by treatment with chlorine, prepared in situ from benzyltributylammonium chloride and trichloroisocyanuric acid, in a suitable solvent such as dichloromethane at 0° C. to provide a sulfonyl chloride, which is then treated with an amine hydrochloride of Formula ($R_4$)($R_8$)NH.HCl followed by aqueous potassium carbonate in a suitable solvent such as dichloromethane to provide a compound of Formula LV wherein —Y— is —S(O)$_2$—N($R_8$)—. The reaction with the amine hydrochloride can be carried out at ambient temperature, and the product can be isolated using conventional methods.

The chloro group on a pyrazolo[3,4-c]quinoline of Formula LIV can also be displaced by an amine of Formula

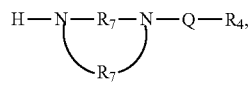

several of which are commercially available. Other amines of this formula can be prepared by conventional methods. The reaction is conveniently carried out by combining a pyrazolo[3,4-c]quinoline of Formula LIV and the amine in the presence of a base such as potassium carbonate and in a suitable solvent such as DMF. Catalytic sodium iodide can optionally be added. The reaction can be carried out at an elevated temperature such as 50° C. or 90-100° C., and the product can be isolated by conventional methods. These reaction conditions can also be used employing a variety of tertiary amines to provide compounds of Formula LV wherein Y is —N($R_8$)—, a variety of phenols to provide compounds of Formula LV wherein Y is —O— and $R_4$ is an unsubstituted or substituted phenyl group, or employing a variety of commercially available cyclic amines in step (8a) to provide compounds of Formula LVa.

In step (9) of Reaction Scheme VIII, the chloro group of a pyrazolo[3,4-c]quinoline of Formula LIV is displaced by potassium phthalimide to provide a pyrazolo[3,4-c]quinoline of Formula LVI. The reaction is conveniently carried out by combining potassium phthalimide, sodium iodide, and a pyrazolo[3,4-c]quinoline of Formula LIV in a suitable solvent such as DMF and heating at an elevated temperature such as 90-100° C. The product or pharmaceutically acceptable salt thereof can be isolated by conventional methods.

In step (10) of Reaction Scheme VIII, the phthalimide protecting group of the pyrazolo[3,4-c]quinoline of Formula LVI is removed to reveal an amine of Formula LVII, a subgenus of Formula I, II, III, and Ia. The deprotection is conveniently carried out by treating the compound of Formula LVI with hydrazine in a suitable solvent such as ethanol. The reaction can be run at an elevated temperature, such as the reflux temperature of the solvent, and the product or pharmaceutically acceptable salt thereof can be isolated using conventional methods.

In step (11) of Reaction Scheme VIII, an aminoalkylpyrazolo[3,4-c]quinoline of Formula LVII or pharmaceutically acceptable salt thereof is converted to an amide, sulfonamide, sulfamide, or urea of Formula LVIII, which is a subgenus of Formulas I, II, III, and Ia. Step (11) of Reaction Scheme VIII can be carried out using the procedures described for step (11) of Reaction Scheme VII. The product or pharmaceutically acceptable salt thereof can be isolated using conventional methods.

Reaction Scheme VIII
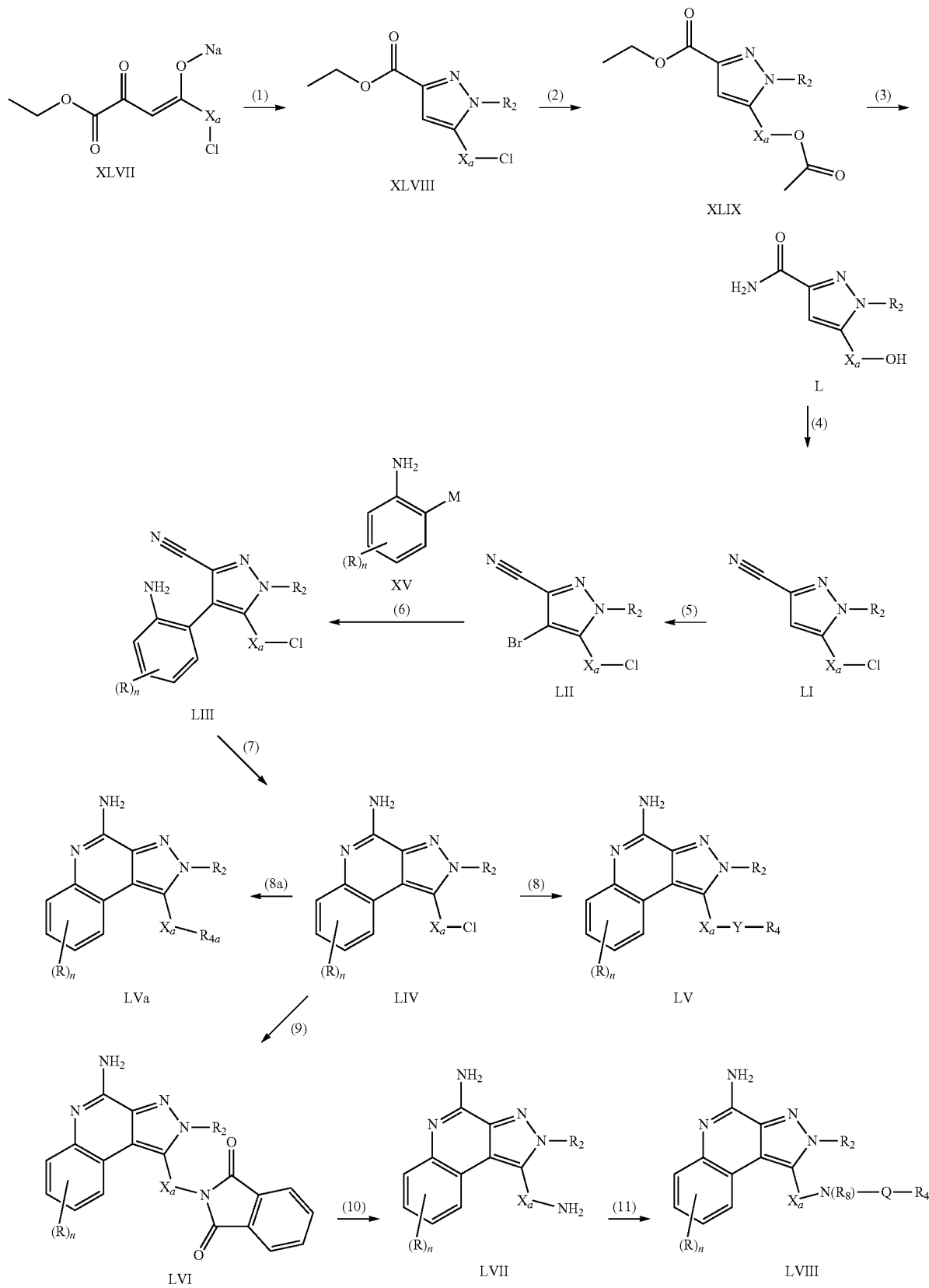

Compounds of the invention are also prepared by Reaction Scheme IX, wherein $R_{2c}$ is —$R_4$, —$X_c$—$R_4$, and —$X_c$—Y—$R_4$; $X_c$ is alkylene optionally terminated with arylene; and R, $R_1$, Y, $R_4$, and n are as defined above. In step (1) of Reaction Scheme IX, the benzyl group of a pyrazolo[3,4-c]quinoline of Formula LIX is cleaved to provide a pyrazolo[3,4-c]quinoline of Formula LX, which is a subgenus of Formulas I, II, III, and Ia. Benzyl pyrazolo[3,4-c]quinolines of Formula LIX are available from the reactions shown in Reaction Schemes I, III, VII, and VIII using benzylhydrazine dihydrochloride in steps (1), (1), (2), and (1), respectively. Step (1) is conveniently carried out by heating the benzyl pyrazolo[3,4-c]quinoline of Formula LIX in the presence of hydrogen bromide and a suitable solvent such as acetic acid at an elevated temperature such as 150° C. Alternatively, the reaction can be carried out under hydrogenolysis conditions by exposing the benzyl pyrazolo[3,4-c]quinoline of Formula LIX to hydrogen pressure in the presence of a catalyst such as palladium on carbon in a suitable solvent such as methanol. The reaction is conveniently carried out in a Parr vessel at ambient temperature or at an elevated temperature such as 50° C. The product of Formula LX or pharmaceutically acceptable salt thereof can be isolated using conventional methods.

In addition to 2-benzyl pyrazolo[3,4-c]quinolines of Formula LIX, 2-tert-butyl pyrazolo[3,4-c]quinolines are also convenient starting materials for Reaction Scheme IX. The cleavage of a tert-butyl group is conveniently carried out with aqueous hydrochloric acid at an elevated temperature, such as 100° C., and the product of Formula LX can be isolated by conventional methods.

In step (2) of Reaction Scheme IX, a pyrazolo[3,4-c]quinoline of Formula LX is alkylated to provide a pyrazolo[3,4-c]quinoline of Formula LXI, a subgenus of Formulas I, II, III, and Ia. The reaction is conveniently carried out by adding an alkyl halide of Formula Halide-$R_4$, Halide-$X_c$—$R_4$, or Halide-$X_c$—Y—$R_4$ to a pyrazolo[3,4-c]quinoline of Formula LX in the presence of a base such as potassium carbonate in a suitable solvent such as DMF. The reaction can be run at ambient temperature. Several alkyl halides of the Formulas Halide-$R_4$, Halide-$X_c$—$R_4$, and Halide-$X_c$—Y—$R_4$ are commercially available, including many substituted alkyl iodides and bromides and substituted benzyl iodides and bromides. Other alkyl halides can be prepared by known synthetic methods. The product or pharmaceutically acceptable salt thereof can be isolated using conventional methods.

Various functional groups can be introduced in step (2) of Reaction Scheme IX, and further synthetic elaboration is possible. For example, an alkyl halide of Formula Cl-alkylene-I can be used in step (2) to provide a compound of Formula LXI, wherein $R_2$ is a chloroalkylenyl group. The chloro group can then be displaced using one of a variety of methods described in steps (8) or (8a) of Reaction Scheme VIII. In another example, 4-bromobutylphthalimide can be used as the alkyl halide in step (2), and the resulting compound of Formula LXI bearing a phthalimide-protected amino group can be treated with hydrazine monohydrate to remove the phthalimide group. The deprotection is conveniently carried out in a suitable solvent such as ethanol at an elevated temperature, such as the reflux temperature. The resulting aminoalkyl-substituted pyrazolo[3,4-c]quinoline of Formula LXI can then be treated according to step (11) of Reaction Scheme VII to provide a compound of Formula LXI wherein $R_{2c}$ is -alkylene-N($R_8$)-Q-$R_4$, and $R_4$, $R_8$, and Q are as defined above.

For some preferred embodiments, a compound of Formula LXI wherein $R_{2c}$ is an ethoxy- or methoxyalkylenyl group is treated with boron tribromide to provide a compound of Formula LXI wherein $R_{2c}$ is a hydroxyalkylenyl group. The reaction is conveniently carried out by adding a solution of boron tribromide to a compound of Formula LXI, wherein $R_{2b}$ is an alkoxyalkylenyl group, in a suitable solvent such as dichloromethane. The reaction can be run at a sub-ambient temperature such as 0° C., and the product or pharmaceutically acceptable salt thereof can be isolated using conventional methods.

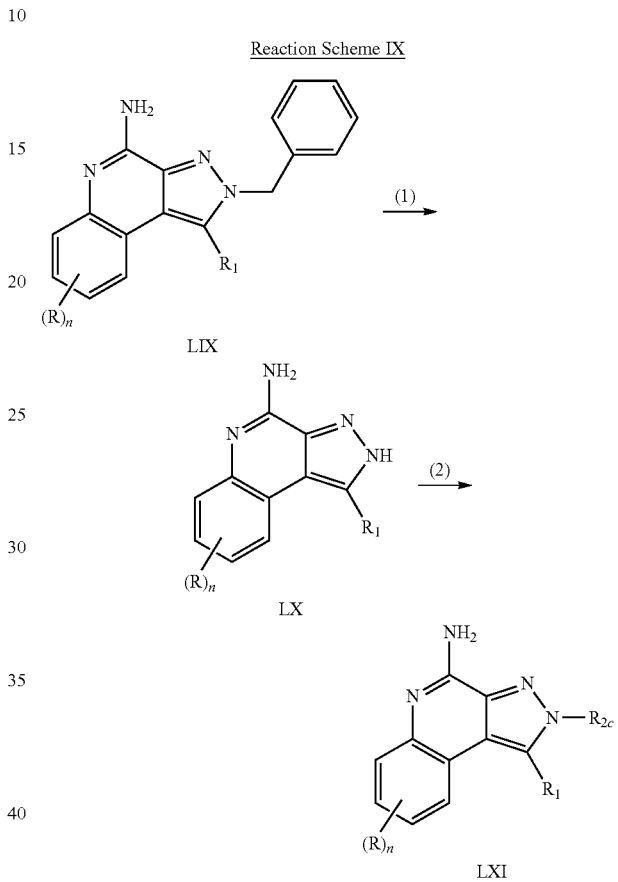

Reaction Scheme IX

For some embodiments, tetrahydroquinolines of the invention can be prepared according to Reaction Scheme X, wherein $R_b$, $R_{2b}$, $R_4$, $R_8$, Q, and n are as defined above and $X_b$ is alkylene optionally interrupted or terminated by heterocyclylene and optionally interrupted by one or more —O— groups. Amino-substituted pyrazolo[3,4-c]quinolines of Formula LXII or pharmaceutically acceptable salts thereof can be prepared using any of the methods shown in Reaction Schemes I, VII, and VIII.

In step (1) of Reaction Scheme X, an amino-substituted pyrazolo[3,4-c]quinoline of Formula LXII is reduced to a tetrahydropyrazolo[3,4-c]quinoline of Formula LXIII according to the method described in Reaction Scheme V. The product or pharmaceutically acceptable salt thereof can be isolated using conventional methods.

In step (2) of Reaction Scheme X, an amino-substituted tetrahydropyrazolo[3,4-c]quinoline of Formula LXIII is converted to an amide, sulfonamide, sulfamide, or urea of Formula LXIV, which is a subgenus of Formulas I, II, VIII, and Ia. Step (2) of Reaction Scheme X can be carried out using the procedures described for step (11) of Reaction Scheme VII. The product or pharmaceutically acceptable salt thereof can be isolated using conventional methods.

Reaction Scheme X

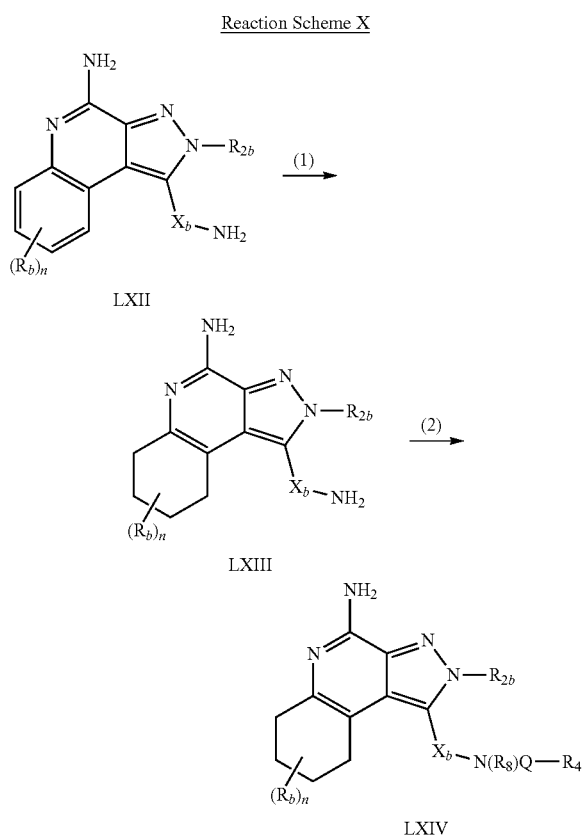

For some embodiments, compounds of the invention can be prepared according to Reaction Scheme XI, wherein n is as defined above; $R_c$ is R for pyrazolo[3,4-c]quinolines or $R_b$ for tetrahydropyrazolo[3,4-c]quinolines; $R_{2d}$ is $R_2$ for pyrazolo [3,4-c]quinolines or $R_{2b}$ for tetrahydropyrazolo[3,4-c]quinolines; $R_{4s}$ is $R_4$ as defined above, with the proviso that the substituent on the alkyl, alkenyl, alkynyl, arylalkylenyl, aryloxyalkylenyl, alkylarylenyl, heteroaryl, heteroarylalkylenyl, heteroaryloxyalkylenyl, alkylheteroarylenyl, or heterocyclyl group is not amino or alkylamino, or two $R_{4s}$ groups in the same molecule can join to form a saturated ring or partially saturated ring system optionally containing one or more heteroatoms; $X_d$ is alkylene optionally interrupted by one or more —O— groups, wherein there are at least two atoms in the linking chain; Boc is tert-butoxycarbonyl; and the bonds represented by dashed lines may be present or absent.

In step (1) of Reaction Scheme XI, the amino group of a pyrazolo[3,4-c]quinoline or tetrahydropyrazolo[3,4-c]quinoline of Formula LIVa is protected with two Boc groups to provide a compound of Formula LXV. Pyrazolo[3,4-c]quinolines of Formula LIVa can be prepared according to steps (1) through (7) of Reaction Scheme VIII. Tetrahydropyrazolo[3,4-c]quinolines of Formula LIVa can be prepared by reducing a pyrazolo[3,4-c]quinoline of Formula LIVa according to the method described in Reaction Scheme V. The protection reaction is conveniently carried out by combining a pyrazolo[3,4-c]quinoline or tetrahydropyrazolo[3,4-c]quinoline of Formula LIVa with di-tert-butyl dicarbonate in the presence of base, such as a combination of triethylamine and catalytic 4-dimethylaminopyridine (DMAP). The reaction can be carried out at ambient temperature in a suitable solvent such as toluene. The product can be isolated by conventional methods.

In step (2) of Reaction Scheme XI, a chloro-substituted compound of Formula LXV is converted to an acetate-substituted pyrazolo[3,4-c]quinoline or tetrahydropyrazolo[3,4-c]quinoline of Formula LXVI according to the method described in step (2) of Reaction Scheme VIII.

In step (3) of Reaction Scheme XI, the acetate protecting group of a compound of Formula LXVI is removed to provide a hydroxy-substituted pyrazolo[3,4-c]quinoline or tetrahydropyrazolo[3,4-c]quinoline of Formula LXVII. The reaction is conveniently carried out by combining a compound of Formula LXVI and potassium carbonate in a suitable solvent such as methanol at ambient temperature. The product or pharmaceutically acceptable salt thereof can be isolated by conventional methods.

In step (4) of Reaction Scheme XI, the alcohol of Formula LXVII is oxidized to an aldehyde-substituted pyrazolo[3,4-c]quinoline or tetrahydropyrazolo[3,4-c]quinoline of Formula LXVIII using conventional methods, for example, Swern oxidation conditions. The Swern oxidation is conveniently carried out by adding a compound of Formula LXVII followed by triethylamine to a mixture of oxalyl chloride and dimethylsulfoxide in a suitable solvent, such as dichloromethane. The reaction can be carried out at sub-ambient temperatures, such as −78° C., and the product can be isolated using conventional methods.

In step (5) of Reaction Scheme XI, an aldehyde-substituted compound of Formula LXVIII is converted to an alkenyl- or alkynyl-substituted compound of Formula LXIX. The conversion to an alkynyl-substituted compound is conveniently carried out by adding diethyl 1-diazo-2-oxopropylphosphonate to the aldehyde-substituted compound of Formula LXVIII in the presence of a mild base such as potassium carbonate. The reaction is carried out in a suitable solvent such as dichloromethane or methanol at ambient temperature. The aldehyde-substituted compound of Formula LXVIII can be converted to an alkenyl-substituted compound of Formula LXIX using synthetic methods well known to those skilled in the art; such methods include the Wittig reaction. The product can be isolated using conventional methods.

In step (6) of Reaction Scheme XI, the alkene or alkyne dipolarophile of Formula LXIX undergoes a cycloaddition reaction with a nitrone of Formula LXX or a nitrile oxide formed from an α-chloroaldoxime of Formula LXXI to provide a isoxazole, isoxazoline, or isoxazolidine-substituted pyrazolo[3,4-c]quinoline or tetrahydropyrazolo[3,4-c]quinoline of Formula LXXII. Nitrones of Formula LXX are known and can be prepared by known methods. See, for example, Dicken, C. M. and DeShong, P., *J. Org. Chem.*, 47, pp. 2047-2051 (1982). Nitrones of Formula LXX wherein two vicinal $R_4$, groups join to form a saturated carbon ring can be prepared according to the literature procedures: Thesing, J.; Sirrenberg, W., *Chem. Ber.*, 92, p. 1748, (1959) and Iwashita, T. et al., *J. Org. Chem.*, 47, p. 230, (1982). The cycloaddition reaction shown in step (6) can be carried out by combining the nitrone of Formula LXX with a compound of Formula LXIX in a suitable solvent such as toluene and heating at an elevated temperature, for example, the reflux temperature of the solvent. Nitrones of Formula LXX can also be prepared in situ by combining a hydroxylamine of Formula $R_{4s}$—NH—OH or a hydrochloride salt thereof and an aldehyde or ketone of Formula $(R_{4s})_2C=O$ with a compound of Formula LXIX in the presence of a base such as sodium bicarbonate and alumina. The reaction can be carried out at an elevated temperature in a suitable solvent such as toluene. The product can be isolated using conventional methods.

α-Chloroaldoximes of Formula LXXI can be prepared by treating an aldoxime of Formula $R_{4s}(H)C=N$—OH with N-chlorosuccinimide at ambient temperature or at a subambient temperature such as 0° C. in a suitable solvent such as DMF or THF. The resulting α-chloroaldoxime of Formula LXXI is combined with a compound of Formula LXIX in the presence of a base such as triethylamine to generate a nitrile oxide in situ and effect the cycloaddition reaction. The reaction can be carried out at ambient temperature in a suitable solvent such as dichloromethane or THF. The product can be isolated using conventional methods. When an alkynyl-substituted compound of Formula LXIX is combined with an α-chloroaldoxime of Formula LXXI under these conditions, the product is an isoxazole of Formula LXXII.

In step (7) of Reaction Scheme XI, the Boc protecting groups are removed from a pyrazolo[3,4-c]quinoline or tetrahydropyrazolo[3,4-c]quinoline of Formula LXXII according to the method described in step (10) of Reaction Scheme VII. The reaction may be run at ambient temperature or at an elevated temperature such as 60° C., and the product of Formula LXXIII or a pharmaceutically acceptable salt thereof can be isolated by conventional methods.

The Boc groups can be removed from other compounds shown in Reaction Scheme XI to provide pyrazolo[3,4-c]quinolines or tetrahydropyrazolo[3,4-c]quinolines of the invention. For example, the conditions described in step (7) can be used to treat compounds of Formula LXVII, LXVIII, or LXIX to reveal pyrazolo[3,4-c]quinolin-4-amines or tetrahydropyrazolo[3,4-c]quinolin-4-amines with a hydroxy, aldehyde, alkene, or alkyne group at $R_1$.

Some compounds shown in Reaction Scheme XI are useful starting materials for the preparation of other compounds of the invention. For example, a hydroxyalkyl-substituted pyrazolo[3,4-c]quinoline or tetrahydropyrazolo[3,4-c]quinoline of Formula LXVII can be treated with N-hydroxyphthalimide under Mitsunobu reaction conditions to provide an N-phthalimide-protected hydroxylamine. The reaction is conveniently carried out by adding triphenylphosphine and N-hydroxyphthalimide to a solution of the alcohol of Formula LXVII in a suitable solvent such as tetrahydrofuran or DMF and then slowly adding diisopropyl azodicarboxylate. The reaction can be carried out at ambient temperature or at an elevated temperature, such as 60° C. The phthalimide group can then be removed from the resulting N-phthalimide-protected hydroxylamine by treatment with hydrazine at ambient temperature in a suitable solvent such as ethanol. The resulting hydroxylamine can then be treated with one of numerous commercially available aldehydes or ketones in a suitable solvent such as methanol to provide an oxime. The Boc protecting groups of the resulting compound can then be removed as described in step (7) of Reaction Scheme XI to provide a compound of the invention, wherein $R_1$ is —X—Y—$R_4$ or —X—$R_5$, where X is $X_d$, which is defined above, Y is —O—N=C($R_4$)—, $R_5$ is

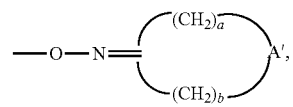

and $R_4$ a, b, and A' are as defined above. Alternatively, the hydroxylamine prepared after the hydrazine deprotection may be treated with one of numerous acid chlorides, sulfonyl chlorides, isocyanates, carbamoyl chlorides, or sulfamoyl chlorides as described in step (11) of Reaction Scheme VII to provide, after removal of the Boc protecting groups, a compound of the invention wherein $R_1$ is —X—Y—$R_4$ where X is $X_d$, Y is —O—NH-Q-, and Q and $R_4$ are as defined above.

In another example, an aldehyde-substituted pyrazolo[3,4-c]quinoline or tetrahydropyrazolo[3,4-c]quinoline of Formula LXVIII can optionally be treated with a Grignard reagent of Formula $R_4$—Mg—X under conventional Grignard conditions to provide a secondary alcohol. It may be necessary to remove the Boc groups prior to this reaction and install different amine protecting groups known to one skilled in the art to be less reactive toward Grignard reagents. The secondary alcohol can then be oxidized under Swern conditions as described in step (4) of Reaction Scheme XI, and the protecting groups may subsequently be removed to provide a ketone, which is a compound of the invention wherein $R_1$ is —X—Y—$R_4$ where X is $X_d$, Y is —C(O)—, and $R_4$ is as defined above. The ketone can then be converted to an oxime by adding an aqueous solution of a hydroxylamine salt of Formula $NH_2OR_8$.HCl to a solution of the ketone in a suitable solvent such as methanol or ethanol and then adding a base such as sodium hydroxide and heating at an elevated temperature to provide a compound of the invention, wherein $R_1$ is —X—Y—$R_4$ where X is $X_d$, Y is —C(=N—$OR_8$)—, and $R_4$ and $R_8$ are as defined above. The oxime so prepared may be reduced with sodium cyanoborohydride in a mixture of ethanol or methanol in acetic acid to provide a hydroxylamine, which may be treated with one of numerous acid chlorides, sulfonyl chlorides, isocyanates, carbamoyl chlorides, or sulfamoyl chlorides as described in step (11) of Reaction Scheme VII to provide a compound of the invention wherein $R_1$ is —X—Y—$R_4$ where X is $X_d$, Y is —CH(—N—($OR_8$)-Q-$R_4$)—, and Q, $R_4$, and $R_8$ are as defined above.

Reaction Scheme XI

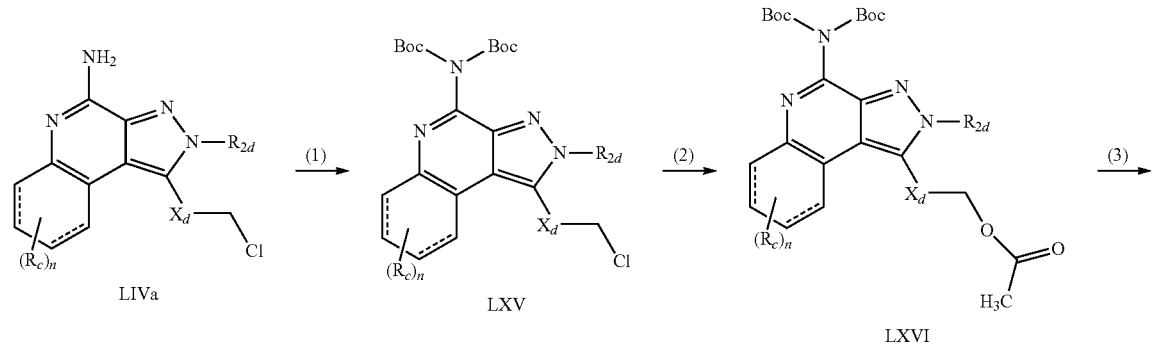

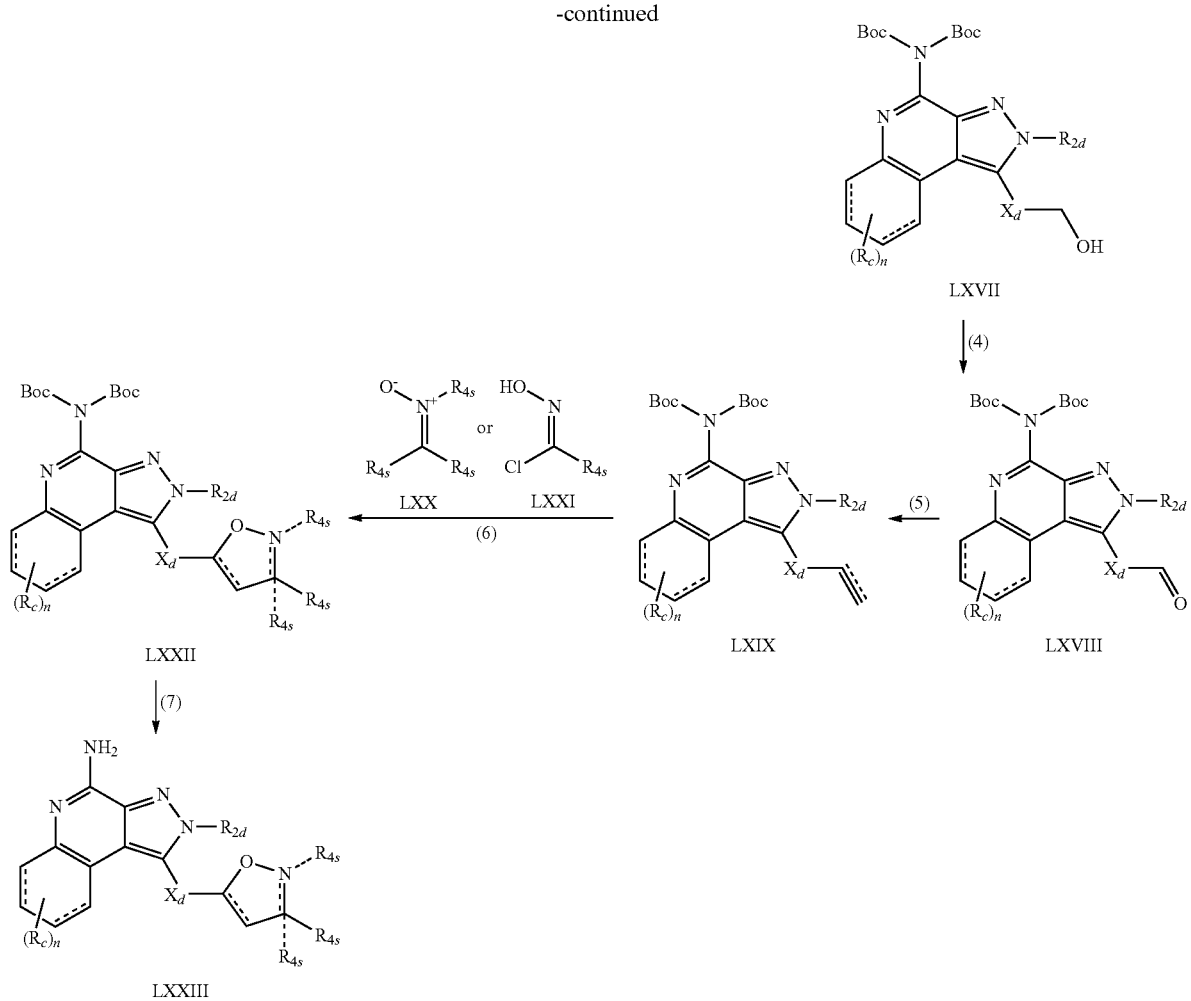

Compounds of the invention can also be prepared according to Reaction Scheme XII, wherein $R_c$, $R_{2d}$, Boc, $R_{4s}$, $X_a$, and n are as defined above, and the bonds represented by dashed lines may be present or absent. In steps (1) and (2) of Reaction Scheme XII, a 1-chloroalkyl-substituted pyrazolo[3,4-c]quinoline or tetrahydropyrazolo[3,4-c]quinoline of Formula LXVa, prepared according to the method described in step (1) of Reaction Scheme XI, is converted to a 1-aminoalkyl-substituted compound of Formula LXXV. Step (1) is conveniently carried out by adding sodium azide and sodium iodide to a 1-chloroalkyl-substituted compound of Formula LXVa in a suitable solvent such as DMF. The reaction can be carried out at an elevated temperature such as 90° C., and the azide of Formula LXXIV can be isolated by conventional methods prior to reduction in step (2). Step (2) is conveniently carried out by adding triphenylphosphine to an azide-substituted pyrazolo[3,4-c]quinoline or tetrahydropyrazolo[3,4-c]quinoline of Formula LXXIV in a suitable solvent or solvent mixture such as tetrahydrofuran/water. The reaction can be carried out at ambient temperature, and the product can be isolated using conventional methods. Aminoalkyl-substituted pyrazolo[3,4-c]quinolines or tetrahydropyrazolo[3,4-c] quinolines of Formula LXXV may also be prepared using methods shown in Reaction Scheme VIII.

In step (3) of Reaction Scheme XII, an aminoalkyl-substituted pyrazolo[3,4-c]quinoline or tetrahydropyrazolo[3,4-c]quinoline of Formula LXXV is converted to an imine by reaction with a ketone or aldehyde of Formula $(R_{4s})_2C=O$ and subsequently treated with an α-chloroaldoxime of Formula LXXI. The reaction is conveniently carried out by combining an aminoalkyl-substituted compound of Formula LXXV with a ketone or aldehyde of Formula $(R_{4s})_2C=O$ at ambient temperature in a suitable solvent such as dichloromethane. The reaction can optionally be carried out in the presence of magnesium sulfate. The resulting imine is then combined with an α-chloroaldoxime of Formula LXXI according to the procedure described in step (6) of Reaction Scheme XI. The product of Formula LXXVI can be isolated using conventional methods.

In step (4) of Reaction Scheme XII, the Boc protecting groups are removed from a pyrazolo[3,4-c]quinoline or tetrahydropyrazolo[3,4-c]quinoline of Formula LXXVI according to the method described in step (7) of Reaction Scheme XI. The product of Formula LXXVII or a pharmaceutically acceptable salt thereof can be isolated by conventional methods.

Reaction Scheme XII

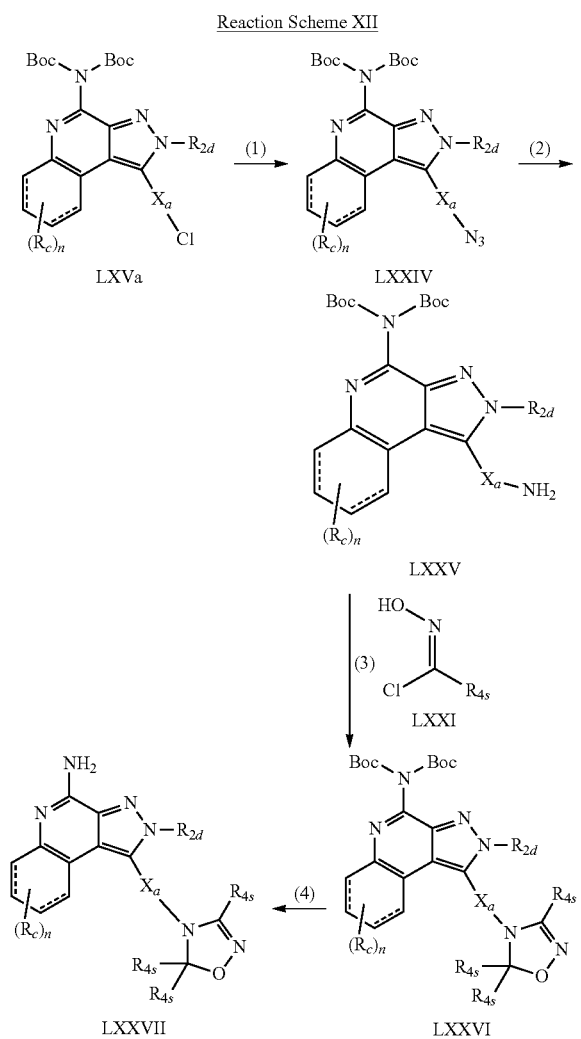

For some embodiments, compounds of the invention are prepared according to Reaction Scheme XIII, wherein $R_1$, $R_2$, and n are defined as above; $R_d$ is selected from the group consisting of halogen, alkyl, alkenyl, trifluoromethyl, and dialkylamino; and $R_{3a}$ and $R_{3b}$ are defined below. In step (1) of Reaction Scheme XIII, a bromo-substituted pyrazole carbonitrile of Formula XIV undergoes a transition-metal catalyzed cross coupling reaction with a reagent of Formula XLIIa. Some compounds of Formula XLIIa are known; see, Adams, L., *J. Heterocyclic Chem.*, 32, p. 1171 (1995). Others can be prepared by known synthetic methods; see, Rocca, P. et al, *Tetrahedron*, 49, pp. 49-64 (1993). The Suzuki coupling reaction can be carried out as described in step (5) of Reaction Scheme I to provide a compound of Formula LXXVIII, and the product can be isolated by conventional methods.

In step (2) of Reaction Scheme XIII, a pivaloylamino-substituted compound of Formula LXXVIII undergoes a base-promoted intramolecular cyclization and subsequent cleavage of the pivaloyl group to provide a pyrazolo[3,4-c]quinoline of Formula XVIIa. The reaction can be carried out as described in Reaction Scheme I, and the product or pharmaceutically acceptable salt thereof can be isolated by conventional methods.

In step (3) of Reaction Scheme XIII, the methoxy group of a pyrazolo[3,4-c]quinoline of Formula XVIIa is demethy-lated to provide a hydroxy-substituted pyrazolo[3,4-c]quinoline of Formula XVIIb. The demethylation is conveniently carried out by treating the compound of Formula XVIIa with a solution of boron tribromide in a suitable solvent such as dichloromethane. The reaction can be carried out at a sub-ambient temperature such as 0° C., and the product or pharmaceutically acceptable salt thereof can be isolated using conventional methods. Alternatively, the demethylation is carried out by heating the compound of Formula XVIIa with anhydrous pyridinium chloride at an elevated temperature, such as 210° C. The product or pharmaceutically acceptable salt thereof can be isolated by conventional methods.

In step (4) of Reaction Scheme XIII, the hydroxy group of a pyrazolo[3,4-c]quinoline of Formula XVIIb is activated by conversion to a trifluoromethanesulfonate (triflate) group. The reaction is conveniently carried out by treating a hydroxy-substituted pyrazolo[3,4-c]quinoline of Formula XVIIb with N-phenyl-bis(trifluoromethanesulfonimide) in the presence of a tertiary amine such as triethylamine. The reaction can be carried out at ambient temperature in a suitable solvent such as DMF, and the triflate of Formula LXXX can be isolated using conventional methods. The activation in step (4) may also be accomplished by converting the hydroxy group to another good leaving group.

Step (5) of Reaction Scheme XIII can be carried out using known palladium-catalyzed coupling reactions such as the Suzuki coupling, Heck reaction, the Stille coupling, and the Sonogashira coupling. For example, a triflate-substituted pyrazolo[3,4-c]quinoline of Formula LXXX undergoes Suzuki coupling with a boronic acid of Formula $R_{3a}$—B(OH)$_2$, an anhydride thereof, or a boronic acid ester of Formula $R_{3a}$—B(O-alkyl)$_2$; wherein $R_{3a}$ is —$R_{4b}$, —$X_f$—Y—$R_4$, or —$X_f$—$R_5$; where $X_e$ is alkenylene; $X_f$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y are as defined above. The coupling is carried out by combining a compound of Formula LXXX with a boronic acid or an ester or anhydride thereof in the presence of palladium (II) acetate, triphenylphosphine, and a base such as aqueous sodium carbonate in a suitable solvent such as n-propanol. The reaction can be carried out at an elevated temperature, for example, at the reflux temperature. Numerous boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods. The product of Formula XVIIc or a pharmaceutically acceptable salt thereof can be isolated by conventional methods.

A compound of Formula XVIIc wherein $R_{3a}$ is a heterocycle attached through a nitrogen atom can be prepared in step (5) by reacting a compound of Formula LXXX with a nitrogen-containing heterocycle in the presence of copper (I) iodide, potassium phosphate, and racemic trans-1,2-diaminocyclohexane in a suitable solvent such as 1,4-dioxane. The reaction can be carried out at an elevated temperature such as 110° C. In addition, this coupling can be carried out using a palladium-mediated coupling by combining a compound of Formula LXXX and the nitrogen-containing heterocyclyl compound in the presence of tris(dibenzylideneacetone)dipalladium, (±)-2,2'-bis(diphenylphosphino)-1,1'-binaphthyl, sodium tert-butoxide, and a suitable solvent such as toluene. The reaction can be carried out at an elevated temperature such as 80° C. The compound or pharmaceutically acceptable salt thereof can be isolated using conventional methods.

Alternatively, the Heck reaction can be used in step (5) of Reaction Scheme XIII to provide compounds of Formula XVIIc, wherein $R_{3a}$ is —$X_e$—$R_{4b}$ or —$X_e$—Y—$R_4$, wherein $X_e$, Y, $R_4$, and $R_{4b}$ are as defined above. The Heck reaction is carried out by coupling a compound of Formula LXXX with a compound of the Formula $H_2C$=C(H)—$R_{4b}$ or $H_2C$=C(H)—Y—$R_4$. Several of these vinyl-substituted compounds are commercially available; others can be prepared by known methods. The reaction is conveniently carried out by combining the compound of Formula LXXX and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere. The product of Formula XVIIc or pharmaceutically acceptable salt thereof can be isolated using conventional methods.

Compounds of Formula XVIIc, wherein $R_{3a}$ is —$X_g$—$R_4$, $X_g$ is alkynylene, and $R_4$ is as defined above, can also be prepared by palladium catalyzed coupling reactions such as the Stille coupling or Sonogashira coupling. These reactions are carried out by coupling a compound of Formula LXXX with a compound of the Formula $(alkyl)_3Sn$—C≡C—$R_4$, $(alkyl)_3Si$—C≡C—$R_4$, or Compounds of Formula XVIIc prepared as described above by palladium-mediated coupling reactions, wherein $R_{3a}$ is —$X_e$—$R_4$, —$X_e$—Y—$R_4$, —$X_{f2}$-Y—$R_4$, —$X_{f2}$-$R_5$, or —$X_g$—$R_4$, where $X_{f2}$ is alkenylene interrupted or terminated by arylene or heteroarylene, and $X_e$, $X_g$, Y, $R_4$, and $R_5$ are as defined above, can undergo reduction of the alkenylene or alkynylene group present to provide compounds of Formula XVIIc wherein $R_{3a}$ is —$X_h$—$R_4$, —$X_h$—Y—$R_4$, —$X_i$—Y—$R_4$, or —$X_i$—$R_5$, where $X_h$ is alkylene; $X_i$ is alkylene interrupted or terminated by arylene or heteroarylene; and $R_4$, $R_5$, and Y are as defined above. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product or pharmaceutically acceptable salt thereof can be isolated using conventional methods.

In step (4a) of Reaction Scheme XIII, a hydroxy-substituted pyrazolo[3,4-c]quinoline of Formula XVIIb is converted to a compound of Formula XVIId, wherein $R_{ab}$ is —O—$R_4$, —O—X—$R_4$, —O—X—Y—$R_4$, or —O—X—$R_5$, and X, Y, $R_4$, and $R_5$ are as defined above, using a Williamson-type ether synthesis. The reaction is effected by treating a hydroxy-substituted pyrazolo[3,4-c]quinoline of Formula XVIIb with an aryl, alkyl, or arylalkylenyl halide of Formula Halide-$R_4$, Halide-alkylene-$R_4$, Halide-alkylene-Y—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, bromo-substituted ketones, esters, and heterocycles, and substituted fluorobenzenes. Other halides of these formulas can be prepared using conventional synthetic methods. The reaction is conveniently carried out by combining an alkyl, arylalkylenyl, or aryl halide with the hydroxy-substituted compound of Formula XVIIb in a solvent such as DMF or N,N-dimethylacetamide in the presence of a suitable base such as cesium carbonate. Optionally, catalytic tetrabutylammonium bromide can be added. The reaction can be carried out at ambient temperature or at an elevated temperature, for example 50° C. or 85° C., depending on the reactivity of the halide reagent.

Step (4a) of Reaction Scheme XIII can alternatively be carried out by treating a compound of Formula XVIIb with an alcohol of Formula HO—$R_{3b}$ under Mitsunobu reaction conditions. Numerous alcohols of formulas HO—X—Y—$R_4$, HO—X—$R_5$, HO—X-Het, and HO—X-HetAr are commercially available; for example, 1-(3-hydroxypropyl)pyrrolidin-2-one, 1-(2-hydroxyethyl)pyrrolidin-2-one, tert-butyl 4-hydroxypiperidine-1-carboxylate, and 3-pyridylcarbinol. Other alcohols of formula HO—$R_{3b}$ can be prepared using conventional synthetic methods. The reaction is conveniently carried out by out by adding triphenylphosphine and an alcohol of Formula HO—$R_{3b}$ to a solution of a compound of Formula XVIIb in a suitable solvent such as tetrahydrofuran and then slowly adding diisopropyl azodicarboxylate or diethyl azodicarboxylate. The reaction can be carried out at ambient temperature or at a sub-ambient temperature, such as 0° C. The product can be isolated using conventional methods.

Compounds prepared in step (4a) can undergo further synthetic elaboration. For example, in a compound of Formula XVIId wherein —$R_{3b}$ is —O—X—N($R_8$)-Boc, prepared as described above, the Boc protecting group can be removed to provide an amino-substituted compound wherein —$R_{3b}$ is —O—X—N($R_8$)H. A compound of Formula XVIId wherein —$R_{3b}$ is —O—X—N($R_8$)H can be converted to a compound of Formula XVIId wherein —$R_{3b}$ is —O—X—N($R_8$)-Q-$R_4$ using conventional methods such as the methods described in step (11) of Reaction Scheme VII. A compound of Formula XVIId wherein —$R_{3b}$ is

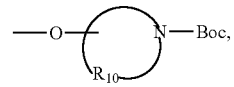

prepared by methods described above, can be converted to a compound of Formula XVIId wherein —$R_{3b}$ is

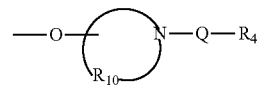

using these same methods.

Alternatively, step (4a) may be carried out using the Ullmann ether synthesis, in which an alkali metal aryloxide prepared from the hydroxy-substituted compound of Formula XVIIb reacts with an aryl halide in the presence of copper salts, to provide a compound of Formula XVIId, where $R_{3b}$ is —O—$R_{4b}$, —O—$X_j$—$R_4$, or —O—$X_j$—Y—$R_4$, wherein $X_j$ is an arylene or heteroarylene and $R_{4b}$ is as defined above. Numerous substituted and unsubstituted aryl halides are commercially available; others can be prepared using conventional methods. The product of Formula XVIId, prepared by either of these methods, or pharmaceutically acceptable salt thereof can be isolated using conventional methods.

Reaction Scheme XIII

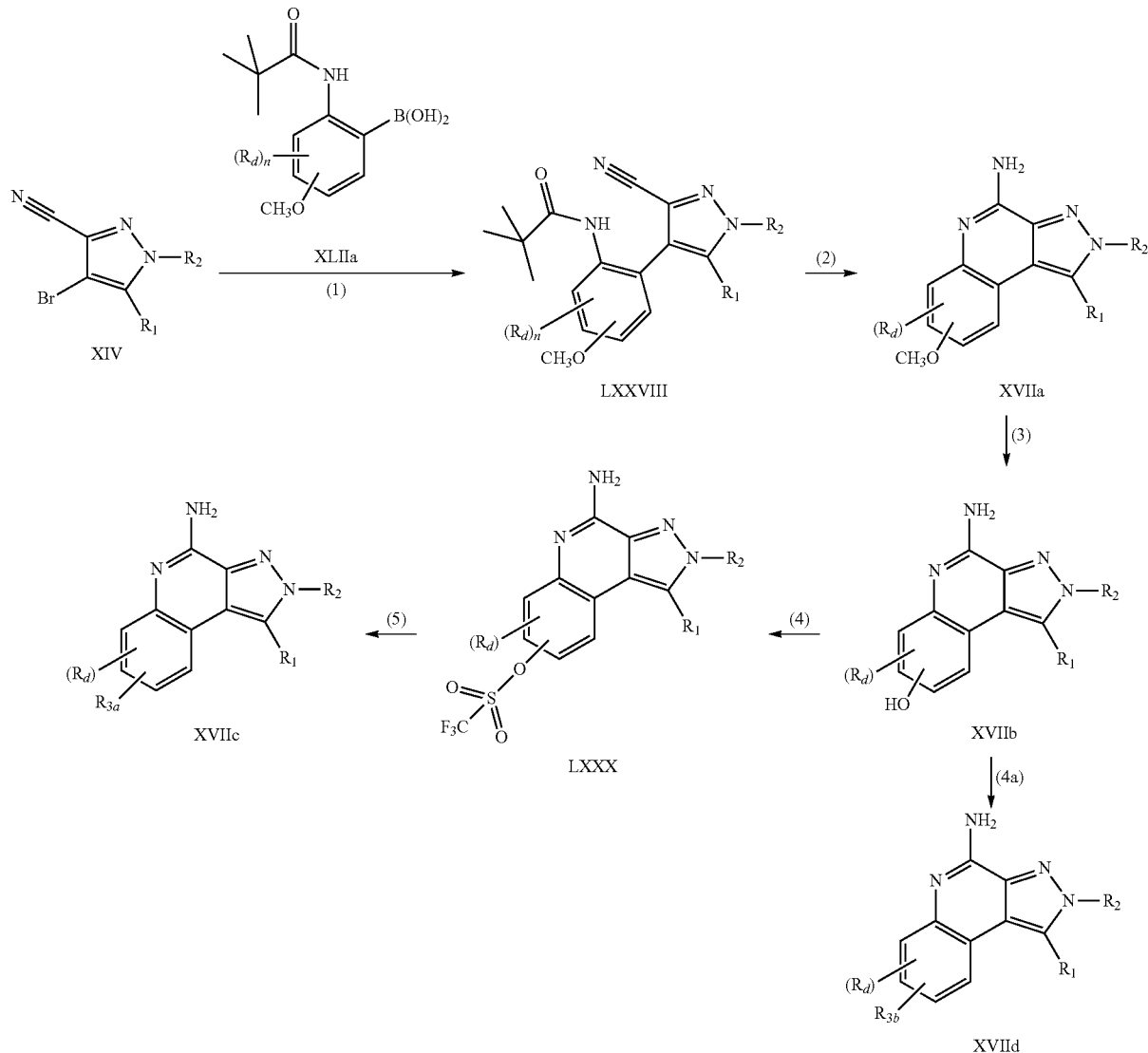

For some embodiments, compounds of the invention can be prepared according to Reaction Scheme XIV, where R, $R_1$, $R_2$, $R_3$, n and m are as defined above.

In step (1) of Reaction Scheme XIV, an indole of Formula LXXXI is acylated to provide an oxalated indole of Formula LXXXII. The reaction can be carried out by adding ethyl chlorooxoacetate to a solution of an indole of Formula LXXXI in a suitable solvent such as diethyl ether in the presence of pyridine. The reaction can be carried out at a sub-ambient temperature such as 0° C. Many indoles of Formula LXXXI are known. Some are commercially available and others can be readily prepared using known synthetic methods.

In step (2) of Reaction Scheme XIV, an oxalated indole of Formula LXXXII is rearranged to a pyrazolo[3,4-c]quinolin-4-one of Formula LXXXIII. The reaction can be carried out by adding a hydrazine of Formula $R_2NHNH_2$ to a solution of an oxalated indole of Formula LXXXII in a solvent or solvent mix such as ethanol/acetic acid in the presence of hydrochloric acid. The reaction can be carried out at an elevated temperature such as at reflux.

If step (2) is carried out using hydrazine, the resulting pyrazolo[3,4-c]quinolin-4-one of Formula LXXXIII where $R_2$ is hydrogen can be further elaborated using known synthetic methods. For example, a pyrazolo[3,4-c]quinolin-4-one of Formula LXXXIII where $R_2$ is hydrogen can be alkylated, for example, as described in step (1) of Reaction Scheme I. Alternatively, a pyrazolo[3,4-c]quinolin-4-one of Formula LXXXIII where $R_2$ is hydrogen can undergo a Buchwald amination with an aryl halide or heteroaryl halide. Numerous alkyl halides, aryl halides, and heteroaryl halides are commercially available; others can be prepared using known synthetic methods.

Step (2) can also be carried out using a hydrazine that will install a removable group at $R_2$. Examples of such hydrazines include benzylhydrazine and tert-butylhydrazine. At a later point in the synthetic pathway the group can be removed using conventional methods to provide a compound in which $R_2$ is hydrogen. The compound may then be further elaborated using the methods described above.

In step (3) of Reaction Scheme XIV, an aldehyde group is installed on a pyrazolo[3,4-c]quinolin-4-one of Formula LXXXIII to provide a pyrazolo[3,4-c]quinolin-4-one of Formula LXXXIV. The reaction can be carried out by deprotonating a pyrazolo[3,4-c]quinolin-4-one of Formula LXXXIII with 2 equivalents of n-butyl lithium followed by treatment with DMF and quenching with hydrochloric acid. The reaction can be carried out at an elevated temperature such as 50° C. in a suitable solvent such as tetrahydrofuran.

In step (4) of Reaction Scheme XIV, a pyrazolo[3,4-c]quinolin-4-one of Formula LXXXIV undergoes further elaboration using conventional synthetic methods to provide a pyrazolo[3,4-c]quinolin-4-one of Formula LXXXV. For example, the aldehyde can be reacted with several different classes of nucleophiles such as phosphonium ylides (Wittig olefination) or phosphonates (Horner Wadsworth olefination) to provide alkenes; amines using reductive amination to provide secondary or tertiary amines; and Grignard reagents or lithiated alkynes or alkenes to provide alcohols which may then be oxidized to provide ketones. When reaction with a nucleophile provides a substituted olefin, the olefin may be reduced using conventional methods such as hydrogenation using a conventional heterogeneous hydrogenation catalyst such as palladium on carbon. Alternatively, the aldehyde can be reduced to the alcohol using known methods, for example, by treating a solution of the aldehyde with sodium borohydride. The alcohol can then be converted to a halide or an oxygen based leaving group such as a triflate, mesylate, or tosylate using conventional methods. The halide or oxygen based leaving group can then be reacted with a variety of nucleophiles.

In step (5) of Reaction Scheme XIV, a pyrazolo[3,4-c]quinolin-4-one of Formula LXXXV is chlorinated to provide to provide a 4-chloropyrazolo[3,4-c]quinoline of Formula LXXXVI. The reaction can be carried out by combining a pyrazolo[3,4-c]quinolin-4-one of Formula LXXXV with phosphorous oxychloride and heating.

In step (6) of Reaction Scheme XIV, a 4-chloropyrazolo[3,4-c]quinoline of Formula LXXXVI is aminated to provide a pyrazolo[3,4-c]quinolin-4-amine of Formula LXXXVII. The reaction can be carried out by treating a compound of Formula LXXXVI with ammonia in a suitable solvent such as ethanol at an elevated temperature, such as 100° C. to 170° C. Pyrazolo[3,4-c]naphthyridines of the invention can be prepared by using an azaindole as the starting material in Reaction Schemes XIV. Azaindoles are known compounds. Some are commercially available and others can be prepared using known synthetic methods. Compounds of Formula LXXXVI wherein $R_3$ is a benzyloxy group are readily prepared using the methods of Reaction Scheme XIV starting with a commercially available compound of Formula LXXXI. The benzyloxy group can be cleaved by hydrogenolysis, and the resulting hydroxy-substituted compound can be treated according to steps (4) and (5) or (4a) of Reaction Scheme XIII.

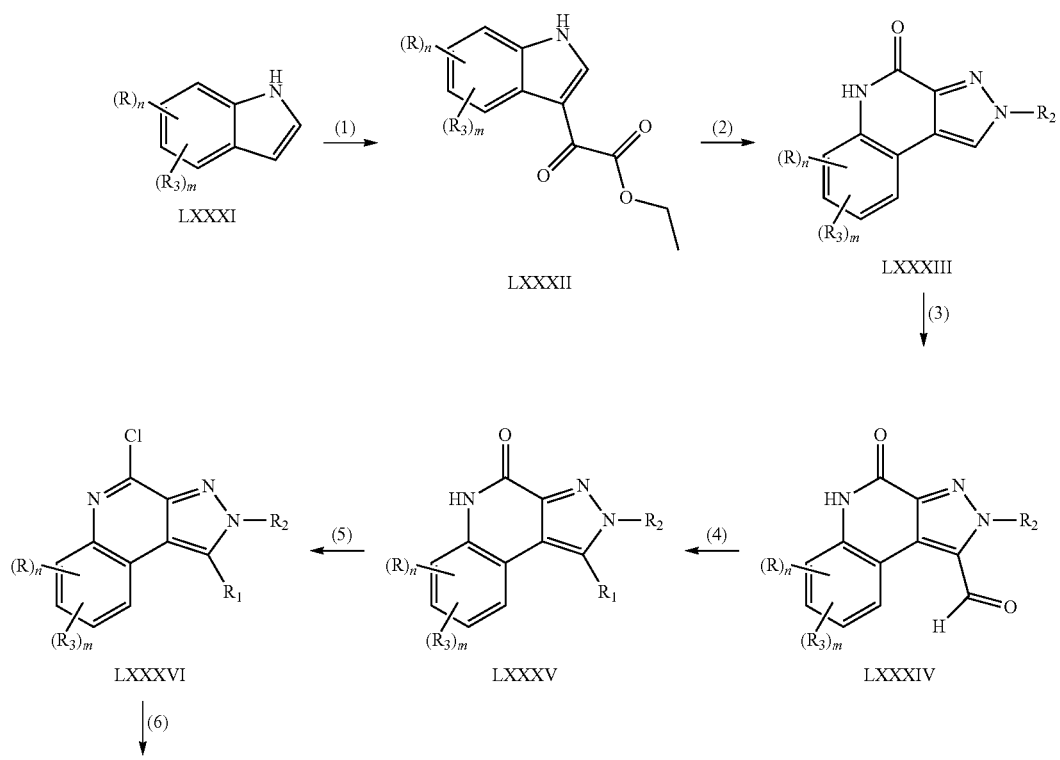

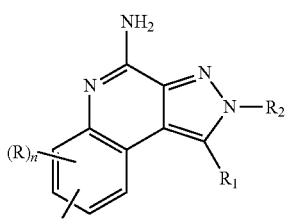

LXXXVII

For some embodiments, compounds of the invention can be prepared according to Reaction Scheme XV, wherein $R_1$, $R_2$, $R_{A1}$, $R_{B1}$, Y''', and $R_{11}$ are as defined above. In Reaction Scheme XV, a pyrazole of Formula II is converted to a compound of Formula II-1 using one of the methods described in step (11) of Reaction Scheme VII. For example, a compound of Formula II can be treated with ethyl chloroformate or acetyl chloride in the presence of triethylamine in a suitable solvent such as dichloromethane. The reaction can be carried out at room temperature, and the product or pharmaceutically acceptable salt thereof can be isolated by conventional methods.

Reaction Scheme XV

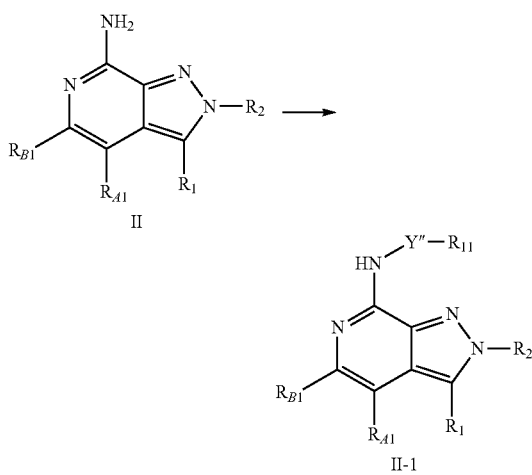

Some compounds of the invention may be transformed in vivo to other compounds of the invention by mechanisms such as hydrolysis in the blood. For example, a compound wherein $R_2$ is —X—O—C($R_6$)—$R_4$, —X—O—C($R_6$)—O—$R_4$, or —X—O—C($R_6$)—N($R_8$)—$R_4$ would likely be transformed in vivo to a compound wherein $R_2$ is —X—OH and therefore would be considered a prodrug of the hydroxy-substituted compound. Compounds of Formula II-1 would be converted to compounds of Formula II.

Other prodrugs can be made from compounds of the invention. For example, a compound bearing a hydroxy substituent may be converted to an ester, a carbonate, a carbamate, or a sulfonate. Particularly useful esters are made from carboxylic acids containing one to six carbon atoms or naturally occurring L-amino acids. In addition, the amino group on the 4-position of the pyrazolo ring compounds can be converted to an amide, amidine, or a carbamate to prepare a prodrug of a compound of the invention. Particularly useful amides and carbamates contain one to four carbon atoms. The preparation of these prodrugs can be carried out by methods well known to one of skill in the art.

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can also be prepared using variations of the synthetic routes shown in Reaction Schemes I through XV that would be apparent to one of skill in the art. For example, the synthetic routes shown in Reaction Schemes VII or VIII for the preparation of quinolines can be used to prepare naphthyridines by using a compound of Formula XVIII or a positional isomer thereof in lieu of a compound of Formula XV. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce or inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, an IRM compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM compounds or salts of the present invention may be particularly helpful in individuals having compromised immune function. For example, certain compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Chromatographic purification was carried out by flash chromatography on either a HORIZON HPFC system (an automated, modular high-performance flash purification product available from Biotage, Inc, Charlottesville, Va., USA) or an Analogix INTELLIFLASH Flash Chromatography System (IFC). The eluent used for each purification is given in the example. In some chromatographic separations, the solvent mixture 80:18:2 chloroform/methanol/concentrated ammonium hydroxide (CMA) was used as the polar component of the eluent. In these separations, CMA was mixed with chloroform in the indicated ratio. For Examples 1 through 6, chromatographic purification was carried out on a HORIZON HPFC system using either a FLASH 40+M cartridge, a FLASH 25+M, or a FLASH 65I Silica cartridge.

Examples 1-4

Part A

Ethyl 6-methyl-2,4-dioxoheptanoate, sodium salt is available from the literature procedure (Claisen, L., *Berichte*, 1909, 42, 59) or can be prepared by the following method. A solution of diethyl oxalate (1 equivalent) and 3-methyl-2-butanone (1 equivalent) was added dropwise with vigorous stirring to a solution of sodium tert-butoxide (1 equivalent) in ethanol. Following the addition, the reaction was stirred for one hour; a precipitate formed. The precipitate was isolated by filtration, washed with ethanol and diethyl ether, and dried to provide ethyl 6-methyl-2,4-dioxoheptanoate, sodium salt.

Part B

Anhydrous hydrazine (3.58 g, 112 mmol) was added dropwise over a period of 30 minutes to a solution of ethyl 6-methyl-2,4-dioxoheptanoate, sodium salt (24.8 g, 112 mmol) in acetic acid (160 mL). The reaction was stirred overnight at ambient temperature, and then the solvent was removed under reduced pressure. The residue was dissolved in a mixture of diethyl ether and water, and solid sodium bicarbonate and sodium carbonate were added to adjust the mixture to pH 8. The aqueous layer was extracted twice with diethyl ether; the combined organic fractions were washed with brine, dried over magnesium sulfate, filtered, and concentrated under reduced pressure. The residue was purified by chromatography on a HORIZON HPFC system (FLASH 65I cartridge, eluting with 50:50 ethyl acetate/hexanes) to provide 21.0 g of ethyl 5-(2-methylpropyl)-1H-pyrazole-3-carboxylate as a solid.

Part C

The alkylating agent from the table below (1.5 equivalents) and a solution of sodium ethoxide in ethanol (21%, 1.1 equivalents) were added to a solution of ethyl 5-(2-methylpropyl)-1H-pyrazole-3-carboxylate (1 equivalent) in ethanol (1M), and the reaction was heated at reflux under a nitrogen atmosphere for 90 minutes to two hours. An analysis by high-performance liquid chromatography (HPLC) indicated the presence of starting material. Additional sodium ethoxide solution (0.1-0.3 equivalents) was added, and the reaction was heated at reflux for an additional 30 minutes to two hours. For example 3, the reaction was stirred at ambient temperature overnight instead of heating at reflux. The solvent was removed under reduced pressure, and the residue was partitioned between aqueous sodium chloride and diethyl ether. The aqueous layer was extracted twice with diethyl ether, and the combined organic fractions were dried over magnesium sulfate, filtered, and concentrated under reduced pressure. The residue was purified by chromatography on a HORIZON HPFC system (FLASH 65I cartridge, eluting with hexane/ethyl acetate ranging in ratios from 80:20 to 50:50) to provide the alkylated pyrazole as a yellow oil.

Part D

Excess 30% ammonium hydroxide was added to a Parr vessel containing the material from Part C and methanol (1-2 M). The vessel was sealed, and the reaction was heated at 100° C. for 12 hours, allowed to cool to ambient temperature over a period of three hours, and then cooled to 0° C. A solid formed and was isolated by filtration, washed with water and hexanes, and air-dried to provide the carboxamides listed below.

Example 1

5-(2-Methylpropyl)-1-propyl-1H-pyrazole-3-carboxamide was obtained as white crystals, mp 141-142.5° C.
Anal. Calcd. for $C_{11}H_{19}N_3O$: C, 63.13; H, 9.15; N, 20.08. Found: C, 62.93; H, 8.89; N, 20.01.

Example 2

1-Ethyl-5-(2-methylpropyl)-1H-pyrazole-3-carboxamide was obtained as white crystals, mp 125-126° C.
Anal. Calcd. for $C_{10}H_{17}N_3O$: C, 61.51; H, 8.78; N, 21.52. Found: C, 61.50; H, 8.86; N, 21.58.

Example 3

At the completion of the reaction, the solvent was removed under reduced pressure. The residue was purified by chromatography on a HORIZON HPFC system (FLASH 65I cartridge, eluting with ethyl acetate/methanol ranging in ratios from 97:3 to 95:5) and subsequently recrystallized from tert-butyl methyl ether to provide 1-methyl-5-(2-methylpropyl)-1H-pyrazole-3-carboxamide as white crystals, mp 118.5-119.5° C.
Anal. Calcd. for $C_9H_{15}N_3O$: C, 59.65; H, 8.34; N, 23.18. Found: C, 59.66; H, 8.66; N, 23.25.

Example 4

At the completion of the reaction, water was added to precipitate the product, 1-butyl-5-(2-methylpropyl)-1H-pyrazole-3-carboxamide, which was isolated as white crystals, mp 122.5-124° C.
Anal. Calcd. for $C_{12}H_{21}N_3O$: C, 64.54; H, 9.48; N, 18.82. Found: C, 64.65; H, 9.52; N, 18.77.

Part E

A mixture of the carboxamide from Part D (5-10 g, 28-45 mmol) and phosphorous oxychloride (21-38 mL) was heated at 90° C. for 90 minutes. The solution was then poured into ice water (250-500 mL), and concentrated ammonium hydroxide was added to adjust the mixture to pH 7-8. The mixture was extracted with dichloromethane (4x), and the combined extracts were dried over magnesium sulfate, filtered, and concentrated under reduced pressure to provide an oil.

Part F

Potassium acetate (1.5 equivalents) and bromine (1.1 equivalents) were added to a solution of the carbonitrile from Part E in acetic acid (0.6 M), and the reaction was stirred for 15-24 hours. Saturated aqueous sodium hydrogensulfite (1 mL) was added, and the mixture was stirred until it became colorless. The acetic acid was removed under reduced pressure, and 2M aqueous sodium carbonate was added to the residue. The resulting solution was extracted with dichloromethane (4x). The combined extracts were dried over magnesium sulfate, filtered, and concentrated under reduced pressure. The resulting oil was purified by chromatography on a HORIZON HPFC system (FLASH 65I cartridge, eluting with hexane/ethyl acetate ranging in ratios from 98:2 to 65:35) to provide an oil. In Example 2, 4-bromo-1-ethyl-5-(2-methylpropyl)-1H-pyrazole-3-carbonitrile crystallized under vacuum and was obtained as a white solid, mp 50-51° C.
Anal. Calcd. for $C_{10}H_{14}N_3Br$: C, 46.89; H, 5.51; N, 16.40. Found: C, 46.95; H, 5.64; N, 16.75.

Part G

Triphenylphosphine (24 mg, 0.09 mmol) and palladium (II) acetate (7 mg, 0.03 mmol) were added to a mixture of the carbonitrile from Part F (10.0 mmol), 2-aminophenylboronic acid (12.0 mmol, Examples 2 and 3) or 2-aminophenylboronic acid hydrochloride (12.0 mmol, Examples 1 and 4), aqueous sodium carbonate (6 mL of 2 M, Examples 2 and 3 or 12 mL of 2M, Examples 1 and 4), propanol (17.5 mL) and water (3.5 mL). The reaction was heated under a nitrogen atmosphere at 100° C. for 12 to 33 hours; in Examples 3 and 4 additional triphenylphosphine, palladium (II) acetate, and boronic acid were added to drive the reaction to completion. The reaction mixture was allowed to cool to ambient temperature and then partitioned between water and chloroform. The aqueous layer was extracted with chloroform (3x). The combined organic fractions were dried over magnesium sulfate, filtered, and concentrated under reduced pressure.

The residue from Example 2 was purified by chromatography on a HORIZON HPFC system (40+M cartridge, eluting with dichloromethane/ethyl acetate ranging in ratios from 100:0 to 85:15). The residue from Example 3 was purified by chromatography on a HORIZON HPFC system (40+M cartridge, eluting with chloroform/CMA ranging in ratios from 99:1 to 95:5).

Part H

A solution of acetyl chloride (1.5 equivalents) in ethanol (0.3 M) was stirred for 15 minutes and added to the material from Part G, and the reaction was heated at reflux under a nitrogen atmosphere for 3.5 to 14 hours. The solvent was removed under reduced pressure, and the residue was partitioned between chloroform and 2 M aqueous sodium carbonate. The aqueous layer was extracted twice with chloroform, and the combined organic fractions were dried over magnesium sulfate, filtered, and concentrated under reduced pressure. The residue was purified by chromatography on a HORIZON HPFC system (40+M cartridge, eluting with chloroform/CMA ranging in ratios from 100:0 to 75:25) and subsequently recrystallized from acetonitrile. The crystals were dried overnight at 6.65 Pa and 98° C. to provide the products listed below.

Example 1

1-(2-Methylpropyl)-2-propyl-2H-pyrazolo[3,4-c]quinolin-4-amine was obtained as white needles, mp 199-200° C.

Anal. Calcd. for $C_{17}H_{22}N_4$: C, 72.31; H, 7.85; N, 19.84. Found: C, 72.13; H, 8.03; N, 19.78.

Example 2

2-Ethyl-1-(2-methylpropyl)-2H-pyrazolo[3,4-c]quinolin-4-amine was obtained as white needles, mp 208-209° C.

Anal. Calcd. for $C_{16}H_{20}N_4$: C, 71.61; H, 7.51; N, 20.88. Found: C, 71.38; H, 7.83; N, 20.79.

Example 3

2-Methyl-1-(2-methylpropyl)-2H-pyrazolo[3,4-c]quinolin-4-amine was obtained as light pink crystals, mp 213-214° C.

Anal. Calcd. for $C_{15}H_{18}N_4$: C, 70.84; H, 7.13; N, 22.03. Found: C, 70.59; H, 7.19; N, 22.05.

Example 4

2-Butyl-1-(2-methylpropyl)-2H-pyrazolo[3,4-c]quinolin-4-amine was obtained as white needles, mp 165-166° C.

Anal. Calcd. for $C_{18}H_{24}N_4$: C, 72.94; H, 8.16; N, 18.90. Found: C, 72.89; H, 7.99; N, 19.08.

Examples 1-4

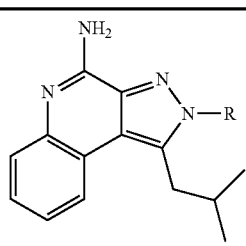

| Example | Alkylating agent in Part C | R |
| --- | --- | --- |
| 1 | 1-Iodopropane | —$CH_2CH_2CH_3$ |
| 2 | 1-Bromoethane | —$CH_2CH_3$ |
| 3 | Iodomethane | —$CH_3$ |
| 4 | 1-Iodobutane | —$CH_2CH_2CH_2CH_3$ |

Example 5

1,2-Dimethyl-2H-pyrazolo[3,4-c]quinolin-4-amine hydrochloride

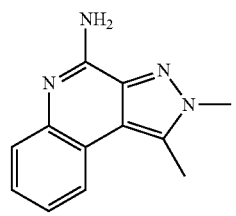 [SMILES: Cc1c2c(nn1C)c(N)nc1ccccc12]

Part A

Ethyl 1,5-dimethyl-1H-pyrazole-3-carboxylate is available from the literature procedure (Huppatz, J. L., *Aust. J. Chem.*, 1983, 36, 135-147). The general method described in Part D of Examples 1 through 4 was used to convert ethyl 1,5-dimethyl-1H-pyrazole-3-carboxylate to 1,5-dimethyl-1H-pyrazole-3-carboxamide.

Part B

The method described in Part E of Examples 1 through 4 was used to treat 1,5-dimethyl-1H-pyrazole-3-carboxamide (5.0 g, 36 mmol) with phosphorous oxychloride (20 mL) to afford 3.9 g of 1,5-dimethyl-1H-pyrazole-3-carbonitrile. A small portion was recrystallized from hexane to provide the following data.

Anal. Calcd. for $C_6H_7N_3$: C, 59.49; H, 5.82; N, 34.69. Found: C, 59.31; H, 5.75; N, 34.48.

Part C

A solution of bromine (5.1 g, 32 mmol) in acetic acid (10 mL) was added dropwise to a solution of potassium acetate (3.9 g, 40 mmol) and 1,5-dimethyl-1H-pyrazole-3-carbonitrile in acetic acid (50 mL). Following the addition, the reaction was stirred for 30 minutes. Saturated aqueous sodium hydrogensulfite was added, and the mixture was stirred until it became colorless. The volatiles were removed under reduced pressure, and the residue was stirred with water to form a solid. The solid was isolated by filtration, washed with water, and recrystallized from ethanol and then from hexane to provide 2.5 g of 4-bromo-1,5-dimethyl-1H-pyrazole-3-carbonitrile as colorless needles, mp 92-94° C. Anal. Calcd. for $C_6H_6BrN_3$: C, 36.03; H, 3.02; N, 21.01. Found: C, 36.04; H, 2.86; N, 20.99.

Part D

Triphenylphosphine (2.4 mg, 0.09 mmol) and palladium (II) acetate (7 mg, 0.03 mmol) were added to a mixture of 4-bromo-1,5-dimethyl-1H-pyrazole-3-carbonitrile (0.600 g, 3.00 mmol), 2-aminophenylboronic acid (0.719 g, 5.25 mmol), aqueous sodium carbonate (1.8 mL of 2 M), propanol (5.25 mL) and water (1.1 mL). The reaction was heated under a nitrogen atmosphere at 100° C. for three hours and then allowed to cool to ambient temperature. The work-up procedure described in Part G of Examples 1-4 was followed. The resulting orange oil was purified by chromatography on a HORIZON HPFC system (25+M cartridge, eluting with ethyl acetate/hexane ranging in ratios from 50:50 to 75:25) to provide 371 mg of 4-(2-aminophenyl)-1,5-dimethyl-1H-pyrazole-3-carbonitrile as a pale yellow solid.

Part E

A solution of acetyl chloride (0.150 g, 1.9 mmol) in ethanol (6.4 mL) was stirred for 15 minutes. 4-(2-Aminophenyl)-1,5-dimethyl-1H-pyrazole-3-carbonitrile (0.270 g, 1.27 mmol) was added, and the reaction was heated at reflux under a nitrogen atmosphere for two hours. A precipitate formed. The mixture was allowed to cool to ambient temperature and then cooled to 0° C. The solid was isolated by filtration, washed with diethyl ether, and dried to provide 285 mg of 1,2-dimethyl-2H-pyrazolo[3,4-c]quinolin-4-amine hydrochloride as a white solid, mp>250° C.
Anal. Calcd. for $C_{12}H_{12}N_4 \cdot HCl$: C, 57.95; H, 5.27; N, 22.53. Found: C, 57.78; H, 5.23; N, 22.34.

Example 6

N-[2-(4-Amino-2-methyl-2H-pyrazolo[3,4-c]quinolin-1-yl)-1,1-dimethylethyl]benzamide

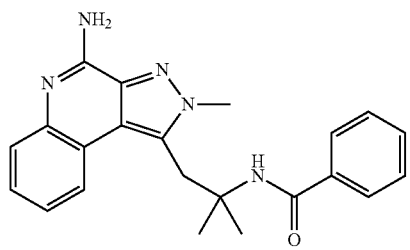 [SMILES: Cn1nc2c(N)nc3ccccc3c2c1CC(C)(C)NC(=O)c1ccccc1]

Part A

4-Methyl-4-benzamido-2-pentanone is available from the literature procedure (Scheuer, P. J. et al., J. Am. Chem. Soc., 1957, 22, 674-676) or from the following method. A mixture of mesityl oxide (19.6 g, 0.200 mol) and benzonitrile (22.0 g, 0.210 mol) was cooled to 0° C.; concentrated sulfuric acid (20 mL) was added in 2 mL increments over a period of ten minutes. The reaction was heated to 35° C., and the reaction temperature rose quickly to 55° C. The reaction temperature was maintained at between 50 and 55° C. for one hour. The viscous liquid was poured into ice water (800 mL), and the mixture was stirred for 90 minutes. A solid formed and was isolated by filtration, washed with water, washed with 2M aqueous sodium carbonate (100 mL), washed again with water until the filtrate was pH neutral, and dried under nitrogen overnight. The solid was then recrystallized from tert-butyl methyl ether (150 mL) to provide 19.0 g of 4-methyl-4-benzamido-2-pentanone as beige needles.

Part B

Sodium tert-butoxide (5.98 g, 62.2 mmol) was added to a solution of 4-methyl-4-benzamido-2-pentanone (12.4 g, 56.5 mmol) and ethyl diethoxyacetate (11.0 g, 62.2 mmol) in ethanol (40 mL), and the reaction was heated at reflux under a nitrogen atmosphere for 3.5 hours. The solvent was removed under reduced pressure, and the residue was partitioned between saturated aqueous ammonium chloride and tert-butyl methyl ether. The aqueous solution was extracted twice with tert-butyl methyl ether, and the combined organic fractions were dried over magnesium sulfate, filtered, and concentrated under reduced pressure to provide 17.5 g of N-(6,6-diethoxy-1,1-dimethyl-3,5-dioxohexyl)benzamide as a brown oil.

Part C

Methyl hydrazine (2.60 g, 56.5 mmol) was added over a period of ten minutes to a solution of the material from Part B in ethanol (56 mL), and the reaction was stirred overnight at ambient temperature. The solvent was removed under reduced pressure, and the residue was purified by chromatography on a HORIZON HPFC system (FLASH 65I cartridge, eluting with ethyl acetate/hexanes ranging in ratios from 50:50 to 90:10) to provide 8.74 g of N-[1-(5-diethoxymethyl-2-methyl-2H-pyrazol-3-yl)-1,1-dimethylethyl]benzamide as a viscous, yellow oil.

Part D

Hydrochloric acid (40 mL of 1 M) was added to a solution of N-[1-(5-diethoxymethyl-2-methyl-2H-pyrazol-3-yl)-1,1-dimethylethyl]benzamide (8.7 g, 24 mmol) in tetrahydrofuran (40 mL), and the reaction was stirred for ten minutes. tert-Butyl methyl ether and 2 M aqueous sodium carbonate (20 mL) were added. The aqueous layer was extracted twice with tert-butyl methyl ether, and the combined organic fractions were dried over magnesium sulfate and filtered. Hexane was added, and the cloudy mixture was stored overnight in the refrigerator. Crystals formed and were isolated in two crops by filtration to provide 5.24 g of N-[1-(5-formyl-2-methyl-2H-pyrazol-3-yl)-1,1-dimethylethyl]benzamide as a white powder, mp 150-151° C.
Anal. Calcd. for $C_{16}H_{19}N_3O_2$: C, 67.35; H, 6.71; N, 14.73. Found: C, 67.22; H, 6.89; N, 14.73.

Part E

The method described in Part F of Examples 1-4 was used to brominate N-[1-(5-formyl-2-methyl-2H-pyrazol-3-yl)-1,1-dimethylethyl]benzamide (4.87 g, 17.1 mmol). The crude product was recrystallized from 50:50 hexane/ethyl acetate (140 mL), and the crystals were washed with hexane and dried for two hours under nitrogen to provide 4.91 g of N-[1-(4-bromo-5-formyl-2-methyl-2H-pyrazol-3-yl)-1,1-dimethylethyl]benzamide as white crystals, mp 150-151° C.
Anal. Calcd. for $C_{16}H_{18}N_3O_2Br$: C, 52.76; H, 4.98; N, 11.54. Found: C, 52.85; H, 5.33; N, 11.54.

Part F

The method described in Part G of Examples 1-4 was used to couple N-[1-(4-bromo-5-formyl-2-methyl-2H-pyrazol-3-yl)-1,1-dimethylethyl]benzamide (3.64 g, 10.0 mmol) and 2-aminophenylboronic acid hydrochloride (2.08 g, 12.0 mmol). The reaction was heated for 4 hours. The product was purified by chromatography on a HORIZON HPFC system (40+M cartridge, eluting sequentially with ethyl acetate and 99:1 ethyl acetate/methanol) to provide 1.81 g of N-[1,1-dimethyl-2-(2-methyl-2H-pyrazolo[3,4-c]quinolin-1-yl) ethyl]benzamide as an orange solid.

Part G

3-Chloroperoxybenzoic acid (2.12 g, available as a 77% pure mixture) (mCPBA) was added to a solution of N-[1,1- dimethyl-2-(2-methyl-2H-pyrazolo[3,4-c]quinolin-1-yl)ethyl]benzamide (2.28 g, 6.36 mmol) in chloroform (25 mL), and the reaction was stirred for 45 minutes at ambient temperature. Brine and 2 M aqueous sodium carbonate were added, and the aqueous layer was separated and extracted with chloroform (6x). The combined organic fractions were dried over magnesium sulfate, filtered, and concentrated under reduced pressure.

Part H

Under a nitrogen atmosphere, trichloroacetyl isocyanate (7.63 mmol) was added to a solution of the material from Part G in anhydrous dichloromethane (30 mL), and the reaction was stirred for 90 minutes at ambient temperature. The solvent was removed under reduced pressure. The residue was dissolved in methanol (15 mL), and a solution of sodium methoxide (1.5 mL, 25% in methanol) was added. The reaction was stirred for two hours, and then the solvent was removed under reduced pressure. The resulting oil was partitioned between dichloromethane and aqueous sodium chloride. The aqueous layer was extracted with dichloromethane (5x), and the combined organic layers were dried over magnesium sulfate, filtered, and concentrated under reduced pressure. The resulting yellow solid was purified by chromatography on a HORIZON HPFC system (40+M cartridge, eluting with chloroform/CMA ranging in ratios from 100:0 to 70:30) and recrystallized twice from acetonitrile (23 mL/g and 14 mL/g). The crystals were dried overnight at 6.65 Pa and 98° C. to provide 687 mg of N-[2-(4-amino-2-methyl-2H-pyrazolo[3,4-c]quinolin-1-yl)-1,1-dimethylethyl]benzamide as beige needles, mp 194-196° C.

Anal. Calcd. for $C_{22}H_{23}N_5O$: C, 70.76; H, 6.21; N, 18.75. Found: C, 70.54; H, 6.09; N, 18.85.

Example 7

2-Butyl-1-methyl-2H-pyrazolo[3,4-c]quinolin-4-amine

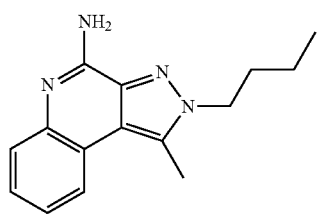 [SMILES: CCCCn1nc2c(N)nc3ccccc3c2c1C]

Part A

Butylhydrazine oxalate (25 g, 140 mmol) was added over a period of 15 minutes to a solution of ethyl 2,4-dioxovalerate (22.2 g, 140 mmol) and triethylamine (210 mmol) in ethanol (140 mL). The resulting solution was stirred overnight at ambient temperature and concentrated under reduced pressure. Hexane was added, and an insoluble solid was removed by filtration. The hexane was removed under reduced pressure; the residue was purified by chromatography on a HORIZON HPFC system (65I cartridge, eluting with hexanes/ethyl acetate in a gradient from 80:20 to 45:55) to provide 18.1 g of ethyl 1-butyl-5-methyl-1H-pyrazole-3-carboxylate as a pale yellow oil.

Part B

A solution of ethyl 1-butyl-5-methyl-1H-pyrazole-3-carboxylate (18.1 g, 86.1 mmol) in methanol (25 mL) was treated with ammonium hydroxide (25 mL) according to a modification of the method described in Part D of Examples 1-4. At the end of the reaction, the methanol was removed under reduced pressure, and the remaining solution was cooled in a refrigerator. A precipitate formed, was isolated by filtration, and was washed with water. The solid (9 g) was recrystallized from hexane (300 mL) and ethyl acetate (30 mL), isolated by filtration, washed with hexane, and air-dried to provide 6.95 g of 1-butyl-5-methyl-1H-pyrazole-3-carboxamide as colorless plates, mp 113.5-114.5° C.

Anal. Calcd for $C_9H_{15}N_3O$: C, 59.65; H, 8.34; N, 23.18. Found: C, 59.79; H, 8.21; N, 23.28.

Part C

A mixture of 1-butyl-5-methyl-1H-pyrazole-3-carboxamide (6.9 g, 38 mmol) and phosphorous oxychloride (34.0 mL) was heated at 90° C. under a nitrogen atmosphere for two hours and then allowed to cool to ambient temperature overnight. The reaction was poured into ice water (300 mL); concentrated ammonium hydroxide (115 mL) was added. The mixture was extracted with chloroform (3x), and the combined extracts were dried over magnesium sulfate, filtered, and concentrated under reduced pressure to provide 6.58 g of 1-butyl-5-methyl-1H-pyrazole-3-carbonitrile as a pale yellow oil.

Part D

1-Butyl-5-methyl-1H-pyrazole-3-carbonitrile (6.58 g, 38 mmol) was treated with potassium acetate (57.2 mmol) and bromine (41.9 mmol) in acetic acid (50 mL) according to a modification of the method described in Part F of Examples 1-4. The reaction provided 9.3 g of 4-bromo-1-butyl-5-methyl-1H-pyrazole-3-carbonitrile as a colorless oil that crystallized upon standing. The crystals were used without purification.

Part E

A modification of the method described in Part G of Examples 1-4 was used to couple 4-bromo-1-butyl-5-methyl-1H-pyrazole-3-carbonitrile (2.42 g, 10.0 mmol) and 2-aminophenylboronic acid hydrochloride (2.43 g, 14.0 mmol). Palladium (II) acetate was added as a 5 mg/mL solution in toluene (1.3 mL). The reaction was heated under nitrogen for 17 hours and combined with the product mixture from another run before being subjected to the work-up procedure. The crude product was purified by chromatography on a HORIZON HPFC system (40+M cartridge, eluting with chloroform:CMA in a gradient from 100:0 to 80:20) to provide 3.17 g of 4-(2-aminophenyl)-1-butyl-5-methyl-1H-pyrazole-3-carbonitrile as an orange oil. A small amount (0.21 g) of 2-butyl-1-methyl-2H-pyrazolo[3,4-c]quinolin-4-amine was also obtained as a beige powder.

Part F

Acetyl chloride (15 mmol) and ethanol (50 mL) were combined and added to 4-(2-aminophenyl)-1-butyl-5-methyl-1H-pyrazole-3-carbonitrile (3.17 g) according to the method described in Part H of Examples 1-4. The reaction was heated for 16 hours.

Following the work-up procedure, chromatographic purification, and recrystallization from acetonitrile (195 mL/g) 873 mg of 2-butyl-1-methyl-2H-pyrazolo[3,4-c]quinolin-4-amine were obtained as white needles, mp 220-222° C.

MS (APCI) m/z 255 (M+H)$^+$;

Anal. Calcd for $C_{15}H_{18}N_4$: C, 70.84; H, 7.13; N, 22.03. Found: C, 70.64; H, 6.94; N, 22.14.

Example 8

2-Benzyl-1-(2-methylpropyl)-2H-pyrazolo[3,4-c]quinolin-4-amine

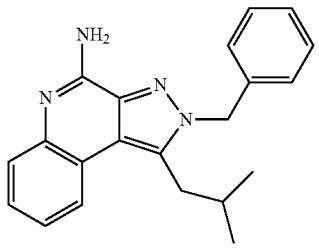 [SMILES: CC(C)Cc1c2c(nn1Cc1ccccc1)c(N)nc1ccccc12]

Part A

Potassium acetate (49.1 g, 0.500 mol) was added with stirring to a solution of ethyl 6-methyl-2,4-dioxoheptanoate, sodium salt (44.4 g, 0.200 mol), prepared as described in Part A of Examples 1-4, in acetic acid (280 mL). The solution was cooled to 10° C., and benzylhydrazine dihydrochloride (39.0 g, 0.200 mol) was added in portions over a period of ten minutes while the reaction temperature was maintained between 10° C. and 13.5° C. The reaction was stirred for 90 minutes at between 6° C. and 13.6° C., allowed to warm to ambient temperature, stirred overnight, and concentrated under reduced pressure. The residue was partitioned between 2 M aqueous sodium carbonate (900 mL) and tert-butyl methyl ether (600 mL). The aqueous layer was extracted with tert-butyl methyl ether (2×300 mL), and the combined organic fractions were dried over magnesium sulfate, filtered, and concentrated under reduced pressure to provide 56.6 g of ethyl 1-benzyl-5-(2-methylpropyl)-1H-pyrazole-3-carboxylate as an oil orange. The product contained 10 mol % of ethyl 2-benzyl-5-(2-methylpropyl)-2H-pyrazole-3-carboxylate.

Part B

A solution of ethyl 1-benzyl-5-(2-methylpropyl)-1H-pyrazole-3-carboxylate (30 g) in methanol (60 mL) was treated with ammonium hydroxide (60 mL) according to a modification of the method described in Part D of Examples 1-4. The reaction was heated for 14 hours. At the end of the reaction, the methanol was removed under reduced pressure, and the remaining solution was extracted with tert-butyl methyl ether (3×). The combined extracts were dried over magnesium sulfate, filtered, and concentrated under reduced pressure. Toluene was added twice and removed under reduced pressure to remove residual water. Hexane was added to the residue; crystals formed and were isolated by filtration, washed with hexane, and air-dried overnight to provide 6.93 g of 1-benzyl-5-(2-methylpropyl)-1H-pyrazole-3-carboxamide as small, off-white crystals.

Part C

A mixture of 1-benzyl-5-(2-methylpropyl)-1H-pyrazole-3-carboxamide (6.77 g, 26.3 mmol) and phosphorous oxychloride (19 mL) was heated at 90° C. under a nitrogen atmosphere for 90 minutes and then allowed to cool to ambient temperature. The reaction was poured into ice water (250 mL); concentrated ammonium hydroxide (64 mL) was added. The mixture was extracted with tert-butyl methyl ether (3×150 mL), and the combined extracts were dried over magnesium sulfate, filtered, and concentrated under reduced pressure to provide 6.28 g of 1-benzyl-5-(2-methylpropyl)-1H-pyrazole-3-carbonitrile as a pale orange oil.

Part D

1-Benzyl-5-(2-methylpropyl)-1H-pyrazole-3-carbonitrile (6.28 g, 26.2 mmol) was treated with potassium acetate (3.9 g, 39 mmol) and bromine (4.61 g, 28.8 mmol) in acetic acid (52 mL) according to the method described in Part F of Examples 1-4. Following chromatographic purification (eluting with hexanes/ethyl acetate in a gradient from 95:5 to 70:30) 7.8 g of 4-bromo-1-benzyl-5-(2-methylpropyl)-1H-pyrazole-3-carbonitrile were obtained as a colorless oil containing 11 mol % of the starting material.

Part E

The method described in Part G of Examples 1-4 was used to couple 4-bromo-1-benzyl-5-(2-methylpropyl)-1H-pyrazole-3-carbonitrile (3.18 g, 10.0 mmol) and 2-aminophenylboronic acid hydrochloride (2.60 g, 15.0 mmol) in the presence of palladium (II) acetate (22.5 mg), triphenylphosphine (79 mg), and 2 M aqueous sodium carbonate (15 mL). The product, 4-2(-aminophenyl)-1-benzyl-5-(2-methylpropyl)-1H-pyrazole-3-carbonitrile, was used without purification.

Part F

The material from Part E was treated according to the method described in Part H of Examples 1-4. Following the work-up procedure and chromatographic purification (eluting with chloroform/CMA in a gradient from 97:3 to 87:13), 1.81 g of product were obtained as a beige solid. A portion (0.63 g) was recrystallized from acetonitrile (28.6 mL/g), isolated by filtration, washed with acetonitrile, and dried for 36 hours in a vacuum oven at 65° C. to provide 559 mg of 2-benzyl-1-(2-methylpropyl)-2H-pyrazolo[3,4-c]quinolin-4-amine as large, beige needles, mp 194-196° C.

MS (APCI) m/z 331 (M+H)$^+$;

Anal. Calcd for $C_{21}H_{22}N_4$: C, 76.33; H, 6.71; N, 16.96. Found: C, 76.03; H, 6.84; N, 16.97.

Example 9

1-(2-Methylpropyl)-2H-pyrazolo[3,4-c]quinolin-4-amine

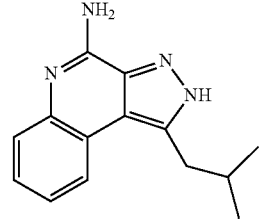 [SMILES: CC(C)Cc1[nH]nc2c(N)nc3ccccc3c12]

Hydrogen bromide (10 mL of 30% by weight in acetic acid) and 2-benzyl-1-(2-methylpropyl)-2H-pyrazolo[3,4-c]

quinolin-4-amine (0.75 g, 2.27 mmol) were combined in a TEFLON-lined Parr vessel and heated at 150° C. for 24 hours and then allowed to cool to ambient temperature over five hours. The reaction was filtered to remove a solid, and the filtrate was adjusted to pH 7 with the addition of 50% sodium hydroxide and 2M aqueous sodium carbonate. A precipitate formed and was isolated by filtration, washed with water, and air-dried. The solid was purified by chromatography on a HORIZON HPFC system (25+M cartridge, eluting with chloroform/CMA in a gradient from 80:20 to 40:60) followed by recrystallization from acetonitrile (19 mL/g) and a small amount of methanol. The crystals were isolated by filtration, washed with acetonitrile, and dried for 36 hours in a vacuum oven at 65° C. to provide 139 mg of 1-(2-methylpropyl)-2H-pyrazolo[3,4-c]quinolin-4-amine as small, pale orange needles, mp 248-249° C.

MS (APCI) m/z 241 (M+H)$^+$;

Anal. Calcd for $C_{14}H_{16}N_4 \cdot 0.17 CH_3OH \cdot 0.16 H_2O$: C, 68.45; H, 6.89; N, 22.53. Found: C, 68.43; H, 6.87; N, 22.53.

Example 10

1-Ethyl-2-methyl-2H-pyrazolo[3,4-c]quinolin-4-amine

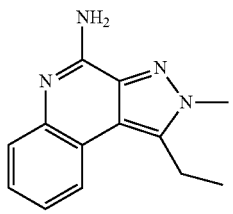 [SMILES: CCc1c2c(nn1C)c(N)nc1ccccc12]

Part A

Sodium tert-butoxide (66.64 g, 0.693 mol) was added over a period of 20 minutes to ethanol (450 mL) under a nitrogen atmosphere. When all solids had dissolved, a mixture of diethyl oxalate (101.28 g, 0.693 mol) and 2-butanone (50.0 g, 0.693 mol) was added over a period of 12 minutes. The reaction was stirred at ambient temperature for 1.5 hours and then used in the next step.

Part B

The solution from Part A was treated with glacial acetic acid (115 mL) and then cooled to 0° C. Methylhydrazine (36.5 mL, 0.693 mmol) was slowly added over a period of 20 minutes. The reaction was allowed to warm to ambient temperature, stirred for two hours, and concentrated under reduced pressure. The residue was made basic with the addition of 2 M aqueous sodium carbonate and extracted with tert-butyl methyl ether (3×400 mL). The combined extracts were dried over sodium sulfate, filtered, and concentrated under reduced pressure to provide 100 g of a red oil. Half of the oil was purified by chromatography on a HORIZON HPFC system (eluting with hexanes:ethyl acetate in a gradient from 100:0 to 0:100 to provide 6.53 g of ethyl 5-ethyl-1-methyl-1H-pyrazole-3-carboxylate as a yellow oil.

Part C

A mixture of ethyl 5-ethyl-1-methyl-1H-pyrazole-3-carboxylate (5.03 g, 27.6 mmol) and ammonium hydroxide (28 mL of 30%) was stirred for 18 hours at ambient temperature. A precipitate formed, was isolated by filtration, and washed with cold hexanes to provide 2.60 g of 5-ethyl-1-methyl-1H-pyrazole-3-carboxamide as a white solid, mp 170-172° C.

Anal. Calcd for $C_7H_{11}N_3O$: C, 54.89; H, 7.24; N, 27.43. Found: C, 54.87; H, 7.56; N, 27.58.

The product was mixed with material from another run.

Part D

5-Ethyl-1-methyl-1H-pyrazole-3-carboxamide (3.8 g, 25 mmol) was treated with phosphorous oxychloride (18 mL, 0.19 mol) according to the method described in Part C of Example 8 to provide 2.68 g of 5-ethyl-1-methyl-1H-pyrazole-3-carbonitrile as a yellow oil.

Part E

5-Ethyl-1-methyl-1H-pyrazole-3-carbonitrile (2.68 g, 19.8 mmol) was treated with potassium acetate (2.91 g, 29.7 mmol) and bromine (3.16 g, 19.8 mmol) in acetic acid (25 mL) according to a modification of the method described in Part F of Examples 1-4. The extraction was carried out with tert-butyl methyl ether, and the combined extracts were dried over sodium sulfate, filtered, and concentrated under reduced pressure to provide 3.8 g of a white solid. A small portion of the solid was recrystallized from ethanol to provide 4-bromo-5-ethyl-1-methyl-1H-pyrazole-3-carbonitrile as long, white needles, mp 72-74° C.

Anal. Calcd for $C_7H_8BrN_3$: C, 39.28; H, 3.77; N, 19.63. Found: C, 39.26; H, 3.55; N, 19.63.

Part F

A modification of the method described in Part G of Examples 1-4 was used to couple 4-bromo-5-ethyl-1-methyl-1H-pyrazole-3-carbonitrile (1.65 g, 7.7 mmol) and 2-aminophenylboronic acid hydrochloride (2.01 g, 11.6 mmol) in the presence of palladium (II) acetate (17.3 mg, 0.077 mmol), triphenylphosphine (60.6 mg, 0.23 mmol), and 2 M aqueous sodium carbonate (11.6 mL). At the end of the reaction, tert-butyl methyl ether was added. The aqueous phase was separated and extracted with tert-butyl methyl ether (2 x); the combined organic fractions were dried over sodium sulfate, filtered, and concentrated under reduced pressure to provide a mixture of 4-(2-aminophenyl)-5-ethyl-1-methyl-1H-pyrazole-3-carbonitrile and 1-ethyl-2-methyl-2H-pyrazolo[3,4-c]quinolin-4-amine.

Part G

Ethanol (12 mL) was cooled to 0° C., and acetyl chloride (0.91 g, 12 mmol) was added. The solution was allowed to warm to ambient temperature and stirred for 30 minutes. A suspension of the material from Part F in ethanol (5 mL) was added, and the mixture was heated at reflux for four hours. The reaction was allowed to cool to ambient temperature. A precipitate was present, isolated by filtration, and combined with material from another run. Chloroform (4 mL) and 2 M aqueous sodium carbonate were added, and the mixture was stirred for six hours. A precipitate formed and was isolated by filtration, washed sequentially with cold water and cold hexanes, and dried in a vacuum oven at 60° C. to provide 0.85 g of 1-ethyl-2-methyl-2H-pyrazolo[3,4-c]quinolin-4-amine as a white solid, mp 257-259° C.

Anal. Calcd for $C_{13}H_{14}N_4 \cdot 0.2\, H_2O$: C, 67.92; H, 6.31; N, 24.37. Found: C, 67.69; H, 6.40; N, 24.76.

Example 11

1,2-Diethyl-2H-pyrazolo[3,4-c]quinolin-4-amine

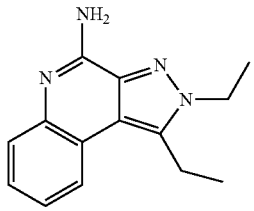 [SMILES: CCc1c2c(nn1CC)c(N)nc1ccccc12]

Part A

A solution of ethyl 2,4-dioxohexanoate (~0.345 mol), prepared as described in Part A of Example 10, in glacial acetic acid (350 mL) was cooled to 0° C. Ethylhydrazine oxalate (41.43 g, 0.276 mol) was added over a period of 20 minutes. The reaction was allowed to warm to ambient temperature, stirred for 20 hours, and concentrated under reduced pressure. The residue was adjusted to pH 10 with the addition of 2 M aqueous sodium carbonate, and chloroform was added. The mixture was filtered to remove a solid. The aqueous filtrate was extracted with chloroform (3×), and the combined organic fractions were dried over sodium sulfate, filtered, and concentrated under reduced pressure to provide 29.4 g of ethyl 1,5-diethyl-1H-pyrazole-3-carboxylate as an orange oil, which was used without purification.

Part B

A mixture of ethyl 1,5-diethyl-1H-pyrazole-3-carboxylate (29.4 g, 0.150 mol) and ammonium hydroxide (150 mL of 30%) was stirred overnight at ambient temperature. An analysis by thin layer chromatography (TLC) indicated the reaction was incomplete. The reaction was then heated for 14 hours at 125° C. in a pressure vessel, allowed to cool to ambient temperature, and cooled to 0° C. A precipitate formed, was isolated by filtration, and washed with cold hexanes to provide 8.3 g of 1,5-diethyl-1H-pyrazole-3-carboxamide as a white solid, mp 129-131° C.

Anal. Calcd for $C_8H_{13}N_3O$: C, 57.47; H, 7.84; N, 25.13. Found: C, 57.37; H, 8.04; N, 25.43.

Part C 1,5-Diethyl-1H-pyrazole-3-carboxamide (8.3 g, 0.050 mol) was treated with phosphorous oxychloride (35 mL) according to the method described in Part C of Example 7. The reaction was heated for 2.5 hours to provide 7.6 g of 1,5-diethyl-1H-pyrazole-3-carbonitrile as a yellow oil, which was used without purification.

Part D

The material from Part C was treated with potassium acetate (7.30 g, 7.44 mmol) and bromine (7.92 g, 49.6 mmol) in acetic acid (60 mL) according to a modification of the method described in Part F of Examples 1-4. The reaction was cooled in an ice bath during the addition of bromine. After the addition, the reaction was stirred at ambient temperature over three days. The extraction was carried out with chloroform (3×100 mL), and the combined extracts were dried over sodium sulfate, filtered, and concentrated under reduced pressure to provide 9.4 g of 4-bromo-1,5-diethyl-1H-pyrazole-3-carbonitrile as an orange oil, which crystallized to an orange solid. The product was used without purification.

Part E

4-Bromo-1,5-diethyl-1H-pyrazole-3-carbonitrile (4.56 g, 20.0 mmol) and 2-aminophenylboronic acid hydrochloride (5.20 g, 30.0 mmol) were coupled in the presence of palladium (II) acetate (45 mg, 0.20 mmol), triphenylphosphine (157 mg, 0.599 mmol), and 2 M aqueous sodium carbonate (30 mL) according to the method described in Part F of Example 10. The product, 4-(2-aminophenyl)-1,5-diethyl-1H-pyrazole-3-carbonitrile, was used without purification.

Part F

The material from Part E was added to a solution of acetyl chloride (2.36 g, 30.0 mmol) in ethanol (30 mL) according to a modification of the method described in Part G of Example 10. The reaction was heated at reflux for six hours and then heated at 81° C. overnight. The crude product was purified by chromatography on a HORIZON HPFC system (eluting with a gradient of chloroform/CMA) followed by recrystallization from acetonitrile. The crystals were heated a second time in acetonitrile in the presence of activated charcoal, which was removed by hot filtration, and recrystallized to provide 0.440 g of 1,2-diethyl-2H-pyrazolo[3,4-c]quinolin-4-amine as an off-white crystalline solid, mp 234-236° C.

Anal. Calcd for $C_{14}H_{16}N_4$: C, 69.97; H, 6.71; N, 23.31. Found: C, 69.93; H, 7.03; N, 23.61.

Example 12

2-Ethyl-1-(2-methanesulfonylethyl)-2H-pyrazolo[3,4-c]quinolin-4-amine

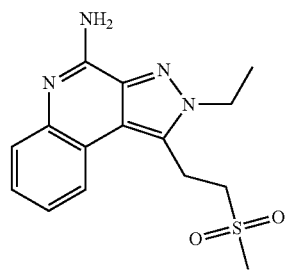 [SMILES: CCn1nc2c(N)nc3ccccc3c2c1CCS(C)(=O)=O]

Part A

Diethyl oxalate (19.8 g, 135 mmol) and 4-methylthio-2-butanone (16 g, 135 mmol) were added to a solution of potassium tert-butoxide (13 g, 135 mmol) in ethanol (97 mL) according to the method described in Part A of Example 10.

Part B

Acetic acid (38 mL) and potassium acetate (20 g, 200 mmol) were sequentially added to the solution from Part A. The resulting suspension was cooled to 0° C., and ethylhydrazine oxalate (20.3 g, 135 mmol) was added with vigorous stirring over a period of ten minutes. The reaction was stirred for 15 minutes at 0° C. and for one hour at ambient temperature and then concentrated under reduced pressure. Saturated aqueous sodium carbonate was added to adjust the residue to pH 9, and water was added. The mixture was extracted with dichloromethane (2×100 mL), and the combined extracts were washed with brine (100 mL), dried over sodium sulfate, filtered, and concentrated under reduced pressure. The resulting dark oil was purified by column chromatography on silica gel (eluting with 1:1 ethyl acetate/hexanes) to provide 8.8 g of ethyl 1-ethyl-5-(2-methylsulfanylethyl)-1H-pyrazole-3-carboxylate as an orange oil.

Part C mCPBA (17.9 g, 72.6 mmol, ~70% pure) was added in portions to a solution of ethyl 1-ethyl-5-(2-methylsulfanylethyl)-1H-pyrazole-3-carboxylate (8.8 g, 36 mmol) over a period of 15 minutes. The reaction was then stirred at ambient temperature for 20 minutes and partitioned between chloroform (100 mL) and saturated aqueous sodium carbonate (100 mL). The organic layer was separated and washed with brine (100 mL), dried over sodium sulfate, filtered, and concentrated under reduced pressure. The crude product was purified by column chromatography on silica gel (eluting with ethyl acetate) to provide 4.6 g of ethyl 1-ethyl-5-(2-methanesulfonylethyl)-1H-pyrazole-3-carboxylate as a white solid.

Part D

The method described in Part C of Example 10 was used to treat ethyl 1-ethyl-5-(2-methanesulfonylethyl)-1H-pyrazole-3-carboxylate (4.6 g, 17 mmol) with ammonium hydroxide (100 mL). The solid was isolated by filtration and washed with water to provide 3.0 g of 1-ethyl-5-(2-methanesulfonylethyl)-1H-pyrazole-3-carboxamide as a white powder, which was mixed with material from another run.

Part E

A modification of the method described in Part E of Examples 1-4 was used to treat 1-ethyl-5-(2-methanesulfonylethyl)-1H-pyrazole-3-carboxamide (3.46 g, 14.1 mmol) with phosphorous oxychloride (10 mL). The reaction was heated for 2.5 hours. After the addition of ammonium hydroxide (35 mL of 28%) a precipitate formed. The mixture was stirred for 30 minutes, and the precipitate was isolated by filtration and washed with water to provide 3.1 g of 1-ethyl-5-(2-methanesulfonylethyl)-1H-pyrazole-3-carbonitrile as a white powder.

Part F

A modification of the method described in Part F of Examples 1-4 was used to treat a solution of 1-ethyl-5-(2-methanesulfonylethyl)-1H-pyrazole-3-carbonitrile (3.1 g, 14 mmol) in acetic acid (27 mL) with potassium acetate (2 g, 20 mmol) and bromine (2.2 g, 14 mmol). The reaction was stirred for 20 minutes before the addition of aqueous sodium hydrogensulfite (1 mL). After the addition of saturated aqueous sodium carbonate, a precipitate formed, was isolated by filtration, and washed with water to provide 2.4 g of a 2:1 mixture of 4-bromo-1-ethyl-5-(2-methanesulfonylethyl)-1H-pyrazole-3-carbonitrile and 1-ethyl-5-(2-methanesulfonylethyl)-1H-pyrazole-3-carbonitrile, which was used without purification.

Part G

Triphenylphosphine (6.1 mg, 0.023 mmol) and palladium (II) acetate (1.75 mg, 0.0018 mmol) were added to a mixture of the material from Part F, 2-aminophenylboronic acid hydrochloride (2.03 g, 11.8 mmol), 2 M aqueous sodium carbonate (23 mL), water (3 mL) and n-propanol (14 mL) according to a modification of the method described in Part G of Examples 1-4. The work-up procedure was carried out by partitioning between dichloromethane (100 mL) and saturated aqueous sodium carbonate (50 mL) and extracting with dichloromethane (50 mL). Following the work-up procedure, the crude product mixture was triturated with ethyl acetate, and a white solid was removed by filtration. The filtrate was concentrated under reduced pressure and purified by column chromatography on silica gel (eluting with 90:10 dichloromethane/methanol) followed by recrystallization from acetonitrile. The crystals were isolated by filtration, washed with acetonitrile, and dried under vacuum for 20 hours at 60° C. to provide 0.05 g of 2-ethyl-1-(2-methanesulfonylethyl)-2H-pyrazolo[3,4-c]quinolin-4-amine as pale yellow needles, mp 220-222° C.

Anal. Calcd for $C_{15}H_{18}N_4O_2S \cdot 0.25\ H_2O$: C, 55.80; H, 5.77; N, 17.35. Found: C, 55.71; H, 5.60; N, 17.41.

Example 13

2-Methyl-1-(2-methylpropyl)-6,7,8,9-tetrahydro-2H-pyrazolo[3,4-c]quinolin-4-amine trifluoroacetate

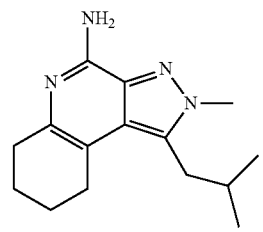 [SMILES: CC(C)Cc1c2c3c(nc(N)c2nn1C)CCCC3]

A solution of 2-methyl-1-(2-methylpropyl)-2H-pyrazolo[3,4-c]quinolin-4-amine (0.6 g, 2 mmol), prepared as described in Example 3, in trifluoroacetic acid (10 mL) was treated with platinum (IV) oxide (0.5 g) and shaken under hydrogen pressure (50 psi, $3.4 \times 10^5$ Pa) for 24 hours. The reaction mixture was diluted with chloroform (20 mL) and filtered through a layer of CELITE filter agent. The filtrate was concentrated under reduced pressure and dissolved in chloroform (50 mL). The solution was adjusted to pH 12 with the addition of ammonium hydroxide and stirred for 20 minutes. The organic layer was separated, dried over magnesium sulfate, filtered, and concentrated under reduced pressure. The resulting solid was recrystallized from acetonitrile to provide 0.3 g of 2-methyl-1-(2-methylpropyl)-6,7,8,9-tetrahydro-2H-pyrazolo[3,4-c]quinolin-4-amine trifluoroacetate as a white powder, mp 204-206° C.

Anal. Calcd for $C_{15}H_{22}N_4 \cdot 0.76\ CF_3COOH$: C, 57.51; H, 6.65; N, 16.24. Found: C, 57.11; H, 7.04; N, 16.23.

Example 14

1,2-Dimethyl-6,7,8,9-tetrahydro-2H-pyrazolo[3,4-c]quinolin-4-amine

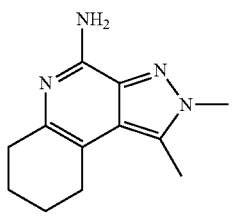 [SMILES: Cc1c2c3c(nc(N)c2nn1C)CCCC3]

A modification of the method described in Example 13 was used to reduce 1,2-dimethyl-2H-pyrazolo[3,4-c]quinolin-4-amine (1.0 g, 4.7 mmol), prepared as described in Example 5. During the work-up procedure, the residue from the filtrate was suspended in 6 M hydrochloric acid and stirred for 30 minutes. The suspension was adjusted to pH 13 with the addition of 50% sodium hydroxide. The resulting solid was isolated by filtration, washed with water, air-dried, and recrystallized from acetonitrile to provide 0.74 g of 1,2-dimethyl-6,7,8,9-tetrahydro-2H-pyrazolo[3,4-c]quinolin-4-amine as an off-white solid, mp 258-259° C.

Anal. Calcd for $C_{12}H_{16}N_4 \cdot 0.1\ H_2O$: C, 66.09; H, 7.49; N, 25.69. Found: C, 65.87; H, 7.52; N, 25.51.

Example 15

2-Methyl-1-(2-methylpropyl)-2H-pyrazolo[3,4-c][1,8]naphthyridin-4-amine

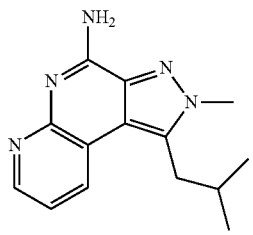 [SMILES: CC(C)Cc1c2c(nn1C)c(N)nc1ncccc12]

Part A tert-Butyl N-(2-pyridyl)carbamate is available from the literature procedure (Moraczewski, A. L. et al, *J. Org. Chem.*, 1998, 63, 7258) or can be prepared by the following method. Under a nitrogen atmosphere, sodium bis(trimethylsilyl)amide (225 mL of a 1.0 M solution in tetrahydrofuran) was added over a period of 20 minutes to a solution of 2-aminopyridine (10.61 g, 108.0 mmol) in dry tetrahydrofuran (THF) (150 mL). The solution was stirred for 15 minutes and then cooled to 0° C. A solution of di-tert-butyl dicarbonate (24.60 g, 112.7 mmol) in THF (50 mL) was added slowly, and the reaction was allowed to warm to ambient temperature slowly and stirred overnight. The THF was removed under reduced pressure, and the residue was partitioned between ethyl acetate (500 mL) and 0.1 M hydrochloric acid (250 mL). The organic layer was separated; washed sequentially with 0.1 M hydrochloric acid (250 mL), water (250 mL), and brine (250 mL); dried over magnesium sulfate; filtered; and concentrated under reduced pressure. The crude product was purified by chromatography on a HORIZON HPFC system (65I cartridge, eluting with 80:20 hexanes/ethyl acetate to provide 17.43 g of tert-butyl N-(2-pyridyl)carbamate as a white solid.

Part B

Under a nitrogen atmosphere, a solution of tert-butyl N-(2-pyridyl)carbamate (15.71 g, 80.9 mmol) and N,N,N',N'-tetramethylethylenediamine (TMEDA, 25.3 g, 218 mmol) in THF (400 mL) was cooled to −78° C. n-Butyllithium (81 mL of a 2.5 M solution in hexanes) was added dropwise over a period of 20 minutes. The solution was stirred for ten minutes, and then the addition funnel was rinsed with additional THF (20 mL). The solution was warmed to −6° C., stirred for two hours, and cooled again to −78° C. Triisopropyl borate (57.7 g, 307 mmol) was added over a period of ten minutes. The resulting solution was warmed to 0° C. and then poured into saturated aqueous ammonium chloride (500 mL). A yellow solid formed and was stirred with diethyl ether (300 mL), isolated by filtration, washed with diethyl ether and water, and air-dried overnight to provide 2-tert-butoxycarbonylamino-3-pyridylboronic acid as a yellow solid.

Part C

A solution of 2-tert-butoxycarbonylamino-3-pyridylboronic acid (7.2 g) and hydrogen chloride (4 M in ethanol) was heated at reflux for 20 minutes. Toluene (50 mL) was added, and the solvents were removed by distillation. The resulting oil was dissolved in water and adjusted to pH 8 with the addition of 2 M aqueous sodium carbonate. The resulting solution was concentrated under reduced pressure to a volume of 20 mL.

Part D

4-Bromo-1-methyl-5-(2-methylpropyl)-1H-pyrazole-3-carbonitrile (2.42 g, 10.0 mmol), prepared as described in Example 3, solid sodium carbonate (1.6 g, 15 mmol), 1-propanol (25 mL), palladium (II) acetate (22 mg, 0.1 mmol), and triphenylphosphine (79 mg, 0.3 mmol) were added to the solution from Part C, and the reaction was heated at 100° C. under a nitrogen atmosphere for 6.5 hours. Additional palladium (II) acetate (22 mg, 0.1 mmol) and triphenylphosphine (79 mg, 0.3 mmol) were added, and the reaction was heated at 100° C. overnight. The work-up procedure described in Part G of Examples 1-4 was followed. The crude product was obtained as a semi-solid and was stirred with tert-butyl methyl ether to form a solid, which was isolated by filtration. The solid was purified by chromatography on a HORIZON HPFC system (40+M cartridge (eluting with acetone/methanol in a gradient from 99:1 to 85:1). The resulting solid (450 mg) was triturated with hot acetonitrile (10 mL), cooled to 0° C., isolated by filtration, and air-dried to provide 365 mg of 2-methyl-1-(2-methylpropyl)-2H-pyrazolo[3,4-c][1,8]naphthyridin-4-amine as a white powder, mp>250° C. MS (APCI) m/z 256 (M+H)$^+$; Anal. Calcd for $C_{14}H_{17}N_5 \cdot 0.4\ H_2O$: C, 64.05; H, 6.83; N, 26.68. Found: C, 64.04; H, 7.27; N, 26.70.

Example 16

2-Ethyl-1-(2-methylpropyl)-2H-pyrazolo[3,4-c][1,8]naphthyridin-4-amine

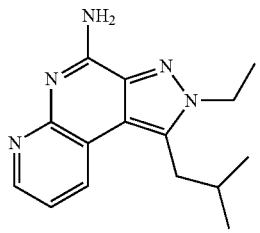 [SMILES: CCn1nc2c(N)nc3ncccc3c2c1CC(C)C]

Hydrochloric acid (15 mL of 1M) was added to a solution of 2-tert-butoxycarbonylamino-3-pyridylboronic acid (3.31 g, 13.9 mmol), prepared as described in Parts A and B of Example 15, in 1-propanol (15 mL), and the resulting mixture was heated at 80° C. for one hour and allowed to cool to ambient temperature. Solid sodium carbonate (2.69 g, 25.4 mmol) was added with stirring followed by a solution of 4-bromo-1-ethyl-5-(2-methylpropyl)-1H-pyrazole-3-carbonitrile (1.78 g, 6.95 mmol), prepared as described in Example 2, in 1-propanol (4 mL). Triphenylphosphine (109 mg, 0.42 mmol) was added, and the reaction was evacuated and backfilled with nitrogen three times and stirred for five minutes. A solution of palladium (II) acetate (31 mg, 0.14 mmol) in warm toluene (0.5 mL) was added. The reaction was twice evacuated and backfilled with nitrogen and then heated at 100° C. overnight. An analysis by HPLC indicated the reaction was incomplete, and additional triphenylphosphine (109 mg, 0.42 mmol) and palladium (II) acetate (31 mg, 0.14 mmol) were added. The reaction was twice evacuated and backfilled with nitrogen at heated at reflux for three days. The 1-propanol was removed under reduced pressure, and the residue was dissolved in chloroform (100 mL). The resulting solution was washed with water, dried over magnesium sulfate, filtered, and concentrated under reduced pressure. The crude product was purified by chromatography on a HORIZON HPFC system as described in Example 15. The resulting solid (200 mg) was recrystallized from acetonitrile (20 mL) after hot filtration, isolated by filtration, washed with cold acetonitrile, and dried overnight in a vacuum oven at 60° C. to provide 0.17 g of 2-ethyl-1-(2-methylpropyl)-2H-pyrazolo[3,4-c][1,8]naphthyridin-4-amine as off-white needles, mp 273-276° C.

Anal. Calcd for $C_{15}H_{19}N_5$: C, 66.89; H, 7.11; N, 26.00. Found: C, 66.77; H, 6.94; N, 26.34.

Example 17

1-(2-Methylpropyl)-2-propyl-2H-pyrazolo[3,4-c][1,8]naphthyridin-4-amine

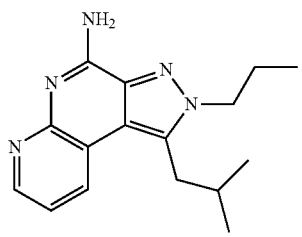 [SMILES: CCCn1nc2c(N)nc3ncccc3c2c1CC(C)C]

A modification of the method described in Example 16 was used to treat 2-tert-butoxycarbonylamino-3-pyridylboronic acid (11.33 mmol) in 1-propanol (10 mL) with hydrochloric acid (12 mL of 1 M) followed by sodium carbonate (1.99 g, 18.8 mmol), 4-bromo-5-(2-methylpropyl)-1-propyl-1H-pyrazole-3-carbonitrile (1.53 g, 5.66 mmol, prepared as described in Example 1) in 1-propanol (5 mL), triphenylphosphine (44.5 mg, 0.17 mmol), and palladium (II) acetate (13 mg, 0.057 mmol) in toluene (0.25 mL). The reaction was complete after it was heated overnight. Following the work-up procedure and purification, 0.18 g of 1-(2-methylpropyl)-2-propyl-2H-pyrazolo[3,4-c][1,8]naphthyridin-4-amine was obtained as off-white needles, mp 257-260° C.

Anal. Calcd for $C_{16}H_{21}N_5$: C, 67.82; H, 7.47; N, 24.71. Found: C, 67.77; H, 7.59; N, 24.52.

Example 18

2-Butyl-1-(2-methylpropyl)-2H-pyrazolo[3,4-c][1,8]naphthyridin-4-amine

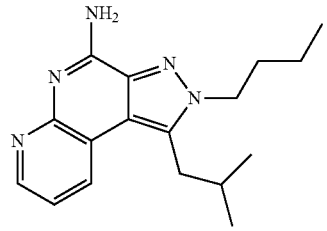 [SMILES: CCCCn1nc2c(N)nc3ncccc3c2c1CC(C)C]

A modification of the method described in Example 16 was used to treat 2-tert-butoxycarbonylamino-3-pyridylboronic acid (2.98 g, 12.5 mmol) in 1-propanol (15 mL) with hydrochloric acid (15 mL of 1 M) followed by sodium carbonate (2.66 g, 25.1 mmol), 4-bromo-1-butyl-5-(2-methylpropyl)-1H-pyrazole-3-carbonitrile (1.91 g, 6.72 mmol, prepared as described in Example 4) in 1-propanol (4 mL), triphenylphosphine (105 mg, 0.400 mmol), and palladium (II) acetate (30 mg, 0.13 mmol). The reaction was complete after it was heated over two nights, and no additional reagents were added. Following the work-up procedure and purification, the crude solid was purified by chromatography on a HORIZON HPFC system (eluting with chloroform/CMA in a gradient from 100:0 to 75:25 to provide 0.48 g of a light yellow solid, which was recrystallized and isolated as described in Example 16 to provide 0.29 g of 2-butyl-1-(2-methylpropyl)-2H-pyrazolo[3,4-c][1,8]naphthyridin-4-amine as off-white needles, mp 219-222° C.

Anal. Calcd for $C_{17}H_{23}N_5$: C, 66.86; H, 7.80; N, 23.55. Found: C, 68.56; H, 8.05; N, 23.88.

Example 19

1-(4-Chlorobutyl)-2-ethyl-2H-pyrazolo[3,4-c]quinolin-4-amine

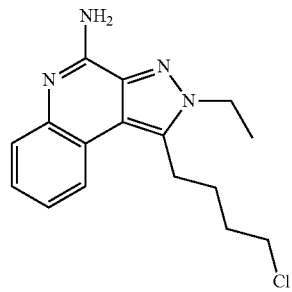 [SMILES: CCn1nc2c(N)nc3ccccc3c2c1CCCCCl]

Part A

Under a nitrogen atmosphere, a mixture sodium tert-butoxide (39.0 g, 0.406 mol) and ethanol (135 mL) was stirred for 30 minutes; most of the solid was dissolved. A solution of diethyl oxalate (25.6 mL, 0.189 mol) and 6-chloro-2-hexanone (25.6 mL, 0.189 mol) in ethanol (20 mL) was added over a period of 20 minutes. The reaction was stirred at ambient temperature for one hour, and potassium acetate (28.0 g, 283 mmol) and acetic acid (95 mL of 2 M) were sequentially added. The reaction was cooled to 0° C., and ethylhydrazine oxalate (31.0 g, 208 mmol) was added in one portion. The reaction was allowed to warm to ambient temperature, stirred for two hours, and then concentrated under reduced pressure. Water was added, and the resulting solution was adjusted to pH 11 with the addition of 2 M aqueous sodium carbonate. The mixture was extracted with chloroform; the combined extracts were dried over sodium sulfate, filtered, and concentrated under reduced pressure to provide ethyl 5-(4-chlorobutyl)-1-ethyl-1H-pyrazole-3-carboxylate as a yellow oil that was used without purification.

Part B

Potassium acetate (92.6 g, 943 mmol), sodium iodide (7.0 g, 47 mmol), and N,N-dimethylformamide (DMF) (943 mL) were added to the material from Part A, and the reaction was heated at 90° C. for four hours under a nitrogen atmosphere and allowed to cool to ambient temperature. Water was added, and the resulting mixture was extracted with diethyl ether. The combined extracts were washed with water (3×), dried over magnesium sulfate, filtered, and concentrated under reduced pressure to provide ethyl 5-(4-acetoxybutyl)-1-ethyl-1H-pyrazole-3-carboxylate, which was used without purification.

Part C

A solution of the material from Part B in methanol (150 mL) was treated with ammonium hydroxide (150 mL) according to a modification of the method described in Part D of Examples 1-4. The reaction was heated overnight at 125° C. and allowed to cool to ambient temperature. The methanol and some water were removed under reduced pressure, and the remaining solution was extracted with chloroform. The combined extracts were dried over sodium sulfate, filtered, and concentrated under reduced pressure to provide 18.0 g of 1-ethyl-5-(4-hydroxybutyl)-1H-pyrazole-3-carboxamide as a dark oil that was used without purification.

Part D

A modification of the method described in Part E of Examples 1-4 was used to treat 1-ethyl-5-(4-hydroxybutyl)-1H-pyrazole-3-carboxamide (18.2 g, 86.1 mmol) with phosphorous oxychloride (60 mL). The reaction was heated for three hours before cooling to 0° C. and pouring into ice water. The mixture was adjusted to pH 12 with the addition of 2 N aqueous sodium carbonate and extracted with chloroform. The combined extracts were passed through a layer of silica gel (eluting first with chloroform and then with 1:1 hexane/ethyl acetate to provide 10.8 g of 5-(4-chlorobutyl)-1-ethyl-1H-pyrazole-3-carbonitrile as a dark oil.

Part E 5-(4-Chlorobutyl)-1-ethyl-1H-pyrazole-3-carbonitrile (10.8 g, 51.0 mmol) was treated with potassium acetate (10.0 g, 102 mmol) and bromine (2.9 mL, 56 mmol) in acetic acid (102 mL), and the reaction was stirred overnight at ambient temperature. The acetic acid was removed under reduced pressure, and the residue was partitioned between water and chloroform. The mixture was adjusted to pH 10 with the addition of 2 N aqueous sodium carbonate. The aqueous layer was extracted with chloroform, and the combined organic layers were dried over sodium sulfate, filtered, and concentrated under reduced pressure. The resulting yellow oil was purified by chromatography on a HORIZON HPFC system (eluting with hexanes/ethyl acetate in a gradient from 95:5 to 50:50) to provide 4-bromo-5-(4-chlorobutyl)-1-ethyl-1H-pyrazole-3-carbonitrile.

Part F

2-Aminophenylboronic acid hydrochloride (1.88 g, 10.8 mmol), potassium phosphate (6.9 g, 32 mmol), tris(dibenzylideneacetone)dipalladium(0) chloroform adduct (186 mg, 0.18 mmol), and bis[(2-diphenylphosphino)phenyl]ether (116 mg, 0.217 mmol) were added to a solution of 4-bromo-5-(4-chlorobutyl)-1-ethyl-1H-pyrazole-3-carbonitrile (2.1 g, 7.2 mmol) in toluene (45 mL). Nitrogen was bubbled through the reaction mixture, and then the reaction was heated at 110° C. for 48 hours. The mixture was filtered through a layer of silica gel (eluting with 3:2 chloroform/methanol). The filtrate was concentrated under reduced pressure and dissolved in ethanol (36 mL). Hydrogen chloride (5.4 mL of a 4 M solution in ethanol) was added to the resulting solution, and the reaction was heated at reflux for two hours and allowed to cool to ambient temperature. The solvent was removed under reduced pressure, and the residue was adjusted to pH 11 with the addition of 2 M aqueous sodium carbonate. The mixture was diluted with brine and extracted with chloroform. The combined extracts were dried over sodium sulfate, filtered, and concentrated under reduced pressure. The crude product was purified by chromatography on a HORIZON HPFC system (40+M cartridge, eluting with chloroform/CMA in a gradient from 100:0 to 70:30). The resulting dark semi-solid was recrystallized from acetonitrile to provide 175 mg of 1-(4-chlorobutyl)-2-ethyl-2H-pyrazolo[3,4-c]quinolin-4-amine as a tan solid.

Anal. Calcd for $C_{16}H_{19}ClN_4$: C, 63.47; H, 6.32; N, 18.50. Found: C, 63.80; H, 6.58; N, 18.38.

Example 20

N-[4-(4-Amino-2-ethyl-2H-pyrazolo[3,4-c]quinolin-1-yl)butyl]methanesulfonamide

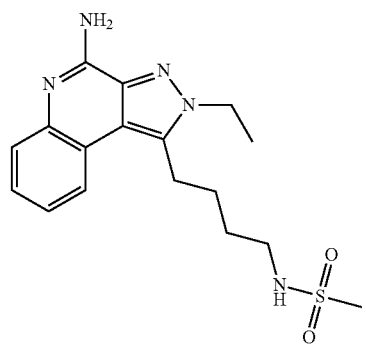 [SMILES: CCn1nc2c(N)nc3ccccc3c2c1CCCCNS(C)(=O)=O]

Methanesulfonamide (1.14 g, 12.0 mmol) was added to a suspension of sodium hydride (60% dispersion in mineral oil, 480 mg, 12.0 mmol) in DMF (5 mL); the reaction was stirred for five minutes. 1-(4-Chlorobutyl)-2-ethyl-2H-pyrazolo[3, 4-c]quinolin-4-amine (0.70 g, 2.4 mmol, prepared as described in Example 19) in DMF (2 mL) and sodium iodide (90 mg, 0.6 mmol) were sequentially added. The reaction was heated at 80° C. for one hour and 90° C. for three hours, allowed to cool to ambient temperature, and poured into ice water (70 mL). A precipitate was removed by filtration, and the filtrate was washed with diethyl ether. A precipitate formed in the aqueous layer over a period of 24 hours and was isolated by filtration and washed with water to provide 200 mg of N-[4-(4-amino-2-ethyl-2H-pyrazolo[3,4-c]quinolin-1-yl)butyl]methanesulfonamide as tan crystals, mp 192-194° C.

MS (APCI) m/z 362 (M+H)$^+$;

Anal. Calcd for $C_{17}H_{23}N_5O_2S$: C, 56.49; H, 6.41; N, 19.37. Found: C, 56.40; H, 6.56; N, 19.24.

Example 21

4-(4-Amino-2-ethyl-2H-pyrazolo[3,4-c]quinolin-1-yl)butan-1-ol

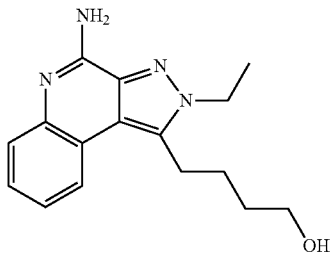 [SMILES: CCn1nc2c(N)nc3ccccc3c2c1CCCCO]

Part A

Potassium acetate (1.69 g, 17.2 mmol), sodium iodide (255 mg, 1.7 mmol), and DMF (17 mL) were added to 4-bromo-5-(4-chlorobutyl)-1-ethyl-1H-pyrazole-3-carbonitrile (1.0 g, 3.4 mmol, prepared as described in Parts A-E of Example 19), and the reaction was heated at 100° C. for two hours under a nitrogen atmosphere and allowed to cool to ambient temperature. Water was added, and the resulting mixture was extracted with diethyl ether. The combined extracts were washed with brine, dried over magnesium sulfate, filtered, and concentrated under reduced pressure. The crude product was purified by chromatography on a HORIZON HPFC system (40+M cartridge, eluting with hexanes/ethyl acetate in a gradient from 90:10 to 60:40) to provide 0.86 g of 4-(4-bromo-5-cyano-2-ethyl-2H-pyrazol-3-yl)butyl acetate.

Part B

Triphenylphosphine (21 mg, 0.082 mmol), 2-aminophenylboronic acid hydrochloride (710 mg, 4.1 mmol), 2 M aqueous sodium carbonate (4.1 mL), n-propanol (4.8 mL), and water (1 mL) were added to 4-(4-bromo-5-cyano-2-ethyl-2H-pyrazol-3-yl)butyl acetate (0.86 mg, 2.7 mmol), and the flask was evacuated and backfilled with nitrogen five times before the addition of palladium (II) acetate (6.0 g, 0.027 mmol). The reaction was evacuated and backfilled with nitrogen three more times and then heated overnight at 100° C. An analysis by HPLC indicated that the reaction was incomplete. Additional triphenylphosphine (10 mg, 0.038 mmol), 2-aminophenylboronic acid hydrochloride (300 mg, 1.73 mmol), solid sodium carbonate (500 mg), and palladium (II) acetate (3.0 g, 0.013 mmol) were added at ambient temperature, and the reaction was heated at reflux for three hours and allowed to cool to ambient temperature. The reaction was diluted with brine and extracted with chloroform. The combined extracts were dried over sodium sulfate, filtered, and concentrated under reduced pressure. Methanol (10 mL) and sodium methoxide (2.2 mL of a 47% solution in methanol) were added to the resulting dark oil. The reaction was heated at reflux for three hours, allowed to cool to ambient temperature, and concentrated under reduced pressure. The residue was diluted with water and extracted with chloroform. The combined extracts were dried over sodium sulfate, filtered, and concentrated under reduced pressure. The crude product was purified by chromatography on a HORIZON HPFC system (40+M cartridge, eluting with chloroform/CMA in a gradient from 100:0 to 75:25) to provide an oil. The oil was crystallized from acetonitrile and recrystallized from acetonitrile to provide 250 mg of 4-(4-amino-2-ethyl-2H-pyrazolo[3,4-c]quinolin-1-yl)butan-1-ol as gold-colored crystals, mp 159-160° C.

MS (APCI) m/z 285 (M+H)$^+$;

Anal. Calcd for $C_{16}H_{20}N_4O$: C, 67.58; H, 7.09; N, 19.70. Found: C, 67.32; H, 7.41; N, 19.80.

Example 22

2-[4-(4-Amino-2-ethyl-2H-pyrazolo[3,4-c]quinolin-1-yl)butyl] isoindole-1,3-dione

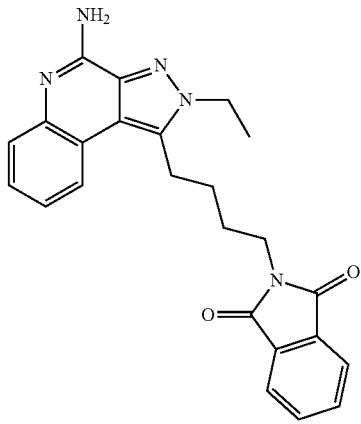 [SMILES: CCn1nc2c(N)nc3ccccc3c2c1CCCCN1C(=O)c2ccccc2C1=O]

Part A

Potassium phthalimide (954 mg, 5.15 mmol), sodium iodide (130 mg, 0.86 mmol), and DMF (5 mL) were added to 4-bromo-5-(4-chlorobutyl)-1-ethyl-1H-pyrazole-3-carbonitrile (1.0 g, 3.4 mmol, prepared as described in Parts A-E of Example 19), and the reaction was heated at 100° C. for 45 minutes under a nitrogen atmosphere and allowed to cool to ambient temperature. Water (50 mL) was added, and the resulting mixture was stirred at 0° C. A precipitate formed, was isolated by filtration, and was dissolved in chloroform. The resulting solution was dried over sodium sulfate, filtered, and concentrated under reduced pressure. An analysis by nuclear resonance spectroscopy (NMR) indicated that starting material was present. The solid was treated with potassium phthalimide (1.27 g, 6.88 mmol), sodium iodide (130 mg, 0.86 mmol), and DMF (5 mL) and heated at 90° C. for three hours. Water (50 mL) was added, and the resulting solid was isolated by filtration to provide 0.97 g of 4-bromo-1-ethyl-5-(4-phthalimidobutyl)-1H-pyrazole-3-carbonitrile as a gray, crystalline solid.

Part B

4-Bromo-1-ethyl-5-(4-phthalimidobutyl)-1H-pyrazole-3-carbonitrile (0.97 g, 2.4 mmol) was treated with 2-aminophenylboronic acid hydrochloride (839 mg, 4.84 mmol), potassium phosphate (2.56 g, 12.1 mmol), tris(dibenzylideneacetone)dipalladium(0) chloroform adduct (124 mg, 0.12 mmol), and bis[(2-diphenylphosphino)phenyl] ether (75 mg, 0.14 mmol) according to the method described in Part F of Example 19. The reaction was heated for 24 hours. Following the purification and recrystallization, 0.157 g of 2-[4-(4-amino-2-ethyl-2H-pyrazolo[3,4-c]quinolin-1-yl)butyl]isoindole-1,3-dione was obtained as brown crystals, mp 216-217° C.

Anal. Calcd for $C_{24}H_{23}N_5O_2$: C, 69.72; H, 5.61; N, 16.94. Found: C, 69.47; H, 5.89; N, 16.94.

Example 23

1-(2-Aminoethyl)-2-ethyl-2H-pyrazolo[3,4-c]quinolin-4-amine dihydrochloride

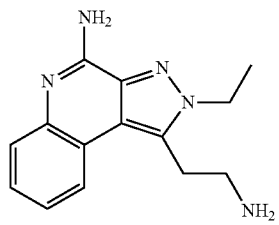 [SMILES: CCn1nc2c(N)nc3ccccc3c2c1CCN]

Part A

4-Phthalimido-2-butanone was obtained from the literature procedure, Eriks et al, *J. Med. Chem.,* 1992, 35, 3239-3246. Sodium tert-butoxide (20.75 g, 0.216 mol) was added over a period of 12 minutes to ethanol (160 mL) under a nitrogen atmosphere. When all solids had dissolved, diethyl oxalate (31.55 g, 0.216 mol) and a suspension of 4-phthalimido-2-butanone (46.9 g, 0.216 mol) were sequentially added. The reaction was stirred at ambient temperature for 2.5 hours. A precipitate was present and was isolated by filtration to provide 37.4 g of ethyl 2,4-dioxo-6-phthalimidohexanoate, sodium salt as a light orange solid.

Part B

A modification of the method described in Part A of Example 11 was followed. A solution of ethyl 2,4-dioxo-6-phthalimidohexanoate, sodium salt (37.64 g, 0.110 mol) in glacial acetic acid (160 L) was cooled to 10° C. before the addition of ethylhydrazine oxalate (16.52 g, 0.110 mol). During the addition, the reaction temperature was maintained between 9 and 11° C. The reaction was complete in two hours. The crude product, a reddish-orange oil, was treated with diethyl ether (150 mL) to form a solid, which was isolated by filtration to provide 26.5 g of ethyl 1-ethyl-5-(2-phthalimidoethyl)-1H-pyrazole-3-carboxylate as a tan solid.

Part C

A solution of ethyl 1-ethyl-5-(2-phthalimidoethyl)-1H-pyrazole-3-carboxylate (10.0 g, 29.3 mmol) in hydrochloric acid (20 mL of 1 M) and acetic acid (60 mL) was heated at 105° C. for 14.5 hours. An analysis by HPLC indicated the presence of starting material; the reaction was heated at 115° C. for three hours and cooled to ambient temperature. The reaction was poured into ice water (200 mL). A precipitate formed and was isolated by filtration, washed with water, and dried in the filter funnel for 1.5 hours to provide 7.64 g of white solid. Toluene (40 mL) and thionyl chloride (20 mL) were added to the white solid, and the mixture was heated at 115° C. for 40 minutes, cooled to ambient temperature, and concentrated under reduced pressure. Toluene was added and removed under reduced pressure. Dichloromethane (60 mL) was added to the residue, and the resulting solution was cooled to 0° C. Concentrated ammonium hydroxide (20 mL) was added, a precipitate formed, and the reaction was stirred for five minutes. The mixture was concentrated under reduced pressure, and the resulting solid was washed with water twice and dried on the filter funnel. The solid was combined with material from another run and recrystallized from ethanol (45 mL/g) to provide 8.5 g of 1-ethyl-5-(2-phthalimidoethyl)-1H-pyrazole-3-carboxamide.

Part D

A solution of 1-ethyl-5-(2-phthalimidoethyl)-1H-pyrazole-3-carboxamide (8.5 g, 27.2 mmol) and thionyl chloride (20 mL) in toluene (40 mL) was heated at reflux for five hours, allowed to cool to ambient temperature, and concentrated under reduced pressure. The residue was dissolved in chloroform and made basic with the addition of 2 M sodium carbonate. The aqueous layer was separated at extracted with chloroform (4×), and the combined organic fractions were washed with brine. The brine was extracted with chloroform (4×). The combined organic fractions were dried over magnesium sulfate, filtered, and concentrated under reduced pressure. The crude product (8.08 g) was purified by chromatography on a HORIZON HPFC system (65I cartridge, eluting with chloroform/CMA in a gradient from 100:0 to 80:20) to provide 7.73 g of 1-ethyl-5-(2-phthalimidoethyl)-1H-pyrazole-3-carbonitrile as a white solid.

Part E

Potassium acetate (3.9 g, 39.5 mmol) was added to a solution of 1-ethyl-5-(2-phthalimidoethyl)-1H-pyrazole-3-carbonitrile (7.73 g, 26.3 mmol) in acetic acid (37.5 mL) and dichloromethane (75 mL). Bromine (5.88 g, 36.8 mmol) was added, and the reaction was stirred for 14 hours. A precipitate was present. Saturated aqueous sodium hydrogensulfite was added, and the dichloromethane was removed under reduced pressure. Water (500 mL) was added with stirring, and the resulting solid was isolated by filtration, washed with water, and dried on the filter funnel to provide 4-bromo-1-ethyl-5-(2-phthalimidoethyl)-1H-pyrazole-3-carbonitrile.

Part F

Hydrazine hydrate (4.26 g, 85.1 mmol) was added to a solution of 4-bromo-1-ethyl-5-(2-phthalimidoethyl)-1H-pyrazole-3-carbonitrile (6.35 g, 17.0 mmol) in ethanol, and the solution was heated at reflux for one hour and cooled to ambient temperature. A precipitate formed and was isolated by filtration and washed with cold ethanol. The filtrate was concentrated under reduced pressure, and the resulting white solid was twice treated with toluene and concentrated under reduced pressure. The combined solids were dissolved in 1-methyl-2-pyrrolidinone (NMP) (30 mL), and di-tert-butyl dicarbonate (4.37 g, 20.0 mmol) was added. The reaction was stirred overnight, and additional di-tert-butyl dicarbonate (0.50 g, 2.3 mmol) was added. The reaction was stirred for 25 minutes and cooled to 0° C. Water (350 mL) was added to form a precipitate, and the mixture was stirred for 30 minutes. The solid was isolated by filtration, washed with water, and purified by chromatography on a HORIZON HPFC system (65I cartridge, eluting with hexanes/ethyl acetate in a gradient from 60:40 to 40:60) to provide 5.73 g of [2-(4-bromo-5-cyano-2-ethyl-2H-pyrazol-3-yl)ethyl]tert-butyl carbamate as a white solid.

Part G

2-[(2,2-Dimethylpropanoyl)amino]phenylboronic acid (also known as 2-pivaloylaminobenzene)boronic acid) was prepared using the literature procedure of Rocca, P. et al, Tetrahedron, 1993, 49, 49-64. The method described in Part G of Examples 1-4 was used to couple [2-(4-bromo-5-cyano-2-ethyl-2H-pyrazol-3-yl)ethyl]tert-butyl carbamate (5.50 g, 16.0 mmol) and (2-pivaloylaminobenzene)boronic acid (5.3 g, 24 mmol) in the presence of palladium (II) acetate (72 mg, 0.32 mmol), triphenylphosphine (252 mg, 0.96 mmol), and 2 M aqueous sodium carbonate (12 mL). After the reaction was heated for nine hours, additional palladium (II) acetate (72 mg, 0.32 mmol), triphenylphosphine (252 mg, 0.96 mmol), and 2-[(2,2-dimethylpropanoyl)amino]phenylboronic acid (1.8 g, 8.1 mmol) were added, and the reaction was heated for an additional 15 hours. The crude product was purified by chromatography on a HORIZON HPFC system (65I cartridge, eluting with hexanes/ethyl acetate in a gradient from 70:30 to 35:65) to provide 4.35 g of tert-butyl 2-(3-cyano-4-{2-[(2,2-dimethylpropanoyl)amino]phenyl}-1-ethyl-1H-pyrazol-5-yl)ethylcarbamate containing small amounts of [2-(4-bromo-5-cyano-2-ethyl-2H-pyrazol-3-yl)ethyl]tert-butyl carbamate and [2-(5-cyano-2-ethyl-2H-pyrazol-3-yl)ethyl] tert-butyl carbamate.

Part H

A solution of the material from Part G in ethanol (50 mL) was treated with sodium tert-butoxide (2 mmol) and heated at 100° C. under a nitrogen atmosphere for 3.5 hours. The reaction was allowed to cool to ambient temperature, and the ethanol was removed under reduced pressure. The residue was partitioned between chloroform and brine. The aqueous layer was separated and extracted with chloroform (4×). The combined organic fractions were dried over magnesium sulfate, filtered, and concentrated under reduced pressure. The crude product was purified by chromatography on a HORIZON HPFC system (40+M cartridge, eluting with chloroform/CMA in a gradient from 95:5 to 60:40) to provide 1.71 g of 2-(4-amino-2-ethyl-2H-pyrazolo[3,4-c]quinolin-1-yl)ethyl tert-butyl carbamate as a white solid containing a small amount of hexane.

Part I

Hydrogen chloride (5 mL of a 4 M solution in ethanol) was added to a suspension of 2-(4-amino-2-ethyl-2H-pyrazolo[3,4-c]quinolin-1-yl)ethyl tert-butyl carbamate (1.71 g) in ethanol (10 mL), and the reaction was heated at reflux for one hour and cooled to ambient temperature. A precipitate formed, and the reaction mixture was cooled to 0° C. The solid was isolated by filtration and washed with diethyl ether to provide 1.521 g of 1-(2-aminoethyl)-2-ethyl-2H-pyrazolo[3,4-c] quinolin-4-amine dihydrochloride.

Examples 23-33

A reagent (0.11 mmol, 1.1 equivalents) from the table below was added to a test tube containing 1-(2-aminoethyl)-2-ethyl-2H-pyrazolo[3,4-c]quinolin-4-amine dihydrochloride (32 mg, 0.10 mmol) and N,N-diisopropylethylamine (0.068 mL, 0.4 mmol) in chloroform (1 mL). The test tubes were capped, shaken for four hours at ambient temperature, and allowed to stand overnight. Two drops of water were added to each test tube, and the solvent was removed by vacuum centrifugation.

The compounds were purified by preparative high-performance liquid chromatography (prep HPLC) using a Waters FractionLynx automated purification system. The prep HPLC fractions were analyzed using a Micromass LC/TOF-MS, and the appropriate fractions were combined and centrifuge evaporated to provide the trifluoroacetate salt of the desired compound. Column. Zorbax BonusRP, 21.2×50 millimeters (mm), 5 micron particle size; non-linear gradient elution from 5 to 95% B where A is 0.05% trifluoroacetic acid/water and B is 0.05% trifluoroacetic acid/acetonitrile; fraction collection by mass-selective triggering. The table below shows the reagent added to each test tube, the structure of the resulting compound, and the observed accurate mass for the isolated trifluoroacetate salt.

Examples 23-33

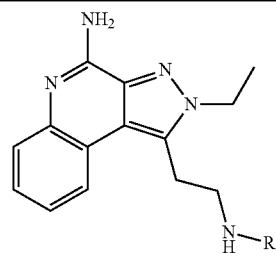

| Example | Reagent | R | Measured Mass (M + H) |
|---|---|---|---|
| 23 | none | H | 256.1570 |
| 24 | Cyclopropanecarbonyl chloride | | 324.1846 |
| 25 | Benzoyl chloride | | 360.1835 |

-continued

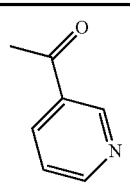

| Example | Reagent | R | Measured Mass (M + H) |
|---|---|---|---|
| 26 | Nicotinoyl chloride hydrochloride | 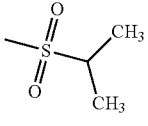 | 361.1784 |
| 27 | Isopropylsulfonyl chloride | 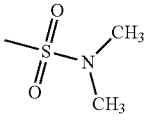 | 362.1665 |
| 28 | Dimethylsulfamoyl chloride | 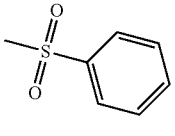 | 363.1611 |
| 29 | Benzenesulfonyl chloride | 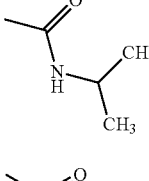 | 396.1493 |
| 30 | Isopropyl isocyanate | 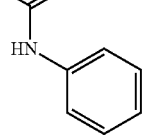 | 341.2103 |
| 31 | Phenyl isocyanate | 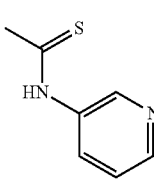 | 375.1952 |
| 32 | 3-Pyridyl isothiocyanate | 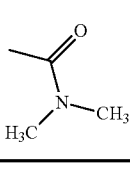 | 392.1692 |
| 33 | N,N-Dimethylcarbamoyl chloride | 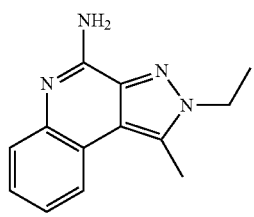 | 327.1965 |

Example 34

1,2-Dimethyl-2H-pyrazolo[3,4-c]quinolin-4-amine

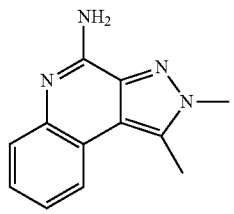 [SMILES: Cc1c2c(nn1C)c(N)nc1ccccc12]

Triphenylphosphine (0.10 g, 0.45 mmol), 2-aminophenylboronic acid hydrochloride (3.89 g, 22.0 mmol), and 4-bromo-1,5-dimethyl-1H-pyrazole-3-carbonitrile (prepared as described in Parts A-C of Example 5, 3.00 g, 15.0 mmol) were placed in a flask. After 1-propanol was added (22 mL), the flask was placed under vacuum and back-filled with nitrogen three times. Palladium (II) acetate (30 mg, 0.15 mmol) was added, followed by aqueous sodium carbonate (22.5 mL of 2 M) and water (4.4 mL). The reaction was heated overnight under a nitrogen atmosphere at 100° C. Additional 2-aminophenylboronic acid hydrochloride (1.0 g), palladium (II) acetate (approximately 10 mg), aqueous sodium carbonate (10 mL of 2 M), and water (5 mL) were added. The reaction was heated at 100° C. for 8 hours, then was allowed to cool to ambient temperature. The reaction mixture was pardoned between dichloromethane and water. The organic layer was concentrated under reduced pressure and the crude product was purified by chromatography on a HORIZON HPFC system (silica gel, gradient elution with 0-30% CMA in chloroform). The appropriate fractions were combined and concentrated under reduced pressure. The residue was dissolved in dichloromethane and concentrated under reduced pressure, which resulted in the formation of a solid. Hexanes were added to the solid, which was isolated by filtration and crystallized from acetonitrile to yield 0.637 g of 1,2-dimethyl-2H-pyrazolo[3,4-c]quinolin-4-amine as white needles, mp>250° C.

$^1$H NMR (500 MHz, DMSO-$d_6$) δ 7.99 (d, J=7.8 Hz, 1H), 7.49 (d, J=8.1 Hz, 1H), 7.32 (t, J=7.2 Hz, 1H), 7.18 (t, J=7.6 Hz, 1H), 6.60 (br s, 2H), 4.07 (s, 3H), 2.80 (s, 3H);

MS (APCI) m/z 213 (M+H)$^+$;

Anal. calcd for $C_{12}H_{12}N_4 \cdot 0.19H_2O$: C, 66.83; H, 5.79; N, 25.98. Found: C, 66.47; H, 5.64; N, 26.02.

Example 35

2-Ethyl-1-methyl-2H-pyrazolo[3,4-c]quinolin-4-amine

Part A

Ethylhydrazine oxalate (23.7 g, 158 mmol) was added slowly to an 11° C. solution of ethyl acetopyruvate (50.0 g, 316 mmol) in ethanol so that the internal temperature did not exceed 14° C. The reaction was allowed to warm to ambient temperature and was stirred overnight. The reaction was concentrated under reduced pressure and 2 M sodium carbonate was added to adjust the mixture to pH 9. The mixture was transferred to a separatory funnel. The aqueous phase was extracted with methyl tert-butyl ether (3×600 mL). The organic layers were combined, dried over magnesium sulfate, filtered, and concentrated under reduced pressure to yield 28.94 g of ethyl 1-ethyl-5-methyl-1H-pyrazole-3-carboxylate as an orange oil that was used without purification in the next reaction.

Part B

A mixture of the material prepared in Part A (28.94 g) and concentrated ammonium hydroxide (275 mL) was heated at 125° C. for 2 days in a pressure vessel. A precipitate formed and was isolated by filtration but was found to contain a mixture of material. The filtrate was stirred at 0° C. for 30 minutes and a white solid formed. The solid was isolated, washed with water, and dried to yield 10.22 g of 1-ethyl-5-methyl-1H-pyrazole-3-carboxamide as a white solid.

Part C

1-Ethyl-5-methyl-1H-pyrazole-3-carboxamide (10.2 g, 66.7 mmol) was treated with phosphorus oxychloride (41 mL) according to the method described in Part C of Example 8. The crude product was purified by chromatography on a HORIZON HPFC system (silica gel, gradient elution with 1-21% ethyl acetate/hexanes followed by 2-25% CMA in chloroform). The appropriate fractions were combined and concentrated under reduced pressure to yield 8.17 g of 1-ethyl-5-methyl-1H-pyrazole-3-carbonitrile as clear colorless crystals.

Part D

1-Ethyl-5-methyl-1H-pyrazole-3-carbonitrile (2.98 g, 22.0 mmol) was treated with potassium acetate (4.93 g, 31.0 mmol) and bromine (3.87 g, 24.0 mmol) in glacial acetic acid (43 mL) according to the general method described in Part F of Examples 1-4. Methyl tert-butyl ether was used instead of dichloromethane in the extraction during the work-up. The organic layers were combined and concentrated under reduced pressure to yield 4-bromo-1-ethyl-5-methyl-1H-pyrazole-3-carbonitrile as a white solid.

Anal. calcd for $C_7H_8BrN_3$: C, 39.28; H, 3.77; N, 19.63. Found: C, 39.30; H, 3.60; N, 19.77.

Part E

4-Bromo-1-ethyl-5-methyl-1H-pyrazole-3-carbonitrile (3.00 g, 14.0 mmol) was treated with triphenylphosphine (0.10 g, 0.42 mmol), 2-aminophenylboronic acid hydrochloride (3.64 g, 21.0 mmol), 1-propanol (22 mL), palladium (II) acetate (30 mg, 0.14 mmol), 2 M aqueous sodium carbonate (22.5 mL, 45 mmol), and water (4.4 mL) according to the general procedure described in Example 34. The reaction time was approximately 18 hours and no additional reagents were added. The crude product mixture was used in the next step without purification.

Part F

A solution of ethanolic HCl, generated from the addition of acetyl chloride (1.65 g, 21.0 mmol) to ethanol (21 mL), was added to the material from Part E according to a modification of the method described in Part G of Example 10. The reaction was heated at reflux and then heated at 81° C. overnight. The reaction mixture was allowed to cool to ambient temperature and a white solid was isolated by filtration and stirred in 2 M aqueous sodium carbonate. The mixture was transferred to a separatory funnel where it was extracted with chloroform twice. The organic layers were combined, dried over magnesium sulfate, filtered, and concentrated under reduced pressure. The resulting light brown solid was recrystallized from acetonitrile and isolated to yield 0.564 g of 2-ethyl-1-methyl-2H-pyrazolo[3,4-c]quinolin-4-amine as an off white powder, mp 217.0-218.0° C.

$^1$H NMR (300 MHz, DMSO-$d_6$) δ 8.01 (dd, J=7.8, 1.2 Hz, 1H), 7.51 (dd, J=8.1, 1.1 Hz, 1H), 7.34 (td, J=7.6, 1.5 Hz, 1H), 7.21 (td, J=7.5, 1.3 Hz, 1H), 6.65 (br s, 2H), 4.43 (q, J=7.2 Hz, 2H), 2.82 (s, 3H), 1.43 (t, J=7.2 Hz, 3H);

MS (APCI) m/z 227 (M+H)$^+$;

Anal. calcd for $C_{13}H_{14}N_4$: C, 69.00; H, 6.24; N, 24.76. Found: C, 68.69; H, 6.21; N, 24.81.

Example 36

2-Benzyl-1-methyl-2H-pyrazolo[3,4-c]quinolin-4-amine

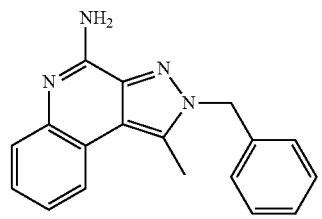 [SMILES: Cc1c2c(nn1Cc1ccccc1)c(N)nc1ccccc12]

Part A

Benzylhydrazine dihydrochloride (123.3 g, 0.632 mol) was added in batches to a 12° C. solution of ethyl acetopyruvate (100.0 g, 0.632 mol) and potassium acetate (155.1 g, 1.58 mol) in glacial acetic acid (1.044 L) so that the internal temperature did not exceed 16° C. The cooling bath was removed and the reaction was allowed to stir overnight at ambient temperature. The mixture was filtered and the filtrate was concentrated under reduced pressure to yield an orange oil to which 2 M aqueous sodium carbonate was added until pH 9 was reached. The mixture was extracted with methyl tert-butyl ether (3×1 L). The combined organic layers were dried over magnesium sulfate, filtered, and concentrated to yield 102.5 g of slightly impure ethyl 1-benzyl-5-methyl-1H-pyrazole-3-carboxylate.

Part B

A mixture of ethyl 1-benzyl-5-methyl-1H-pyrazole-3-carboxylate (57.57 g, 0.236 mol), concentrated ammonium hydroxide (114 mL), and methanol (114 mL) was heated at 125° C. for 39 hours in a pressure vessel. After cooling to ambient temperature, the vessel was placed in an ice bath and the reaction solution was stirred for 30 minutes until a precipitate formed. The precipitate was isolated by filtration and washed with water to yield 28.22 g of 1-benzyl-5-methyl-1H-pyrazole-3-carboxamide.

Part C

1-Benzyl-5-methyl-1H-pyrazole-3-carboxamide (28.22 g, 0.131 mol) was treated with phosphorus oxychloride (112 mL) according to the general method described in Part C of Example 8. The mixture was heated for 3 hours at 90° C. The crude product was purified by chromatography on a HORIZON HPFC system (silica gel, gradient elution with 1-25% ethyl acetate in hexanes). The appropriate fractions were combined, dried over magnesium sulfate, and concentrated under reduced pressure to yield 3.38 g of 1-benzyl-5-methyl-1H-pyrazole-3-carbonitrile as a white solid.

Part D

1-Benzyl-5-methyl-1H-pyrazole-3-carbonitrile (3.38 g, 17.1 mmol) was treated with potassium acetate (2.35 g, 24.0 mmol) and bromine (3.01 g, 18.9 mmol) in glacial acetic acid (48 mL) according to the method described in Part F of Examples 1-4. After the 2 M aqueous sodium carbonate was added in the work-up, a white solid was isolated by filtration and washed with water to yield 4.49 g of 1-benzyl-4-bromo-5-methyl-1H-pyrazole-3-carbonitrile.

Anal, calcd for $C_{12}H_{10}BrN_3$: C, 52.20; H, 3.65; N, 15.22. Found: C, 51.98; H, 3.45; N, 15.27.

Part E

1-Benzyl-4-bromo-5-methyl-1H-pyrazole-3-carbonitrile (3.00 g, 10.9 mmol) was treated with triphenylphosphine (85 mg, 0.32 mmol), 2-[(2,2-dimethylpropanoyl)amino]phenylboronic acid (prepared as described in Part G of Example 23, 2.15 g, 16.3 mmol), 1-propanol (22 mL), palladium (II) acetate (24 mg, 0.11 mmol), aqueous sodium carbonate (6.5 mL of 2 M, 13 mmol), and water (4.4 mL) according to the general procedure described in Example 34. The reaction time was approximately 16 hours and no additional reagents were added. The reaction was allowed to cool to ambient temperature and methyl tert-butyl ether (25 mL) was added. After the mixture was stirred for about 10 minutes, the layers were separated. The organic layer was dried over magnesium sulfate, filtered, and concentrated to yield a brown oil. The crude product was purified by chromatography on a HORIZON HPFC system (silica gel, gradient elution 1-30% ethyl acetate in hexanes). The appropriate fractions were combined, dried over magnesium sulfate, filtered, and concentrated to yield 2.40 g of N-[2-(1-benzyl-3-cyano-5-methyl-1H-pyrazol-4-yl)phenyl]-2,2-dimethylpropanamide as an oil that solidified upon standing at ambient temperature.

Part F

A solution of N-[2-(1-benzyl-3-cyano-5-methyl-1H-pyrazol-4-yl)phenyl]-2,2-dimethylpropanamide (2.40 g, 6.44 mmol) and sodium tert-butoxide (0.743 g, 7.73 mmol) in ethanol (28 mL) was heated at reflux for 1 day, then was allowed to cool to ambient temperature. A precipitate formed that was isolated by filtration and washed with water followed by water/ethanol (8:1) to provide 1.33 g of 2-benzyl-1-methyl-2H-pyrazolo[3,4-c]quinolin-4-amine as a white powder, mp>250° C.

$^1$H NMR (300 MHz, DMSO-$d_6$) δ 8.00 (dd, J=7.9, 1.2 Hz, 1H), 7.51 (dd, J=8.1, 1.1 Hz, 1H), 7.38-7.28 (m, 4H), 7.21-7.15 (m, 3H), 6.70 (br s, 2H), 5.70 (br s, 2H), 2.77 (s, 3H); MS (APCI) m/z 289 (M+H)$^+$;

Anal. calcd for $C_{18}H_{16}N_4$: C, 74.98; H, 5.59; N, 19.43. Found: C, 74.80; H, 5.65; N, 19.55.

Examples 37-39

Part A

Diethyl oxalate and 4,4-dimethyl-2-pentanone were treated with sodium tert-butoxide in ethanol according to the procedure described in Part A of Examples 1-4. The product was isolated, washed with ethanol, and dried under vacuum to provide ethyl 4-hydroxy-6,6-dimethyl-2-oxohept-3-enoate, sodium salt as a white solid.

Part B

A hydrazine reagent from the table below (1 equivalent) was added slowly to a 11° C. stirred 0.65 M solution of ethyl 4-hydroxy-6,6-dimethyl-2-oxohept-3-enoate, sodium salt (1 equivalent) in glacial acetic acid such that the internal temperature did not exceed 14° C. In Example 38, the acetic acid solution also contained potassium acetate (1.5 equivalents). When the addition was complete, the ice bath was removed and the reaction was allowed to stir overnight at ambient temperature. The solution was concentrated under reduced pressure. To the resulting oil was added 2 M aqueous sodium carbonate the mixture reached pH 9. The mixture was extracted with methyl tert-butyl ether three times. The combined organic layers were dried over magnesium sulfate, filtered, and concentrated to yield an oil.

Part C

The material from Part B (37.8-45.4 g, 169-190 mmol) in a 1:1 mixture of concentrated ammonium hydroxide/methanol (150-200 mL) was heated at 125° C. for 24 hours in a pressure vessel. After cooling to ambient temperature, the vessel was placed in an ice bath. The reaction mixture was stirred for 30 minutes and a precipitate formed. The precipitate was isolated by filtration and washed with water to yield a carboxamide.

Part D

A mixture of the carboxamide (7.05-13.27 g, 29.7-63.5 mmol) and phosphorous oxychloride (28-52 mL) was heated at 90° C. for 3 hours. The mixture was allowed to cool to ambient temperature and was poured onto ice water (360-680 mL). Additional ice was added. Concentrated ammonium hydroxide was added to adjust the mixture to pH 8-9. The mixture was extracted with methyl tert-butyl ether. The organic layers were combined, dried over magnesium sulfate, filtered, and concentrated under reduced pressure to provide an oil.

Part E

Potassium acetate (1.4 equivalents) followed by bromine (1.1 equivalents) were added to a 0.4 M solution of the material from Part D in acetic acid. The reaction was stirred for 18-72 hours at ambient temperature. Saturated aqueous sodium hydrogensulfite was added to reduce the residual bromine. The mixture was concentrated under reduced pressure and 2 M aqueous sodium bicarbonate was added to adjust the mixture to pH 9. A white solid formed and was isolated by filtration and washed with water to provide a 1-alkyl-4-bromo-5-(2,2-dimethylpropyl)-1H-pyrazole-3-carbonitrile.

Example 38

4-Bromo-1-ethyl-5-(2,2-dimethylpropyl)-1H-pyrazole-3-carbonitrile was obtained as a white solid.
Anal. calcd for $C_{11}H_{16}BrN_3$: C, 48.90; H, 5.97; N, 15.55. Found: C, 48.88; H, 6.26; N, 15.52.

Example 39

4-Bromo-1-butyl-5-(2,2-dimethylpropyl)-1H-pyrazole-3-carbonitrile was obtained as a white solid.
Anal. calcd for $C_{13}H_{20}BrN_3$: C, 52.36; H, 6.76; N, 14.09. Found: C, 52.06; H, 7.02; N, 13.78.

Part F

Triphenylphosphine (0.03 equivalent), 2-aminophenylboronic acid hydrochloride (1.5-2.0 equivalents), and the material from Part E (1 equivalent) were placed in a flask. After 1-propanol was added (so that the concentration of material from Part E was 0.55 M), the flask was placed under vacuum and back-filled with nitrogen three times. Palladium (II) acetate (0.01 equivalent) was added, followed by 2 M aqueous sodium carbonate (3 equivalents) and water (⅕ of the amount of 1-propanol). The reaction was heated overnight under a nitrogen atmosphere at 100° C. The reaction was allowed to cool to ambient temperature and methyl tert-butyl ether was added. After the mixture was stirred for about 10 minutes, the layers were separated. The organic layer was dried over magnesium sulfate, filtered, and concentrated to yield a brown oil. In Examples 37 and 38 the oil was used directly in the next step. In Example 39, the crude product was purified by chromatography on a HORIZON HPFC system (silica gel, gradient elution with 0-20% ethyl acetate in hexanes). The appropriate fractions were combined, dried over magnesium sulfate, filtered, and concentrated to yield an oil.

Part G

The oil prepared in Part F was converted into a 2-alkyl-1-(2,2-dimethylpropyl)-2H-pyrazolo[3,4-c]quinolin-4-amine using the general procedure described in Part H of Examples 1-4.

Example 37

2-Methyl-1-(2,2-dimethylpropyl)-2H-pyrazolo[3,4-c]quinolin-4-amine was isolated as an off-white powder, mp 254.0-255.0° C.
$^1$H NMR (300 MHz, DMSO-$d_6$) δ 8.16 (dd, J=7.9, 1.1 Hz, 1H), 7.50 (dd, J=8.1, 1.2 Hz, 1H), 7.31 (td, J=7.1, 1.3 Hz, 1H), 7.17 (td, J=8.1, 1.4 Hz, 1H), 6.67 (br s, 2H), 4.10 (s, 3H), 3.25 (s, 2H), 1.02 (s, 9H);
MS (APCI) m/z 269 (M+H)$^+$;
Anal. calcd for $C_{16}H_{20}N_4$: C, 71.61; H, 7.51; N, 20.88. Found: C, 71.37; H, 7.50; N, 21.04.

Example 38

No chromatographic purification was necessary. After crystallization from acetonitrile, 2-ethyl-1-(2,2-dimethylpropyl)-2H-pyrazolo[3,4-c]quinolin-4-amine was isolated as a off-white needles, mp 239.8-240.2° C.
$^1$H NMR (300 MHz, DMSO-$d_6$) δ 8.15 (dd, J=8.0, 1.2 Hz, 1H), 7.48 (dd, J=8.1, 1.3 Hz, 1H), 7.30 (dt, J=7.1, 1.4 Hz, 1H), 7.16 (dt, J=8.0, 1.4 Hz, 1H), 6.61 (br s, 2H), 4.43 (q, J=7.1 Hz, 2H), 3.26 (br s, 2H), 1.46 (t, J=7.1 Hz, 3H), 1.01 (s, 9H).
Anal. calcd for $C_{17}H_{22}N_4$: C, 72.31; H, 7.85; N, 19.84. Found: C, 71.94; H, 8.01; N, 19.80.

Example 39

No chromatography or crystallization steps necessary. 2-Butyl-1-(2,2-dimethylpropyl)-2H-pyrazolo[3,4-c]quinolin-4-amine was isolated as a white powder, mp 163.0-164.0° C.
$^1$H NMR (300 MHz, DMSO-$d_6$) δ 8.15 (dd, J=7.9, 0.7 Hz, 1H), 7.49 (dd, J=8.1, 1.0 Hz, 1H), 7.30 (td, J=8.1, 1.1 Hz, 1H), 7.16 (td, J=8.0, 1.1 Hz, 1H), 6.62 (br s, 2H), 4.39 (t, J=6.9 Hz, 2H), 3.27 (br s, 2H), 1.87 (pentet, J=7.2 Hz, 2H), 1.28 (sextet, J=7.5 Hz, 2H), 1.00 (s, 9H), 0.89 (t, J=7.3 Hz, 3H);
MS (APCI) m/z 311 (M+H)$^+$;
Anal. calcd for $C_{19}H_{26}N_4$: C, 73.51; H, 8.44; N, 18.05. Found: C, 73.34; H, 8.21; N, 18.19.

Examples 37-39

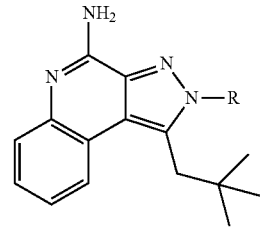

| Example | Hydrazine reagent in Part B | R |
|---|---|---|
| 37 | Methylhydrazine | —CH$_3$ |
| 38 | Ethylhydrazine oxalate | —CH$_2$CH$_3$ |
| 39 | Butylhydrazine oxalate | —CH$_2$CH$_2$CH$_2$CH$_3$ |

Examples 40-42

Part A

Diethyl oxalate and benzylacetone were treated with sodium tert-butoxide in ethanol according to the procedure described in Part A of Examples 1-4. The reaction solution was stirred for 90 minutes and a precipitate formed. The precipitate was isolated to provide ethyl-4-hydroxy-2-oxo-6-phenylhex-3-enoate, sodium salt as a white solid.

Part B

A hydrazine reagent from the table below (1 equivalent) was added to a solution of ethyl-4-hydroxy-2-oxo-6-phenyl-hex-3-enoate, sodium salt (1 equivalent) in glacial acetic acid according to the procedure described in Part B of Examples 37-39. The product was isolated as an oil.

Part C

The material from Part B was treated with a 1:1 mixture of concentrated ammonium hydroxide/methanol (150-200 mL)

according to the procedure described in Part C of Examples 37-39 to yield a carboxamide. Example 40 was heated for 2 days, Example 41 was heated for 18 hours, and Example 42 was heated for 1 day.

Part D

The carboxamide from Part C was treated with phosphorous oxychloride according to the procedure described in Part D of Examples 37-39 to yield the nitrile as an oil.

Part E

The material from Part D was brominated according to the procedure described in Part E of Examples 37-39. During the work-up in Examples 41 and 42, the mixture at pH 9 was extracted with methyl tert-butyl ether twice. The organic layers were combined, dried over magnesium sulfate, and concentrated to give a brown oil.

Part F

The material from Part E (3.00 g) was treated with triphenylphosphine (0.03 equivalent), 2-[(2,2-dimethylpropanoyl)amino]phenylboronic acid (prepared as described in Part G of Example 23, 1.5 equivalents), 1-propanol (22 mL), palladium (II) acetate (0.01 equivalent), 2 M aqueous sodium carbonate (1.2 equivalents), and water (4.4 mL) according to the general procedure described in Examples 37-39. The crude product was purified by chromatography on a HORIZON HPFC system (silica gel, gradient elution with 0-25% ethyl acetate in hexanes) to yield an oil.

Part G

To a 0.2 M solution of the material from Part F in ethanol was added sodium tert-butoxide (1.2 equivalents). The solution was heated at reflux for 1 day, then was allowed to cool to ambient temperature. A precipitate formed that was isolated by filtration and washed with a small amount of water and ethanol. The solid was dried at 70° C. in a vacuum oven overnight to provide the product products listed below.

Example 40

2-Methyl-1-(2-phenylethyl)-2H-pyrazolo[3,4-c]quinolin-4-amine was isolated as pale yellow powder, mp 210.5-212.5° C.
$^1$H NMR (300 MHz, DMSO-$d_6$) δ 7.97 (dd, J=7.8, 0.9 Hz, 1H), 7.53 (dd, J=8.1, 1.0 Hz, 1H), 7.37-7.15 (m, 7H), 6.67 (br s, 2H), 3.77 (s, 3H), 3.51 (t, J=7.5 Hz, 2H), 3.01 (t, J=7.5 Hz, 2H);
MS (APCI) m/z 303 (M+H)$^+$;
Anal. calcd for $C_{19}H_{18}N_4 \cdot 0.17H_2O$: C, 74.71; H, 6.05; N, 18.34. Found: C, 74.40; H, 5.83; N, 18.31.

Example 41

2-Ethyl-1-(2-phenylethyl)-2H-pyrazolo[3,4-c]quinolin-4-amine was isolated as a white powder, mp 179.0-181.0° C.
$^1$H NMR (300 MHz, DMSO-$d_6$) δ 7.97 (dd, J=7.8, 1.1 Hz, 1H), 7.53 (dd, J=8.1, 1.2 Hz, 1H), 7.37-7.20 (m, 7H), 6.65 (br s, 2H), 4.17 (q, J=7.2 Hz, 2H), 3.53 (t, J=7.5 Hz, 2H), 3.01 (t, J=7.7 Hz, 2H), 1.32 (t, J=7.2 Hz, 3H);
Anal. calcd for $C_{20}H_{20}N_4$: C, 75.92; H, 6.37; N, 17.71. Found: C, 75.71; H, 6.75; N, 17.82.

Example 42

1-(2-Phenylethyl)-2-propyl-2H-pyrazolo[3,4-c]quinolin-4-amine was isolated as a white powder, mp 175.0-176.0° C.
$^1$H NMR (300 MHz, DMSO-$d_6$) δ 7.97 (dd, J=7.8, 1.1 Hz, 1H), 7.54 (dd, J=8.1, 1.2 Hz, 1H), 7.37-7.20 (m, 7H), 6.65 (br s, 2H), 4.07 (t, J=7.2 Hz, 2H), 3.53 (t, J=7.4 Hz, 2H), 3.03 (t, J=7.7 Hz, 2H), 1.75 (sextet, J=7.3 Hz, 2H), 0.85 (t, J=7.3 Hz, 3H);
Anal. calcd for $C_{21}H_{22}N_4$: C, 76.33; H, 6.71; N, 16.96. Found: C, 76.10; H, 6.69; N, 16.90.

Examples 40-42

| Example | Hydrazine reagent in Part B | R |
|---|---|---|
| 40 | Methylhydrazine | —CH$_3$ |
| 41 | Ethylhydrazine oxalate | —CH$_2$CH$_3$ |
| 42 | Propylhydrazine oxalate | —CH$_2$CH$_2$CH$_3$ |

Example 43

1-Butyl-2-tert-butyl-2H-pyrazolo[3,4-c]quinolin-4-amine

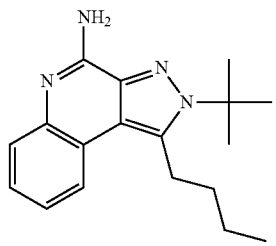 [SMILES: CCCCc1c2c(nn1C(C)(C)C)c(N)nc1ccccc12]

Part A

Diethyl oxalate and 2-hexanone were treated with sodium tert-butoxide in ethanol according to the procedure described in Part A of Examples 1-4. The reaction solution was stirred for 90 minutes and a precipitate formed. The precipitate was isolated to provide 1-ethoxy-1,2-dioxooct-3-en-4-olate, sodium salt as a white solid.

Part B

1-Ethoxy-1,2-dioxooct-3-en-4-olate, sodium salt (332.8 g, 1.50 mol) was treated with tert-butylhydrazine hydrochloride (186.6 g, 1.50 mol) according to the procedure described in Part B of Examples 37-39 to yield ethyl 5-butyl-1-ten-butyl-1H-pyrazole-3-carboxylate as a brown oil.

Part C

Ethyl 5-butyl-1-tert-butyl-1H-pyrazole-3-carboxylate (60 g, 0.24 mol) in a 1:1 mixture of concentrated ammonium hydroxide/methanol (238 mL) was heated at 125° C. for 37 hours in a pressure vessel. After cooling to ambient temperature, the vessel was placed in an ice bath. The reaction mixture was stirred for 30 minutes, then was concentrated under reduced pressure to a brown oil. The oil was dissolved in dichloromethane and the solution was washed with water and brine. The organic layer was dried over magnesium sulfate, filtered, and concentrated under reduced pressure to give a wet brown solid. Hexanes were added, the mixture was stirred, and 18.67 g of 5-butyl-1-tert-butyl-1H-pyrazole-3-carboxamide was isolated by filtration as an off-white solid.

Part D

A solution of trifluoroacetic anhydride (13.5 mL, 95.4 mmol) in dichloromethane (84 mL) was added over 15 minutes to a 0° C. solution of 5-butyl-1-tert-butyl-1H-pyrazole-3-carboxamide (18.7 g, 86.7 mmol) and triethylamine (36.3 mL, 260 mmol) in dichloromethane (167 mL). The reaction was allowed to stir for 10 minutes before the ice bath was removed. The reaction was stirred at ambient temperature for 1 hour and then 2 M aqueous sodium carbonate was added. The mixture was transferred to a separatory funnel and was extracted with dichloromethane three times. The combined organic layers were dried over magnesium sulfate, filtered, and concentrated. The crude product was purified by chromatography on a HORIZON HPFC system (silica gel, eluted with 20% ethyl acetate in hexanes). The appropriate fractions were combined, dried over magnesium sulfate, and concentrated under reduced pressure to yield 11.00 g of 5-butyl-1-tert-butyl-1H-pyrazole-3-carbonitrile as an orange oil.

Part E

5-Butyl-1-tert-butyl-1H-pyrazole-3-carbonitrile (11.00 g, 53.6 mmol) was converted into 4-bromo-5-butyl-1-tert-butyl-1H-pyrazole-3-carbonitrile using the procedure described in Part E of Examples 37-39.

Part F

4-Bromo-5-butyl-1-tert-butyl-1H-pyrazole-3-carbonitrile (3.0 g, 10.6 mmol) was treated with triphenylphosphine (0.085 g, 0.32 mmol), 2-[(2,2-dimethylpropanoyl)amino]phenylboronic acid (prepared as described in Part G of Example 23, 2.41 g, 15.8 mmol), 1-propanol (22 mL), palladium (II) acetate (0.024 g, 0.11 mmol), 2 M aqueous sodium carbonate (6.5 mL, 13.0 mmol), and water (4.4 mL) according to the general procedure described in Examples 37-39. The crude product was purified by chromatography on a HORIZON HPFC system (silica gel, gradient elution with 0-25% ethyl acetate in hexanes) to yield 1.63 g of N-[2-(5-butyl-1-tert-butyl-3-cyano-1H-pyrazol-4-yl)phenyl]-2,2-dimethylpropanamide as an oil.

Part G

To a solution of N-[2-(5-butyl-1-tert-butyl-3-cyano-1H-pyrazol-4-yl)phenyl]-2,2-dimethylpropanamide (1.63 g, 4.28 mmol) in ethanol was added sodium tert-butoxide (0.494 g, 5.14 mmol). The solution was heated at reflux for 1 day, then was allowed to cool to ambient temperature. A precipitate formed that was isolated by filtration and washed with a small amount of water (24 mL) and ethanol (3 mL) to yield 0.4667 g of 1-butyl-2-tert-butyl-2H-pyrazolo[3,4-c]quinolin-4-amine as off-white crystals, mp 222.0-223.0° C.

$^1$H NMR (300 MHz, DMSO-$d_6$ at 46° C.) δ 7.83 (dd, J=7.9, 1.1 Hz, 1H), 7.50 (dd, J=8.1, 1.3 Hz, 1H), 7.34 (td, J=7.2, 1.4 Hz, 1H), 7.23 (td, J=7.9, 1.4 Hz, 1H), 6.52 (br s, 2H), 3.39-3.34 (m, 2H), 1.76 (s, 9H), 1.72-1.56 (m, 4H), 1.01 (t, J=7.1 Hz, 3H);

MS (APCI) m/z 297 (M+H)$^+$;

Anal. calcd for $C_{18}H_{24}N_4$: C, 72.94; H, 8.16; N, 18.90. Found: C, 72.67; H, 8.29; N, 19.01.

Example 44

1-Ethyl-2-propyl-2H-pyrazolo[3,4-c]quinolin-4-amine

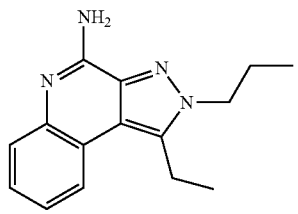 [SMILES: CCCn1nc2c(N)nc3ccccc3c2c1CC]

Part A

A solution of ethyl 2,4-dioxohexanoate (~0.464 mol), prepared as described in Part A of Example 10, in glacial acetic acid (300 mL) was cooled to 0° C. Hydrazine (8.91 g, 0.278 mol) was added dropwise. The reaction was allowed to warm to ambient temperature, stirred overnight, and concentrated under reduced pressure. The residue was adjusted to pH 10 with the addition of 2 M aqueous sodium carbonate. The mixture was extracted with chloroform (3×250 mL). The combined organic layers were dried over sodium sulfate, filtered, and concentrated under reduced pressure to provide 27.0 g of ethyl 5-ethyl-1H-pyrazole-3-carboxylate, which was used without purification.

Part B

Propyl iodide (0.43 mL, 4.46 mmol) and a solution of sodium ethoxide in ethanol (21%, 0.95 g, 3.27 mmol) were added to a solution of ethyl 5-ethyl-1H-pyrazole-3-carboxylate (0.5 g, 2.97 mmol) in ethanol (5 mL) at ambient temperature. The reaction was stirred overnight, and additional propyl iodide (0.05 mL) and sodium ethoxide in ethanol (21%, 0.1 g) were added. After 3 hours, the solvent was removed under reduced pressure and the residue was partitioned between an aqueous sodium chloride solution and methyl tert-butyl ether. The aqueous phase was extracted with methyl tert-butyl ether twice. The organic phases were combined, dried over sodium sulfate, filtered, and concentrated under reduced pressure to yield impure ethyl 5-ethyl-1-propyl-1H-pyrazole-3-carboxylate.

Part C

Ethyl 5-ethyl-1-propyl-1H-pyrazole-3-carboxylate (13.0 g, 62 mmol) in a 4:1 mixture of concentrated ammonium hydroxide/methanol (50 mL) was heated at 125° C. for 18 hours in a pressure vessel. After cooling to ambient temperature, the contents of the vessel were poured into a flask and a precipitate formed immediately. The precipitate was isolated by filtration to yield 5.02 g of analytically pure 5-ethyl-1-propyl-1H-pyrazole-3-carboxamide as off-white crystals, mp 105-106° C. MS (APCI) m/z 182.1 (M+H)$^+$; Anal. calcd for $C_9H_{15}N_3O$: C, 59.64; H, 8.34; N, 23.19. Found: C, 59.59; H, 8.54; N, 23.39. An additional 0.50 g of product was obtained in the second crop from the filtrate.

Part D

5-Ethyl-1-propyl-1H-pyrazole-3-carboxamide (5.50 g, 30.35 mmol) was treated with phosphorous oxychloride (20 mL) according to the procedure described in Part D of Examples 37-39 to yield 4.89 g of 5-ethyl-1-propyl-1H-pyrazole-3-carbonitrile as an oil.

Part E

5-Ethyl-1-propyl-1H-pyrazole-3-carbonitrile (4.89 g, 30.0 mmol) was dissolved in glacial acetic acid (30 mL) and treated with potassium acetate (4.41 g, 44.9 mmol) and bromine (4.79 g, 30.0 mmol). During the slow addition of bromine, an exotherm occurred and ice bath was used to cool the reaction. After the addition of bromine was complete, the reaction was allowed to warm to ambient temperature and stir for 5 hours. Saturated aqueous sodium hydrogensulfite was added to reduce the residual bromine. The mixture was concentrated under reduced pressure and 2 M aqueous sodium carbonate was added to adjust the mixture to pH 9. The mixture was extracted with chloroform (3×100 mL). The organic layers were combined, dried over sodium sulfate, filtered, and concentrated to yield 6.12 g of 4-bromo-5-ethyl-1-propyl-1H-pyrazole-3-carbonitrile as a yellow oil.

Part F

A mixture of 4-bromo-5-ethyl-1-propyl-1H-pyrazole-3-carbonitrile (4.00 g, 16.5 mmol), 2-aminophenylboronic acid hydrochloride (4.30 g, 24.8 mmol), triphenylphosphine (0.26 g, 0.99 mmol), palladium (II) acetate (0.074 g, 0.33 mmol), 2 M aqueous sodium carbonate (24.8 mL, 49.5 mmol), 1-propanol (35 mL), and water (5 mL) was heated at reflux for 18 hours. Additional triphenylphosphine (0.26 g) and palladium (II) acetate (0.074 g) were added and the mixture was heated at reflux for 22 hours. The mixture was allowed to cool to ambient temperature and methyl tert-butyl ether (100 mL) was added.

The mixture was transferred to a separatory funnel and the organic layer was isolated and washed with water and brine. The aqueous layers were combined and back-extracted with methyl tert-butyl ether (2×40 mL). The combined organic layers were dried over magnesium sulfate, filtered, and concentrated to provide a red oil that was used in the next step without purification.

Part G

The oil prepared in Part F was converted into 1-ethyl-2-propyl-2H-pyrazolo[3,4-c]quinolin-4-amine using the general procedure described in Part H of Examples 1-4. 1-Ethyl-2-propyl-2H-pyrazolo[3,4-c]quinolin-4-amine (0.34 g) was isolated an off-white solid, mp 219-220° C.

$^1$H-NMR (300 MHz, DMSO-d$_6$) δ 7.91 (dd, J=7.8, 1.1 Hz, 1H), 7.50 (dd, J=8.1, 1.1 Hz, 1H), 7.37-7.27 (m, 1H), 7.25-7.15 (m, 1H), 6.64 (br s, 2H), 4.34 (t, J=7.2 Hz, 2H), 3.25 (q, J=7.5 Hz, 2H), 1.92 (sextet, J=7.3 Hz, 2H), 1.29 (t, J=7.5 Hz, 3H), 0.92 (t, J=7.4 Hz, 3H);

$^{13}$C-NMR (75 MHz, DMSO-d$_6$) δ 150.5, 143.7, 139.0, 135.5, 125.5, 121.6, 119.6, 116.0, 50.7, 23.6, 18.2, 13.1, 10.9.

MS (APCI) m/z 255.2 (M+H)$^+$;

Anal. calcd for $C_{15}H_{18}N_4$: C, 70.84; H, 7.13; N, 22.03. Found: C, 70.49; H, 7.38; N, 22.12.

Example 45

2-Butyl-1-ethyl-2H-pyrazolo[3,4-c]quinolin-4-amine

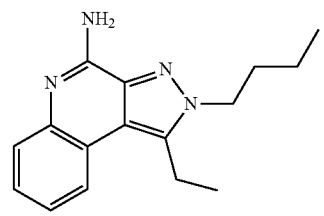 [SMILES: CCCCn1nc2c(N)nc3ccccc3c2c1CC]

Part A

A solution of ethyl 2,4-dioxohexanoate (approximately 60% pure, 45.0 g, 0.232 mol), prepared as described in Part A of Example 10, in glacial acetic acid (150 mL) was cooled to 0° C. Butylhydrazine oxalate (25.0 g, 0.139 mol) was added slowly. The reaction was allowed to warm to ambient temperature, stirred overnight, and concentrated under reduced pressure. The residue was adjusted to pH 10 with the addition of 2 M aqueous sodium carbonate. The mixture was extracted with chloroform and an emulsion that contained solid material formed. The solid was isolated by filtration, and the filtrate was transferred to the separatory funnel. The organic layer was separated. The aqueous layer was extracted with chloroform three times. The combined organic layers were dried over sodium sulfate, filtered, and concentrated under reduced pressure to provide an oil that was purified by chromatography on a HORIZON HPFC system (silica gel, gradient elution with CMA in chloroform) to yield 13.27 g of ethyl 5-ethyl-1-butyl-1H-pyrazole-3-carboxylate as a yellow oil.

Part B

Ethyl 5-ethyl-1-butyl-1H-pyrazole-3-carboxylate (13.27 g, 59.2 mmol) in concentrated ammonium hydroxide (50 mL) was heated at 125° C. for 14 hours in a pressure vessel. After the vessel was allowed to cool to ambient temperature, methanol (40 mL) was added and the vessel was heated at 125° C. for 1 day. After cooling to ambient temperature, the vessel was cooled in an ice bath and the product began to crystallize from the reaction mixture. Two crops of crystals were isolated to provide 5.50 g of 5-ethyl-1-butyl-1H-pyrazole-3-carboxamide as off-white crystals, mp 60-61° C. MS (APCI) m/z 196.1 (M+H)$^+$; Anal. calcd for $C_{10}H_{17}N_3O$: C, 61.51; H, 8.78; N, 21.52.

Found: C, 61.32; H, 9.04; N, 21.71.

Part C

5-Ethyl-1-butyl-1H-pyrazole-3-carboxamide (5.44 g, 27.9 mmol) was treated with phosphorous oxychloride (20 mL) according to the procedure described in Part D of Examples 37-39 to yield 5.20 g of an oil. Chloroform was used in place of methyl tert-butyl ether in the work-up.

Part D

Potassium acetate (4.11 g, 41.9 mmol) followed by bromine (4.46 g, 27.9 mmol) were added to a cooled solution of the material from Part C in acetic acid (35 mL). The reaction was stirred for 48 hours at ambient temperature. The solution was concentrated under reduced pressure and 2 M aqueous sodium bicarbonate was added to adjust the mixture to pH 9-10. The mixture was extracted with methyl tert-butyl ether (250 mL). The organic layer was dried over sodium sulfate, filtered, and concentrated under reduced pressure to yield 5.87 g of 4-bromo-1-butyl-5-ethyl-1H-pyrazole-3-carbonitrile as a yellow oil that was used in the next step without purification.

Part E

A flask containing a mixture of 4-bromo-1-butyl-5-ethyl-1H-pyrazole-3-carbonitrile (2.56 g, 10 mmol), 2-[(2,2-dimethylpropanoyl)amino]phenylboronic acid (2.87 g, 15 mmol), triphenylphosphine (0.079 g, 0.30 mmol), 2 M aqueous sodium carbonate (15 mL, 30 mmol), water (3 mL) and 1-propanol (20 mL) was placed under vacuum and back-filled with nitrogen three times. Palladium (II) acetate (0.023 g, 0.10 mmol) was added. Again, the flask was placed under vacuum and back-filled with nitrogen. The mixture was heated overnight under a nitrogen atmosphere at 100° C. The reaction was allowed to cool to ambient temperature and methyl tert-butyl ether was added. After the mixture was stirred for about 10 minutes, the layers were separated. The organic layer was dried over magnesium sulfate, filtered, and concentrated to yield a brown oil. Hexanes were added to the brown oil, causing the formation of a tan solid that was isolated by filtration. The filtrate was concentrated to an oil that was purified by chromatography on a HORIZON HPFC system (silica gel, eluted with ethyl acetate/hexanes) to provide 0.45 g of N-[2-(5-ethyl-1-butyl-3-cyano-1H-pyrazol-4-yl)phenyl]-2,2-dimethylpropanamide, which was used in the next step without further purification.

Part F

To a solution of N-[2-(5-ethyl-1-butyl-3-cyano-1H-pyrazol-4-yl)phenyl]-2,2-dimethylpropanamide (0.45 g, 1.28 mmol) in ethanol (8 mL) was added sodium ethoxide in ethanol (21 wt % solution in ethanol, 1.03 g, 3.19 mmol). The solution was heated at reflux overnight, then was allowed to cool to ambient temperature. The solvent was removed under reduced pressure and the residue was triturated with water. A precipitate formed that was isolated by filtration and washed with water, then was purified by chromatography on a HORIZON HPFC system (silica gel, gradient elution with 0-35% CMA in chloroform) to yield 0.14 g of 1-ethyl-2-butyl-2H-pyrazolo[3,4-c]quinolin-4-amine as a white crystalline solid, mp 215-216° C.

$^1$H-NMR (300 MHz, DMSO-$d_6$) δ 7.90 (dd, J=7.8, 1.2 Hz, 1H), 7.49 (dd, J=8.1, 1.1 Hz, 1H), 7.37-7.27 (m, 1H), 7.24-7.16 (m, 1H), 6.63 (br s, 2H), 4.37 (t, J=7.3 Hz, 2H), 3.25 (q, J=7.5 Hz, 2H), 1.93-1.80 (m, 2H), 1.43-1.30 (m, 2H), 1.29 (t, J=7.5 Hz, 3H), 0.93 (t, J=7.3 Hz, 3H);

$^{13}$C-NMR (75 MHz, DMSO-$d_6$) δ 150.5, 143.7, 138.8, 135.4, 125.5, 121.6, 119.6, 116.0, 49.0, 32.3, 19.3, 18.3, 13.5, 13.1;

MS (APCI) m/z 269.3 (M+H)$^+$;

Anal. calcd for $C_{16}H_{20}N_4$: C, 71.61; H, 7.51; N, 20.88. Found: C, 71.5; H, 7.54; N, 20.94.

Example 46

1-(4-Chlorobutyl)-2-propyl-2H-pyrazolo[3,4-c]quinolin-4-amine

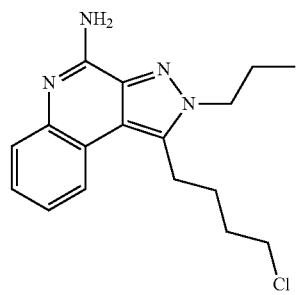 [SMILES: CCCn1nc2c(N)nc3ccccc3c2c1CCCCCl]

Part A

Ethyl 5-(4-chlorobutyl)-1-propyl-1H-pyrazole-3-carboxylate was prepared using a modification of the procedure described in Part A of Example 19. Propylhydrazine oxalate was used instead of ethylhydrazine oxalate. After all the reagents were added, the reaction mixture was stirred overnight instead of two hours. Crude ethyl 5-(4-chlorobutyl)-1-propyl-1H-pyrazole-3-carboxylate was isolated as an impure brown oil, MS (APCI) m/z 273.1 (M+H)$^+$.

Part B

To a solution of the material from Part A (85.05 g, 0.312 mol) in ethanol (500 mL) was added 6 M aqueous sodium hydroxide (104 mL, 0.624 mol). The solution was stirred at ambient temperature for 2 hours. The ethanol was removed under reduced pressure and water (200 mL) was added. The aqueous solution was transferred to a separatory funnel and washed with diethyl ether (100 mL). The aqueous layer was acidified with 6 M aqueous hydrochloric acid to pH 3, causing a precipitate to form. After 10 minutes, the precipitate was isolated by filtration, washed with water, and dried under vacuum at 60° C. overnight to yield 57.1 g of a brown oil which was used without purification in the next step.

Part C

To a solution of the material from Part B (57.1 g, 0.233 mol) in dichloromethane (600 mL) at 0° C. was added slowly a solution of oxalyl chloride (61.0 mL, 0.700 mol) in dichloromethane (20 mL). The reaction was stirred for 10 minutes at 0° C., then at ambient temperature for 4 hours. The solution was concentrated under reduced pressure, then was concentrated from dichloromethane twice. The residue was dissolved in dichloromethane (15 mL) and added dropwise to a flask containing concentrated ammonium hydroxide (250 mL) cooled in an ice bath. The reaction was stirred at ambient temperature overnight. The mixture was extracted with dichloromethane (600 mL, then 2×100 mL). The organic layers were combined, washed with water and brine, dried over sodium sulfate, filtered, and concentrated under reduced pressure to yield a brown solid that was purified by trituration with diethyl ether/hexanes. A tan solid was isolated by filtration to provide 30.98 g of 5-(4-chlorobutyl)-1-propyl-1H-pyrazole-3-carboxamide. $^1$H-NMR (300 MHz, CDCl$_3$) δ 6.70 (br s, 1H), 6.59 (s, 1H), 5.32 (br s, 1H), 3.99 (t, J=7.3 Hz, 2H), 3.61-3.54 (m, 2H), 2.69-2.59 (m, 2H), 1.94-1.76 (m, 6H), 0.94 (t, J=7.4 Hz, 3H).

Part D 5-(4-Chlorobutyl)-1-propyl-1H-pyrazole-3-carboxamide (30.95 g, 0.127 mol) in toluene (250 mL) was treated with phosphorous oxychloride (24.86 mL, 0.267 mol). The solution was heated at reflux for 40 minutes. The reaction was worked-up as described in Part D of Examples 37-39, with the exception that chloroform was used in place of methyl tert-butyl ether, to yield 5.20 g of 5-(4-chlorobutyl)-1-propyl-1H-pyrazole-3-carbonitrile as an oil. $^1$H-NMR (300 MHz, CDCl$_3$) δ 6.43 (s, 1H), 4.04 (t, J=7.3 Hz, 2H), 3.62-3.53 (m, 2H), 2.70-2.58 (m, 2H), 1.94-1.76 (m, 6H), 0.93 (t, J=7.4 Hz, 3H).

Part E 5-(4-Chlorobutyl)-1-propyl-1H-pyrazole-3-carbonitrile (14.00 g, 62.0 mmol) was converted into 4-bromo-5-(4-chlorobutyl)-1-propyl-1H-pyrazole-3-carbonitrile according the procedure described in Part F of Examples 1-4. Chloroform was used instead of dichloromethane in the extraction step during the work-up. The crude product was purified by chromatography on a HORIZON HPFC system (silica gel, gradient elution with 10-25% ethyl acetate in hexanes) to provide 14.80 g of 4-bromo-5-(4-chlorobutyl)-1-propyl-1H-pyrazole-3-carbonitrile as a yellow oil. $^1$H-NMR (300 MHz, CDCl$_3$) δ 4.07 (t, J=7.3 Hz, 2H), 3.59 (t, J=6.1 Hz, 2H), 2.79-2.69 (m, 2H), 1.96-1.69 (m, 6H), 0.95 (t, J=7.4 Hz, 3H).

Part F

To a mixture of 4-bromo-5-(4-chlorobutyl)-1-propyl-1H-pyrazole-3-carbonitrile (8.25 g, 27.1 mmol) and powdered molecular sieves (1 g) in toluene (170 mL) was added 2-aminophenylboronic acid hydrochloride (9.40 g, 54.2 mmol), potassium phosphate (28.62 g, 135 mmol), tris(dibenzylideneacetone)dipalladium(0)-chloroform adduct (0.701 g, 0.677 mmol) and bis(2-diphenylphosphinophenyl)ether (0.437 g, 0.812 mmol). Nitrogen gas was bubbled through the mixture for 5 minutes. The mixture was heated at 110° C. for 22 hours. After cooling to ambient temperature, the mixture was filtered through a plug of CELITE filter agent with 3:2 chloroform/methanol. The filtrate was concentrated under reduced pressure to yield a residue that was used in the next step.

Part G

Acetyl chloride (6.38 g, 81.3 mmol) was added to ethanol (20 mL) at 0° C. The resulting solution was added to the residue from Part F. The solution was heated at reflux overnight. Upon cooling to ambient temperature, the solution was concentrated under reduced pressure. The residue was partitioned between chloroform and 2 M aqueous sodium carbonate. The aqueous layer was extracted twice with chloroform, and the combined organic layers were dried over sodium sulfate, filtered, and concentrated under reduced pressure. The crude product was purified by chromatography on a HORIZON HPFC system (silica gel, gradient elution with 0-30% CMA in chloroform) followed by recrystallization from acetonitrile to afford 4.31 g of 1-(4-chlorobutyl)-2-propyl-2H-pyrazolo[3,4-c]quinolin-4-amine as off-white crystals, mp 172-173° C.

$^1$H-NMR (300 MHz, DMSO-d$_6$) δ 7.93 (dd, J=7.8, 1.1 Hz, 1H), 7.49 (dd, J=8.1, 1.2 Hz, 1H), 7.36-7.27 (m, 1H), 7.24-7.15 (m, 1H), 6.62 (br s, 2H), 4.35 (t, J=7.2 Hz, 2H), 3.73 (t, J=6.4 Hz, 2H), 3.31-3.23 (m, 2H), 2.01-1.86 (m, 4H), 1.84-1.72 (m, 2H), 0.92 (t, J=7.4 Hz, 3H);

$^{13}$C-NMR (75 MHz, DMSO-d$_6$) δ 150.5, 143.7, 137.3, 135.5, 125.60, 125.55, 121.7, 121.5, 119.5, 116.3, 50.7, 44.9, 31.3, 25.7, 23.9, 23.5, 10.9;

MS (APCI) m/z 317.1 (M+H)$^+$;

Anal. calcd for C$_{17}$H$_{21}$ClN$_4$: C, 64.45; H, 6.68; N, 17.68. Found: C, 64.44; H, 6.88; N, 17.79.

Example 47

1-(2-Methylpropyl)-2-propyl-6,7,8,9-tetrahydro-2H-pyrazolo[3,4-c]quinolin-4-amine

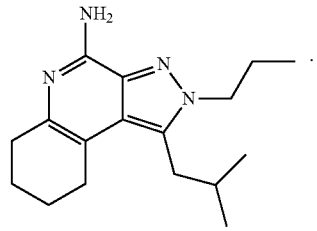 [SMILES: CCCn1nc2c(N)nc3c(c2c1CC(C)C)CCCC3]

A solution of 1-(2-methylpropyl)-2-propyl-2H-pyrazolo[3,4-c]quinolin-4-amine (0.8 g, 3 mmol), prepared as described in Example 1, in trifluoroacetic acid (10 mL) was treated with platinum (IV) oxide (0.5 g) and shaken under hydrogen pressure (50 psi, 3.4×10$^5$ Pa) for 24 hours on a Parr apparatus. The reaction mixture was diluted with chloroform (20 mL) and methanol (10 mL) and filtered through a layer of CELITE filter agent. The filtrate was concentrated under reduced pressure. The residue was suspended in 6 M aqueous hydrochloric acid (5 mL), stirred for 30 minutes, and treated with 50% aqueous sodium hydroxide to adjust the mixture to pH 13. A precipitate formed and was isolated by filtration, washed with water, and dried. The crude product was purified by chromatography on a HORIZON HPFC system (silica gel, gradient elution with 0-35% CMA in chloroform) to yield 0.55 g of 1-(2-methylpropyl)-2-propyl-6,7,8,9-tetrahydro-2H-pyrazolo[3,4-c]quinolin-4-amine as an off-white powder, mp 167-168° C.

$^1$H-NMR (300 MHz, CDCl$_3$) δ 5.02 (br s, 2H), 4.26-4.16 (m, 2H), 2.94-2.83 (m, 4H), 2.79-2.69 (m, 2H), 2.05-1.92 (m, 3H), 1.89-1.76 (m, 4H), 0.97 (d, J=6.7 Hz, 6H) 0.95 (t, J=7.5 Hz, 3H); $^{13}$C-NMR (75 MHz, CDCl$_3$) δ 148.3, 141.2, 135.3, 134.9, 123.1, 112.1, 51.9, 34.2, 32.0, 30.7, 25.5, 23.9, 23.3, 23.0, 22.3, 11.2;

MS (APCI) m/z 287.2 (M+H)$^+$;

Anal. calcd for C$_{17}$H$_{26}$N$_4$,0.01 CF$_3$COOH: C, 71.09; H, 9.12; N, 19.48; F, 0.20. Found: C, 70.77; H, 9.37; N, 19.27; F, 0.22.

Example 48

2-Ethyl-1-(2-methylpropyl)-6,7,8,9-tetrahydro-2H-pyrazolo[3,4-c]quinolin-4-amine

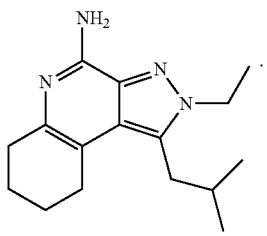 [SMILES: CCn1nc2c(N)nc3c(c2c1CC(C)C)CCCC3]

2-Ethyl-1-(2-methylpropyl)-2H-pyrazolo[3,4-c]quinolin-4-amine (0.700 g, 1.61 mmol), prepared as described in Example 2, was reduced using the procedure described in Example 47. After chromatographic purification, the product was crystallized from acetonitrile to yield 0.39 g of 2-ethyl-1-(2-methylpropyl)-6,7,8,9-tetrahydro-2H-pyrazolo[3,4-c]quinolin-4-amine as a white crystalline solid, mp 206-207° C.

$^1$H-NMR (300 MHz, CDCl$_3$) δ 14.58 (br s, 1H), 10.88 (br s, 1H), 6.21 (br s, 1H), 4.33 (q, J=7.3 Hz, 2H), 2.88 (d, J=7.6 Hz, 2H), 2.86-2.71 (m, 4H), 1.95 (heptet, J=6.9 Hz, 1H), 1.88-1.76 (m, 4H), 1.56 (t, J=7.3 Hz, 3H), 0.99 (d, J=6.7 Hz, 6H);

$^{13}$C-NMR (75 MHz, CDCl$_3$) δ 149.2, 137.0, 133.2, 131.6, 122.7, 112.2, 45.9, 33.9, 30.5, 26.5, 24.4, 22.3, 22.0, 21.6, 15.4;

MS (APCI) m/z 273.2 (M+H)$^+$;

Anal. calcd for C$_{16}$H$_{24}$N$_4$ · 1.02 CF$_3$COOH: C, 55.74; H, 6.49; N, 14.41; F, 14.96. Found: C, 55.41; H, 6.90; N, 14.38; F, 14.68.

Example 49

1-(2-Cyclohexylethyl)-2-methyl-6,7,8,9-tetrahydro-2H-pyrazolo[3,4-c]quinolin-4-amine

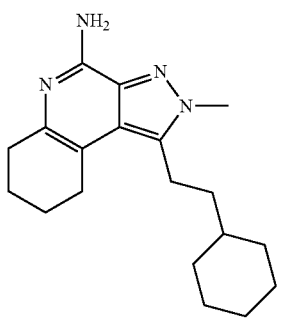 [SMILES: Cn1nc2c(N)nc3c(c2c1CCC1CCCCC1)CCCC3]

2-Methyl-1-(2-phenylethyl)-2H-pyrazolo[3,4-c]quinolin-4-amine (0.79 g, 2.6 mmol), prepared as described in Example 40, was reduced using the procedure described in Example 47. After chromatographic purification, the product was crystallized from acetonitrile to yield 0.44 g of 1-(2-cyclohexylethyl)-2-methyl-6,7,8,9-tetrahydro-2H-pyrazolo[3,4-c]quinolin-4-amine as a white powder, mp 230-231° C.

$^1$H-NMR (300 MHz, CDCl$_3$) δ 4.96 (br s, 2H), 4.02 (s, 3H), 3.03-2.93 (m, 2H), 2.91-2.81 (m, 2H), 2.78-2.68 (m, 2H), 1.91-1.61 (m, 9H), 1.54-1.10 (m, 6H), 1.08-0.89 (m, 2H);

$^{13}$C-NMR (75 MHz, CDCl$_3$) δ 148.0, 141.3, 136.4, 135.2, 122.8, 112.0, 38.2, 37.8, 37.3, 33.1, 31.9, 26.5, 26.2, 25.1, 23.3, 22.9;

MS (APCI) m/z 313.2 (M+H)$^+$;

Anal. calcd for C$_{19}$H$_{28}$N$_4$ · 0.12 H$_2$O: C, 72.53; H, 9.05; N, 17.81. Found: C, 72.27; H, 9.16; N, 17.41.

Example 50

1-(2-Aminoethyl)-2-methyl-6,7,8,9-tetrahydro-2H-pyrazolo[3,4-c]quinolin-4-amine

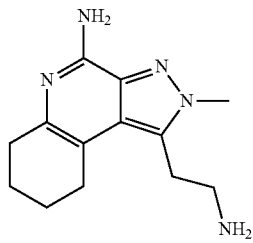 [SMILES: Cn1nc2c(N)nc3c(c2c1CCN)CCCC3]

Part A

A modification of the method described in Part A of Example 11 was followed. A mixture of ethyl 2,4-dioxo-6-phthalimidohexanoate, sodium salt (prepared as described in Part A of Example 23, 100 g, 295 mmol) in glacial acetic acid (0.3 L) was cooled to 9° C. before the addition of methylhydrazine (16.0 mL, 300 mmol). During the addition, the reaction temperature did not exceed 16° C. Solids were rinsed from the inside of the flask walls into the mixture with acetic acid (50 mL) and the mixture was allowed to warm to ambient temperature and stir overnight. Water was added to the mixture and additional solid precipitated. The solid was isolated by filtration, dried, and recrystallized from ethanol. The solid was isolated and dried to yield 75.2 g of ethyl 5-[2-(1,3-dioxo-1,3-dihydro-2H-isoindol-2-yl)ethyl]-1-methyl-1H-pyrazole-3-carboxylate.

Part B

A solution of ethyl 5-[2-(1,3-dioxo-1,3-dihydro-2H-isoindol-2-yl)ethyl]-1-methyl-1H-pyrazole-3-carboxylate (75.2 g, 230 mmol) in 1 M aqueous hydrochloric acid (450 mL) and acetic acid (450 mL) was heated at 100° C. (internal temperature) for 5.2 hours, cooled to ambient temperature, and stirred for about 12 hours. A white solid was isolated by filtration, washed with water, and dried to provide 52.6 g of 5-[2-(1,3-dioxo-1,3-dihydro-2H-isoindol-2-yl)ethyl]-1-methyl-1H-pyrazole-3-carboxylic acid.

Part C

Toluene (250 mL) and thionyl chloride (30.4 mL, 418 mmol) were added to 5-[2-(1,3-dioxo-1,3-dihydro-2H-isoindol-2-yl)ethyl]-1-methyl-1H-pyrazole-3-carboxylic acid (50.0 g, 167 mmol). The mixture was heated at reflux for 2 hours, cooled to ambient temperature, and poured onto ice. A solid was isolated by filtration, washed with water, and dried to afford 47.5 g of a white solid.

Part D

To a solid from Part C (25.0 g) in dichloromethane (250 mL) at 0° C. was added concentrated ammonium hydroxide (50 mL) in one portion. The mixture was stirred for 5 minutes, then hexanes (200 mL) was added and the mixture was filtered, washed with water, then dried to provide 13.07 g of 5-[2-(1,3-dioxo-1,3-dihydro-2H-isoindol-2-yl)ethyl]-1-methyl-1H-pyrazole-3-carboxamide as a white powder.

Part E

To a mixture of 5-[2-(1,3-dioxo-1,3-dihydro-2H-isoindol-2-yl)ethyl]-1-methyl-1H-pyrazole-3-carboxamide (10.5 g, 35.2 mmol) and pyridine (5.69 mL, 70.4 mmol) in dichloromethane (200 mL) at 0° C. was added trifluoroacetic anhydride (5.47 mL, 38.7 mmol) over two minutes. The solution was stirred at 0° C. for about 20 minutes, then was allowed to warm to ambient temperature. After 2 hours, more pyridine (2.8 mL) and trifluoroacetic anhydride (1.5 mL) were added. The reaction was quenched by adding 2 M sodium carbonate (200 mL). The mixture was extracted with chloroform. The organic layers were combined, dried over magnesium sulfate, filtered, and concentrated under reduced pressure to a volume of about 50 mL. A white solid was present. Heptane (150 mL) was added, and the mixture was concentrated to a volume of about 25 mL, then hexanes were added and the solid was collected by filtration. The white solid was washed with hexanes and dried to provide 8.50 g of 5-[2-(1,3-dioxo-1,3-dihydro-2H-isoindol-2-yl)ethyl]-1-methyl-1H-pyrazole-3-carbonitrile that contained a small amount of an impurity.

Part F

To a mixture of 5-[2-(1,3-dioxo-1,3-dihydro-2H-isoindol-2-yl)ethyl]-1-methyl-1H-pyrazole-3-carbonitrile (8.50 g, 30.3 mmol) and potassium acetate (4.50 g, 45.5 mmol) in acetic acid (40 mL) and dichloromethane (120 mL) was slowly added bromine (6.79 g, 42.5 mmol). The mixture was stirred overnight. Saturated aqueous sodium hydrogensulfite was added until the mixture became colorless, then the mixture was concentrated under reduced pressure to form a slurry. Water (200 mL) was added to the slurry and a white solid was isolated by filtration, washed with water, and dried to afford 9.15 g of 4-bromo-5-[2-(1,3-dioxo-1,3-dihydro-2H-isoindol-2-yl)ethyl]-1-methyl-1H-pyrazole-3-carbonitrile as a white solid.

Part G

A mixture of hydrazine hydrate (6.40 g, 127 mmol) and 4-bromo-5-[2-(1,3-dioxo-1,3-dihydro-2H-isoindol-2-yl)ethyl]-1-methyl-1H-pyrazole-3-carbonitrile (9.15 g, 25.5 mmol) in ethanol (200 mL) was heated at reflux for 80 minutes, then was allowed to cool to ambient temperature in a water bath. A precipitate formed and was isolated by filtration and washed with cold ethanol. The filtrate was concentrated under reduced pressure, and the resulting white solid was twice treated with toluene and concentrated under reduced pressure then dried under vacuum to provide 5.74 g of 5-(2-aminoethyl)-4-bromo-1-methyl-1H-pyrazole-3-carbonitrile as an off-white solid.

Part H

Di-tert-butyl dicarbonate (13.3 g, 60.9 mmol) was added to a mixture of 5-(2-aminoethyl)-4-bromo-1-methyl-1H-pyrazole-3-carbonitrile (11.62 g, 50.7 mmol) in 1-methyl-2-pyrrolidinone at 0° C. The mixture was allowed to warm to ambient temperature and was stirred for 20 minutes; a solution formed. Water was added to the stirred solution, causing a solid to form. The mixture was cooled and the solid was isolated by filtration, washed with water, and dried. The crude product was purified by chromatography on a HORIZON HPFC system (silica gel, gradient elution with 60-75% ethyl acetate in hexanes). The appropriate fractions were combined and concentrated under reduced pressure to provide 12.0 g of tert-butyl 2-(4-bromo-3-cyano-1-methyl-1H-pyrazol-5-yl)ethylcarbamate as a white solid.

Part I

A mixture of tert-butyl 2-(4-bromo-3-cyano-1-methyl-1H-pyrazol-5-yl)ethylcarbamate (19.1 g, 58.0 mmol), 2-aminophenylboronic acid hydrochloride (15.09 g, 87.03 mmol), triphenylphosphine (1.37 g, 5.22 mmol), palladium (II) acetate (390 mg, 1.74 mmol), 2 M aqueous sodium carbonate (87 mL, 174 mmol), 1-propanol (100 mL), and water (20 mL) was heated at 100° C. for 4 hours under a nitrogen atmosphere. Additional 1-propanol (100 mL) and water (20 mL) were added and the mixture was heated at 100° C. overnight. The mixture was allowed to cool to ambient temperature and chloroform (200 mL) was added. After 10 minutes, the mixture was transferred to a separatory funnel and the organic layer was isolated and washed with water (200 mL) and brine (200 mL). The combined organic layers were dried over sodium sulfate, filtered, and concentrated to provide an oil that was purified by flash chromatography (silica gel, eluting sequentially with chloroform, 10% CMA in chloroform, and finally 40% CMA in chloroform) to yield an oil that was used in the next step.

Part J

Acetyl chloride (7.8 g, 100 mmol) was added to ethanol (100 mL) at 0° C. The resulting solution was added to the oil from Part I. The solution was heated at reflux overnight. Upon cooling to ambient temperature, a precipitate formed that was isolated by filtration, washed with a small amount of cold ethanol, and dried under vacuum at 75° C. for 4 hours to give 7.34 g of 1-(2-aminoethyl)-2-methyl-2H-pyrazolo[3,4-c]quinolin-4-amine dihydrochloride as a white solid.

Part K

A solution of 1-(2-aminoethyl)-2-methyl-2H-pyrazolo[3,4-c]quinolin-4-amine dihydrochloride (7.20 g, 22.9 mmol) in trifluoroacetic acid (75 mL) was treated with platinum (IV) oxide (7.0 g) and shaken under hydrogen pressure (50 psi, $3.4 \times 10^5$ Pa) for 24 hours on a Parr apparatus. The reaction mixture was diluted with chloroform (50 mL) and methanol (25 mL) and filtered through a layer of CELITE filter agent. The filtrate was concentrated under reduced pressure. The residue was suspended in concentrated hydrochloric acid (5 mL), stirred for 2 hours, treated with 50% aqueous sodium hydroxide to adjust the pH to 13, and stirred at ambient temperature overnight. The mixture was diluted with water (100 mL) and was extracted with chloroform (5×150 mL). The combined organic layers were dried over sodium sulfate, filtered, and concentrated under reduced pressure to yield 5.10 g of 1-(2-aminoethyl)-2-methyl-6,7,8,9-tetrahydro-2H-pyrazolo[3,4-c]quinolin-4-amine as an off-white foam.

¹H-NMR (300 MHz, DMSO-d₆) δ 6.12-3.20 (br abs., 4H), 4.04 (s, 3H), 3.21-3.10 (m, 2H), 2.91-2.76 (m, 4H), 2.61-2.52 (m, 2H), 1.80-1.67 (m, 4H);
MS (APCI) m/z 246.3 (M+H)⁺.

Example 51

1-(2-Aminoethyl)-2-propyl-6,7,8,9-tetrahydro-2H-pyrazolo[3,4-c]quinolin-4-amine

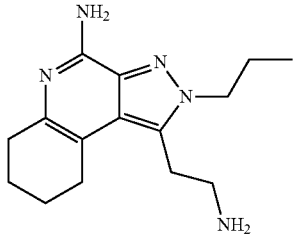 [SMILES: CCCn1nc2c(N)nc3c(c2c1CCN)CCCC3]

Part A

A modification of the method described in Part A of Example 11 was followed. A mixture of ethyl 2,4-dioxo-6-phthalimidohexanoate, sodium salt (prepared as described in Part A of example 23, 67.9 g, 200 mmol) in glacial acetic acid (0.2 L) was cooled to 9° C. before the addition of propylhydrazine oxalate (32.8 g, 200 mmol). During the addition, the reaction temperature did not exceed 17° C. The mixture was allowed to warm to ambient temperature and stir for 4 hours. Water (600 mL) was added to the mixture and additional solid precipitated. The solid was isolated by filtration, washed with water, and dried to yield 67.4 g of a yellow solid. The solid was stirred in 1 M aqueous potassium acetate (311 mL), isolated by filtration, washed with water, dried, and recrystallized from ethanol/heptane. The final solid was isolated, washed with 2:1 heptane/ethyl acetate, and dried to yield 45.2 g of ethyl 5-[2-(1,3-dioxo-1,3-dihydro-2H-isoindol-2-yl)ethyl]-1-propyl-1H-pyrazole-3-carboxylate.

Part B

A stirred solution of ethyl 5-[2-(1,3-dioxo-1,3-dihydro-2H-isoindol-2-yl)ethyl]-1-propyl-1H-pyrazole-3-carboxylate (45.1 g, 127 mmol) in 1 M aqueous hydrochloric acid (157 mL) and acetic acid (157 mL) was heated at 95° C. (internal temperature) for 10 hours and then cooled to 10° C. Water (300 mL) was added and a white solid was isolated by filtration, washed with water and diethyl ether, and dried. The solid was treated with toluene (150 mL) and heated at reflux for 3 hours with a Dean-Stark trap. The mixture was cooled in an ice bath to 10° C. and a solid was isolated by filtration and dried to provide 28.85 g of 5-[2-(1,3-dioxo-1,3-dihydro-2H-isoindol-2-yl)ethyl]-1-propyl-1H-pyrazole-3-carboxylic acid.

Part C

Toluene (70 mL) and thionyl chloride (70 mL) were added to 5-[2-(1,3-dioxo-1,3-dihydro-2H-isoindol-2-yl)ethyl]-1-propyl-1H-pyrazole-3-carboxylic acid (28.8 g, 87.8 mmol) and the mixture was heated at reflux for 1 hour, cooled to ambient temperature, and concentrated under reduced pressure to yield a yellow solid. The solid was dissolved in dichloromethane (200 mL). The solution was cooled to 0° C., then concentrated ammonium hydroxide (125 mL) was added in one portion. The resulting mixture was stirred for 1 hour at 0° C. The dichloromethane was removed under reduced pressure. A solid was isolated by filtration, washed with water, and dried to afford 28.70 g of 5-[2-(1,3-dioxo-1,3-dihydro-2H-isoindol-2-yl)ethyl]-1-propyl-1H-pyrazole-3-carboxamide.

Part D

To a mixture of 5-[2-(1,3-dioxo-1,3-dihydro-2H-isoindol-2-yl)ethyl]-1-propyl-1H-pyrazole-3-carboxamide (16.3 g, 50.0 mmol) and pyridine (20.9 mL, 150 mmol) in dichloromethane (100 mL) at 0° C. was added a solution of trifluoroacetic anhydride (9.89 mL, 70.0 mmol) in dichloromethane (100 mL) over ten minutes. The solution was stirred at 0° C. for about 15 minutes, then was allowed to warm to ambient temperature. After 45 minutes, saturated aqueous sodium bicarbonate (200 mL) was added and the dichloromethane was removed under reduced pressure. A white solid was isolated by filtration, washed with water, and dried. The solid was recrystallized from 1:1 heptane/ethyl acetate to yield 5-[2-(1,3-dioxo-1,3-dihydro-2H-isoindol-2-yl)ethyl]-1-propyl-1H-pyrazole-3-carbonitrile.

Part E

To a solution of 5-[2-(1,3-dioxo-1,3-dihydro-2H-isoindol-2-yl)ethyl]-1-propyl-1H-pyrazole-3-carbonitrile (14.1 g, 45.7 mmol) and potassium acetate (6.73 g, 68.6 mmol) in acetic acid (91 mL) and dichloromethane (46 mL) was slowly added bromine (3.28 g, 64.0 mmol). The mixture was stirred for one day. Saturated aqueous sodium hydrogensulfite was added until the mixture became colorless, then the mixture was concentrated under reduced pressure to form a slurry. Water (450 mL) was added to the slurry and a white solid was isolated by filtration, washed with water, and dried to afford 17.24 g of 4-bromo-5-[2-(1,3-dioxo-1,3-dihydro-2H-isoindol-2-yl)ethyl]-1-propyl-1H-pyrazole-3-carbonitrile as a white solid.

Part F

A mixture of hydrazine hydrate (11.1 g, 222 mmol) and 4-bromo-5-[2-(1,3-dioxo-1,3-dihydro-2H-isoindol-2-yl)ethyl]-1-propyl-1H-pyrazole-3-carbonitrile (17.2 g, 44.4 mmol) in ethanol (570 mL) was heated at reflux for 90 minutes, then was allowed to cool to ambient temperature. A precipitate was isolated by filtration and washed with cold ethanol. The filtrate was concentrated under reduced pressure to generate an off-white solid that was suspended in dichloromethane (133 mL). Di-tert-butyl dicarbonate (11.6 g, 53.3 mmol) was added to the mixture, which was then stirred overnight. The mixture was filtered and the filtrate was concentrated under reduced pressure to yield a yellow oil. The crude product was purified by chromatography on a HORIZON HPFC system (silica gel, gradient elution with 40-60% ethyl acetate in hexanes). The appropriate fractions were combined and concentrated under reduced pressure to provide 15.8 g of tert-butyl 2-(4-bromo-3-cyano-1-propyl-1H-pyrazol-5-yl)ethylcarbamate as a colorless oil.

Part G

A flask containing a mixture of tert-butyl 2-(4-bromo-3-cyano-1-propyl-1H-pyrazol-5-yl)ethylcarbamate (15.8 g, 44.2 mmol), 2-aminophenylboronic acid hydrochloride (11.5 g, 66.3 mmol), triphenylphosphine (1.04 g, 3.98 mmol), palladium (II) acetate (299 mg, 1.33 mmol), 2 M aqueous sodium carbonate (67 mL, 133 mmol), 1-propanol (77.4 mL), and water (15.5 mL) was heated overnight under a nitrogen atmosphere in a 100° C. oil bath. The reaction was allowed to cool to ambient temperature and water (300 mL) was added. The mixture was extracted with chloroform, dried over magnesium sulfate, filtered, and concentrated to provide an oil that was purified twice by flash chromatography (silica gel, first column: eluted sequentially with 0-10% CMA in chloroform, and then 25% CMA in chloroform; second column: gradient elution with 50-60% ethyl acetate in hexanes) to yield 7.3 g of tert-butyl 2-(4-amino-2-propyl-2H-pyrazolo[3,4-c]quinolin-1-yl)ethylcarbamate as a yellow resin.

Part H

Acetyl chloride (7.1 mL, 100 mmol) was added to ethanol (100 mL) at 0° C. The resulting solution was added to the tert-butyl 2-(4-amino-2-propyl-2H-pyrazolo[3,4-c]quinolin-1-yl)ethylcarbamate from Part G. The solution was heated at reflux for 9.5 hours. Upon cooling to ambient temperature, a precipitate formed that was isolated after two days by filtration, washed with a small amount of cold ethanol, and dried to yield 5.78 g of 1-(2-aminoethyl)-2-propyl-2H-pyrazolo[3,4-c]quinolin-4-amine dihydrochloride as a white solid.

Part I 1-(2-Aminoethyl)-2-propyl-2H-pyrazolo[3,4-c]quinolin-4-amine dihydrochloride (2.50 g, 7.30 mmol) was reduced using the procedure described in Example 47. After the reaction was filtered and concentrated, the residue was triturated with diethyl ether to precipitate a solid that was isolated by filtration, washed with diethyl ether, and dried under vacuum. After chromatographic purification, the product was crystallized from acetonitrile to yield 0.44 g of the bis-trifluoroacetic acid salt of 1-(2-aminoethyl)-2-propyl-6,7,8,9-tetrahydro-2H-pyrazolo[3,4-c]quinolin-4-amine as a white powder, 228-230° C.

$^1$H-NMR (300 MHz, DMSO-$d_6$) δ 13.13 (s, 1H), 9.30-6.50 (br peaks, 5H), 4.42 (t, J=7.2 Hz, 2H), 3.47-3.33 (m, 2H), 3.11-2.92 (m, 2H), 2.87-2.75 (m, 2H), 2.68-2.57 (m, 2H), 1.99-1.86 (m, 2H) 1.86-1.68 (m, 4H);

MS (APCI) m/z 274.3 (M+H)$^+$.

Examples 52-55

A mixture of tert-butoxycarbonylamino-3-pyridylboronic acid (prepared as described in Parts A and B of Example 15, 1.9 equivalents) in 1-propanol (15 mL) and 1 M aqueous HCl (15 mL) was heated at 80° C. for 1 hour. The reaction was allowed to cool to ambient temperature and solid sodium carbonate (1.5 equivalents) was added with stirring. A solution of a 4-bromo-1,5-disubstitued-1H-pyrazole-3-carbonitrile (1.51-2.07 g, 6.63-7.80 mmol, 1 equivalent) shown in the table below in 1-propanol (4-5 mL) was added, followed by triphenylphosphine (0.06 equivalent) and palladium (II) acetate (0.02 equivalent). In Example 55, tetrakis(triphenylphosphine)palladium(0) (0.05 equivalent) was used instead of triphenylphosphine and palladium (II) acetate. The flask was fitted with a reflux condenser and a nitrogen inlet line, then was placed under vacuum and back-filled with nitrogen three times. The pale yellow solution was heated under a nitrogen atmosphere at 100° C. for 18-21 hours. The 1-propanol was evaporated under reduced pressure. The remaining liquid was dissolved in chloroform (100 mL), washed with water (100 mL), dried over magnesium sulfate, filtered, and concentrated under reduced pressure. The crude product was purified by chromatography on a HORIZON HPFC system (silica gel, gradient elution using 0-30% CMA in chloroform). In Example 55, a gradient elution with 0-25% CMA in chloroform was used. The appropriate fractions were combined and concentrated to yield a pale yellow solid that was recrystallized from boiling acetonitrile. White crystals were isolated, washed with cold acetonitrile, and dried overnight at 60° C. in a vacuum oven to provide the product.

Example 52

Isolated 0.18 g of 1,2-diethyl-2H-pyrazolo[3,4-c]-1,8-naphthyridin-4-amine as off-white needles, mp 286-288° C.

$^1$H NMR (300 MHz, $d_6$-DMSO) δ 8.46 (dd, J=4.7, 1.9, 1H), 8.24 (dd, J=7.8, 1.9, 1H), 7.16 (dd, J=7.8, 4.7, 1H), 7.05 (s, 2H), 4.42 (q, J=7.1, 2H), 3.24 (q, J=7.5, 2H), 1.47 (t, J=7.1, 3H), 1.24 (t, J=7.5, 3H);

$^{13}$C NMR (75 MHz, $d_6$-DMSO) δ 154.6, 153.0, 146.9, 139.8, 135.2, 129.8, 117.0, 115.8, 114.2, 44.5, 18.2, 15.9, 13.1;

Anal. calcd for $C_{13}H_{15}N_5$: C, 64.71; H, 6.27; N, 29.02. Found: C, 64.49; H, 6.31; N, 29.19.

Example 53

Isolated 90 mg of 1-ethyl-2-propyl-2H-pyrazolo[3,4-c]-1,8-naphthyridin-4-amine as off-white needles, mp 303-305° C.

$^1$H NMR (300 MHz, $d_6$-DMSO) δ 8.46 (dd, J=4.7, 1.9, 1H), 8.24 (dd, J=7.8, 1.9, 1H), 7.16 (dd, J=7.8, 4.7, 1H), 7.06 (s, 2H), 4.34 (q, J=6.9, 2H), 3.24 (q, J=7.5, 2H), 1.90 (sextet, J=7.1, 2H), 1.26 (t, J=7.8, 3H), 0.91 (t, J=7.5, 3H);

$^{13}$C NMR (75 MHz, $d_6$-DMSO) δ 153.0, 149.5, 146.9, 140.3, 135.2, 129.8, 117.0, 115.7, 114.2, 50.9, 23.6, 18.2, 13.1, 10.9;

Anal. calcd for $C_{14}H_{17}N_5$: C, 65.86; H, 6.71; N, 27.43. Found: C, 65.80; H, 6.67; N, 27.50.

Example 54

Isolated 0.156 g of 2-methyl-1-(2,2-dimethylpropyl)-2H-pyrazolo[3,4-c]-1,8-naphthyridin-4-amine as off-white needles, mp 323-326° C. $^1$H NMR (300 MHz, $d_6$-DMSO) δ 8.49 (dd, J=7.9, 1.9, 1H), 8.44 (dd, J=4.6, 1.6, 1H), 7.12 (dd, J=7.8, 4.7, 1H), 7.08 (s, 2H), 4.10 (s, 3H), 3.23 (s, 2H), 0.99 (s, 9H); $^{13}$C NMR (75 MHz, $d_6$-DMSO) δ 154.8, 153.0, 147.0, 137.5, 135.0, 130.5, 117.5, 116.4, 114.4, 38.4, 37.0, 35.3, 29.4;

Anal. calcd for $C_{15}H_{19}N_5$: C, 66.89; H, 7.11; N, 26.00. Found: C, 66.95; H, 6.95; N, 26.08.

Example 55

Isolated 0.24 g of 2-benzyl-1-(2-methylpropyl)-2H-pyrazolo[3,4-c]-1,8-naphthyridin-4-amine as off-white needles, mp 232-235° C. $^1$H NMR (300 MHz, $d_6$-DMSO) δ 8.46 (dd, J=4.4, 1.6, 1H), 8.28 (dd, J=7.8, 1.9, 1H), 7.36-7.27 (m, 3H), 7.19-7.13 (m, 5H), 5.70 (s, 2H), 3.12 (d, J=8.5, 2H), 1.95 (septet, J=6.9, 1H), 0.92 (d, J=6.6, 6H);

$^{13}$C NMR (75 MHz, d$_6$-DMSO) δ 154.8, 153.1, 147.1, 138.9, 136.9, 135.6, 130.2, 128.6, 127.6, 126.7, 116.9, 114.1, 53.3, 33.2, 28.6, 21.8;

Anal. calcd for C$_{20}$H$_{21}$N$_5$: C, 72.48; H, 6.39; N, 21.13. Found: C, 72.24; H, 6.56; N, 21.18.

Examples 52-55

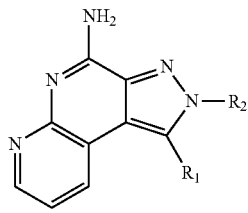

| Example | Starting Material | R$_1$ | R$_2$ |
|---|---|---|---|
| 52 | 4-Bromo-1,5-diethyl-1H-pyrazole-3-carbonitrile (prepared Example 11) | —CH$_2$CH$_3$ | —CH$_2$CH$_3$ |
| 53 | 4-Bromo-5-ethyl-1-propyl-1H-pyrazole-3-carbonitrile (prepared in Example 44) | —CH$_2$CH$_3$ | —CH$_2$CH$_2$CH$_3$ |
| 54 | 4-Bromo-1-methyl-5-(2,2-dimethylpropyl)-1H-pyrazole-3-carbonitrile (prepared in Example 37) | —CH$_2$C(CH$_3$)$_3$ | —CH$_3$ |
| 55 | 4-Bromo-1-benzyl-5-(2-methylpropyl)-1H-pyrazole-3-carbonitrile (prepared in Example 8) | —CH$_2$CH(CH$_3$)$_2$ | —CH$_2$C$_6$H$_5$ |

Example 56

2-Butyl-1-(2-methylpropyl)-2H-pyrazolo[3,4-c]-1,6-naphthyridin-4-amine

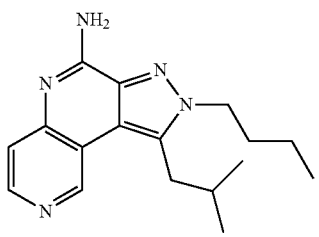 [SMILES: CCCCn1nc2c(N)nc3ccncc3c2c1CC(C)C]

Part A

A 2.5 M solution of n-butyl lithium in hexane (100 mL, 250 mmol) was added over 20 minutes to a stirred solution of tert-butyl pyridin-4-ylcarbamate (19.4 g, 100 mmol) and N,N,N',N'-tetramethylethylenediamine (31.4 g, 270 mmol) in THF (500 mL) at −78° C. tert-Butyl pyridin-4-ylcarbamate is available from a literature procedure (Spivey, A. C. et al. *J. Org. Chem.* 1999, 64, 9430-9443). A white solid appeared and the mixture was stirred for 10 minutes at −78° C., then was allowed to warm slowly to −4° C. before cooling to −78° C. again. Trimethyl borate (39.5 g, 380 mmol) was added over 15 minutes. The solution was allowed to warm to 0° C., then was poured into saturated aqueous ammonium chloride (500 mL). The mixture was stirred for 2 minutes. After standing at ambient temperature overnight, the mixture was partitioned between diethyl ether and brine. The organic layer was separated and washed with brine. A white solid formed in the organic layer and was isolated by filtration. The solid was washed sequentially with diethyl ether, water, and diethyl ether, then was dried to provide 17.1 g of 4-[(tert-butoxycarbonyl)amino]pyridin-3-ylboronic acid as a white solid.

Part B

2-Butyl-1-(2-methylpropyl)-2H-pyrazolo[3,4-c]-1,6-naphthyridin-4-amine was synthesized from 4-[(tert-butoxycarbonyl)amino]pyridin-3-ylboronic acid (2.48 g, 10.4 mmol) and 4-bromo-1-butyl-5-(2-methylpropyl)-1H-pyrazole-3-carbonitrile (prepared as described in Parts A-F of Example 4, 1.56 g, 5.49 mmol) according to the reaction conditions described in Examples 52-54. Additional palladium (II) acetate (50 mg) and triphenylphosphine (170 mg) were added after the reaction had been heated for 23 hours. After the addition, the flask was placed under vacuum and back-filled with nitrogen twice. The solution was heated at 100° C. for an additional 29 hours. The reaction was worked-up and purified as described in Example 54, but was not recrystallized from acetonitrile, to provide 25 mg of 2-butyl-1-(2-methylpropyl)-2H-pyrazolo[3,4-c]-1,6-naphthyridin-4-amine as an off-white solid.

$^1$H NMR (300 MHz, d$_6$-DMSO) δ 9.10 (s, 1H), 8.31 (d, J=5.4, 1H), 7.30 (d, J=5.4, 1H), 7.25 (s, 2H), 4.37 (t, J=7.2, 2H), 3.17 (d, J=7.5, 2H), 2.10-1.86 (m, 3H), 1.39-1.32 (m, 2H), 0.99 (d, J=6.6, 6H), 0.92 (t, J=7.6, 3H);

HRMS Measured Mass (M+H)$^+$298.2023.

Example 57

2-Propyl-1-[3-(3-pyridin-3-ylisoxazol-5-yl)propyl]-2H-pyrazolo[3,4-c]quinolin-4-amine

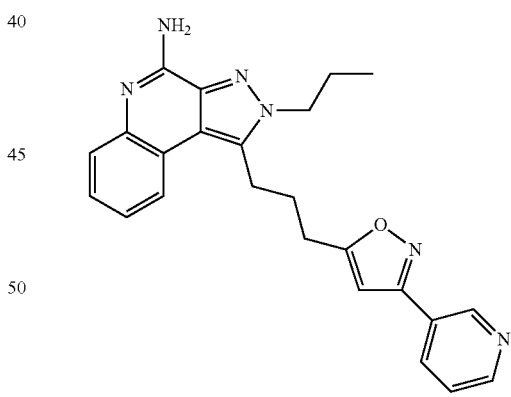

Part A

A mixture of 1-(4-chlorobutyl)-2-propyl-2H-pyrazolo[3,4-c]quinolin-4-amine (prepared as described in Example 46, 5.00 g, 15.8 mmol), 4-dimethylaminopyridine (0.04 g, 0.316 mmol), di-tert-butyldicarbonate (13.8 g, 63.12 mmol), and triethylamine (5.50 mL, 39.5 mmol) was heated at 90° C. for 20 minutes and a solution formed. The temperature was decreased to 60° C. and the solution was heated for 1 hour. The solution was allowed to cool to ambient temperature and was concentrated under reduced pressure. The resulting oil was partitioned between dichloromethane and 1 M aqueous potassium hydroxide. The organic layer was washed with water and brine, dried over sodium sulfate, filtered, and concentrated to a yield an oil that was dried under vacuum. The oil was triturated with an approximately 1:1 diethyl ether/hexanes solution, resulting in the formation of a solid that was isolated by filtration and dried to provide 5.68 g of di(tert-butyl) 1-(4-chlorobutyl)-2-propyl-2H-pyrazolo[3,4-c]quinolin-4-ylimidodicarbonate as a tan solid.

Part B

Potassium acetate (0.83 g, 8.432 mmol) and sodium iodide (16 g, 1.05 mmol) was added to a solution of di(tert-butyl) 1-(4-chlorobutyl)-2-propyl-2H-pyrazolo[3,4-c]quinolin-4-ylimidodicarbonate (2.18 g, 4.22 mmol) in DMF (15 mL). The reaction mixture was heated at 90° C. under a nitrogen atmosphere for 4.5 hours. The reaction was allowed to cool to ambient temperature and the volatiles were removed under reduced pressure. The resulting oil was partitioned between ethyl acetate and water. The organic layer was isolated and washed with water (2×25 mL) and brine (3×20 mL), dried over magnesium sulfate, filtered, and concentrated under reduced pressure to yield an oil that was dried under vacuum to provide 1.76 g of 4-{4-[bis(tert-butoxycarbonyl)amino]-2-propyl-2H-pyrazolo[3,4-c]quinolin-1-yl} butyl acetate.

Part C

Potassium carbonate (6 mg, 0.041 mmol) was added to a solution of 4-{4-[bis(tert-butoxycarbonyl)amino]-2-propyl-2H-pyrazolo[3,4-c]quinolin-1-yl}butyl acetate (0.8823 g, 1.632 mmol) in methanol (5 mL). The mixture was stirred at ambient temperature for 1.3 hours. The volatiles were removed under reduced pressure. The resulting oil was purified by flash chromatography (silica gel, eluted with 100% ethyl acetate) to yield 0.1466 g of di(tert-butyl) 1-(4-hydroxybutyl)-2-propyl-2H-pyrazolo[3,4-c]quinolin-4-ylimidodicarbonate in about 87% purity.

Part D

To dichloromethane (5 mL) at −78° C. was added dimethylsulfoxide (0.12 mL, 1.6 mmol) and oxalyl chloride (0.11 mL, 1.2 mmol). After several minutes, a solution di(tert-butyl) 1-(4-hydroxybutyl)-2-propyl-2H-pyrazolo[3,4-c]quinolin-4-ylimidodicarbonate (0.5449 g, 1.093 mmol) and triethylamine (0.46 mL, 3.3 mmol) in dichloromethane (5 mL) was added dropwise to the −78° C. solution. After 15 minutes, the cooling bath was removed and the solution was allowed to warm to ambient temperature, during which time more dichloromethane (20 mL) was added. The solution was transferred to a separatory funnel and washed with aqueous potassium carbonate, water, and brine. The solution was dried over sodium sulfate, filtered, and concentrated under reduced pressure. The resulting oil was dried under vacuum to yield 0.5845 g of di(tert-butyl) 1-(4-oxobutyl)-2-propyl-2H-pyrazolo[3,4-c]quinolin-4-ylimidodicarbonate that contained a small amount of dimethylsulfoxide, but was used without further purification.

Part E

Diethyl 1-diazo-2-oxopropylphosphonate (0.28 g, 1.3 mmol) was prepared by the method of Bestmann, H. J. et al., *Synlett*, 1996, 6, 521-522 and added to a stirred mixture of di(tert-butyl) 1-(4-oxobutyl)-2-propyl-2H-pyrazolo[3,4-c]quinolin-4-ylimidodicarbonate (0.543 g, 1.09 mmol) and potassium carbonate (0.31 g, 2.2 mmol) in methanol (5 mL) at ambient temperature. After 4 hours, the reaction was concentrated under reduced pressure. The oil was dissolved in dichloromethane, washed with water and brine, dried over sodium sulfate, filtered, and concentrated under reduced pressure. The crude product was purified by flash chromatography (silica gel, eluted with 5% ethyl acetate in dichloromethane) to yield 0.2498 g of a white solid that was used without further purification in the next step.

Part F

N-Chlorosuccinimide (0.15 g, 1.0 mmol) was added to a solution of 3-pyridine aldoxime (0.13 g, 1.0 mmol) in THF (5 mL). The solution was stirred at ambient temperature for 1 day. The material from Part E (0.2498 g, 0.5071 mmol) and anhydrous triethylamine (0.16 mL, 1.1 mmol) were added and the solution was heated at 60° C. for 20 hours. The volatiles were removed under reduced pressure to yield a brown oil that was purified by flash chromatography (silica gel, sequential elution with 40% ethyl acetate in hexanes, 40% ethyl acetate in dichloromethane, and finally 100% ethyl acetate) to yield 0.1105 g of material that was used without further purification in the next step.

Part G

A solution of the material from Part F (0.1105 g) in a solution of 1:1 ethanol/concentrated hydrochloric acid was heated at 60° C. under a nitrogen atmosphere for 2 hours. The volatiles were removed under reduced pressure. The resulting oil was dissolved in water and 1 drop of 50% aqueous sodium hydroxide was added to adjust the pH to 14. The mixture was extracted with dichloromethane several times. The organic layers were combined, washed with water and brine, dried over magnesium sulfate, filtered, and concentrated under reduced pressure to yield an oil. The oil was dried under vacuum, then triturated with hexanes to yield a solid that was isolated by filtration. The solid was dried under vacuum at 70° C. to yield 0.0376 g of 2-propyl-1-[3-(3-pyridin-3-ylisoxazol-5-yl)propyl]-2H-pyrazolo[3,4-c]quinolin-4-amine as a white powder, mp 192.0-193.0° C.

$^1$H NMR (300 MHz, CDCl$_3$) δ 8.99 (dm, J=1.5 Hz, 1H), 8.68 (dm, J=3.2 Hz, 1H), 8.11 (dm, J=8.0 Hz, 1H), 7.81 (d, J=6.7 Hz, 1H), 7.70 (d, J=7.1 Hz, 1H), 7.40-7.43 (m, 2H), 7.23-7.28 (m, 1H), 6.38 (s, 1H), 5.36 (s, 2H), 4.29 (t, J=7.4 Hz, 2H), 3.47 (t, J=7.9 Hz, 2H), 3.03 (t, J=73 Hz, 2H), 2.26 (t, J=7.9 Hz, 2H), 1.98 (q, J=7.3 Hz, 2H), 0.99 (t, J=7.4 Hz, 3H); MS (APCI) m/z 412 (M+H)$^+$;

Anal. calcd for C$_{24}$H$_{24}$N$_6$O.0.2C$_2$H$_6$O: C, 69.50; H, 6.02; N, 19.93. Found: C, 69.15; H, 5.75; N, 20.09.

Example 58

1-(2-Cyclohexylethyl)-2-ethyl-6,7,8,9-tetrahydro-2H-pyrazolo[3,4-c]quinolin-4-amine

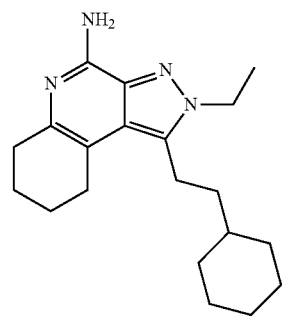 [SMILES: CCn1nc2c(N)nc3c(c2c1CCC1CCCCC1)CCCC3]

A mixture of 2-ethyl-1-(2-phenylethyl)-2H-pyrazolo[3,4-c]quinolin-4-amine (prepared as described in Example 41, 575 mg, 1.81 mmol) and platinum (IV) oxide (290 mg) in trifluoroacetic acid (8 mL) was shaken under hydrogen pressure (50 psi, 3.4×10$^5$ Pa) for 22.5 hours on a Parr apparatus. The reaction mixture was filtered through a poly(tetrafluoroethylene) membrane to remove the catalyst. The filtrate was concentrated under reduced pressure. The crude product was purified by chromatography on a HORIZON HPFC system (silica gel, gradient elution using 0-30% CMA in chloroform) and the appropriate fractions were concentrated to yield a solid that was slurried in hot acetonitrile. The mixture was allowed to cool to ambient temperature with stirring, then 318 mg of 1-(2-cyclohexylethyl)-2-ethyl-6,7,8,9-tetrahydro-2H-pyrazolo[3,4-c]quinolin-4-amine was isolated as a white powder, mp 177.0-179.0° C.

MS (APCI) m/z 327 (M+H)$^+$;

Anal. calcd for $C_{20}H_{30}N_4$: C, 73.58; H, 9.26; N, 17.16. Found: C, 73.48; H, 9.01; N, 17.16.

Example 59

1-(2-Cyclohexylethyl)-2-propyl-6,7,8,9-tetrahydro-2H-pyrazolo[3,4-c]quinolin-4-amine

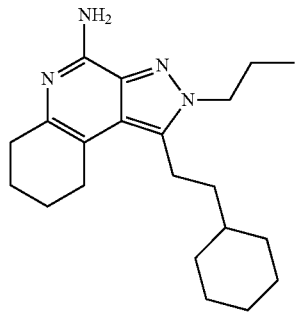 [SMILES: CCCn1nc2c(N)nc3c(c2c1CCC1CCCCC1)CCCC3]

A mixture of 1-(2-phenylethyl)-2-propyl-2H-pyrazolo[3,4-c]quinolin-4-amine (prepared as described in Example 42, 400 mg, 1.21 mmol) and platinum (IV) oxide (200 mg) in trifluoroacetic acid (8 mL) was shaken under hydrogen pressure (50 psi, 3.4×10$^5$ Pa) on a Parr apparatus for 18 hours and worked up using the method described in Example 58 to afford 217 mg of 1-(2-cyclohexylethyl)-2-propyl-6,7,8,9-tetrahydro-2H-pyrazolo[3,4-c]quinolin-4-amine as a white powder, mp 173-174.5° C.

MS (APCI) m/z 341 (M+H)$^+$;

Anal. calcd for $C_{21}H_{32}N_4$: C, 74.07; H, 9.47; N, 16.45. Found: C, 73.77; H, 9.73; N, 16.49.

Example 60

2-Butyl-1-[2-(propylsulfonyl)ethyl]-2H-pyrazolo[3,4-c]quinolin-4-amine

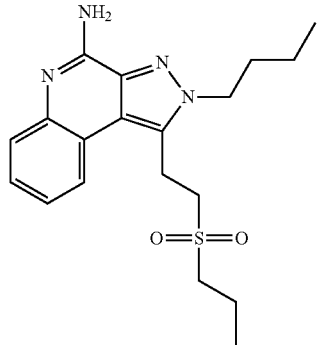 [SMILES: CCCCn1nc2c(N)nc3ccccc3c2c1CCS(=O)(=O)CCC]

Part A

Solid sodium hydride (60% dispersion in oil, 2.90 g, 72.3 mmol) was added in portions over 5 minutes to a stirred solution of 1-propanethiol (6.00 g, 78.8 mmol) in tetrahydrofuran (262 mL). After 15 minutes, a thick white suspension had formed. To the suspension was added 1-chloro-3-butanone (7.00 g, 65.7 mmol), which caused the reaction mixture to warm and a cloudy solution to form. After 30 minutes, the cloudy solution was partitioned between ethyl acetate (100 mL) and water (100 mL). The layers were separated and the organic layer was washed with saturated aqueous sodium bicarbonate (100 mL) and brine (100 mL), dried over sodium sulfate, filtered, and concentrated under reduced pressure to afford a pale brown oil. The crude product was purified by flash chromatography (silica gel, elution with 20% ethyl acetate in hexanes) to provide 9.0 g of 4-(propylthio)butan-2-one as a clear liquid.

Part B

A neat mixture of 4-(propylthio)butan-2-one (9.00 g, 61.5 mmol) and diethyl oxalate (9.00 g, 61.5 mmol) was added dropwise to a stirred solution of sodium tert-butoxide (5.90 g, 61.5 mmol) in ethanol (44 mL) at ambient temperature. Following the addition, the reaction was stirred for two hours. Acetic acid (35 mL) was added, followed by potassium acetate (7.24 g, 73.8 mmol). The mixture was cooled in a cold water bath. Butylhydrazine (11.0 g, 61.5 mmol) was added in portions. After 15 minutes, the mixture was allowed to warm to ambient temperature and was stirred for 2 hours. The volatiles were removed under reduced pressure to yield an oil. Saturated aqueous sodium carbonate was added to the oil until a pH of 10 was reached. The mixture was extracted with dichloromethane (3×50 mL). The combined organic layers were washed with brine, dried over sodium sulfate, filtered, and concentrated under reduced pressure. The orange oil was purified by flash chromatography (silica gel, elution with 20% ethyl acetate in hexanes) to provide 10.6 g of ethyl 1-butyl-5-[2-(propylthio)ethyl]-1H-pyrazole-3-carboxylate as an orange oil.

Part C

To a stirred solution of 1-butyl-5-[2-(propylthio)ethyl]-1H-pyrazole-3-carboxylate (10.6 g, 35.5 mmol) in chloroform (355 mL) was added mCPBA (20.4 g, 71.0 mmol) in portions over 15 minutes. After 1 hour, the mixture was partitioned between chloroform and saturated aqueous sodium carbonate (100 mL). The layers were separated and the organic layer was washed with saturated aqueous sodium carbonate (100 mL) and brine (100 mL), dried over anhydrous sodium sulfate, filtered, and concentrated under reduced pressure to afford an oil. The crude product was purified by flash chromatography (silica gel, elution with 20% ethyl acetate in hexanes) to afford 5.65 g of ethyl 1-butyl-5-[2-(propylsulfonyl)ethyl]-1H-pyrazole-3-carboxylate.

Part D

To a solution of ethyl 1-butyl-5-[2-(propylsulfonyl)ethyl]-1H-pyrazole-3-carboxylate (5.00 g, 15.1 mmol) in ethanol (76 mL) at ambient temperature was added 6 M aqueous sodium hydroxide (5.0 mL, 30 mmol). The solution was stirred for 2 hours, then the volatiles were removed under reduced pressure and the resulting oil was dissolved in water (100 mL). The aqueous solution was washed with dichloromethane (50 mL) and then the pH was adjusted with 1 M hydrochloric acid to pH 4. A precipitate formed and the mixture was stirred for 1 hour. The solid was isolated by filtration, washed with water, and dried to provide 4.6 g of 1-butyl-5-[2-(propylsulfonyl)ethyl]-1H-pyrazole-3-carboxylic acid as a white powder.

Part E

To a solution of 1-butyl-5-[2-(propylsulfonyl)ethyl]-1H-pyrazole-3-carboxylic acid (4.00 g, 13.22 mmol) in dichloromethane (66 mL) was added oxalyl chloride (3.5 mL, 39.7 mmol) and a drop of DMF. The solution bubbled vigorously and was stirred at ambient temperature for 30 minutes. The solution was concentrated under reduced pressure. The residue was dissolved in dichloromethane (66 mL) and the resulting solution was cooled in an ice bath, then concentrated ammonium hydroxide (66 mL) was added dropwise. After the addition was complete, the ice bath was removed and the mixture was stirred at ambient temperature for 2 hours. The volatiles were removed under reduced pressure to afford a slurry that was extracted with chloroform (2×100 mL). The organic layers were combined and concentrated under reduced pressure to afford 4.0 g of 1-butyl-5-[2-(propylsulfonyl)ethyl]-1H-pyrazole-3-carboxamide as a white solid.

Part F

1-Butyl-5-[2-(propylsulfonyl)ethyl]-1H-pyrazole-3-carboxamide (4.00 g, 13.27 mmol) in toluene (66 mL) was treated with phosphorous oxychloride (2.50 mL, 26.5 mmol). The solution was heated at reflux for 1 hour. The reaction mixture was allowed to cool to ambient temperature and the volatiles were removed under reduced pressure. The resulting oil was diluted with water (50 mL) and saturated aqueous sodium bicarbonate. The mixture was extracted with dichloromethane (2×50 mL). The organic layers were combined, washed with saturated aqueous sodium bicarbonate (50 mL), dried over sodium sulfate, filtered, and concentrated under reduced pressure to provide 3.8 g of 1-butyl-5-[2-(propylsulfonyl)ethyl]-1H-pyrazole-3-carbonitrile as a brown oil.

Part G

Bromine (0.8 mL, 14.7 mmol) was added dropwise to a stirred solution of potassium acetate (2.00 g, 20.1 mmol) and 1-butyl-5-[2-(propylsulfonyl)ethyl]-1H-pyrazole-3-carbonitrile (3.80 g, 13.4 mmol) in acetic acid (27 mL). The reaction was stirred at ambient temperature, then was concentrated under reduced pressure to afford a solid. Saturated aqueous sodium bicarbonate was added to the solid until the mixture was pH 9. The mixture was extracted with dichloromethane (2×50 mL). The organic layers were combined and concentrated under reduced pressure to afford a brown oil. The crude product was purified by flash chromatography (silica gel, elution with 40% ethyl acetate in hexanes) to yield 2.85 g of 4-bromo-1-butyl-5-[2-(propylsulfonyl)ethyl]-1H-pyrazole-3-carbonitrile as a white solid.

Part H

To a mixture of 4-bromo-1-butyl-5-[2-(propylsulfonyl)ethyl]-1H-pyrazole-3-carbonitrile (2.35 g, 6.49 mmol) and powdered molecular sieves (1 g) in toluene (41 mL) was added 2-aminophenylboronic acid hydrochloride (2.25 g, 12.97 mmol), potassium phosphate (6.90 g, 32.5 mmol), tris (dibenzylideneacetone)dipalladium(0) (0.148 g, 0.162 mmol) and bis(2-diphenylphosphinophenyl)ether (0.105 g, 0.195 mmol). Nitrogen gas was bubbled through the mixture for 5 minutes. The mixture was heated at 110° C. for 20 hours. After cooling to ambient temperature, the mixture was filtered through a plug of CELITE filter agent, which was rinsed until clear with a solution of dichloromethane and methanol. The filtrate was concentrated under reduced pressure to yield a residue that was used in the next step.

Part I

The material from Part H was dissolved in ethanol (24 mL) and a solution of hydrogen chloride in ethanol (2.7 M, 7.0 mL, 19 mmol) was added. The solution was heated at reflux for 2.5 hours. Upon cooling to ambient temperature, the solution was concentrated under reduced pressure. The resulting oil was dissolved in water and the pH was adjusted with saturated aqueous sodium carbonate to pH 10. The solution was extracted with dichloromethane (3×50 mL). The organic layers were combined, dried over sodium sulfate, filtered, and concentrated under reduced pressure. The crude product was purified by flash chromatography (silica gel, elution with 5% methanol in dichloromethane) to yield an off-white foam (1.50 g) that was crystallized from ethanol (20 mL). The crystals were isolated by filtration, washed with ethanol, and dried under vacuum at 65° C. for 10 hours to yield 2-butyl-1-[2-(propylsulfonyl)ethyl]-2H-pyrazolo[3,4-c]quinolin-4-amine as tan crystalline plates, mp 169-171° C.

$^1$H NMR (300 MHz, DMSO-d$_6$) δ 7.90 (d, J=8.1 Hz, 1H), 7.51 (d, J=8.1 Hz, 1H), 7.35 (t, J=8.1 Hz, 1H), 7.21 (t, J=8.1 Hz, 1H), 6.69 (bs, 2H), 4.42 (t, J=7.5 Hz, 2H), 3.70-3.66 (m, 2H), 3.51-3.46 (m, 2H), 3.23-3.18 (m, 2H) 1.90 (pentet, J=7.5 Hz, 2H), 1.74 (sextet, J=7.5 Hz, 2H), 1.37 (sextet, J=7.5 Hz, 2H), 0.99 (t, J=7.5 Hz, 3H), 0.95 (t, J=7.5 Hz, 3H);

MS (ESI) m/z 375 (M+H)$^+$;

Anal. Calcd for C$_{19}$H$_{26}$N$_4$O$_2$S: C, 60.94; H, 7.00; N, 14.96. Found: C, 60.85; H, 6.92; N, 14.90.

Example 61

2-Butyl-1-[2-(propylsulfonyl)ethyl]-6,7,8,9-tetrahydro-2H-pyrazolo[3,4-c]quinolin-4-amine

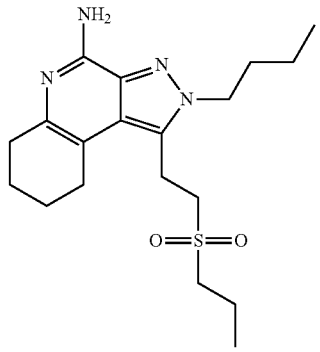 [SMILES: CCCCn1nc2c(N)nc3c(c2c1CCS(=O)(=O)CCC)CCCC3]

A solution of 2-butyl-1-[2-(propylsulfonyl)ethyl]-2H-pyrazolo[3,4-c]quinolin-4-amine (prepared as described in Example 60, 0.50 g, 1.3 mmol) in trifluoroacetic acid (6 mL) was treated with platinum (IV) oxide (0.5 g) and shaken under hydrogen pressure (50 psi, 3.4×10$^5$ Pa) for 20 hours on a Parr apparatus. The reaction mixture was filtered through a layer of CELITE filter agent, and the CELITE filter agent was rinsed with dichloromethane (100 mL) until the rinses were clear. The filtrate was concentrated under reduced pressure. The oil was suspended in water (20 mL) and treated with 50% aqueous sodium hydroxide to adjust the mixture to pH 14, causing a precipitate to form. The mixture was stirred for 1 hour, then the precipitate was isolated by filtration and washed with water. The white powder was recrystallized from acetonitrile (5 mL). The crystals were isolated by filtration, washed with acetonitrile, and dried under vacuum at 65° C. to afford 0.40 g of 2-butyl-1-[2-(propylsulfonyl)ethyl]-6,7,8,9-tetrahydro-2H-pyrazolo[3,4-c]quinolin-4-amine as white crystals, mp 173-175° C. $^1$H NMR (300 MHz, DMSO-d$_6$) δ 6.02 (bs, 2H), 4.28 (t, J=7.5 Hz, 2H), 3.43-3.37 (m, 4H), 3.19-3.14 (m, 2H), 2.85 (bs, 2H) 2.56 (bs, 2H), 1.85 (pentet, J=7.5 Hz, 2H), 1.77-1.70 (m, 6H), 1.33 (sextet, J=7.5 Hz, 2H), 1.00 (t, J=7.5 Hz, 3H), 0.93 (t, J=7.5 Hz, 3H);

MS (ESI) m/z 379 (M+H)$^+$;

Anal. Calcd for C$_{19}$H$_{30}$N$_4$O$_2$S: C, 60.29; H, 7.99; N, 14.80. Found: C, 59.98; H, 8.34; N, 15.11.

Example 62

1-(4-Amino-2-ethyl-2H-pyrazolo[3,4-c]quinolin-1-yl)-2-methylpropan-2-ol

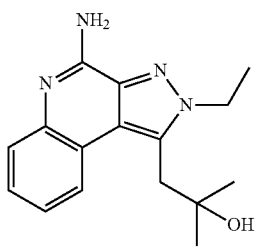 [SMILES: CCn1nc2c(N)nc3ccccc3c2c1CC(C)(C)O]

Part A

A solution of mesityl oxide (30.0 mL, 262 mmol) and diethyl oxalate (35.6 mL, 262 mmol) was added dropwise to a stirred solution of sodium tert-butoxide (54.1 g, 563 mmol) in ethanol (187 mL) at ambient temperature according to the procedure described in Part B of Example 60. The reaction was stirred for 1 hour, then was treated with acetic acid (131 mL), potassium acetate (38.6 g, 393 mmol), and ethylhydrazine oxalate (43.2 g, 288.2 mmol) according to the procedure described in Part B of Example 60. The mixture was stirred overnight at ambient temperature. The volatiles were removed under reduced pressure and the residue was diluted with water and chloroform. 2 M aqueous sodium carbonate was added until pH 11 was reached. The mixture was extracted with chloroform. The combined organic layers were dried over sodium sulfate, filtered, and concentrated under reduced pressure to yield a black oil that was used without purification in the next step.

Part B

A mixture of the material from Part A, concencentrated ammonium hydroxide (500 mL) and methanol (200 mL) were stirred at ambient temperature for 16 hours. A white solid was isolated from the mixture by filtration. More solid was isolated from the filtrate to yield a total for 13.9 g of 1-ethyl-5-(2-methylprop-1-enyl)-1H-pyrazole-3-carboxamide.

Part C

A mixture of 1-ethyl-5-(2-methylprop-1-enyl)-1H-pyrazole-3-carboxamide (5.0 g, 25.9 mmol) and phosphorous oxychloride (18.5 mL) was heated at 90° C. for 20 minutes. The reaction vessel was cooled in an ice bath and reaction mixture was poured over ice (100 mL) The quenched reaction mixture was made basic with 2 M aqueous sodium carbonate and was extracted with chloroform. The organic layers were dried over sodium sulfate, filtered, and concentrated under reduced pressure to provide 1-ethyl-5-(2-methylprop-1-enyl)-1H-pyrazole-3-carbonitrile, all of which was used in the next step.

Part D

A solution of the material from Part C and mCPBA (11.7 g, 34.0 mmol) in dichloromethane (115 mL) was stirred at ambient temperature overnight. The resulting mixture was diluted with water and the pH was made basic with 2 M aqueous sodium carbonate. The solution was extracted with chloroform. The combined organic layers were dried over sodium sulfate, filtered, and concentrated under reduced pressure to yield 5-(3,3-dimethyloxiran-2-yl)-1-ethyl-1H-pyrazole-3-carbonitrile, all of which was used in the next step.

Part E

Bromine (1.7 mL, 33.0 mmol) was added to a solution of the material from Part D in chloroform at 0° C. The red solution was stirred at ambient temperature for 2 hours, then saturated aqueous sodium bisulfite was added and the mixture was concentrated under reduced pressure. The residue was diluted with chloroform (100 mL) and the pH was adjusted with 2 M aqueous sodium carbonate to pH 11. The cloudy mixture was diluted with water (50 mL) and was extracted with chloroform (3×75 mL). The combined organic layers were dried over sodium sulfate, filtered, and concentrated under reduced pressure to yield 4.4 g of a cloudy oil that was used without purification in the next step.

Part F

To a mixture of the material from Part E in toluene (62 mL) at ambient temperature was added azobisisobutyronitrile (AIBN, 512 mg, 3.12 mmol) and tributyltin hydride (4.0 mL, 15.0 mmol). Bubbles were observed for a short period of time. The pale yellow solution was heated at 90° C. for 1 hour. The solution was allowed to cool to ambient temperature and subjected to chromatography on a HORIZON HPFC system (silica gel, gradient elution with 0-50% ethyl acetate in hexanes to afford 1.1 g of 4-bromo-1-ethyl-5-(2-hydroxy-2-methylpropyl)-1H-pyrazole-3-carbonitrile as a colorless oil.

Part G

To a mixture of 4-bromo-1-ethyl-5-(2-hydroxy-2-methylpropyl)-1H-pyrazole-3-carbonitrile (1.0 g, 3.7 mmol) and powdered molecular sieves (1 g) in toluene (23 mL) was added 2-aminophenylboronic acid hydrochloride (1.28 g, 7.4 mmol), potassium phosphate (3.92 g, 18.5 mmol), tris(dibenzylideneacetone)dipalladium(0) chloroform adduct (96 mg, 0.093 mmol) and bis(2-diphenylphosphinophenyl)ether (60 mg, 0.111 mmol). Nitrogen gas was bubbled through the mixture for 5 minutes. The mixture was heated at 110° C. for 1 day. After cooling to ambient temperature, the mixture was filtered through a plug of silica gel, which was rinsed with a solution of 3:2 chloroform/methanol. The filtrate was concentrated under reduced pressure to yield a residue that was used in the next step.

Part H

The material from Part G was dissolved in ethanol (20 mL) and a solution of hydrogen chloride in ethanol (4 M, 2.8 mL, 11 mmol) was added. The solution was heated at reflux for 2 hours. Upon cooling to ambient temperature, the solution was concentrated under reduced pressure. To the resulting oil was added 2 M aqueous sodium carbonate until the pH was basic, then brine was added and the mixture was extracted with chloroform. The organic layers were combined, dried over sodium sulfate, filtered, and concentrated under reduced pressure. The crude product was purified by chromatography on a HORIZON HPFC system (silica gel, gradient elution with 0-30% CMA in chloroform) then was recrystallized from acetonitrile to yield 0.2 g of 1-(4-amino-2-ethyl-2H-pyrazolo [3,4-c]quinolin-1-yl)-2-methylpropan-2-ol as light tan crystals, mp 223-225° C.

MS (APCI) m/z 285 (M+H)$^+$;

Anal. calcd for $C_{16}H_{20}N_4O$: C, 67.58; H, 7.09; N, 19.70. Found: C, 67.38; H, 7.39; N, 19.94.

Example 63

2-Ethyl-1-[4-(4-pyridin-2-ylpiperazin-1-yl)butyl]-2H-pyrazolo[3,4-c]quinolin-4-amine

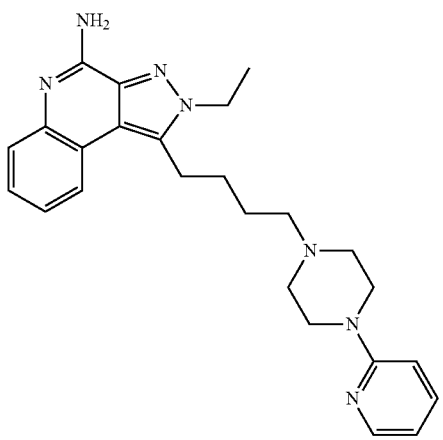 [SMILES: CCn1nc2c(N)nc3ccccc3c2c1CCCCN1CCN(c2ccccn2)CC1]

A mixture of 1-(4-chlorobutyl)-2-ethyl-2H-pyrazolo[3,4-c]quinoline-4-amine (prepared as described in Example 19, 1.0 g, 3.3 mmol), 1-(2-pyridyl)piperazine (0.752 mL, 4.95 mmol), potassium carbonate (1.8 g, 13.2 mmol), and sodium iodide (123 mg, 0.825 mmol) in DMF (6 mL) was heated at 60° C. for 1 hour, then at 90° C. for 2 hours. The reaction was allowed to cool to ambient temperature and white solid formed. Water (100 mL) was added to the mixture. The mixture was stirred for 30 min and the solid was isolated by filtration and dried to yield 1.4 g of 2-ethyl-1-[4-(4-pyridin-2-ylpiperazin-1-yl)butyl]-2H-pyrazolo[3,4-c]quinolin-4-amine monohydrate as a white solid, mp 183-184° C.

MS (APCI) m/z 430 (M+H)$^+$;

Anal. calcd for $C_{25}H_{31}N_7 \cdot H_2O$: C, 67.09; H, 7.43; N, 21.91. Found: C, 66.86; H, 7.66; N, 22.11.

Example 64

1-(2-Amino-2-methylpropyl)-2-propyl-2H-pyrazolo[3,4-c]quinolin-4-amine

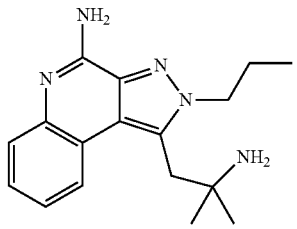 [SMILES: CCCn1nc2c(N)nc3ccccc3c2c1CC(C)(C)N]

Part A

A neat mixture of tert-butyl 1,1-dimethyl-3-oxobutylcarbamate (prepared as described in B. Peschke et al., *Eur. J. Med. Chem.*, 1999, 34, 363-380, 14.0 g, 65.0 mmol) and diethyl oxalate (9.50 g, 65.0 mmol) was added in one portion, followed by an ethanol rinse (20 mL), to a stirred solution of sodium tert-butoxide (6.25 g, 65.0 mmol) in ethanol (46 mL). A precipitate formed immediately. The mixture was stirred for 2 hours, then acetic acid (66.4 mL) was added. The resulting solution was cooled to 10° C. and propylhydrazine oxalate (10.7 g, 65.0 mmol) was added in one portion. The reaction was stirred for 45 minutes and the internal temperature reached 19° C. The volatiles were removed under reduced pressure and water was added. The mixture was stirred while 2 M aqueous sodium carbonate was added until carbon dioxide evolution ceased. The mixture was extracted three times with tert-butyl methyl ether. The organic layers were combined, dried over magnesium sulfate, filtered, and concentrated to yield 17.9 g of a yellow solid that was recrystallized from hexanes (130 mL). The crystals were isolated by filtration, washed with cold hexanes, and dried to yield 11.68 g of ethyl 5-{2[(tert-butoxycarbonyl)amino]2-methylpropyl}-1-propyl-1H-pyrazole-3-carboxylate as a white solid, mp 109-111° C. MS (APCI) m/z 354 (M+H)$^+$; Anal. calcd for $C_{18}H_{31}N_3O_4$: C, 61.17; H, 8.84; N, 11.89. Found: C, 61.18; H, 9.17; N, 11.97.

Part B

Methanol (39.9 mL), lithium hydroxide (5.06 g, 121 mmol), and water (13.3 mL) were added to ethyl 5-{2-[(tert-butoxycarbonyl)amino]-2-methylpropyl}-1-propyl-1H-pyrazole-3-carboxylate (10.65 g, 30.1 mmol) in a 500 mL round bottom flask. The mixture was stirred vigorously for 5.5 hours. Acetic acid (8.0 mL) and water (200 mL) were added. A white solid formed and more acetic acid (61 mL) was added. The solid was isolated by filtration, washed with water, and dried. A second crop of solid was isolated from the filtrate. The crops were combined to yield 8.77 g of 5-{2-[(tert-butoxycarbonyl)amino]-2-methylpropyl}-1-propyl-1H-pyrazole-3-carboxylic acid as a white solid, mp 151-152° C. MS (APCI) m/k 326 (M+H)$^+$; Anal. calcd for $C_{16}H_{27}N_3O_4$: C, 59.06; H, 8.36; N, 12.91. Found: C, 58.93; H, 8.59; N, 12.94.

Part C 1-(3-Dimethylaminopropyl)-3-ethylcarbodiimide hydrochloride (5.68 g, 29.6 mmol.) was added to a solution of 5-{2-[(tert-butoxycarbonyl)amino]-2-methylpropyl}-1-propyl-1H-pyrazole-3-carboxylic acid (8.77 g, 27.0 mmol) and 1-hydroxybenzotriazole (4.00 g, 29.6 mmol) in DMF (44 mL) at ambient temperature. The mixture was stirred for 5.5 hours until a solution formed, then was cooled in an ice bath. Concentrated ammonium hydroxide (5.5 mL) was added and the cloudy solution was stirred for 10 minutes, then was allowed to warm to ambient temperature and stir overnight. Water (150 mL) was added and the mixture was extracted with chloroform (4×75 mL). The organic layers were combined, dried over magnesium sulfate, filtered, and concentrated under reduced pressure. The residue was concentrated twice from xylene under reduced pressure to afford an oil that was purified on chromatography on a HORIZON HPFC system (silica gel, elution with ethyl acetate) to yield 8.21 g of tert-butyl 2-[3-(aminocarbonyl)-1-propyl-1H-pyrazol-5-yl]-1,1-dimethylethylcarbamate as a white solid.

Part D

A solution of trifluoroacetic anhydride (3.93 mL, 27.8 mmol) in dichloromethane (51 mL) was added slowly to a 0° C. solution of tert-butyl 2-[3-(aminocarbonyl)-1-propyl-1H-pyrazol-5-yl]-1,1-dimethylethylcarbamate (8.21 g, 25.3 mmol) and triethylamine (10.6 mL, 75.9 mmol) in dichloromethane (51 mL). After the addition was complete, the cooling bath was removed and the solution was stirred for 90 minutes. The solution was transferred to a separatory funnel and washed with 2 M aqueous sodium carbonate (200 mL). The aqueous layer was extracted twice with chloroform. The organic layers were combined, dried over magnesium sulfate, filtered, and concentrated under reduced pressure to yield an off white solid that was recrystallized from 10% ethyl acetate in hexanes, isolated by filtration, and dried to yield 6.77 g of tert-butyl 2-(3-cyano-1-propyl-1H-pyrazol-5-yl)-1,1-dimethylethylcarbamate as a white crystals, mp 115-116° C. MS (ESI) m/z 307 (M+H)$^+$; Anal. Calcd for $C_{16}H_{26}N_4O_2$: C, 62.72; H, 8.55; N, 18.28. Found: C, 62.61; H, 8.46; N, 18.52.

Part E tert-Butyl 2-(3-cyano-1-propyl-1H-pyrazol-5-yl)-1,1-dimethylethylcarbamate (5.15 g, 16.8 mmol) was brominated using a modified version of the method described in Part F of Examples 1-4. In the reaction, 1.4 equivalents of bromine were used instead of 1.1 equivalents, chloroform was used instead of dichloromethane in the work-up, and no chromatographic purification was performed. The product, tert-butyl 2-(4-bromo-3-cyano-1-propyl-1H-pyrazol-5-yl)-1,1-dimethylethylcarbamate (6.97 g), was isolated as a clear, colorless oil that may have contained some chloroform.

Part F

The material from Part E (approximately 16.8 mmol) was dissolved in 1-propanol and concentrated under reduced pressure twice, then was diluted with approximately 29 mL of 1-propanol. To the resulting solution was added 2 M aqueous sodium carbonate (25.2 mL, 50.4 mmol), then water (5.88 mL), triphenylphosphine (397 mg, 1.51 mmol), palladium (II) acetate (113 mg, 0.504 mmol), and 2-aminophenylboronic acid hydrochloride (4.37 g, 25.2 mmol). The flask was equipped with a reflux condenser with a nitrogen inlet and was placed under vacuum and back-filled with nitrogen four times. The reaction was heated under a nitrogen atmosphere at 100° C. for 8 hours. The reaction was allowed to cool to ambient temperature and tetrakis(triphenylphosphine)palladium(0) (388 mg), 2 M aqueous sodium carbonate (25.2 mL), and 2-aminophenylboronic acid hydrochloride (4.37 g) were added. The mixture was heated at 100° C. for 11 hours. The reaction was allowed to cool to ambient temperature, then was extracted with chloroform four times. The organic layers were combined, dried over magnesium sulfate, filtered, and concentrated to yield a brown oil. The crude product was purified by chromatography on a HORIZON HPFC system (silica gel, gradient elution with 40-50% ethyl acetate in hexanes followed by 20% CMA in chloroform). The appropriate fractions were combined and concentrated to yield an oil that was purified again by chromatography on a HORIZON HPFC system (silica gel, gradient elution with 35-40% ethyl acetate in hexanes) to afford 2.65 g of a light brown oil.

Part G

A solution of the material from Part F in 1 M HCl in ethanol (50 mL) was heated at reflux for 3 hours, then was allowed to stand at ambient temperature overnight before being concentrated under reduced pressure to yield a solid suspended in ethanol (approximately 5 mL). The suspension was cooled in an ice bath and diethyl ether (75 mL) was added. The solid was collected by filtration, washed with diethyl ether, and dried to yield 2.3 g of a white solid. The solid was dissolved in water and 2 M aqueous sodium carbonate was added. The mixture was extracted with chloroform five times. The organic layers were dried over sodium sulfate, filtered, and concentrated under reduced pressure to yield a white solid that was purified by chromatography on a HORIZON HPFC system (silica gel, gradient elution with 20-30% CMA in chloroform). The appropriate fractions were combined and concentrated to a volume of a few mL. A solid was precipitated with hexanes and was isolated by filtration and dried. The white powder was recrystallized form aceonitrile to yield 1.17 g of 1-(2-amino-2-methylpropyl)-2-propyl-2H-pyrazolo[3,4-c]quinolin-4-amine as white granular crystals, mp 193-195° C.

MS (APCI) m/z 298 (M+H)$^+$;

Anal. Calcd for $C_{17}H_{23}N_5$: C, 68.66; H, 7.80; N, 23.55. Found: C, 68.59; H, 7.50; N, 23.30.

Example 65

N-[2-(4-Amino-2-propyl-2H-pyrazolo[3,4-c]quinolin-1-yl)-1,1-dimethylethyl]acetamide

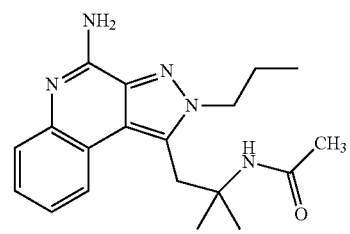 [SMILES: CCCn1nc2c(N)nc3ccccc3c2c1CC(C)(C)NC(C)=O]

Acetyl chloride (221 µL, 3.14 mmol) was added to a 0° C. stirred solution of 1-(2-amino-2-methylpropyl)-2-propyl-2H-pyrazolo[3,4-c]quinolin-4-amine (prepared as described in Example 64, 840 mg, 2.82 mmol) and triethylamine (591

μL, 4.24 mmol) in dichloromethane (25.2 mL). The solution was stirred for 20.5 h at ambient temperature, then was concentrated under reduced pressure to yield a foam that was dissolved in methanol. To the solution was added concentrated hydrochloric acid (2 mL). The solution was stirred at ambient temperature for 90 minutes, then heated at reflux for 40 minutes. After cooling to ambient temperature, the solution was concentrated under reduced pressure and 2 M aqueous sodium carbonate was added until the pH was basic. The solution was extracted with chloroform. The organic layers were dried over sodium sulfate, filtered, and concentrated under reduced pressure. The residue was dissolved in dichloromethane (10 mL), then triethylamine (786 mL) and acetyl chloride (300 mL) were added. The reaction was worked up as before, then methanol (20 mL) and concentrated hydrochloric acid (2 mL) were added. The solution was heated at reflux for 30 minutes, left to stand at ambient temperature overnight, then heated at reflux again for 30 minutes. After cooling to ambient temperature, the solution was concentrated under reduced pressure and 2M aqueous sodium carbonate was added until the pH was adjusted to pH 10-11. The solution was extracted with chloroform three times. The organic layers were dried over sodium sulfate, filtered, and concentrated under reduced pressure. The crude product was purified twice by chromatography on a HORIZON HPFC system (silica gel, gradient elution with 20-30% CMA in chloroform for the first column; gradient elution with 4-10% methanol in chloroform for the second column). The appropriate fractions were combined and concentrated under reduced pressure to yield a colorless foam that was crystallized from ethyl acetate/hexanes. A white solid was isolated and dried under vacuum at elevated temperature to yield 698 mg of N-[2-(4-amino-2-propyl-2H-pyrazolo[3,4-c]quinolin-1-yl)-1,1-dimethylethyl]acetamide as a white solid, mp 182-183° C.

MS (APCI) m/z 340 (M+H)$^+$;

Anal. Calcd for $C_{19}H_{25}N_5O.0.25H_2O$: C, 66.35; H, 7.47; N, 20.36. Found: C, 66.29; H, 7.68; N, 20.09.

Example 66

N-[2-(4-Amino-2-propyl-2H-pyrazolo[3,4-c]quinolin-1-yl)-1,1-dimethylethyl]methanesulfonamide

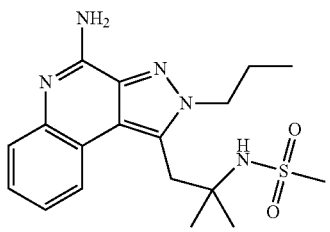 [SMILES: CCCn1nc2c(N)nc3ccccc3c2c1CC(C)(C)NS(C)(=O)=O]

Methanesulfonyl chloride (232 μL, 3.00 mmol) was added to a 0° C. stirred solution of 1-(2-amino-2-methylpropyl)-2-propyl-2H-pyrazolo[3,4-c]quinolin-4-amine (prepared as described in Example 64, 892 mg, 3.00 mmol) and triethylamine (627 μL, 4.5 mmol) in dichloromethane (26.7 mL). After 3 hours at 0° C., the solution was stirred for 2 days at ambient temperature. To the solution was added 2 M aqueous sodium carbonate. The mixture was extracted with chloroform four times. The organic layers were combined, dried over sodium sulfate, filtered, and concentrated under reduced pressure to yield a white solid. The crude product was purified by IFC (silica gel, elution with 10% CMA in chloroform). The appropriate fractions were combined and concentrated under reduced pressure to provide a white foam that was crystallized from acetonitrile, isolated by filtration, and dried to yield 600 mg of N-[2-(4-amino-2-propyl-2H-pyrazolo[3,4-c]quinolin-1-yl)-1,1-dimethylethyl]methanesulfonamide as a white solid, mp 130-139° C.

MS (APCI) m/z 376 (M+H)$^+$;

Anal. Calcd for $C_{18}H_{25}N_5O_2S.0.25H_2O$: C, 56.89; H, 6.76; N, 18.43. Found: C, 56.85; H, 7.09; N, 18.40.

Example 67

N-[2-(4-Amino-2-propyl-2H-pyrazolo[3,4-c]quinolin-1-yl)-1,1-dimethylethyl]cyclohexanecarboxamide

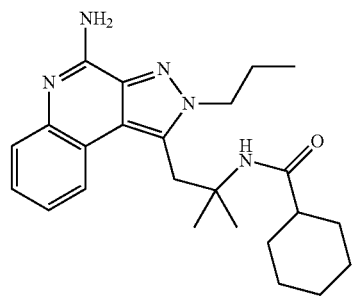 [SMILES: CCCn1nc2c(N)nc3ccccc3c2c1CC(C)(C)NC(=O)C1CCCCC1]

Cyclohexanecarbonyl chloride (401 μL, 3.00 mmol) was added to a 0° C. stirred solution of 1-(2-amino-2-methylpropyl)-2-propyl-2H-pyrazolo[3,4-c]quinolin-4-amine (prepared as described in Example 64, 892 mg, 3.00 mmol) and triethylamine (627 μL, 4.5 mmol) in dichloromethane (26.7 mL). After 3 hours at 0° C., the solution was stirred for 2 days at ambient temperature. More triethylamine (697 μL) and cyclohexanecarbonyl chloride (602 μL) was added. After 30 minutes, 2 M aqueous sodium carbonate was added to the solution. The mixture was extracted with chloroform four times. The organic layers were combined, dried over sodium sulfate, filtered, and concentrated under reduced pressure. Methanol (20 mL) and concentrated hydrochloric acid (2 mL) were added. The solution was heated at reflux for 4 hours, then left to stand at ambient temperature overnight, then heated at reflux again for brief periods of time during the next 2 days. In all, the solution was heated at reflux for a total of 7 hours. After cooling to ambient temperature, 2 M aqueous sodium carbonate was added to adjust the mixture to pH 10-11. The mixture was concentrated under reduced pressure to remove the methanol. Water was added and a solid was isolated from the mixture by filtration. The solid was washed with water. Chloroform was added to the solid, and the mixture was filtered. The filtrate was concentrated under reduced pressure and purified by IFC. The appropriate fractions were combined and concentrated to a white solid that was recrystallized from 50% ethyl acetate/hexanes. The crystals were isolated by filtration and dried to yield 896 mg of N-[2-(4-amino-2-propyl-2H-pyrazolo[3,4-c]quinolin-1-yl)-1,1-dimethylethyl]cyclohexanecarboxamide as a white solid, mp 190-191° C.

MS (APCI) m/z 408 (M+H)$^+$;

Anal. Calcd for $C_{24}H_{33}N_5O$: C, 70.73; H, 8.16; N, 17.18. Found: C, 70.58; H, 8.30; N, 16.91.

Example 68

N-[2-(4-Amino-2-propyl-2H-pyrazolo[3,4-c]quinolin-1-yl)-1,1-dimethylethyl]nicotinamide

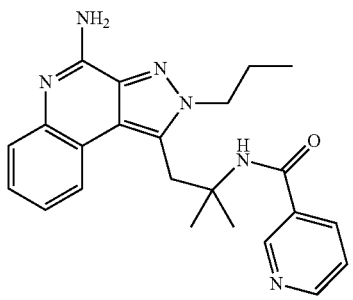 [SMILES: CCCn1nc2c(N)nc3ccccc3c2c1CC(C)(C)NC(=O)c1cccnc1]

Nicotinoyl chloride hydrochloride (1.62 g, 9.08 mmol) was added to a stirred solution of 1-(2-amino-2-methylpropyl)-2-propyl-2H-pyrazolo[3,4-c]quinolin-4-amine (prepared as described in Example 64, 1.08 g, 3.63 mmol) and triethylamine (2.8 mL, 20 mmol) in dichloromethane (32.4 mL). After 2 h, the solution was concentrated under reduced pressure. The residue was dissolved in methanol (20 mL). Concentrated hydrochloric acid (4 mL) was added and the solution was heated at reflux for 30 minutes, then was allowed to cool to ambient temperature. To the solution was added 2 M aqueous sodium carbonate until the pH was basic, then water was added. The mixture was extracted with chloroform four times. The organic layers were combined, dried over sodium sulfate, filtered, and concentrated to yield a brown oil that was purified by IFC (silica gel, elution with CMA in chloroform). The appropriate fractions were combined and concentrated to produce a yellow foam that was crystallized from ethyl acetate/hexanes. The solid was isolated by filtration and dried to yield 418 mg of N-[2-(4-amino-2-propyl-2H-pyrazolo[3,4-c]quinolin-1-yl)-1,1-dimethylethyl]nicotinamide as a pale yellow solid, mp 203-205° C.

MS (APCI) m/z 403 (M+H)$^+$;

Anal. Calcd for $C_{23}H_{26}N_6O \cdot 1.5H_2O$: C, 64.31; H, 6.80; N, 19.57. Found: C, 64.06; H, 6.56; N, 19.64.

Example 69

N-[2-(4-Amino-2-propyl-2H-pyrazolo[3,4-c]quinolin-1-yl)-1,1-dimethylethyl]-2-methylpropanamide

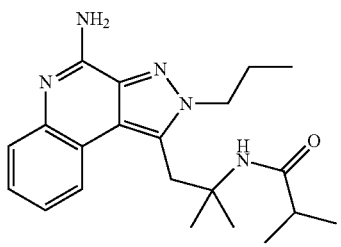 [SMILES: CCCn1nc2c(N)nc3ccccc3c2c1CC(C)(C)NC(=O)C(C)C]

2-Methylpropanoyl chloride (786 μL, 7.50 mmol) was added to a 0° C. stirred solution of 1-(2-amino-2-methylpropyl)-2-propyl-2H-pyrazolo[3,4-c]quinolin-4-amine (prepared as described in Example 64, 892 mg, 3.00 mmol) and triethylamine (1.32 mL, 9.5 mmol) in dichloromethane (26.7 mL). After 10 minutes at 0° C., the solution was stirred for 2 hours at ambient temperature. The solution was concentrated to afford a white solid that was dissolved in methanol (20 mL) and concentrated hydrochloric acid (4 mL). The solution was heated at reflux for 3.5 hours, then was left to stand at ambient temperature overnight. To the solution was added 2 M aqueous sodium carbonate until the pH was basic. The mixture was concentrated under reduced pressure to remove the methanol. The mixture was extracted with chloroform four times. The organic layers were combined, dried over sodium sulfate, filtered, and concentrated to yield an off-white solid that was purified by IFC (silica gel, eluted with CMA in chloroform). The appropriate fractions were combined and concentrated under reduced pressure to yield a white foam that was crystallized from 50% ethyl acetate in hexanes. The solid was isolated by filtration, washed with 50% ethyl acetate in hexanes, and dried to yield 815 mg of N-[2-(4-amino-2-propyl-2H-pyrazolo[3,4-c]quinolin-1-yl)-1,1-dimethylethyl]-2-methylpropanamide as a white solid, mp 177-178.5° C.

MS (APCI) m/z 368 (M+H)$^+$;

Anal. Calcd for $C_{21}H_{29}N_5O$: C, 68.64; H, 7.95; N, 19.06. Found: C, 68.49; H, 8.23; N, 18.97.

Example 70

N-[2-(4-Amino-2-propyl-2H-pyrazolo[3,4-c]quinolin-1-yl)-1,1-dimethylethyl]N'-isopropylurea

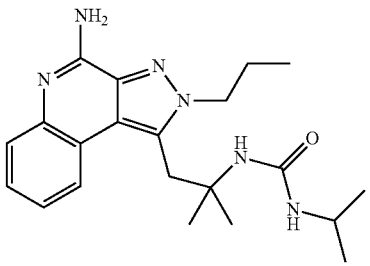 [SMILES: CCCn1nc2c(N)nc3ccccc3c2c1CC(C)(C)NC(=O)NC(C)C]

Isopropyl isocyanate (255 mg, 3.00 mmol) was added to a 0° C. stirred solution of 1-(2-amino-2-methylpropyl)-2-propyl-2H-pyrazolo[3,4-c]quinolin-4-amine (prepared as described in Example 64, 892 mg, 3.00 mmol) in dichloromethane (26.7 mL). After 4 hours at 0° C., the solution was stirred overnight at ambient temperature. The solution was concentrated to afford a colorless resin that was purified by IFC (silica gel, elution with CMA in chloroform). The appropriate fractions were combined and concentrated to yield a solid that was recrystallized from ethyl acetate in hexanes. The solid was isolated by filtration, washed with ethyl acetate/hexanes, and dried to yield 130 mg of N-[2-(4-amino-2-propyl-2H-pyrazolo[3,4-c]quinolin-1-yl)-1,1-dimethylethyl]-N'-isopropylurea as a white solid, mp 190-191° C.

MS (APCI) m/z 383 (M+H)$^+$;

Anal. Calcd for $C_{21}H_{30}N_6O \cdot 0.25H_2O$: C, 65.17; H, 7.94; N, 21.72. Found: C, 65.15; H, 8.03; N, 21.76.

Examples 71-85

A reagent (0.11 mmol, 1.1 equivalents) from the table below was added to a test tube containing 1-(2-methylpropyl)-2H-pyrazolo[3,4-c]quinolin-4-amine (prepared as described in Example 9, 23 mg, 0.10 mmol) and potassium carbonate (approximately 40 mg, 0.29 mmol) in DMF (1 mL). A stirbar was added to each test tube. The test tubes were capped and stirred overnight at ambient temperature. The solvent was removed by vacuum centrifugation.

The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent added to each test tube, the structure of the resulting compound, and the observed accurate mass for the isolated trifluoroacetate salt.

Examples 71-85

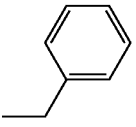

| Example | Reagent | R | Measured Mass (M + H) |
|---|---|---|---|
| 71 | none | —H | 241.1455 |
| 72 | Benzyl bromide | 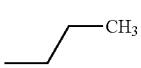 | 331.1935 |
| 73 | 1-Bromopropane | 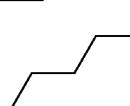 | 283.1894 |
| 74 | 1-Bromopentane | 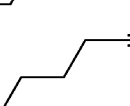 | 311.2221 |
| 75 | 5-Bromovaleronitrile | 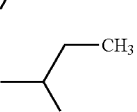 | 322.2037 |
| 76 | 2-Iodobutane | 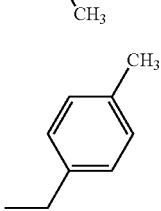 | 297.2060 |
| 77 | 4-Methylbenzyl bromide | 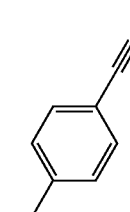 | 345.2080 |
| 78 | 4-Cyanobenzyl bromide | 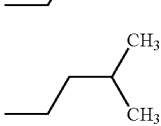 | 356.1867 |
| 79 | 1-Iodo-3-methylbutane | | 311.2220 |

-continued

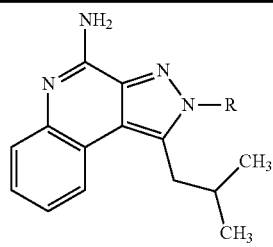

| Example | Reagent | R | Measured Mass (M + H) |
|---|---|---|---|
| 80 | 3-Methoxybenzyl bromide | 3-methoxybenzyl | 361.2035 |
| 81 | beta-Bromophenetole | 2-phenoxyethyl | 361.2040 |
| 82 | 4-Chlorobenzyl bromide | 4-chlorobenzyl | 365.1545 |
| 83 | Methyl 4-(bromomethyl)benzoate | 4-(methoxycarbonyl)benzyl | 389.1986 |
| 84 | 4-(Trifluoromethyl)benzyl bromide | 4-(trifluoromethyl)benzyl | 399.1820 |
| 85 | 3,4-Dichlorobenzyl bromide | 3,4-dichlorobenzyl | 399.1148 |

Examples 86-197

A reagent (0.11 mmol, 1.1 equivalents) from the table below was added to a test tube containing 1-(2-aminoethyl)-2-methyl-2H-pyrazolo[3,4-c]quinolin-4-amine dihydrochloride (prepared as described in Parts A-J of Example 50, 31 mg, 0.10 mmol) and N,N-diisopropylethylamine (0.069 mL, 0.40 mmol) in DMF (1 mL). The test tubes were capped, shaken for four hours at ambient temperature. The solvent was removed by vacuum centrifugation. The compounds were purified as described in Examples 71-85. The table below shows the reagent added to each test tube, the structure of the resulting compound, and the observed accurate mass for the isolated trifluoroacetate salt.

Examples 86-197
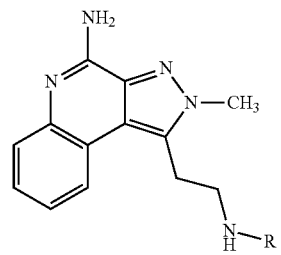
| Example | Reagent | R | Measured Mass (M + H) |
|---|---|---|---|
| 86 | none | –H | 242.1400 |
| 87 | Acetyl chloride | –C(=O)OH | 284.1511 |
| 88 | Methyl chloroformate | –C(=O)OCH₃ | 300.1460 |
| 89 | Cyclopropanecarbonyl chloride | –C(=O)-cyclopropyl | 310.1672 |
| 90 | Butryl chloride | –C(=O)CH₂CH₂CH₃ | 312.1812 |
| 91 | Ethyl chloroformate | –C(=O)OCH₂CH₃ | 314.1607 |
| 92 | Methoxyacetyl chloride | –C(=O)CH₂OCH₃ | 314.1599 |
| 93 | Cyclobutanecarbonyl chloride | –C(=O)-cyclobutyl | 324.1807 |
| 94 | Pivaloyl chloride | –C(=O)C(CH₃)₃ | 326.1982 |

-continued
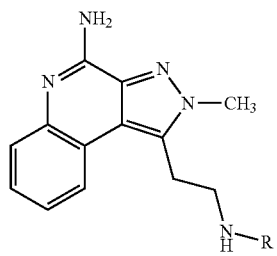
| Example | Reagent | R | Measured Mass (M + H) |
|---|---|---|---|
| 95 | 2-Furoyl chloride | (2-furyl C(=O)−) | 336.1455 |
| 96 | 3-Furoyl chloride | (3-furyl C(=O)−) | 336.1483 |
| 97 | Benzoyl chloride | (phenyl C(=O)−) | 346.1654 |
| 98 | Cyclopentylacetyl chloride | (cyclopentyl-CH₂-C(=O)−) | 352.2130 |
| 99 | Cyclohexanecarbonyl chloride | (cyclohexyl C(=O)−) | 352.2140 |
| 100 | m-Toluoyl chloride | (3-methylphenyl C(=O)−) | 360.1840 |
| 101 | p-Toluoyl chloride | (4-methylphenyl C(=O)−) | 360.1839 |

-continued
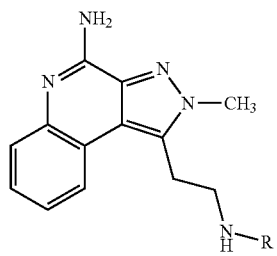
| Example | Reagent | R | Measured Mass (M + H) |
|---|---|---|---|
| 102 | Phenylacetyl chloride | benzyl C(=O)– | 360.1836 |
| 103 | o-Toluoyl chloride | 2-methylphenyl-C(=O)– | 360.1823 |
| 104 | 4-Cyanobenzoyl chloride | 4-cyanophenyl-C(=O)– | 371.1636 |
| 105 | 3-Cyanobenzoyl chloride | 3-cyanophenyl-C(=O)– | 371.1608 |
| 106 | Cinnamoyl chloride | PhCH=CH-C(=O)– | 372.1824 |
| 107 | Hydrocinnamoyl chloride | PhCH₂CH₂-C(=O)– | 374.1956 |

-continued
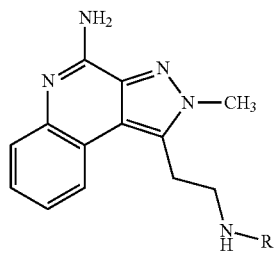
| Example | Reagent | R | Measured Mass (M + H) |
|---|---|---|---|
| 108 | 3-Methoxybenzoyl chloride | 3-methoxybenzoyl group | 376.1795 |
| 109 | p-Anisoyl chloride | 4-methoxybenzoyl group | 376.1804 |
| 110 | 2-Chlorobenzoyl chloride | 2-chlorobenzoyl group | 380.1255 |
| 111 | 3-Chlorobenzoyl chloride | 3-chlorobenzoyl group | 380.1294 |
| 112 | 4-Chlorobenzoyl chloride | 4-chlorobenzoyl group | 380.1310 |
| 113 | Isonicotinoyl chloride hydrochloride | isonicotinoyl group | 347.1617 |

-continued
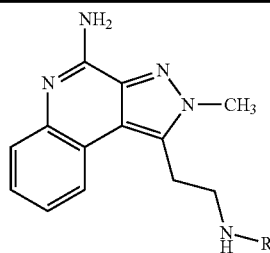
| Example | Reagent | R | Measured Mass (M + H) |
|---|---|---|---|
| 114 | Nicotinoyl chloride hydrochloride | 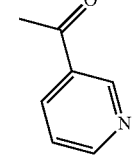 | 347.1597 |
| 115 | Picolinoyl chloride hydrochloride | 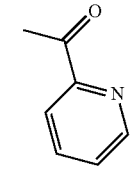 | 347.1585 |
| 116 | trans-2-Phenyl-1-cyclopropanecarbonyl chloride | 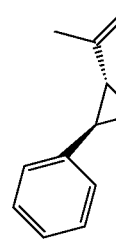 | 386.1975 |
| 117 | 4-Dimethylaminobenzoyl chloride | 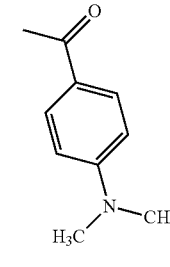 | 389.2125 |
| 118 | 3-Dimethylaminobenzoyl chloride | 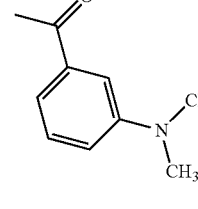 | 389.2104 |
| 119 | (Phenylthio)acetyl chloride | 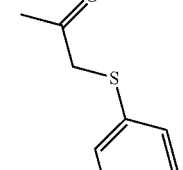 | 392.1530 |

-continued
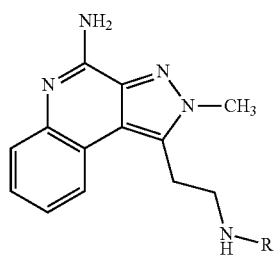
| Example | Reagent | R | Measured Mass (M + H) |
|---|---|---|---|
| 120 | 2-Naphthoyl chloride | (2-naphthyl carbonyl) | 396.1837 |
| 121 | 2,4-Dimethoxybenzoyl chloride | (2,4-dimethoxyphenyl carbonyl) | 406.1906 |
| 122 | 3-(Trifluoromethyl)benzoyl chloride | (3-trifluoromethylphenyl carbonyl) | 414.1536 |
| 123 | 3,4-Dichlorobenzoyl chloride | (3,4-dichlorophenyl carbonyl) | 414.0906 |
| 124 | 2,4-Dichlorobenzoyl chloride | (2,4-dichlorophenyl carbonyl) | 414.0908 |

-continued
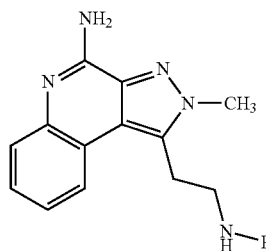
| Example | Reagent | R | Measured Mass (M + H) |
|---|---|---|---|
| 125 | 2,6-Dichlorobenzoyl chloride | 2,6-dichlorobenzoyl | 414.0900 |
| 126 | 3,5-Dichlorobenzoyl chloride | 3,5-dichlorobenzoyl | 414.0910 |
| 127 | 4-Biphenylcarbonyl chloride | 4-biphenylcarbonyl | 422.2006 |
| 128 | Methanesulfonyl chloride | -S(O)$_2$CH$_3$ | 320.1184 |
| 129 | Ethanesulfonyl chloride | -S(O)$_2$CH$_2$CH$_3$ | 334.1332 |
| 130 | 1-Propanesulfonyl chloride | -S(O)$_2$CH$_2$CH$_2$CH$_3$ | 348.1492 |
| 131 | Isopropylsulfonyl chloride | -S(O)$_2$CH(CH$_3$)$_2$ | 348.1521 |

-continued
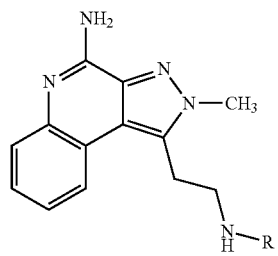
| Example | Reagent | R | Measured Mass (M + H) |
|---|---|---|---|
| 132 | Dimethylsulfamoyl chloride | -S(O)₂N(CH₃)₂ | 349.1465 |
| 133 | 1-Butanesulfonyl chloride | -S(O)₂(CH₂)₃CH₃ | 362.1653 |
| 134 | Trifluoromethanesulfonyl chloride | -S(O)₂CF₃ | 374.0889 |
| 135 | Benzenesulfonyl chloride | -S(O)₂C₆H₅ | 382.1341 |
| 136 | 2,2,2-Trifluoroethanesulfonyl chloride | -S(O)₂CH₂CF₃ | 388.1060 |
| 137 | 2-Thiophenesulfonyl chloride | -S(O)₂-(2-thienyl) | 388.0883 |
| 138 | 3-Methylbenzenesulfonyl chloride | -S(O)₂-(3-methylphenyl) | 396.1499 |

-continued

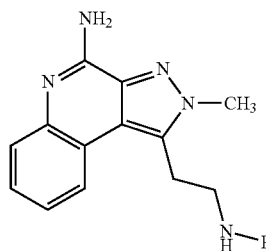

| Example | Reagent | R | Measured Mass (M + H) |
|---|---|---|---|
| 139 | alpha-Toluenesulfonyl chloride | benzyl methylsulfonyl | 396.1493 |
| 140 | o-Toluenesulfonyl chloride | 2-methylphenylsulfonyl | 396.1525 |
| 141 | p-Toluenesulfonyl chloride | 4-methylphenylsulfonyl | 396.1475 |
| 142 | 2-Fluorobenzenesulfonyl chloride | 2-fluorophenylsulfonyl | 400.1256 |
| 143 | 3-Fluorobenzenesulfonyl chloride | 3-fluorophenylsulfonyl | 400.1277 |
| 144 | 4-Fluorobenzenesulfonyl chloride | 4-fluorophenylsulfonyl | 400.1235 |

-continued
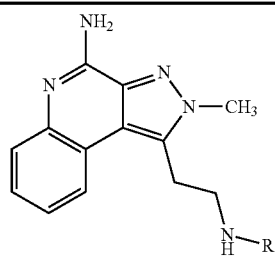
| Example | Reagent | R | Measured Mass (M + H) |
|---|---|---|---|
| 145 | 3-Cyanobenzenesulfonyl chloride | 3-cyanophenylsulfonyl | 407.1299 |
| 146 | 4-Cyanobenzenesulfonyl chloride | 4-cyanophenylsulfonyl | 407.1327 |
| 147 | beta-Styrenesulfonyl chloride | styrylsulfonyl | 408.1498 |
| 148 | 3-Methoxybenzenesulfonyl chloride | 3-methoxyphenylsulfonyl | 412.1471 |
| 149 | 4-Methoxybenzenesulfonyl chloride | 4-methoxyphenylsulfonyl | 412.1478 |

-continued
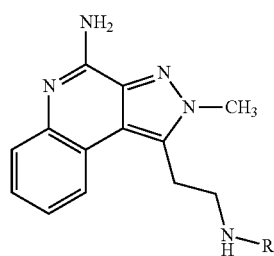
| Example | Reagent | R | Measured Mass (M + H) |
|---|---|---|---|
| 150 | 2-Chlorobenzenesulfonyl chloride | 2-Cl-C6H4-SO2- | 416.0967 |
| 151 | 3-Chlorobenzenesulfonyl chloride | 3-Cl-C6H4-SO2- | 416.0960 |
| 152 | 4-Chlorobenzenesulfonyl chloride | 4-Cl-C6H4-SO2- | 416.0978 |
| 153 | 1-Naphthalenesulfonyl chloride | 1-naphthyl-SO2- | 432.1494 |
| 154 | 2-Naphthalenesulfonyl chloride | 2-naphthyl-SO2- | 432.1490 |

-continued

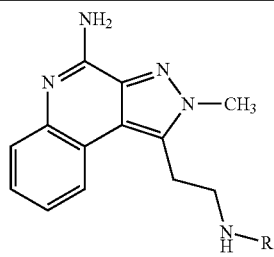

| Example | Reagent | R | Measured Mass (M + H) |
|---|---|---|---|
| 155 | 2,5-Dimethoxybenzenesulfonyl chloride | 2,5-dimethoxyphenylsulfonyl | 442.1533 |
| 156 | 3,4-Dimethoxybenzenesulfonyl chloride | 3,4-dimethoxyphenylsulfonyl | 442.1549 |
| 157 | 3-(Trifluoromethyl)benzenesulfonyl chloride | 4-(trifluoromethoxy)phenylsulfonyl | 450.1183 |
| 158 | (Trifluoromethyl)benzenesulfonyl chloride | 2-(trifluoromethyl)phenylsulfonyl | 450.1194 |
| 159 | 4-(Trifluoromethyl)benzenesulfonyl chloride | 4-(trifluoromethyl)phenylsulfonyl | 450.1187 |

-continued

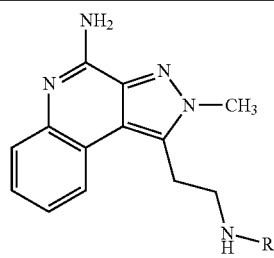

| Example | Reagent | R | Measured Mass (M + H) |
|---|---|---|---|
| 160 | 2,3-Dichlorobenzenesulfonyl chloride | 2,3-dichlorophenylsulfonyl | 450.0583 |
| 161 | 2,4-Dichlorobenzenesulfonyl chloride | 2,4-dichlorophenylsulfonyl | 450.0587 |
| 162 | 2,5-Dichlorobenzenesulfonyl chloride | 2,5-dichlorophenylsulfonyl | 450.0571 |
| 163 | 2,6-Dichlorobenzenesulfonyl chloride | 2,6-dichlorophenylsulfonyl | 450.0598 |
| 164 | 3,4-Dichlorobenzenesulfonyl chloride | 3,4-dichlorophenylsulfonyl | 450.0583 |
| 165 | 10-Camphorsulfonyl chloride | 10-camphorsulfonyl | 456.2094 |

-continued
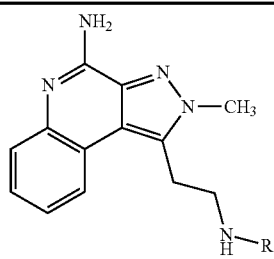
| Example | Reagent | R | Measured Mass (M + H) |
|---|---|---|---|
| 166 | 4-(Trifluoromethoxy)benzenesulfonyl chloride | (4-(trifluoromethoxy)phenyl)sulfonyl | 466.1161 |
| 167 | Methyl isocyanate | -C(O)NHCH₃ | 299.1630 |
| 168 | Ethyl isocyanate | -C(O)NHCH₂CH₃ | 313.1789 |
| 169 | Isopropyl isocyanate | -C(O)NHCH(CH₃)₂ | 327.1940 |
| 170 | Pentyl isocyanate | -C(O)NH(CH₂)₄CH₃ | 355.2246 |
| 171 | Phenyl isocyanate | -C(O)NHPh | 361.1775 |
| 172 | Cyclohexyl isocyanate | -C(O)NH-cyclohexyl | 367.2263 |

-continued
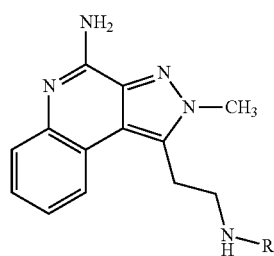
| Example | Reagent | R | Measured Mass (M + H) |
|---|---|---|---|
| 173 | Benzyl isocyanate | acetamide-N-benzyl | 375.1959 |
| 174 | m-Tolyl isocyanate | acetamide-N-(3-methylphenyl) | 375.1939 |
| 175 | o-Tolyl isocyanate | acetamide-N-(2-methylphenyl) | 375.1937 |
| 176 | p-Tolyl isocyanate | acetamide-N-(4-methylphenyl) | 375.1939 |
| 177 | 3-Pyridyl isothiocyanate | thioacetamide-N-(3-pyridyl) | 378.1530 |
| 178 | 4-Cyanophenyl isocyanate | acetamide-N-(4-cyanophenyl) | 386.1752 |

-continued
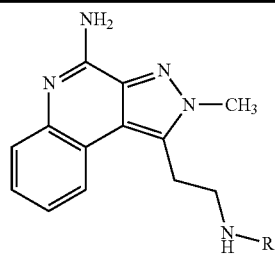
| Example | Reagent | R | Measured Mass (M + H) |
|---|---|---|---|
| 179 | Benzoyl isocyanate | -C(=O)-NH-C(=O)-C6H5 | 389.1724 |
| 180 | (R)-(+)-alpha-Methylbenzyl isocyanate | -C(=O)-NH-CH(CH3)-C6H5 (Chiral) | 389.2057 |
| 181 | 2-Phenyl ethylisocyanate | -C(=O)-NH-CH2CH2-C6H5 | 389.2061 |
| 182 | 2-Methoxyphenyl isocyanate | -C(=O)-NH-(2-OMe-C6H4) | 391.1881 |
| 183 | 3-Methoxyphenyl isocyanate | -C(=O)-NH-(3-OMe-C6H4) | 391.1856 |
| 184 | 4-Methoxyphenyl isocyanate | -C(=O)-NH-(4-OMe-C6H4) | 391.1888 |

-continued

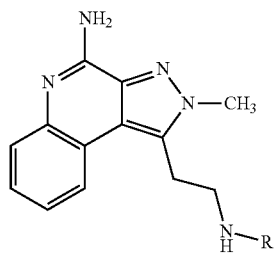

| Example | Reagent | R | Measured Mass (M + H) |
|---|---|---|---|
| 185 | 2-Chlorophenyl isocyanate | 2-chlorophenyl carbamoyl | 395.1394 |
| 186 | 3-Chlorophenyl isocyanate | 3-chlorophenyl carbamoyl | 395.1395 |
| 187 | 4-Chlorophenyl isocyanate | 4-chlorophenyl carbamoyl | 395.1357 |
| 188 | 3,4-Difluorophenyl isocyanate | 3,4-difluorophenyl carbamoyl | 397.1572 |
| 189 | trans-2-Phenylcyclopropyl isocyanate | trans-2-phenylcyclopropyl carbamoyl | 401.2105 |
| 190 | 3-Acetylphenyl isocyanate | 3-acetylphenyl carbamoyl | 403.1882 |

-continued
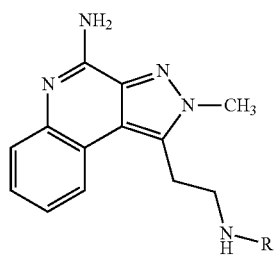
| Example | Reagent | R | Measured Mass (M + H) |
|---|---|---|---|
| 191 | 1-Naphthyl isocyanate | | 411.1963 |
| 192 | 2-Morpholinoethyl isothiocyanate | | 414.2108 |
| 193 | 3-Carbomethoxyphenyl isocyanate | | 419.1846 |
| 194 | 4-(Dimethylamino)isothiocyanate | | 420.1989 |
| 195 | 3,4-Dimethoxyphenyl isocyanate | | 421.1974 |

-continued

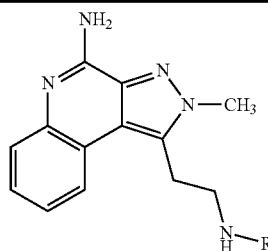

| Example | Reagent | R | Measured Mass (M + H) |
|---|---|---|---|
| 196 | 3,5-Dimethoxyphenyl isocyanate | ![structure with acetamide linked to 3,5-dimethoxyphenyl] | 421.1998 |
| 197 | 4-Methyl-1-piperazinecarbonyl chloride | ![structure with acetyl-4-methylpiperazine] | 368.2194 |

Examples 198-270

A reagent (0.11 mmol, 1.1 equivalents) from the table below was added to a test tube containing 1-(2-aminoethyl)-2-methyl-6,7,8,9-tetrahydro-2H-pyrazolo[3,4-c]quinolin-4-amine (prepared as described in Example 50, 25 mg, 0.10 mmol) and N,N-diisopropylethylamine (0.035 mL, 0.20 mmol) in chloroform (1 mL). The test tubes were capped, shaken for four hours at ambient temperature, and then were shaken overnight. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

Examples 198-270

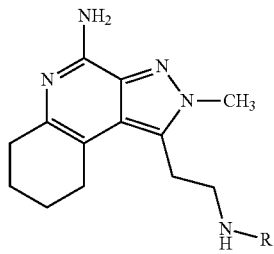

| Example | Reagent | R | Measured Mass (M + H) |
|---|---|---|---|
| 198 | none | H | 246.1712 |
| 199 | Acetyl chloride | COCH₃ | 288.1845 |

-continued
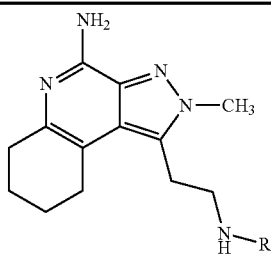
| Example | Reagent | R | Measured Mass (M + H) |
|---|---|---|---|
| 200 | Propionyl chloride | CH2CH3 | 302.1989 |
| 201 | Cyclopropanecarbonyl chloride | C(=O)-cyclopropyl | 314.1982 |
| 202 | Butyryl chloride | C(=O)CH2CH2CH3 | 316.2153 |
| 203 | Methoxyacetyl chloride | C(=O)CH2OCH3 | 318.1920 |
| 204 | Methyl chlorothiolformate | C(=O)SCH3 | 320.1528 |
| 205 | Cyclopentylacetyl chloride | C(=O)CH2-cyclopentyl | 356.2448 |
| 206 | m-Toluoyl chloride | C(=O)-(3-methylphenyl) | 364.2139 |
| 207 | p-Toluoyl chloride | C(=O)-(4-methylphenyl) | 364.2139 |

-continued
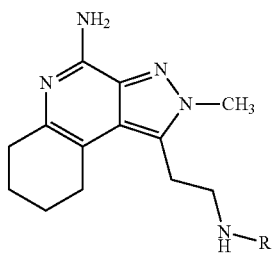
| Example | Reagent | R | Measured Mass (M + H) |
|---|---|---|---|
| 208 | Phenylacetyl chloride | ![benzyl ketone] | 364.2135 |
| 209 | 3-Fluorobenzoyl chloride | ![3-fluorobenzoyl] | 368.1854 |
| 210 | 4-Fluorobenzoyl chloride | ![4-fluorobenzoyl] | 368.1859 |
| 211 | 3-Cyanobenzoyl chloride | ![3-cyanobenzoyl] | 375.1942 |
| 212 | Hydrocinnamoyl chloride | ![hydrocinnamoyl] | 378.2286 |
| 213 | 2-Methoxybenzoyl chloride | ![2-methoxybenzoyl] | 380.2076 |

-continued
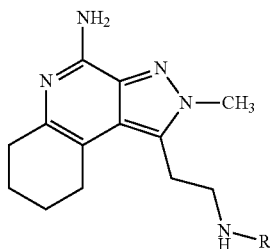
| Example | Reagent | R | Measured Mass (M + H) |
|---|---|---|---|
| 214 | 3-Methoxybenzoyl chloride | 3-methoxybenzoyl | 380.2078 |
| 215 | p-Anisoyl chloride | 4-methoxybenzoyl | 380.2050 |
| 216 | 2-Chlorobenzoyl chloride | 2-chlorobenzoyl | 384.1574 |
| 217 | Isonicotinoyl chloride hydrochloride | isonicotinoyl | 351.1942 |
| 218 | Nicotinoyl chloride hydrochloride | nicotinoyl | 351.1934 |
| 219 | Picolinoyl chloride hydrochloride | picolinoyl | 351.1912 |

-continued

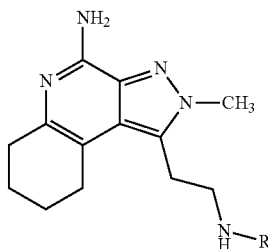

| Example | Reagent | R | Measured Mass (M + H) |
|---|---|---|---|
| 220 | trans-2-Phenyl-1-cyclopropanecarbonyl chloride | (trans-2-phenylcyclopropyl)carbonyl | 390.2289 |
| 221 | 3,4-Dimethoxybenzoyl chloride | 3,4-dimethoxybenzoyl | 410.2179 |
| 222 | 3-(Trifluoromethyl)benzoyl chloride | 3-(trifluoromethyl)benzoyl | 418.1834 |
| 223 | 2,4-Dichlorobenzoyl chloride | 2,4-dichlorobenzoyl | 418.1243 |
| 224 | Methanesulfonyl chloride | methanesulfonyl | 324.1476 |
| 225 | Ethanesulfonyl chloride | ethanesulfonyl | 338.1645 |

-continued

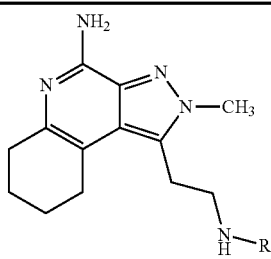

| Example | Reagent | R | Measured Mass (M + H) |
|---|---|---|---|
| 226 | 1-Propanesulfonyl chloride | -S(O)$_2$CH$_2$CH$_2$CH$_3$ | 352.1780 |
| 227 | Dimethylsulfamoyl chloride | -S(O)$_2$N(CH$_3$)$_2$ | 353.1751 |
| 228 | 1-Butanesulfonyl chloride | -S(O)$_2$CH$_2$CH$_2$CH$_2$CH$_3$ | 366.1972 |
| 229 | Trifluoromethanesulfonyl chloride | -S(O)$_2$CF$_3$ | 378.1198 |
| 230 | 1-Methylimidazole-4-sulphonyl chloride | -S(O)$_2$-(1-methylimidazol-4-yl) | 390.1730 |
| 231 | 2,2,2-Trifluoroethanesulfonyl chloride | -S(O)$_2$CH$_2$CF$_3$ | 392.1344 |
| 232 | 3-Methylbenzenesulfonyl chloride | -S(O)$_2$-(3-methylphenyl) | 400.1787 |

-continued
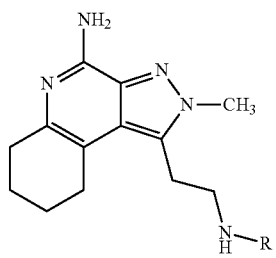
| Example | Reagent | R | Measured Mass (M + H) |
|---|---|---|---|
| 233 | alpha-Toluenesulfonyl chloride | 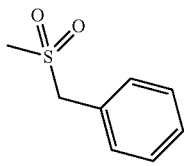 | 400.1801 |
| 234 | 2-Fluorobenzenesulfonyl chloride | 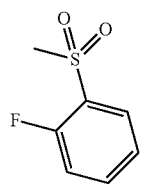 | 404.1536 |
| 235 | 3-Fluorobenzenesulfonyl chloride | 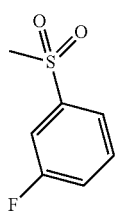 | 404.1560 |
| 236 | 4-Fluorobenzenesulfonyl chloride | 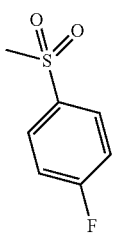 | 404.1543 |
| 237 | 3-Cyanobenzenesulfonyl chloride | 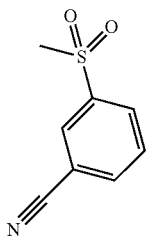 | 411.1613 |

-continued
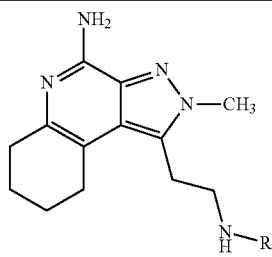
| Example | Reagent | R | Measured Mass (M + H) |
|---|---|---|---|
| 238 | 4-Cyanobenzenesulfonyl chloride | | 411.1631 |
| 239 | beta-Styrenesulfonyl chloride | | 412.1797 |
| 240 | 3-Methoxybenzenesulfonyl chloride | | 416.1752 |
| 241 | 4-Methoxybenzenesulfonyl chloride | | 416.1774 |
| 242 | 2-Chlorobenzenesulfonyl chloride | | 420.1244 |

-continued

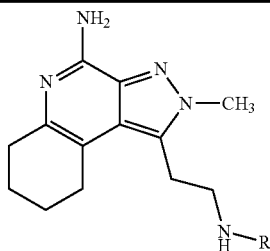

| Example | Reagent | R | Measured Mass (M + H) |
|---|---|---|---|
| 243 | 3-Chlorobenzenesulfonyl chloride | 3-chlorophenylsulfonyl | 420.1227 |
| 244 | 2-Naphthalenesulfonyl chloride | 2-naphthylsulfonyl | 436.1782 |
| 245 | N-Acetylsulfanilyl chloride | 4-acetamidophenylsulfonyl | 443.1829 |
| 246 | 3,4-Dimethoxybenzenesulfonyl chloride | 3,4-dimethoxyphenylsulfonyl | 446.1832 |
| 247 | 3-(Trifluoromethyl)benzenesulfonyl chloride | 3-(trifluoromethyl)phenylsulfonyl | 454.1510 |

-continued

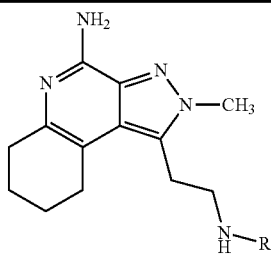

| Example | Reagent | R | Measured Mass (M + H) |
|---|---|---|---|
| 248 | 3,4-Dichlorobenzenesulfonyl chloride | 3,4-dichlorophenylsulfonyl | 454.0905 |
| 249 | 3,5-Dichlorobenzenesulfonyl chloride | 3,5-dichlorophenylsulfonyl | 454.0891 |
| 250 | Methyl isocyanate | C(O)NHCH₃ | 303.1942 |
| 251 | Ethyl isocyanate | C(O)NHCH₂CH₃ | 317.2078 |
| 252 | Isopropyl isocyanate | C(O)NHCH(CH₃)₂ | 331.2234 |
| 253 | Cyclopropyl isothiocyanate | C(S)NH-cyclopropyl | 345.1847 |
| 254 | Cyclopropylmethyl isothiocyanate | C(S)NHCH₂-cyclopropyl | 359.2050 |

-continued
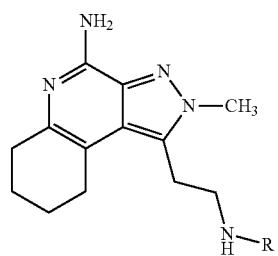
| Example | Reagent | R | Measured Mass (M + H) |
|---|---|---|---|
| 255 | Phenyl isocyanate | -C(=O)NH-phenyl | 365.2102 |
| 256 | Benzyl isocyanate | -C(=O)NH-CH2-phenyl | 379.2238 |
| 257 | m-Tolyl isocyanate | -C(=O)NH-(3-methylphenyl) | 379.2245 |
| 258 | p-Tolyl isocyanate | -C(=O)NH-(4-methylphenyl) | 379.2234 |
| 259 | Phenyl isothiocyanate | -C(=S)NH-phenyl | 381.1844 |
| 260 | 3-Pyridyl isothiocyanate | -C(=S)NH-(3-pyridyl) | 382.1807 |

-continued
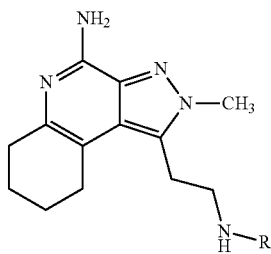
| Example | Reagent | R | Measured Mass (M + H) |
|---|---|---|---|
| 261 | 3-Methoxyphenyl isocyanate | 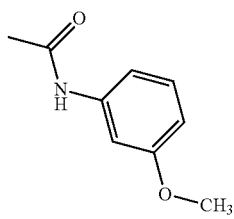 | 395.2202 |
| 262 | 4-Methoxyphenyl isocyanate | 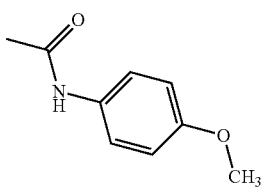 | 395.2234 |
| 263 | 3-Chlorophenyl isocyanate |  | 399.1696 |
| 264 | 1-Naphthyl isocyanate | 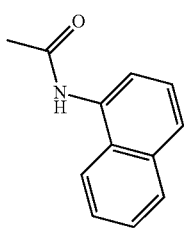 | 415.2243 |
| 265 | 2-Morpholinoethyl isothiocyanate | 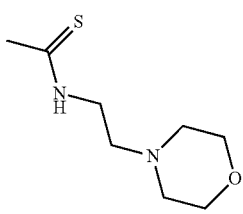 | 418.2388 |

-continued

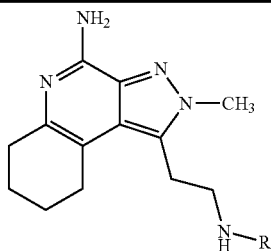

| Example | Reagent | R | Measured Mass (M + H) |
|---|---|---|---|
| 266 | N,N-Dimethylcarbamoyl chloride | (C(=O)N(CH3)2) | 317.2071 |
| 267 | 1-Piperidinecarbonyl chloride | (piperidinecarbonyl) | 357.2418 |
| 268 | 4-Morpholinylcarbonyl chloride | (morpholinylcarbonyl) | 359.2209 |
| 269 | 4-Methyl-1-piperazinecarbonyl chloride | (4-methylpiperazinecarbonyl) | 372.2527 |
| 270 | N-Methyl-N-phenylcarbamoyl chloride | (N-methyl-N-phenylcarbamoyl) | 379.2267 |

Examples 271-306

A reagent (0.14 mmol, 1.1 equivalents) from the table below was added to a test tube containing 1-(2-methylpropyl)-2H-pyrazolo[3,4-c]quinolin-4-amine (prepared as described in Example 9, 32 mg, 0.13 mmol) and potassium carbonate (approximately 55 mg, 0.40 mmol) in DMF (1 mL). A stirbar was added to each test tube. The test tubes were capped and stirred overnight (approximately 18 hours) at ambient temperature. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

Examples 271-306

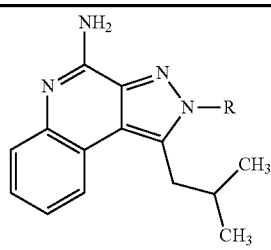

| Example | Reagent | R | Measured Mass (M + H) |
|---|---|---|---|
| 271 | 2-Bromoethyl methyl ether | —CH₂CH₂OCH₃ | 299.1857 |
| 272 | Iodomethane | —CH₃ | 255.1599 |
| 273 | Cyclobutylmethyl bromide | —CH₂-cyclobutyl | 309.2067 |
| 274 | 2-Bromopropanamide | —CH(CH₃)C(O)NH₂ | 312.1841 |
| 275 | Methyl bromoacetate | —CH₂C(O)OCH₃ | 313.1661 |
| 276 | Iodoethane | —CH₂CH₃ | 269.1758 |
| 277 | 2-Iodoethanol | —CH₂CH₂OH | 285.1724 |
| 278 | 2-Bromo-4-hydroxyvaleric acid gamma-lactone | gamma-lactone | 339.1794 |
| 279 | 1-Iodobutane | —(CH₂)₃CH₃ | 297.2073 |
| 280 | (1-Bromoethyl)benzene | —CH(CH₃)Ph | 345.2084 |
| 281 | alpha-Bromo-m-xylene | —CH₂-(3-methylphenyl) | 345.2065 |

-continued

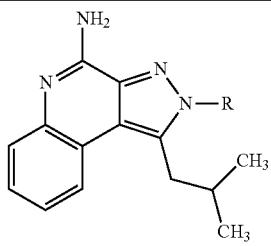

| Example | Reagent | R | Measured Mass (M + H) |
|---|---|---|---|
| 282 | alpha-Bromo-o-xylene | 2-methylbenzyl | 345.2049 |
| 283 | Iodoacetic acid | carboxymethyl | 299.1503 |
| 284 | 2-Cyclohexylethyl bromide | 2-cyclohexylethyl | 351.2532 |
| 285 | alpha-Bromo-m-tolunitrile | 3-cyanobenzyl | 356.1871 |
| 286 | 2-Chlorobenzyl bromide | 2-chlorobenzyl | 365.1530 |
| 287 | 3-Chlorobenzyl bromide | 3-chlorobenzyl | 365.1534 |
| 288 | 2,3-Difluorobenzyl bromide | 2,3-difluorobenzyl | 367.1741 |
| 289 | 2,4-Difluorobenzyl bromide | 2,4-difluorobenzyl | 367.1734 |
| 290 | 2,6-Difluorobenzyl bromide | 2,6-difluorobenzyl | 367.1718 |

-continued

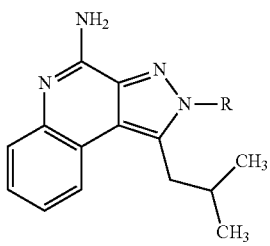

| Example | Reagent | R | Measured Mass (M + H) |
|---|---|---|---|
| 291 | 3,4-Difluorobenzyl bromide | 3,4-difluorobenzyl | 367.1704 |
| 292 | 4-Nitrobenzyl bromide | 4-nitrobenzyl | 376.1784 |
| 293 | 2-(Bromomethyl)naphthalene | naphthalen-2-ylmethyl | 381.2071 |
| 294 | 1-Iodo-3,3,3-trifluoropropane | 3,3,3-trifluoropropyl | 337.1628 |
| 295 | 4-(tert-Butyl)benzyl bromide | 4-tert-butylbenzyl | 387.2564 |
| 296 | Methyl 3-(bromomethyl)benzoate | 3-(methoxycarbonyl)benzyl | 389.1986 |
| 297 | 2-(Trifluoromethyl)benzyl bromide | 2-(trifluoromethyl)benzyl | 399.1796 |

-continued

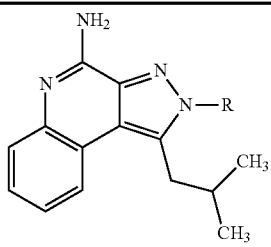

| Example | Reagent | R | Measured Mass (M + H) |
|---|---|---|---|
| 298 | 3-(Trifluoromethyl)benzyl bromide | 3-(trifluoromethyl)benzyl | 399.1790 |
| 299 | 2,6-Dichlorobenzyl bromide | 2,6-dichlorobenzyl | 399.1157 |
| 300 | 4-Bromomethylbiphenyl | 4-biphenylmethyl | 407.2252 |
| 301 | Bromodiphenylmethane | diphenylmethyl | 407.2248 |
| 302 | 3-(Trifluoromethoxy)benzyl bromide | 3-(trifluoromethoxy)benzyl | 415.1747 |
| 303 | 4-(Trifluoromethoxy)benzyl bromide | 4-(trifluoromethoxy)benzyl | 415.1759 |
| 304 | 1-Adamantyl bromomethyl ketone | 1-adamantylcarbonylmethyl | 417.2643 |

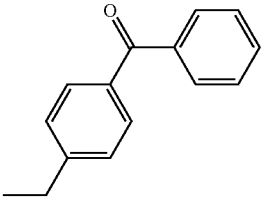 [SMILES: CCc1ccc(C(=O)c2ccccc2)cc1]

| Example | Reagent | R | Measured Mass (M + H) |
|---|---|---|---|
| 305 | 4-(Bromomethyl)benzophenone | 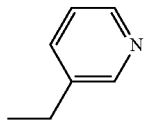 | 435.2195 |
| 306 | 2-(Bromoacetyl)pyridine hydrobromide | 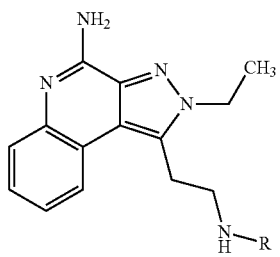 | 332.1870 |

Examples 307-348

A solution of 1-(2-aminoethyl)-2-ethyl-2H-pyrazolo[3,4-c]quinolin-4-amine dihydrochloride (prepared as described in Example 23, 33 mg, 0.10 mmol) and N,N-diisopropylethylamine (0.070 mL, 0.40 mmol) in chloroform (1 mL) was treated with a reagent (0.11 mmol, 1.1 equivalents) from the table below using the procedure described in Examples 23-33. The test tubes were capped and shaken overnight at ambient temperature, then were worked up and purified as described in Examples 23-33. The table below shows the reagent added to each test tube, the structure of the resulting compound, and the observed accurate mass for the isolated trifluoroacetate salt.

Examples 307-348

| Example | Reagent | R | Measured Mass (M + H) |
|---|---|---|---|
| 307 | Acetyl chloride | 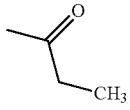 | 298.1668 |
| 308 | Propionyl chloride | 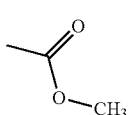 | 312.1841 |
| 309 | Methyl chloroformate | 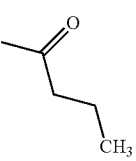 | 314.1601 |
| 310 | Butryl chloride | | 326.1995 |

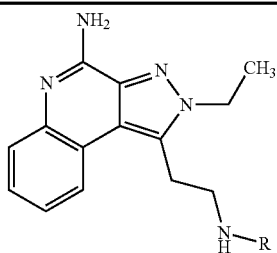

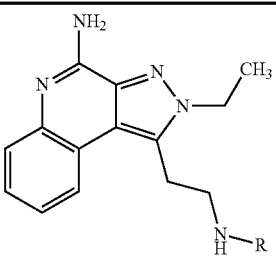

| Example | Reagent | R | Measured Mass (M + H) |
|---|---|---|---|
| 311 | Cyclobutane-carbonyl chloride |  | 338.1966 |
| 312 | Cyclopentylacetyl chloride | 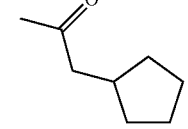 | 366.2291 |
| 313 | m-Toluoyl chloride | 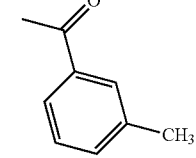 | 374.2002 |
| 314 | 3-Cyanobenzoyl chloride | 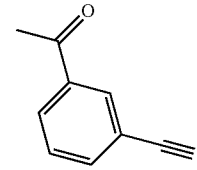 | 385.1764 |
| 315 | Hydrocinnamoyl chloride | 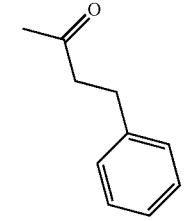 | 388.2147 |
| 316 | 3-Methoxybenzoyl chloride | 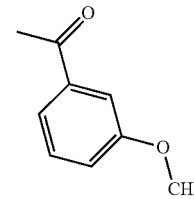 | 390.1935 |
| 317 | 3-Chlorobenzoyl chloride | 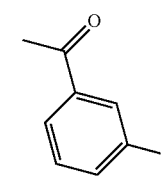 | 394.1436 |
| 318 | 4-Chlorobenzoyl chloride | 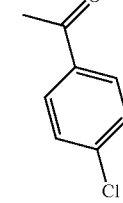 | 394.1441 |
| 319 | Isonicotinoyl chloride hydrochloride | 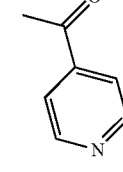 | 361.1778 |
| 320 | Picolinoyl chloride hydrochloride | 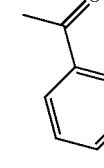 | 361.1762 |
| 321 | 3-Dimethylamino-benzoyl chloride | 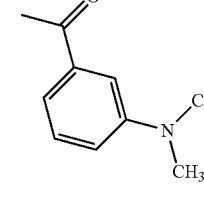 | 403.2254 |
| 322 | Methanesulfonyl chloride | 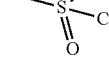 | 334.1329 |
| 323 | Ethanesulfonyl chloride | 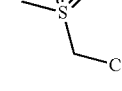 | 348.1497 |
| 324 | 1-Propanesulfonyl chloride | 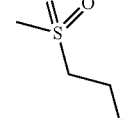 | 362.1642 |

-continued

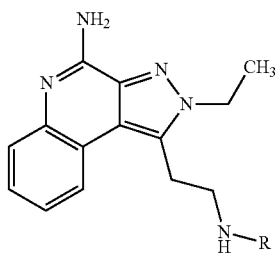

| Example | Reagent | R | Measured Mass (M + H) |
|---|---|---|---|
| 325 | 1-Butanesulfonyl chloride | -S(O)₂-CH₂CH₂CH₂CH₃ | 376.1806 |
| 326 | Trifluoromethanesulfonyl chloride | -S(O)₂-CF₃ | 388.1048 |
| 327 | 1-Methylimidazole-4-sulfonyl chloride | -S(O)₂-(1-methylimidazol-4-yl) | 400.1549 |
| 328 | 3-Methylbenzenesulfonyl chloride | -S(O)₂-(3-methylphenyl) | 410.1651 |
| 329 | alpha-Toluenesulfonyl chloride | -S(O)₂-CH₂-phenyl | 410.1644 |
| 330 | 3-Cyanobenzenesulfonyl chloride | -S(O)₂-(3-cyanophenyl) | 421.1447 |
| 331 | 3-Methoxylbenzenesulfonyl chloride | -S(O)₂-(3-methoxyphenyl) | 426.1591 |
| 332 | 3-Chlorobenzenesulfonyl chloride | -S(O)₂-(3-chlorophenyl) | 430.1097 |
| 333 | Methyl isocyanate | -C(O)-NH-CH₃ | 313.1771 |
| 334 | Ethyl isocyanate | -C(O)-NH-CH₂CH₃ | 327.1921 |
| 335 | Methyl isothiocyanate | -C(S)-NH-CH₃ | 329.1542 |
| 336 | Cyclopropyl isothiocyanate | -C(S)-NH-cyclopropyl | 355.1706 |
| 337 | Pentyl isocyanate | -C(O)-NH-CH₂CH₂CH₂CH₂CH₃ | 369.2397 |

259

-continued

[Structure: 4-amino-2-ethyl-2H-pyrazolo[3,4-c]quinoline with ethyl-NH-R substituent]

| Example | Reagent | R | Measured Mass (M + H) |
|---------|---------|---|------------------------|
| 338 | Cyclopropylmethyl isothiocyanate | -C(=S)-NH-CH2-cyclopropyl | 369.1848 |
| 339 | Cyclohexyl isocyanate | -C(=O)-NH-cyclohexyl | 381.2404 |
| 340 | Benzyl isocyanate | -C(=O)-NH-CH2-phenyl | 389.2104 |
| 341 | m-Tolyl isocyanate | -C(=O)-NH-(3-methylphenyl) | 389.2086 |
| 342 | Phenyl isothiocyanate | -C(=S)-NH-phenyl | 391.1704 |
| 343 | Cyclohexyl isothiocyanate | -C(=S)-NH-cyclohexyl | 397.2166 |

260

-continued

[Structure: 4-amino-2-ethyl-2H-pyrazolo[3,4-c]quinoline with ethyl-NH-R substituent]

| Example | Reagent | R | Measured Mass (M + H) |
|---------|---------|---|------------------------|
| 345 | 3-Methoxyphenyl isocyanate | -C(=O)-NH-(3-methoxyphenyl) | 405.2052 |
| 346 | trans-2-Phenylcyclopropyl isocyanate | -C(=O)-NH-(trans-2-phenylcyclopropyl) | 415.2250 |
| 347 | 4-Morpholinyl-carbonyl chloride | -C(=O)-morpholinyl | 369.2028 |
| 348 | N-Methyl-N-phenylcarbamoyl chloride | -C(=O)-N(CH3)-phenyl | 389.2051 |

Examples 349-453

Part A

2-[4-(4-Amino-2-ethyl-2H-pyrazolo[3,4-c]quinolin-1-yl)butyl]isoindole-1,3-dione (prepared as described in Example 22, 7.10 g, 17.2 mmol), hydrazine hydrate (4.20 mL, 85.9 mmol), and ethanol (213 mL) were combined and heated at reflux for 30 minutes. The solution was allowed to cool to ambient temperature, then was cooled to 0° C. A white solid precipitated from the solution and was isolated by filtration and washed with ethanol. The crude product was purified by chromatography on a HORIZON HPFC system (silica, gradient elution with 10%-75% CMA in chloroform). The appropriate fractions were combined and concentrated under reduced pressure to afford 4.25 g of 1-(4-aminobutyl)-2-ethyl-2H-pyrazolo[3,4-c]quinolin-4-amine.

Part B

A reagent (0.11 mmol, 1.1 equivalents) from the table below was added to a test tube containing 1-(4-aminobutyl)-

2-ethyl-2H-pyrazolo[3,4-c]quinolin-4-amine (28 mg, 0.10 mmol) and N,N-diisopropylethylamine (0.026 mL, 0.15 mmol) in chloroform (1 mL). The test tubes were capped and the test tubes were shaken overnight at room temperature and then two drops of water were added to each test tube. The solvent was removed by vacuum centrifugation. The compounds were purified as described in Examples 71-85. The table below shows the reagent added to each test tube, the structure of the resulting compound, and the observed accurate mass for the isolated trifluoroacetate salt.

Examples 349-453

| Example | Reagent | R | Measured Mass (M + H) |
|---|---|---|---|
| 349 | none | H | 284.1877 |
| 350 | Acetyl chloride | -C(O)CH₃ | 326.1978 |
| 351 | Propionyl chloride | -C(O)CH₂CH₃ | 340.2140 |
| 352 | Methyl chloroformate | -C(O)OCH₃ | 342.1937 |
| 353 | Cyclopropanecarbonyl chloride | -C(O)-cyclopropyl | 352.2149 |
| 354 | Butyryl chloride | -C(O)CH₂CH₂CH₃ | 354.2276 |
| 355 | Methoxyacetyl chloride | -C(O)CH₂OCH₃ | 356.2112 |
| 356 | Cyclobutanecarbonyl chloride | -C(O)-cyclobutyl | 366.2305 |

-continued
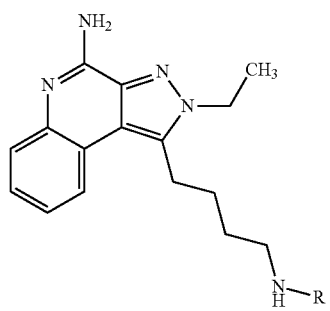
| Example | Reagent | R | Measured Mass (M + H) |
|---|---|---|---|
| 357 | Pivaloyl chloride | *C(=O)C(CH3)3 | 368.2444 |
| 358 | 3-Furoyl chloride | *C(=O)-3-furyl | 378.1927 |
| 359 | Hexanoyl chloride | *C(=O)(CH2)4CH3 | 382.2627 |
| 360 | Benzoyl chloride | *C(=O)Ph | 388.2150 |
| 361 | Cyclohexanecarbonyl chloride | *C(=O)Cy | 394.2607 |
| 362 | m-Toluoyl chloride | *C(=O)-m-tolyl | 402.2298 |

-continued
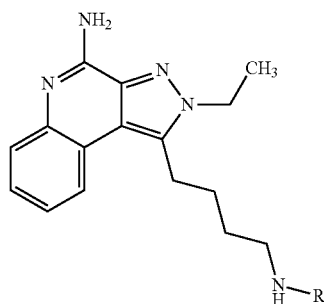
| Example | Reagent | R | Measured Mass (M + H) |
|---|---|---|---|
| 363 | p-Toluoyl chloride | 4-methylbenzoyl | 402.2291 |
| 364 | Phenylacetyl chloride | phenylacetyl | 402.2286 |
| 365 | 4-Cyanobenzoyl chloride | 4-cyanobenzoyl | 413.2110 |
| 366 | 3-Cyanobenzoyl chloride | 3-cyanobenzoyl | 413.2065 |
| 367 | Cinnamoyl chloride | cinnamoyl | 414.2303 |

-continued
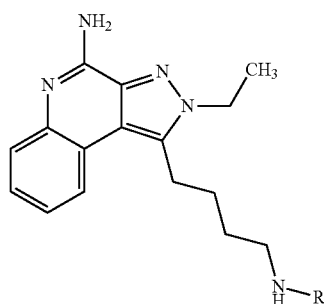
| Example | Reagent | R | Measured Mass (M + H) |
|---|---|---|---|
| 368 | Hydrocinnamoyl chloride | (C(=O)CH2CH2-phenyl) | 416.2462 |
| 369 | 2-Methoxybenzoyl chloride | (C(=O)-2-methoxyphenyl) | 418.2260 |
| 370 | 3-Methoxybenzoyl chloride | (C(=O)-3-methoxyphenyl) | 418.2227 |
| 371 | Benzyl chloroformate | (C(=O)OCH2-phenyl) | 418.2251 |
| 372 | p-Anisoyl chloride | (C(=O)-4-methoxyphenyl) | 418.2253 |

-continued
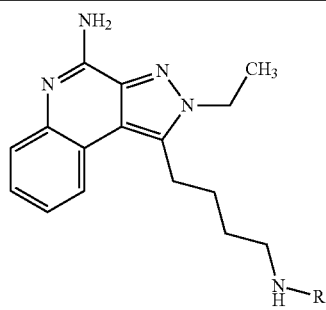
| Example | Reagent | R | Measured Mass (M + H) |
|---|---|---|---|
| 373 | 2-Chlorobenzoyl chloride | 2-chlorobenzoyl | 422.1730 |
| 374 | 3-Chlorobenzoyl chloride | 3-chlorobenzoyl | 422.1746 |
| 375 | 4-Chlorobenzoyl chloride | 4-chlorobenzoyl | 422.1752 |
| 376 | Isonicotinoyl chloride hydrochloride | isonicotinoyl | 389.2069 |
| 377 | Nicotinoyl chloride hydrochloride | nicotinoyl | 389.2081 |
| 378 | Picolinoyl chloride hydrochloride | picolinoyl | 389.2097 |

-continued

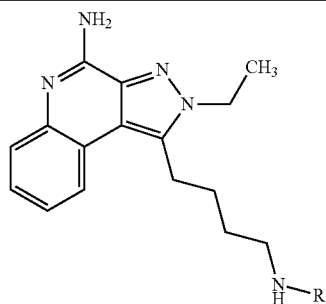

| Example | Reagent | R | Measured Mass (M + H) |
|---|---|---|---|
| 379 | trans-2-Phenyl-1-cyclopropanecarbonyl chloride | ![R group with phenylcyclopropane carbonyl] | 428.2440 |
| 380 | 3-Dimethylaminobenzoyl chloride | ![R group with 3-dimethylaminobenzoyl] | 431.2560 |
| 381 | 2-Naphthoyl chloride | ![R group with 2-naphthoyl] | 438.2295 |
| 382 | 3,4-Dimethoxybenzoyl chloride | ![R group with 3,4-dimethoxybenzoyl] | 448.2343 |
| 383 | 3-(Trifluoromethyl)benzoyl chloride | ![R group with 3-trifluoromethylbenzoyl] | 456.2019 |

-continued
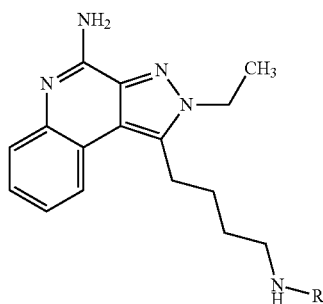
| Example | Reagent | R | Measured Mass (M + H) |
|---|---|---|---|
| 384 | 4-Biphenylcarbonyl chloride | (4-biphenylcarbonyl) | 464.2492 |
| 385 | 3-(Trifluoromethoxy)benzoyl chloride | (3-(trifluoromethoxy)benzoyl) | 472.1953 |
| 386 | Methanesulfonyl chloride | (methanesulfonyl) | 362.1651 |
| 387 | Ethanesulfonyl chloride | (ethanesulfonyl) | 376.1832 |
| 388 | 1-Propanesulfonyl chloride | (1-propanesulfonyl) | 390.1955 |
| 389 | Isopropylsulfonyl chloride | (isopropylsulfonyl) | 390.1954 |

-continued
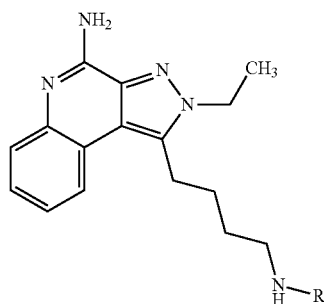
| Example | Reagent | R | Measured Mass (M + H) |
|---|---|---|---|
| 390 | Dimethylsulfamoyl chloride | —S(O)(O)N(CH₃)₂ | 391.1898 |
| 391 | 1-Butanesulfonyl chloride | —S(O)(O)CH₂CH₂CH₂CH₃ | 404.2154 |
| 392 | Trifluoromethanesulfonyl chloride | —S(O)(O)CF₃ | 416.1362 |
| 393 | Benzenesulfonyl chloride | —S(O)(O)Ph | 424.1826 |
| 394 | 1-Methylimidazole-4-sulfonyl chloride | —S(O)(O)-(1-methylimidazol-4-yl) | 428.1883 |
| 395 | 2,2,2-Trifluoroethanesulfonyl chloride | —S(O)(O)CH₂CF₃ | 430.1515 |

-continued
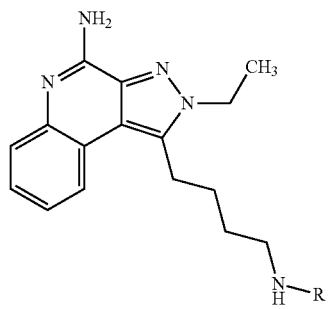
| Example | Reagent | R | Measured Mass (M + H) |
|---|---|---|---|
| 396 | 3-Methylbenzenesulfonyl chloride | 3-methylphenylsulfonyl | 438.1981 |
| 397 | alpha-Toluenesulfonyl chloride | benzylsulfonyl | 438.1944 |
| 398 | p-Toluenesulfonyl chloride | 4-methylphenylsulfonyl | 438.2003 |
| 399 | 3-Fluorobenzenesulfonyl chloride | 3-fluorophenylsulfonyl | 442.1712 |
| 400 | 4-Fluorobenzenesulfonyl chloride | 4-fluorophenylsulfonyl | 442.1740 |

-continued
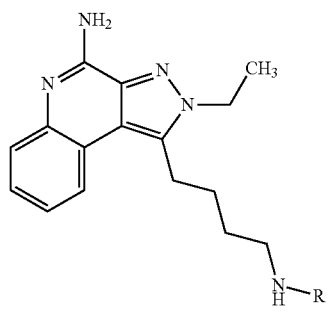
| Example | Reagent | R | Measured Mass (M + H) |
|---|---|---|---|
| 401 | 3-Cyanobenzenesulfonyl chloride | 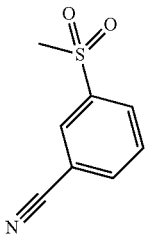 | 449.1736 |
| 402 | 4-Cyanobenzenesulfonyl chloride | 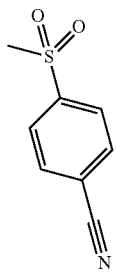 | 449.1800 |
| 403 | beta-Styrenesulfonyl chloride | 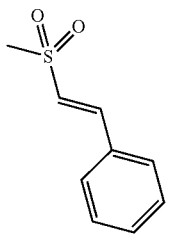 | 450.1969 |
| 404 | 3-Methoxybenzenesulfonyl chloride | 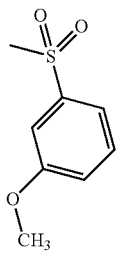 | 454.1942 |

-continued

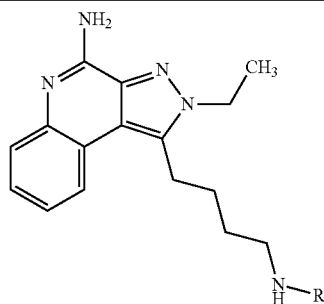

| Example | Reagent | R | Measured Mass (M + H) |
|---|---|---|---|
| 405 | 4-Methoxybenzenensulfonyl chloride | ![R group: 4-methoxyphenylsulfonyl] | 454.1910 |
| 406 | 2-Chlorobenzenesulfonyl chloride | ![R group: 2-chlorophenylsulfonyl] | 458.1417 |
| 407 | 3-Chlorobenzenesulfonyl chloride | ![R group: 3-chlorophenylsulfonyl] | 458.1423 |
| 408 | 4-Chlorobenzenesulfonyl chloride | ![R group: 4-chlorophenylsulfonyl] | 458.1418 |
| 409 | 2-Naphthalenesulfonyl chloride | ![R group: 2-naphthylsulfonyl] | 474.1969 |

-continued
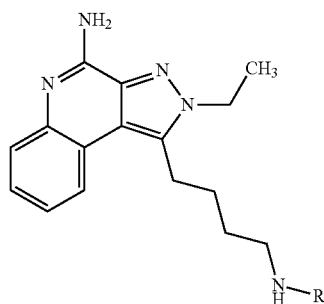
| Example | Reagent | R | Measured Mass (M + H) |
|---|---|---|---|
| 410 | 3,4-Dichlorobenzenesulfonyl chloride | | 492.1036 |
| 411 | 10-Camphorsulfonyl chloride | | 498.2510 |
| 412 | 3-(Trifluoromethoxy)benzenesulphonyl chloride | | 508.1635 |
| 413 | Methyl isocyanate | | 341.2076 |
| 414 | Ethyl isocyanate | | 355.2278 |
| 415 | Methyl isothiocyanate | | 357.1883 |

-continued
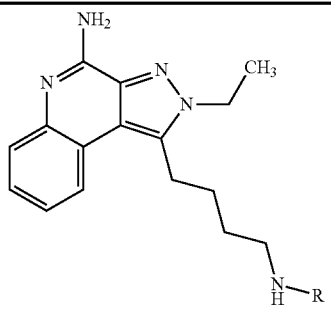
| Example | Reagent | R | Measured Mass (M + H) |
|---|---|---|---|
| 416 | Isopropyl isocyanate | –C(O)NH–CH(CH₃)₂ | 369.2388 |
| 417 | Ethyl isothiocyanate | –C(S)NH–CH₂CH₃ | 371.2035 |
| 418 | Cyclopropyl isothiocyanate | –C(S)NH–cyclopropyl | 383.2018 |
| 419 | Isopropyl isothiocyanate | –C(S)NH–CH(CH₃)₂ | 385.2171 |
| 420 | Pentyl isocyanate | –C(O)NH–(CH₂)₄CH₃ | 397.2738 |
| 421 | Cyclopropyl isothiocyanate | –C(S)NH–CH₂-cyclopropyl | 397.2174 |
| 422 | Isobutyl isothiocyanate | –C(S)NH–CH₂CH(CH₃)₂ | 399.2336 |

-continued
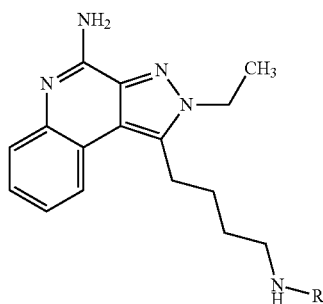
| Example | Reagent | R | Measured Mass (M + H) |
|---------|---------|---|----------------------|
| 423 | Phenyl isocyanate | *-C(O)-NH-phenyl* | 403.2256 |
| 424 | Cyclohexyl isocyanate | *-C(O)-NH-cyclohexyl* | 409.2725 |
| 425 | Benzyl isocyanate | *-C(O)-NH-CH₂-phenyl* | 417.2388 |
| 426 | m-Tolyl isocyanate | *-C(O)-NH-(3-methylphenyl)* | 417.2409 |
| 427 | o-Tolyl isocyanate | *-C(O)-NH-(2-methylphenyl)* | 417.2403 |
| 428 | p-Tolyl isocyanate | *-C(O)-NH-(4-methylphenyl)* | 417.2428 |

-continued
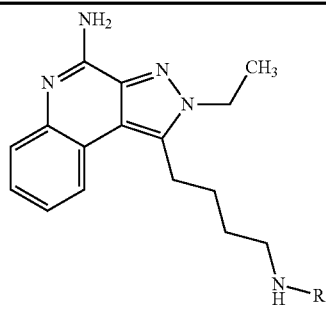
| Example | Reagent | R | Measured Mass (M + H) |
|---|---|---|---|
| 429 | Phenyl isothiocyanate | ![R group: C(=S)NH-phenyl] | 419.2035 |
| 430 | 3-Pyridyl isothiocyanate | ![R group: C(=S)NH-3-pyridyl] | 420.1951 |
| 431 | Benzoyl isocyanate | ![R group: C(=O)NH-C(=O)-phenyl] | 431.2180 |
| 432 | 2-Phenylethyl isocyanate | ![R group: C(=O)NH-CH2CH2-phenyl] | 431.2529 |
| 433 | 2-Methoxyphenyl isocyanate | ![R group: C(=O)NH-2-methoxyphenyl] | 433.2350 |
| 434 | 3-Methoxyphenyl isocyanate | ![R group: C(=O)NH-3-methoxyphenyl] | 433.2338 |

-continued
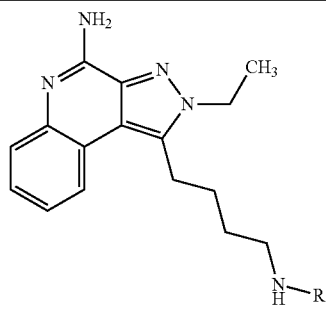
| Example | Reagent | R | Measured Mass (M + H) |
|---|---|---|---|
| 435 | 4-Methoxyphenyl isocyanate | carbamoyl) | 433.2359 |
| 436 | 2-(Thien-2-yl)ethyl isocyanate | ethyl)carbamoyl) | 437.2132 |
| 437 | 2-Chlorophenyl isocyanate | carbamoyl) | 437.1870 |
| 438 | 3-Chlorophenyl isocyanate | carbamoyl) | 437.1870 |
| 439 | 4-Chlorophenyl isocyanate | carbamoyl) | 437.1896 |
| 440 | 3,4-Difluorophenyl isocyanate | carbamoyl) | 439.2064 |

-continued
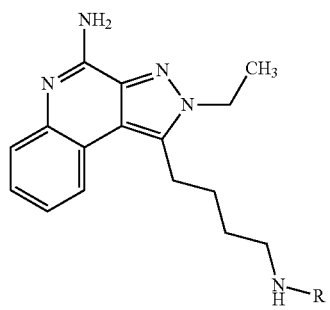
| Example | Reagent | R | Measured Mass (M + H) |
|---|---|---|---|
| 441 | trans-2-Phenylcyclopropyl isocyanate | | 443.2563 |
| 442 | 3-Cyanophenyl isothiocyanate | | 444.1997 |
| 443 | 3-Acetylphenyl isocyanate | | 445.2336 |
| 444 | 2-Morpholinoethyl isothiocyanate | | 456.2535 |
| 445 | 3-Carbomethoxyphenyl isocyanate | | 461.2263 |

-continued

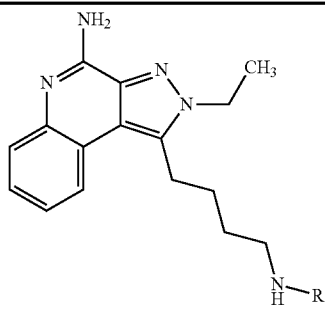

| Example | Reagent | R | Measured Mass (M + H) |
|---|---|---|---|
| 446 | 4-(Dimethylamino)phenyl isocyanate | (thioamide-C6H4-N(CH3)2) | 462.2433 |
| 447 | N,N-Dimethylcarbamoyl chloride | (C(=O)N(CH3)2) | 355.2226 |
| 448 | Dimethylthiocarbamoyl chloride | (C(=S)N(CH3)2) | 371.2020 |
| 449 | 1-Piperidinecarbonyl chloride | (C(=O)-piperidinyl) | 395.2556 |
| 450 | 2-Oxo-1-imidazolidinecarbonyl chloride | (C(=O)-2-oxoimidazolidinyl) | 396.2154 |
| 451 | 4-Methyl-1-piperazinecarbonyl chloride | (C(=O)-4-methylpiperazinyl) | 410.2647 |
| 452 | N-Methyl-N-phenylcarbamoyl chloride | (C(=O)N(CH3)Ph) | 417.2386 |

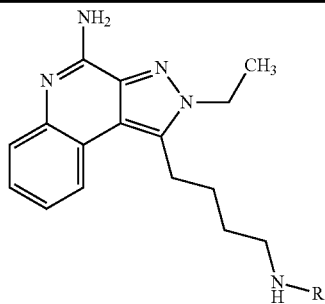

| Example | Reagent | R | Measured Mass (M + H) |
|---|---|---|---|
| 453 | N-Methyl-N-phenylthiocarbamoyl chloride | ![structure] | 433.2192 |

Example 454-488

Part A

Ethyl 5-(4-chlorobutyl)-1-methyl-1H-pyrazole-3-carboxylate was prepared from 6-chloro-2-hexanone (50.0 g, 357 mmol) and diethyl oxalate (48.4 mL, 357 mmol) according to the procedure described in Part A of Example 19 using methyl hydrazine (19.0 mL, 357 mmol) in place of ethylhydrazine oxalate. Ethyl 5-(4-chlorobutyl)-1-methyl-1H-pyrazole-3-carboxylate was isolated as a dark oil that was used without purification in the next step.

Part B

The material from Part A was converted into ethyl 5-[4-(acetyloxy)butyl]-1-methyl-1H-pyrazole-3-carboxylate according to the procedure used in Part B of Example 19. The crude product was used without purification in the next step.

Part C

A solution of the material from Part B in methanol (175 mL) was treated with ammonium hydroxide (250 mL) according to a modification of the method described in Part D of Examples 1-4. The reaction was heated overnight at 125° C. and allowed to cool to ambient temperature. The methanol and water were removed under reduced pressure.

Acetonitrile was added and the mixture was filtered through a plug of silica gel (eluted with 20% methanol in chloroform). The filtrate was concentrated to yield 5-(4-hydroxybutyl)-1-methyl-1H-pyrazole-3-carboxamide that was used in the next step without further purification.

Part D

A modification of the method described in Part E of Examples 1-4 was used to treat 5-(4-hydroxybutyl)-1-methyl-1H-pyrazole-3-carboxamide (42.9 g, 218 mmol) with phosphorous oxychloride (130 mL). The reaction was heated for two hours at 90° C. before cooling to 0° C. and pouring into ice water. The mixture was adjusted to pH 12 with the addition of 2 N aqueous sodium carbonate and 50% aqueous sodium hydroxide. The mixture was extracted with chloroform. The combined extracts were passed through a layer of silica gel (eluting first with chloroform and then with ethyl acetate to provide 23.0 g of 5-(4-chlorobutyl)-1-methyl-1H-pyrazole-3-carbonitrile as a dark oil that was used in the next step without further purification.

Part E

A modification of the method described in Part E of Example 19 was used to convert the material from Part D (23.0 g) into 4-bromo-5-(4-chlorobutyl)-1-methyl-1H-pyrazole-3-carbonitrile. The reaction was allowed to stir for one day before an aqueous solution of sodium bisulfite was added to quench the excess bromine. The reaction was worked up as described for Part E of Example 19, except that after the combined organic layers were dried over sodium sulfate, they were passed through a plug of silica gel (eluted with 1:1 ethyl acetate/hexanes). The filtrate was concentrated and the crude product was purified by chromatography on a HORIZON HPFC system (silica gel, gradient elution with 10-50% ethyl acetate/hexanes. The appropriate fractions were combined and concentrated to yield 7.3 g of 4-bromo-5-(4-chlorobutyl)-1-methyl-1H-pyrazole-3-carbonitrile as a clear oil.

Part F

2-Aminophenylboronic acid hydrochloride (9.20 g, 53.0 mmol), potassium phosphate (28.0 g, 133 mmol), tris(dibenzylideneacetone)dipalladium(0) chloroform adduct (685 mg, 0.662 mmol), and bis[(2-diphenylphosphino)phenyl]ether (428 mg, 0.795 mmol) were added to a mixture of 4-bromo-5-(4-chlorobutyl)-1-methyl-1H-pyrazole-3-carbonitrile (7.30 g, 26.5 mmol) and powdered molecular sieves (1 g) in toluene (165 mL). Nitrogen was bubbled through the reaction mixture, and then the reaction was heated at 110° C. for 24 hours. The mixture was filtered through a layer of silica gel (eluting with 3:2 chloroform/methanol). The filtrate was concentrated under reduced pressure and dissolved in ethanol (130 mL). Hydrogen chloride (20 mL of a 4 M solution in ethanol) was added to the solution and the reaction was heated at reflux for two hours and allowed to cool to ambient temperature. The reaction was worked up as described in Part F of Example 19. After purification by chromatography on a HORIZON HPFC system, the solid was stirred in acetonitrile and filtered to provide 1.0 g of 1-(4-chlorobutyl)-2-methyl-2H-pyrazolo[3,4-c]quinolin-4-amine that was used in the next step. The filtrate was concentrated to provide an additional 4.0 g of product.

Part G

A reagent (0.15 mmol, 1.5 equivalents) from the table below was added to a test tube containing 1-(4-chlorobutyl)-2-methyl-2H-pyrazolo[3,4-c]quinolin-4-amine (29 mg, 0.10 mmol) and potassium carbonate (approximately 55 mg, 0.40 mmol) in DMF (1 mL).

The test tubes were capped and heated at 100° C. for approximately 22 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

Examples 454-488

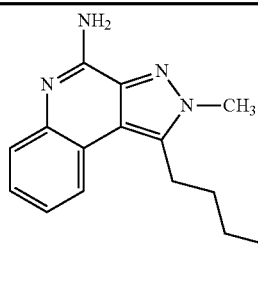

| Example | Reagent | R | Measured Mass (M + H) |
|---|---|---|---|
| 454 | none | \Cl | 289.1205 |
| 455 | Piperidine | | 338.2332 |
| 456 | (R)-3-Hydroxypyrrolidine | Chiral | 340.2130 |
| 457 | Morpholine | | 340.2120 |
| 458 | Thiazolidine | | 342.1721 |
| 459 | 1-Methylpiperazine | | 353.2425 |
| 460 | 4-Hydroxypiperidine | | 354.2310 |
| 461 | 3-Hydroxypiperidine | | 354.2268 |
| 462 | Thiomorpholine | | 356.1884 |
| 463 | N-Methylfurfurylamine | | 364.2134 |
| 464 | N,N'-Dimethyl-3-aminopyrrolidine | | 367.2619 |

301
-continued

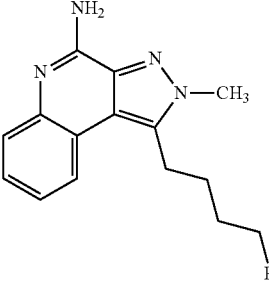

| Example | Reagent | R | Measured Mass (M + H) |
|---|---|---|---|
| 465 | 2,6-Dimethyl-morpholine | 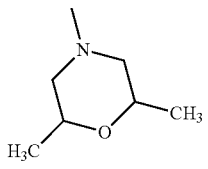 | 368.2448 |
| 466 | 2-Piperidine-methanol | 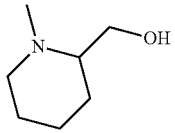 | 368.2426 |
| 467 | 3-(Hydroxymethyl)piperidine | 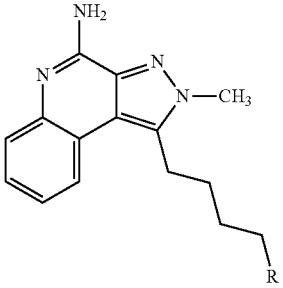 | 368.2443 |
| 468 | 4-(Hydroxymethyl)piperidine | 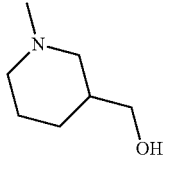 | 368.2437 |
| 469 | 3-Azabicyclo[3.2.2]nonane | 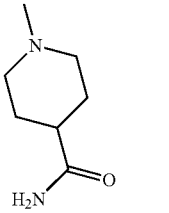 | 378.2622 |
| 470 | 1-Acetylpiperazine | 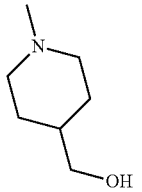 | 381.2406 |

302
-continued

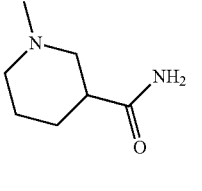

| Example | Reagent | R | Measured Mass (M + H) |
|---|---|---|---|
| 471 | Isonipecotamide | 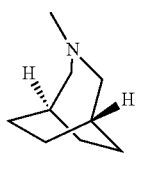 | 381.2375 |
| 472 | Nipecotamide | 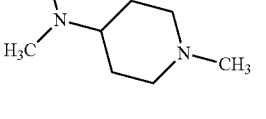 | 381.2426 |
| 473 | 1-Methyl-4-(methylamino)piperidine | 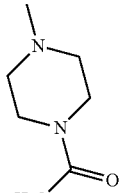 | 381.2733 |
| 474 | Nipecotic acid | 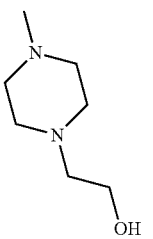 | 382.2213 |
| 475 | N-(2-Hydroxyethyl)piperazine | 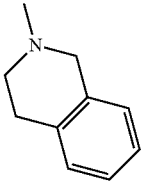 | 383.2571 |
| 476 | 1,2,3,4-Tetrahydroisoquinoline | 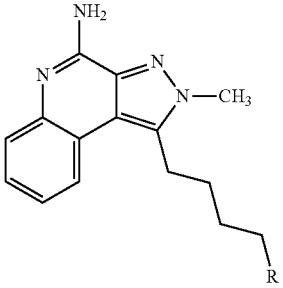 | 386.2333 |

303
-continued

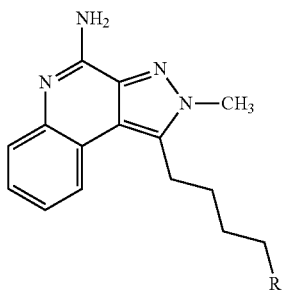

| Example | Reagent | R | Measured Mass (M + H) |
|---|---|---|---|
| 477 | 2-(2-Methylamino-ethyl)pyridine | -N(CH3)-CH2CH2-(2-pyridyl) | 389.2438 |
| 478 | N-(2-Piperidylmethyl)dimethylamine | (1-methylpiperidin-2-yl)-CH2-N(CH3)2 | 395.2915 |
| 479 | 4-(1-Pyrrolidinyl)-piperidine | 4-(pyrrolidin-1-yl)piperidin-1-yl | 407.2894 |
| 480 | 1-(2-Ethoxy-ethyl)piperazine | 4-(2-ethoxyethyl)piperazin-1-yl | 411.2862 |
| 481 | 1-Phenyl-piperazine | 4-phenylpiperazin-1-yl | 415.2572 |

304
-continued

| Example | Reagent | R | Measured Mass (M + H) |
|---|---|---|---|
| 482 | 1-(2-Pyrdiyl)piperazine | 4-(pyridin-2-yl)piperazin-1-yl | 416.2568 |
| 483 | 4-Benzyl-piperidine | 4-benzylpiperidin-1-yl | 428.2816 |
| 484 | 1-(2-Furoyl)piperazine | 4-(furan-2-ylcarbonyl)piperazin-1-yl | 433.2371 |
| 485 | 2-Piperidin-1-ylmethyl-piperidine | 2-(piperidin-1-ylmethyl)piperidin-1-yl | 435.3229 |
| 486 | N,N-Diethyl-nipecotamide | 3-(N,N-diethylcarbamoyl)piperidin-1-yl | 437.3021 |

-continued

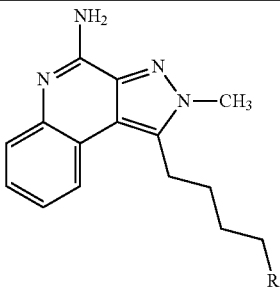

| Example | Reagent | R | Measured Mass (M + H) |
|---|---|---|---|
| 487 | N-Isopropyl-1-piperazine-acetamide | ![structure] | 438.3000 |
| 488 | 1-Cinnamyl-piperazine | ![structure] | 455.2915 |

Example 489-518

Part A

Potassium phthalimide (4.90 mg, 26.4 mmol), sodium iodide (495 mg, 3.30 mmol), and DMF (22 mL) were added to 1-(4-chlorobutyl)-2-methyl-2H-pyrazolo[3,4-c]quinolin-4-amine (4.00 g, 13.2 mmol, prepared as described in Parts A-F of Examples 454-489), and the reaction was heated at 90° C. for two hours under a nitrogen atmosphere and allowed to cool to ambient temperature. Water (100 mL) was added and a precipitate formed and was isolated by filtration to yield 3.7 g of 2-[4-(4-amino-2-methyl-2H-pyrazolo[3,4-c]quinolin-1-yl)butyl]-1H-isoindole-1,3(2H)-dione that was used in the next step.

Part B

A solution of the material from Part A (3.7 g, 8.9 mmol) and hydrazine hydrate (2.15 mL, 44.5 mmol) in ethanol (111 mL) was heated at reflux for 30 minutes, then was cooled to 0° C. and a white solid formed. The solid was isolated and washed with ethanol. The solid was combined with some material from another experiment and was purified by chromatography on a HORIZON HPFC system (silica gel, gradient elution with 5-50% CMA in chloroform). The appropriate fractions were combined, concentrated, and triturated with acetonitrile to afford a solid that was isolated by filtration to yield 880 mg of 1-(4-aminobutyl)-2-methyl-2H-pyrazolo[3,4-c]quinolin-4-amine as a tan powder.

$^1$H NMR (300 MHz, DMSO-$d_6$) δ 8.23 (dd, J=7.6, 1.2 Hz, 1H), 7.48 (dd, J=7.6, 1.2 Hz, 1H), 7.31 (td, J=7.2, 1.5 Hz, 1H), 7.19 (td, J=8.1, 1.4 Hz, 1H), 6.62 (br s, 2H), 4.10 (s, 3H), 3.31 (s, 2H), 3.23 (t, J=7.6 Hz, 2H), 2.57 (t, J=6.9 Hz, 2H), 1.71 (m, 2H), 1.49 (m, 2H);

MS (APCI) m/z 270 (M+H)$^+$.

Part C

A reagent (0.11 mmol, 1.1 equivalents) from the table below was added to a test tube containing 1-(4-aminobutyl)-2-methyl-2H-pyrazolo[3,4-c]quinolin-4-amine (27 mg, 0.10 mmol) and N,N-diisopropylethylamine (0.033 mL, 0.20 mmol) in chloroform (1 mL). The test tubes were capped and shaken overnight at room temperature and then two drops of water were added to each test tube. The solvent was removed by vacuum centrifugation. The compounds were purified as described in Examples 71-85. The table below shows the reagent added to each test tube, the structure of the resulting compound, and the observed accurate mass for the isolated trifluoroacetate salt.

Examples 489-518

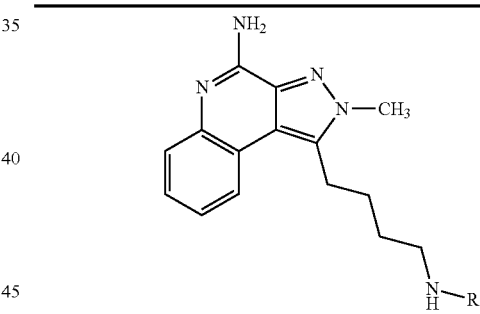

| Example | Reagent | R | Measured Mass (M + H) |
|---|---|---|---|
| 489 | none | H | 270.1720 |
| 490 | Acetyl chloride | ![structure] | 312.1822 |
| 491 | Propionyl chloride | ![structure] | 326.1971 |
| 492 | Cyclopropanecarbonyl chloride | ![structure] | 338.1985 |

307

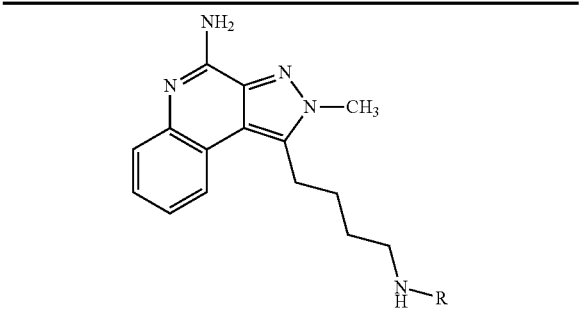

| Example | Reagent | R | Measured Mass (M + H) |
|---|---|---|---|
| 493 | Butyryl chloride | -C(O)CH2CH2CH3 | 340.2134 |
| 494 | Cyclobutanecarbonyl chloride | -C(O)-cyclobutyl | 352.2128 |
| 495 | 3-Chlorobenzoyl chloride | -C(O)-(3-Cl-C6H4) | 408.1593 |
| 496 | 4-Chlorobenzoyl chloride | -C(O)-(4-Cl-C6H4) | 408.1610 |
| 497 | Isonicotinoyl chloride hydrochloride | -C(O)-(4-pyridyl) | 375.1924 |
| 498 | Nicotinoyl chloride hydrochloride | -C(O)-(3-pyridyl) | 375.1945 |
| 499 | Methanesulfonyl chloride | -S(O)2CH3 | 348.1503 |

308

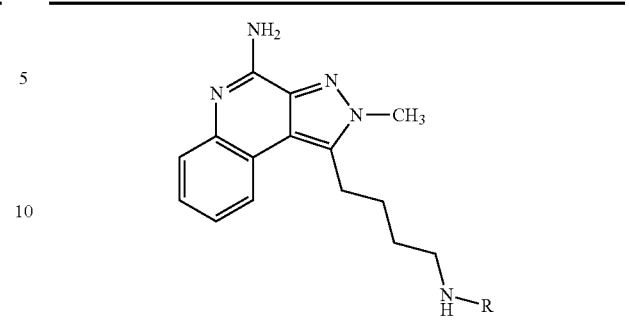

| Example | Reagent | R | Measured Mass (M + H) |
|---|---|---|---|
| 500 | Ethanesulfonyl chloride | -S(O)2CH2CH3 | 362.1656 |
| 501 | 1-Propanesulfonyl chloride | -S(O)2CH2CH2CH3 | 376.1838 |
| 502 | 1-Butanesulfonyl chloride | -S(O)2(CH2)3CH3 | 390.1973 |
| 503 | Trifluoromethanesulfonyl chloride | -S(O)2CF3 | 402.1238 |
| 504 | Benzenesulfonyl chloride | -S(O)2-C6H5 | 410.1693 |
| 505 | 3-Fluorobenzenesulfonyl chloride | -S(O)2-(3-F-C6H4) | 428.1566 |

-continued

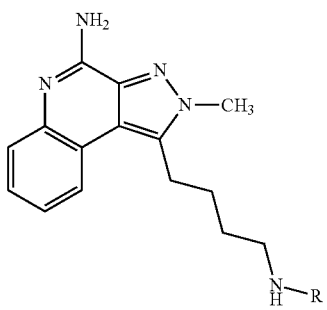

| Example | Reagent | R | Measured Mass (M + H) |
|---|---|---|---|
| 506 | 3-Cyanobenzene-sulfonyl chloride | 3-cyanophenyl-SO2- | 435.1588 |
| 507 | 3-Chlorobenzene-sulfonyl chloride | 3-chlorophenyl-SO2- | 444.1227 |
| 508 | Methyl isocyanate | -C(O)NH-CH3 | 327.1951 |
| 509 | Ethyl isocyanate | -C(O)NH-CH2CH3 | 341.2088 |
| 510 | Isopropyl isocyanate | -C(O)NH-CH(CH3)2 | 355.2279 |
| 511 | Pentyl isocyanate | -C(O)NH-(CH2)4CH3 | 383.2570 |

-continued

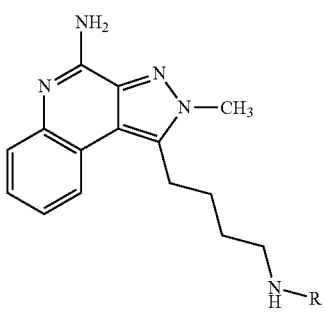

| Example | Reagent | R | Measured Mass (M + H) |
|---|---|---|---|
| 512 | Phenyl isocyanate | -C(O)NH-phenyl | 389.2083 |
| 513 | Cyclohexyl isocyanate | -C(O)NH-cyclohexyl | 395.2576 |
| 514 | Benzyl isocyanate | -C(O)NH-CH2-phenyl | 403.2261 |
| 515 | 2-Phenylethyl isocyanate | -C(O)NH-CH2CH2-phenyl | 417.2420 |
| 516 | N,N-Dimethyl-carbamoyl chloride | -C(O)N(CH3)2 | 341.2114 |
| 517 | 4-Morpholinyl-carbonyl chloride | -C(O)-morpholinyl | 383.2235 |

-continued

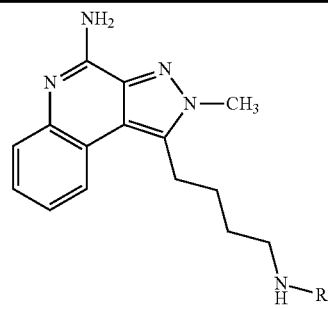

| Example | Reagent | R | Measured Mass (M + H) |
|---|---|---|---|
| 518 | 4-Methyl-1-piperazinecarbonyl chloride | *piperazine-C(=O)- with N-CH3* | 396.2516 |

Examples 519-572

A reagent (0.11 mmol, 1.1 equivalents) from the table below was added to a test tube containing the bis-trifluoroacetic acid salt of 1-(2-aminoethyl)-2-propyl-6,7,8,9-tetrahydro-2H-pyrazolo[3,4-c]quinolin-4-amine (50 mg, 0.10 mmol, prepared as described in Example 51) and N,N-diisopropylethylamine (0.070 mL, 0.40 mmol) in chloroform (1 mL). The test tubes were capped and shaken overnight at room temperature and then two drops of water were added to each test tube. The solvent was removed by vacuum centrifugation. The compounds were purified as described in Examples 71-85. The table below shows the reagent added to each test tube, the structure of the resulting compound, and the observed accurate mass for the isolated trifluoroacetate salt.

Examples 519-572

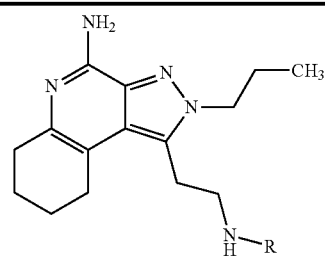

| Example | Reagent | R | Measured Mass (M + H) |
|---|---|---|---|
| 519 | none | H | 274.2038 |
| 520 | Acetyl chloride | -C(=O)CH3 | 316.2154 |

-continued

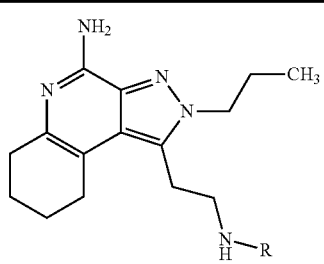

| Example | Reagent | R | Measured Mass (M + H) |
|---|---|---|---|
| 521 | Propionyl chloride | -C(=O)CH2CH3 | 330.2310 |
| 522 | Cyclopropanecarbonyl chloride | -C(=O)-cyclopropyl | 342.2291 |
| 523 | Butyryl chloride | -C(=O)CH2CH2CH3 | 344.2472 |
| 524 | Benzoyl chloride | -C(=O)-phenyl | 378.2303 |
| 525 | Cyclopentylacetyl chloride | -C(=O)CH2-cyclopentyl | 384.2774 |
| 526 | Cyclohexanecarbonyl chloride | -C(=O)-cyclohexyl | 384.2748 |
| 527 | Phenylacetyl chloride | -C(=O)CH2-phenyl | 392.2445 |

313
-continued

Structure: pyrazoloquinoline core with NH2, N-propyl, and -CH2CH2-NH-R substituent

| Example | Reagent | R | Measured Mass (M + H) |
|---|---|---|---|
| 528 | 3-Fluoro-benzoyl chloride | 3-fluorobenzoyl | 396.2219 |
| 529 | 4-Fluoro-benzoyl chloride | 4-fluorobenzoyl | 396.2224 |
| 530 | 4-Cyano-benzoyl chloride | 4-cyanobenzoyl | 403.2255 |
| 531 | 3-Cyano-benzoyl chloride | 3-cyanobenzoyl | 403.2243 |
| 532 | 3-Methoxy-benzoyl chloride | 3-methoxybenzoyl | 408.2416 |
| 533 | 3-Chloro-benzoyl chloride | 3-chlorobenzoyl | 412.1931 |

314
-continued

| Example | Reagent | R | Measured Mass (M + H) |
|---|---|---|---|
| 534 | 4-Chloro-benzoyl chloride | 4-chlorobenzoyl | 412.1929 |
| 535 | Isonicotinoyl chloride hydrochloride | isonicotinoyl | 379.2278 |
| 536 | Nicotinoyl chloride hydrochloride | nicotinoyl | 379.2258 |
| 537 | Picolinoyl chloride hydrochloride | picolinoyl | 379.2265 |
| 538 | Methane-sulfonyl chloride | methanesulfonyl | 352.1819 |
| 539 | Ethanesulfonyl chloride | ethanesulfonyl | 366.1990 |
| 540 | 1-Propane-sulfonyl chloride | 1-propanesulfonyl | 380.2133 |

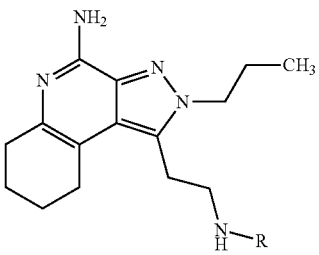
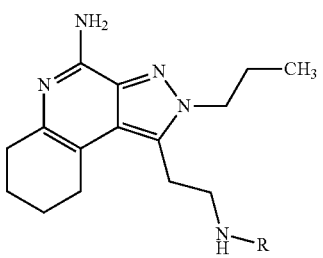

| Example | Reagent | R | Measured Mass (M + H) |
|---|---|---|---|
| 541 | Isopropyl-sulfonyl chloride | | 380.2134 |
| 542 | Dimethyl-sulfamoyl chloride | | 381.2080 |
| 543 | 1-Butane-sulfonyl chloride | | 394.2316 |
| 544 | Trifluoro-methane-sulfonyl chloride | | 406.1540 |
| 545 | Benzene-sulfonyl chloride | | 414.1985 |
| 546 | 1-Methyl-imidazole-4-sulfonyl chloride | | 418.2029 |
| 547 | 3-Methyl-benzene-sulfonyl chloride | | 428.2123 |
| 548 | 3-Fluoro-benzene-sulfonyl chloride | | 432.1890 |
| 549 | 4-Cyano-benzene-sulfonyl chloride | | 439.1953 |
| 550 | 3-Methoxy-benzene-sulfonyl chloride | | 444.2095 |
| 551 | 3-Chloro-benzene-sulfonyl chloride | | 448.1604 |
| 552 | 4-Chloro-benzene-sulfonyl chloride | | 448.1575 |

317
-continued

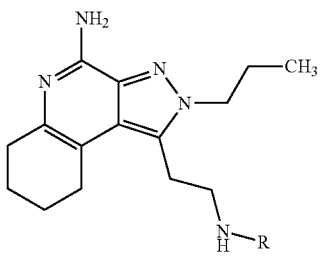

| Example | Reagent | R | Measured Mass (M + H) |
|---|---|---|---|
| 553 | Methyl isocyanate | —C(O)NHCH₃ | 331.2267 |
| 554 | Ethyl isocyanate | —C(O)NHCH₂CH₃ | 345.2419 |
| 555 | Isopropyl isocyanate | —C(O)NHCH(CH₃)₂ | 359.2592 |
| 556 | Pentyl isocyanate | —C(O)NH(CH₂)₄CH₃ | 387.2903 |
| 557 | Phenyl isocyanate | —C(O)NHPh | 393.2431 |
| 558 | Cyclohexyl isocyanate | —C(O)NHCyclohexyl | 399.2892 |
| 559 | Benzyl isocyanate | —C(O)NHCH₂Ph | 407.2554 |

318
-continued

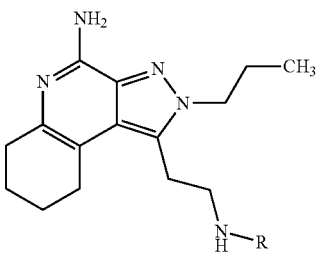

| Example | Reagent | R | Measured Mass (M + H) |
|---|---|---|---|
| 560 | m-Tolyl isocyanate | —C(O)NH(3-methylphenyl) | 407.2596 |
| 561 | 3-Pyridyl isothiocycante | —C(S)NH(3-pyridyl) | 410.2142 |
| 562 | 2-Phenylethyl isocyanate | —C(O)NHCH₂CH₂Ph | 21.2730 |
| 563 | 2-Methoxyl-phenyl isocyanate | —C(O)NH(2-methoxyphenyl) | 423.2517 |
| 564 | 3-Methoxy-phenyl isocyanate | —C(O)NH(3-methoxyphenyl) | 423.2527 |
| 565 | 4-Methoxy-phenyl isocyanate | —C(O)NH(4-methoxyphenyl) | 423.2525 |

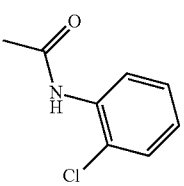

| Example | Reagent | R | Measured Mass (M + H) |
|---|---|---|---|
| 566 | 2-Chlorophenyl isocyanate | 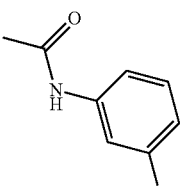 | 427.2018 |
| 567 | 3-Chlorophenyl isocyanate | 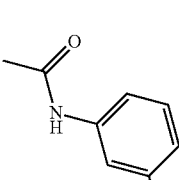 | 427.2028 |
| 568 | 3,4-Difluorophenyl isocyanate | 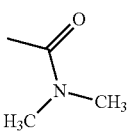 | 429.2248 |
| 569 | N,N-Dimethylcarbamoyl chloride | 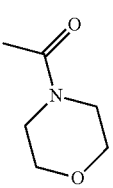 | 345.2408 |
| 570 | 4-Morpholinylcarbonyl chloride | 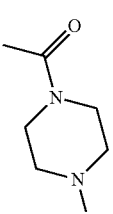 | 387.2500 |
| 571 | 4-Methyl-1-piperazinecarbonyl chloride | | 400.2845 |
| 572 | N-Methyl-N-phenylcarbamoyl chloride | 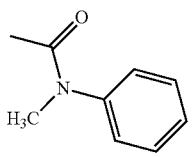 | 407.2571 |

Example 573

1,2-Diethyl-7-methoxy-2H-pyrazolo[3,4-c]quinolin-4-amine

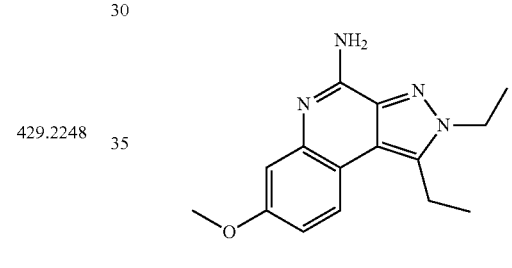

Part A

To a stirred solution of N-(2-bromo-5-methoxyphenyl)-2,2-dimethylpropanamide (2.82 g, 9.85 mmol) in tetrahydrofuran (20 mL) at −78° C. was added slowly a solution of n-butyllithium in hexanes (2.5 M, 8.30 mL, 20.7 mmol). The solution was stirred for 30 minutes in a −40° C. bath, then was cooled back to −78° C. Triisopropyl borate (6.82 mL, 29.6 mmol) was added slowly. The solution was stirred for 1 hour at −40° C., then was stirred at 0° C. for 30 minutes. Saturated aqueous ammonium chloride was added. The mixture was extracted with diethyl ether. The organic layers were combined, dried over sodium sulfate, filtered, and concentrated to afford a residue that was triturated with hexanes. The hexanes were decanted and the residue was stirred in methanol/water to precipitate a white solid that was isolated by filtration, washed with water, and dried to yield 1.36 g of 2-[(2,2-dimethylpropanoyl)amino]-4-methoxyphenylboronic acid, m.p. 256-257° C. The material was used in the next step without further purification.

Part B

A 50 mL round bottom flask containing a mixture of 4-bromo-1,5-diethyl-1H-pyrazole-3-carbonitrile (prepared as described in Part E of Example 11, 1.12 g, 4.91 mmol) and 2-[(2,2-dimethylpropanoyl)amino]-4-methoxyphenylboronic acid (1.36 g, 5.40 mmol) in 1-propanol (25 mL) was evacuated and backfilled with nitrogen. To the flask was added triphenylphosphine (38.6 mg, 0.147 mmol), 2 M aqueous sodium carbonate (7.4 mL), water (5 mL), and palladium (II) acetate (11 mg, 0.048 mmol). The yellow suspension was heated at 100° C. After 3 hours, the reaction mixture was allowed to cool to room temperature, water (10 mL) was added, and the 1-propanol was removed under reduced pressure. The water layer was extracted with ethyl acetate (2×30 mL). The organic layers were combined, washed with 2 M aqueous sodium carbonate (50 mL), water (50 mL), and brine (50 mL), then dried over sodium sulfate. The organic layer was concentrated under reduced pressure. The crude product was purified by chromatography on a HORIZON HPFC system (silica gel, gradient elution with 0-40% ethyl acetate in hexanes) to provide 0.54 g of N-[2-(3-cyano-1,5-diethyl-1H-pyrazol-4-yl)-5-methoxyphenyl]-2,2-dimethylpropanamide as a colorless liquid. MS (ESI) m/z 355.28 (M+H)$^+$ Part C A solution of sodium ethoxide in ethanol (21% by weight, 2.29 mL, 13.9 mmol) was added to a solution of N-[2-(3-cyano-1,5-diethyl-1H-pyrazol-4-yl)-5-methoxyphenyl]-2,2-dimethylpropanamide (0.5 g, 1.41 mmol) in ethanol (10 mL). The reaction mixture was stirred at room temperature for 20 minutes and then heated at reflux overnight. The reaction mixture was allowed to cool to room temperature and was concentrated under reduced pressure. The resulting residue was triturated with water to provide a solid that was isolated by filtration, washed with water, and dried. The material was purified by chromatography on a HORIZON HPFC system (silica gel, gradient elution with 0-20% CMA in chloroform) followed by crystallization from acetonitrile to yield 0.23 g of 1,2-diethyl-7-methoxy-2H-pyrazolo[3,4-c]quinolin-4-amine as beige needles, mp 210-211° C.

$^1$H NMR (500 MHz, DMSO-d$_6$) δ 7.8 (d, J=8.7 Hz, 1H), 7.0 (d, J=2.7 Hz, 1H), 6.80 (dd, J=8.6, 2.7 Hz, 1H), 7.00 (s, 2H), 4.40 (q, J=7.2 Hz, 2H), 3.80 (s, 1H), 3.21 (q, J=7.5 Hz, 2H), 1.46 (t, J=7.2 Hz, 3H), 1.28 (t, J=7.5 Hz, 3H);

$^{13}$C-NMR (75 MHz, CDCl$_3$) δ158.0, 151.4, 145.6, 137.9, 135.3, 122.8, 116.8, 113.6, 110.6, 108.7, 55.3, 44.7, 18.6, 16.4, 13.6;

MS (ESI) m/z 271.2 (M+H)$^+$;

Anal. calcd for C$_{15}$H$_{18}$N$_4$O: C, 66.65; H, 6.71; N, 20.73. Found: C, 66.27; H, 6.59; N, 20.72.

Example 574

2-Ethyl-7-methoxy-1-(2-phenylethyl)-2H-pyrazolo[3,4-c]quinolin-4-amine

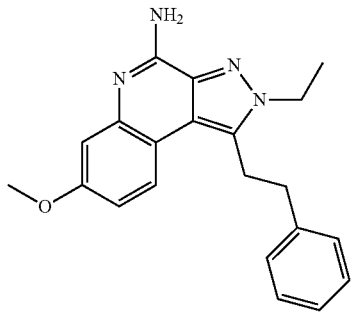 [SMILES: CCn1nc2c(N)nc3cc(OC)ccc3c2c1CCc1ccccc1]

Part A

Using a modification on the method described in Part B of Example 573, 4-bromo-1-ethyl-5-(2-phenylethyl)-1H-pyrazole-3-carbonitrile (prepared as described in Part E of Example 41, 10.3 g, 33.9 mmol) was coupled with 2-[(2,2-dimethylpropanoyl)amino]-4-methoxyphenylboronic acid (prepared as described in Part A of Example 573, 15.3 g, 60.9 mmol). The reaction was worked up and purified as described in Part B of Example 573 to yield 1.7 g of N-{2-[3-cyano-1-ethyl-5-(2-phenylethyl)-1H-pyrazol-4-yl]-5-methoxyphenyl}-2,2-dimethylpropanamide as a colorless liquid, MS (ESI) m/z 431.17 (M+H)$^+$.

Part B

A modification of the method described in Part C of Example 573 was used to convert the material from Part A into 2-ethyl-7-methoxy-1-(2-phenylethyl)-2H-pyrazolo[3,4-c]quinolin-4-amine. The crude product was purified by chromatography on a HORIZON HPFC system (silica gel, gradient elution with 0-30% CMA in chloroform) followed by crystallization from acetonitrile to yield 0.57 g of 2-ethyl-7-methoxy-1-(2-phenylethyl)-2H-pyrazolo[3,4-c]quinolin-4-amine as an off-white solid, mp 162-163° C. MS (ESI) m/z 347.32 (M+H)$^+$; Anal. calcd for C$_{21}$H$_{22}$N$_4$O: C, 72.81; H, 6.40; N, 16.17. Found: C, 72.60; H, 6.53; N, 16.32.

Example 575

4-Amino-2-ethyl-1-(2-phenylethyl)-2H-pyrazolo[3,4-c]quinolin-7-ol hydrochloride

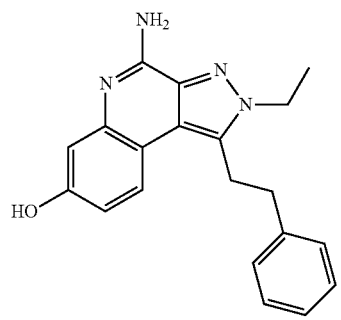 [SMILES: CCn1nc2c(N)nc3cc(O)ccc3c2c1CCc1ccccc1]

2-Ethyl-7-methoxy-1-(2-phenylethyl)-2H-pyrazolo[3,4-c]quinolin-4-amine (0.37 g, 1.07 mmol) was added in one portion to boiling pyridinium chloride (3.70 g, 32.0 mmol). The mixture was heated at reflux for 4 hours, and then was allowed to cool to room temperature. The mixture was triturated with ice water and the precipitate was isolated by filtration, washed with water, and dried to yield 0.38 g of 4-amino-2-ethyl-1-(2-phenylethyl)-2H-pyrazolo[3,4-c]quinolin-7-ol hydrochloride as a light grey solid, mp>300° C.

MS (ESI) m/z 333.31 (M+H)$^+$;

Anal. calcd for C$_{20}$H$_{20}$N$_4$O.1.1HCl.0.25H$_2$O: C, 63.72; H, 5.78; N, 14.86; Cl, 10.34.

Found: C, 63.75; H, 5.96; N, 15.10; Cl, 10.61.

Example 576

4-Amino-2-ethyl-1-(2-phenylethyl)-2H-pyrazolo[3,4-c]quinolin-7-yl trifluoromethanesulfonate

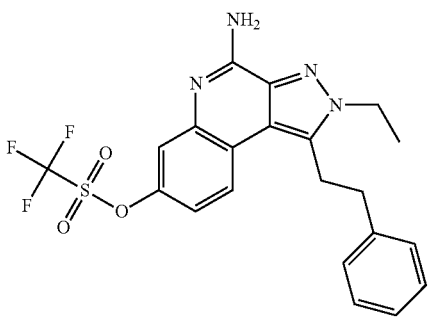 [SMILES: CCn1nc2c(N)nc3cc(OS(=O)(=O)C(F)(F)F)ccc3c2c1CCc1ccccc1]

N-Phenyl-bis(trifluoromethanesulfonamide) (0.187 g, 0.447 mmol) was added to a stirred solution of 4-amino-2-ethyl-1-(2-phenylethyl)-2H-pyrazolo[3,4-c]quinolin-7-ol hydrochloride (0.15 g, 0.41 mmol) and triethylamine (0.280 mL, 2.03 mmol) in DMF (5 mL). After 6 hours, water (25 mL) was added and a precipitate formed that was isolated by filtration, washed with water, and dried to yield 0.175 g of 4-amino-2-ethyl-1-(2-phenylethyl)-2H-pyrazolo[3,4-c]quinolin-7-yl trifluoromethanesulfonate as a white powder, mp 178-179° C.

$^1$H NMR (300 MHz, DMSO-$d_6$) δ 8.05 (d, J=8.8 Hz, 1H), 7.43 (d, J=2.7 Hz, 1H), 7.25 (m, 6H), 7.09 (s, 2H), 4.18 (q, J=7.0 Hz, 2H), 3.54 (t, J=7.3 Hz, 2H), 3.00 (t, J=7.6 Hz, 2H), 1.32 (t, J=7.2 Hz, 3H).

MS (APCI) m/z 465.13 (M+H)$^+$.

Example 577

1-(4-Aminobutyl)-2-propyl-2H-pyrazolo[3,4-c]quinolin-4-amine

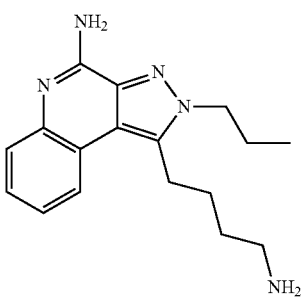 [SMILES: CCCn1nc2c(N)nc3ccccc3c2c1CCCCN]

Part A

A mixture of potassium phthalimide (6.61 g, 35.7 mmol), sodium iodide (0.669 g, 4.46 mmol) and 1-(4-chlorobutyl)-2-propyl-2H-pyrazolo[3,4-c]quinolin-4-amine (prepared as described in Example 46, 5.65 g, 17.8 mmol) in DMF (30 mL) was heated at 90° C. for 3 hours. The reaction mixture was allowed to cool to room temperature overnight, then was diluted with ice water (300 mL) and stirred for 10 minutes. A solid formed that was collected by filtration and dried to yield 7.14 g of 2-[4-(4-amino-2-propyl-2H-pyrazolo[3,4-c]quinolin-1-yl)butyl]-1H-isoindole-1,3(2H)-dione as a tan solid, mp 204-206° C. $^1$H-NMR (300 MHz, CDCl$_3$) δ 7.86-7.70 (m, 5H), 7.69-7.64 (m, 1H), 7.43-7.36 (m, 1H), 7.29-7.22 (m, 1H), 5.37 (br s, 2H), 4.30 (t, J=7.3 Hz, 2H), 3.77 (t, J=6.8 Hz, 2H), 3.31-3.21 (m, 2H), 2.05-1.75 (m, 6H), 0.98 (t, J=7.4 Hz, 3H).

Part B

A mixture of 2-[4-(4-amino-2-propyl-2H-pyrazolo[3,4-c]quinolin-1-yl)butyl]-1H-isoindole-1,3(2H)-dione (7.21 g, 16.9 mmol) and hydrazine hydrate (4.22 g, 84.3 mmol) in ethanol (400 mL) was heated at reflux for 2 hours. The resulting solution was allowed to cool to room temperature, filtered, and concentrated under reduced pressure to yield 3.52 g of 1-(4-aminobutyl)-2-propyl-2H-pyrazolo[3,4-c]quinolin-4-amine as a yellow solid, mp 137-139° C.

MS (APCI) m/z 298.2 (M+H)$^+$.

Example 578

1-(4-Aminobutyl)-2-propyl-6,7,8,9-tetrahydro-2H-pyrazolo[3,4-c]quinolin-4-amine

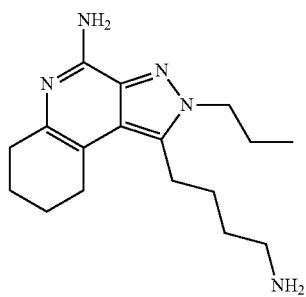 [SMILES: CCCn1nc2c(N)nc3c(c2c1CCCCN)CCCC3]

A solution of 1-(4-aminobutyl)-2-propyl-2H-pyrazolo[3,4-c]quinolin-4-amine (2.40 g, 8.06 mmol) in trifluoroacetic acid (20 mL) was treated with platinum (IV) oxide. The mixture was hydrogenated on a Parr apparatus at 50 psi (3.5×10$^5$ Pa) for 1 day, and then was diluted with chloroform (50 mL) and methanol (25 mL). The mixture was filtered through CELITE filter agent. The filtrate was concentrated under reduced pressure to yield 6.0 g the bis-trifluoroacetic acid salt of 1-(4-aminobutyl)-2-propyl-6,7,8,9-tetrahydro-2H-pyrazolo[3,4-c]quinolin-4-amine in residual trifluoroacetic acid as a yellow liquid.

MS (APCI) m/z 302.3 (M+H)$^+$.

Examples 579-581

Part A

A solution of 1-butyl-2-tert-butyl-2H-pyrazolo[3,4-c]quinolin-4-amine (prepared as described in Example 43, 1.43 g, 4.60 mmol) in 6 M HCl in water (40 mL) was heated at 100° C. overnight. The reaction mixture was allowed too cool to room temperature and a white solid was isolated by filtration, washed with water to provide 1-butyl-2H-pyrazolo[3,4-c]quinolin-4-amine hydrochloride that was used in the next step without extensive drying. Alternatively, the product can be dried in a vacuum oven at 95° C.

Anal. calcd for C$_{14}$H$_{16}$N$_4$·0.8HCl: C, 56.31; H, 5.67; N, 18.76. Found: C, 56.64; H, 5.10; N, 18.68.

Part B

A solution of 1-butyl-2H-pyrazolo[3,4-c]quinolin-4-amine hydrochloride (1 equivalent, 0.06 M), sodium tert-butoxide (3 equivalents), and an alkyl iodide from the table below (3 equivalents) in ethanol was heated at reflux for 1-4 days. Additional alkyl iodide was added if necessary. The reaction mixture was allowed to cool to room temperature and a precipitate was isolated by filtration, washed with water, and dried. The crude product was purified by IFC (silica gel, gradient elution with CMA in chloroform). In Example 579, the product was further purified by precipitation from ethanol/water. In Examples 580 and 581, the product was further purified by reverse phase chromatography (gradient elution with acetonitrile in water containing 0.5% formic acid). In all examples, the final product was dried at 90° C. under vacuum.

Example 579

1,2-Dibutyl-2H-pyrazolo[3,4-c]quinolin-4-amine was obtained as a white powder, mp 143.0-145.0° C.

$^1$H NMR (500 MHz, DMSO-d$_6$) δ 7.89 (dd, J=7.9, 1.1 Hz, 1H), 7.50 (dd, J=8.1, 1.1 Hz, 1H), 7.33 (td, J=7.2, 1.4 Hz, 1H), 7.22 (td, J=8.0, 1.3 Hz, 1H), 6.59 (br s, 2H), 4.36 (t, J=7.3 Hz, 2H), 3.23 (t, J=8.1 Hz, 2H), 1.91-1.85 (m, 2H), 1.69-1.63 (m, 2H), 1.48 (sextet, J=7.5 Hz, 2H), 1.36 (sextet, J=7.6 Hz, 2H), 0.95 (t, J=7.3 Hz, 3H), 0.93 (t, J=7.4 Hz, 3H);

MS (APCI) m/z 297 (M+H)$^+$;

Anal. calcd for C$_{18}$H$_{24}$N$_4$: C, 72.94; H, 8.16; N, 18.90. Found: C, 72.70; H, 8.08; N, 19.05.

Example 580

The formic acid salt of 1-butyl-2-propyl-2H-pyrazolo[3,4-c]quinolin-4-amine was obtained as a white powder, mp 164-166° C.

$^1$H NMR (700 MHz, DMSO-d$_6$) δ 8.17 (s, 0.8H), 7.90-7.89 (m, 1H), 7.50-7.49 (m, 1H), 7.34-7.31 (m, 1H), 7.23-7.21 (m, 1H), 6.83 (br s, 2H), 4.34 (t, J=7 Hz, 2H), 3.23 (t, J=7.6 Hz, 2H), 1.95 (sextet, J=7.3 Hz, 2H), 1.67 (pentet, J=7.9 Hz, 2H), 1.46 (sextet, J=7.5 Hz, 2H), 0.95 (t, 7.3 Hz, 3H), 0.92 (t, J=7.3 Hz, 3H);

$^{13}$C NMR (175 MHz, DMSO) δ 163.34, 150.49, 143.04, 137.98, 135.33, 125.69, 125.12, 121.74, 121.65, 119.48, 116.25, 50.76, 30.62, 24.57, 23.53, 21.83, 13.66, 10.89;

MS (APCI) m/z 283 (M+H)$^+$;

Anal. calcd for C$_{17}$H$_{22}$N$_4$·1.0 CH$_2$O$_2$·0.2H$_2$O: C, 65.12; H, 7.41; N, 16.87. Found: C, 64.73; H, 7.53; N, 16.92.

Example 581

The formic acid salt of 1-butyl-2-methyl-2H-pyrazolo[3,4-c]quinolin-4-amine was obtained as a white powder, mp 202-203° C.

$^1$H NMR (500 MHz, DMSO-d$_6$) δ 8.17 (s, 0.8H), 7.92 (dd, J=7.9, 1.2 Hz, 1H), 7.50 (dd, J=8.1, 1.1 Hz, 1H), 7.34 (td, J=7.1, 1.4 Hz, 1H), 7.23 (td, J=7.9, 1.3 Hz, 1H), 6.83 (br s, 2H), 4.10 (s, 3H), 3.23 (t, J=7.6 Hz, 2H), 1.67 (pentet, J=7.9 Hz, 2H), 1.46 (sextet, J=7.5 Hz, 2H), 0.94 (t, J=7.3 Hz, 3H);

$^{13}$C NMR (125 MHz, DMSO) δ 163.29, 150.38, 142.94, 138.15, 134.96, 125.70, 125.05, 121.73, 121.54, 119.39, 116.46, 37.23, 30.10, 24.67, 21.76, 13.62;

MS (APCI) m/z 255 (M+H)$^+$;

Anal. calcd for C$_{15}$H$_{18}$N$_4$·0.8 CH$_2$O$_2$·0.02H$_2$O: C, 65.10; H, 6.79; N, 19.22. Found: C, 64.75; H, 6.74; N, 19.22.

Examples 579-581

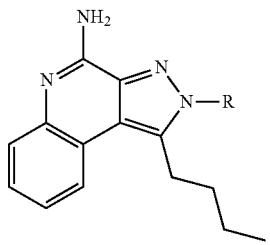

| Example | Alkylating agent in Part B | R |
|---|---|---|
| 579 | 1-iodobutane | —CH$_2$CH$_2$CH$_2$CH$_3$ |
| 580 | 1-iodopropane | —CH$_2$CH$_2$CH$_3$ |
| 581 | iodomethane | —CH$_3$ |

Examples 582

2-Isopropyl-1-methyl-2H-pyrazolo[3,4-c]quinolin-4-amine

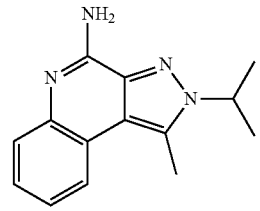 [SMILES: Cc1c2c(nn1C(C)C)c(N)nc1ccccc12]

Part A

A poly(tetrafluoroethylene)-lined steel pressure vessel containing a solution of 2-benzyl-1-methyl-2H-pyrazolo[3,4-c]quinolin-4-amine (prepared as described in Example 36, 0.8821 g, 3.06 mmol) in anhydrous hydrogen bromide in acetic acid (10 mL) was heated in a 140° C. oven for 17 hours. The vessel was allowed to cool to room temperature. A solid formed that was isolated by filtration and washed with water to yield 1-methyl-2H-pyrazolo[3,4-c]quinolin-4-amine that was used in the next step.

Part B

The general method described in Part B of Examples 579-581 was used to convert the material from Part A into 2-isopropyl-1-methyl-2H-pyrazolo[3,4-c]quinolin-4-amine, using 2-iodopropane as the alkyl iodide. The purification method described for Example 579 was used to provide 0.0398 g of 2-isopropyl-1-methyl-2H-pyrazolo[3,4-c]quinolin-4-amine as a white powder, mp 221.0-222.0° C.

$^1$H NMR (500 MHz, DMSO-d$_6$) δ 8.02 (dd, J=7.9, 1.2 Hz, 1H), 7.49 (dd, J=8.1, 1.0 Hz, 1H), 7.32 (td, J=7.1, 1.5 Hz, 1H), 7.20 (td, J=7.9, 1.3 Hz, 1H), 6.52 (br s, 2H), 4.94 (septet, J=6.6 Hz, 1H), 2.84 (s, 3H), 1.53 (d, J=6.6 Hz, 6H);

MS (APCI) m/z 241 (M+H)$^+$;

Anal. calcd for $C_{14}H_{16}N_4 \cdot 0.15H_2O$: C, 69.21; H, 6.76; N, 23.06. Found: C, 68.81; H, 6.60; N, 22.85.

Example 583

4-(4-Amino-2-ethyl-2H-pyrazolo[3,4-c]quinolin-1-yl)butyl acetate

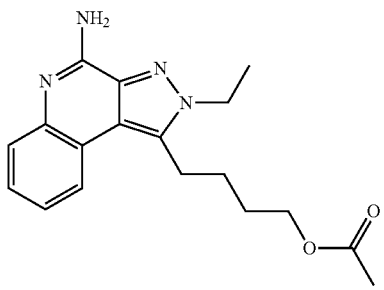 [SMILES: CCn1nc2c(N)nc3ccccc3c2c1CCCCOC(C)=O]

1-(4-Chlorobutyl)-2-ethyl-2H-pyrazolo[3,4-c]quinolin-4-amine (3.8 g, 12.5 mmol, prepared as described in Example 19) was combined with potassium acetate (3.68 g, 37.5 mmol), sodium iodide (470 mg, 3.12 mmol), and DMF (21 mL). The mixture was heated at 90° C. for 2 hours, allowed to cool to ambient temperature, diluted with water (100 mL), stirred for 20 minutes, and then filtered to remove a black solid. The filtrate was allowed to stand for 1 week at which time crystals had formed. The crystals were isolated by filtration, purified by chromatography on a HORIZON HPFC system (25+M cartridge eluting with chloroform/CMA in a gradient from 100:0 to 70:30), and then recrystallized from acetonitrile to provide 55 mg of 4-(4-amino-2-ethyl-2H-pyrazolo[3,4-c]quinolin-1-yl)butyl acetate as a tan crystalline solid, mp 128-129° C. MS (APCI) m/z 327 $(M+H)^+$;

Anal. calcd for $C_{18}H_{22}N_4O_2$: C, 66.24; H, 6.79; N, 17.17. Found: C, 66.01; H, 6.89; N, 17.24.

Example 584

N-[3-(4-Amino-2-tert-butyl-2H-pyrazolo[3,4-c]quinolin-1-yl)propyl]methanesulfonamide

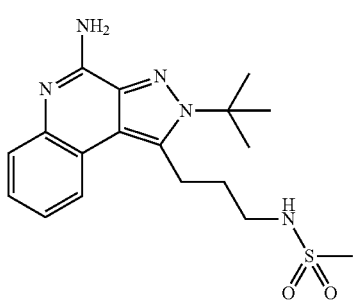 [SMILES: CC(C)(C)n1nc2c(N)nc3ccccc3c2c1CCCNS(C)(=O)=O]

Part A

Under a nitrogen atmosphere, a mixture sodium tert-butoxide (88.45 g, 0.920 mol) and ethanol (625 mL) was stirred for 5 minutes and then cooled to 0° C. A solution of diethyl oxalate (119 mL, 0.877 mol) and 6-chloro-2-pentanone (100 mL, 0.877 mol) in a minimal amount of ethanol was added and a precipitate formed immediately. The reaction was stirred for 5 minutes, then acetic acid (438 mL of 2 M) was added and a solution was obtained. Potassium acetate (129.0 g, 1.314 mol) was added and the reaction mixture was stirred for 3 minutes at which time it solidified. tert-Butylhydrazine oxalate hydrochloride (120.1 g, 0.964 mol) was added. The reaction was allowed to warm to ambient temperature with stirring overnight and then concentrated under reduced pressure. The residue was diluted with dichloromethane and water and the mixture was adjusted to pH 11 with the addition of 2 M aqueous sodium carbonate. The aqueous layer was extracted with dichloromethane; the combined organics were dried over sodium sulfate, filtered, and concentrated under reduced pressure to provide ethyl 1-tert-butyl-5-(3-chloropropyl)-1H-pyrazole-3-carboxylate that was used without purification.

Part B

The material from Part A was combined with 6 M sodium hydroxide (292 mL) and ethanol (219 mL), stirred at ambient temperature for 4 hours, and then concentrated under reduced pressure. The residue was dissolved in water. The solution was extracted with diethyl ether (2×100 mL) and then acidified to pH 4 with 3 N hydrochloric acid. A precipitate formed; the mixture was stirred for 30 minutes and then filtered. The isolated solid was washed with water and then air dried for 48 hours to provide 65.9 g of 1-tert-butyl-5-(3-chloropropyl)-1H-pyrazole-3-carboxylic acid as a tan solid.

Part C 1-(3-Dimethylaminopropyl)-3-ethylcarbodiimide hydrochloride (8.63 g, 45.0 mmol) was added to a solution of material from Part B (10 g, 40.9 mmol) and 1-hydroxybenzotriazole hydrate (6.08 g, 45.0 mmol) in DMF (70 mL). The solution was stirred for 30 minutes and then cooled to 0° C. Ammonium hydroxide (8.1 mL of 15 M, 123 mmol) was added and the solution was stirred at ambient temperature for 2 hours. The reaction mixture was diluted with water (200 mL) and then extracted with diethyl ether (4×150 mL). The combined extracts were dried over magnesium sulfate, filtered, and concentrated under reduced pressure to provide 1-tert-butyl-5-(3-chloropropyl)-1H-pyrazole-3-carboxamide as a brown oil.

Part D

The material from Part C, triethylamine (17.1 mL, 123 mmol), and dichloromethane (136 mL) were combined and then cooled to 0° C. Trifluoroacetic anhydride (6.3 mL, 45 mmol) was added dropwise over a period of 1 minute. The reaction mixture was stirred for 2 hours and then quenched with saturated ammonium chloride solution (30 mL). The reaction mixture was diluted with water and then extracted with dichloromethane. The combined extracts were dried over sodium sulfate, filtered, and then concentrated under reduced pressure to provide 1-tert-butyl-5-(3-chloropropyl)-1H-pyrazole-3-carbonitrile.

Part E

Bromine (2.5 mL, 49 mmol) was added in a single portion to a mixture of the material from Part D, potassium acetate (8.0 g, 82 mmol), and acetic acid (82 mL). The reaction mixture was stirred for 24 hours, quenched with sodium bisulfate, and then concentrated under reduced pressure. The residue was diluted with dichloromethane and water and the mixture was adjusted to pH 11 with aqueous sodium carbonate. The aqueous layer was extracted with dichloromethane. The combined organics were dried over sodium sulfate, filtered, and then concentrated under reduced pressure to provide a black oil. The oil was purified by column chromatography (silica gel eluting with 7:3 hexanes:ethyl acetate) to provide 7.5 g of a dark yellow oil. Analysis by NMR indicated that the oil contained 4-bromo-1-tert-butyl-5-(3-chloropropyl)-1H-pyrazole-3-carbonitrile and starting material in about a 9:1 ratio.

Part F

2-Aminophenylboronic acid hydrochloride (8.5 g, 49.2 mmol), potassium phosphate (15.6 g, 73.8 mmol), tris(dibenzylideneacetone)dipalladium(0) chloroform adduct (563 mg, 0.615 mmol), and bis[(2-diphenylphosphino)phenyl]ether (397 mg, 0.738 mmol) were added to a solution of the material from Part E in toluene (153 mL) containing powdered molecular sieves (1 g). Nitrogen was bubbled through the reaction mixture, and then the reaction was heated at 110° C. for 24 hours. The mixture was cooled to ambient temperature and then filtered through a layer of silica gel (eluting with 3:2 chloroform/methanol). The filtrate was concentrated under reduced pressure and the residue was dissolved in ethanol (120 mL). Hydrogen chloride (20 mL of a 4 M solution in ethanol) was added to the resulting solution, and the reaction was heated at reflux for two hours and then allowed to cool to ambient temperature. The solvent was removed under reduced pressure and the residue was adjusted to pH 10 with the addition of 2 M aqueous sodium carbonate. The mixture was diluted with brine and extracted with dichloromethane. The combined extracts were dried over sodium sulfate, filtered, and concentrated under reduced pressure. The crude product was purified by chromatography on a HORIZON HPFC system (65+M cartridge, eluting with chloroform/CMA in a gradient from 100:0 to 70:30). The cleanest fractions were combined and concentrated under reduced pressure. The residue was recrystallized from acetonitrile to provide 250 mg of off white crystals. The remaining fractions and the mother liquor from the recrystallization were combined and concentrated to provide 2 g of 2-tert-butyl-1-(3-chloropropyl)-2H-pyrazolo[3,4-c]quinolin-4-amine as a yellow solid.

Part G

Methanesulfonamide (3.0 g, 31.5 mmol) was added to a chilled (0° C.) suspension of sodium hydride (60% dispersion in mineral oil, 1.2 g, 31.5 mmol) in DMF (10 mL); the reaction was stirred at ambient temperature for five minutes. The yellow solid from Part F, DMF (4 mL) and sodium iodide (235 mg, 1.57 mmol) were sequentially added. The reaction was heated at 90° C. for three hours, allowed to cool to ambient temperature, and then poured into ice water (100 mL). The mixture was stirred at ambient temperature for 1 hour at which time a precipitate formed. The solid was isolated by filtration and then dissolved in a mixture of dichloromethane and chloroform. The solution was dried over sodium sulfate and then purified by chromatography on a HORIZON HPFC system (40+M cartridge eluting with chloroform/CMA in a gradient from 100:0 to 70:30). The resulting solid was recrystallized from acetonitrile to provide 80 mg of N-[3-(4-amino-2-tert-butyl-2H-pyrazolo[3,4-c]quinolin-1-yl)propyl]methanesulfonamide as gray crystals, mp 223-224° C. MS (APCI) m/z 376 (M+H)$^+$; Anal. calcd for $C_{18}H_{25}N_5O_2S$: C, 57.58; H, 6.71; N, 18.65 Found: C, 57.71; H, 7.00; N, 18.81.

Example 585

1-(4-Amino-2-methyl-2H-pyrazolo[3,4-c]quinolin-1-yl)-2-methylpropan-2-ol

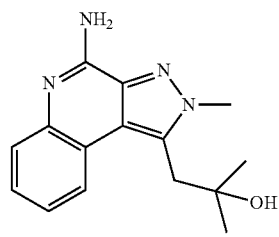 [SMILES: Cn1nc2c(N)nc3ccccc3c2c1CC(C)(C)O]

Part A

Under a nitrogen atmosphere, sodium tert-butoxide (54.1 g, 0.564 mol) and ethanol (187 mL) were combined at 0° C. The mixture was stirred at ambient temperature for 30 minutes. A mixture of mesityl oxide (30 mL, 0.26 mol) and diethyl oxalate (35.6 mL, 0.26 mol) in ethanol (40 mL) was added over a period of 1 minute. The reaction mixture was stirred for 2.5 hours at ambient temperature and then cooled to 0° C. Acetic acid (131 mL) and methyl hydrazine (15.3 mL, 0.288 mol) were added. The reaction was allowed to warm to ambient temperature with stirring overnight and then concentrated under reduced pressure. The residue was diluted with chloroform (500 mL) and water (1 L) and the mixture was adjusted to pH 11 with the addition of 50% sodium hydroxide. The aqueous layer was extracted with chloroform (3×250 mL); the combined organics were dried over sodium sulfate, filtered, and concentrated under reduced pressure to provide ethyl 1-methyl-5-(2-methylprop-1-enyl)-1H-pyrazole-3-carboxylate as a black oil that was used without purification.

Part B

The material from Part B was combined with 6 M sodium hydroxide (87 mL) and ethanol (655 mL), stirred at ambient temperature for 2 hours, and then concentrated under reduced pressure. The residue was dissolved in water and the solution acidified to pH 4 by the addition of 3 N hydrochloric acid. A precipitate formed; the mixture was stirred for 30 minutes and then filtered. The isolated solid was washed with water and then air dried for 24 hours to provide 39 g of 1-methyl-5-(2-methylprop-1-enyl)-1H-pyrazole-3-carboxylic acid as a tan solid.

Part C

The material from Part B was combined with dichloromethane (870 mL) and a drop of DMF. Oxalyl chloride (45.8 mL, 525 mmol) was added. The reaction mixture was stirred at ambient temperature for 30 minutes and then cooled to 0° C. Chilled (0° C.) ammonium hydroxide (250 mL of 15 M) was added in a single portion. The reaction mixture was stirred for 1 hour and then extracted with chloroform. The combined extracts were dried and then concentrated under reduced pressure to provide 31.9 g of 1-methyl-5-(2-methyl-prop-1-enyl)-1H-pyrazole-3-carboxamide as a brown oil.

Part D

The material from Part C was combined with toluene (250 mL) and stirred until a solution was obtained. Phosphorous oxychloride (28.5 mL, 302 mmol) was added and the reaction mixture was heated at reflux for 4 hours. The toluene layer was poured into ice water; the mixture was made basic by the addition of 2 N aqueous sodium carbonate and then extracted with chloroform. The extracts were dried over sodium sulfate, filtered, and then concentrated under reduced pressure to provide 1-methyl-5-(2-methylprop-1-enyl)-1H-pyrazole-3-carbonitrile as a dark oil.

Part E mCPBA (57 g of 50%) was added in a single portion to a solution of the material from Part D in dichloromethane (750 mL). The reaction mixture was stirred at ambient temperature overnight and then filtered to remove the chlorobenzoic acid. The filter cake was rinsed with a small amount of dichloromethane. The filtrate was washed with aqueous saturated sodium bicarbonate. The aqueous layer was extracted with dichloromethane (1×200 mL). The combined organics were dried over sodium sulfate, filtered, and then concentrated under reduced pressure to provide 5-(3,3-dimethyloxiran-2-yl)-1-methyl-1H-pyrazole-3-carbonitrile.

Part F

Bromine (16.14 mL, 315 mmol) was added to a solution of the material from Part E in acetic acid (300 mL) at 0° C. The red solution was stirred at ambient temperature for 2 hours, and then saturated aqueous sodium bisulfite was added until the red color was gone. The mixture was concentrated under reduced pressure to remove the acetic acid. The residue was diluted with chloroform (100 mL) and the pH was adjusted with 2 M aqueous sodium carbonate to pH 11. The cloudy mixture was diluted with water (50 mL) and extracted with chloroform (3×75 mL). The combined organic layers were dried over sodium sulfate, filtered, and concentrated under reduced pressure to a cloudy oil. The oil was combined with acetonitrile (300 mL) and aqueous hydrogen bromide (35 mL of 48%) and stirred for 1 hour. Aqueous saturated sodium bicarbonate was added until the mixture was basic. The resulting solution was diluted with water and then extracted with dichloromethane. The extracts were dried and concentrated under reduced pressure to provide a dark yellow oil. The oil was purified by chromatography on a HORIZON HPFC system (eluting with hexanes/ethyl acetate in a gradient from 9:1 to 1:1) to provide 10.5 g of crude 4-bromo-5-(1-bromo-2-hydroxy-2-methylpropyl)-1-methyl-1H-pyrazole-3-carbonitrile.

Part G

Azobisisobutyronitrile (600 mg, 3.6 mmol) and tributyltin hydride (7.3 mL, 27.3 mmol) were added to a mixture of portion of the material from Part F (6.4 g, 18 mmol) and toluene (91 mL). After bubbling had ceased, the pale yellow solution was heated at 90° C. for 1 hour. Analysis by TLC indicated that starting material was still present. An additional equivalent of tributyltin hydride was added and the reaction mixture was heated for an additional 30 minutes; this was repeated. The reaction mixture was purified by chromatography on a HORIZON HPFC system (65+M cartridge eluting with hexanes/ethyl acetate in a gradient from all hexane to 1:1) to provide 2.7 g of 4-bromo-5-(2-hydroxy-2-methylpropyl)-1-methyl-1H-pyrazole-3-carbonitrile as a colorless oil.

Part H

2-Aminophenylboronic acid hydrochloride (3.6 g, 20.8 mmol), potassium phosphate (11.0 g, 52.0 mmol), tris(dibenzylideneacetone)dipalladium(0) chloroform adduct (238 mg, 0.26 mmol), and bis[(2-diphenylphosphino)phenyl]ether (167 mg, 0.312 mmol) were added to a solution of the material from Part G in toluene (65 mL) containing powdered molecular sieves (1 g). Nitrogen was bubbled through the reaction mixture, and then the reaction was heated at 110° C. for 24 hours. The mixture was cooled to ambient temperature and then filtered through a layer of silica gel (eluting with 3:2 chloroform/methanol). The filtrate was concentrated under reduced pressure and dissolved in ethanol (52 mL). Hydrogen chloride (4.8 mL of a 4 M solution in ethanol) was added to the resulting solution, and the reaction was heated at reflux for two hours and allowed to cool to ambient temperature. The solvent was removed under reduced pressure and the residue was adjusted to pH 10 with the addition of 2 M aqueous sodium carbonate. The mixture was diluted with brine and chloroform. A white solid that did not dissolve in either layer was isolated by filtration and then recrystallized from ethanol to provide 300 mg of 1-(4-amino-2-methyl-2H-pyrazolo[3,4-c]quinolin-1-yl)-2-methylpropan-2-ol as gray crystals, mp 256-257° C. MS (APCI) m/z 271 (M+H)$^+$; Anal. calcd for $C_{15}H_{18}N_4O$: C, 66.65; H, 6.71; N, 20.73. Found: C, 66.51; H, 6.89; N, 20.79.

Example 586

1-(4-Amino-2-methyl-6,7,8,9-tetrahydro-2H-pyrazolo[3,4-c]quinolin-1-yl)-2-methylpropan-2-ol

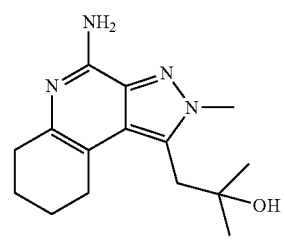 [SMILES: Cn1nc2c(N)nc3c(c2c1CC(C)(C)O)CCCC3]

The mother liquor from Example 585 Part H was concentrated to provide 1 g of 1-(4-amino-2-methyl-2H-pyrazolo[3,4-c]quinolin-1-yl)-2-methylpropan-2-ol. This material was combined with platinum oxide (750 mg) and trifluoroacetic acid (25 mL) and shaken under hydrogen pressure on a Parr apparatus for 2 days. The reaction mixture was filtered through a layer of CELITE filter agent and the filter cake was rinsed with dichloromethane. The filtrate was concentrated under reduced pressure. The residue was diluted with water (10 mL), the pH was adjusted to pH 12 with 50% sodium hydroxide, and the mixture was extracted with dichloromethane. The extracts were dried over sodium sulfate and then purified by chromatography on a HORIZON HPFC system (40+M cartridge eluting with a gradient of 0 to 30% CMA in chloroform). The resulting solid was recrystallized from acetonitrile to provide 160 mg of 1-(4-amino-2-methyl-6,7,8,9-tetrahydro-2H-pyrazolo[3,4-c]quinolin-1-yl)-2-methylpropan-2-ol as tan crystals, mp 228-234° C. MS (APCI) m/z 275 (M+H)$^+$; Anal. calcd for $C_{15}H_{22}N_4O$: C, 65.67; H, 8.08; N, 20.42. Found: C, 65.53; H, 8.19; N, 20.47.

Example 587

1-(4-Amino-2-ethyl-6,7,8,9-tetrahydro-2H-pyrazolo[3,4-c]quinolin-1-yl)-2-methylpropan-2-ol

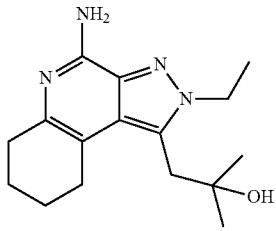 [SMILES: CCn1nc2c(N)nc3c(c2c1CC(C)(C)O)CCCC3]

Using the method of Example 586, 1-(4-amino-2-ethyl-2H-pyrazolo[3,4-c]quinolin-1-yl)-2-methylpropan-2-ol (100 mg, prepared as described in Example 62) was reduced and purified to provide 25 mg of 1-(4-amino-2-ethyl-6,7,8,9-tetrahydro-2H-pyrazolo[3,4-c]quinolin-1-yl)-2-methylpropan-2-ol as a white powder, mp 202-204° C. $^1$H NMR (500 MHz, DMSO-$d_6$) δ 5.96 (s, 2H), 4.55 (s, 1H), 4.46 (q, J=7.2 Hz, 2H), 3.12 (s, 2H), 2.82 (m, 2H), 2.57 (m, 2H), 1.72 (m, 4H), 1.39 (t, J=7.2 Hz, 3H), 1.34 (s, 6H); $^{13}$C NMR (75 MHz, DMSO-$d_6$) δ 149.11, 141.0, 135.20, 132.16, 123.77, 110.30, 70.70, 45.56, 37.93, 32.09, 30.18, 25.10, 23.46, 23.15, 15.91; MS (APCI) m/z 289 (M+H)$^+$; Anal. calcd for $C_{16}H_{24}N_4O$: C, 66.64; H, 8.39; N, 19.43. Found: C, 66.46; H, 8.58; N, 19.23.

Example 588

5-Butyl-2,3-dimethyl-2H-pyrazolo[3,4-c]pyridin-7-amine

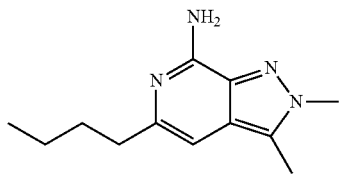 [SMILES: CCCCc1cc2c(C)n(C)nc2c(N)n1]

Part A

Methylhydrazine (6.2 mL, 117 mmol) was added to a chilled (0° C.) solution of methyl pyruvic acetate (15.0 mL, 107 mmol) in acetic acid (210 mL). The reaction mixture was stirred for 1 hour and then concentrated under reduced pressure. The residue was diluted with water, made basic (pH 11) by the addition of aqueous saturated sodium carbonate, and then extracted with dichloromethane. The combined extracts were dried over sodium sulfate, filtered, and concentrated under reduced pressure to provide 14.6 g of ethyl 1,5-dimethyl-1H-pyrazole-3-carboxylate as a dark oil.

Part B

The material from Part A (3.0 g, 17.8 mmol) was combined in a stainless steel reactor with 7 N ammonia in methanol (30 mL). The reaction was sealed and heated at 150° C. for 24 hours. The reaction mixture was concentrated under reduced pressure to provide 2.5 g of crude 1,5-dimethyl-1H-pyrazole-3-carboxamide as a dark brown solid.

Part C

The material from Part B, triethylamine (7.5 mL, 54 mmol), and dichloromethane (60 mL) were combined and then cooled to 0° C. Trifluoroacetic anhydride (3.8 mL, 27 mmol) was added dropwise over a period of 1 minute. The reaction mixture was stirred for 2 hours and then quenched with saturated ammonium chloride solution (30 mL). The reaction mixture was diluted with water and then extracted with dichloromethane. The combined extracts were dried over sodium sulfate, filtered, and then concentrated under reduced pressure. The crude product was purified by chromatography on a HORIZON HPFC system (40+M cartridge, eluting with a gradient of 0 to 50% ethyl acetate in hexanes) to provide 1,5-dimethyl-1H-pyrazole-3-carbonitrile as a white solid.

Part D

A solution of iodine monochloride (3.9 g, 24.6 mmol) in dichloromethane (12 mL) was added to a mixture of material from Part C (1.5 g, 12.3 mmol), dichloromethane (20 mL) and freshly ground potassium carbonate (3.2 g, 23 mmol). After 1 hour the reaction mixture was quenched with sodium bisulfite until all color was gone, diluted with water, and then extracted with dichloromethane. The combined extracts were dried over sodium sulfate, filtered, and then concentrated under reduced pressure. The crude product was purified by chromatography on a HORIZON HPFC system (40+M cartridge, eluting with a gradient of 0 to 50% ethyl acetate in hexanes) to provide 2.5 g of 4-iodo-1,5-dimethyl-1H-pyrazole-3-carbonitrile as a white solid.

Part E

Under a nitrogen atmosphere, material from Part D (200 mg, 0.81 mmol), hexyne (0.18 mL, 1.6 mmol), copper(I) iodide (30 mg, 0.16 mmol), dichlorobis(triphenylphosphine)palladium(II) (57 mg, 0.081 mmol), triethylamine (0.24 mL, 2.4 mmol) and acetonitrile (4 mL) were combined and then heated at reflux for 1 hour. The reaction mixture was cooled to ambient temperature, diluted with 7:3 hexanes:ethyl acetate, and then filtered through a layer of CELITE filter agent. The filtrate was concentrated under reduced pressure. The residue was purified by chromatography on a HORIZON HPFC system (25+M cartridge, eluting with a gradient of 0 to 50% ethyl acetate in hexanes) to provide 140 mg of 4-(hex-1-ynyl)-1,5-dimethyl-1H-pyrazole-3-carbonitrile as a brown oil.

Part F

The material from Part E was combined in a stainless steel reactor with 7 N ammonia in methanol (10 mL). The reaction was sealed and heated at 150° C. for 58 hours. The reaction mixture was concentrated under reduced pressure to provide a brown oil. The oil was purified by chromatography on a HORIZON HPFC system (40+M cartridge, eluting with a gradient of 0 to 20% CMA in chloroform) to provide a tan solid. This material was triturated with acetonitrile to provide 60 mg of 5-butyl-2,3-dimethyl-2H-pyrazolo[3,4-c]pyridin-7-amine as a tan powder, mp 130-131° C. $^1$H NMR (500 MHz, DMSO-$d_6$) δ 6.45 (s, 1H), 6.17 (s, 2H), 4.00 (s, 3H), 2.46-2.49 (m, 5H), 1.16 (m, 2H), 1.30 (m, 2H), 0.89 (t, J=7.25 Hz, 3H); $^{13}$C NMR (75 MHz, DMSO-d$_6$) δ 149.15, 146.42, 133.04, 129.13, 122.17, 97.71, 36.10, 36.05, 30.44, 20.79, 12.80, 8.39; MS (APCI) m/z 219.2 (M+H)$^+$; HRMS (ESI) calcd for C$_{12}$H$_{18}$N$_4$+H, 219.161. found 219.1594. Anal. calcd for C$_{12}$H$_{18}$N$_4$·0.15H$_2$O: C, 65.22; H, 8.35; N, 25.35. Found: C, 65.52; H, 8.72; N, 25.64.

Example 589

N-[4-(4-Amino-2-methyl-6,7,8,9-tetrahydro-2H-pyrazolo[3,4-c]quinolin-1-yl)butyl]morpholine-4-carboxamide

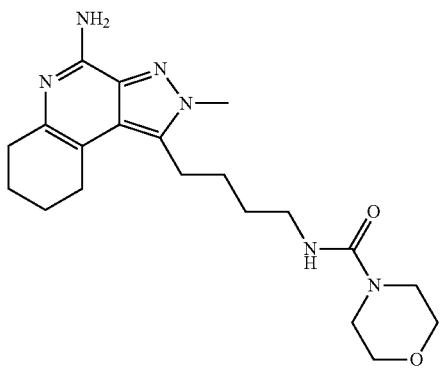 [SMILES: Cn1nc2c(N)nc3c(c2c1CCCCNC(=O)N1CCOCC1)CCCC3]

Part A

A mixture of 1-(4-chlorobutyl)-2-methyl-2H-pyrazolo[3,4-c]quinoline-4-amine (2.8 g, 8.6 mmol, prepared as described in Part F of Examples 454-488), platinum oxide, and trifluoroacetic acid was shaken under hydrogen pressure on a Parr apparatus for 2 days. The reaction mixture was filtered through a layer of CELITE filter agent and the filter cake was rinsed with methanol. The filtrate was concentrated under reduced pressure. The residue was diluted with water (10 mL), the pH was adjusted to pH 12 with 50% sodium hydroxide, and the mixture was extracted with dichloromethane. The extracts were dried over sodium sulfate and concentrated under reduce pressure. The residue was purified by chromatography on a HORIZON HPFC system (40+M cartridge eluting with a gradient of 0 to 20% CMA in chloroform) to provide 2.0 g of 1-(4-chlorobutyl)-2-methyl-6,7,8,9-tetrahydro-2H-pyrazolo[3,4-c]quinoline-4-amine as a yellow solid.

Part B

A mixture of 1-(4-chlorobutyl)-2-methyl-6,7,8,9-tetrahydro-2H-pyrazolo[3,4-c]quinoline-4-amine (385 mg, 1.31 mmol), potassium phthalimide (362 mg, 1.96 mmol), sodium iodide (50 mg, 0.327 mmol), and DMF (2 mL) was heated at 90° C. for 4 hours. The reaction mixture was cooled to ambient temperature and then diluted with water (30 mL) while stirring in an ice bath. A precipitate was isolated by filtration to obtain 2-[4-(4-amino-2-methyl-6,7,8,9-tetrahydro-2H-pyrazolo[3,4-c]quinolin-1-yl)butyl]-1H-isoindole-1,3(2H)-dione as a yellow solid.

Part C

The material from Part B was combined with hydrazine hydrate (0.3 mL, 6.55 mmol) and ethanol (15 mL) and heated at reflux for 30 minutes. The reaction mixture was chilled to 0° C. A precipitate was removed by filtration and the filter cake was rinsed with ethanol. The filtrate was purified by chromatography on a HORIZON HPFC system (25+M cartridge eluting with a gradient of 0 to 40% CMA in chloroform) to provide 290 mg of 1-(4-aminobutyl)-2-methyl-6,7,8,9-tetrahydro-2H-pyrazolo[3,4-c]quinoline-4-amine.

Part D

Under a nitrogen atmosphere, a mixture of the material from Part C, triethylamine (290 μL, 2.12 mmol), and dichloromethane (5 mL) was cooled to 0° C. 4-Morpholinecarbonyl chloride (124 μL, 1.06 mmol) was added in 3 portions spaced 5 minutes apart. The reaction mixture was warmed to ambient temperature and stirred for 1 hour. The reaction mixture was quenched with saturated aqueous ammonium chloride, diluted with water, and then extracted with chloroform. The extract was dried over sodium sulfate, filtered, and then purified by chromatography on a HORIZON HPFC system (25+M cartridge eluting with a gradient of 0 to 20% CMA in chloroform) to provide a clear oil. The oil was dissolved in acetonitrile. The acetonitrile was removed under reduced pressure and the residue was placed under high vacuum with gentle heating to provide N-[4-(4-amino-2-methyl-6,7,8,9-tetrahydro-2H-pyrazolo[3,4-c]quinolin-1-yl)butyl]morpholine-4-carboxamide as a white powder, mp 95° C. $^1$H NMR (300 MHz, DMSO-d$_6$) δ 6.48 (t, J=5.3 Hz, 1H), 5.99 (s, 2H), 4.00 (s, 3H), 3.51 (t, J=4.5 Hz, 4H), 3.22 (t, J=5.0 Hz, 4H), 3.07 (q, J=5.6 Hz, 2H), 3.00 (t, J=7.3 Hz, 2H), 2.80 (bs, 2H), 2.56 (bs, 2H), 1.74 (m, 4H) 1.51 (m, 4H); $^{13}$C NMR (75 MHz, DMSO-d$_6$) δ 156.51, 147.42, 139.56, 134.11, 133.45, 120.94, 108.33, 64.81, 42.72, 39.56, 36.15, 30.41, 28.38, 26.42, 23.40, 23.23, 21.90, 21.57; MS (APCI) m/z 387 (M+H)$^+$; Anal. calcd for C$_{20}$H$_{30}$N$_6$O$_2$·H$_2$O: C, 59.39; H, 7.97; N, 20.78. Found: C, 59.04; H, 7.89; N, 20.74.

Example 590

1-(2-Amino-2-methylpropyl)-2-(2-methoxyethyl)-2H-pyrazolo[3,4-c]quinolin-4-amine

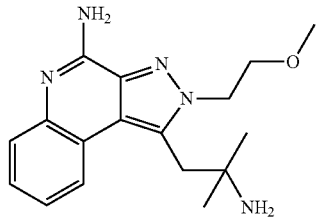 [SMILES: COCCn1nc2c(N)nc3ccccc3c2c1CC(C)(C)N]

Part A

Under a nitrogen atmosphere, 2-bromoethyl methyl ether (19.7 g, 142 mmol) was added to a mixture of ethyl 5-{2-[(tert-butoxycarbonyl)amino]-2-methylpropyl}-1H-pyrazole-3-carboxylate (40 g, 129 mmol, prepared according to the method of Example 64 Part A using hydrazine hydrate in lieu of propylhydrazine oxalate) and sodium tert-butoxide (12.4 g, 129 mmol) in ethanol (128 mL). The reaction mixture was heated at reflux for 5 hours; an additional 0.2 equivalents of both sodium tert-butoxide and 2-bromoethyl methyl ether were added, and the reaction mixture was heated at reflux for an additional 21 hours. The reaction mixture was concentrated under reduced pressure and the residue was partitioned between water and tert-butyl methyl ether. The aqueous layer was extracted with tert-butyl methyl ether (×3). The combined organics were dried over magnesium sulfate, filtered, and concentrated under reduced pressure to provide 46.0 g of a yellow oil. The oil was dissolved in 1:1 tert-butyl methyl ether:hexanes and purified by IFC (65 cartridge eluting with 1:1 tert-butyl methyl ether:hexanes) to provide a pale yellow oil. This material was triturated with 40 mL of 1:1 tert-butyl methyl ether:hexanes, seeded with product from an earlier run, stirred until a white solid formed, and then concentrated under reduced pressure to provide 24.83 g of ethyl 5-{2-[(tert-butoxycarbonyl)amino]-2-methylpropyl}-1-(2-methoxyethyl)-1H-pyrazole-3-carboxylate as a white solid, mp 92-93° C. MS (APCI) m/z 370 (M+H)$^+$; Anal. Calcd for $C_{18}H_{31}N_3O_5$: C, 58.52; H, 8.46; N, 11.37. Found: C, 58.65; H, 8.69; N, 11.47.

Part B

Lithium hydroxide (17.1 g, 407 mmol) was added to a solution of ethyl 5-{2-[(tert-butoxycarbonyl)amino]-2-methylpropyl}-1-(2-methoxyethyl)-1H-pyrazole-3-carboxylate (37.6 g, 102 mmol) in methanol (141 mL) and water (47 mL). The reaction mixture was stirred for 2 days and then most of the methanol was removed under reduced pressure. The aqueous residue was cooled in an ice bath and then combined with 1 N hydrochloric acid (350 mL) and tert-butyl methyl ether. The layers were separated. The volume of the organic layer was reduced under vacuum and then diluted with hexanes. A precipitate was isolated by filtration, washed with water, and suction dried to provide 13.09 g of 5-{2-[(tert-butoxycarbonyl)amino]-2-methylpropyl}-1-(2-methoxyethyl)-1H-pyrazole-3-carboxylic acid as a white solid. The aqueous layer was extracted with chloroform while maintaining the pH of the aqueous layer at pH 4-5 by the addition of 1 N hydrochloric acid. The chloroform extracts were combined, dried over sodium sulfate and magnesium sulfate, filtered, and concentrated under reduced pressure. The residue was dissolved in tert-butyl methyl ether, diluted with hexanes, and then concentrated under reduced pressure. A white solid was isolated by filtration, washed with hexanes, and suction dried to provide an additional 21.8 g of product.

Part C 1-(3-Dimethylaminopropyl)-3-ethylcarbodiimide hydrochloride (21.5 g, 112 mmol) was added to a solution of 5-{2-[(tert-butoxycarbonyl)amino]-2-methylpropyl}-1-(2-methoxyethyl)-1H-pyrazole-3-carboxylic acid (34.8 g, 102 mmol) and 1-hydroxybenzotriazole (15.2 g, 112 mmol) in DMF (174 mL) at ambient temperature. The mixture was stirred for 2.5 hours until a solution formed and then it was cooled in an ice bath. Concentrated ammonium hydroxide (20.4 mL) was added and the reaction mixture was stirred for 30 minutes. Water (445 mL) was added and the mixture was extracted with tert-butyl methyl ether (×12). The extracts were combined, dried over sodium sulfate, filtered, and concentrated under reduced pressure. The residue was concentrated twice from xylene under reduced pressure to provide 38 g of an oil. The oil was combined with 100 mL of 1:1 tert-butyl methyl ether:hexanes, warmed until a solution was obtained, and then let stand. An oil formed; the mixture was concentrated under reduced pressure. The residue was dried under vacuum at 50° C. until a solid formed. The solid was slurried with hexanes, isolated by filtration, washed with hexanes, and suction dried to provide 31.3 g of tert-butyl 2-[3-(aminocarbonyl)-1-(2-methoxyethyl)-1H-pyrazol-5-yl]-1,1-dimethylethylcarbamate as a white solid.

Part D

Using the method of Example 64 Part D, tert-butyl 2-[3-(aminocarbonyl)-1-(2-methoxyethyl)-1H-pyrazol-5-yl]-1,1-dimethylethylcarbamate (31.1 g) was dehydrated. The crude product was purified by IFC (65+M cartridge eluting with a gradient of 50 to 60% ethyl acetate in hexanes) to provide 28.12 g of tert-butyl 2-[3-cyano-1-(2-methoxyethyl)-1H-pyrazol-5-yl]-1,1-dimethylethylcarbamate as a white solid.

Part E

Bromine (19.5 g, 122 mmol) was added in a single portion to a solution of tert-butyl 2-[3-cyano-1-(2-methoxyethyl)-1H-pyrazol-5-yl]-1,1-dimethylethylcarbamate (28.07 g, 87.1 mmol) and potassium acetate (12.8 g, 131 mmol) in acetic acid (174.2 mL). After 16 hours saturated aqueous sodium bisulfate was added until the reaction mixture was colorless. The acetic acid was removed under reduced pressure at about 30° C. The residue was made basic with 2 M sodium carbonate and then extracted with tert-butyl methyl ether (×3). The extracts were combined, dried over magnesium sulfate, and concentrated under reduced pressure. Analysis by HPLC indicated that the BOC group had been partially removed. The material was dissolved in dichloromethane (50 mL), combined with di-tert-butyl dicarbonate, and stirred for 9 hours. The reaction mixture was concentrated under reduced pressure and the residue was purified by IFC (65+M cartridge eluting with a gradient of 40 to 50% tert-butyl methyl ether in hexanes) to provide 32.1 g of tert-butyl 2-[4-bromo-3-cyano-1-(2-methoxyethyl)-1H-pyrazol-5-yl]-1,1-dimethylethylcarbamate as a colorless, viscous resin.

Part F

Using the method of Example 64 Part F, tert-butyl 2-[4-bromo-3-cyano-1-(2-methoxyethyl)-1H-pyrazol-5-yl]-1,1-dimethylethylcarbamate (32.1 g, 80.0 mmol) was coupled with 2-aminophenylboronic acid. The reaction mixture was partitioned between water and tert-butyl methyl ether. The aqueous layer was extracted with tert-butyl methyl ether (×2). The combined extracts were dried over magnesium sulfate, filtered, and concentrated to provide a brown oil. The oil was purified by chromatography on a HORIZON HPFC system (65+M cartridge eluting with a gradient of 1 to 20% CMA in chloroform) to provide 11.4 g of an orange resin. This material was purified IFC (65+M cartridge eluting with a gradient of 35 to 55% ethyl acetate in hexanes) to provide 4.85 g of tert-butyl 2-[4-(2-aminophenyl)-3-cyano-1-(2-methoxyethyl)-1H-pyrazol-5-yl]-1,1-dimethylethylcarbamate as an orange glassy resin.

Part G

Under a nitrogen atmosphere, acetyl chloride (100 mmol) was added to ice cold ethanol (100 mL). The ice bath was removed; the mixture was stirred for 3 hours and then combined with the material from Part F. The reaction mixture was heated at reflux for 2 hours and then concentrated under reduced pressure. The residue was combined with 2 M aqueous sodium carbonate (50 mL) and then extracted with chloroform (×4). The combined extracts were dried over sodium sulfate, filtered, and concentrated to provide 3.84 g of an orange solid. This material was purified by IFC (40+M cartridge eluting with a gradient of 25 to 55% CMA in chloroform) to provide 2.15 g of a white solid. This material was refluxed with 3:1 ethyl acetate:hexanes (100 mL), chilled in an ice bath, isolated by filtration, rinsed with a small amount of the solvent mixture, and then suction dried to provide 1.94 g of a white solid. A portion (165 mg) of this material was recrystallized from acetonitrile (10 mL) to provide 109 mg of 1-(2-amino-2-methylpropyl)-2-(2-methoxyethyl)-2H-pyrazolo[3,4-c]quinolin-4-amine as a white solid, mp 199-200° C.

MS (APCI) m/z 314 (M+H)$^+$; Anal. Calcd for $C_{17}H_{23}N_5O$: C, 65.15; H, 7.40; N, 22.35.

Found: C, 64.83; H, 7.38; N, 22.70.

Example 591

N-{2-[4-Amino-2-(2-methoxyethyl)-2H-pyrazolo[3,4-c]quinolin-1-yl]-1,1-dimethylethyl}isonicotinamide

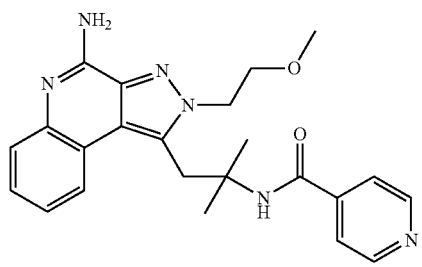 [SMILES: COCCn1nc2c(N)nc3ccccc3c2c1CC(C)(C)NC(=O)c1ccncc1]

Using the method of Example 68, isonicotinoyl chloride hydrochloride (710 mg, 4.00 mmol) was reacted with 1-(2-amino-2-methylpropyl)-2-(2-methoxyethyl)-2H-pyrazolo[3,4-c]quinolin-4-amine (500 mg, 1.60 mmol, prepared as described in Example 590). The crude product was purified as described in Example 68 to provide 551 mg of N-{2-[4-amino-2-(methoxyethyl)-2H-pyrazolo[3,4-c]quinolin-1-yl]-1,1-dimethylethyl}isonicotinamide as a white solid, mp 166-168° C. MS (ESI) m/z 419 (M+H)$^+$; Anal. Calcd for $C_{23}H_{26}N_6O_2$: C, 66.01; H, 6.26; N, 20.08. Found: C, 65.93; H, 6.41; N, 20.44.

Example 592

N-{2-[4-Amino-2-(2-methoxyethyl)-2H-pyrazolo[3,4-c]quinolin-1-yl]-1,1-dimethylethyl}methanesulfonamide

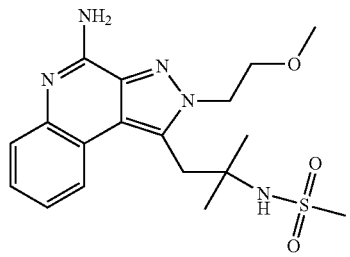 [SMILES: COCCn1nc2c(N)nc3ccccc3c2c1CC(C)(C)NS(C)(=O)=O]

Using the method of Example 66, methanesulfonyl chloride (399 mg, 3.48 mmol) was reacted with 1-(2-amino-2-methylpropyl)-2-(2-methoxyethyl)-2H-pyrazolo[3,4-c]quinolin-4-amine (1.09 g, 3.48 mmol, prepared as described in Example 590). The crude product was purified by IFC (40M cartridge eluting with a gradient of 15 to 35% CMA in chloroform) to provide a white foam. The foam was refluxed with 35% ethyl acetate in hexanes (50 mL), ethyl acetate was added until a free flowing white solid appeared, and then the mixture was cooled on ice. The solid was isolated by filtration and dried to provide 809 mg of N-{2-[4-amino-2-(methoxyethyl)-2H-pyrazolo[3,4-c]quinolin-1-yl]-1,1-dimethylethyl}methanesulfonamide as a white solid, mp 211-213° C. MS (ESI) m/z 392 (M+H)$^+$; Anal. Calcd for $C_{18}H_{25}N_5O_3S$: C, 55.22; H, 6.44; N, 17.89. Found: C, 55.05; H, 6.38; N, 17.98.

Example 593

4-(4-Amino-2-propyl-2H-pyrazolo[3,4-c]quinolin-1-yl)butan-1-ol

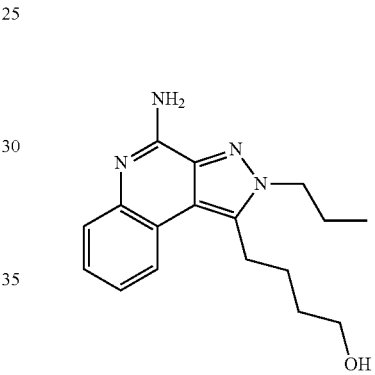

A solution of di(tert-butyl) 1-(4-hydroxybutyl)-2-propyl-2H-pyrazolo[3,4-c]quinolin-4-ylimidodicarbonate (prepared as described in Parts A-C of Example 57, 0.507 g, 1.02 mmol) in 6 M HCl in ethanol (5 mL) was heated at 60° C. for 1.5 hours. The solution was allowed to cool to room temperature, and then was concentrated under reduced pressure to yield an oil. The oil was triturated with ether to obtain a solid that was isolated by filtration. The solid was dissolved in methanol and the solution was adjusted to approximately pH 14 with 50% aqueous sodium hydroxide. The solution was concentrated under reduced pressure and the crude product was purified by chromatography (silica gel, elution with 5% CMA in chloroform) followed by crystallization from hexanes/ethyl acetate to provide 0.084 g of 4-(4-amino-2-propyl-2H-pyrazolo[3,4-c]quinolin-1-yl)butan-1-ol as white needles, mp 135.0-136.0° C.

$^1$H NMR (300 MHz, DMSO) δ 7.92 (d, J=7.0 Hz, 1H), 7.48 (d, J=8.0 Hz, 1H), 7.32 (t, J=7.0 Hz, 1H), 7.20 (t, J=7.0 Hz, 1H), 6.64 (s, 2H), 4.43 (t, J=5.0 Hz, 1H), 4.34 (t, J=7.2 Hz, 2H), 3.47 (q, J=5.8 Hz, 2H), 3.25 (t, J=7.5 Hz, 2H), 1.85-1.99 (m, 2H), 1.70-1.77 (m, 2H), 1.56-1.66 (m, 2H), 0.92 (t, J=7.4 Hz, 3H);

MS (APCI) m/z 299 (M+H)$^+$;

Anal. calcd for $C_{17}H_{22}N_4O$: C, 68.43; H, 7.43; N, 18.78. Found: C, 68.47; H, 7.62; N, 18.84.

Example 594

4-(4-Amino-2-propyl-6,7,8,9-tetrahydro-2H-pyrazolo[3,4-c]quinolin-1-yl)butan-1-ol

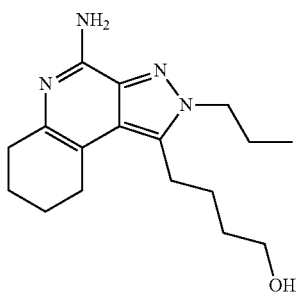 [SMILES: CCCn1nc2c(N)nc3c(c2c1CCCCO)CCCC3]

4-(4-Amino-2-propyl-2H-pyrazolo[3,4-c]quinolin-1-yl)butan-1-ol (prepared as described in Example 593, 0.118 g, 0.396 mmol) was hydrogenated for 1.8 days using the method described in Example 59. The catalyst was removed by filtration, and the filtrate was concentrated under reduced pressure to yield an oil that was dissolved in 6 M aqueous sodium hydroxide (20 mL). The mixture was stirred for 1 day, then a white solid was isolated by filtration, washed with water, and dried at 70° C. under vacuum to provide 0.719 g of 4-(4-amino-2-propyl-6,7,8,9-tetrahydro-2H-pyrazolo[3,4-c]quinolin-1-yl)butan-1-ol as a white powder, mp 194.0-200.0° C.

$^1$H NMR (300 MHz, DMSO) δ 5.95 (s, 2H), 4.41 (t, J=4.7 Hz, 1H), 4.22 (t, J=7.2 Hz, 2H), 3.44 (m, 2H), 3.00 (t, J=7.5 Hz, 2H), 2.82 (s, 2H), 2.57 (s, 2H), 1.82-1.91 (m, 2H), 1.74 (s, 4H), 1.49-1.59 (m, 4H), 0.89 (t, J=7.4 Hz, 3H);

MS (APCI) m/z 303 (M+H)$^+$;

Anal. calcd for $C_{17}H_{26}N_4O \cdot 0.2H_2O_2 \cdot 0.3\ C_2F_3HO_2$: C, 62.13; H, 7.91; N, 16.47. Found: C, 62.10; H, 7.75; N, 16.40.

Example 595

1-[3-(3-Methylisoxazol-5-yl)propyl]-2-propyl-2H-pyrazolo[3,4-c]quinolin-4-amine

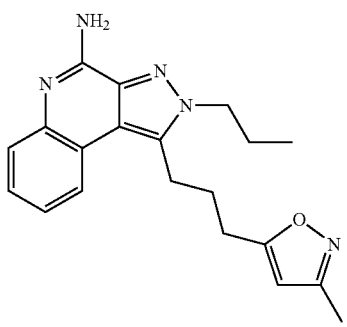 [SMILES: CCCn1nc2c(N)nc3ccccc3c2c1CCCc1cc(C)no1]

Part A

A solution of acetaldoxime (1.00 g, 16.9 mmol) and N-chlorosuccinimide (2.26 g, 16.9 mmol) in DMF (50 mL) was heated at 50° C. for 1.5 hours. The solution was allowed to cool to room temperature and was partitioned between water and ethyl acetate. The layers were separated and the aqueous layer was extracted with ethyl acetate. The organic layers were combined, dried over magnesium sulfate, filtered, and concentrated to yield 1.0545 g of α-chloroacetaldoxime as a clear colorless oil that was used directly in the next step.

Part B

The oil from Part A (0.14 g, 1.5 mmol) was added to a solution of di(tert-butyl) 1-pent-4-ynyl-2-propyl-2H-pyrazolo[3,4-c]quinolin-4-ylimidodicarbonate (prepared as described in Parts A-E of Example 57, 0.590 g, 1.20 mmol) and triethylamine (0.25 mL, 1.8 mmol) in dichloromethane (10 mL). The solution was heated at 40° C. for 42 hours, during which time more of the material from Part A (0.357 g) was added. The solution was allowed to cool to room temperature, and then was diluted with dichloromethane. The solution was washed with an aqueous potassium carbonate solution, water, and brine, then was dried over sodium sulfate, filtered, and concentrated under reduced pressure. The crude product was purified by chromatography (silica gel, eluted with 40% ethyl acetate in hexanes) to provide 0.4705 g of di(tert-butyl) 1-[3-(3-methylisoxazol-5-yl)propyl]-2-propyl-2H-pyrazolo[3,4-c]quinolin-4-ylimidodicarbonate as a colorless oil.

Part C

A solution of di(tert-butyl) 1-[3-(3-methylisoxazol-5-yl)propyl]-2-propyl-2H-pyrazolo[3,4-c]quinolin-4-ylimidodicarbonate (0.471 g, 0.856 mmol) in 6 M HCl in ethanol (5 mL) was heated at 60° C. for 1 hour. The solution was allowed to cool to room temperature, then was concentrated under reduced pressure to yield an oil that was dissolved in water (20 mL). The solution was adjusted to pH 12 with a few drops of 50% aqueous potassium hydroxide and then to pH 14 with 1 M aqueous potassium hydroxide. A precipitate formed that was isolated by filtration and crystallized from ethyl acetate/hexanes. The crystals were isolated by filtration and dried under vacuum at 70° C. to afford 0.123 g 1-[3-(3-methylisoxazol-5-yl)propyl]-2-propyl-2H-pyrazolo[3,4-c]quinolin-4-amine as white needles, mp 183.0-184.0° C.

$^1$H NMR (300 MHz, CDCl$_3$) δ 7.78 (d, J=7.9 Hz, 1H), 7.70 (d, J=7.5 Hz, 1H), 7.42 (t, J=7.1 Hz, 1H), 7.24-7.30 (m, 1H), 5.85 (s, 1H), 5.33 (s, 2H), 4.26 (t, J=7.3 Hz, 2H), 3.25 (t, J=8.1 Hz, 2H), 2.91 (t, J=7.2 Hz, 2H), 2.30 (s, 3H), 2.11-2.24 (m, 2H), 1.93-2.04 (m, 2H), 0.93 (t, J=7.4 Hz, 3H);

MS (APCI) m/z 350 (M+H)$^+$;

Anal. calcd for $C_{20}H_{23}N_5O$: C, 68.75; H, 6.63; N, 20.04. Found: C, 68.62; H, 6.80; N, 20.00.

Example 596

1-[3-(3-Phenylisoxazol-5-yl)propyl]-2-propyl-2H-pyrazolo[3,4-c]quinolin-4-amine

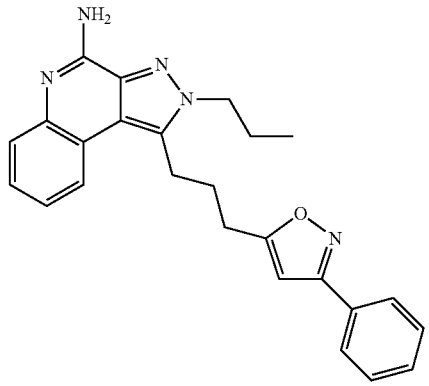 [SMILES: CCCn1nc2c(N)nc3ccccc3c2c1CCCc1cc(-c2ccccc2)no1]

Part A

α-Chlorobenzaldoxime was prepared according to the method described in Part A of Example 595 by reacting benzaldoxime (11.5 g, 94.9 mmol) in DMF (20 mL) with N-chlorosuccinimide (12.6 g, 94.9 mmol). α-Chlorobenzaldoxime (13.7 g, 93%) was obtained as a white solid.

Part B

α-Chlorobenzaldoxime (0.64 g, 4.1 mmol) was added to a solution of di(tert-butyl) 1-pent-4-ynyl-2-propyl-2H-pyrazolo[3,4-c]quinolin-4-ylimidodicarbonate (prepared as described in Parts A-E of Example 57, 1.36 g, 2.76 mmol) and triethylamine (0.60 mL, 4.14 mmol) in dichloromethane (10 mL). The solution was heated at 40° C. for 19 hours, during which time additional α-chlorobenzaldoxime (0.65 g) was added. The reaction was worked up as described in Part B of Example 595. The crude product was purified by chromatography (silica gel, sequential elution with 20% then 40% ethyl acetate in hexanes) to provide 1.35 g of di(tert-butyl) 1-[3-(3-phenylisoxazol-5-yl)propyl]-2-propyl-2H-pyrazolo[3,4-c]quinolin-4-ylimidodicarbonate as a white solid.

Part C

A solution of the material from Part B in 6 M hydrochloric acid in ethanol (10 mL) was heated at 60° C. for 45 minutes. The reaction mixture was concentrated under reduced pressure. The residue was slurried with 1 N potassium hydroxide for 16 hours. The resulting solid was isolated by filtration, rinsed with a 6:4 mixture of hexanes/ethyl acetate, and dried at 80° for 3 hours to provide 0.7353 g of 1-[3-(3-phenylisoxazol-5-yl)propyl]-2-propyl-2H-pyrazolo[3,4-c]quinolin-4-amine as a white powder, mp 176-178.0° C.
$^1$H NMR (300 MHz, CDCl$_3$) δ 7.77-7.83 (m, 3H), 7.71 (d, J=7.4 Hz, 1H), 7.39-7.48 (m, 4H), 7.23-7.80 (m, 1H), 6.35 (s, 1H), 5.37 (s, 2H), 4.27 (t, J=7.3 Hz, 2H), 3.32 (t, J=8.0 Hz, 2H), 3.01 (t, J=7.2 Hz, 2H), 2.24 (p, J=7.6 Hz, 2H), 1.99 (q, J=7.4 Hz, 2H), 0.98 (t, J=7.4 Hz, 3H);
MS (APCI) m/z 412 (M+H)$^+$;
Anal. calcd for C$_{25}$H$_{25}$N$_5$O.0.6 H2O: C, 71.10; H, 6.25; N, 16.58. Found: C, 70.93; H, 6.36; N, 16.48.

Example 597

1-Pent-4-ynyl-2-propyl-2H-pyrazolo[3,4-c]quinolin-4-amine

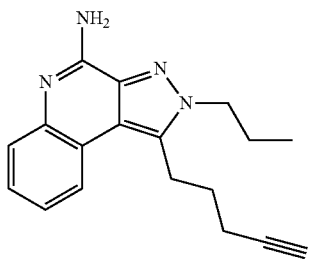 [SMILES: C#CCCCc1c2c(nn1CCC)c(N)nc1ccccc12]

A solution of di(tert-butyl) 1-pent-4-ynyl-2-propyl-2H-pyrazolo[3,4-c]quinolin-4-ylimidodicarbonate (prepared as described in Parts A-E of Example 57, 0.400 g, 0.812 mmol) in 6 M HCl in ethanol (3 mL) was heated at 60° C. for 1.7 hours. The solution was allowed to cool to room temperature, and then was concentrated under reduced pressure to yield an oil. The oil was treated with 1 M aqueous potassium hydroxide to generate a white precipitate, which was isolated by filtration. The crude product was purified by chromatography (silica gel, gradient elution with 5-10% CMA in chloroform) followed by crystallization from hexanes/ethyl acetate to afford 0.061 g of 1-pent-4-ynyl-2-propyl-2H-pyrazolo[3,4-c]quinolin-4-amine as white crystals, mp 144.0-145.0° C.
$^1$H NMR (300 MHz, DMSO) δ 7.96 (d, J=7.4 Hz, 1H), 7.70 (d, J=7.5 Hz, 1H), 7.43 (t, J=7.5 Hz, 1H), 7.29 (t, J=7.2 Hz, 1H), 5.41 (s, 2H), 4.34 (t, J=7.4 Hz, 2H), 3.35 (t, J=8.0 Hz, 2H), 2.35-2.41 (m, 2H), 2.14 (t, J=2.6 Hz, 1H), 1.95-2.03 (m, 4H), 1.00 (t, J=7.4 Hz, 3H);
MS (APCI) m/z 293 (M+H)$^+$;
Anal. calcd for C$_{18}$H$_{20}$N$_4$: C, 73.94; H, 6.89; N, 19.16. Found: C, 73.58; H, 6.90; N, 19.24.

Example 598

1-[4-(3-Methyl-1-oxa-2,4-diazaspiro[4.4]non-2-en-4-yl)butyl]-2-propyl-2H-pyrazolo[3,4-c]quinolin-4-amine

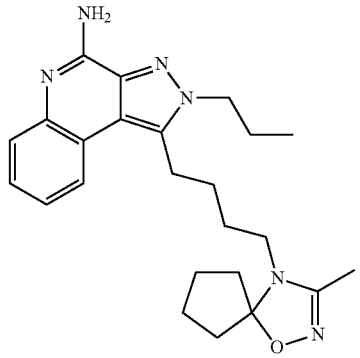 [SMILES: CCCn1nc2c(N)nc3ccccc3c2c1CCCCN1C(C)=NOC12CCCC2]

Part A

A mixture of di(tert-butyl) 1-(4-chlorobutyl)-2-propyl-2H-pyrazolo[3,4-c]quinolin-4-ylimidodicarbonate (prepared as described in Part A of Example 57, 6.82 g, 13.2 mmol), sodium azide (1.74 g, 26.4 mmol), and sodium iodide (0.50 g, 3.30 mmol) in DMF (20 mL) was heated at 90° C. for 21 hours. The mixture was allowed to cool to room temperature, then was poured into water (500 mL) and extracted with ethyl acetate. The organic layers were combined, washed with water and brine, dried over magnesium sulfate, filtered, concentrated under reduced pressure, and dried under vacuum to afford 6.21 g of a brown solid that was used without further purification in the next step.

Part B

A mixture of the material from Part A (6.21 g, 11.9 mmol), triphenylphosphine (4.7 g, 17.8 mmol), water (7 mL), and tetrahydrofuran (70 mL) was stirred at room temperature for 5 hours. The reaction mixture was concentrated under reduced pressure and the resulting oil was dissolved in dichloromethane. The solution was washed with water and brine, dried over sodium sulfate, and filtered. The filtrate was placed onto a column of silica gel and was eluted with ethyl acetate, followed by 5% methanol in dichloromethane, followed by 15% methanol in dichloromethane. The appropriate fractions were combined and concentrated to afford 3.37 g of di(tert-butyl) 1-(4-aminobutyl)-2-propyl-2H-pyrazolo[3,4-c]quinolin-4-ylimidodicarbonate.

Part C

A mixture of di(tert-butyl) 1-(4-aminobutyl)-2-propyl-2H-pyrazolo[3,4-c]quinolin-4-ylimidodicarbonate (1.50 g, 3.01 mmol), cyclopentanone (1 mL, 11.31 mmol), and magnesium sulfate in dichloromethane (9 mL) was stirred at room temperature for 1 day. The mixture was filtered and the filtrate was concentrated under reduced pressure; and the residue was dissolved in dichloromethane (10 mL). To the solution was added α-chloroacetaldoxime (prepared as described in Part A of Example 595, 0.56 g, 6.03 mmol). The solution was cooled to 0° C. and triethylamine (1.00 mL, 7.54 mmol) was added. The mixture was allowed to warm to room temperature and was stirred for 1 day. The mixture was transferred to a separatory funnel, washed with an aqueous solution of potassium carbonate, water, and brine, then dried over sodium sulfate, filtered, and concentrated under reduced pressure. The crude product was purified by chromatography (silica gel, elution with 40% hexanes in ethyl acetate) to afford a 0.75 g of material that was used in the next step.

Part D

A solution of the material from Part C (0.75 g, 1.21 mmol) in 6 M HCl in ethanol (6 mL) was heated at 60° C. for 2 hours. The solution was allowed to cool to room temperature, then was concentrated under reduced pressure to yield an oil. The oil was treated with 6 M aqueous potassium hydroxide. The aqueous solution was extracted with dichloromethane several times. The organic layers were combined, washed with water and brine, dried over sodium sulfate, filtered, and concentrated under reduced pressure. The crude product was purified by chromatography (silica gel, gradient elution with 5-15% CMA in chloroform) to afford 0.131 g of 1-[4-(3-methyl-1-oxa-2,4-diazaspiro[4.4]non-2-en-4-yl)butyl]-2-propyl-2H-pyrazolo[3,4-c]quinolin-4-amine as a white powder, mp 101.0-105.0° C.
$^1$H NMR (300 MHz, CDCl$_3$) δ 7.87 (d, J=7.9 Hz, 1H), 7.71 (d, J=7.4 Hz, 1H), 7.44 (t, J=7.5 Hz, 1H), 7.29 (t, J=7.0 Hz, 1H), 5.41 (s, 2H), 4.29 (t, J=7.3 Hz, 2H), 3.25 (t, J=7.4 Hz, 2H), 3.03 (t, J=7.1 Hz, 2H), 2.02 (q, J=7.3 Hz, 2H), 1.56-1.89 (m, 15H), 1.00 (t, J=7.4 Hz, 3H);
MS (APCI) m/z 421 (M+H)$^+$;
Anal. calcd for C$_{24}$H$_{32}$N$_6$O.0.8 H2O: C, 66.27; H, 7.79; N, 19.32. Found: C, 66.34; H, 7.62; N, 19.21.

Example 599

N-{2-[4-Amino-2-(2-methoxyethyl)-2H-pyrazolo[3,4-c]quinolin-1-yl]-1,1-dimethylethyl}acetamide

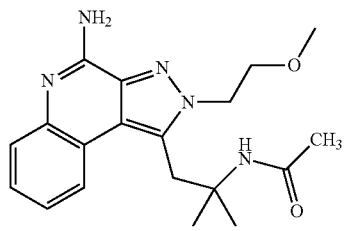 [SMILES: COCCn1nc2c(N)nc3ccccc3c2c1CC(C)(C)NC(C)=O]

Triethylamine (5 mmol) and acetyl chloride (4.0 mmol) were added to a solution of 1-(2-amino-2-methylpropyl)-2-(2-methoxyethyl)-2H-pyrazolo[3,4-c]quinolin-4-amine (496 mg, 1.60 mmol, prepared as described in Example 590) in dichloromethane (20 mL). The reaction mixture was stirred for 30 minutes and then concentrated under reduced pressure. The residue was dissolved in methanol (10 mL), and then combined with concentrated hydrochloric acid (2 mL). The mixture was heated at reflux for 2 hours, diluted with 2 M aqueous sodium carbonate, and then concentrated under reduced pressure. The residue was extracted with chloroform. The extract was dried over magnesium sulfate, filtered, and concentrated under reduced pressure. The residue was purified by IFC (RS-90 column, eluting with a gradient of 20 to 35% CMA in chloroform) to provide 0.67 g of a colorless resin. This material was refluxed with 35% ethyl acetate in hexanes (50 mL), cooled to ambient temperature, and then the mixture was cooled on ice. The resulting solid was isolated by filtration, rinsed with some of the solvent mix, and dried to provide 443 mg of N-{2-[4-amino-2-(methoxyethyl)-2H-pyrazolo[3,4-c]quinolin-1-yl]-1,1-dimethylethyl}acetamide as a white solid, mp 170-171° C. MS (ESI) m/z 356 (M+H)$^+$; Anal. Calcd for C$_{19}$H$_{25}$N$_5$O$_2$: C, 64.20; H, 7.09; N, 19.70. Found: C, 63.89; H, 7.41; N, 19.63.

Example 600

N-{2-[4-Amino-2-(2-methoxyethyl)-2H-pyrazolo[3,4-c]quinolin-1-yl]-1,1-dimethylethyl}nicotinamide

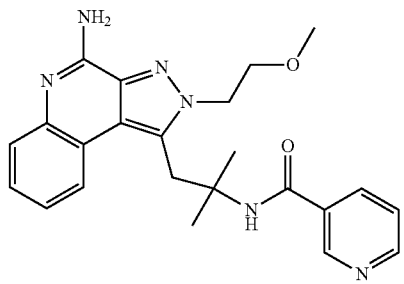 [SMILES: COCCn1nc2c(N)nc3ccccc3c2c1CC(C)(C)NC(=O)c1cccnc1]

Using the method of Example 68, nicotinoyl chloride hydrochloride (668 mg, 4.75 mmol) was reacted with 1-(2-amino-2-methylpropyl)-2-(2-methoxyethyl)-2H-pyrazolo[3,4-c]quinolin-4-amine (470 mg, 1.5 mmol, prepared as described in Example 590). The crude product was purified by IFC (silica gel eluting with a gradient of 10 to 40% CMA in chloroform) to provide a pale yellow resin. The resin was refluxed with 35% ethyl acetate in hexanes (50 mL) and ethyl acetate (75 mL) and cooled to ambient temperature with stirring. The resulting solid was isolated by filtration, rinsed with 35% ethyl acetate in hexanes, and dried to provide 278 mg of N-{2-[4-amino-2-(methoxyethyl)-2H-pyrazolo[3,4-c]quinolin-1-yl]-1,1-dimethylethyl}nicotinamide as a light beige solid, mp 212-214° C. MS (APCI) m/z 419 (M+H)$^+$; Anal. Calcd for C$_{23}$H$_{26}$N$_6$O$_2$: C, 66.01; H, 6.26; N, 20.08. Found: C, 65.74; H, 6.50; N, 20.09.

Example 601

N-[2-(4-Amino-2-propyl-2H-pyrazolo[3,4-c]quinolin-1-yl)-1,1-dimethylethyl]-4-fluorobenzamide

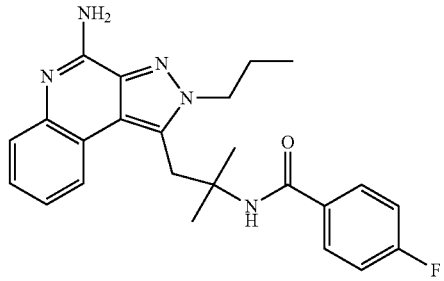 [SMILES: CCCn1nc2c(N)nc3ccccc3c2c1CC(C)(C)NC(=O)c1ccc(F)cc1]

Using the general method of Example 68, except that the acid chloride was added at 0° C., 1-(2-amino-2-methylpropyl)-2-propyl-2H-pyrazolo[3,4-c]quinolin-4-amine (prepared as described in Example 64, 770 mg, 2.59 mmol) was reacted with 4-fluorobenzoyl chloride (1.03 g, 6.48 mmol) to provide 2.1 g of crude product as pale yellow resin. This material was purified by IFC (silica gel eluting with a gradient of 5 to 20% CMA in chloroform) to provide about 1 g of a white foam. The foam was stirred with 35% ethyl acetate in hexanes. The resulting solid was isolated by filtration, rinsed with the same solvent mix, and then dried to provide 503 mg of a white solid (A). The filtrate was concentrated under reduced pressure to provide a white solid. This material was dissolved in dichloromethane, precipitated with hexanes, isolated by filtration, rinsed with hexanes, and dried to provide 340 mg of a white solid (B). White solids A and B were combined, refluxed in 20% ethyl acetate in hexanes, cooled to ambient temperature, and then in an ice bath. The resulting solid was isolated by filtration, rinsed with 20% ethyl acetate in hexanes, and dried to provide 706 mg of N-[2-(4-amino-2-propyl-2H-pyrazolo[3,4-c]quinolin-1-yl)-1,1-dimethylethyl]-4-fluorobenzamide as a white solid, mp 168-169° C. MS (APCI) m/z 420 (M+H)$^+$; Anal. Calcd for $C_{24}H_{26}FN_5O$: C, 68.72; H, 6.25; N, 16.69. Found: C, 68.69; H, 6.15; N, 16.90.

Example 602

N-[2-(4-Amino-2-propyl-2H-pyrazolo[3,4-c]quinolin-1-yl)-1,1-dimethylethyl]-3,4-difluorobenzamide

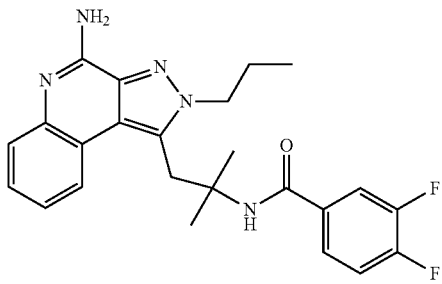 [SMILES: CCCn1nc2c(N)nc3ccccc3c2c1CC(C)(C)NC(=O)c1ccc(F)c(F)c1]

Using the method of Example 601, 1-(2-amino-2-methylpropyl)-2-propyl-2H-pyrazolo[3,4-c]quinolin-4-amine (prepared as described in Example 64, 770 mg, 2.59 mmol) was reacted with 3,4-difluorobenzoyl chloride (1.14 g, 6.48 mmol). The crude product was purified as described in Example 601 to provide 896 mg of N-[2-(4-amino-2-propyl-2H-pyrazolo[3,4-c]quinolin-1-yl)-1,1-dimethylethyl]-3,4-difluorobenzamide as a white solid, mp 165-166° C. MS (APCI) m/z 438 (M+H)$^+$; Anal. Calcd for $C_{24}H_{25}F_2N_5O$: C, 65.89; H, 5.76; N, 16.01. Found: C, 65.84; H, 5.58; N, 15.92.

Example 603

N-[2-(4-Amino-2-propyl-2H-pyrazolo[3,4-c]quinolin-1-yl)-1,1-dimethylethyl]isonicotinamide

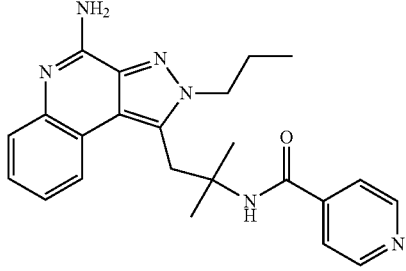 [SMILES: CCCn1nc2c(N)nc3ccccc3c2c1CC(C)(C)NC(=O)c1ccncc1]

Using the method of Example 68, 1-(2-amino-2-methylpropyl)-2-propyl-2H-pyrazolo[3,4-c]quinolin-4-amine (prepared as described in Example 64, 770 mg, 2.59 mmol) was reacted with isonicotinoyl chloride hydrochloride (1.15 mg, 6.48 mmol). The crude product was purified as described in Example 68 to provide 708 mg of N-[2-(4-amino-2-propyl-2H-pyrazolo[3,4-c]quinolin-1-yl)-1,1-dimethylethyl]isonicotinamide as an off-white solid, mp 148-150° C. MS (APCI) m/z 403 (M+H)$^+$; Anal. Calcd for $C_{23}H_{26}N_6O$: C, 68.63; H, 6.51; N, 20.88. Found: C, 68.30; H, 6.49; N, 20.92.

Example 604

N-{2-[4-Amino-2-(2-methoxyethyl)-2H-pyrazolo[3,4-c]quinolin-1-yl]-1,1-dimethylethyl}-3,4-difluorobenzamide

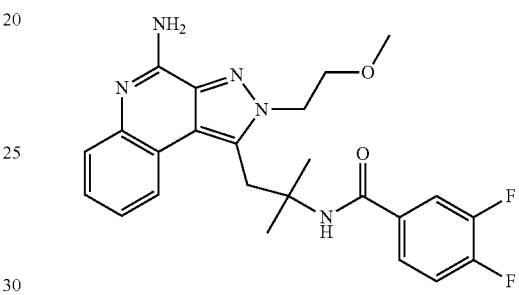

Using the general method of Example 599, 1-(2-amino-2-methylpropyl)-2-(2-methoxyethyl)-2H-pyrazolo[3,4-c]quinolin-4-amine (0.52 g, 1.66 mmol, prepared as described in Example 590) was reacted with 3,4-difluorobenzoyl chloride. The crude product was purified as described in Example 599 to provide 382 mg of N-{2-[4-amino-2-(methoxyethyl)-2H-pyrazolo[3,4-c]quinolin-1-yl]-1,1-dimethylethyl}-3,4-difluorobenzamide as a white solid, mp 199-200° C. MS (ESI) m/z 454 (M+H)$^+$; Anal. Calcd for $C_{24}H_{25}F_2N_5O_2$: C, 63.57; H, 5.56; N, 15.44. Found: C, 63.37; H, 5.50; N, 15.58.

Example 605

N-[2-(4-Amino-2-propyl-2H-pyrazolo[3,4-c]quinolin-1-yl)-1,1-dimethylethyl]propionamide

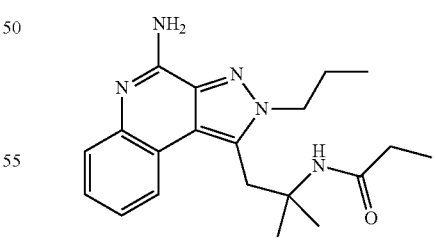

Using the method of Example 68, 1-(2-amino-2-methylpropyl)-2-propyl-2H-pyrazolo[3,4-c]quinolin-4-amine (prepared as described in Example 64, 595 mg, 2.00 mmol) was reacted with propionyl chloride (463 mg, 5.00 mmol). The crude product was purified by IFC (silica gel eluting with a gradient of 15 to 25% CMA in chloroform) followed by recrystallization from ethyl acetate/hexanes to provide 545 mg of N-[2-(4-amino-2-propyl-2H-pyrazolo[3,4-c]quinolin- 1-yl)-1,1-dimethylethyl]propionamide as a white solid, mp 158-159° C. MS (APCI) m/z 354 (M+H)$^+$; Anal. Calcd for C$_{20}$H$_{27}$N$_5$O: C, 67.96; H, 7.70; N, 19.81. Found: C, 67.80; H, 8.08; N, 19.77

Example 606

N-{2-[4-Amino-2-(2-methoxyethyl)-2H-pyrazolo[3,4-c]quinolin-1-yl]-1,1-dimethylethyl}propionamide

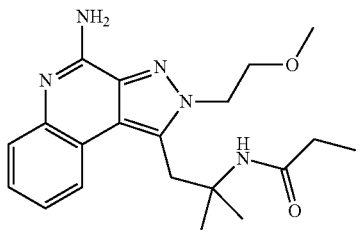 [SMILES: CCC(=O)NC(C)(C)Cc1c2c(nn1CCOC)c(N)nc1ccccc12]

Using the general method of Example 599, 1-(2-amino-2-methylpropyl)-2-(2-methoxyethyl)-2H-pyrazolo[3,4-c]quinolin-4-amine (500 mg, 1.60 mmol, prepared as described in Example 590) was reacted with propionyl chloride (370 mg, 4.00 mmol). The crude product was purified by IFC (silica gel eluting with a gradient of 15 to 50% CMA in chloroform) followed by recrystallization from ethyl acetate/hexanes to provide 434 mg of N-{2-[4-amino-2-(methoxyethyl)-2H-pyrazolo[3,4-c]quinolin-1-yl]-1,1-dimethylethyl}propionamide as a white solid, mp 157-158° C. MS (APCI) m/z 370 (M+H)$^+$; Anal. Calcd for C$_{20}$H$_{27}$N$_5$O$_2$: C, 65.02; H, 7.37; N, 18.96. Found: C, 64.79; H, 7.58; N, 18.94.

Example 607

N-{2-[4-Amino-2-(2-methoxyethyl)-2H-pyrazolo[3,4-c]quinolin-1-yl]-1,1-dimethylethyl}-4-fluorobenzamide

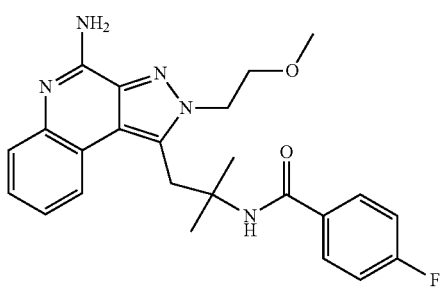 [SMILES: COCCn1nc2c(N)nc3ccccc3c2c1CC(C)(C)NC(=O)c1ccc(F)cc1]

Using the general method of Example 599, 1-(2-amino-2-methylpropyl)-2-(2-methoxyethyl)-2H-pyrazolo[3,4-c]quinolin-4-amine (500 mg, 1.60 mmol, prepared as described in Example 590) was reacted with 4-fluorobenzoyl chloride (634 mg, 4.00 mmol). The crude product was purified by IFC (silica gel eluting with a gradient of 5 to 20% CMA in chloroform) followed by recrystallization from ethyl acetate/hexanes to provide 551 mg of N-{2-[4-amino-2-(methoxyethyl)-2H-pyrazolo[3,4-c]quinolin-1-yl]-1,1-dimethylethyl}-4-fluorobenzamide as a white solid, mp 187-189° C. MS (ESI) m/z 436 (M+H)$^+$; Anal. Calcd for C$_{24}$H$_{26}$FN$_5$O$_2$: C, 66.19; H, 6.02; N, 16.08. Found: C, 65.92; H, 5.93; N, 15.87.

Example 608

N-{2-[4-Amino-2-(2-hydroxyethyl)-2H-pyrazolo[3,4-c]quinolin-1-yl]-1,1-dimethylethyl}methanesulfonamide

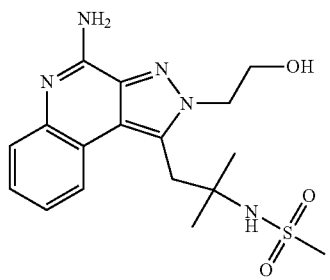 [SMILES: CC(C)(Cc1c2c(nn1CCO)c(N)nc1ccccc12)NS(C)(=O)=O]

Boron tribromide (1 M in dichloromethane, 2.15 mL, 2.15 mmol) was added over a period of 2 minutes to a chilled (0° C.) slurry of N-{2-[4-amino-2-(2-methoxyethyl)-2H-pyrazolo[3,4-c]quinolin-1-yl]-1,1-dimethylethyl}methanesulfonamide (337 mg, 0.861 mmol, prepared as described in Example 592) in dichloromethane (10 mL). The reaction mixture was stirred for 14 hours and then concentrated under reduced pressure. The residue was combined with 6 M hydrochloric acid and stirred for 3 hours. The reaction mixture was diluted with 2 M aqueous sodium carbonate. The resulting precipitate was isolated by filtration and rinsed with water and chloroform. The precipitate was combined with the chloroform layer and concentrated under reduced pressure. The residue was purified by IFC (silica gel eluting with a gradient of CMA in chloroform) followed by recrystallization from ethyl acetate/hexanes/acetonitrile to provide 184 mg of N-{2-[4-amino-2-(2-hydroxyethyl)-2H-pyrazolo[3,4-c]quinolin-1-yl]-1,1-dimethylethyl}methanesulfonamide as a white solid, mp 203-204° C. MS (ESI) m/z 378 (M+H)$^+$; Anal. Calcd for C$_{27}$H$_{23}$N$_5$O$_3$S: C, 54.09; H, 6.14; N, 18.55. Found: C, 54.11; H, 5.97; N, 18.42.

Example 609

2-(4-Amino-1-methyl-2H-pyrazolo[3,4-c]quinolin-2-yl)ethanol

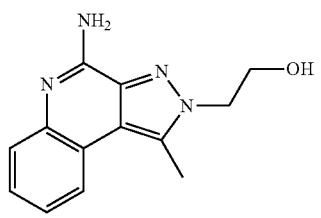 [SMILES: Cc1c2c(nn1CCO)c(N)nc1ccccc12]

Part A

A solution of 2-hydroxyethylhydrazine (15.2 g, 200 mmol) in ethanol (50 mL) was added over a period of 30 minutes to a solution of ethyl 2,4-dioxopentanoate (31.6 g, 200 mmol) in ethanol (200 mL). The reaction mixture was stirred for an additional 20 minutes and then concentrated under reduced pressure to provide 45 g of ethyl 1-(2-hydroxyethyl)-5-methyl-1H-pyrazole-3-carboxylate a light brown oil. A portion (31.1 g) of this material was combined in a Parr vessel with methanol (25 mL) and concentrated ammonium hydroxide (25 mL). The vessel was sealed and the mixture was heated for 12 hours. The reaction mixture was concentrated under reduced pressure to provide a brown resin. The resin was stirred with a mixture of chloroform and methanol until a solid appeared. The solid was isolated by filtration and then recrystallized from isopropanol to provide 7.01 g of 1-(2-hydroxyethyl)-5-methyl-1H-pyrazole-3-carboxamide as a white solid. The rest of the ester was purified by IFC (silica gel eluting with a gradient of 50 to 100% ethyl acetate in hexanes) to provide 6.6 g of a pale yellow oil. This material was dissolved in concentrated ammonium hydroxide (25 mL) and allowed to stand at ambient temperature for 48 hours. A precipitate was isolated by filtration, rinsed with water, and dried to provide 3.74 g of 1-(2-hydroxyethyl)-5-methyl-1H-pyrazole-3-carboxamide as white needles, mp 170-172° C. Anal. Calcd for $C_7H_{11}N_3O_2$: C, 49.70; H, 6.55; N, 24.84. Found: C, 49.59; H, 6.65; N, 24.92.

Part B

Under a nitrogen atmosphere, triethylamine (17.9 g, 177 mmol) was added to a slurry of 1-(2-hydroxyethyl)-5-methyl-1H-pyrazole-3-carboxamide (7.0 g, 41.4 mmol) in dichloromethane (70 mL). The mixture was cooled in an ice bath and then a solution of trifluoroacetic anhydride (15.6 g, 74.2 mmol) in dichloromethane (70 mL) was added over a period of 10 minutes. All of the solids dissolved to provide a cloudy solution. After 1 hour additional triethylamine (70.6 mmol) was added and the reaction mixture was cooled in an ice bath. Trifluoroacetic anhydride (35.3 mmol) was added neat over a period of 5 minutes. The reaction mixture was stirred for 10 minutes then the ice bath was removed and the reaction mixture was stirred for 30 minutes. The reaction mixture was diluted with 2 M aqueous sodium carbonate (100 mL) and water (100 mL) then extracted with chloroform (×3). The extracts were combined, dried over magnesium sulfate, filtered, and concentrated under reduced pressure to provide 11.5 g of 1-(2-hydroxyethyl)-5-methyl-1H-pyrazole-3-carbonitrile a brown oil.

Part C

Potassium acetate (5.2 g, 53 mmol) and bromine (7.9 g, 49.4 mmol) were added sequentially to a solution of the material from Part B in acetic acid (70 mL). The reaction mixture was stirred for 20 hours and then quenched with aqueous saturated sodium bisulfite. The acetic acid was removed under reduced pressure. The residue was made basic with 2 M aqueous sodium carbonate and then extracted with chloroform (×3). The extracts were combined, dried over magnesium sulfate, filtered, and concentrated under reduced pressure to provide 11 g of a brown oil. The oil was purified by IFC (silica gel eluting with a gradient of 50 to 75% ethyl acetate in hexanes) to provide 3.48 g of 4-bromo-1-(2-hydroxyethyl)-5-methyl-1H-pyrazole-3-carbonitrile as a yellow oil.

Part D

2 M aqueous sodium carbonate (11.8 mL), 2-aminophenylboronic acid hydrochloride (2.04 g, 11.8 mmol), water (2.76 mL), triphenylphosphine (186 mg, 0.709 mmol), and palladium (II) acetate (53 mg, 0.236 mmol) were added sequentially to a solution of 4-bromo-1-(2-hydroxyethyl)-5-methyl-1H-pyrazole-3-carbonitrile (1.812 g, 7.88 mmol) in propanol (13.8 mL) in a 100 mL round bottom flask. The flask was evacuated then filled with nitrogen. The reaction mixture was heated at reflux for 22 hours. The reaction mixture was extracted with chloroform (×4). The extracts were combined, dried over magnesium sulfate, filtered, and concentrated under reduced pressure to provide a yellow oil. The oil was refluxed with tert-butyl methyl ether to provide about 1 g of a gummy solid. This material was purified by IFC (silica gel eluting with a gradient of 30 to 75% CMA in chloroform) to provide about 400 mg of a pale yellow solid. This material was recrystallized from acetonitrile (50 mL) to provide 187 mg of 2-(4-amino-1-methyl-2H-pyrazolo[3,4-c]quinolin-2-yl)ethanol as a white solid, mp 226-228° C. MS (APCI) m/z 243 (M+H)⁺; Anal. Calcd for $C_{13}H_{14}N_4O$: C, 64.45; H, 5.82; N, 23.12.

Found: C, 64.31; H, 6.01; N, 23.18.

Example 610

2-Ethyl-1-(2,2-dimethylpropyl)-2H-pyrazolo[3,4-c]-1,7-naphthyridin-4-amine

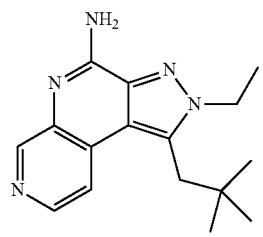 [SMILES: CCn1nc2c(N)nc3cnccc3c2c1CC(C)(C)C]

Propanol (5 mL) and 2 M hydrochloric acid (1.6 mL) were added to 3-[(tert-butoxycarbonyl)amino]pyridin-4-ylboronic acid (1.04 g, 4.37 mmol), prepared as described in Example 15 using tert-butyl N-(3-pyridyl)carbamate in lieu of tert-butyl N-(2-pyridyl)carbamate. The mixture was refluxed for 30 minutes to remove the BOC group. Solid sodium carbonate (710 mg, 6.7 mol), 4-bromo-1-ethyl-5-(2,2-dimethylpropyl)-1H-pyrazole-3-carbonitrile (786 mg, 2.91 mmol), prepared as described in Example 38, bis[(2-diphenylphosphino)phenyl]ether (47 mg, 0.087 mmol), and palladium (II) acetate (19.5 mg, 0.087 mmol) were added. The flask was evacuated and then filled with nitrogen three times. The reaction mixture was heated at reflux for 18 hours and then partitioned between water and chloroform. The aqueous layer was extracted with chloroform (×3). The combined organics were dried over magnesium sulfate, filtered, and concentrated under reduced pressure to provide a yellow oil. The oil was purified by IFC (silica gel eluting with a gradient of 2 to 45% CMA in chloroform) to provide 180 mg of a yellow resin. This material was purified by IFC (silica gel eluting with 15% CMA in chloroform) to provide 120 mg of product. This material was refluxed in 35% ethyl acetate in hexanes (15 mL) then diluted with hexanes (15 mL) and chilled. The resulting solid was isolated by filtration and dried to provide 54 mg of a white solid. Analysis by ¹H NMR and IR indicated the presence of the biaryl intermediate and a nitrile group. Acetyl chloride (393 mg) and anhydrous ethanol (5 mL) were combined and stirred for 30 minutes. The white solid was added and the mixture was refluxed under nitrogen for 5 hours. The reaction mixture was allowed to stand for 48 hours; then it was diluted with 2 M aqueous sodium carbonate and concentrated under reduced pressure. The residue was extracted with chloroform (×4). The combined extracts were dried over magnesium sulfate, filtered, and concentrated under reduced pressure to provide a white solid. This material was dissolved in a minimal amount of dichloromethane and then precipitated with hexanes. The solid was isolated by filtration and dried to provide 28 mg of 2-ethyl-1-(2,2-dimethylpropyl)-2H-pyrazolo[3,4-c]-1,7-naphthyridin-4-amine as a white solid, mp>260° C. HRMS (ESI) Calcd for $C_{16}H_{21}N_5$+H 284.1875. found 284.1860.

Example 611

1-(3-Benzenesulfonylpropyl)-2-butyl-2H-pyrazolo[3,4-c]quinolin-4-amine

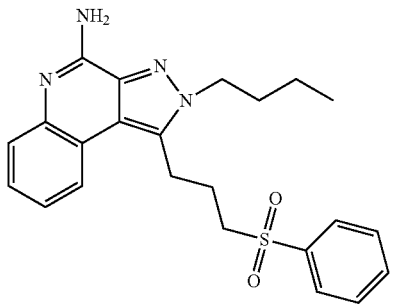 [SMILES: CCCCn1nc2c(N)nc3ccccc3c2c1CCCS(=O)(=O)c1ccccc1]

Part A

Sodium metal (23 mg, 1 mmol) was added to 25 mL of methanol. After the sodium metal was consumed, methyl acetoacetate (1.16 g, 10 mmol) was added to the mixture and stirred for 15 minutes. A solution of phenyl vinyl sulfone (1.68 g, 10 mmol) was added dropwise to the solution and maintained for several hours. The slightly yellow solution was concentrated under reduced pressure, and the residue was diluted with ethyl acetate and washed with saturated aqueous ammonium chloride. The aqueous layer was extracted with ethyl acetate and the combined organic layers were washed with brine, dried over magnesium sulfate, filtered and concentrated to afford a clear oil. The material was purified via flash column chromatography on silica gel (eluting with hexane:ethyl acetate in a gradient from 3:2 to 2:3) to afford 1.40 g of ethyl 2-(2-benzenesulfonylethyl)-3-oxo-butyrate.

Part B

Hydrochloric acid was added (150 mL of 3 N) to a solution of ethyl 2-(2-benzenesulfonylethyl)-3-oxo-butyrate (21.7 g, 76.3 mmol) in 100 mL of ethanol and heated to reflux overnight. The reaction was cooled to ambient temperature and the mixture was concentrated under reduced pressure. The residue was extracted with several portions of ethyl acetate, and the combined organic layers were washed with saturated aqueous sodium bicarbonate, washed with brine, dried over magnesium sulfate, filtered, and concentrated under reduced pressure to afford 16.8 g of 5-benzenesulfonylpentan-2-one as a yellow oil.

Part C

Sodium tert-butoxide (15.4 g, 160 mmol) was combined with ethanol (53 mL) and allowed to stir for 30 minutes. 5-Benzenesulfonylpentan-2-one (16.8 g, 74.2 mmol) and diethyl oxalate (10.1 mL, 74.2 mmol) were added to the reaction mixture in 20 mL of ethanol via an addition funnel. The reaction was maintained for 1 hour and the solution changed in color from orange to red. Potassium acetate (10.9 g, 111 mmol) was added to the reaction mixture, followed by addition of acetic acid (37 mL, 2M). The reaction mixture was then cooled to 0° C. and butyl hydrazine oxalate (13.2 g, 74.2 mmol) was added. The resultant slurry was stirred for 2 hours and turned yellow. The reaction mixture was concentrated under reduced pressure, diluted with water, and the pH of the mixture was adjusted to 11 by addition of sodium carbonate. The reaction mixture was extracted with chloroform while adding additional water to minimize elusion formation. The combined organic layers were washed with brine, dried over magnesium sulfate, filtered, and concentrated under reduced pressure to afford a red oil. The material was purified by column chromatography on silica gel (eluting with hexane:ethyl acetate in a gradient from 3:1 to 1:1) to yield 13.3 g of ethyl 5-(3-benzenesulfonylpropyl)-1-butyl-1H-pyrazole-3-carboxylate as an orange oil.

Part D

Sodium hydroxide (12 mL, 6M) was added to a solution of ethyl 5-(3-benzenesulfonylpropyl)-1-butyl-1H-pyrazole-3-carboxylate (13.3 g, 35.1 mmol) in 100 mL of ethanol and heated to reflux overnight. The reaction mixture was concentrated under reduced pressure and the residue was diluted with 100 mL of water. The aqueous layer was extracted with several portions of ethyl acetate. The pH of the aqueous layer was adjusted to approximately 2-3 with aqueous hydrochloric acid and was then extracted with several portions of ethyl acetate. The combined organic layers originating from extraction of the aqueous layer were washed with brine, dried over magnesium sulfate, filtered, and concentrated to afford 10.5 g of 5-(3-benzenesulfonylpropyl)-1-butyl-1H-pyrazole-3-carboxylic acid.

Part E

Oxalyl chloride (7.8 mL, 90.0 mmol) was added slowly via syringe to a solution of 5-(3-benzenesulfonylpropyl)-1-butyl-1H-pyrazole-3-carboxylic acid (10.5 g, 30.0 mmol) in 100 mL of dichloromethane containing one drop of DMF. After 2 hours of stirring, saturated ammonium chloride (100 mL) was added to the reaction mixture and the reaction was maintained for 1 hour. The reaction mixture was concentrated under reduced pressure, diluted with dichloromethane and washed with water. The combined organic layers were washed with brine, dried over magnesium sulfate, filtered, and concentrated to afford 10.4 g of 5-(3-benzenesulfonylpropyl)-1-butyl-1H-pyrazole-3-carboxamide.

Part F

Phosphorus oxychloride (25 mL) was added to 5-(3-benzenesulfonylpropyl)-1-butyl-1H-pyrazole-3-carboxamide (10.4 g, 30.0 mmol) and heated to 90° C. for 2.5 hours. The reaction mixture was then cooled to ambient temperature and poured into ice water cooled by an ice bath. Additional ice was added to the reaction mixture and the pH of the mixture was adjusted to 8-9 by addition of 30% saturated aqueous ammonium hydroxide. The mixture was extracted with ethyl acetate and the combined organic layers were dried over magnesium sulfate, filtered, and concentrated under reduced pressure to afford 8.60 g of 5-(3-benzenesulfonylpropyl)-1-butyl-1H-pyrazole-3-carbonitrile.

Part G

Potassium acetate (3.82 g, 38.9 mmol) was added to a solution of 5-(3-benzenesulfonylpropyl)-1-butyl-1H-pyrazole-3-carbonitrile (8.60 g, 25.9 mmol) in 50 mL of acetic acid. The reaction mixture was stirred until all solids had dissolved, followed by dropwise addition of bromine (1.33 mL, 25.9 mmol) over 5 minutes. The resultant red solution was stirred for 5 hours and aqueous sodium thiosulfate was added to quench excess bromine. The reaction mixture was concentrated under reduced pressure and the residue was diluted with 200 mL of water. The pH of the mixture was adjusted to 8-9 by slow addition of solid sodium carbonate followed by extraction with several portions of ethyl acetate. The combined organic layers were washed with brine, dried over magnesium sulfate, filtered, and concentrated under reduced pressure to afford an orange oil. Purification via flash column chromatography on silica gel (eluting with hexane:ethyl acetate in a gradient from 3:1 to 1:1) afforded 4.80 g of 5-(3-benzenesulfonylpropyl)-4-bromo-1-butyl-1H-pyrazole-3-carbonitrile as a colorless oil that crystallized upon standing.

Part H

2-Aminophenyl boronic acid hydrochloride (693 mg, 4.00 mmol) and potassium phosphate tribasic (2.12 g, 10.0 mmol) were added sequentially to a solution of 5-(3-benzenesulfonylpropyl)-4-bromo-1-butyl-1H-pyrazole-3-carbonitrile (550 mg, 1.30 mmol) in 15 mL of toluene in a pressure tube. Nitrogen was bubbled through the resultant slurry for 15 minutes. Tris(dibenzylideneacetone)dipalladium(0) (104 mg, 0.10 mmol), bis[(2-diphenylphosphino)phenyl]ether (65 mg, 0.12 mmol), and 4 angstrom molecular sieves were then added to the reaction mixture. The pressure tube was sealed and heated in a 110° C. oil bath. After 20 hours, the reaction mixture was cooled to ambient temperature, diluted with ethyl acetate and filtered through CELITE filter aid. The filtrate was diluted with ethyl acetate and washed with saturated aqueous sodium bicarbonate. The aqueous layer was extracted with additional ethyl acetate and the combined organic layers were washed with brine, dried over magnesium sulfate, filtered, and concentrated to an orange oil. Purification via flash column chromatography on silica gel (eluting with hexane:ethyl acetate in a gradient from 2:1 to 2:3) afforded 550 mg of 4-(2-aminophenyl)-5-(3-benzenesulfonylpropyl)-1-butyl-1H-pyrazole-3-carbonitrile as a thick pale yellow oil.

Part I

Hydrochloric acid (0.98 mL, 3.90 mmol) in ethanol was added dropwise to a solution of 4-(2-aminophenyl)-5-(3-benzenesulfonylpropyl)-1-butyl-1H-pyrazole-3-carbonitrile (550 mg, 1.30 mmol) in 10 mL of ethanol. The resultant solution was stirred for 2 hours, concentrated under reduced pressure, and diluted with water. The pH of the mixture was adjusted to 8-9 by slow addition of solid sodium carbonate. The aqueous layer was extracted with several portions of dichloromethane. The combined organic layers were washed with brine, dried over magnesium sulfate, filtered, and concentrated under reduced pressure to afford a pale yellow solid. The material was purified via flash column chromatography on silica gel (eluting with a 97:3 mixture of dichloromethane/methanol) to afford 350 mg of 1-(3-benzenesulfonylpropyl)-2-butyl-2H-pyrazolo[3,4-c]quinolin-4-amine as a white crystalline solid, mp 206-207° C. $^1$H NMR (300 MHz, CDCl$_3$) δ 7.87 (d, J=6.9 Hz, 2H), 7.77 (dd, J=1.2, 8.1 Hz, 1H), 7.69 (dd, J=0.9, 8.1 Hz, 1H), 7.63 (m, 1H), 7.53 (m, 2H), 5.37 (br s, 2H), 4.35 (app t, J=7.2 Hz, 2H), 3.45 (m, 2H), 3.22 (t, J=7.1 Hz, 2H), 2.23 (m, 2H), 1.94 (m, 2H), 1.40 (qd, J=7.2, 14.6 Hz, 2H), 0.98 (t. J=7.3 Hz, 3H); MS (APCI) m/z 423 (M+H$^+$); Anal. calcd for C$_{23}$H$_{26}$N$_4$O$_2$S: C, 65.38; H, 6.20; N, 13.26. Found: C, 65.40; H, 6.01; N, 13.26.

Example 612

1-(4-Methanesulfonylbutyl)-2-propyl-2H-pyrazolo[3,4-c]quinolin-4-amine

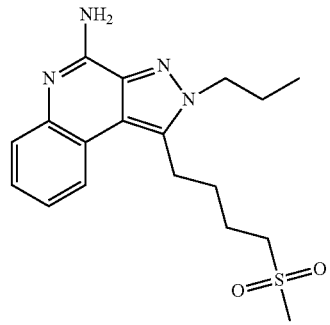 [SMILES: CCCn1nc2c(N)nc3ccccc3c2c1CCCCS(C)(=O)=O]

Part A

2-Aminophenyl boronic acid hydrochloride (9.10 mg, 26.3 mmol) and freshly ground potassium phosphate tribasic (27.8 g, 131 mmol) were added sequentially to a solution of 4-bromo-5-(4-chlorobutyl)-1-propyl-1H-pyrazole-3-carbonitrile (8.00 g, 26.3 mmol), prepared as described in Example 46, in 100 mL of toluene in a pressure tube. Nitrogen was bubbled through the resultant slurry for 15 minutes. Tris(dibenzylideneacetone)dipalladium(0) (1.36 g, 1.31 mmol), bis[(2-diphenylphosphino)phenyl]ether (851 mg, 1.58 mmol), and 4 angstrom molecular sieves were then added to the reaction mixture. The pressure tube was sealed and heated in a 110° C. oil bath. After 24 hours, the reaction mixture was cooled to ambient temperature, diluted with ethyl acetate and filtered through CELITE filter aid. The filtrate was diluted with ethyl acetate and washed with saturated aqueous sodium bicarbonate. The aqueous layer was extracted with additional ethyl acetate and the combined organic layers were washed with brine, dried over magnesium sulfate, filtered, and concentrated to a red oil. Purification via flash column chromatography on silica gel (eluting with 2:1 hexane:ethyl acetate) afforded 7.60 g of 4-(2-aminophenyl)-5-(4-chlorobutyl)-1-propyl-1H-pyrazole-3-carbonitrile as a red oil.

Part B

Hydrochloric acid (18 mL, 71.0 mmol) in ethanol was added dropwise to a solution of 4-(2-aminophenyl)-5-(4-chlorobutyl)-1-propyl-1H-pyrazole-3-carbonitrile (7.50 g, 23.7 mmol) in 150 mL of ethanol. The resultant solution was heated to reflux overnight, concentrated under reduced pressure, and diluted with water. The pH of the mixture was adjusted to 9-10 by slow addition of solid sodium carbonate. The aqueous layer was extracted with several portions of dichloromethane. The combined organic layers were washed with brine, dried over magnesium sulfate, filtered, and concentrated under reduced pressure to afford a reddish solid.

The material was purified via flash column chromatography on silica gel (eluting with a 96:4 mixture of dichloromethane/methanol) to afford 4.78 g of 1-(4-chlorobutyl)-2-propyl-2H-pyrazolo[3,4-c]quinolin-4-amine.

Part C

Sodium thiomethoxide (0.3 g, 3.79 mmol) was added to a solution of 1-(4-chlorobutyl)-2-propyl-2H-pyrazolo[3,4-c]quinolin-4-amine (1.0 g, 3.16 mmol) in 15 mL of DMF and heated for 3 hours at 80° C. The reaction mixture was allowed to cool to ambient temperature, diluted with dichloromethane, and washed with water. The aqueous layer was extracted with several additional portions of dichloromethane and the combined organic layers were washed with water, washed with brine, dried over magnesium sulfate, and concentrated to afford 1.04 g of 1-(4-methylthiobutyl)-2-propyl-2H-pyrazolo[3,4-c]quinolin-4-amine as a yellow solid.

Part D

3-Chloroperoxybenozic acid (mCPBA) (75% pure, 1.60 g, 6.97 mmol, 2.2 eq) was added portion wise to a solution of 1-(4-methylthiobutyl)-2-propyl-2H-pyrazolo[3,4-c]quinolin-4-amine (1.04 g, 3.16 mmol) in 50 mL of chloroform over several minutes. The resulting reaction mixture was stirred at ambient temperature for 2 hours and became darker red in color. The mixture was then washed with saturated aqueous sodium bicarbonate, the layers were separated, and the aqueous layer was further extracted with dichloromethane. The combined organic layers were washed with brine, dried over magnesium sulfate, filtered, and concentrated under reduced pressure to afford a dark oil. The material was purified via flash column chromatography on silica gel (eluting with dichloromethane/methanol in a gradient from 97:3 to 93:7), diluted with acetonitrile, washed with saturated aqueous sodium bicarbonate, and purified a second time via flash column chromatography on silica gel (eluting with dichloromethane/methanol in a gradient from 97:3 to 93:7). The product was recrystallized from acetonitrile to afford 960 mg of 1-(4-methanesulfonylbutyl)-2-propyl-2H-pyrazolo[3,4-c]quinolin-4-amine as a yellow crystalline solid, mp 155-157° C. $^1$H NMR (300 MHz, CDCl$_3$) δ 7.85 (m, 1H), 7.73 (dd, J=1.2, 8.1 Hz, 1H), 7.46 (dt, J=1.2, 6.9 Hz, 1H), 7.32 (dt, J=1.2, 7.5 Hz, 1H), 5.54 (br s, 2H), 4.31 (t, J=7.2 Hz, 2H), 3.29 (t, J=7.5 Hz, 2H), 3.07 (t, J=7.5 Hz, 2H), 2.90 (s, 3H), 2.12-1.93 (m, 6H), 1.02 (t, J=7.2 Hz, 3H); MS (APCI) m/z 361 (M+H)$^+$; Anal. calcd for C$_{18}$H$_{24}$N$_4$O$_2$S (containing 0.5 CH$_3$CN): C, 59.90; H, 6.75; N, 16.54. Found: C, 59.89; H, 6.83; N, 16.77.

Example 613

Alternative preparation of 1-(4-Aminobutyl)-2-propyl-2H-pyrazolo[3,4-c]quinolin-4-amine

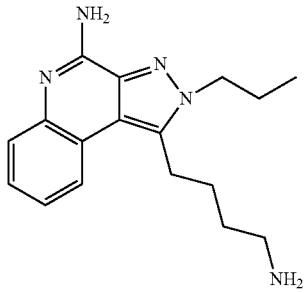 [SMILES: CCCn1nc2c(N)nc3ccccc3c2c1CCCCN]

Using the method of Example 593, the protecting groups were removed from di(tert-butyl) 1-(4-aminobutyl)-2-propyl-2H-pyrazolo[3,4-c]quinolin-4-ylimidodicarbonate (0.368 mg), prepared as described in Example 598. The crude product was purified by column chromatography (silica gel eluting with chloroform/CMA in a gradient of 95:5 to 8:2) to provide 0.0993 g of 1-(4-aminobutyl)-2-propyl-2H-pyrazolo[3,4-c]quinolin-4-amine as a white powder, mp 156.0-157.0° C. $^1$H NMR (500 MHz, DMSO-d$_6$) δ 7.90 (d, J=7.9 Hz, 1H), 7.46 (d, J=7.5 Hz, 1H), 7.31 (t, J=7.7 Hz, 1H), 7.19 (t, J=8.1 Hz, 1H), 6.62 (s, 2H), 4.34 (t, J=7.3 Hz, 2H), 3.23 (t, J=7.8 Hz, 2H), 2.69 (t, J=6.9 Hz, 2H), 1.92 (t, J=7.3 Hz, 2H), 1.67-1.71 (m, 2H), 1.49-1.57 (m, 4H), 0.92 (t, J=7.4 Hz, 3H); MS (APCI) m/z 298 (M+H)$^+$; Anal. calcd for C$_{17}$H$_{23}$N$_5$·0.3 H$_2$O: C, 67.43; H, 7.86; N, 23.13. Found: C, 67.61; H, 7.98; N, 23.20.

Example 614

2-Propyl-1-[4-(3,5,5-trimethyl-1,2,4-oxadiazol-4(5H)-yl)butyl]-2H-pyrazolo[3,4-c]quinolin-4-amine

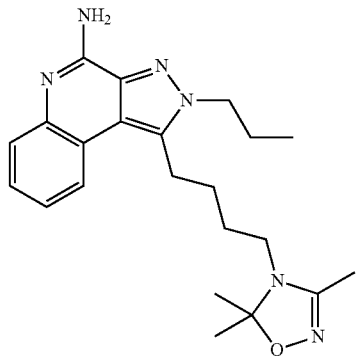 [SMILES: CCCn1nc2c(N)nc3ccccc3c2c1CCCCN1C(C)=NOC1(C)C]

Part A

Using the general method of Example 598 Part C, di(tert-butyl) 1-(4-aminobutyl)-2-propyl-2H-pyrazolo[3,4-c]quinolin-4-ylimidodicarbonate (1.50 g, 3.01 mmol), prepared as described in Example 598, was reacted with acetone to form an imine intermediate and the imine was treated with α-chloroacetaldoxime. The crude product was purified by chromatography (silica gel, elution with a gradient of 40 to 80% ethyl acetate in hexanes) to provide 0.66 g of di(tert-butyl) 2-propyl-1-[4-(3,5,5-trimethyl-1,2,4-oxadiazol-4(5H)-yl)butyl]-2H-pyrazolo[3,4-c]quinolin-4-ylimidodicarbonate as a white solid.

Part B

The Boc protecting groups were removed from the material from Part A by acid hydrolysis as described in Example 598 Part D. The crude product was purified by chromatography (silica gel, elution with 9:1 chloroform/CMA) and dried under high vacuum at 65° C. to provide 0.0874 g of 2-propyl-1-[4-(3,5,5-trimethyl-1,2,4-oxadiazol-4(5H)-yl)butyl]-2H-pyrazolo[3,4-c]quinolin-4-amine as a white solid, mp 144.0-146.0° C. $^1$H NMR (300 MHz, CDCl$_3$) δ 7.77 (d, J=7.3 Hz, 1H), 7.64 (d, J=8.1 Hz, 1H), 7.37 (t, J=8.0 Hz, 1H), 7.22 (t, J=7.8 Hz, 1H), 5.44 (s, 2H), 4.22 (t, J=7.3 Hz, 2H), 3.18 (t, J=7.5 Hz, 2H), 2.95 (t, J=7.9 Hz, 2H), 1.94 (q, J=7.3 Hz, 2H), 1.63-1.77 (m, 7H), 1.32 (s, 6H), 0.93 (t, J=7.4 Hz, 3H); MS (APCI) m/z 395 (M+H)+; Anal. calcd for $C_{22}H_{30}N_6O \cdot 0.3$ H2O: C, 66.07; H, 7.71; N, 21.01. Found: C, 65.82; H, 7.74; N, 20.90.

Example 615

1-Pent-4-ynyl-2-propyl-6,7,8,9-tetrahydro-2H-pyrazolo[3,4-c]quinolin-4-amine

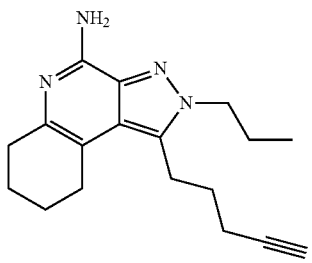 [SMILES: C#CCCCc1c2c3c(nc(N)c2nn1CCC)CCCC3]

Part A

A mixture of 1-(4-chlorobutyl)-2-propyl-2H-pyrazolo[3,4-c]quinolin-4-amine (19.45 g, 61.39 mmol), prepared as described in Example 46, platinum oxide (10.00 g) and trifluoroacetic acid (200 mL) was placed under hydrogen pressure (50 psi, $3.4 \times 10^5$ Pa) for 2 days. The reaction mixture was filtered through CELITE filter aid. The filtrate was concentrated under reduced pressure to provide a dark oil. The oil was chilled in an ice bath, ice was added, and the mixture was made basic (pH 14) by the addition of 1 N potassium hydroxide. The resulting solid was isolated by filtration and then dissolved in dichloromethane. The solution was washed sequentially with 1 N potassium hydroxide, water, and brine, dried over magnesium sulfate, filtered, and concentrated under reduced pressure. The residue was dried under vacuum for 2 days to provide 18.0 g of 1-(4-chlorobutyl)-2-propyl-6,7,8,9-tetrahydro-2H-pyrazolo[3,4-c]quinolin-4-amine as an oil.

Part B

Using the method of Example 57 Part A, the material from Part A was reacted with di-tert-butyl dicarbonate (49 g, 4 eq) to provide a quantitative yield of di(tert-butyl) 1-(4-chlorobutyl)-2-propyl-6,7,8,9-2H-pyrazolo[3,4-c]quinolin-4-ylimidodicarbonate as a black oil.

Part C

Using the method of Example 57 Part B, the material from Part B was reacted with potassium acetate (11.0 g, 2.0 eq) to provide 29.25 g of 4-{4-[bis(tert-butoxycarbonyl)amino]-2-propyl-6,7,8,9-tetrahydro-2H-pyrazolo[3,4-c]quinolin-1-yl}butyl acetate as a black oil.

Part D

Using the method of Example 57 Part C, the acetate protecting group was removed from the material from Part C to provide 24.2 g of di(tert-butyl) 1-(4-hydroxybutyl)-2-propyl-6,7,8,9-tetrahydro-2H-pyrazolo[3,4-c]quinolin-4-ylimidodicarbonate as a brown solid.

Part E

The material from Part D was oxidized using the method of Example 57 Part D. The crude product was purified by chromatography (silica gel, elution with 1:1 hexanes/ethyl acetate) and dried under vacuum at ambient temperature over the weekend to provide 15.5 g of di(tert-butyl) 1-(4-oxobutyl)-2-propyl-6,7,8,9-tetrahydro-2H-pyrazolo[3,4-c]quinolin-4-ylimidodicarbonate as an amber, glassy, semi-solid.

Part F

Using the method of Example 58 Part E, the material from Part E was reacted with freshly prepared diethyl 1-diazo-2-oxopropylphosphonate (10.22 g, 1.5 eq) to provide 15.33 g of di(tert-butyl) 1-pent-4-ynyl-2-propyl-6,7,8,9-tetrahydro-2H-pyrazolo[3,4-c]quinolin-4-ylimidodicarbonate as a tan solid.

Part G

Under a nitrogen atmosphere, a solution of a portion (0.75 g) of the material from Part F in 6 M hydrochloric acid in ethanol (10 mL) was heated at 60° C. for 1.7 hours. The reaction mixture was concentrated under reduced pressure. The residue was made basic with 1 N potassium hydroxide and then extracted with dichloromethane. The combined extracts were washed sequentially with water and brine, dried over sodium sulfate, filtered, and concentrated under reduced pressure. The residue was purified by chromatography (silica gel, elution with a gradient of 5-20% CMA in chloroform) to provide 0.327 g of a tan solid. This material was twice triturated with boiling diethyl ether and isolated by filtration to provide 0.2823 g of 1-pent-4-ynyl-2-propyl-6,7,8,9-tetrahydro-2H-pyrazolo[3,4-c]quinolin-4-amine as a white solid, mp 167.0-169.0° C. $^1$H NMR (300 MHz, CDCl$_3$) δ 5.07 (s, 2H), 4.25 (t, J=7.5 Hz, 2H), 3.15 (t, J=8.1 Hz, 2H), 2.81-2.84 (m, 2H), 2.64-2.70 (m, 2H), 2.22-2.29 (m, 2H), 2.00 (t, J=2.5 Hz, 1H), 1.99 (q, J=7.4 Hz, 2H), 1.81-1.87 (m, 6H), 0.97 (t, J=7.4 Hz, 3H); MS (APCI) m/z 297 (M+H)+; Anal. calcd for $C_{18}H_{24}N_4 \cdot 0.3H_2O$: C, 71.63; H, 8.22; N, 18.56. Found: C, 71.60; H, 7.96; N, 18.71.

Example 616

1-[3-(3-Methylisoxazol-5-yl)propyl]-2-propyl-6,7,8,9-tetrahydro-2H-pyrazolo[3,4-c]quinolin-4-amine

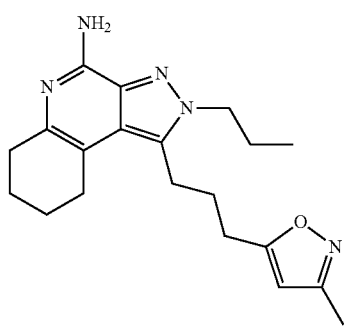 [SMILES: CCCn1nc2c(N)nc3c(c2c1CCCc1cc(C)no1)CCCC3]

Part A

Using the method of Example 595 Part B, di(tert-butyl) 1-pent-4-ynyl-2-propyl-6,7,8,9-tetrahydro-2H-pyrazolo[3, 4-c]quinolin-4-ylimidodicarbonate (4.00 g, 8.05 mmol), prepared as described in Example 615, was reacted with α-chloroacetaldoxime (1.13 g, 12.1 mmol). The crude product was purified by chromatography (silica gel, elution with a gradient of 20-40% ethyl acetate in hexanes) to provide 1.55 g of di(tert-butyl) 1-[3-(3-methylisoxazol-5-yl)propyl]-2-propyl-6,7,8,9-tetrahydro-2H-pyrazolo[3,4-c]quinolin-4-ylimidodicarbonate as a glassy solid.

Part B

Under a nitrogen atmosphere, a solution of the material from Part A in 6 M hydrochloric acid in ethanol (10 mL) was heated at 60° C. for 2 hours. The reaction mixture was concentrated under reduced pressure. The residue was made basic with 1 N potassium hydroxide and then extracted with dichloromethane. The combined extracts were washed sequentially with water and brine, dried over sodium sulfate, filtered, and concentrated under reduced pressure. The residue was dried under vacuum over the weekend and then triturated with a mixture of hexanes and diethyl ether. The resulting solid was isolated by filtration and dried to provide 0.3342 g of 1-[3-(3-methylisoxazol-5-yl)propyl]-2-propyl-6,7,8,9-tetrahydro-2H-pyrazolo[3,4-c]quinolin-4-amine as a white solid, mp 144.0-145.0° C. $^1$H NMR (300 MHz, CDCl$_3$) δ 5.86 (s, 1H), 5.06 (bs, 2H), 4.17 (t, J=7.4 Hz, 2H), 3.05 (t, J=8.1 Hz, 2H), 2.79-2.86 (m, 4H), 2.71-2.75 (m, 2H), 2.28 (s, 3H), 1.89-2.07 (m, 4H), 1.80-1.84 (m, 4H), 0.95 (t, J=7.4 Hz, 3H); MS (APCI) m/z 354 (M+H)$^+$; Anal. calcd for C$_{20}$H$_{27}$N$_5$O: C, 67.96; H, 7.70; N, 19.81. Found: C, 67.67; H, 7.83; N, 19.68.

Example 617

1-[3-(3-Phenylisoxazol-5-yl)propyl]-2-propyl-6,7,8,9-tetrahydro-2H-pyrazolo[3,4-c]quinolin-4-amine

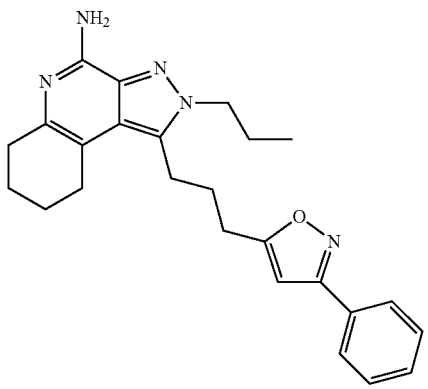 [SMILES: CCCn1nc2c(N)nc3c(c2c1CCCc1cc(-c2ccccc2)no1)CCCC3]

Part A

Under a nitrogen atmosphere, a mixture of di(tert-butyl) 1-pent-4-ynyl-2-propyl-6,7,8,9-tetrahydro-2H-pyrazolo[3,4-c]quinolin-4-ylimidodicarbonate (4.00 g, 8.05 mmol), prepared as described in Example 615, α-chlorobenzaldoxime (2.51 g, 16.1 mmol), prepared as described in Example 596, anhydrous triethylamine (1.7 mL, 12.1 mmol), and anhydrous dichloromethane (25 mL) was heated at 40° C. for 18 hours. The reaction mixture was diluted with dichloromethane, washed sequentially with potassium carbonate, water, and brine, dried over sodium sulfate, and filtered. The filtrate was loaded onto a silica gel column (250 g) and eluted with a gradient of 30-40% ethyl acetate in hexanes. The fractions containing product were combined and concentrated under reduced pressure to provide 2.97 g of di(tert-butyl) 1-[3-(3-phenylisoxazol-5-yl)propyl]-2-propyl-6,7,8,9-tetrahydro-2H-pyrazolo[3,4-c]quinolin-4-ylimidodicarbonate as a pale yellow solid.

Part B

Under a nitrogen atmosphere, a solution of the material from Part A in 6 M hydrochloric acid in ethanol (20 mL) was heated at 60° C. for 1.7 hours. The reaction mixture was concentrated under reduced pressure. The residue was made basic with 1 N potassium hydroxide and then extracted with dichloromethane. The combined extracts were washed sequentially with water and brine, dried over sodium sulfate, filtered, and concentrated under reduced pressure to provide 1.75 g of a yellow solid. This material was purified by column chromatography (silica gel, elution with a gradient of 10-20% CMA in chloroform) to provide 1.324 g of product. This material was triturated twice with hot diethyl ether to provide 0.85 g of a pale yellow solid. The solid was recrystallized twice from ethanol to provide 1-[3-(3-phenylisoxazol-5-yl)propyl]-2-propyl-6,7,8,9-tetrahydro-2H-pyrazolo[3,4-c]quinolin-4-amine as a white solid, mp 154.0-155.0° C. $^1$H NMR (300 MHz, CDCl$_3$) δ 7.75-7.80 (m, 2H), 7.42-7.49 (m, 3H), 6.34 (s, 1H), 5.01 (bs, 2H), 4.19 (t, J=7.4 Hz, 2H), 3.11 (t, J=8.2 Hz, 2H), 2.94 (t, J=7.3 Hz, 2H), 2.83 (m, 2H), 2.73 (m, 2H), 2.09 (p, J=8.0 Hz, 2H), 1.95 (q, J=7.4 Hz, 2H), 1.80-1.84 (m, 4H), 0.95 (t, J=7.4 Hz, 3H); MS (APCI) m/z 416 (M+H)$^+$.

Example 618

2-Propyl-1-[3-(3-pyridin-3-ylisoxazol-5-yl)propyl]-6,7,8,9-tetrahydro-2H-pyrazolo[3,4-c]quinolin-4-amine

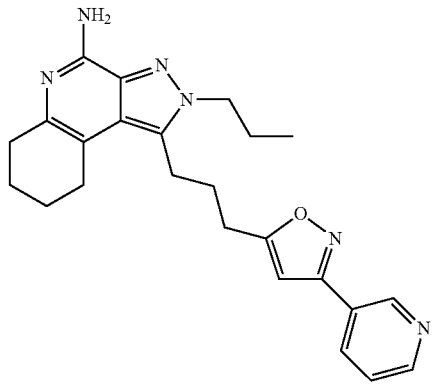 [SMILES: CCCn1nc2c(N)nc3c(c2c1CCCc1cc(-c2cccnc2)no1)CCCC3]

Part A

Under a nitrogen atmosphere, N-chlorosuccinimide (2.1 g, 16 mmol) was added to a solution of 3-pyridine aldoxime (2.0 g, 16 mmol) in THF (10 mL). The solution was stirred at ambient temperature for 4 hours. A solution of di(tert-butyl) 1-pent-4-ynyl-2-propyl-6,7,8,9-tetrahydro-2H-pyrazolo[3,4-c]quinolin-4-ylimidodicarbonate (4.00 g, 8.05 mmol), prepared as described in Example 615, and anhydrous triethylamine (2.5 mL, 18 mmol) in THF (10 mL) was added and the reaction solution was heated at 60° C. for 18 hours. The reaction solution was concentrated under reduced pressure to provide a black oil. The oil was dissolved in dichloromethane, washed sequentially with potassium carbonate, water, and brine, dried over sodium sulfate, and filtered. The filtrate was purified by column chromatography (silica gel, elution with a gradient of 20-80% ethyl acetate in hexanes) to provide 1.0877 g of di(tert-butyl) 2-propyl-1-[3-(3-pyridin-3-ylisoxazol-5-yl)propyl]-6,7,8,9-tetrahydro-2H-pyrazolo[3,4-c]quinolin-4-ylimidodicarbonate.

Part B

Under a nitrogen atmosphere, a solution of the material from Part A in 6 M hydrochloric acid in ethanol (20 mL) was heated at 60° C. for 1.5 hours. The reaction mixture was concentrated under reduced pressure. The residue was made basic with 1 N potassium hydroxide and then extracted with dichloromethane. The combined extracts were washed sequentially with water and brine, dried over sodium sulfate, filtered, and concentrated under reduced pressure. The residue was purified by column chromatography (silica gel, elution with a gradient of 5-20% CMA in chloroform) to provide 0.385 g of product. This material was triturated twice with hot diethyl ether to provide 0.2185 g of 2-propyl-1-[3-(3-pyridin-3-ylisoxazol-5-yl)propyl]-6,7,8,9-tetrahydro-2H-pyrazolo[3,4-c]quinolin-4-amine as a white solid, mp 168.0-170.0° C. $^1$H NMR (300 MHz, CDCl$_3$) δ 8.98-9.01 (md, 1H), 8.68-8.7 (mt, 1H), 8.11-8.15 (md, 1H), 7.38-7.43 (m, 1H), 6.38 (s, 1H), 5.17 (bs, 2H), 4.20 (t, J=7.3 Hz, 2H), 3.12 (t, J=8.2 Hz, 2H), 2.97 (t, J=7.3 Hz, 2H), 2.80-2.85 (m, 2H), 2.70-2.75 (m, 2H), 2.11 (p, J=8.0 Hz, 2H), 1.96 (q, J=7.4 Hz, 2H), 1.70-1.89 (m, 4H), 0.96 (t, J=7.4 Hz, 3H); MS (APCI) m/z 417 (M+H)$^+$; Anal. calcd for $C_{24}H_{28}N_6O \cdot 0.6H_2O$: C, 67.46; H, 6.89; N, 19.67. Found: C, 67.19; H, 6.61; N, 19.65.

Examples 619-643

A reagent (0.15 mmol, 1.5 equivalents) from the table below was added to a test tube containing 1-(4-chlorobutyl)-2-propyl-6,7,8,9-tetrahydro-2H-pyrazolo[3,4-c]quinoline-4-amine (32 mg, 0.10 mmol, prepared as described in Example 615 Part A) and potassium carbonate (approximately 55 mg, 0.40 mmol) in N,N-dimethylacetamide (1 mL). The test tubes were capped and heated at 90° C. for approximately 16 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

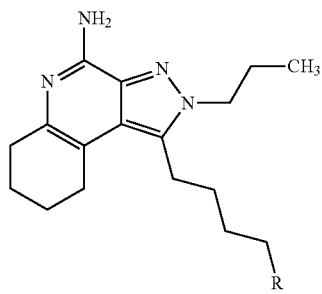

| Example | Reagent | R | Measured Mass (M + H) |
|---|---|---|---|
| 619 | None—starting material | Cl | 321.1830 |
| 620 | Pyrrolidine | N-pyrrolidinyl | 356.2833 |
| 621 | Piperidine | N-piperidinyl | 370.2978 |
| 622 | Morpholine | N-morpholinyl | 372.2796 |

-continued
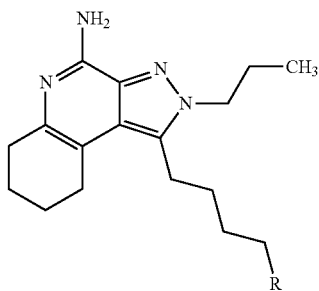
| Example | Reagent | R | Measured Mass (M + H) |
|---|---|---|---|
| 623 | Hexamethyleneimine | | 384.3158 |
| 624 | 3-Hydroxypiperidine | | 386.2952 |
| 625 | 4-Hydroxypiperidine | | 386.2952 |
| 626 | Thiomorpholine | | 388.2558 |
| 627 | 1-Methylpiperazine | | 385.3067 |
| 628 | 3-(Dimethylamino)pyrrolidine | | 399.3262 |
| 629 | N,N-Dimethyl-3-aminopyrrolidine | | 399.3273 |

-continued
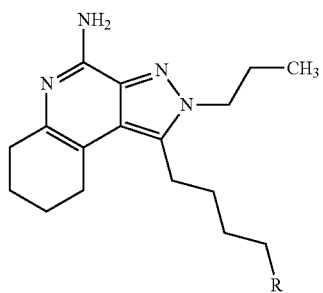
| Example | Reagent | R | Measured Mass (M + H) |
|---|---|---|---|
| 630 | N-Methylhomopiperazine | (N-methylhomopiperazinyl) | 399.3264 |
| 631 | 3-(Hydroxymethyl)piperidine | (3-(hydroxymethyl)piperidinyl) | 400.3107 |
| 632 | Isonipecotamide | (4-carbamoylpiperidinyl) | 413.3041 |
| 633 | Nipecotamide | (3-carbamoylpiperidinyl) | 413.3047 |
| 634 | 1-Acetylpiperazine | (4-acetylpiperazinyl) | 413.3029 |
| 635 | bis(2-Methoxyethyl)amine | (bis(2-methoxyethyl)amino) | 418.3217 |

-continued
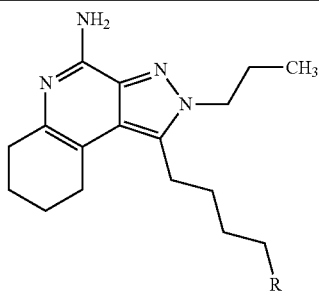
| Example | Reagent | R | Measured Mass (M + H) |
|---|---|---|---|
| 636 | 2-(2-Methylaminoethyl)pyridine | N-methyl-N-(2-(pyridin-2-yl)ethyl)amino | 421.3109 |
| 637 | 1-(2-Methoxyethyl)piperazine | 4-(2-methoxyethyl)piperazin-1-yl (N-methyl) | 429.3309 |
| 638 | 4-(1-Pyrrolidinyl)-piperidine | 4-(pyrrolidin-1-yl)piperidin-1-yl (N-methyl) | 439.3506 |
| 639 | 4-Phenylpiperidine | 4-phenylpiperidin-1-yl (N-methyl) | 446.3255 |
| 640 | 1-(2-Pyridyl)piperazine | 4-(pyridin-2-yl)piperazin-1-yl (N-methyl) | 448.3183 |

-continued

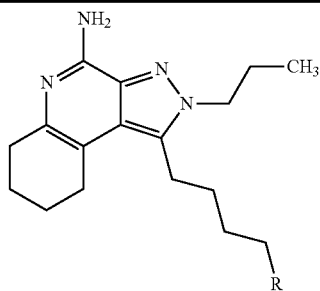

| Example | Reagent | R | Measured Mass (M + H) |
|---|---|---|---|
| 641 | 1-(4-Pyridyl)-piperazine | 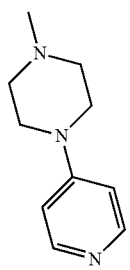 | 448.3232 |
| 642 | 1-(2-Pyrimidyl)piperazine | 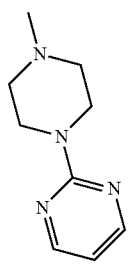 | 449.3107 |
| 643 | 4-Chlorophenol | 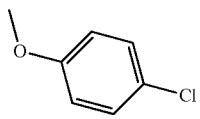 | 413.2120 |

Examples 644-700

Part A

A mixture of 1-(4-chlorobutyl)-2-ethyl-2H-pyrazolo[3,4-c]quinolin-4-amine (3 g, prepared as described in Example 19), platinum (IV) oxide (3 g), and trifluoroacetic acid (50 mL) was placed under hydrogen pressure (50 psi, $3.4 \times 10^5$ Pa) on a Parr shaker for 2 days. The reaction mixture was filtered through a layer of CELITE filter agent and the filter cake was rinsed with dichloromethane. The filtrate was concentrated under reduced pressure. The residue was made basic (pH 14) by the addition of 50% sodium hydroxide and then extracted with chloroform. The extract was dried over sodium sulfate and then purified by chromatography on a HORIZON HPFC system (eluting with chloroform/CMA in a gradient from 100:0 to 70:30) to provide 1.75 g of 1-(4-chlorobutyl)-2-ethyl-6,7,8,9-tetrahydro-2H-pyrazolo[3,4-c]quinolin-4-amine as a light yellow solid.

Part B

A reagent (0.15 mmol, 1.5 equivalents) from the table below was added to a test tube containing 1-(4-chlorobutyl)-2-ethyl-6,7,8,9-tetrahydro-2H-pyrazolo[3,4-c]quinolin-4-amine (31 mg, 0.10 mmol) and potassium carbonate (approximately 55 mg, 0.40 mmol) in N,N-dimethylacetamide (1 mL). The test tubes were capped and heated at 70° C. for approximately 17 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

US 9,145,410 B2

| Example | Reagent | R | Measured Mass (M + H) |
|---|---|---|---|
| 644 | None—starting material | 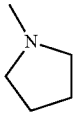 | 307.1694 |
| 645 | Pyrrolidine | 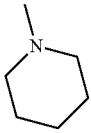 | 342.2682 |
| 646 | Piperidine | 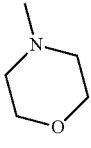 | 356.2845 |
| 647 | Morpholine | 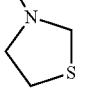 | 358.2638 |
| 648 | Thiazolidine | 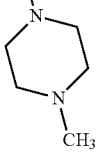 | 360.2237 |
| 649 | 1-Methyl-piperazine | 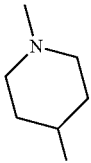 | 371.2937 |
| 650 | 4-Hydroxy-piperidine | 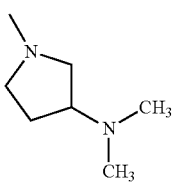 | 372.2795 |
| 651 | 3-(Dimethylamino)pyrrolidine | 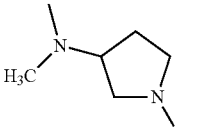 | 385.3103 |

-continued

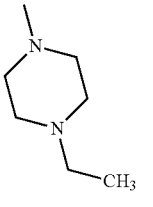

| Example | Reagent | R | Measured Mass (M + H) |
|---|---|---|---|
| 652 | N,N-Dimethyl-3-aminopyrrolidine | 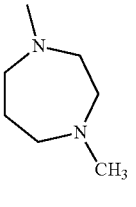 | 385.3098 |
| 653 | N-Ethylpiperazine | 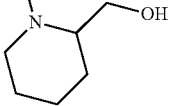 | 385.3092 |
| 654 | N-Methylhomo-piperazine | 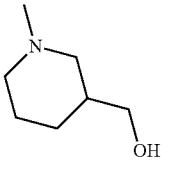 | 385.3118 |
| 655 | 2-Piperidine-methanol | 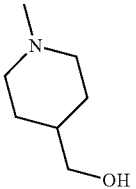 | 386.2896 |
| 656 | 3-(Hydroxymethyl)piperidine | | 386.2888 |
| 657 | 4-(Hydroxymethyl)piperidine | | 386.2893 |

-continued

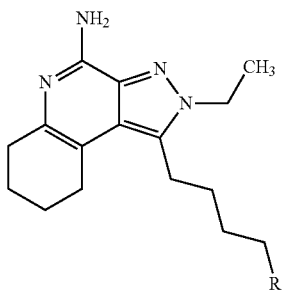

| Example | Reagent | R | Measured Mass (M + H) |
|---|---|---|---|
| 658 | N-Methylbenzylamine | 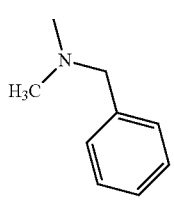 | 392.2845 |
| 659 | Isonipecotamide | 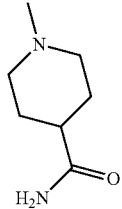 | 399.2902 |
| 660 | Nipecotamide | 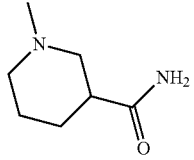 | 399.2894 |
| 661 | (3S)-(−)-3-Acetamido-pyrrolidine | Chiral 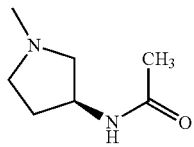 | 399.2876 |
| 662 | 1-Acetyl-piperazine | 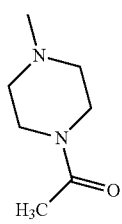 | 399.2906 |
| 663 | 1-Methyl-4-(Methylamino)piperidine | 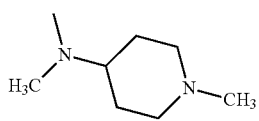 | 399.3218 |

-continued

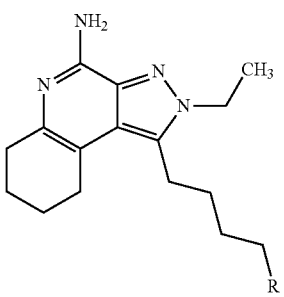

| Example | Reagent | R | Measured Mass (M + H) |
|---|---|---|---|
| 664 | 2-Piperidine-ethanol | 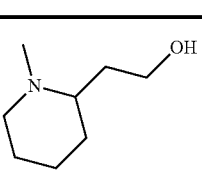 | 400.3098 |
| 665 | 4-Piperidine-ethanol | 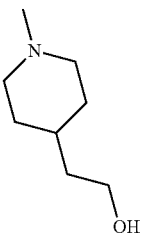 | 400.3116 |
| 666 | N-(2-Hydroxyethyl)piperazine | 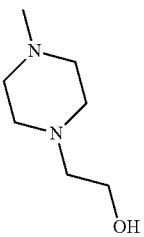 | 401.3050 |
| 667 | 1,2,3,4-Tetrahydro-isoquinoline | 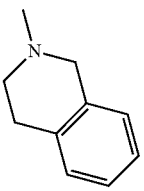 | 404.2845 |
| 668 | (R)-(+)-N-Methyl-1-Phenylethyl-amine | Chiral 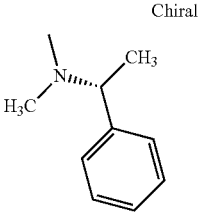 | 406.3002 |

377
-continued
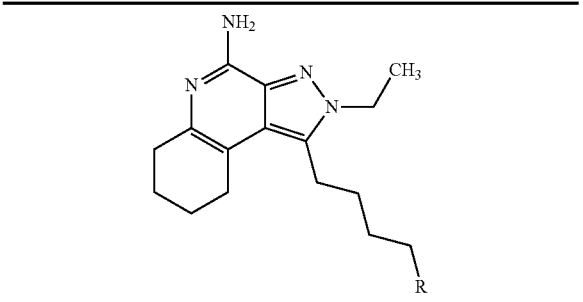
| Example | Reagent | R | Measured Mass (M + H) |
|---|---|---|---|
| 669 | (S)-(−)-N-Methyl-1-Phenylethyl-amine | Chiral 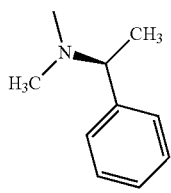 | 406.3007 |
| 670 | 4-(Ethylamino-methyl)pyridine | 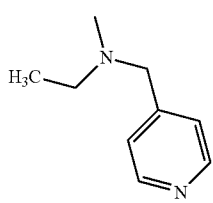 | 407.2958 |
| 671 | 4-(1-Pyrrolidinyl)-piperidine | 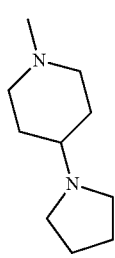 | 425.3405 |
| 672 | 1-(2-Ethoxy-ethyl)piperazine | 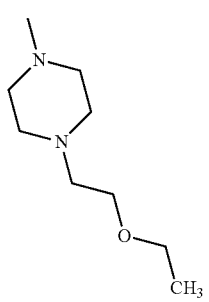 | 429.3372 |
| 673 | 1-Phenyl-piperazine | | 433.3121 |
378
-continued
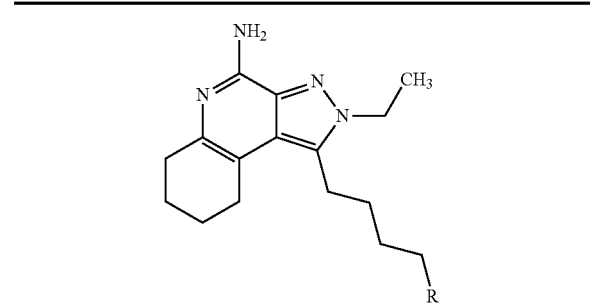
| Example | Reagent | R | Measured Mass (M + H) |
|---|---|---|---|
| 674 | 1-(2-Pyridyl)piperazine | 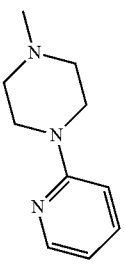 | 434.3068 |
| 675 | 1-(4-Pyridyl)-piperazine | 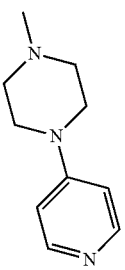 | 434.3066 |
| 676 | 1-(2-Pyrimdyl)piperazine | 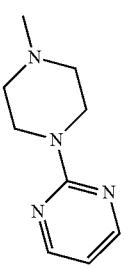 | 435.3006 |
| 677 | 4-Piperidino-piperidine | 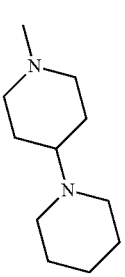 | 439.3589 |

379
-continued
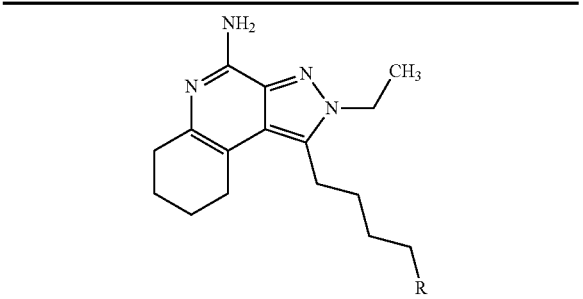
| Example | Reagent | R | Measured Mass (M + H) |
|---|---|---|---|
| 678 | 4-Benzyl-piperidine | 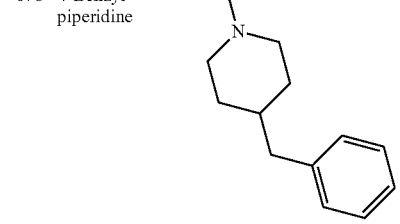 | 446.3323 |
| 679 | 4-Hydroxy-4-phenyl-piperidine | 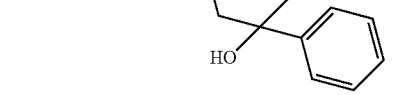 | 448.3083 |
| 680 | 1-(2-Furoyl)piperazine | 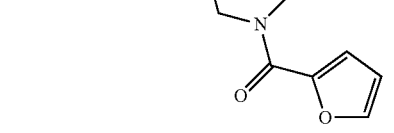 | 451.2848 |
| 681 | Phenol | 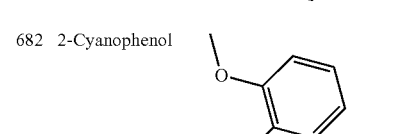 | 365.2370 |
| 682 | 2-Cyanophenol | 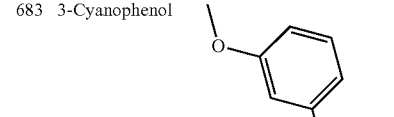 | 390.2276 |
| 683 | 3-Cyanophenol | | 390.2332 |
380
-continued
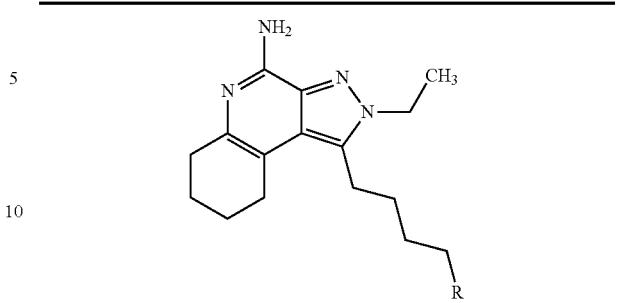
| Example | Reagent | R | Measured Mass (M + H) |
|---|---|---|---|
| 684 | 4-Cyanophenol | 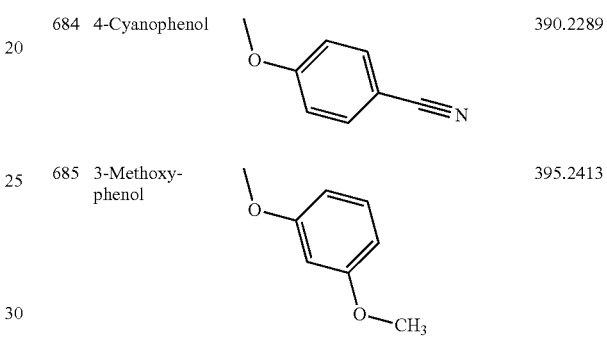 | 390.2289 |
| 685 | 3-Methoxyphenol | | 395.2413 |
| 686 | 4-Methoxyphenol | | 395.2477 |
| 687 | Guaiacol | | 395.2485 |
| 688 | 2-Chlorophenol |  | 399.1955 |
| 689 | 3-Chlorophenol | 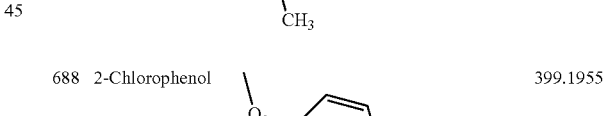 | 399.1946 |
| 690 | 4-Chlorophenol | 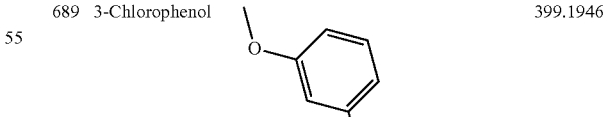 | 399.1913 |

-continued

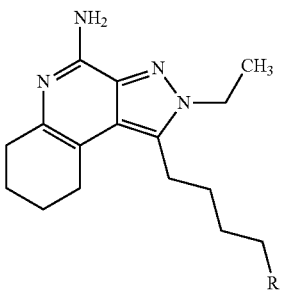

| Example | Reagent | R | Measured Mass (M + H) |
|---|---|---|---|
| 691 | 4-Hydroxy-benzamide | | 408.2427 |
| 692 | Salicylamide | | 408.2430 |
| 693 | 2-Acetamido-phenol | | 422.2584 |
| 694 | 3-Acetamido-phenol | | 422.2597 |
| 695 | 4-Hydroxy-phenyl-acetamide | | 422.2587 |
| 696 | Acetaminophen | | 422.2594 |

-continued

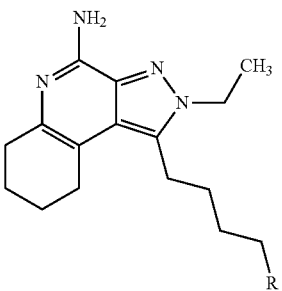

| Example | Reagent | R | Measured Mass (M + H) |
|---|---|---|---|
| 697 | Dimethylamino-methylphenol | | 422.2943 |
| 698 | 4-Dimethylamino-methylphenol | | 422.2960 |
| 699 | 3,4-Dichloro-phenol | | 433.1546 |
| 700 | 4-Hydroxy-benzene-sulfonamide | | 444.2099 |

Examples 701-775

A reagent (0.15 mmol, 1.5 equivalents) from the table below was added to a test tube containing 1-(4-chlorobutyl)-2-propyl-2H-pyrazolo[3,4-c]quinoline-4-amine (32 mg, 0.10 mmol, prepared as described in Example 46) and potassium carbonate (approximately 55 mg, 0.40 mmol) in N,N-dimethylacetamide (1 mL). The test tubes were capped and heated at 85° C. for approximately 18 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 701 | None—starting material | Cl | 317.1542 |
| 702 | 2-(Methylamino)ethanol | N(CH3)CH2CH2OH | 356.2476 |
| 703 | Piperidine | piperidinyl | 366.2679 |
| 704 | (R)-3-Hydroxypyrrolidine | (R)-3-hydroxypyrrolidinyl (Chiral) | 368.2467 |
| 705 | Morpholine | morpholinyl | 368.2443 |
| 706 | 2-Ethylaminoethanol | N(Et)CH2CH2OH | 370.2610 |
| 707 | 1-Methylpiperazine | 4-methylpiperazinyl | 381.2777 |
| 708 | 4-Hydroxypiperidine | 4-hydroxypiperidinyl | 382.2585 |
| 709 | 3-Hydroxypiperidine | 3-hydroxypiperidinyl | 382.2575 |
| 710 | Thiomorpholine | thiomorpholinyl | 384.2242 |
| 711 | N-Methylfurfurylamine | N(CH3)CH2-furan | 392.2450 |
| 712 | N-Methylcyclohexylamine | N(CH3)-cyclohexyl | 394.2995 |
| 713 | N-Propylcyclopropanemethylamine | N(Pr)CH2-cyclopropyl | 394.3004 |
| 714 | N,N'-Dimethyl-3-aminopyrrolidine | 3-(N,N-dimethylamino)-1-methylpyrrolidinyl | 395.2964 |
| 715 | N-Ethylpiperazine | 4-ethylpiperazinyl | 395.2957 |

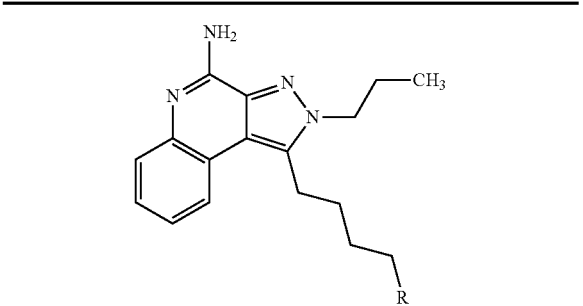
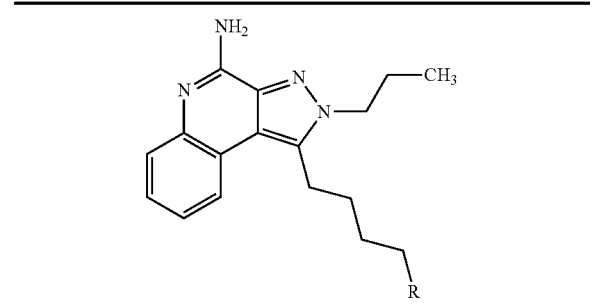
| Example | Reagent | R | Measured Mass (M + H) |
|---|---|---|---|
| 716 | N-Methyl-homopiperazine | | 395.2915 |
| 717 | 2,6-Dimethyl-morpholine | | 396.2796 |
| 718 | 3-(Hydroxymethyl)piperidine | | 396.2732 |
| 719 | 4-(Hydroxymethyl)piperidine | | 396.2764 |
| 720 | N-Ethylaniline | | 402.2686 |
| 721 | N-Methyl-benzylamine | | 402.2680 |
| 722 | 1-Acetylpiperazine | | 409.2697 |
| 723 | Isonipecotamide | | 409.2709 |
| 724 | Nipecotamide | | 409.2695 |
| 725 | 1-Methyl-4-(methylamino)piperidine | | 409.3067 |
| 726 | 2-Piperidineethanol | | 410.2938 |
| 727 | 4-Piperidineethanol | | 410.2953 |

387
-continued

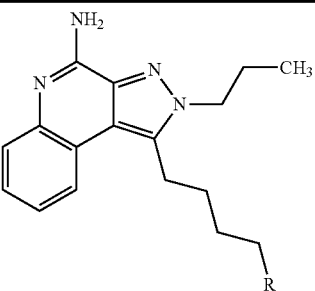

| Example | Reagent | R | Measured Mass (M + H) |
|---|---|---|---|
| 728 | N-(2-Hydroxyethyl)piperazine | 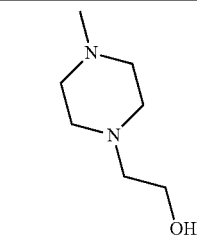 | 411.2862 |
| 729 | N-Methyl-phenethylamine | 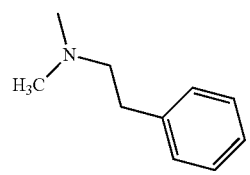 | 416.2831 |
| 730 | 2-(2-Methylaminoethyl)pyridine | 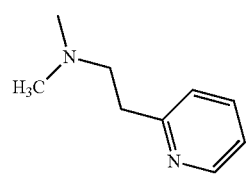 | 417.2759 |
| 731 | 4-(Ethylaminomethyl)pyridine | 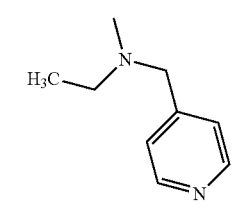 | 417.2796 |
| 732 | 2-Amino-1-phenylethanol | 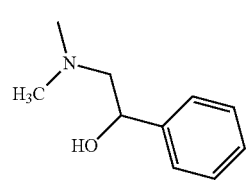 | 432.2751 |
| 733 | 1-(2-Ethoxyethyl)piperazine | 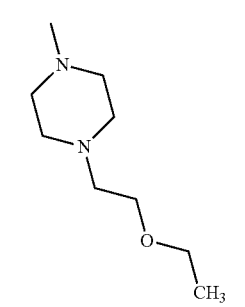 | 439.3194 |

388
-continued

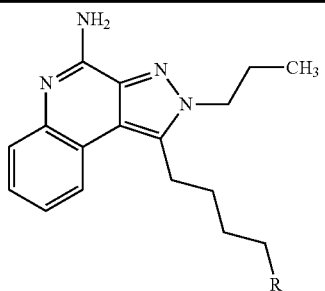

| Example | Reagent | R | Measured Mass (M + H) |
|---|---|---|---|
| 734 | 1-Phenylpiperazine | 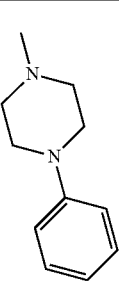 | 443.2926 |
| 735 | 1-(2-Pyridyl)piperazine | 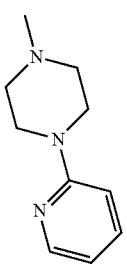 | 444.2854 |
| 736 | 4-Piperidino-piperidine | 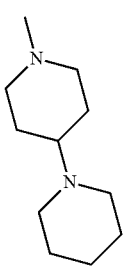 | 449.3390 |
| 737 | 4-Benzylpiperidine | 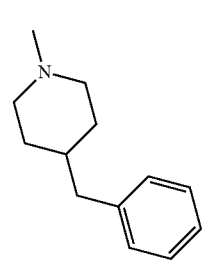 | 456.3132 |
| 738 | 4-Hydroxy-4-phenylpiperidine | 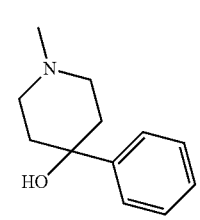 | 458.2898 |

389

-continued

[Structure: 4-amino-2-propyl-1-(R-butyl)-2H-pyrazolo[3,4-c]quinoline]

| Example | Reagent | R | Measured Mass (M + H) |
|---|---|---|---|
| 739 | 1-(2-Furoyl)piperazine | N-methylpiperazine with 2-furoyl carbonyl | 461.2658 |
| 740 | N-Isopropyl-1-piperazine-acetamide | N-methylpiperazine-CH₂-C(O)-NH-iPr | 466.3321 |
| 741 | Dibenzylamine | N(CH₂Ph)₂ with methyl | 478.3015 |
| 742 | 2,2'-Dipicolylamine | N(CH₂-2-pyridyl)₂ with methyl | 480.2880 |
| 743 | Phenol | OPh | 375.2155 |
| 744 | m-Cresol | O-(3-methylphenyl) | 389.2325 |

390

-continued

[Structure: 4-amino-2-propyl-1-(R-butyl)-2H-pyrazolo[3,4-c]quinoline]

| Example | Reagent | R | Measured Mass (M + H) |
|---|---|---|---|
| 745 | o-Cresol | O-(2-methylphenyl) | 389.2318 |
| 746 | p-Cresol | O-(4-methylphenyl) | 389.2358 |
| 747 | 2-Fluorophenol | O-(2-fluorophenyl) | 393.2096 |
| 748 | 3-Fluorophenol | O-(3-fluorophenyl) | 393.2087 |
| 749 | 4-Fluorophenol | O-(4-fluorophenyl) | 393.2070 |
| 750 | 2-Cyanophenol | O-(2-cyanophenyl) | 400.2164 |
| 751 | 3-Cyanophenol | O-(3-cyanophenyl) | 400.2127 |
| 752 | 4-Cyanophenol | O-(4-cyanophenyl) | 400.2151 |

391
-continued

[Structure: 4-amino-2-propyl-1-(4-R-butyl)-2H-pyrazolo[3,4-c]quinoline]

| Example | Reagent | R | Measured Mass (M + H) |
|---|---|---|---|
| 753 | 2,4-Dimethylphenol | 4-methoxy-2,5-dimethylphenoxy (OMe, 2-CH₃, 5-CH₃ substituted phenyl ether) | 403.2482 |
| 754 | 3,4-Dimethylphenol | 4-methoxy-2,3-dimethylphenoxy | 403.2458 |
| 755 | 3-Methoxyphenol | 3,5-dimethoxyphenoxy | 405.2332 |
| 756 | 2-Methoxyphenol | 2,3-dimethoxyphenoxy | 405.2296 |
| 757 | 4-Methoxyphenol | 2,5-dimethoxyphenoxy | 405.2310 |
| 758 | 2-Chlorophenol | 2-methoxy-3-chlorophenoxy | 409.1817 |
| 759 | 3-Chlorophenol | 3-methoxy-5-chlorophenoxy | 409.1787 |

392
-continued

[Structure: 4-amino-2-propyl-1-(4-R-butyl)-2H-pyrazolo[3,4-c]quinoline]

| Example | Reagent | R | Measured Mass (M + H) |
|---|---|---|---|
| 760 | 4-Chlorophenol | 2-methoxy-5-chlorophenoxy | 409.1805 |
| 761 | 4-Hydroxybenzamide | 4-carbamoyl-2-methoxyphenoxy | 418.2222 |
| 762 | Salicylamide | 3-carbamoyl-2-methoxyphenoxy | 418.2272 |
| 763 | 3-Dimethyl-aminophenol | 3-(dimethylamino)-5-methoxyphenoxy | 418.2630 |
| 764 | 3-tert-Butylphenol | 3-tert-butyl-5-methoxyphenoxy | 431.2794 |
| 765 | 4-Hydroxy-phenylacetamide | 4-(carbamoylmethyl)-2-methoxyphenoxy | 432.2422 |
| 766 | 4-Acetamidophenol | 4-acetamido-2-methoxyphenoxy | 432.2377 |

-continued

| Example | Reagent | R | Measured Mass (M + H) |
|---|---|---|---|
| 767 | 2-Acetamidophenol | 2-methoxy-phenyl with NHC(O)CH3 | 432.2415 |
| 768 | 3-Acetamidophenol | 3-methoxy-phenyl with NHC(O)CH3 | 432.2396 |
| 769 | 2-Dimethyl-aminomethylphenol | 2-methoxy-phenyl with CH2N(CH3)2 | 432.2734 |
| 770 | 3-Hydroxy-benzotrifluoride | 3-methoxy-phenyl with CF3 | 443.2042 |
| 771 | 4-Hydroxy benzotrifluoride | 4-methoxy-phenyl with CF3 | 443.2050 |
| 772 | 2,3-Dichlorophenol | 2-methoxy-3-chlorophenyl with Cl | 443.1438 |

-continued

| Example | Reagent | R | Measured Mass (M + H) |
|---|---|---|---|
| 773 | 2,4-Dichlorophenol | 2-methoxy-4-chlorophenyl with Cl | 443.1372 |
| 774 | 2,5-Dichlorophenol | 2-methoxy-5-chlorophenyl with Cl | 443.1427 |
| 775 | 3,4-Dichlorophenol | 3-methoxy-4-chlorophenyl with Cl | 443.1422 |

Examples 776-799

Part A

Platinum (IV) oxide (4 g) was added to a solution of 1-(4-aminobutyl)-2-ethyl-2H-pyrazolo[3,4-c]quinolin-4-amine (approximately 24 mmol, prepared as described in Part A of Examples 349-453) in trifluoroacetic acid (80 mL), and the mixture was shaken under hydrogen pressure (50 psi, 3.4×10$^5$ Pa) for two days and subsequently filtered through a layer of CELITE filter agent. The filter cake was washed with methanol, and the filtrate was concentrated under reduced pressure. Water (10 mL) was added, and the resulting solution was adjusted to pH 14 with the addition of 50% aqueous sodium hydroxide. The resulting mixture was extracted with dichloromethane, and the extracts were dried over sodium sulfate, filtered, and concentrated under reduced pressure to provide 1-(4-aminobutyl)-2-ethyl-6,7,8,9-tetrahydro-2H-pyrazolo[3,4-c]quinolin-4-amine.

Part B

A reagent (0.048 mmol, 1.1 equivalents) from the table below was added to a test tube containing 1-(4-aminobutyl)-2-ethyl-6,7,8,9-tetrahydro-2H-pyrazolo[3,4-c]quinolin-4-amine (12.5 mg, 0.044 mmol) and N,N-diisopropylethylamine (approximately 15 µL, 2 equivalents) in chloroform (1 mL). The test tubes were capped and shaken for four hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

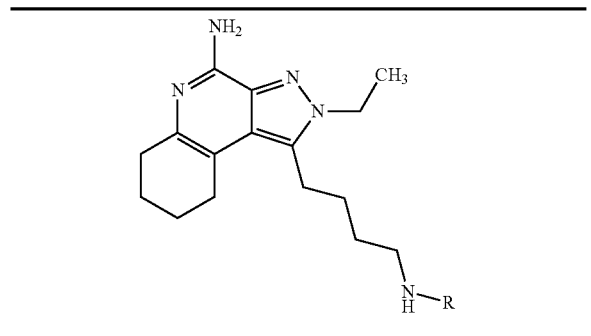

| Example | Reagent | R | Measured Mass (M + H) |
|---|---|---|---|
| 776 | Acetyl chloride | –C(=O)CH₃ | 330.2275 |
| 777 | Cyclopropane-carbonyl chloride | –C(=O)-cyclopropyl | 356.2417 |
| 778 | Isobutyryl chloride | –C(=O)CH(CH₃)₂ | 358.2600 |
| 779 | Cyclopentane-carbonyl chloride | –C(=O)-cyclopentyl | 384.2771 |
| 780 | Cyclohexane-carbonyl chloride | –C(=O)-cyclohexyl | 398.2882 |
| 781 | Phenylacetyl chloride | –C(=O)CH₂Ph | 406.2586 |
| 782 | 3-(Trifluoromethyl)-benzoyl chloride | –C(=O)-C₆H₄-CF₃ | 460.2296 |

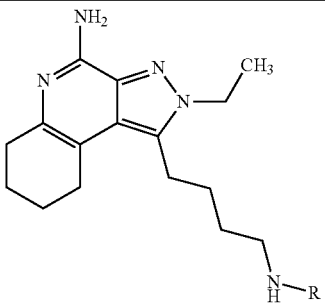

| Example | Reagent | R | Measured Mass (M + H) |
|---|---|---|---|
| 783 | 1-Propanesulfonyl chloride | –S(O)₂CH₂CH₂CH₃ | 394.2255 |
| 784 | Isopropylsulfonyl chloride | –S(O)₂CH(CH₃)₂ | 394.2260 |
| 785 | 1-Butanesulfonyl chloride | –S(O)₂(CH₂)₃CH₃ | 408.2441 |
| 786 | Trifluoro-methanesulfonyl chloride | –S(O)₂CF₃ | 420.1678 |
| 787 | Benzenesulfonyl chloride | –S(O)₂Ph | 428.2078 |
| 788 | 2,2,2-Trifluoroethane-sulfonyl chloride | –S(O)₂CH₂CF₃ | 434.1819 |
| 789 | alpha-Toluene-sulfonyl chloride | –S(O)₂CH₂Ph | 442.2266 |

397
-continued

| Example | Reagent | R | Measured Mass (M + H) |
|---|---|---|---|
| 790 | Ethyl isocyanate | -C(O)NH-CH2CH3 | 359.2540 |
| 791 | Isopropyl isocyanate | -C(O)NH-CH(CH3)2 | 373.2689 |
| 792 | N-Propyl isocyanate | -C(O)NH-CH2CH2CH3 | 373.2713 |
| 793 | N-Butyl isocyanate | -C(O)NH-(CH2)3CH3 | 387.2856 |
| 794 | Cyclopentyl isocyanate | -C(O)NH-cyclopentyl | 399.2846 |
| 795 | Phenyl isocyanate | -C(O)NH-phenyl | 407.2519 |
| 796 | Cyclohexyl isocyanate | -C(O)NH-cyclohexyl | 413.3038 |

398
-continued

| Example | Reagent | R | Measured Mass (M + H) |
|---|---|---|---|
| 797 | p-Tolyl isocyanate | -C(O)NH-(4-methylphenyl) | 421.2720 |
| 798 | 3-Methoxyphenyl isocyanate | -C(O)NH-(3-methoxyphenyl) | 437.2661 |
| 799 | 3-Chlorophenyl isocyanate | -C(O)NH-(3-chlorophenyl) | 441.2194 |

Examples 800-819

A reagent (0.11 mmol, 1.1 equivalents) from the table below was added to a test tube containing 1-butyl-2H-pyrazolo[3,4-c]quinolin-4-amine hydrochloride (27.6 mg, 0.10 mmol, prepared as described in Part A of Examples 579-581) and potassium carbonate (55 mg, 0.40 mmol) in DMF (1 mL). The test tubes were capped and shaken overnight at ambient temperature. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

399

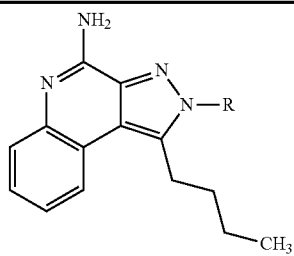

| Example | Reagent | R | Measured Mass (M + H) |
|---|---|---|---|
| 800 | None—starting material | —H | 241.1441 |
| 801 | 1-Bromopentane | -CH2CH2CH2CH2CH3 | 311.2222 |
| 802 | 2-Iodoethanol | -CH2CH2OH | 285.1711 |
| 803 | 1-Iodobutane | -CH2CH2CH2CH3 | 297.2054 |
| 804 | 2-Iodobutane | -CH(CH3)CH2CH3 | 297.2053 |
| 805 | 1-(3-Bromopropyl)pyrrole | -(CH2)3-pyrrole | 348.2174 |
| 806 | 2-Cyclohexylethyl bromide | -CH2CH2-cyclohexyl | 351.2527 |
| 807 | 2-Cyanobenzyl bromide | -CH2-(2-CN-C6H4) | 356.1855 |
| 808 | 2-Bromo-acetophenone | -CH2C(O)C6H5 | 359.1871 |
| 809 | 1-Bromo-3-Phenylpropane | -(CH2)3C6H5 | 359.2220 |
| 810 | 3-Chlorobenzyl bromide | -CH2-(3-Cl-C6H4) | 365.1521 |

400

-continued

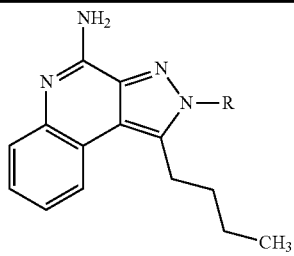

| Example | Reagent | R | Measured Mass (M + H) |
|---|---|---|---|
| 811 | 4-Chlorobenzyl bromide | -CH2-(4-Cl-C6H4) | 365.1548 |
| 812 | 2,6-Difluorobenzyl bromide | -CH2-(2,6-F2-C6H3) | 367.1742 |
| 813 | 2-Bromo-4'-methyl-acetophenone | -CH2C(O)-(4-CH3-C6H4) | 373.1996 |
| 814 | 2-Bromo-4'-fluoro-acetophenone | -CH2C(O)-(4-F-C6H4) | 377.1789 |
| 815 | 4-Cyanophenacyl bromide | -CH2C(O)-(4-CN-C6H4) | 384.1801 |
| 816 | 2-Bromo-3'-Methoxy-acetophenone | -CH2C(O)-(3-OCH3-C6H4) | 389.2006 |
| 817 | 2-Bromo-4'-Methoxy-acetophenone | -CH2C(O)-(4-OCH3-C6H4) | 389.1953 |
| 818 | 2,6-Dichlorobenzyl bromide | -CH2-(2,6-Cl2-C6H3) | 399.1115 |
| 819 | 3,4-Dichlorobenzyl bromide | -CH2-(3,4-Cl2-C6H3) | 399.1170 |

Examples 820-904

A reagent (0.11 mmol, 1.1 equivalents) from the table below was added to a test tube containing 1-(2-aminoethyl)-

401

2-propyl-2H-pyrazolo[3,4-c]quinolin-4-amine dihydrochloride (34 mg, 0.098 mmol, prepared as described in Parts A through H of Example 51) and N,N-diisopropylethylamine (approximately 70 μL, 4 equivalents) in chloroform (1 mL). The test tubes were capped and shaken for six hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

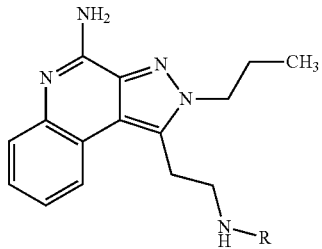

| Example | Reagent | R | Measured Mass (M + H) |
|---|---|---|---|
| 820 | None - starting material | H | 270.1707 |
| 821 | Acetyl chloride | | 312.1855 |
| 822 | Propionyl chloride | | 326.1965 |
| 823 | Cyclopropanecarbonyl chloride | | 338.1994 |
| 824 | Butyryl chloride | | 340.2110 |
| 825 | Methoxyacetyl chloride | | 342.1953 |
| 826 | Pivaloyl chloride | | 354.2304 |
| 827 | Benzoyl chloride | | 374.1986 |
| 828 | Cyclopentylacetyl chloride | | 380.2487 |
| 829 | Cyclohexanecarbonyl chloride | | 380.2419 |
| 830 | m-Toluoyl chloride | | 388.2146 |
| 831 | Phenylacetyl chloride | | 388.2168 |
| 832 | 3-Fluorobenzoyl chloride | | 392.1925 |
| 833 | 4-Fluorobenzoyl chloride | | 392.1896 |

-continued

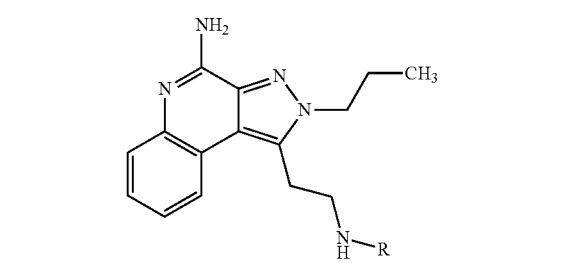

| Example | Reagent | R | Measured Mass (M + H) |
|---|---|---|---|
| 834 | 4-Cyanobenzoyl chloride | 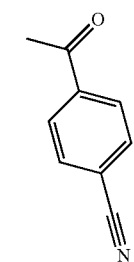 | 399.1963 |
| 835 | Hydrocinnamoyl chloride | 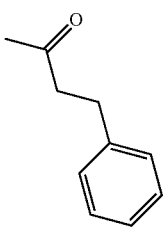 | 402.2307 |
| 836 | 3-Methoxybenzoyl chloride | 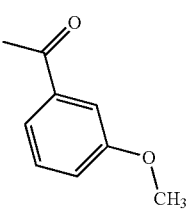 | 404.2108 |
| 837 | p-Anisoyl chloride | 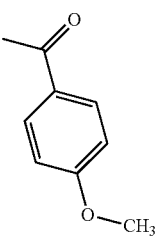 | 404.2093 |
| 838 | 3-Chlorobenzoyl chloride | 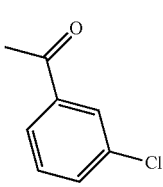 | 408.1565 |

-continued

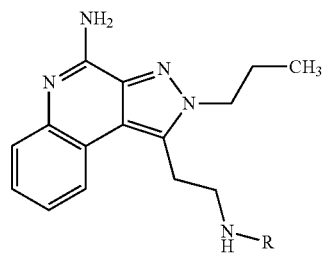

| Example | Reagent | R | Measured Mass (M + H) |
|---|---|---|---|
| 839 | 4-Chlorobenzoyl chloride | 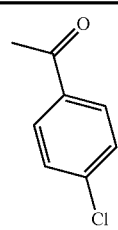 | 408.1616 |
| 840 | Isonicotinoyl chloride hydrochloride | 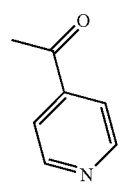 | 375.1937 |
| 841 | Nicotinoyl chloride hydrochloride | 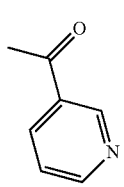 | 375.1913 |
| 842 | Picolinoyl chloride hydrochloride | 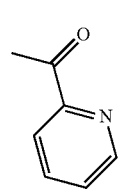 | 375.1948 |
| 843 | trans-2-Phenyl-1-cyclopropane-carbonyl chloride |  | 414.2304 |
| 844 | 3-Dimethyl-aminobenzoyl chloride | 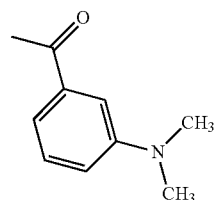 | 417.2423 |

-continued

[Structure: pyrazoloquinoline core with NH2, N-propyl, and CH2CH2-NH-R substituent]

| Example | Reagent | R | Measured Mass (M + H) |
|---|---|---|---|
| 845 | 4-Chloro-phenylacetyl chloride | (4-chlorophenyl)acetyl group | 422.1747 |
| 846 | 3-(Trifluoromethyl)benzoyl chloride | 3-(trifluoromethyl)benzoyl group | 442.1840 |
| 847 | 3,4-Dichlorobenzoyl chloride | 3,4-dichlorobenzoyl group | 442.1196 |
| 848 | 4-(Trifluoromethoxy)benzoyl chloride | 4-(trifluoromethoxy)benzoyl group | 458.1784 |
| 849 | Methanesulfonyl chloride | methanesulfonyl group | 348.1522 |
| 850 | Ethanesulfonyl chloride | ethanesulfonyl group | 362.1672 |
| 851 | 1-Propane-sulfonyl chloride | propanesulfonyl group | 376.1812 |

-continued

[Structure: pyrazoloquinoline core with NH2, N-propyl, and CH2CH2-NH-R substituent]

| Example | Reagent | R | Measured Mass (M + H) |
|---|---|---|---|
| 852 | Isopropyl-sulfonyl chloride | isopropylsulfonyl group | 376.1808 |
| 853 | Dimethyl-sulfamoyl chloride | dimethylsulfamoyl group | 377.1767 |
| 854 | 1-Butanesulfonyl chloride | butanesulfonyl group | 390.2003 |
| 855 | Trifluoro-methanesulfonyl chloride | trifluoromethanesulfonyl group | 402.1206 |
| 856 | Benzenesulfonyl chloride | phenylsulfonyl group | 410.1689 |
| 857 | 1-Methylimidazole-4-sulfonyl chloride | 1-methylimidazole-4-sulfonyl group | 414.1732 |
| 858 | 2,2,2-Trifluoro-methanesulfonyl chloride | 2,2,2-trifluoroethylsulfonyl group | 416.1376 |

407

-continued

| Example | Reagent | R | Measured Mass (M + H) |
|---|---|---|---|
| 859 | 2-Thiophenesulfonyl chloride | (methylsulfonyl-thiophene) | 416.1233 |
| 860 | alpha-Toluenesulfonyl chloride | (methylsulfonyl-benzyl) | 424.1842 |
| 861 | 3-Fluoro-benzenesulfonyl chloride | (3-fluorophenyl sulfonyl) | 428.1556 |
| 862 | 4-Fluoro-benzenesulfonyl chloride | (4-fluorophenyl sulfonyl) | 428.1568 |
| 863 | 3-Cyano-benzenesulfonyl chloride | (3-cyanophenyl sulfonyl) | 435.1585 |

408

-continued

| Example | Reagent | R | Measured Mass (M + H) |
|---|---|---|---|
| 864 | 4-Cyano-benzenesulfonyl chloride | (4-cyanophenyl sulfonyl) | 435.1617 |
| 865 | 3-Methoxy-benzenesulfonyl chloride | (3-methoxyphenyl sulfonyl) | 440.1798 |
| 866 | 4-Methoxy-benzenesulfonyl chloride | (4-methoxyphenyl sulfonyl) | 440.1721 |
| 867 | 2-Chloro-benzenesulfonyl chloride | (2-chlorophenyl sulfonyl) | 444.1277 |
| 868 | 3-Chloro-benzenesulfonyl chloride | (3-chlorophenyl sulfonyl) | 444.1272 |

409
-continued

| Example | Reagent | R | Measured Mass (M + H) |
|---|---|---|---|
| 869 | 4-Chloro-benzenesulfonyl chloride | methylsulfonyl-4-chlorophenyl | 444.1278 |
| 870 | 3-(Trifluoromethyl)benzenesulfonyl chloride | methylsulfonyl-3-trifluoromethylphenyl | 478.1482 |
| 871 | 4-(Trifluoromethyl)benzenesulfonyl chloride | methylsulfonyl-4-trifluoromethylphenyl | 478.1519 |
| 872 | 2,4-Dichloro-benzenesulfonyl chloride | methylsulfonyl-2,4-dichlorophenyl | 478.0887 |
| 873 | 2,6-Dichloro-benzenesulfonyl chloride | methylsulfonyl-2,6-dichlorophenyl | 478.0858 |

410
-continued

| Example | Reagent | R | Measured Mass (M + H) |
|---|---|---|---|
| 874 | 3,4-Dichloro-benzenesulfonyl chloride | methylsulfonyl-3,4-dichlorophenyl | 478.0838 |
| 875 | 3,5-Dichloro-benzenesulfonyl chloride | methylsulfonyl-3,5-dichlorophenyl | 478.0890 |
| 876 | Methyl isocyanate | C(=O)NHCH₃ | 327.1915 |
| 877 | Ethyl isocyanate | C(=O)NHCH₂CH₃ | 341.2110 |
| 878 | Isopropyl isocyanate | C(=O)NHCH(CH₃)₂ | 355.2263 |
| 879 | Cyclopropyl isothiocyanate | C(=S)NH-cyclopropyl | 369.1870 |
| 880 | Pentyl isocyanate | C(=O)NH-pentyl | 383.2596 |

-continued

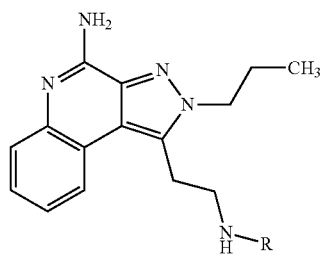

| Example | Reagent | R | Measured Mass (M + H) |
|---|---|---|---|
| 881 | Isobutyl isothiocyanate | —C(=S)NH—CH₂CH(CH₃)₂ | 385.2207 |
| 882 | Phenyl isocyanate | —C(=O)NH-phenyl | 389.2116 |
| 883 | Cyclohexyl isocyanate | —C(=O)NH-cyclohexyl | 395.2597 |
| 884 | Benzyl isocyanate | —C(=O)NH-benzyl | 403.2283 |
| 885 | m-Tolyl isocyanate | —C(=O)NH-(3-methylphenyl) | 403.2268 |
| 886 | o-Tolyl isocyanate | —C(=O)NH-(2-methylphenyl) | 403.2238 |

-continued

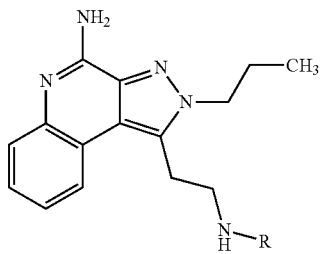

| Example | Reagent | R | Measured Mass (M + H) |
|---|---|---|---|
| 887 | Phenyl isothiocyanate | —C(=S)NH-phenyl | 405.1867 |
| 888 | 3-Pyridyl isothiocyanate | —C(=S)NH-(3-pyridyl) | 406.1828 |
| 889 | 2-Phenethyl isocyanate | —C(=O)NH-CH₂CH₂-phenyl | 417.2416 |
| 890 | 2-Methoxyphenyl isocyanate | —C(=O)NH-(2-methoxyphenyl) | 419.2187 |
| 891 | 3-Methoxyphenyl isocyanate | —C(=O)NH-(3-methoxyphenyl) | 419.2167 |
| 892 | 2-Chlorophenyl isocyanate | —C(=O)NH-(2-chlorophenyl) | 423.1716 |

413
-continued

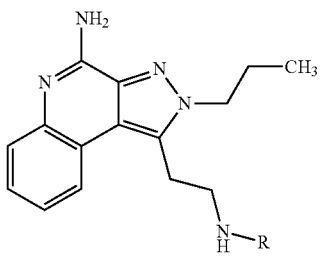

| Example | Reagent | R | Measured Mass (M + H) |
|---|---|---|---|
| 893 | 3-Chlorophenyl isocyanate | 3-chlorophenyl urea-acetyl | 423.1736 |
| 894 | 4-Chlorophenyl isocyanate | 4-chlorophenyl urea-acetyl | 423.1716 |
| 895 | 3,4-Difluorophenyl isocyanate | 3,4-difluorophenyl urea-acetyl | 425.1877 |
| 896 | trans-2-Phenyl-cyclopropyl isocyanate | trans-2-phenylcyclopropyl urea-acetyl | 429.2428 |
| 897 | 3-Carbomethoxyphenyl isocyanate | 3-carbomethoxyphenyl urea-acetyl | 447.2178 |
| 898 | 3,4-Dimethoxy-phenyl isocyanate | 3,4-dimethoxyphenyl urea-acetyl | 449.2318 |

414
-continued

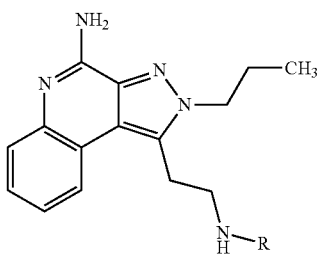

| Example | Reagent | R | Measured Mass (M + H) |
|---|---|---|---|
| 899 | 3,5-Dimethoxyl-phenyl isocyanate | 3,5-dimethoxyphenyl urea-acetyl | 449.2270 |
| 900 | 2-(Trifluoro-methoxy)phenyl isocyanate | 2-(trifluoromethoxy)phenyl urea-acetyl | 473.1876 |
| 901 | N,N-Dimethyl-carbamoyl chloride | N,N-dimethyl urea-acetyl | 341.2104 |
| 902 | 2-Oxo-1-imidazolidine-carbonyl chloride | 2-oxoimidazolidinyl-acetyl | 382.1967 |
| 903 | 4-Methyl-1-piperazine-carbonyl chloride | 4-methylpiperazinyl-acetyl | 396.2530 |
| 904 | N-Methyl-N-Phenyl-carbamoyl chloride | N-methyl-N-phenyl urea-acetyl | 403.2245 |

Examples 905-941

A reagent (0.15 mmol, 1.5 equivalents) from the table below was added to a test tube containing 1-(4-chlorobutyl)-2-ethyl-2H-pyrazolo[3,4-c]quinoline-4-amine (31 mg, 0.10 mmol, prepared as described in Example 19) and potassium carbonate (approximately 55 mg, 0.40 mmol) in DMF (1 mL). The test tubes were capped and heated at 50° C. for approximately 18 hours and then at 85° C. for 5 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

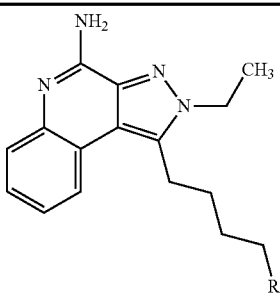

| Example | Reagent | R | Measured Mass (M + H) |
|---|---|---|---|
| 905 | None—starting material | 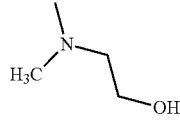 | 303.1352 |
| 906 | 2-(Methylamino)ethanol | 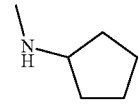 | 342.2295 |
| 907 | Cyclopentylamine | 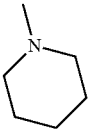 | 352.2509 |
| 908 | Piperidine | 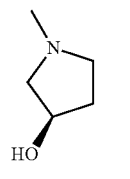 | 352.2497 |
| 909 | (R)-3-Hydroxypyrrolidine | Chiral 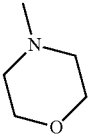 | 354.2297 |
| 910 | Morpholine | 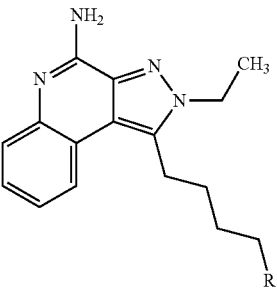 | 354.2301 |

-continued

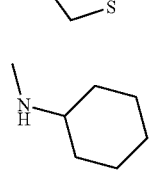

| Example | Reagent | R | Measured Mass (M + H) |
|---|---|---|---|
| 911 | Thiazolidine | 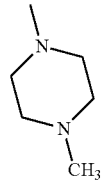 | 356.1942 |
| 912 | Cyclohexylamine | 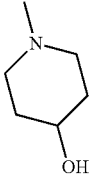 | 366.2661 |
| 913 | 1-Methylpiperazine | 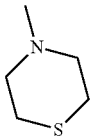 | 367.2617 |
| 914 | 4-Hydroxypiperidine | 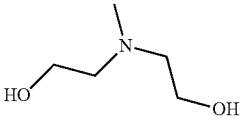 | 368.2452 |
| 915 | Thiomorpholine | 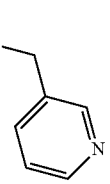 | 370.2053 |
| 916 | Diethanolamine |  | 372.2402 |
| 917 | 3-Picolylamine |  | 375.2289 |

-continued

[Structure: 4-amino-2-ethyl-1-(4-R-butyl)-2H-pyrazolo[3,4-c]quinoline]

| Example | Reagent | R | Measured Mass (M + H) |
|---|---|---|---|
| 918 | N-Methyl-furfurylamine | N-methyl-N-(furan-2-ylmethyl)amino | 378.2289 |
| 919 | N-Ethylpiperazine | 4-ethylpiperazin-1-yl | 381.2749 |
| 920 | N-Methyl-homopiperazine | 4-methyl-1,4-diazepan-1-yl | 381.2764 |
| 921 | 2,6-Dimethyl-morpholine | 2,6-dimethylmorpholin-4-yl | 382.2625 |
| 922 | N,N-Dimethyl-N'-ethylethylene-diamine | N-ethyl-N-(2-(dimethylamino)ethyl)amino | 383.2944 |
| 923 | N-Methyl-benzylamine | N-methyl-N-benzylamino | 388.2493 |

-continued

[Structure: 4-amino-2-ethyl-1-(4-R-butyl)-2H-pyrazolo[3,4-c]quinoline]

| Example | Reagent | R | Measured Mass (M + H) |
|---|---|---|---|
| 924 | 3-Azabicyclo[3.2.2]nonane | 3-azabicyclo[3.2.2]non-3-yl | 392.2816 |
| 925 | 1-Acetyl-piperazine | 4-acetylpiperazin-1-yl | 395.2555 |
| 926 | Iso-nipecotamide | 4-carbamoylpiperidin-1-yl | 395.2561 |
| 927 | 1-Methyl-4-(methylamino)piperidine | N-methyl-N-(1-methylpiperidin-4-yl)amino | 395.2888 |
| 928 | 4-Piperidine-ethanol | 4-(2-hydroxyethyl)piperidin-1-yl | 396.2765 |
| 929 | 4-(2-Aminoethyl)morpholine | N-(2-morpholinoethyl)amino | 397.2720 |

419
-continued
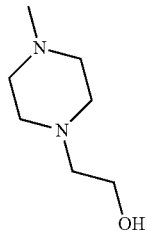
| Example | Reagent | R | Measured Mass (M + H) |
|---|---|---|---|
| 930 | N-(2-Hydroxyethyl)piperazine | 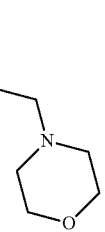 | 397.2731 |
| 931 | bis(2-Methoxyethyl)amine | 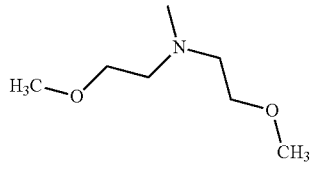 | 400.2716 |
| 932 | 1,2,3,4-Tetrahydroisoquinoline | 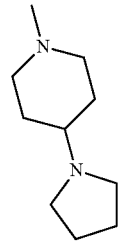 | 400.2487 |
| 933 | 1,1-Dioxidotetrahydrothien-3-ylamine | 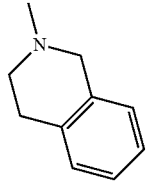 | 402.1963 |
| 934 | Methyl isonipecotate | 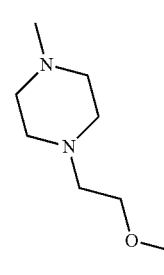 | 410.2554 |
420
-continued
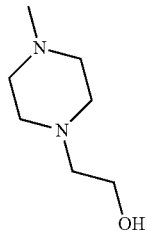
| Example | Reagent | R | Measured Mass (M + H) |
|---|---|---|---|
| 935 | N-(3-Aminopropyl)morpholine | 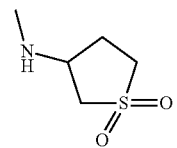 | 411.2876 |
| 936 | 4-(1-Pyrrolidinyl)-piperidine | 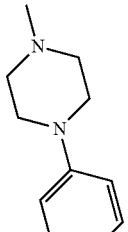 | 421.3071 |
| 937 | 1-(2-Ethoxyethyl)piperazine | 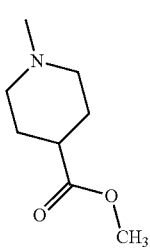 | 425.3028 |
| 938 | 1-Phenyl-piperazine | | 429.2729 |

421

Structure: 4-amino-2-ethyl-2H-pyrazolo[3,4-c]quinoline with 1-(4-R-butyl) substituent

| Example | Reagent | R | Measured Mass (M + H) |
|---|---|---|---|
| 939 | 1-(2-Pyridyl)piperazine | N-methylpiperazinyl-2-pyridyl group | 430.2732 |
| 940 | 4-Benyzyl-piperidine | 4-benzylpiperidinyl group | 442.2974 |
| 941 | 1-(2-Furoyl)piperazine | 4-(2-furoyl)piperazinyl group | 447.2495 |

422

Examples 942-1019

A reagent (0.11 mmol, 1.1 equivalents) from the table below was added to a test tube containing 1-(4-aminobutyl)-2-methyl-6,7,8,9-tetrahydro-2H-pyrazolo[3,4-c]quinolin-4-amine (27 mg, 0.10 mmol, prepared as described in Example 589) and N,N-diisopropylethylamine (approximately 34 µL, 2 equivalents) in chloroform (1 mL). The test tubes were capped and shaken for about 16 hours. Water (50 µL) was added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

Structure: 4-amino-2-methyl-6,7,8,9-tetrahydro-2H-pyrazolo[3,4-c]quinoline with 1-(4-(NHR)butyl) substituent

| Example | Reagent | R | Measured Mass (M + H) |
|---|---|---|---|
| 942 | None - starting material | H | 274.2038 |
| 943 | Propionyl chloride | C(=O)CH₂CH₃ | 330.2314 |
| 944 | Methyl chloroformate | C(=O)OCH₃ | 332.2068 |
| 945 | Cyclopropanecarbonyl chloride | C(=O)-cyclopropyl | 342.2281 |
| 946 | Butyryl chloride | C(=O)CH₂CH₂CH₃ | 344.2462 |
| 947 | Isobutyryl chloride | C(=O)CH(CH₃)₂ | 344.2468 |
| 948 | Methoxyacetyl chloride | C(=O)CH₂OCH₃ | 346.2242 |
| 949 | Methyl chlorothiolformate | C(=O)SCH₃ | 348.1872 |
| 950 | Cyclobutanecarbonyl chloride | C(=O)-cyclobutyl | 356.2471 |

423
-continued

[Structure: 4-amino-2-methyl-2,5,6,7,8-pentahydropyrazolo-quinoline with 1-(CH₂)₃-NH-R substituent]

| Example | Reagent | R | Measured Mass (M + H) |
|---|---|---|---|
| 951 | Isovaleryl chloride | -C(O)-CH₂-CH(CH₃)₂ | 358.2617 |
| 952 | Cyclopentanecarbonyl chloride | -C(O)-cyclopentyl | 370.2637 |
| 953 | Benzoyl chloride | -C(O)-phenyl | 378.2315 |
| 954 | Cyclohexanecarbonyl chloride | -C(O)-cyclohexyl | 384.2777 |
| 955 | 2-Fluorobenzoyl chloride | -C(O)-(2-F-phenyl) | 396.2228 |
| 956 | 3-Fluorobenzoyl chloride | -C(O)-(3-F-phenyl) | 396.2219 |

424
-continued

[Structure: same scaffold as 423]

| Example | Reagent | R | Measured Mass (M + H) |
|---|---|---|---|
| 957 | 4-Fluorobenzoyl chloride | -C(O)-(4-F-phenyl) | 396.2228 |
| 958 | 3-Cyanobenzoyl chloride | -C(O)-(3-CN-phenyl) | 403.2255 |
| 959 | 4-Cyanobenzoyl chloride | -C(O)-(4-CN-phenyl) | 403.2274 |
| 960 | Hydrocinnamoyl chloride | -C(O)-CH₂CH₂-phenyl | 406.2613 |
| 961 | 2-Methoxybenzoyl chloride | -C(O)-(2-OCH₃-phenyl) | 408.2415 |

-continued

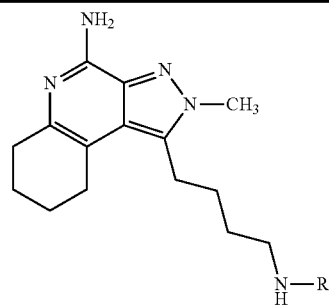

| Example | Reagent | R | Measured Mass (M + H) |
|---|---|---|---|
| 962 | 3-Methoxybenzoyl chloride |  | 408.2403 |
| 963 | p-Anisoyl chloride | 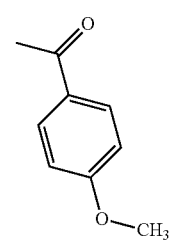 | 408.2409 |
| 964 | 2-Chlorobenzoyl chloride | 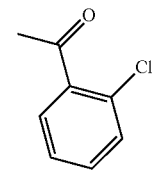 | 412.1929 |
| 965 | 3-Chlorobenzoyl chloride | 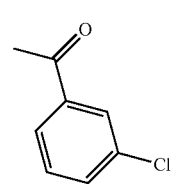 | 412.1936 |
| 966 | 4-Chlorobenzoyl chloride | 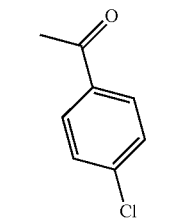 | 412.1929 |
| 967 | Isonicotinoyl chloride hydrochloride | 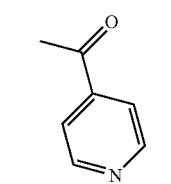 | 379.2263 |

-continued

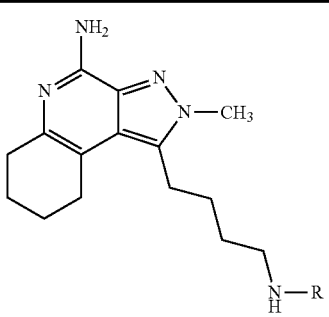

| Example | Reagent | R | Measured Mass (M + H) |
|---|---|---|---|
| 968 | Nicotinoyl chloride hydrochloride | 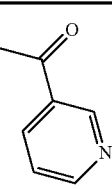 | 379.2217 |
| 969 | Picolinoyl chloride hydrochloride | 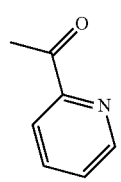 | 379.2234 |
| 970 | Methanesulfonyl chloride | 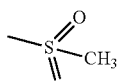 | 352.1825 |
| 971 | Ethanesulfonyl chloride | 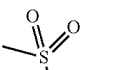 | 366.1987 |
| 972 | 1-Propanesulfonyl chloride | 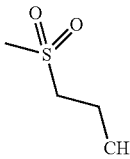 | 380.2142 |
| 973 | Isopropylsulfonyl chloride | 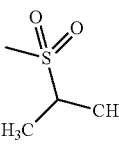 | 380.2150 |
| 974 | Dimethylsulfamoyl chloride | 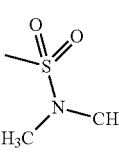 | 381.2038 |

427
-continued

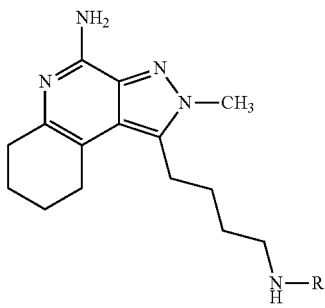

| Example | Reagent | R | Measured Mass (M + H) |
|---|---|---|---|
| 975 | 1-Butanesulfonyl chloride | –S(O)₂–CH₂CH₂CH₂CH₃ | 394.2293 |
| 976 | Benzenesulfonyl chloride | –S(O)₂–Ph | 414.1946 |
| 977 | 1-Methylimidazole-4-sulfonyl chloride | –S(O)₂–(1-methylimidazol-4-yl) | 418.2022 |
| 978 | 2,2,2-Trifluoro-ethanesulfonyl chloride | –S(O)₂–CH₂CF₃ | 420.1650 |
| 979 | alpha-Toluenesulfonyl chloride | –S(O)₂–CH₂Ph | 428.2090 |
| 980 | o-Toluenesulfonyl chloride | –S(O)₂–(2-methylphenyl) | 428.2122 |

428
-continued

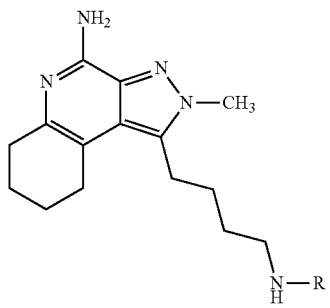

| Example | Reagent | R | Measured Mass (M + H) |
|---|---|---|---|
| 981 | p-Toluenesulfonyl chloride | –S(O)₂–(4-methylphenyl) | 428.2105 |
| 982 | 2-Fluoro-benzenesulfonyl chloride | –S(O)₂–(2-fluorophenyl) | 432.1891 |
| 983 | 3-Fluoro-benzenesulfonyl chloride | –S(O)₂–(3-fluorophenyl) | 432.1877 |
| 984 | 4-Fluoro-benzenesulfonyl chloride | –S(O)₂–(4-fluorophenyl) | 432.1838 |
| 985 | 3-Cyano-benzenesulfonyl chloride | –S(O)₂–(3-cyanophenyl) | 439.1921 |

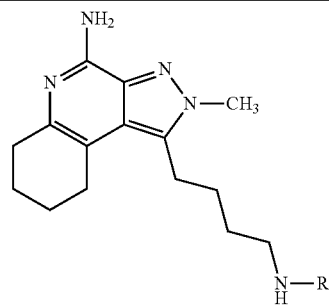

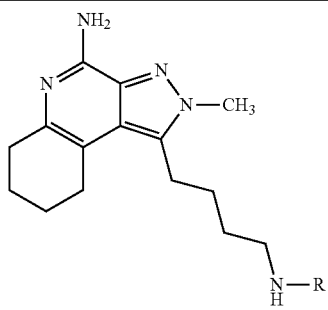

| Example | Reagent | R | Measured Mass (M + H) |
|---|---|---|---|
| 986 | 4-Cyano-benzenesulfonyl chloride | 4-cyanophenyl sulfonyl | 439.1921 |
| 987 | 3-Methoxy-benzenesulfonyl chloride | 3-methoxyphenyl sulfonyl | 444.2036 |
| 988 | 4-Methoxy-benzenesulfonyl chloride | 4-methoxyphenyl sulfonyl | 444.2082 |
| 989 | 2-Chloro-benzenesulfonyl chloride | 2-chlorophenyl sulfonyl | 448.1583 |
| 990 | 3-Chloro-benzenesulfonyl chloride | 3-chlorophenyl sulfonyl | 448.1584 |

| Example | Reagent | R | Measured Mass (M + H) |
|---|---|---|---|
| 991 | 4-Chloro-benzenesulfonyl chloride | 4-chlorophenyl sulfonyl | 448.1583 |
| 992 | Methyl isocyanate | methylcarbamoyl | 331.2276 |
| 993 | Ethyl isocyanate | ethylcarbamoyl | 345.2416 |
| 994 | Isopropyl isocyanate | isopropylcarbamoyl | 359.2588 |
| 995 | N-Propyl isocyanate | n-propylcarbamoyl | 359.2568 |
| 996 | Isopropyl isothiocyanate | isopropylthiocarbamoyl | 375.2342 |
| 997 | Cyclopentyl isocyanate | cyclopentylcarbamoyl | 385.2722 |

-continued

| Example | Reagent | R | Measured Mass (M + H) |
|---|---|---|---|
| 998 | Cyclopropylmethyl isothiocyanate | (thioamide N-CH2-cyclopropyl) | 387.2356 |
| 999 | Phenyl isocyanate | (amide N-phenyl) | 393.2427 |
| 1000 | Cyclohexyl isocyanate | (amide N-cyclohexyl) | 399.2901 |
| 1001 | Benzyl isocyanate | (amide N-benzyl) | 407.2578 |
| 1002 | m-Tolyl isocyanate | (amide N-m-tolyl) | 407.2584 |
| 1003 | o-Tolyl isocyanate | (amide N-o-tolyl) | 407.2581 |

-continued

| Example | Reagent | R | Measured Mass (M + H) |
|---|---|---|---|
| 1004 | p-Tolyl isocyanate | (amide N-p-tolyl) | 407.2563 |
| 1005 | Phenyl isothiocyanate | (thioamide N-phenyl) | 409.2182 |
| 1006 | 3-Pyridyl isothiocyanate | (thioamide N-3-pyridyl) | 410.2164 |
| 1007 | 2-Methoxyphenyl isocyanate | (amide N-2-methoxyphenyl) | 423.2523 |
| 1008 | 3-Methoxyphenyl isocyanate | (amide N-3-methoxyphenyl) | 423.2486 |
| 1009 | 4-Methoxyphenyl isocyanate | (amide N-4-methoxyphenyl) | 423.2512 |

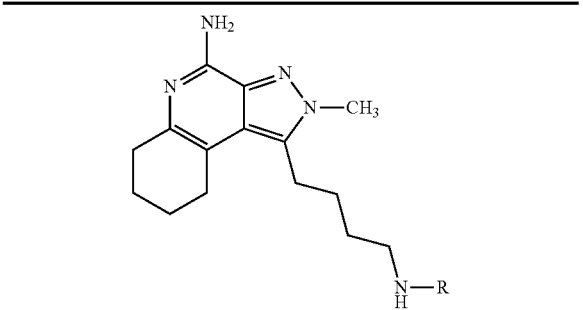

| Example | Reagent | R | Measured Mass (M + H) |
|---|---|---|---|
| 1010 | 2-Chlorophenyl isocyanate | -C(=O)-NH-(2-Cl-C6H4) | 427.2027 |
| 1011 | 3-Chlorophenyl isocyanate | -C(=O)-NH-(3-Cl-C6H4) | 427.2027 |
| 1012 | 4-Chlorophenyl isocyanate | -C(=O)-NH-(4-Cl-C6H4) | 427.2030 |
| 1013 | trans-2-Phenyl-cyclopropyl isocyanate | -C(=O)-NH-(trans-2-phenylcyclopropyl) | 433.2676 |
| 1014 | N,N-Dimethyl-carbamoyl chloride | -C(=O)-N(CH3)2 | 345.2416 |
| 1015 | 1-Pyrrolidine-carbonyl chloride | -C(=O)-N(pyrrolidine) | 371.2584 |
| 1016 | 2-Oxo-1-imidazolidine-carbonyl chloride | -C(=O)-N(2-oxoimidazolidine) | 386.2310 |

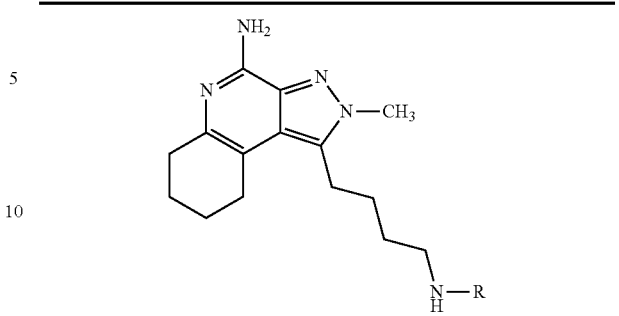

| Example | Reagent | R | Measured Mass (M + H) |
|---|---|---|---|
| 1017 | 4-Morpholinyl-carbonyl chloride | -C(=O)-N(morpholine) | 387.2515 |
| 1018 | 4-Methyl-1-Piperazinecarbonyl chloride | -C(=O)-N(4-methylpiperazine) | 400.2810 |
| 1019 | N-Methyl-N-Phenylcarbamoyl chloride | -C(=O)-N(CH3)(C6H5) | 407.2577 |

Examples 1020-1097

A reagent (0.12 mmol, 1.2 equivalents) from the table below was added to a test tube containing 1-(4-aminobutyl)-2-propyl-6,7,8,9-tetrahydro-2H-pyrazolo[3,4-c]quinolin-4-amine tris-trifluoroacetate (64 mg, 0.10 mmol, prepared as described in Example 578) and N,N-diisopropylethylamine (approximately 90 μL, 5 equivalents) in N,N-dimethylacetamide (1 mL). The test tubes were capped and shaken for about 16 hours. Water (30 μL) was added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

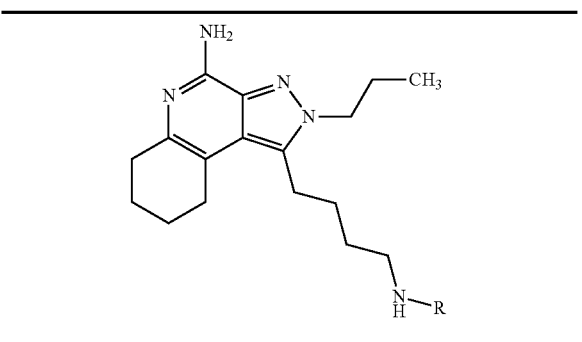

| Example | Reagent | R | Measured Mass (M + H) |
|---|---|---|---|
| 1020 | None—starting material | H | 302.2356 |
| 1021 | Methyl chloroformate | —C(O)—O—CH₃ | 360.2431 |
| 1022 | Cyclopropanecarbonyl chloride | —C(O)-cyclopropyl | 370.2581 |
| 1023 | Butyryl chloride | —C(O)—CH₂CH₂CH₃ | 372.2793 |
| 1024 | Isobutyryl chloride | —C(O)—CH(CH₃)₂ | 372.2797 |
| 1025 | Ethyl chloroformate | —C(O)—O—CH₂CH₃ | 374.2581 |
| 1026 | Methoxyacetyl chloride | —C(O)—CH₂—O—CH₃ | 374.2524 |
| 1027 | Methyl chlorothiolformate | —C(O)—S—CH₃ | 376.2200 |
| 1028 | Cyclobutanecarbonyl chloride | —C(O)-cyclobutyl | 384.2800 |

-continued

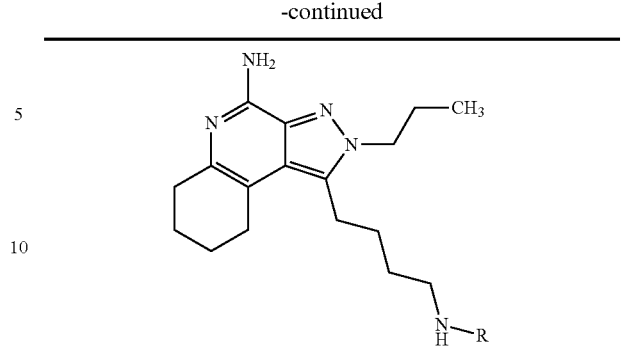

| Example | Reagent | R | Measured Mass (M + H) |
|---|---|---|---|
| 1029 | Isovaleryl chloride | —C(O)—CH₂—CH(CH₃)₂ | 386.2942 |
| 1030 | Pentanoyl chloride | —C(O)—CH₂CH₂CH₂CH₃ | 386.2930 |
| 1031 | Pivaloyl chloride | —C(O)—C(CH₃)₃ | 386.2955 |
| 1032 | tert-Butylacetyl chloride | —C(O)—CH₂—C(CH₃)₃ | 400.3100 |
| 1033 | Benzoyl chloride | —C(O)-phenyl | 406.2637 |
| 1034 | Cyclohexanecarbonyl chloride | —C(O)-cyclohexyl | 412.3082 |
| 1035 | 3-Cyanobenzoyl chloride | —C(O)-(3-cyanophenyl) | 431.2566 |

-continued

| Example | Reagent | R | Measured Mass (M + H) |
|---|---|---|---|
| 1036 | 4-Cyanobenzoyl chloride | 4-cyanobenzoyl | 431.2582 |
| 1037 | Cinnamoyl chloride | cinnamoyl | 432.2789 |
| 1038 | Hydrocinnamoyl chloride | hydrocinnamoyl | 434.2884 |
| 1039 | 2-Methoxylbenzoyl chloride | 2-methoxybenzoyl | 436.2724 |
| 1040 | 2-Chlorobenzoyl chloride | 2-chlorobenzoyl | 440.2225 |

-continued

| Example | Reagent | R | Measured Mass (M + H) |
|---|---|---|---|
| 1041 | 3-Chlorobenzoyl chloride | 3-chlorobenzoyl | 440.2231 |
| 1042 | 4-Chlorobenzoyl chloride | 4-chlorobenzoyl | 440.2261 |
| 1043 | Isonicotinoyl chloride hydrochloride | isonicotinoyl | 407.2575 |
| 1044 | Nicotinoyl chloride hydrochloride | nicotinoyl | 407.2576 |
| 1045 | Picolinoyl chloride hydrochloride | picolinoyl | 407.2582 |
| 1046 | trans-2-Phenyl-1-cyclopropanecarbonyl chloride | trans-2-phenylcyclopropanecarbonyl | 446.2876 |

439

-continued

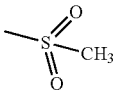

| Example | Reagent | R | Measured Mass (M + H) |
|---|---|---|---|
| 1047 | Methanesulfonyl chloride | 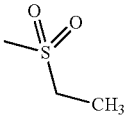 | 380.2112 |
| 1048 | Ethanesulfonyl chloride | 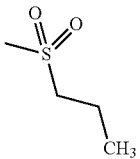 | 394.2269 |
| 1049 | 1-Propanesulfonyl chloride | 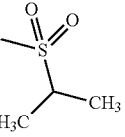 | 408.2450 |
| 1050 | Isopropylsulfonyl chloride | 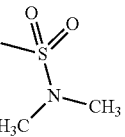 | 408.2448 |
| 1051 | Dimethylsulfamoyl chloride | 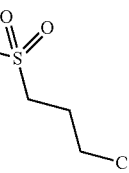 | 409.2384 |
| 1052 | 1-Butanesulfonyl chloride | 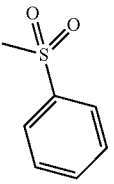 | 422.2617 |
| 1053 | Benzenesulfonyl chloride | 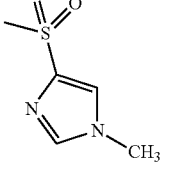 | 442.2272 |

440

-continued

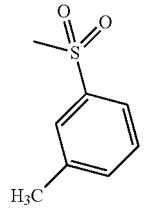

| Example | Reagent | R | Measured Mass (M + H) |
|---|---|---|---|
| 1054 | 1-Methylimidazole-4-sulfonyl chloride | 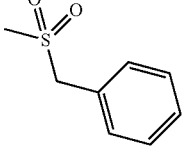 | 446.2353 |
| 1055 | 3-Methyl-benzenesulfonyl chloride | | 456.2474 |
| 1056 | alpha-Toluenesulfonyl chloride | 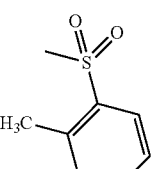 | 456.2435 |
| 1057 | o-Toluenesulfonyl chloride | | 456.2475 |
| 1058 | p-Toluenesulfonyl chloride | 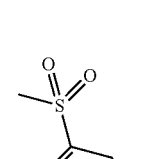 | 456.2390 |

-continued

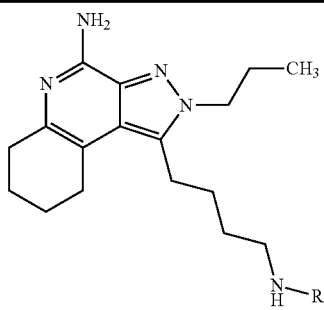

| Example | Reagent | R | Measured Mass (M + H) |
|---|---|---|---|
| 1059 | 3-Cyano-benzenesulfonyl chloride | 3-cyanophenylsulfonyl | 467.2200 |
| 1060 | 4-Cyano-benzenesulfonyl chloride | 4-cyanophenylsulfonyl | 467.2187 |
| 1061 | 3-Methoxy-benzenesulfonyl chloride | 3-methoxyphenylsulfonyl | 472.2384 |
| 1062 | 4-Methoxy-benzenesulfonyl chloride | 4-methoxyphenylsulfonyl | 472.2398 |
| 1063 | 2-Chloro-benzenesulfonyl chloride | 2-chlorophenylsulfonyl | 476.1908 |

-continued

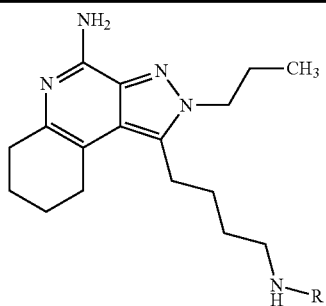

| Example | Reagent | R | Measured Mass (M + H) |
|---|---|---|---|
| 1064 | 3-Chloro-benzenesulfonyl chloride | 3-chlorophenylsulfonyl | 476.1861 |
| 1065 | 4-Chloro-benzenesulfonyl chloride | 4-chlorophenylsulfonyl | 476.1846 |
| 1066 | 1-Naphthalene-sulfonyl chloride | 1-naphthylsulfonyl | 492.2451 |
| 1067 | 2-Naphthalene-sulfonyl chloride | 2-naphthylsulfonyl | 492.2414 |
| 1068 | N-Acetylsulfanilyl chloride | 4-acetamidophenylsulfonyl | 499.2519 |

-continued

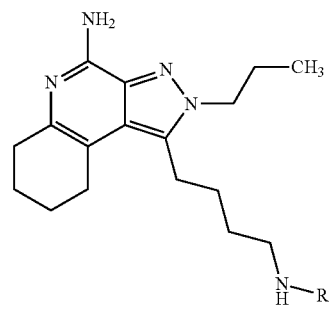

| Example | Reagent | R | Measured Mass (M + H) |
|---|---|---|---|
| 1069 | Methyl isocyanate | —C(=O)NH—CH₃ | 359.2596 |
| 1070 | Ethyl isocyanate | —C(=O)NH—CH₂CH₃ | 373.2702 |
| 1071 | Isopropyl isocyanate | —C(=O)NH—CH(CH₃)₂ | 387.2855 |
| 1072 | N-Propyl isocyanate | —C(=O)NH—CH₂CH₂CH₃ | 387.2852 |
| 1073 | N-Butyl isocyanate | —C(=O)NH—(CH₂)₃CH₃ | 401.3009 |
| 1074 | sec-Butyl isocyanate | —C(=O)NH—CH(CH₃)CH₂CH₃ | 401.3026 |
| 1075 | Cyclopropyl isothiocyanate | —C(=S)NH—cyclopropyl | 401.2458 |
| 1076 | Cyclopentyl isocyanate | —C(=O)NH—cyclopentyl | 413.2993 |
| 1077 | Cyclopropylmethyl isothiocyanate | —C(=S)NH—CH₂-cyclopropyl | 415.2605 |
| 1078 | Phenyl isocyanate | —C(=O)NH—phenyl | 421.2702 |
| 1079 | Cyclohexyl isocyanate | —C(=O)NH—cyclohexyl | 427.3229 |
| 1080 | m-Tolyl isocyanate | —C(=O)NH—(m-tolyl) | 435.2876 |
| 1081 | Phenyl isothiocyanate | —C(=S)NH—phenyl | 437.2459 |
| 1082 | 3-Pyridyl isothiocyanate | —C(=S)NH—(3-pyridyl) | 438.2480 |

-continued

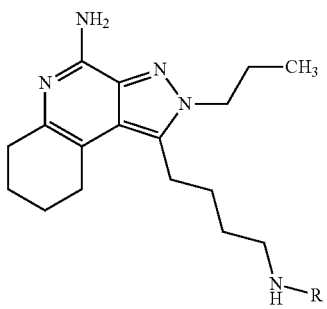

| Example | Reagent | R | Measured Mass (M + H) |
|---|---|---|---|
| 1083 | 2-Tetrahydro-furfuryl isothiocyanate | (thiourea with tetrahydrofuran-2-ylmethyl) | 445.2741 |
| 1084 | Benzoyl isocyanate | (benzoyl urea) | 449.2674 |
| 1085 | 2-Phenylethyl isocyanate | (phenethyl urea) | 449.3064 |
| 1086 | 2-Methoxylphenyl isocyanate | (2-methoxyphenyl urea) | 451.2864 |
| 1087 | 3-Methoxylphenyl isocyanate | (3-methoxyphenyl urea) | 451.2798 |

-continued

| Example | Reagent | R | Measured Mass (M + H) |
|---|---|---|---|
| 1088 | 4-Methoxylphenyl isocyanate | (4-methoxyphenyl urea) | 451.2860 |
| 1089 | 3-Chlorophenyl isocyanate | (3-chlorophenyl urea) | 455.2350 |
| 1090 | 4-Chlorophenyl isocyanate | (4-chlorophenyl urea) | 455.2345 |
| 1091 | trans-2-Phenyl-cyclopropyl isocyanate | (trans-2-phenylcyclopropyl urea) | 461.3076 |
| 1092 | 3-Carbomethoxyphenyl isocyanate | (3-methoxycarbonylphenyl urea) | 479.2800 |
| 1093 | N,N-Dimethyl-carbamoyl chloride | (N,N-dimethyl urea) | 373.2736 |

447

-continued

[Structure: 4-amino-pyrazoloquinoline core with tetrahydro ring, 2-propyl, and 1-(4-aminobutyl)-NH-R substituent]

| Example | Reagent | R | Measured Mass (M + H) |
|---|---|---|---|
| 1094 | 1-Pyrrolidine-carbonyl chloride | [pyrrolidine carbonyl] | 399.2891 |
| 1095 | 1-Piperidine-carbonyl chloride | [piperidine carbonyl] | 413.2986 |
| 1096 | 4-Morpholine-carbonyl chloride | [morpholine carbonyl] | 415.2802 |
| 1097 | 4-Methyl-1-Piperazinecarbonyl chloride | [4-methylpiperazine carbonyl] | 428.3176 |

Examples 1098-1115

A reagent (0.11 mmol, 1.1 equivalents) from the table below was added to a test tube containing 1-(4-aminobutyl)-2-propyl-2H-pyrazolo[3,4-c]quinolin-4-amine (30 mg, 0.10 mmol, prepared as described in Example 577) and N,N-diisopropylethylamine (approximately 36 μL, 2 equivalents) in chloroform (1 mL). The test tubes were capped and shaken for about 4 hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

448

[Structure: 4-amino-2H-pyrazolo[3,4-c]quinoline core with 2-propyl and 1-(4-aminobutyl)-NH-R substituent]

| Example | Reagent | R | Measured Mass (M + H) |
|---|---|---|---|
| 1098 | None—starting material | H | 298.2036 |
| 1099 | Propionyl chloride | [propionyl] | 354.2326 |
| 1100 | Cyclobutanecarbonyl chloride | [cyclobutanecarbonyl] | 380.2464 |
| 1101 | Benzoyl chloride | [benzoyl] | 402.2332 |
| 1102 | Cyclohexanecarbonyl chloride | [cyclohexanecarbonyl] | 408.2801 |
| 1103 | Nicotinoyl chloride hydrochloride | [nicotinoyl] | 403.2280 |
| 1104 | Methanesulfonyl chloride | [methanesulfonyl] | 376.1839 |
| 1105 | 1-Propanesulfonyl chloride | [propanesulfonyl] | 404.2154 |

449 -continued

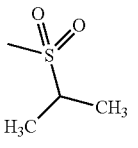

| Example | Reagent | R | Measured Mass (M + H) |
|---|---|---|---|
| 1106 | Isopropylsulfonyl chloride | 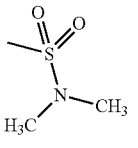 | 404.2087 |
| 1107 | Dimethylsulfamoyl chloride | 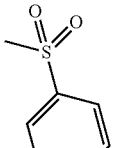 | 405.2098 |
| 1108 | Benzenesulfonyl chloride | 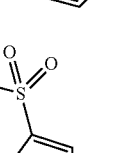 | 438.1996 |
| 1109 | 1-Methylimidazole-4-sulfonyl chloride | 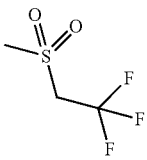 | 442.2025 |
| 1110 | 2,2,2-Trifluoroethanesulfonyl chloride | 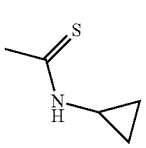 | 444.1700 |
| 1111 | Cyclopropyl isothiocyanate | 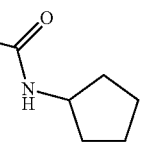 | 397.2207 |
| 1112 | Cyclopentyl isocyanate | 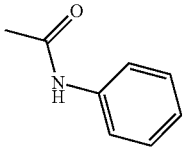 | 409.2737 |

450 -continued

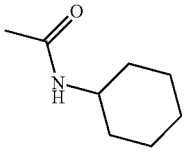

| Example | Reagent | R | Measured Mass (M + H) |
|---|---|---|---|
| 1113 | Phenyl isocyanate | 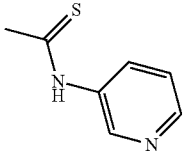 | 417.2438 |
| 1114 | Cyclohexyl isocyanate | | 423.2903 |
| 1115 | 3-Pyridyl isothiocyanate | | 434.2153 |

Examples 1116-1129

A reagent (0.11 mmol, 1.1 equivalents) from the table below was added to a test tube containing 1-(2-amino-2-methylpropyl)-2-propyl-2H-pyrazolo[3,4-c]quinolin-4-amine (32 mg, 0.10 mmol, prepared as described in Example 64) and N,N-diisopropylethylamine (approximately 27 μL, 1.5 equivalents) in N,N-dimethylacetamide (1 mL). The test tubes were capped and shaken for about 4 hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 1116 | None—starting material | 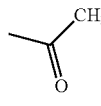 | 298.2029 |
| 1117 | Acetyl chloride | 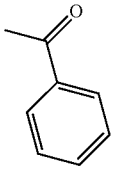 | 340.2144 |
| 1118 | Benzoyl chloride | 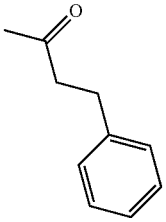 | 402.2336 |
| 1119 | Hydrocinnamoyl chloride | 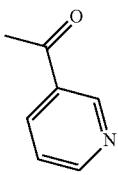 | 430.2639 |
| 1120 | Nicotinoyl chloride hydrochloride | 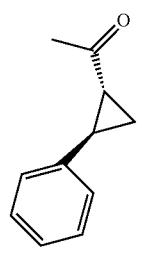 | 403.2256 |
| 1121 | trans-2-Phenyl-1-cyclopropanecarbonyl chloride | 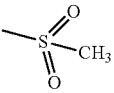 | 442.2607 |
| 1122 | Methanesulfonyl chloride | 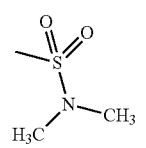 | 376.1814 |
| 1123 | Dimethylsulfamoyl chloride | 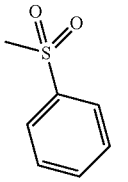 | 405.2071 |

-continued

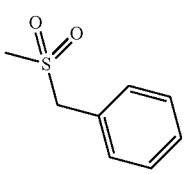

| Example | Reagent | R | Measured Mass (M + H) |
|---|---|---|---|
| 1124 | Benzenesulfonyl chloride | 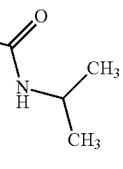 | 438.1994 |
| 1125 | alpha-Toluenesulfonyl chloride | 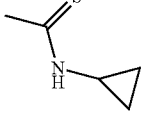 | 452.2145 |
| 1126 | Isopropyl isocyanate | 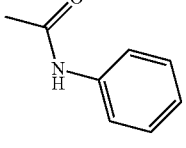 | 383.2566 |
| 1127 | Cyclopropyl isothiocyanate | 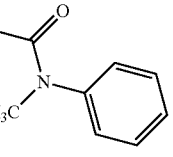 | 397.2189 |
| 1128 | Phenyl isocyanate | | 417.2445 |
| 1129 | N-Methyl-N-Phenylcarbomoyl chloride | | 431.2592 |

Examples 1130-1176

Part A

A mixture of 1-(4-chlorobutyl)-2-methyl-2H-pyrazolo[3,4-c]quinolin-4-amine hydrochloride (2.8 g, prepared as described in Examples 454-488), platinum (IV) oxide (2.1 g), and trifluoroacetic acid (43 mL) was placed under hydrogen pressure (50 psi, $3.4 \times 10^5$ Pa) on a Parr shaker for 2 days. The reaction mixture was filtered through a layer of CELITE filter agent and the filter cake was rinsed with methanol. The filtrate was concentrated under reduced pressure. The residue was diluted with water (10 mL), made basic (pH 14) by the addition of 50% sodium hydroxide and then extracted with dichloromethane. The extract was dried over sodium sulfate and concentrated under reduced pressure. The residue was purified by chromatography on a HORIZON HPFC system (40+M cartridge eluting with chloroform/CMA in a gradient from 100:0 to 80:20) to provide 2.0 g of 1-(4-chlorobutyl)-2-methyl-6,7,8,9-tetrahydro-2H-pyrazolo[3,4-c]quinolin-4-amine as a light yellow solid.

Part B

A reagent (0.15 mmol, 1.5 equivalents) from the table below was added to a test tube containing 1-(4-chlorobutyl)-2-methyl-6,7,8,9-tetrahydro-2H-pyrazolo[3,4-c]quinolin-4-amine (29 mg, 0.10 mmol) and potassium carbonate (approximately 55 mg, 0.40 mmol) in N,N-dimethylacetamide (1 mL). The test tubes were capped and heated at 70° C. (amines) or 85° C. (phenols) for approximately 17 hours. The reaction mixtures were filtered and the solvent was removed from the filtrates by vacuum centrifugation. The compounds were purified as described in Examples 71-85. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 1130 | None—starting material | | 293.1557 |
| 1131 | Pyrrolidine | | 328.2524 |
| 1132 | Piperidine | | 342.2643 |
| 1133 | Morpholine | | 344.2464 |
| 1134 | 2-Ethylaminoethanol | | 346.2614 |
| 1135 | 3-Hydroxypiperidine | | 358.2613 |
| 1136 | 4-Hydroxypiperidine | | 358.2633 |
| 1137 | 3-(Dimethylamino)pyrrolidine | | 371.2914 |
| 1138 | N-Methylhomopiperazine | | 371.2959 |
| 1139 | 2-Piperidinemethanol | | 372.2749 |
| 1140 | 3-(Hydroxymethyl)piperidine | | 372.2794 |

455
-continued

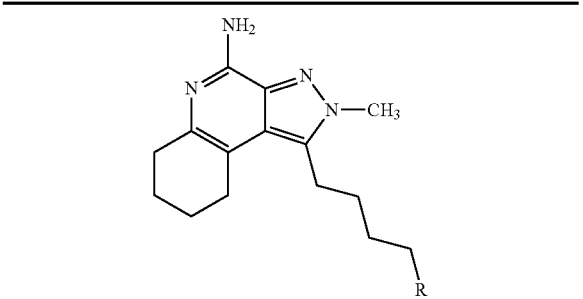

| Example | Reagent | R | Measured Mass (M + H) |
|---|---|---|---|
| 1141 | 4-(Hydroxymethyl)piperidine | (N-methylpiperidin-4-yl)methanol group | 372.2793 |
| 1142 | N-Methylbenzylamine | N-methyl-N-benzylamino | 378.2680 |
| 1143 | Isonipecotamide | 1-methylpiperidine-4-carboxamide | 385.2697 |
| 1144 | (3S)-(−)-3-Acetamido-pyrrolidine | (3S)-1-methyl-3-acetamidopyrrolidine (Chiral) | 385.2710 |
| 1145 | 1-Acetylpiperazine | 4-acetyl-1-methylpiperazine | 385.2723 |
| 1146 | 2-Piperidineethanol | 2-(1-methylpiperidin-2-yl)ethanol | 386.2931 |

456
-continued

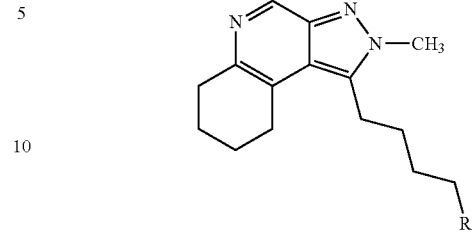

| Example | Reagent | R | Measured Mass (M + H) |
|---|---|---|---|
| 1147 | 4-Piperidineethanol | 2-(1-methylpiperidin-4-yl)ethanol | 386.2928 |
| 1148 | N-(2-Hydroxyethyl)piperazine | 4-(2-hydroxyethyl)-1-methylpiperazine | 387.2910 |
| 1149 | 4-(Ethylamino-methyl)pyridine | N-ethyl-N-(pyridin-4-ylmethyl)methylamine | 393.2790 |
| 1150 | 1-(2-Methoxyethyl)piperazine | 4-(2-methoxyethyl)-1-methylpiperazine | 401.3011 |
| 1151 | 4-(1-Pyrrolidinyl)-piperidine | 1-methyl-4-(pyrrolidin-1-yl)piperidine | 411.3260 |

457
-continued
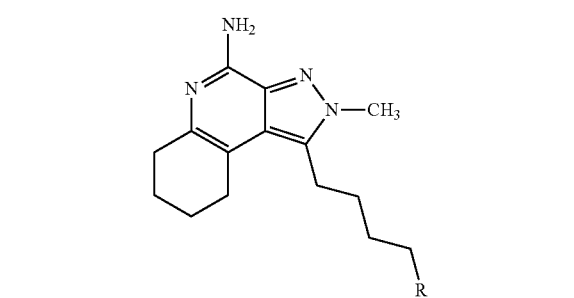
| Example | Reagent | R | Measured Mass (M + H) |
|---|---|---|---|
| 1152 | 1-(2-Ethoxyethyl)piperazine | 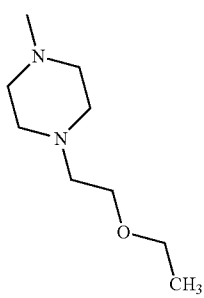 | 415.3208 |
| 1153 | 1-Phenylpiperazine | 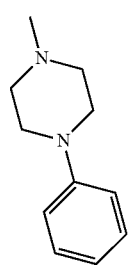 | 419.2944 |
| 1154 | 1-(2-Pyridyl)piperazine | 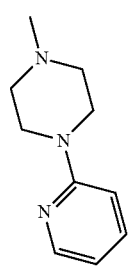 | 420.2886 |
| 1155 | 4-Piperidinopiperidine | 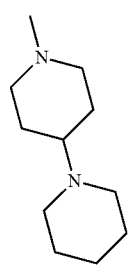 | 425.3397 |
458
-continued
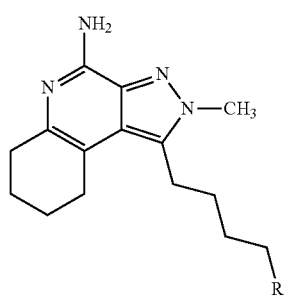
| Example | Reagent | R | Measured Mass (M + H) |
|---|---|---|---|
| 1156 | 1-Hydroxyethyl-ethoxypiperazine |  | 431.3148 |
| 1157 | 1-(2-Furoyl)piperazine | 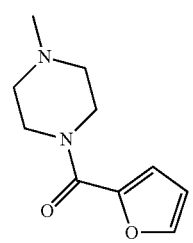 | 437.2685 |
| 1158 | 2-Piperidin-1-ylmethyl-piperidine | 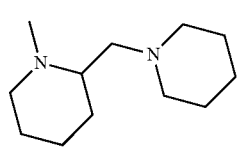 | 439.3556 |
| 1159 | 1-Cinnamylpiperazine | 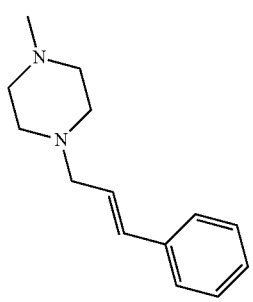 | 459.3239 |

-continued
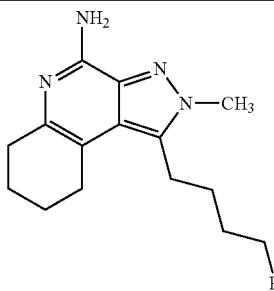
| Example | Reagent | R | Measured Mass (M + H) |
|---|---|---|---|
| 1160 | 1-Phenyl-1,3,8-triazospiro[4.5]decan-4-one | | 488.3132 |
| 1161 | Phenol | | 351.2188 |
| 1162 | 2-Cyanophenol | | 376.2125 |
| 1163 | 3-Cyanophenol | | 376.2157 |
| 1164 | 4-Cyanophenol | | 376.2140 |
| 1165 | 3-Methoxyphenol | | 381.2270 |
| 1166 | 4-Methoxyphenol | | 381.2278 |
| 1167 | Guaiacol | | 381.2270 |
| 1168 | 2-Chlorophenol | | 385.1785 |
| 1169 | 4-Chlorophenol | | 385.1780 |
| 1170 | 4-Hydroxybenzamide | | 394.2255 |
| 1171 | 3-Dimethylaminophenol | | 394.2589 |
| 1172 | 2,4-Dichlorophenol | | 419.1378 |
| 1173 | 2,5-Dichlorophenol | | 419.1363 |

-continued

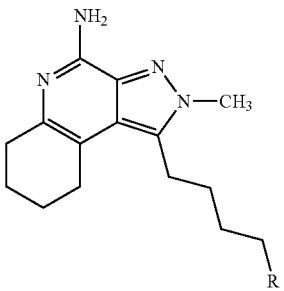

| Example | Reagent | R | Measured Mass (M + H) |
|---|---|---|---|
| 1174 | 3,4-Dichlorophenol | (3,4-dichlorophenoxy) | 419.1374 |
| 1175 | 3,5-Dichlorophenol | (3,5-dichlorophenoxy) | 419.1381 |
| 1176 | 4-Hydroxybenzene-sulfonamide | (4-sulfamoylphenoxy) | 430.1886 |

Examples 1177-1191

Part A

DMF (50 mL) was added to a mixture of 1-(2-methylpropyl)-2H-pyrazolo[3,4-c]quinolin-4-amine (3 g, 12.5 mmol, prepared as described in Example 9), 4-bromobutylphthalimide (3.9 g, 13.7 mmol), and potassium carbonate (5.2 g, 37.5 mmol). The reaction mixture was heated at 60° C. with stirring under a nitrogen atmosphere for about 18 hours. The reaction mixture was filtered to remove excess potassium carbonate. The filtrate was diluted with water and then extracted with ethyl acetate. The extract was dried over magnesium sulfate, filtered, and concentrated under reduced pressure. The residue was purified by chromatography on a HORIZON HPFC system (silica gel, eluting first with ethyl acetate and then with a gradient of methanol in ethyl acetate) to provide 2.0 g of 2-{4-[4-amino-1-(2-methylpropyl)-2H-pyrazolo[3,4-c]quinolin-2-yl]butyl}-1H-isoindole-1,3 (2H)-dione

Part B

The material from Part A was combined with hydrazine monohydrate (1.1 mL, 5 eq) and ethanol (100 mL). The reaction mixture was heated at reflux for 2 hours and then allowed to cool to ambient temperature overnight. The reaction mixture was filtered and the filtrate was concentrated under reduced pressure to provide 0.8 g of 2-(4-aminobutyl)-1-(2-methylpropyl)-2H-pyrazolo[3,4-c]quinolin-4-amine.

Part C

A reagent (0.11 mmol, 1.1 equivalents) from the table below was added to a test tube containing 2-(4-aminobutyl)-1-(2-methylpropyl)-2H-pyrazolo[3,4-c]quinolin-4-amine (31 mg, 0.10 mmol) and N,N-diisopropylethylamine (approximately 35 µL, 2 equivalents) in N,N-dimethylacetamide (1 mL). The test tubes were capped and shaken for about 16 hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 1177 | None—starting material | H | 312.2203 |
| 1178 | Acetyl chloride | acetyl | 354.2316 |
| 1179 | Benzoyl chloride | benzoyl | 416.2444 |
| 1180 | Hydrocinnamoyl chloride | hydrocinnamoyl | 444.2769 |
| 1181 | Nicotinoyl chloride hydrochloride | nicotinoyl | 417.2406 |
| 1182 | Isopropylsulfonyl chloride | isopropylsulfonyl | 418.2296 |
| 1183 | Dimethylsulfamoyl chloride | dimethylsulfamoyl | 419.2213 |
| 1184 | Trifluoro-methanesulfonyl chloride | trifluoromethanesulfonyl | 444.1689 |

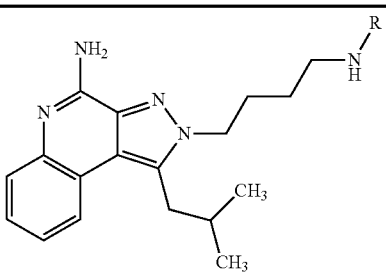

| Example | Reagent | R | Measured Mass (M + H) |
|---|---|---|---|
| 1185 | Benzenesulfonyl chloride | | 452.2150 |
| 1186 | alpha-Toluenesulfonyl chloride | | 466.2242 |
| 1187 | Ethyl isocyanate | | 383.2586 |
| 1188 | Cyclopropyl isothiocyanate | | 411.2358 |
| 1189 | Cyclopropylmethyl isothiocyanate | | 425.2496 |
| 1190 | Phenyl isocyanate | | 431.2590 |
| 1191 | Benzyl isocyanate | | 445.2752 |

Examples 1192-1197

A reagent (0.12 mmol, 1.2 equivalents) from the table below and a solution of potassium tert-butoxide (150 µL of 1 M in THF, 1.5 eq) were added to a test tube containing 1-(4-chlorobutyl)-2-ethyl-2H-pyrazolo[3,4-c]quinoline-4-amine (30 mg, 0.10 mmol) in DMF (1 mL). The tubes were capped and stirred (magnetic stir bar) at ambient temperature for about 65 hours. Aqueous hydrochloric acid (300 µL of 1 N) and peracetic acid (57 µL of 32 wt %) were added to each tube; then stirring was continued for an additional 3 hours. The solvent was removed by vacuum centrifugation. The compounds were purified as described in Examples 71-85. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 1192 | None—starting material | | 303.1352 |
| 1193 | Ethanethiol | | 361.1699 |
| 1194 | 2-Propanethiol | | 375.1861 |
| 1195 | Methyl thioglycolate | | 405.1585 |
| 1196 | Thiophenol | | 409.1690 |
| 1197 | Furfuryl mercaptan | | 413.1659 |

Example 1198

Under a nitrogen atmosphere, potassium tert-butoxide (218 µL of 1 M in THF, 1.5 eq) was added to a solution of 1-(4-chlorobutyl)-2-ethyl-2H-pyrazolo[3,4-c]quinoline-4-amine (44 mg, 0.145 mmol) and butanethiol (19 µL, 0.174 mmol) in DMF (1.5 mL). The reaction mixture was stirred at ambient temperature overnight. Peracetic acid (76 µL of 32 wt %) was added and the reaction mixture was stirred for 2 hours. The reaction mixture was acidified (pH 3) by the addition of 1 N hydrochloric acid and then loaded onto a solid phase extraction cartridge (Waters, MCX 6 cc). The reaction mixture was pushed through the cartridge with light nitrogen pressure to provide fraction 1. The cartridge was eluted sequentially with methanol (5 mL) and ammonia/methanol (5 mL of 1 N) to provide fractions 2 and 3 respectively. The solvent was removed by vacuum centrifugation to provide 1-[4-(butylsulfonyl)butyl]-2-ethyl-2H-pyrazolo[3,4-c]quinolin-4-amine, measured mass (M+H): 389.1989.

Example 1199

4-Amino-1,2-diethyl-2H-pyrazolo[3,4-c]quinolin-7-ol

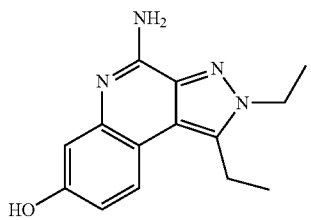 [SMILES: CCc1c2c(nn1CC)c(N)nc1cc(O)ccc12]

Dichloromethane (1 mL) was added to a vial containing 1,2-diethyl-7-methoxy-2H-pyrazolo[3,4-c]quinolin-4-amine (20 mg, 0.074 mmol, prepared as described in Example 573). The reaction mixture was stirred at 0° C. for 5 minutes. Cold boron tribromide (370 µL of 1 M in dichloromethane, 0.37 mmol) was added dropwise and the reaction mixture was stirred at 0° C. for 20 minutes. The ice bath was removed and the reaction mixture was stirred for about 3 hours. The solvent was evaporated. The residue was combined with methanol (2 mL) and 6 N hydrochloric acid (500 µL); and then stirred for 1 hour. The mixture was made basic by the addition of 6 M sodium hydroxide and a portion of the solvent was evaporated. The residue was partitioned between dichloromethane (25 mL) and water (25 mL). The layers were separated. The aqueous layer was evaporated to provide a yellow solid. The solid was suspended in methanol. The methanol was evaporated and the residue was purified as described in Examples 71-85 to provide the trifluoroacetate salt of 4-amino-1,2-diethyl-2H-pyrazolo[3,4-c]quinolin-7-ol, measured mass (M+H): 257.1408.

Example 1200

7-(Benzyloxy)-1,2-diethyl-2H-pyrazolo[3,4-c]quinolin-4-amine

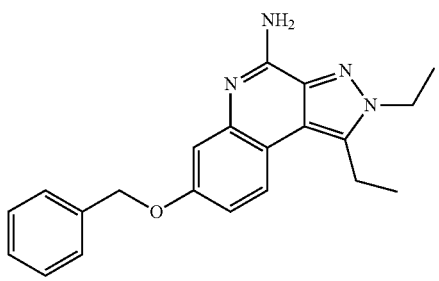 [SMILES: CCc1c2c(nn1CC)c(N)nc1cc(OCc3ccccc3)ccc12]

Chloroform (2 mL) and cesium carbonate (32.6 mg, 0.1 mmol) were added to a vial containing 4-amino-1,2-diethyl-2H-pyrazolo[3,4-c]quinolin-7-ol (17 mg, 0.05 mmol) and the mixture was stirred at ambient temperature for 5 minutes. Benzyl bromide (6.54 µL, 0.055 mmol) was added and the reaction mixture was stirred at 50° C. for 30 minutes. Analysis by LCMS indicated that only a small amount of product had formed. The chloroform was evaporated and the residue was dissolved in N,N-dimethylacetamide. The reaction mixture was stirred at 50° C. for about 1 hour. The solvent was evaporated and the residue was purified as described in Examples 71-85 to provide the trifluoroacetate salt of 7-(benzyloxy)-1,2-diethyl-2H-pyrazolo[3,4-c]quinolin-4-amine, measured mass (M+H): 423.2190.

Examples 1201 & 1202

N,N-Dimethylacetamide (2 mL) and cesium carbonate (32.6 mg, 0.1 mmol) were added to vials containing 4-amino-1,2-diethyl-2H-pyrazolo[3,4-c]quinolin-7-ol (17 mg, 0.05 mmol) and the mixture was stirred at ambient temperature for 5 minutes. A reagent (6.54 µL, 0.055 mmol) from the table below was added to a vial and the reaction mixture was stirred at 50° C. for 4 hours. The solvent was evaporated and the residue was purified as described in Examples 71-85. The table below shows the reagents used, the structure of the resulting compound, and the observed accurate mass for the isolated trifluoroacetate salt.

| Example | Reagent | R | Measured Mass (M + H) |
|---|---|---|---|
| 1201 | alpha-Bromo-p-xylene | H₃C–⟨benzyl⟩–CH₂– | 437.2349 |
| 1202 | 4-Chlorobenzyl bromide | Cl–⟨benzyl⟩–CH₂– | 457.1809 |

Examples 1203-1206

A boronic acid (2.1 eq, 0.11 mmol) from the table below and n-propyl alcohol (720 µL) were added to a vial containing 4-amino-2-ethyl-1-(2-phenylethyl)-2H-pyrazolo[3,4-c]quinolin-7-yl trifluoromethanesulfonate (23 mg, 0.05 mmol, prepared as described in Example 576). The vial was purged with nitrogen. Palladium (II) acetate (1.12 mg, 10 mole %), 2 M aqueous sodium carbonate (250 µL), water (50 µL), and triphenylphosphine (2.6 mg (20 mole %) in 100 µL of n-propyl alcohol) were sequentially added. The reaction mixture was heated at 80° C. with stirring for 1 hour, allowed to cool to ambient temperature, and then filtered through a plug of glass wool. The plug was washed with n-propyl alcohol, methanol, and dichloromethane. The filtrate was evaporated and the residue was purified as described in Examples 71-85. The table below shows the reagents used, the structure of the resulting compound, and the observed accurate mass for the isolated trifluoroacetate salt.

described in Examples 71-85. The table below shows the reagent added to each test tube, the structure of the resulting compound, and the observed accurate mass for the isolated trifluoroacetate salt.

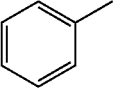

| Example | Reagent | R | Measured Mass (M + H) |
|---|---|---|---|
| 1203 | Phenylboronic acid | 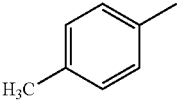 | 393.2108 |
| 1204 | 4-Methyl-phenylboronic acid | 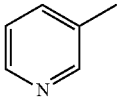 | 407.2201 |
| 1205 | Pyridine-3-boronic acid | 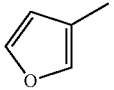 | 394.2031 |
| 1206 | Furan-3-boronic acid | 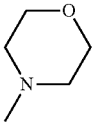 | 383.1852 |

Examples 1207-1216

Part A 1-(2-Methylpropyl)-2H-pyrazolo[3,4-c]quinolin-4-amine (2.4 g, 9.99 mmol, prepared as described in Example 9), potassium carbonate (5.5 g, 39.9 mmol), 3-chloroiodopropane (1.2 mL, 11.0 mmol), and DMF (110 mL) were combined and heated at 40° C. overnight. The reaction mixture was diluted with water and then extracted with ethyl acetate. The combined extracts were washed with water and concentrated under reduced pressure. The residue was purified twice by chromatography on a HORIZON HPFC system (silica gel eluting with ethyl acetate) to provide 2-(3-chloropropyl)-1-(2-methylpropyl)-2H-pyrazolo[3,4-c]quinolin-4-amine.

Part B

A reagent (0.15 mmol, 1.5 equivalents) from the table below was added to a test tube containing 2-(3-chloropropyl)-1-(2-methylpropyl)-2H-pyrazolo[3,4-c]quinolin-4-amine (32 mg, 0.10 mmol) and potassium carbonate (approximately 55 mg, 0.40 mmol) in N,N-dimethylacetamide (1 mL). The test tubes were capped and heated at 70° C. (amines) or 85° C. (phenols) for approximately 18 hours. The reaction mixtures were filtered and the solvent was removed from the filtrates by vacuum centrifugation. The compounds were purified as

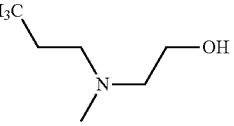

| Example | Reagent | R | Measured Mass (M + H) |
|---|---|---|---|
| 1207 | Morpholine | 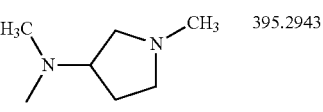 | 368.2472 |
| 1208 | 2-(Propylamino)ethanol | 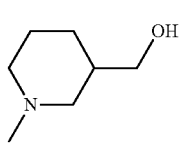 | 384.2784 |
| 1209 | N,N'-Dimethyl-3-amino-pyrrolidine | 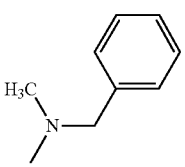 | 395.2943 |
| 1210 | 3-(Hydroxymethyl)piperidine | 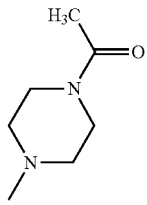 | 396.2797 |
| 1211 | N-Methyl-benzylamine | 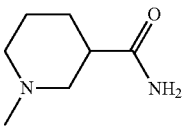 | 402.2664 |
| 1212 | 1-Acetylpiperazine | 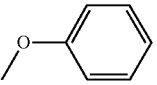 | 409.2721 |
| 1213 | Nipecotamide | | 409.2733 |
| 1214 | Phenol | | 375.2200 |

-continued

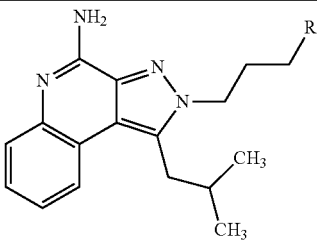

| Example | Reagent | R | Measured Mass (M + H) |
|---|---|---|---|
| 1215 | 3-Methoxyphenol | (3-methoxyphenoxy group) | 405.2329 |
| 1216 | 3-Chlorophenol | (3-chlorophenoxy group) | 409.1805 |

Examples 1217-1241

Part A

A mixture of 2-tert-butoxycarbonylamino-3-pyridylboronic acid (11.37 g, 47.78 mmol, prepared as described in Example 15), n-propanol (80 mL), and 1 M hydrochloric acid (60 mL) was heated in an oil bath at 80° C. for 1 hour and then allowed to cool to ambient temperature. Solid sodium carbonate was added with stirring to neutralize the hydrochloric acid and to serve as a base in the next step.

Part B tert-Butyl 2-(4-bromo-3-cyano-1-propyl-1H-pyrazol-5-yl)ethylcarbamate (11.36 g, 31.84 mmol, prepared as described in Example 51), n-propanol (20 mL), and palladium (II) acetate (143 mg, 0.64 mmol) were added to the mixture from Part A. The reaction mixture was degassed and backfilled with nitrogen three times and then heated at 100° C. for 2 days. The reaction mixture was allowed to cool to ambient temperature and the n-propanol was removed under reduced pressure. The residue was diluted with chloroform (250 mL), washed with water (2×100 mL), dried over magnesium sulfate, filtered, and then concentrated under reduced pressure to provide a light yellow solid. This material was purified by chromatography on a HORIZON HPFC system (silica gel eluting with a gradient of 0-45% of 80:20 CMA:chloroform in chloroform) to provide 2.47 g of a light yellow solid. This material was suspended in acetonitrile (25 mL), sonicated for about 15 seconds, isolated by filtration, rinsed with acetonitrile, and dried to provide 2.25 g of tert-butyl 2-(4-amino-2-propyl-2H-pyrazolo[3,4-c]-1,8-naphthyridin-1-yl)ethylcarbamate as a white solid.

Part C

Hydrochloric acid (3 mL of 2.7 M in ethanol) was added to a suspension of tert-butyl 2-(4-amino-2-propyl-2H-pyrazolo[3,4-c]-1,8-naphthyridin-1-yl)ethylcarbamate (0.52 g) in ethanol (10 mL). The mixture was heated at 80° C. for about 1 hour and then concentrated under reduced pressure. The residue was partitioned between water (50 mL) and dichloromethane (30 mL). The layers were separated. The aqueous layer was made basic with ammonium hydroxide and then extracted with dichloromethane (2×50 mL). The combined organics were washed with brine (1×50 mL), dried over magnesium sulfate, filtered, and then concentrated under reduced pressure to provide 0.29 g of crude product as a white solid. The reaction was repeated using 2.05 g of starting material to provide 1.18 g of crude product as a white solid. The two lots were combined and purified by chromatography on a HORIZON HPFC system (silica gel eluting with a gradient of 20-60% of 80:20 CMA:chloroform in chloroform) to provide 0.48 g of 1-(2-aminoethyl)-2-propyl-2H-pyrazolo[3,4-c]-1,8-naphthyridin-4-amine as a white solid.

Part D

A reagent (0.11 mmol, 1.1 equivalents) from the table below was added to a test tube containing 1-(2-aminoethyl)-2-propyl-2H-pyrazolo[3,4-c]-1,8-naphthyridin-4-amine (26 mg, 0.10 mmol) and N,N-diisopropylethylamine (approximately 36 µL, 2 equivalents) in chloroform (2 mL). The test tubes were capped and shaken for about 4 hours. Two drops of water were added to each test tube, and the solvent was removed by vacuum centrifugation. The compounds were purified as described in Examples 71-85. The table below shows the reagent added to each test tube, the structure of the resulting compound, and the observed accurate mass for the isolated trifluoroacetate salt.

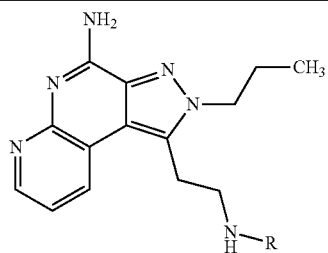

| Example | Reagent | R | Measured Mass (M + H) |
|---|---|---|---|
| 1217 | None—starting material only | H | 271.1696 |
| 1218 | Acetyl chloride | (acetyl) | 313.1781 |
| 1219 | Propionyl chloride | (propionyl) | 327.1962 |
| 1220 | Cyclopropanecarbonyl chloride | (cyclopropanecarbonyl) | 339.1948 |

471
-continued

| Example | Reagent | R | Measured Mass (M + H) |
|---|---|---|---|
| 1221 | Butyryl chloride | -C(=O)-CH2-CH2-CH3 | 341.2108 |
| 1222 | Isobutyryl chloride | -C(=O)-CH(CH3)2 | 341.2107 |
| 1223 | Benzoyl chloride | -C(=O)-C6H5 | 375.1966 |
| 1224 | Cyclohexanecarbonyl chloride | -C(=O)-cyclohexyl | 381.2433 |
| 1225 | Nicotinoyl chloride hydrochloride | -C(=O)-(3-pyridyl) | 376.1888 |
| 1226 | Methanesulfonyl chloride | -S(=O)2-CH3 | 349.1472 |
| 1227 | Ethanesulfonyl chloride | -S(=O)2-CH2CH3 | 363.1638 |
| 1228 | 1-Propanesulfonyl chloride | -S(=O)2-CH2CH2CH3 | 377.1736 |

472
-continued

| Example | Reagent | R | Measured Mass (M + H) |
|---|---|---|---|
| 1229 | Isopropylsulfonyl chloride | -S(=O)2-CH(CH3)2 | 377.1794 |
| 1230 | 1-Butanesulfonyl chloride | -S(=O)2-CH2CH2CH2CH3 | 391.1938 |
| 1231 | Benzenesulfonyl chloride | -S(=O)2-C6H5 | 411.1636 |
| 1232 | 2,2,2-Trifluoroethanesulfonyl chloride | -S(=O)2-CH2-CF3 | 417.1358 |
| 1233 | Methyl isocyanate | -C(=O)-NH-CH3 | 328.1909 |
| 1234 | Ethyl isocyanate | -C(=O)-NH-CH2CH3 | 342.2059 |
| 1235 | Isopropyl isocyanate | -C(=O)-NH-CH(CH3)2 | 356.2222 |
| 1236 | N-Propyl isocyanate | -C(=O)-NH-CH2CH2CH3 | 356.2213 |

| Example | Reagent | R | Measured Mass (M + H) |
|---|---|---|---|
| 1237 | Cyclopentyl isocyanate | | 382.2394 |
| 1238 | Cyclohexyl isocyanate | | 396.2547 |
| 1239 | 1-Pyrrolidinecarbonyl chloride | | 368.2217 |
| 1240 | 1-Piperidinecarbonyl chloride | | 382.2379 |
| 1241 | 4-Morpholinecarobonyl chloride | | 384.2181 |

Example 1242

N-[2-(4-Amino-2-propyl-2H-pyrazolo[3,4-c]quinolin-1-yl)-1,1-dimethylethyl]cyclopropylamide

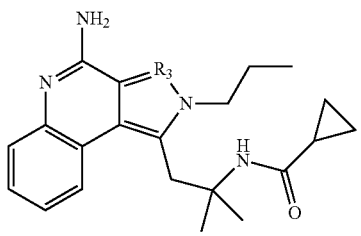

Cyclopropanecarbonyl chloride (454 μL, 5.00 mmol) was added to a stirred solution of 1-(2-amino-2-methylpropyl)-2-propyl-2H-pyrazolo[3,4-c]quinolin-4-amine (prepared as described in Example 64, 595 mg, 2.00 mmol) and triethylamine (895 μL, 6.4 mmol) in dichloromethane (18 mL). The solution was stirred for 15 minutes at room temperature and then was concentrated under reduced pressure to yield a yellow solid that was dissolved in methanol (20 mL). Concentrated hydrochloric acid (4 mL) was added to the resulting solution, and the reaction was heated at reflux for 20 hours and allowed to cool to room temperature. Aqueous sodium carbonate (15 mL of 2 M) was added, and the methanol was removed under reduced pressure. The resulting mixture was extracted four times with chloroform. The combined extracts were dried over sodium sulfate, filtered, and concentrated under reduced pressure. The crude product (1.2 g) was purified by IFC using a silica cartridge followed by recrystallization from 35% ethyl acetate in hexanes (50 mL). The crystals were dried overnight on the filter funnel and then dried overnight under vacuum at 98° C. to provide 463 mg of N-[2-(4-amino-2-propyl-2H-pyrazolo[3,4-c]quinolin-1-yl)-1,1-dimethylethyl]cyclopropylamide as a white solid, mp 192-193° C.

MS (APCI) m/z 366 (M+H)+;

Anal. Calcd for $C_{21}H_{27}N_5O$: C, 69.01; H, 7.45; N, 19.16. Found: C, 68.66; H, 7.46; N, 19.13.

Example 1243

N-{2-[4-Amino-2-(2-methoxyethyl)-2H-pyrazolo[3,4-c]quinolin-1-yl]-1,1-dimethylethyl}cyclopropylamide

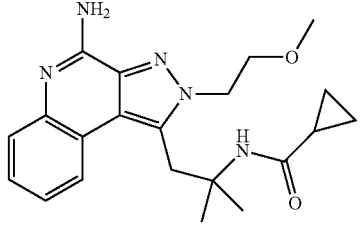 [SMILES: COCCn1nc2c(N)nc3ccccc3c2c1CC(C)(C)NC(=O)C1CC1]

The methods described in Example 1242 were used treat 1-(2-amino-2-methylpropyl)-2-(2-methoxyethyl)-2H-pyrazolo[3,4-c]quinolin-4-amine (0.500 g, 1.60 mmol), prepared as described in Example 590, with cyclopropanecarbonyl chloride and to isolate and purify the final product to provide 267 mg of N-{2-[4-amino-2-(2-methoxyethyl)-2H-pyrazolo[3,4-c]quinolin-1-yl]-1,1-dimethylethyl}cyclopropylamide as a white solid, mp 180-181° C.

MS (APCI) m/z 382 (M+H)+;

Anal. Calcd for $C_{21}H_{27}N_5O_2$: C, 66.12; H, 7.13; N, 18.36. Found: C, 66.06; H, 7.48; N, 18.35.

Example 1244

1-(2-Amino-2-methylpropyl)-2-ethyl-2H-pyrazolo[3,4-c]quinolin-4-amine

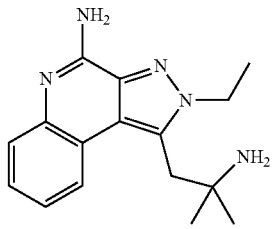 [SMILES: CCn1nc2c(N)nc3ccccc3c2c1CC(C)(C)N]

The methods described in Parts A through C of Example 64 were followed using ethylhydrazine oxalate in lieu of propylhydrazine oxalate in Part A to provide tert-butyl 2-[3-(aminocarbonyl)-1-ethyl-1H-pyrazol-5-yl]-1,1-dimethylethylcarbamate, which was recrystallized from 75:25 ethyl acetate:hexanes to yield a white solid, mp 178-180° C. Anal. Calcd for $C_{15}H_{26}N_4O_3$: C, 58.04; H, 8.44; N, 18.05. Found: C, 58.08; H, 8.72; N, 18.14.

The methods described in Parts D through G of Example 64 were then used to convert tert-butyl 2-[3-(aminocarbonyl)-1-ethyl-1H-pyrazol-5-yl]-1,1-dimethylethylcarbamate to 1-(2-amino-2-methylpropyl)-2-ethyl-2H-pyrazolo[3,4-c]quinolin-4-amine. The final crude product (5.08 g) was recrystallized from a mixture of 35% ethyl acetate in hexanes (100 mL) and ethyl acetate (200 mL). The mother liquor was concentrated under reduced pressure, and the residue was purified by IFC (silica cartridge) to provide 1-(2-amino-2-methylpropyl)-2-ethyl-2H-pyrazolo[3,4-c]quinolin-4-amine as a beige solid, mp 234-235° C.

MS (APCI) m/z 284 (M+H)$^+$;

Anal. Calcd for $C_{16}H_{21}N_5$: C, 67.82; H, 7.47; N, 24.71. Found: C, 67.60; H, 7.38; N, 24.57.

Examples 1245-1251

The method described in Example 65 can be used to treat 1-(2-amino-2-methylpropyl)-2-ethyl-2H-pyrazolo[3,4-c]quinolin-4-amine with the acid chlorides shown in the following table to provide the compounds shown in the following table.

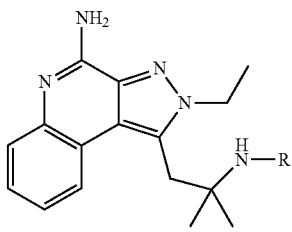

| Example | Reagent | Name | R |
|---|---|---|---|
| 1245 | Acetyl chloride | N-[2-(4-Amino-2-ethyl-2H-pyrazolo[3,4-c]quinolin-1-yl)-1,1-dimethylethyl]acetamide | |
| 1246 | Nicotinoyl chloride hydrochloride | N-[2-(4-Amino-2-ethyl-2H-pyrazolo[3,4-c]quinolin-1-yl)-1,1-dimethylethyl]nicotinamide | |
| 1247 | Isonicotinoyl chloride hydrochloride | N-[2-(4-Amino-2-ethyl-2H-pyrazolo[3,4-c]quinolin-1-yl)-1,1-dimethylethyl]isonicotinamide | |

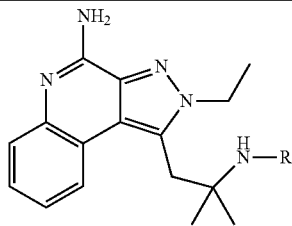

| Example | Reagent | Name | R |
|---|---|---|---|
| 1248 | 4-Fluorobenzoyl chloride | N-[2-(4-Amino-2-ethyl-2H-pyrazolo[3,4-c]quinolin-1-yl)-1,1-dimethylethyl]-4-fluorobenzamide | |
| 1249 | 3,4-Difluorobenzoyl chloride | N-[2-(4-Amino-2-ethyl-2H-pyrazolo[3,4-c]quinolin-1-yl)-1,1-dimethylethyl]-3,4-difluorobenzamide | |
| 1250 | Propionyl chloride | N-[2-(4-Amino-2-ethyl-2H-pyrazolo[3,4-c]quinolin-1-yl)-1,1-dimethylethyl]propionamide | |
| 1251 | Cyclopropanecarbonyl chloride | N-[2-(4-Amino-2-ethyl-2H-pyrazolo[3,4-c]quinolin-1-yl)-1,1-dimethylethyl]cyclopropylamide | |

Example 1252

N-[2-(4-Amino-2-ethyl-2H-pyrazolo[3,4-c]quinolin-1-yl)-1,1-dimethylethyl]methanesulfonamide

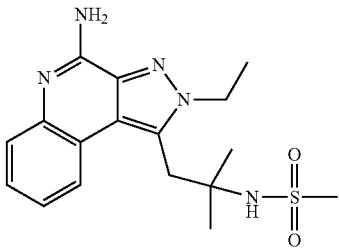 [SMILES: CCn1nc2c(N)nc3ccccc3c2c1CC(C)(C)NS(C)(=O)=O]

Under a nitrogen atmosphere, a solution of 1-(2-amino-2-methylpropyl)-2-ethyl-2H-pyrazolo[3,4-c]quinolin-4-amine (609 mg, 2.15 mmol) in dichloromethane (60 mL) was cooled to 0° C. Triethylamine (326 mg, 3.22 mmol) and methanesulfonyl chloride (246 mg, 2.15 mmol) were sequentially added. The reaction was stirred at 0° C. for five hours and then allowed to warm to room temperature slowly and stirred overnight. Water was added, and the aqueous layer was separated and extracted four times with chloroform. The combined organic fractions were dried over magnesium sulfate, filtered, and concentrated under reduced pressure. The crude product was purified by TFC (silica cartridge) followed by recrystallization from acetonitrile. The crystals were dried overnight on the vacuum filter funnel to provide 363 mg of N-[2-(4-amino-2-ethyl-2H-pyrazolo[3,4-c]quinolin-1-yl)-1,1-dimethylethyl]methanesulfonamide as a white solid, mp 229-230° C.

MS (APCI) m/z 362 (M+H)$^+$;

Anal. Calcd for $C_{17}H_{23}N_5O_2S$: C, 56.49; H, 6.41; N, 19.37. Found: C, 56.46; H, 6.77; N, 19.70.

Example 1253

1-(4-Chlorobutyl)-2-methyl-2H-pyrazolo[3,4-c]quinolin-4-amine

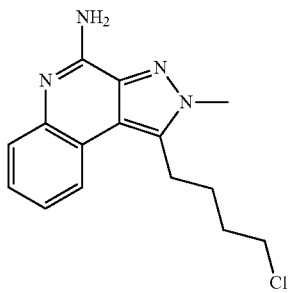 [SMILES: Cn1nc2c(N)nc3ccccc3c2c1CCCCCl]

Part A

Ethyl 5-(4-chlorobutyl)-1-methyl-1H-pyrazole-3-carboxylate (163 g) was prepared using a modification of the procedure described in Part A of Example 19. Methylhydrazine was used instead of ethylhydrazine oxalate. After all the reagents were added, the reaction mixture was stirred overnight instead of two hours. Dichloromethane was used for extraction during the work-up procedure, and the combined extracts were not dried. The product was obtained as a dark oil, which was treated according to the method of Part B of Example 46 to provide 5-(4-chlorobutyl)-1-methyl-1H-pyrazole-3-carboxylic acid.

Part B

To a solution of the carboxylic acid from Part A (0.666 mol) in dichloromethane (1 L) and DMF (0.5 mL) at 0° C. was added oxalyl chloride (64.0 mL, 0.73 mol). The reaction was stirred for one hour at ambient temperature. An analysis by HPLC indicated the presence of starting material, and additional oxalyl chloride (35 mL) was added. The reaction was stirred at ambient temperature for one hour and concentrated under reduced pressure. The residue was dissolved in a small volume of dichloromethane and added slowly to concentrated ammonium hydroxide (888 mL of 15 M) cooled to approximately 0° C. The reaction was stirred at ambient temperature for two days. A precipitate was present and was isolated by filtration and washed with water. The filtrate was extracted with dichloromethane. The organic fraction was dried over sodium sulfate, filtered, and concentrated under reduced pressure to yield a tan solid that was combined with the isolated precipitate to provide 103 g of 5-(4-chlorobutyl)-1-methyl-1H-pyrazole-3-carboxamide.

Part C

A solution of 5-(4-chlorobutyl)-1-methyl-1H-pyrazole-3-carboxamide (39 g, 0.181 mol) and triethylamine (75 mL, 0.54 mol) in dichloromethane (600 mL) was cooled to approximately 0° C., and trifluoroacetic anhydride (31 mL, 0.22 mol) was added. The reaction was stirred for one hour, and then saturated aqueous ammonium chloride (50 mL) was added. The mixture was diluted with water and extracted with dichloromethane. The combined organic fractions were dried over sodium sulfate and concentrated under reduced pressure to 5-(4-chlorobutyl)-1-methyl-1H-pyrazole-3-carbonitrile as a dark brown oil.

Part D

Potassium acetate (35.5 g, 0.362 mol) and bromine (12 mL, 0.235 mol) were added to a solution of the material from Part C in acetic acid (362 mL), and the reaction was stirred for two hours at ambient temperature. An analysis by LC/MS indicated the presence of starting material, and additional bromine (0.5 equivalent) was added. The reaction was stirred for two more hours and again was found to be incomplete. Additional bromine (0.5 equivalent) was added, and the reaction was stirred for one hour. Aqueous sodium bisulfite (1 mL) was added, and the mixture was stirred until it became colorless. The acetic acid was removed under reduced pressure, and water was added to the residue. The resulting mixture was extracted with dichloromethane. The combined extracts were dried over sodium sulfate, filtered, and concentrated under reduced pressure. The crude product was purified through a plug of silica gel (eluting with 70:30 hexanes:ethyl acetate) to provide 51 g of 4-bromo-5-(4-chlorobutyl)-1-methyl-1H-pyrazole-3-carbonitrile as a dark oil.

Part E

The method described in Part F of Example 46 was used to couple 4-bromo-5-(4-chlorobutyl)-1-methyl-1H-pyrazole-3-carbonitrile (16.0 g, 60.0 mmol) and 2-aminophenylboronic acid hydrochloride (20.8 g, 0.120 mol). After the mixture was heated at 115° C. for 24 hours, it was cooled to ambient temperature and filtered through a plug of silica gel (eluting with 3:2 chloroform/methanol). The filtrate was concentrated under reduced pressure and dissolved in ethanol (300 mL). Hydrogen chloride (45 mL of a 4 M solution in ethanol) was added to the solution, and the reaction was heated at reflux for two hours and then cooled to ambient temperature. A precipitate formed and was isolated by filtration and washed with ethanol to provide 1-(4-chlorobutyl)-2-methyl-2H-pyrazolo[3,4-c]quinolin-4-amine hydrochloride. The filtrate was concentrated under reduced pressure and the resulting solid was dissolved in dichloromethane and water. The pH of the solution was raised to 14 using 50% aqueous NaOH while keeping the temperature at 0° C. by adding ice. The layers were separated, the aqueous layer was extracted with additional dichloromethane, the organic layers were combined, dried over $Na_2SO_4$, filtered and concentrated to a dark yellow oily solid. The residue was purified by chromatography using a HORIZON HPFC system (40+M cartridge, eluting with 0-30% CMA in chloroform) followed by recrystallization from acetonitrile to provide 1-(4-chlorobutyl)-2-methyl-2H-pyrazolo[3,4-c]quinolin-4-amine. This solid was purified as light tan crystals, mp 188-189° C.

MS (APCI) m/z 289 (M+H)

Anal. calcd for $C_{15}H_{17}ClN_4$: C, 62.39; H, 5.93; N, 19.40. Found: C, 62.60; H, 5.99; N, 19.67. +;

Example 1254

N-[4-(4-Amino-2-methyl-2H-pyrazolo[3,4-c]quinolin-1-yl)butyl]methanesulfonamide

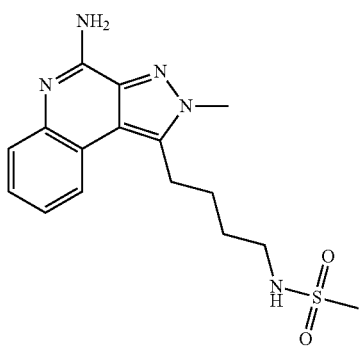 [SMILES: Cn1nc2c(N)nc3ccccc3c2c1CCCCNS(C)(=O)=O]

Methanesulfonamide (1.5 g, 16.5 mmol) was added to a suspension of sodium hydride (60% dispersion in mineral oil, 0.660 g, 16.5 mmol) in DMF (10 mL); the reaction was stirred for five minutes. 1-(4-Chlorobutyl)-2-methyl-2H-pyrazolo [3,4-c]quinolin-4-amine (0.952 g, 3.3 mmol) in DMF (1 mL) and sodium iodide (123 mg, 0.825 mmol) were sequentially added. The reaction was heated at 80° C. for four hours, allowed to cool to ambient temperature, and poured into ice water (70 mL). The resulting mixture was extracted with dichloromethane (6×50 mL), and the combined extracts were dried over sodium sulfate, filtered, and concentrated under reduced pressure. The residue was purified twice by chromatography using a HORIZON HPFC system (40+M cartridge, eluting with 0-30% CMA in chloroform first and 5-10% methanol in dichloromethane second) followed by recrystallization from acetonitrile to provide 440 mg of N-[4-(4-amino-2-methyl-2H-pyrazolo[3,4-c]quinolin-1-yl)butyl] methanesulfonamide as light tan crystals, mp 188-189° C.

MS (APCI) m/z 289 (M+H)$^+$;

Anal. calcd for $C_{15}H_{17}ClN_4$: C, 62.39; H, 5.93; N, 19.40. Found: C, 62.60; H, 5.99; N, 19.67.

Example 1255

1-(4-Chlorobutyl)-2-(2-methoxyethyl)-2H-pyrazolo [3,4-c]quinolin-4-amine

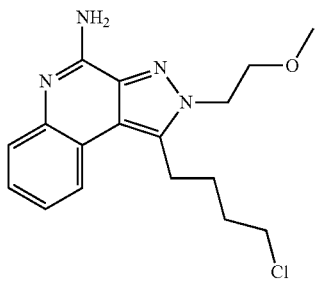 [SMILES: COCCn1nc2c(N)nc3ccccc3c2c1CCCCCl]

Part A

Ethyl 5-(4-chlorobutyl)-1-(2-hydroxyethyl)-1H-pyrazole-3-carboxylate (175 g) was prepared using a modification of the procedure described in Part A of Example 19. Hydroxyethylhydrazine was used instead of ethylhydrazine oxalate. After all the reagents were added, the reaction mixture was stirred overnight instead of two hours.

Part B

A solution of ethyl 5-(4-chlorobutyl)-1-(2-hydroxyethyl)-1H-pyrazole-3-carboxylate (165 g, 0.600 mol) and iodomethane (187 mL, 3.00 mol) in THF (1.2 L) was cooled to 0° C. Sodium hydride (28.8 g of a 60% dispersion in mineral oil, 0.720 mol) was added slowly while maintaining the temperature below 10° C. The reaction was allowed to warm to ambient temperature and stirred overnight. Aqueous ammonium chloride and water were added, and the mixture was extracted with dichloromethane. The combined extracts were dried over sodium sulfate, filtered, and concentrated under reduced pressure to provide ethyl 5-(4-chlorobutyl)-1-(2-methoxyethyl)-1H-pyrazole-3-carboxylate as a dark brown oil.

Part C

A solution of the material from Part B in ethanol (500 mL) was combined with 6 M aqueous sodium hydroxide (200 mL, 1.20 mol), and the reaction was stirred at ambient temperature for 5 hours. The ethanol was removed under reduced pressure, and the residue was stirred with water for five minutes. The solution was adjusted with 3 N aqueous hydrochloric acid to pH 4; a precipitate formed. The mixture was stirred for 30 minutes, and the precipitate was then isolated by filtration, washed with water, dried on the filter funnel for two hours to provide 5-(4-chlorobutyl)-1-(2-methoxyethyl)-1H-pyrazole-3-carboxylic acid, which was dissolved in dichloromethane. The resulting solution was dried over sodium sulfate, filtered, and then used in Part D.

Part D

A modification of the method described in Part B of Example 1253 was followed. After the second additional of oxalyl chloride, the reaction was stirred for 18 hours at ambient temperature. After the reaction with ammonium hydroxide was stirred for three hours, the precipitate was not isolated by filtration, but the mixture was extracted several times with dichloromethane. The combined extracts were dried, filtered, and concentrated to provide 5-(4-chlorobutyl)-1-(2-methoxyethyl)-1H-pyrazole-3-carboxamide as a dark oil, which was treated with trifluoroacetic anhydride according to the method of Part C of Examples 1253 to provide 5-(4-chlorobutyl)-1-(2-methoxyethyl)-1H-pyrazole-3-carbonitrile as a dark brown oil.

Part E

Potassium acetate (193 g, 1.97 mol) and bromine (69 mL, 1.4 mol) were added to a solution of the carbonitrile from Part D in acetic acid (1 L), and the reaction was stirred for 24 hours at ambient temperature. An analysis by LC/MS indicated the presence of starting material, and additional bromine (15 mL) was added. The reaction again was found to be incomplete. Additional bromine (15 mL) was added, and the reaction was then treated according to the work-up procedure described in Part D of Example 1253 to provide 144 g of 4-bromo-5-(4-chlorobutyl)-1-(2-methoxyethyl)-1H-pyrazole-3-carbonitrile as a brown oil, which was used without purification.

Part F

2-Aminophenylboronic acid hydrochloride (16.2 g, 93.5 mmol), potassium carbonate (42.5 g, 308 mmol), DME (333 mL), water (166 mL), and 4-bromo-5-(4-chlorobutyl)-1-(2-methoxyethyl)-1H-pyrazole-3-carbonitrile (30 g, 93.5 mmol) were combined in a flask, which was then evacuated three times and filled with nitrogen. Dichlorobis(triphenylphosphine)palladium(II) (0.65 g, 0.94 mmol) was then added, and the reaction was heated at 110° C. for one hour. An analysis by HPLC indicated the presence of starting material, and additional 2-aminophenylboronic acid hydrochloride (16.2 g, 93.5 mmol) and dichlorobis(triphenylphosphine)palladium(II) (0.65 g, 0.94 mmol) were added. The reaction was then heated at reflux overnight and allowed to cool to ambient temperature. Water (30 mL) was added, and the mixture was extracted with ethyl acetate. The combined extracts were dried over sodium sulfate, filtered through a layer of CELITE filter agent, and concentrated under reduced pressure. The crude product was purified by column chromatography on silica gel (eluting sequentially with 25% ethyl acetate in hexanes and 75% ethyl acetate in hexanes) to provide 18 g of 4-(2-aminophenyl)-5-(4-chlorobutyl)-1-(2-methoxyethyl)-1H-pyrazole-3-carbonitrile as a maroon oil.

Part G

Acetyl chloride (15 mL, 216 mmol) was added to ethanol (170 mL) at 0° C. A solution of the material from Part F in ethanol (100 mL) was added, and the resulting solution was heated at reflux for two hours and allowed to cool to ambient temperature overnight. The ethanol was removed under reduced pressure. The residue was diluted with dichloromethane (100 mL) and adjusted to pH 12 with the addition of ice and 50% w/w aqueous sodium hydroxide. The aqueous fraction was extracted with dichloromethane (3×100 mL), and the combined organic fractions dried over sodium sulfate, filtered, and concentrated under reduced pressure to provide a semi-solid. The semi-solid was triturated with diethyl ether and isolated by filtration to provide 10 g of 1-(4-chlorobutyl)-2-(2-methoxyethyl)-2H-pyrazolo[3,4-c]quinolin-4-amine. A small portion of the product was recrystallized from acetonitrile to provide white crystals, mp 156-157° C.

MS (APCI) m/z 333 (M+H)$^+$;

Anal. calcd for $C_{17}H_{21}ClN_4O$: C, 61.35; H, 6.36; N, 16.83. Found: C, 61.51; H, 6.65; N, 17.01.

Example 1256

N-{-4-[4-Amino-2-(2-methoxyethyl)-2H-pyrazolo[3,4-c]quinolin-1-yl]butyl}methanesulfonamide

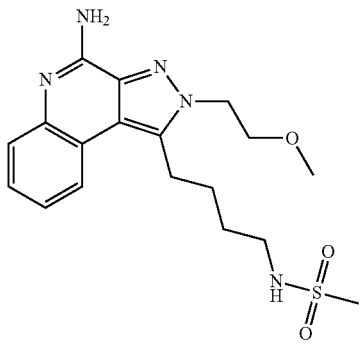 [SMILES: COCCn1nc2c(N)nc3ccccc3c2c1CCCCNS(C)(=O)=O]

The method described in Example 1254 was used to treat 1-(4-chlorobutyl)-2-(2-methoxyethyl)-2H-pyrazolo[3,4-c]quinolin-4-amine (1.1 g, 3.3 mmol) with methanesulfonamide pretreated with sodium hydride in the presence of sodium iodide. The crude was purified by chromatography using a HORIZON HPFC system (40+M cartridge, eluting with 0-30% CMA in chloroform) followed by recrystallization from acetonitrile to provide 600 mg of N-{4-[4-amino-2-(2-methoxyethyl)-2H-pyrazolo[3,4-c]quinolin-1-yl]butyl}methanesulfonamide as white crystals, mp 159-161° C.

MS (APCI) m/z 392 (M+H)$^+$;

Anal. calcd for $C_{18}H_{25}N_5O_3S$: C, 55.22; H, 6.44; N, 17.89. Found: C, 55.40; H, 6.33; N, 18.13.

Example 1257

N-[3-(4-Amino-2H-pyrazolo[3,4-c]quinolin-1-yl)propyl]methanesulfonamide hydrochloride

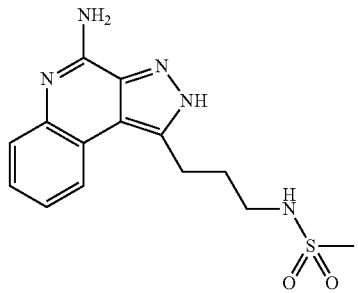 [SMILES: CS(=O)(=O)NCCCc1[nH]nc2c(N)nc3ccccc3c12]

A mixture of N-[3-(4-amino-2-tert-butyl-2H-pyrazolo[3,4-c]quinolin-1-yl)propyl]methanesulfonamide (Example 584, 0.410 g, 1.37 mmol), hydrogen bromide (0.7 mL of a 48% solution in water, 13.7 mmol) and acetonitrile (7 mL) was stirred overnight at ambient temperature. The solvent was removed under reduced pressure, and the residue was dissolved in water and treated with 50% w/w aqueous sodium hydroxide. The resulting solution was washed with dichloromethane and then adjusted to pH 4 with the addition of concentrated hydrochloric acid. A precipitate formed, was isolated by filtration, and was dried on the filter funnel to provide 0.39 g of N-[3-(4-amino-2H-pyrazolo[3,4-c]quinolin-1-yl)propyl]methanesulfonamide hydrochloride as a white powder, mp>250° C.

MS (APCI) m/z 320 (M+H)$^+$;

Anal. calcd for $C_{14}H_{17}N_5O_2S \cdot H_2O \cdot HCl$: C, 44.98; H, 5.39; N, 18.73. Found: C, 44.88; H, 5.27; N, 18.57.

Example 1258

1-(4-Amino-2-butyl-2H-pyrazolo[3,4-c]quinolin-1-yl)-2-methylpropan-2-ol

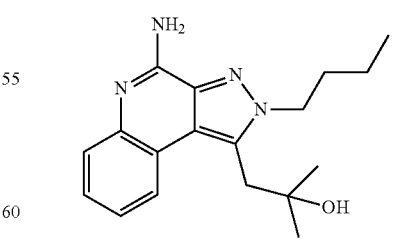

Part A

A mixture sodium tert-butoxide (23.0 g, 0.240 mol) and ethanol (200 mL) was stirred for 30 minutes at 0° C.; most of the solid was dissolved. A mixture of diethyl oxalate (32.6 mL, 0.240 mol) and 4-hydroxy-4-methyl-2-pentanone (25.0 mL, 0.200 mol) was added slowly, and the reaction was stirred for ten minutes at 0° C. before the addition of acetic acid (100 mL). The reaction was warmed to ambient temperature and stirred for ten minutes. Potassium acetate (29.4 g, 0.300 mol) and butylhydrazine oxalate (30.0 g, 0.200 mol) were sequentially added. The reaction was stirred overnight at ambient temperature, and the acetic acid was removed under reduced pressure. The residue was adjusted to pH 14 with the addition of 50% w/w aqueous sodium hydroxide while maintaining the temperature at 0° C. with the addition of ice. The mixture was extracted with dichloromethane; the combined extracts were dried over sodium sulfate, filtered, and concentrated under reduced pressure. The crude product was purified by chromatography on a HORIZON HPFC system (65+M cartridge, eluting with 0 to 70% ethyl acetate in hexanes) to provide 26 g of ethyl 1-butyl-5-(2-hydroxy-2-methylpropyl)-1H-pyrazole-3-carboxylate as a yellow oil.

Part B

Ethyl 1-butyl-5-(2-hydroxy-2-methylpropyl)-1H-pyrazole-3-carboxylate (26 g, 97 mmol) and ammonia (160 mL of a 7 N solution in methanol) were heated at 150° C. in a stainless steel reactor for 42 hours and allowed to cool to ambient temperature. The volatiles were removed under reduced pressure to provide 1-butyl-5-(2-hydroxy-2-methylpropyl)-1H-pyrazole-3-carboxamide as a black oil, which was treated with trifluoroacetic anhydride (40 mL, 289 mmol) and triethylamine (53 mL, 386 mmol) according to a modification of the method of Part C of Example 1253 to provide 2-(1-butyl-3-cyano-1H-pyrazol-5-yl)-1,1-dimethylethyl trifluoroacetate as a dark brown oil. The reaction with trifluoroacetic anhydride was stirred for three hours.

Part C

Potassium carbonate (20 g, 145 mmol) was added to a solution of the trifluoroacetate from Part B in ethanol (192 mL) and water (57 mL), and the mixture was stirred at ambient temperature for two hours and then filtered to remove a solid. The filtrate was concentrated under reduced pressure, and the residue was partitioned between dichloromethane and water. The aqueous fraction was extracted with dichloromethane, and the combined organic fractions were dried over sodium sulfate, filtered, and concentrated under reduced pressure. The crude product was purified by chromatography on a HORIZON HPLC system (601 cartridge, eluting with 0 to 50% ethyl acetate in hexanes to provide 18 g of 1-butyl-5-(2-hydroxy-2-methylpropyl)-1H-pyrazole-3-carbonitrile as a yellow oil.

Part D

The method described in Part F of Examples 1 through 4 was used to treat 1-butyl-5-(2-hydroxy-2-methylpropyl)-1H-pyrazole-3-carbonitrile (18 g, 81 mmol) with potassium acetate (16.7 g, 171 mmol) and bromine (4.6 mL, 89 mmol). After the acetic acid was removed under reduced pressure, the residue was diluted with dichloromethane (100 mL) and adjusted to pH 12 with the addition of 50% w/w aqueous sodium hydroxide and ice while maintaining the temperature at 0° C. The resulting mixture was extracted with dichloromethane, and the combined extracts were dried over sodium sulfate, filtered, and concentrated under reduced pressure. The crude product was purified by chromatography on a HORIZON HPFC system (601 cartridge, eluting with 0 to 50% ethyl acetate in hexanes to provide 13 g of 1-butyl-4-bromo-5-(2-hydroxy-2-methylpropyl)-1H-pyrazole-3-carbonitrile as a yellow oil.

Part E

A modification of the method described in Part H of Example 1255 was used to treat 1-butyl-4-bromo-5-(2-hydroxy-2-methylpropyl)-1H-pyrazole-3-carbonitrile (2.7 g, 9.2 mmol). Two equivalents of 2-aminophenylboronic acid hydrochloride (3.2 g, 18.4 mmol) and 2 mol % dichlorobis(triphenylphosphine)palladium(II) (0.126 g, 0.18 mmol) were added at the beginning of the reaction, and the reaction was heated at reflux for five hours. The crude product was purified by chromatography on a HORIZON HPFC system (40+M cartridge, eluting with 0 to 50% ethyl acetate in hexanes to provide 4-(2-aminophenyl)-1-butyl-5-(2-hydroxy-2-methylpropyl)-1H-pyrazole-3-carbonitrile.

Part F

The method described in Part G of Example 1255 was used to treat the material from Part E with the modification that the reaction was heated at reflux for three hours. The crude product was purified by chromatography and recrystallization according to the methods described in Example 1256 to provide 210 mg of 1-(4-amino-2-butyl-2H-pyrazolo[3,4-c]quinolin-1-yl)-2-methylpropan-2-ol as white crystals, mp 171-172° C.

MS (APCI) m/z 313 (M+H)$^+$;

Anal. calcd for $C_{18}H_{24}N_4O$: C, 69.20; H, 7.74; N, 17.93. Found: C, 69.00; H, 8.07; N, 18.13.

The mother liquor from the recrystallization was concentrated to provide an additional 0.78 g of product.

Example 1259

1-(4-Amino-2-butyl-6,7,8,9-tetrahydro-2H-pyrazolo[3,4-c]quinolin-1-yl)-2-methylpropan-2-ol

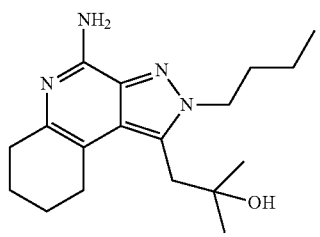 [SMILES: CCCCn1nc2c(N)nc3c(c2c1CC(C)(C)O)CCCC3]

The methods described in Example 586 were used to hydrogenate 1-(4-amino-2-butyl-2H-pyrazolo[3,4-c]quinolin-1-yl)-2-methylpropan-2-ol (0.78 g, 2.5 mmol) in the presence of platinum (IV) oxide (0.78 g) and trifluoroacetic acid (20 mL) and purify the product to provide 0.21 g of 1-(4-amino-2-butyl-2H-pyrazolo[3,4-c]quinolin-1-yl)-2-methylpropan-2-ol as off-white crystals, mp 130° C.

MS (APCI) m/z 317 (M+H)$^+$

Anal. calcd for $C_{18}H_{28}N_4O \cdot 0.12\ H_2O$: C, 67.86; H, 8.93; N, 17.58. Found: C, 67.54; H, 9.15; N, 17.57. ;

Example 1260

1-[4-Amino-2-(2-methoxyethyl)-2H-pyrazolo[3,4-c]quinolin-1-yl]-2-methylpropan-2-ol

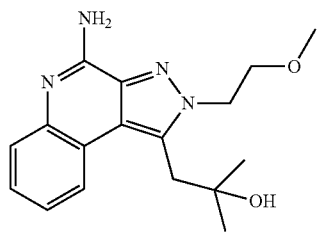 [SMILES: COCCn1nc2c(N)nc3ccccc3c2c1CC(C)(C)O]

Part A

The method described in Part A of Example 1258 was followed using hydroxyethylhydrazine (13.5 mL, 0.200 mol) instead of butylhydrazine oxalate. The crude product was purified by chromatography on a HORIZON HPFC system (65+M cartridge, eluting with 0 to 70% ethyl acetate in hexanes followed by ethyl acetate) to provide 24 g of ethyl 1-(2-hydroxyethyl)-5-(2-hydroxy-2-methylpropyl)-1H-pyrazole-3-carboxylate as a dark yellow oil.

Part B

A solution of ethyl 1-(2-hydroxyethyl)-5-(2-hydroxy-2-methylpropyl)-1H-pyrazole-3-carboxylate (24.6 g, 95.9 mmol) in THF (191 mL) was cooled to 0° C. Sodium hydride (4.6 g of a 60% dispersion in mineral oil, 110 mmol) was added, and iodomethane (6.6 mL, 105 mmol) was added dropwise over a period of ten minutes. The reaction was allowed to warm to ambient temperature and stirred for six hours. The work-up procedure described in Part B of Example 1255 was followed to provide ethyl 5-(2-hydroxy-2-methylpropyl)-1-(2-methoxyethyl)-1H-pyrazole-3-carboxylate as a light brown oil.

Part C

The methods described in Part B of Example 1258 were used to treat the material from Part B with ammonia (160 mL of a 7 N solution in methanol) followed by trifluoroacetic anhydride (60 mL, 287 mmol) to provide 2-[3-cyano-1-(2-methoxyethyl)-1H-pyrazol-5-yl]-1,1-dimethylethyl trifluoroacetate.

Part D

The method described in Part C of Example 1258 was used to treat the trifluoroacetate from Part C with the modification that the reaction was stirred overnight. The product, 5-(2-hydroxy-2-methylpropyl)-1-(2-methoxyethyl)-1H-pyrazole-3-carbonitrile, was treated according to the method described in Part D of Example 1258 with the modification that the crude product was not purified. 4-Bromo-5-(2-hydroxy-2-methylpropyl)-1-(2-methoxyethyl)-1H-pyrazole-3-carbonitrile (10 g) was obtained as a yellow oil.

Part E

The methods described in Parts E and F of Example 1258 were followed using 4-bromo-5-(2-hydroxy-2-methylpropyl)-1-(2-methoxyethyl)-1H-pyrazole-3-carbonitrile (7.0 g, 23 mmol) as the starting material to provide 2.0 g of 1-[4-amino-2-(2-methoxyethyl)-2H-pyrazolo[3,4-c]quinolin-1-yl]-2-methylpropan-2-ol as tan crystals, mp 171-172° C.
MS (APCI) m/z 315 (M+H)$^+$;
Anal. calcd for $C_{17}H_{22}N_4O_2$: C, 64.95; H, 7.05; N, 17.82. Found: C, 64.79; H, 6.99; N, 17.89.
The mother liquor from the recrystallization of the final product was concentrated to provide additional material.

Example 1261

1-[4-Amino-2-(2-methoxyethyl)-6,7,8,9-tetrahydro-2H-pyrazolo[3,4-c]quinolin-1-yl]-2-methylpropan-2-ol

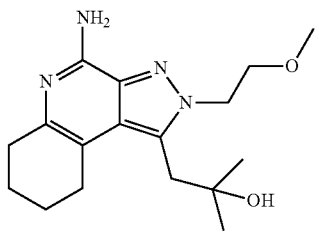 [SMILES: COCCn1nc2c(N)nc3c(c2c1CC(C)(C)O)CCCC3]

The methods described in Example 586 were used to hydrogenate 1-[4-amino-2-(2-methoxyethyl)-2H-pyrazolo[3,4-c]quinolin-1-yl]-2-methylpropan-2-ol (1.75 g, 5.5 mmol) in the presence of platinum (IV) oxide (1.5 g) and trifluoroacetic acid (20 mL) and purify the product with the modification that before recrystallization, the product was also triturated with acetonitrile. 1-[4-Amino-2-(2-methoxyethyl)-6,7,8,9-tetrahydro-2H-pyrazolo[3,4-c]quinolin-1-yl]-2-methylpropan-2-ol (1.0 g) was obtained as white crystals, mp 163-165° C.
MS (APCI) m/z 319 (M+H)$^+$;
Anal. calcd for $C_{17}H_{26}N_4O_2$: C, 64.13; H, 8.23; N, 17.6. Found: C, 64.01; H, 8.37; N, 17.74.

Example 1262

1-[4-Amino-2-(2-hydroxyethyl)-2H-pyrazolo[3,4-c]quinolin-1-yl]-2-methylpropan-2-ol

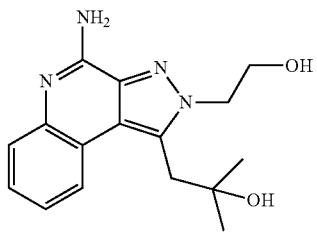 [SMILES: CC(C)(O)Cc1c2c(nn1CCO)c(N)nc1ccccc12]

Under a nitrogen atmosphere, boron tribromide (6 mL of a 1 M solution in dichloromethane) was added to a solution of 1-[4-amino-2-(2-methoxyethyl)-2H-pyrazolo[3,4-c]quinolin-1-yl]-2-methylpropan-2-ol (0.500 g, 1.59 mmol) in dichloromethane (8 mL), and the reaction was stirred for four hours. The dichloromethane was removed under reduced pressure, and the residue was dissolved in a mixture of ethanol and 3 N hydrochloric acid. A solution of 7 N ammonia in methanol was added, and then the solvent was removed under reduced pressure. The treatment with ammonia and the concentration were repeated two more times. The crude product was purified by chromatography using a HORIZON HPFC system (40+M cartridge, eluting with 0-30% CMA in chloroform) followed by trituration with acetonitrile and recrystallization from acetonitrile to provide 115 mg of 1-[4-amino-2-(2-hydroxyethyl)-2H-pyrazolo[3,4-c]quinolin-1-yl]-2-methylpropan-2-ol as white crystals, mp 196-198° C.

MS (APCI) m/z 301 (M+H)$^+$;

Anal. calcd for $C_{16}H_{20}N_4O$: C, 63.98; H, 6.71; N, 18.65. Found: C, 64.05; H, 6.97; N, 18.82.

Example 1263

1-(7-Amino-2-ethyl-5-methyl-2H-pyrazolo[3,4-c]pyridin-3-yl)-2-methylpropan-2-ol

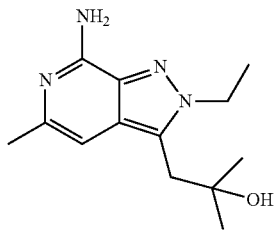 [SMILES: CCn1nc2c(N)nc(C)cc2c1CC(C)(C)O]

Part A

The method described in Part A of Example 1258 was followed using ethylhydrazine oxalate (100 g, 666 mmol) instead of butylhydrazine oxalate. The crude product was purified by chromatography on silica gel (1.6 kg, eluting sequentially with 30% ethyl acetate in hexanes and ethyl acetate) to provide 75 g of ethyl 1-ethyl-5-(2-hydroxy-2-methylpropyl)-1H-pyrazole-3-carboxylate.

Part B

The methods described in Part B of Example 1258 were used to treat the material from Part A with ammonia (500 mL of a 7 N solution in methanol) followed by trifluoroacetic anhydride (132 mL, 936 mmol) and triethylamine (174 mL, 1.25 mol) to provide 2-(3-cyano-1-ethyl-1H-pyrazol-5-yl)-1,1-dimethylethyl trifluoroacetate.

Part C

The method described in Part C of Example 1258 was used to treat the trifluoroacetate from Part B with potassium carbonate (65 g, 470 mmol). The crude product was purified by chromatography on silica gel (600 g, eluting sequentially with 30% ethyl acetate in hexanes and 50% ethyl acetate in hexanes) to provide 44 g of 1-ethyl-5-(2-hydroxy-2-methylpropyl)-1H-pyrazole-3-carbonitrile as a dark yellow oil.

Part D

A solution of iodine monochloride in dichloromethane (10.8 mL of 2 M, 21.6 mmol) was added to a mixture of 1-ethyl-5-(2-hydroxy-2-methylpropyl)-1H-pyrazole-3-carbonitrile (2.0 g, 10.3 mmol), dichloromethane (17 mL) and freshly ground potassium carbonate (2.9 g, 22 mmol). The reaction was stirred for 18 hours. The work-up and purification procedures described in Part D of Example 588 were followed to provide 1.8 g of 1-ethyl-5-(2-hydroxy-2-methylpropyl)-4-iodo-1H-pyrazole-3-carbonitrile as a white solid.

Part E

Under a nitrogen atmosphere, 1-ethyl-5-(2-hydroxy-2-methylpropyl)-4-iodo-1H-pyrazole-3-carbonitrile (900 mg, 2.81 mmol), propargyltrimethylsilane (0.8 mL, 5.6 mmol), copper(I) iodide (107 mg, 0.562 mmol), dichlorobis(triphenylphosphine)palladium(II) (197 mg, 0.281 mmol), triethylamine (1.2 mL, 8.4 mmol) and acetonitrile (14 mL) were combined and then heated at reflux for five hours. The reaction mixture was cooled to ambient temperature, diluted with ethyl acetate, and then filtered through a layer of silica gel. The filtrate was concentrated under reduced pressure. The residue was purified by chromatography on a HORIZON HPFC system (40+M cartridge, eluting with a gradient of 0 to 80% ethyl acetate in hexanes) to provide 1-ethyl-5-(2-hydroxy-2-methylpropyl)-4-(3-trimethylsilylprop-1-ynyl)-1H-pyrazole-3-carbonitrile as a yellow oil.

Part F

The method described in Part F of Example 588 was used to treat the material from Part E with ammonia (30 mL of a 7 N solution in methanol) with the modification that the reaction was heated for 48 hours. Following chromatographic purification according to the method described in Part F of Example 588, the product was recrystallized from acetonitrile to provide 40 mg of 1-(7-amino-2-ethyl-5-methyl-2H-pyrazolo[3,4-c]pyridin-3-yl)-2-methylpropan-2-ol as yellow crystals, mp 134-135° C.

MS (APCI) m/z 249 (M+H)$^+$;

Anal. calcd for $C_{13}H_{20}N_4O$: C, 62.88; H, 8.12; N, 22.56. Found: C, 62.86; H, 8.03; N, 22.62.

Examples 1264-1273

Part A 1-(2-Aminoethyl)-2-propyl-2H-pyrazolo[3,4-c]quinolin-4-amine dihydrochloride, prepared according to the method described in Parts A through H of Example 51 was stirred with aqueous sodium hydroxide at pH 13. The mixture was adjusted to pH 8 with the addition of hydrochloric acid, and the resulting mixture was extracted with dichloromethane. The extracts were concentrated under reduced pressure to provide 1-(2-aminoethyl)-2-propyl-2H-pyrazolo[3,4-c]quinolin-4-amine.

Part B

Under a nitrogen atmosphere, a solution of 1-(2-aminoethyl)-2-propyl-2H-pyrazolo[3,4-c]quinolin-4-amine (1.0 equivalent) and triethylamine (3.0 equivalents) in chloroform (starting material is at a concentration of 0.008 M) was cooled to 0° C., and a solution of a reagent from the table below (1.0 equivalent) in chloroform was added. The reaction was stirred for between two and four hours and then concentrated under reduced pressure. In some examples, the residue was mixed with water and extracted twice with chloroform or dichloromethane. The combined extracts were then concentrated under reduced pressure. For each example, the residue was purified by chromatography once or twice using an INTELLIFLASH system (eluting with a gradient of either CMA in chloroform or methanol in chloroform). The pure product was dried in a vacuum oven overnight at 75° C. to 90° C. to provide the product shown in the table below. Additional purification methods, and analytical data for each compound are given below the table.

Examples 1264-1973

| Example | Reagent | R |
|---|---|---|
| 1264 | Cyclopropanecarbonyl chloride | |
| 1265 | Isopropyl isocyanate | |
| 1266 | 3,4-Difluorophenyl isocyanate | |
| 1267 | Nicotinoyl chloride hydrochloride | |
| 1268 | Acetyl chloride | |
| 1269 | Propionyl chloride | |
| 1270 | Methanesulfonyl chloride | |

-continued

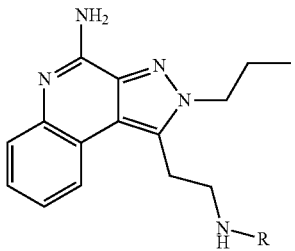

| Example | Reagent | R |
|---|---|---|
| 1271 | Ethyl isocyanate | |
| 1272 | 4-Fluorophenyl isocyanate | |
| 1273 | Ethyl chloroformate | |

Example 1264

The reaction was carried out with the starting material at a concentration of 0.3 M. N,N-Diisopropylethylamine (4 equivalents) was used instead of triethylamine. The chromatography fractions were concentrated to a small volume, and hexanes were added to form a precipitate. The precipitate was collected by filtration and dried as described above to provide N-[2-(4-amino-2-propyl-2H-pyrazolo[3,4-c]quinolin-1-yl)ethyl]cyclopropanecarboxamide was obtained as a white powder, mp 215-217° C.

MS (APCI) m/z 338 (M+H)$^+$;

Anal. calcd for $C_{19}H_{23}N_5O_1$: C, 67.63; H, 6.87; N, 20.76. Found: C, 67.30; H, 6.73; N, 20.51.

Example 1265

N-[2-(4-Amino-2-propyl-2H-pyrazolo[3,4-c]quinolin-1-yl)ethyl]-N'-isopropylurea was obtained as a white powder, mp 197.0-198.0° C.

MS (APCI) m/z 355 (M+H)$^+$;

Anal. calcd for $C_{19}H_{26}N_6O_1$: C, 64.38; H, 7.39; N, 23.71. Found: C, 64.06; H, 7.65; N, 23.73.

Example 1266

The chromatography fractions were concentrated to a small volume, and hexanes were added to form a precipitate. The precipitate was collected by filtration and dried as described above in Part B to provide N-[2-(4-amino-2-propyl-2H-pyrazolo[3,4-c]quinolin-1-yl)ethyl]-N'-(3,4-difluorophenyl)urea as a white powder, mp 211-212° C.

MS (APCI) m/z 425 (M+H)+;
Anal. calcd for $C_{22}H_{22}F_2N_6O_1$: C, 62.25; H, 5.22; N, 19.8. Found: C, 61.90; H, 5.08; N, 19.57.

Example 1267

N-[2-(4-Amino-2-propyl-2H-pyrazolo[3,4-c]quinolin-1-yl)ethyl]nicotinamide was obtained as a white powder, mp 219.0-221.0° C.
MS (APCI) m/z 375 (M+H)+;
Anal. calcd for $C_{21}H_{22}N_6O_1$: C, 67.36; H, 5.92; N, 22.44. Found: C, 67.08; H, 5.84; N, 22.32.

Example 1268

N-[2-(4-Amino-2-propyl-2H-pyrazolo[3,4-c]quinolin-1-yl)ethyl]acetamide was obtained as a white powder, mp 185.0-186.0° C.
MS (APCI) m/z 312 (M+H)+;
Anal. calcd for $C_{17}H_{21}N_5O_1$: C, 65.57; H, 6.80; N, 22.49. Found: C, 65.42; H, 6.70; N, 22.69.

Example 1269

After the product was dried, it was dissolved in 2 M sodium carbonate, and the resulting solution was extracted twice with chloroform. The combined extracts were concentrated to a small volume, and hexanes were added to form a precipitate. The precipitate was collected by filtration and dried as described above in Part B to provide N-[2-(4-amino-2-propyl-2H-pyrazolo[3,4-c]quinolin-1-yl)ethyl]propanamide as an off-white solid, mp 184.0-185.0° C.
MS (APCI) m/z 326 (M+H)+;
Anal. calcd for $C_{18}H_{23}N_5O_1$: C, 64.44; H, 7.24; N, 20.88. Found: C, 64.13; H, 6.91; N, 20.94.

Example 1270

The addition purification methods described for Example 1269 were followed to provide N-[2-(4-amino-2-propyl-2H-pyrazolo[3,4-c]quinolin-1-yl)ethyl]methanesulfonamide as a white powder, mp 187.0-188.0° C.
MS (APCI) m/z 355 (M+H)+;
Anal. calcd for $C_{16}H_{21}N_5O_2S_1$: C, 55.31; H, 6.09; N, 20.16. Found: C, 55.05; H, 6.22; N, 20.13.

Example 1271

After the product was purified twice by chromatography as described in Part B above, it was recystallized from acetonitrile. The crystals were dried in a vacuum oven for two days at 90° C. to provide N-[2-(4-amino-2-propyl-2H-pyrazolo[3,4-c]quinolin-1-yl)ethyl]-N-ethylurea as a white powder, mp 206.0-207.0° C.
MS (APCI) m/z 341 (M+H)+;
Anal. calcd for $C_{18}H_{24}N_6O_1$: C, 63.51; H, 7.11; N, 24.69. Found: C, 63.58; H, 6.89; N, 24.78.

Example 1272

The addition purification methods described for Example 1269 were followed. Before the precipitate was dried, it was purified by chromatography using a HORIZON HPFC system (eluting with 0% to 15% methanol in chloroform). It was then dried as described in Part B above to provide N-[2-(4-amino-2-propyl-2H-pyrazolo[3,4-c]quinolin-1-yl)ethyl]-N-(4-fluorophenyl)urea as a white solid, mp 201.0-202.0° C.

MS (APCI) m/z 407 (M+H)+;
Anal. calcd for $C_{22}H_{23}F_1N_6O_1$: C, 65.01; H, 5.70; N, 20.68. Found: C, 64.64; H, 5.72; N, 20.63.

Example 1273

It was determined that much of the product remained in the aqueous layer during the work-up procedure. The aqueous layer was adjusted to pH 9 with the addition of 2 M aqueous sodium carbonate and then extracted three times with dichloromethane. The combined extracts were concentrated to a small volume, and hexanes were added to form a precipitate. The precipitate was collected by filtration and dried as described above in Part B to provide ethyl 2-(4-amino-2-propyl-2H-pyrazolo[3,4-c]quinolin-1-yl)ethylcarbamate as a light yellow solid, mp 143-144° C.
MS (APCI) m/z 342 (M+H)+;
Anal. calcd for $C_{18}H_{23}N_5O_2$: C, 63.32; H, 6.79; N, 20.51. Found: C, 62.98; H, 6.84; N, 20.37.

Example 1274

N-[2-(4-Amino-2-propyl-2H-pyrazolo[3,4-c]quinolin-1-yl)ethyl]-4-fluorobenzamide

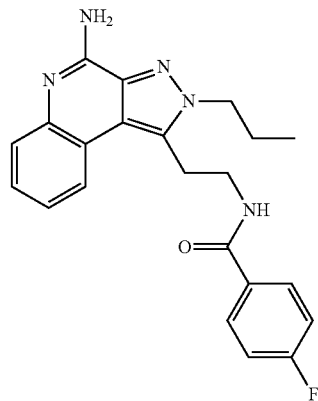 [SMILES: CCCn1nc2c(N)nc3ccccc3c2c1CCNC(=O)c1ccc(F)cc1]

Under a nitrogen atmosphere, a solution of 1-(2-aminoethyl)-2-propyl-2H-pyrazolo[3,4-c]quinolin-4-amine (0.250 g, 0.928 mmol), triethylamine (0.30 g, 3.0 mmol), and 4-fluorobenzoyl chloride (0.18 g, 1.1 mmol) in dichloromethane (7 mL) was stirred for two hours and then concentrated under reduced pressure. The residue was dissolved in methanol, and 1 N hydrochloric acid was added. The reaction was stirred for three days at room temperature and then heated at reflux overnight. A precipitate was present and was isolated by filtration and stirred with 2 M aqueous sodium carbonate. The resulting mixture was extracted with dichloromethane. The combined extracts were then concentrated under reduced pressure. The residue was purified by chromatography using an INTELLIFLASH system (eluting with 0% to 30% CMA in chloroform). The pure product was dried in a vacuum oven overnight at 90° C. to provide N-[2-(4-amino-2-propyl-2H-pyrazolo[3,4-c]quinolin-1-yl)ethyl]-4-fluorobenzamide as a white powder, mp 198-199° C.

MS (APCI) m/z 392 (M+H)+;

Anal. calcd for $C_{22}H_{22}FN_5O$: C, 67.50; H, 5.66; N, 17.89. Found: C, 67.20; H, 6.01; N, 18.10.

Example 1275

1-[2-(1,1-Dioxidoisothiazolidin-2-yl)ethyl]-2-propyl-2H-pyrazolo[3,4-c]quinolin-4-amine

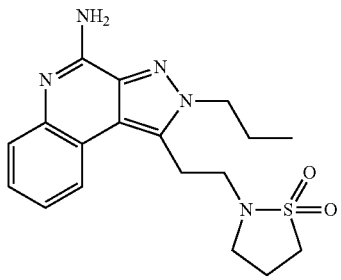 [SMILES: CCCn1nc2c(N)nc3ccccc3c2c1CCN1CCCS1(=O)=O]

Part A

Under a nitrogen atmosphere, a solution of 1-(2-aminoethyl)-2-propyl-2H-pyrazolo[3,4-c]quinolin-4-amine (0.228 g, 0.848 mmol) and N,N-diisopropylethylamine (0.604 mL, 3.39 mmol) in chloroform (6.67 mL) was cooled to 0° C. A solution of 3-chloropropanesulfonyl chloride (0.113 mL, 0.933 mmol) in chloroform (10 mL) was added. An analysis by HPLC indicated that the reaction was not progressing. N-Methylpyrrolidone (12 mL) was added, and the reaction went to completion. The solvents were removed under reduced pressure to provide N-[2-(4-amino-2-propyl-2H-pyrazolo[3,4-c]quinolin-1-yl)ethyl]-3-chloropropane-1-sulfonamide.

Part B

Under a nitrogen atmosphere, a solution of the material from Part A and 1,8-diazabicyclo[5,4,0]undec-7-ene (0.161 g, 1.1 mmol) in DMF (2.5 mL). The reaction was stirred overnight at room temperature. The solvent was removed under reduced pressure, and the residue was purified by chromatography twice using an INTELLIFLASH system (eluting with 0% to 40% CMA in chloroform). The chromatography fractions were concentrated to a small volume, and hexanes were added to form a precipitate. The precipitate was collected by filtration and dried in a vacuum oven overnight at 90° C. to provide 1-[2-(1,1-dioxidoisothiazolidin-2-yl)ethyl]-2-propyl-2H-pyrazolo[3,4-c]quinolin-4-amine as a white powder, mp 201-202° C.

MS (APCI) m/z 374 (M+H)+;

Anal. calcd for $C_{18}H_{23}N_5O_2S$: C, 57.89; H, 6.21; N, 18.75. Found: C, 57.78; H, 6.51; N, 18.56.

Example 1276

(4-Amino-2-ethyl-2H-pyrazolo[3,4-c]quinolin-1-yl)methanol

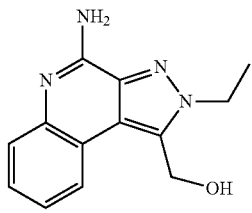 [SMILES: CCn1nc2c(N)nc3ccccc3c2c1CO]

Part A

Pyridine (40 mL, 492 mmol) was added in a single portion to a chilled solution (0° C.) solution of indole (48 g, 410 mmol) in diethyl ether (820 mL). Ethyl chlorooxoacetate (50 mL, 451 mmol) was added dropwise. The resulting suspension was allowed to warm to ambient temperature over a period of 20 hours. The solid was isolated by filtration and washed with diethyl ether. The solid was combined with water (1 L), stirred for 1 hour, and then isolated by filtration to provide 75 g of ethyl (1H-indol-3-yl)(oxo)acetate.

Part B

Acetyl chloride (19 mL, 273 mmol), acetic acid (30 mL), and ethylhydrazine oxalate (41 g, 272 mmol) were added sequentially to a suspension of methyl 1H-indol-3-yl(oxo)acetate (37 g, 180 mmol) in ethanol (910 mL). The reaction mixture was heated at reflux for 18 hours, cooled to ambient temperature, and concentrated under reduced pressure to a small volume. Dichloromethane (100 mL) and ice were added, and the mixture was adjusted to pH 14 with the addition of 50% w/w sodium hydroxide. A precipitate formed. The dichloromethane was removed under reduced pressure, and the precipitate was isolated by filtration, triturated with hot acetonitrile, and isolated by filtration to provide 26 g of 2-ethyl-2,5-dihydro-4H-pyrazolo[3,4-c]quinolin-4-one as a tan solid.

Part C

Under a nitrogen atmosphere, a mixture of 2-ethyl-2,5-dihydro-4H-pyrazolo[3,4-c]quinolin-4-one (10 g, 46.8 mmol), N,N,N,N-tetramethylethylenediamine (31 mL), and THF (520 mL) was chilled to 0° C. A solution of n-butyllithium in hexanes (56 mL of 2.5 M) was added dropwise. After the addition was complete the reaction mixture was stirred for 5 minutes and then DMF (72 mL) was added dropwise. The reaction mixture was warmed to ambient temperature and stirred for 1 hour. 1 N hydrochloric acid was added and the reaction mixture was stirred for 1 hour. The reaction mixture was concentrated under reduced pressure to about half the original volume and then diluted with water and extracted with dichloromethane. The combined extracts were dried over sodium sulfate, filtered, and then concentrated under reduced pressure to provide a dark yellow oil. The oil was combined with acetonitrile and stirred for 20 minutes. A bright yellow solid was isolated by filtration to provide 4 g of 2-ethyl-4-oxo-4,5-dihydro-2H-pyrazolo[3,4-c]quinoline-1-carbaldehyde as a yellow powder. An additional 3 g of material was isolated from the mother liquor.

Part D

2-Ethyl-4-oxo-4,5-dihydro-2H-pyrazolo[3,4-c]quinoline-1-carbaldehyde (1.0 g, 4.1 mmol) was combined with phosphorus oxychloride (4 mL) and heated at 90° C. for 10 minutes. Analysis by LCMS showed the desired product with a small amount of a trichloro species in which chloride had replaced the 4-hydroxy group and the aldehyde to provide a geminal dichloride group. The reaction mixture was cooled to ambient temperature, poured into a mixture of ammonium hydroxide (50 mL) and ice, and then stirred for 20 minutes. A solid was isolated by filtration and air dried to provide a tan solid.

Part E

Sodium borohydride (310 mg) was added in portions over a period of 20 minutes to a suspension of material from Part D in methanol (20 mL). The reaction was stirred for 30 minutes; a precipitate was present. The precipitate was isolated by filtration and dried on the vacuum filter funnel to provide (4-chloro-2-ethyl-2H-pyrazolo[3,4-c]quinolin-1-yl)methanol.

Part F

The material from Part E was combined with ammonia (50 mL of a 7 N solution in methanol), and the reaction was heated in a pressure vessel for 18 hours at 150° C., allowed to cool to room temperature, and further cooled to 0° C. A precipitate was present and was isolated by filtration, washed with a small volume of methanol, and recrystallized from a mixture of acetonitrile and methanol to provide 0.19 g of (4-amino-2-ethyl-2H-pyrazolo[3,4-c]quinolin-1-yl)methanol as gold crystals, mp 255-256° C.
MS (APCI) m/z 243 (M+H)$^+$;
Anal. calcd for $C_{13}H_{14}N_4O$: C, 64.45; H, 5.82; N, 23.12. Found: C, 64.31; H, 5.66; N, 23.14.

Examples 1277-1281

Part A

Acetyl chloride (2 equivalents), acetic acid (methyl 1H-indol-3-yl(oxo)acetate is at a concentration of 6 M), and the hydrazine or hydrazine salt indicated in the table below (1.5 equivalents) were added sequentially to a 0.2 M suspension of methyl 1H-indol-3-yl(oxo)acetate in ethanol. The reaction mixture was heated at reflux for 18 hours. The reaction mixture was cooled to ambient temperature, and further cooled to 0° C. if necessary to form a precipitate. For Examples 1278 and 1281, acetonitrile was added after most of the reaction solvent was removed under reduced pressure to cause the precipitate to form. The product was purified according to the method shown in the table below.

Part B

A 0.3 M solution of the material from Part A in phosphorus oxychloride was heated at 90° C. for 30 minutes. The reaction mixture was cooled to room temperature, poured into a mixture of ammonium hydroxide (50 mL) and ice, and then stirred for 20 minutes to one hour. A solid was isolated by filtration and air-dried. For Example 1278, the reaction was heated at reflux for three hours, and the ammonium hydroxide mixture was extracted with dichloromethane. The combined extracts were dried over sodium sulfate, filtered, concentrated under reduced pressure, purified by chromatography on a HORIZON HPFC system (40+M column, eluting with 0% to 30% CMA in chloroform), and dried under high vacuum.

Part C

The material from Part B was combined with ammonia (7 N solution in methanol), and the reaction was heated in a pressure vessel for 18 to 24 hours at 150° C. and allowed to cool to room temperature. The table below shows the structure of the product. The isolation and purification of the product are given below the table.

Examples 1277-1281

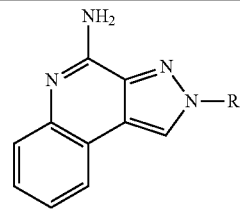

| Example | Hydrazine | Purification Method in Part A | R |
|---|---|---|---|
| 1277 | Methylhydrazine | Trituration with acetonitrile | —CH$_3$ |
| 1278 | Ethylhydrazine oxalate | Chromatography (silica gel, eluting with 0% to 30% CMA in chloroform) | —CH$_2$CH$_3$ |
| 1279 | Propylhydrazine oxalate | Recrystallized from acetonitrile | —CH$_2$CH$_2$CH$_3$ |
| 1280 | Butylhydrazine oxalate | Recrystallized from acetonitrile | —CH$_2$CH$_2$CH$_2$CH$_3$ |
| 1281 | Methoxyethyl hydrazine dihydrochloride | None | —CH$_2$CH$_2$OCH$_3$ |

Example 1277

Upon cooling to room temperature, a precipitate formed. The precipitate was isolated by filtration and recrystallized from 9:1 acetonitrile:methanol to provide 2-methyl-2H-pyrazolo[3,4-c]quinolin-4-amine as tan crystals, mp 218-219° C.
MS (APCI) m/z 199 (M+H)$^+$;
Anal. calcd for $C_{11}H_{10}N_4$: C, 66.65; H, 5.08; N, 28.26. Found: C, 66.70; H, 5.13; N, 28.22.

Example 1278

The solvent was removed under reduced pressure, and the residue was partitioned dichloromethane and water. The aqueous layer was extracted with dichloromethane, and the combined organic fractions were dried over sodium sulfate, filtered, and concentrated under reduced pressure to provide a white solid. The solid was purified by chromatography on a HORIZON HPFC system (40+M column, eluting with 0% to 30% CMA in chloroform) followed by recrystallization from acetonitrile to provide 2-ethyl-2H-pyrazolo[3,4-c]quinolin-4-amine as white crystals, mp 240-241° C.

MS (APCI) m/z 213 (M+H)$^+$;

Anal. calcd for $C_{12}H_{12}N_4$: C, 67.91; H, 5.70; N, 26.40. Found: C, 67.69; H, 5.80; N, 26.60.

Example 1279

Crystals formed upon cooling to room temperature, and the crystals were dissolved in hot methanol and purified by chromatography using an INTELLIFLASH system (silica gel, eluting with 0% to 30% CMA in chloroform) followed by recrystallization from a mixture of acetonitrile and methanol to provide 2-propyl-2H-pyrazolo[3,4-c]quinolin-4-amine as colorless needles, mp 225-227° C.

MS (APCI) m/z 227 (M+H)$^+$;

Anal. calcd for $C_{13}H_{14}N_4$: C, 69.00; H, 6.24; N, 24.76. Found: C, 69.24; H, 6.27; N, 25.04.

Example 1280

Crystals formed upon cooling to room temperature, and the crystals were dissolved in hot methanol and purified by chromatography using an INTELLIFLASH system (silica gel, eluting with 0% to 30% CMA in chloroform) followed by recrystallization from acetonitrile to provide 2-butyl-2H-pyrazolo[3,4-c]quinolin-4-amine as pink crystals, mp 194-195° C.

MS (APCI) m/z 241 (M+H)$^+$;

Anal. calcd for $C_{14}H_{16}N_4$: C, 69.97; H, 6.71; N, 23.31. Found: C, 69.92; H, 6.74; N, 23.49.

Example 1281

Upon cooling to 0° C., a precipitate formed. A portion of the precipitate was recrystallized from acetonitrile to provide 2-(2-methoxyethyl)-2H-pyrazolo[3,4-c]quinolin-4-amine as tan crystals, mp 230-231° C.

MS (APCI) m/z 243 (M+H)$^+$;

Anal. calcd for $C_{13}H_{14}N_4O$: C, 64.45; H, 5.82; N, 23.12. Found: C, 64.43; H, 5.93; N, 23.02.

Example 1282

2-(4-Amino-2H-pyrazolo[3,4-c]quinolin-2-yl)ethanol

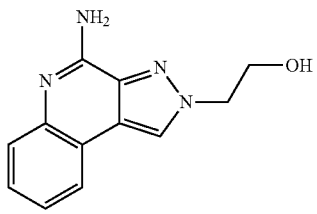 [SMILES: Nc1nc2ccccc2c2cn(CCO)nc12]

2-(2-Methoxyethyl)-2H-pyrazolo[3,4-c]quinolin-4-amine was treated with boron tribromide to give 2-(4-amino-2H-pyrazolo[3,4-c]quinolin-2-yl)ethanol.

Anal. calcd for $C_{12}H_{12}N_4O$: C, 63.15; H, 5.30; N, 24.55. Found: C, 63.06; H, 5.27; N, 24.69.

Example 1283

1-(4-Amino-2-ethyl-2H-pyrazolo[3,4-c][1,7]naphthyridin-1-yl)-2-methylpropan-2-ol

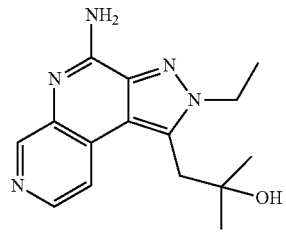 [SMILES: CCn1nc2c(N)nc3cnccc3c2c1CC(C)(C)O]

4-Bromo-1-ethyl-5-(2-hydroxy-2-methylpropyl)-1H-pyrazole-3-carbonitrile (Parts A-F of Example 62) (1.36 g, 5.00 mmol), 3-[(tert-butoxycarbonyl)amino]pyridin-4-ylboronic acid (Example 610) (2.38 g, 10.0 mmol), potassium carbonate (1.04 g, 7.50 mmol), DME (16 mL), water (8 mL), and dichlorobis(triphenylphosphine)palladium(II) (0.0175 g, 0.025 mmol) were combined in a flask, which was then evacuated three times and filled with nitrogen. The reaction was heated at 95° C. for two days. Water was added, and the aqueous layer was separated and extracted four times with chloroform. The combined organic fractions were dried over magnesium sulfate, filtered, and concentrated under reduced pressure. The crude product was purified by IFC (silica cartridge) to provide 211 mg of a yellow solid. The solid was heated at reflux in 1 M hydrogen chloride in ethanol for 19 hours. Aqueous sodium carbonate (35 mL of 2 M) was added, and the ethanol was removed under reduced pressure. The mixture was extracted four times with chloroform, and the combined extracts were treated as described above. The crude product was purified by chromatography on a HORIZON HPFC system (silica cartridge) followed by recrystallization from acetonitrile to provide 130 mg of 1-(4-amino-2-ethyl-2H-pyrazolo[3,4-c][1,7]naphthyridin-1-yl)-2-methylpropan-2-ol as a white solid, mp 277-279° C. MS (APCI) m/z 286 (M+H)$^+$;

Anal. Calcd for $C_{15}H_{19}N_5O$: C, 63.14; H, 6.71; N, 24.54. Found: C, 62.98; H, 7.02; N, 24.77.

Example 1284

N-[2-(4-Amino-2-propyl-2H-pyrazolo[3,4-c][1,7]naphthyridin-1-yl)ethyl]-4-fluorobenzamide

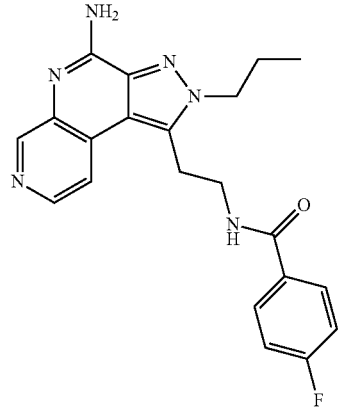 [SMILES: CCCn1nc2c(N)nc3cnccc3c2c1CCNC(=O)c1ccc(F)cc1]

Part A

A modification of the method described in Example 610 was used to couple tert-butyl 2-(4-amino-2-propyl-2H-pyrazolo[3,4-c]quinolin-1-yl)ethylcarbamate (2.08 g, 5.82 mmol) (Example 51, Parts A through G) with 3-[(tert-butoxycarbonyl)amino]pyridin-4-ylboronic acid (2.77 g, 11.6 mmol). After the first purification by IFC, 0.44 g of tert-butyl 2-(4-amino-2-propyl-2H-pyrazolo[3,4-c][1,7]naphthyridin-1-yl) ethylcarbamate was obtained as a yellow solid.

Part B

The material from Part A was mixed with methanol (20 mL) and concentrated hydrochloric acid (2 mL) and heated at reflux for 30 minutes and allowed to cool to room temperature. Dichloromethane (25 mL), triethylamine (3 mL), and 4-fluorobenzoyl chloride (0.476 g, 3.0 mmol) were sequentially added. The reaction was carried out as described in Example 1242. Following purification by IFC, the product was purified by chromatography again using HORIZON HPFC system (40+M cartridge, eluting with methanol in chloroform) followed by recrystallization from 1:1 ethanol:propyl acetate. The crystals were isolated by filtration, washed with ethanol:propyl acetate, and dried overnight on the vacuum filter funnel to provide 114 mg of N-[2-(4-amino-2-propyl-2H-pyrazolo[3,4-c][1,7]naphthyridin-1-yl)ethyl]-4-fluorobenzamide as a white solid, mp 317-318° C.

MS (APCI) m/z 393 (M+H)+;
Anal. Calcd for $C_{21}H_{21}FN_6O$: C, 64.27; H, 5.39; N, 21.41. Found: C, 64.11; H, 5.45; N, 21.67.

Example 1285

3-(4-Amino-2-propyl-2H-pyrazolo[3,4-c]quinolin-1-yl)-2,2-dimethylpropanenitrile

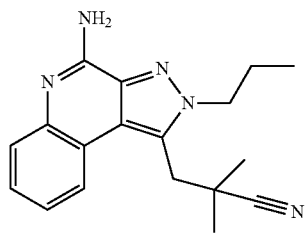 [SMILES: CCCn1nc2c(N)nc3ccccc3c2c1CC(C)(C)C#N]

Part A 4,4-Dimethyl-5-nitropentan-2-one was made according to the literature procedure; see Kloetzel, M. C. *J. Am. Chem. Soc.*, 69, pp. 2271-2275 (1947). Under a nitrogen atmosphere, a solution of nitropentanone (9.55 g, 60.0 mmol) was cooled to 0° C. Diethyl azodicarboxylate (11.5 g, 66 mmol) and tributylphosphine (26.71 g, 132 mmol) were sequentially added. The reaction was stirred for one hour at 0° C. and then for one hour at room temperature. The solvent was removed under reduced pressure, and the residue was purified by chromatography on a HORIZON HPFC system (65I cartridge, eluting with dichloromethane). The resulting oil was treated with hexane; a precipitate formed and was removed by fitration. The filtrate was concentrated under reduced pressure, and the residue was purified by chromatography on a HORIZON HPFC system (65I cartridge, eluting with 45% to 55% ethyl acetate in hexane) to provide 5.17 g of 2,2-dimethyl-4-oxopentanenitrile as a pale yellow oil.

Part B

The methods described in Parts A through C of Example 64 were followed. In the final step, the product precipitated from the reaction mixture and was isolated by filtration, washed with water, and dried on the vacuum filter funnel to provide 3.50 g of 5-(2-cyano-2-methylpropyl)-1-propyl-1H-pyrazole-3-carboxamide as a white solid.

Anal. Calcd for $C_{12}H_{18}N_4O$: C, 61.52; H, 7.74; N, 23.91. Found: C, 61.31; H, 7.54; N, 24.18. The filtrate was concentrated and treated according to the work-up and purification procedures described in Part C of Example 64.

Part C

The methods described in Parts D and E of Example 64 were used to convert 5-(2-cyano-2-methylpropyl)-1-ethyl-1H-pyrazole-3-carboxamide (4.9 g, 20.9 mmol) into 5.88 g of 4-bromo-5-(2-cyano-2-methylpropyl)-1-propyl-1H-pyrazole-3-carbonitrile. Purification by IFC was carried out after each step.

Part D

A modification of the method described in Example 1283 was used to couple 4-bromo-5-(2-cyano-2-methylpropyl)-1-propyl-1H-pyrazole-3-carbonitrile (1.48 g, 5.00 mmol) with 2-aminophenylboronic acid hydrochloride (1.73 g, 10.0 mmol). The reaction was completed in one hour. The coupling product was purified by IFC (silica cartridge, eluting with 40% to 60% ethyl acetate in hexane). The reaction with hydrogen chloride was heated at reflux for a total of about seven hours. 3-(4-Amino-2-propyl-2H-pyrazolo[3,4-c]quinolin-1-yl)-2,2-dimethylpropanenitrile (840 mg) was obtained as a white solid, mp 248-250° C.

MS (APCI) m/z 308 (M+H)+;
Anal. Calcd for $C_{18}H_{21}N_5$: C, 70.33; H, 6.89; N, 22.78. Found: C, 70.18; H, 6.88; N, 23.02.

Example 1286

3-[4-Amino-2-(2-methoxyethyl)-2H-pyrazolo[3,4-c]quinolin-1-yl]-2,2-dimethylpropanenitrile

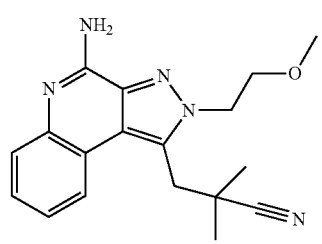 [SMILES: COCCn1nc2c(N)nc3ccccc3c2c1CC(C)(C)C#N]

Part A

The method described in Part A of Example 64 was used to convert 2,2-dimethyl-4-oxopentanenitrile (8.19 g, 65.4 mmol) into 13.7 g of ethyl 5-(2-cyano-2-methylpropyl)-1-(2-hydroxyethyl)-1H-pyrazole-3-carboxylate.

Part B

A solution of ethyl 5-(2-cyano-2-methylpropyl)-1-(2-hydroxyethyl)-1H-pyrazole-3-carboxylate (6.12 g, 23.1 mmol) in THF (50 mL) was cooled to approximately 0° C. under nitrogen, and iodomethane (3.28 g, 23.1 mmol) was added. Sodium hydride (0.924 g of 60% in mineral oil, 23.1 mmol) was added in one portion. The mixture was allowed to warm to room temperature slowly and stirred overnight. Saturated aqueous ammonium chloride was added, and the mixture was extracted three times with tert-butyl methyl ether.

The combined extracts were dried over magnesium sulfate, filtered, and concentrated under reduced pressure to provide a yellow oil. The oil was purified by chromatography on a HORIZON HPFC system (65I cartridge, eluting with ethyl acetate) to provide 3.68 g of ethyl 5-(2-cyano-2-methylpropyl)-1-(2-methoxyethyl)-1H-pyrazole-3-carboxylate as a pale yellow oil.

Part C

The methods described in Parts B and C of Example 64 were used to treat ethyl 5-(2-cyano-2-methylpropyl)-1-(2-methoxyethyl)-1H-pyrazole-3-carboxylate (3.66 g, 13.1 mmol). The final product was not purified by chromatography but was recrystallized from a mixture of 50% ethyl acetate in hexane (100 mL) and ethyl acetate (35 mL). The crystals were washed with 50% ethyl acetate in hexane and dried on the vacuum filter funnel to provide 2.676 g of 5-(2-cyano-2-methylpropyl)-1-(2-methoxyethyl)-1H-pyrazole-3-carboxamide, mp 130-131° C.

Anal. Calcd for $C_{12}H_{18}N_4O_2$: C, 57.58; H, 7.25; N, 22.38. Found: C, 57.78; H, 6.92; N, 22.44.

Part D

The methods described in Parts D and E of Example 64 were used to convert 5-(2-cyano-2-methylpropyl)-1-(2-methoxyethyl)-1H-pyrazole-3-carboxamide into 4-bromo-5-(2-cyano-2-methylpropyl)-1-(2-methoxyethyl)-1H-pyrazole-3-carbonitrile. Purification by IFC was carried out after each step.

Part E

A modification of the method described in Part B of Example 1283 was used to couple 4-bromo-5-(2-cyano-2-methylpropyl)-1-(2-methoxyethyl)-1H-pyrazole-3-carbonitrile (1.56 g, 5.00 mmol) with 2-aminophenylboronic acid hydrochloride (1.73 g, 10.0 mmol). The reaction was completed in one hour. The coupling product was purified by IFC (silica cartridge, eluting with 50% to 90% ethyl acetate in hexane). The reaction with hydrogen chloride was heated at reflux for two hours and allowed to cool to room temperature overnight. 3-[4-Amino-2-(2-methoxyethyl)-2H-pyrazolo[3,4-c]quinolin-1-yl]-2,2-dimethylpropanenitrile (676 mg) was obtained as white crystals, mp 206-208° C.

MS (APCI) m/z 324 (M+H)$^+$;

Anal. Calcd for $C_{18}H_{21}N_5O$: C, 66.85; H, 6.55; N, 21.66. Found: C, 66.81; H, 6.67; N, 21.82.

Example 1287

3-(4-Amino-2-propyl-2H-pyrazolo[3,4-c]quinolin-1-yl)-2,2-dimethylpropanamide

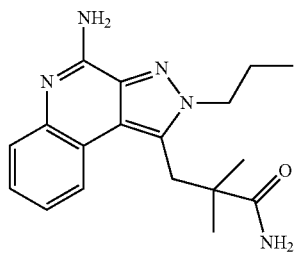 [SMILES: CCCn1nc2c(N)nc3ccccc3c2c1CC(C)(C)C(N)=O]

3-(4-Amino-2-propyl-2H-pyrazolo[3,4-c]quinolin-1-yl)-2,2-dimethylpropanenitrile (657 mg, 2.14 mmol), ethanol (10 mL), concentrated ammonium hydroxide (2.1 mL), and 30% w/w hydrogen peroxide (2.8 g) were combined in a sealed glass tube and heated at 70° C. for seven hours. During this time, the reaction was periodically cooled and the pressure released. Additional hydrogen peroxide (1.4 g) was added, and the reaction was heated at 70° C. for five hours, with periodic cooling and venting. The reaction was cooled to 0° C., and water (25 mL) was added. A precipitate formed and was isolated by filtration, washed with water, purified by chromatography on a HORIZON HPFC instrument (40M cartridge), and recrystallized from acetonitrile. The crystals were dried on the vacuum filter funnel for two hours to provide 485 mg of 3-(4-amino-2-propyl-2H-pyrazolo[3,4-c]quinolin-1-yl)-2,2-dimethylpropanamide as a white solid, mp 224-225° C.

MS (APCI) m/z 326 (M+H)$^+$;

Anal. Calcd for $C_{18}H_{23}N_5O \cdot 0.25\ H_2O$: C, 65.53; FL 7.18; N, 21.23. Found: C, 65.52; H, 7.30; N, 21.19.

Example 1288

3-[4-Amino-2-(2-methoxyethyl)-2H-pyrazolo[3,4-c]quinolin-1-yl]-2,2-dimethylpropanamide

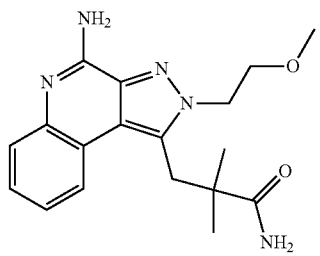 [SMILES: COCCn1nc2c(N)nc3ccccc3c2c1CC(C)(C)C(N)=O]

3-[4-Amino-2-(2-methoxyethyl)-2H-pyrazolo[3,4-c]quinolin-1-yl]-2,2-dimethylpropanenitrile (436 mg, 1.35 mmol), ethanol (5 mL), sodium hydroxide (0.056 mL of 6 N), and 30% w/w hydrogen peroxide (0.54 mL, 4.7 mmol) were combined and heated at 50° C. for 18.5 hours. Water was added, and the ethanol was removed under reduced pressure. The mixture was extracted with chloroform, and the combined extracts were dried over magnesium sulfate, filtered, and concentrated under reduced pressure. The residue was purified by IFC (silica cartridge) and recrystallized from 75% ethyl acetate in hexane. The crystals were washed with 50% ethyl acetate in hexane, dried on the vacuum filter funnel overnight, and further dried under vacuum at 9 Pa and 98° C. to provide 3-[4-amino-2-(2-methoxyethyl)-2H-pyrazolo[3,4-c]quinolin-1-yl]-2,2-dimethylpropanamide as a white solid, mp 225-226° C.

MS (APCI) m/z 342 (M+H)$^+$;

Anal. Calcd for $C_{18}H_{23}N_5O_2$: C, 63.32; H, 6.79; N, 20.51. Found: C, 63.05; H, 6.86; N, 20.55.

Example 1289

1-(Aminomethyl)-2-methyl-2H-pyrazolo[3,4-c]quinolin-4-amine hydrochloride

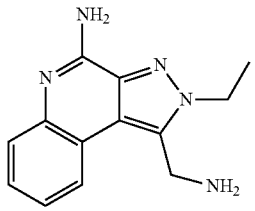

Part A

The method of Examples 1-4 Part A was followed to treat 2-(2-oxopropyl)-1H-isoindole-1,3(2H)-dione (10.2 g, 50.0 mmol) with a solution of sodium tert-butoxide (5.77 g, 60.0 mmol) in ethanol (60 mL) and diethyl oxalate (8.77 g, 60.0 mmol). Ethyl 541, 3-dioxo-1,3-dihydro-2H-isoindol-2-yl)-2,4-dioxopentanoate sodium salt (14.00 g) was obtained as an orange solid.

Part B

The method described in Part B of Examples 1-4 was used to treat a 0° C. solution of the material from Part A (14.00 g, 43 mmol) in acetic acid (43 mL) with methylhydrazine (1.98 g, 43 mmol). During the addition over a period of ten minutes, the reaction temperature was maintained below 15° C. The crude product was treated with 50% ethyl acetate in hexane to yield a powder. The solvents were removed under reduced pressure, and the residue was recrystallized from ethanol to provide 8.13 g of ethyl 5-[(1,3-dioxo-1,3-dihydro-2H-isoindol-2-yl)methyl]-1-methyl-1H-pyrazole-3-carboxylate.

Part C

A solution of ethyl 5-[(1,3-dioxo-1,3-dihydro-2H-isoindol-2-yl)methyl]-1-methyl-1H-pyrazole-3-carboxylate (8.13 g, 25.9 mmol) in hydrochloric acid (33 mL of 1 M) and acetic acid (33 mL) was heated at reflux intermittently for six hours and allowed to cool to room temperature; a precipitate formed. Water was added, and the solid was isolated by filtration, washed with water, and dried on the vacuum filter funnel for two days to provide 3.79 g of 5-[(1,3-dioxo-1,3-dihydro-2H-isoindol-2-yl)methyl]-1-methyl-1H-pyrazole-3-carboxylic acid as a brown solid.

Part D

A solution of 5-[(1,3-dioxo-1,3-dihydro-2H-isoindol-2-yl)methyl]-1-methyl-1H-pyrazole-3-carboxylic acid (3.79 g, 13.3 mmol) and thionyl chloride (10 mL) in toluene (10 mL) was heated at 90° C. for 30 minutes under nitrogen and allowed to cool to ambient temperature. A precipitate formed upon cooling, and the precipitate was isolated by filtration, washed with toluene, and suspended in dichloromethane (40 mL). The suspension was poured into concentrated ammonium hydroxide (40 mL) that was cooled to 0° C. The reaction was stirred for ten minutes. A precipitate formed and was isolated by filtration, washed with water, and dried. The crude product was purified by chromatography on a HORIZON HPFC system (40M cartridge) to provide 1.67 g of 5-[(1,3-dioxo-1,3-dihydro-2H-isoindol-2-yl)methyl]-1-methyl-1H-pyrazole-3-carboxamide as an off-white solid.

Part E

A solution of trifluoroacetic anhydride (0.996 mL, 7.05 mmol) in dichloromethane (15 mL) was added slowly to a 0° C. solution of 5-[(1,3-dioxo-1,3-dihydro-2H-isoindol-2-yl)methyl]-1-methyl-1H-pyrazole-3-carboxamide (1.67 g, 5.87 mmol) and triethylamine (1.78 g, 17.6 mmol) in dichloromethane (15 mL). The resulting solution was stirred for 30 minutes, and water (50 mL) was added. The work-up procedure described in Part D of Example 64 was followed. Hexane (100 mL) was added to the resulting off-white solid, which was isolated by filtration and washed with hexane. The resulting light-brown solid was purified by chromatography using a HORIZON HPFC system (40M cartridge, eluting with 1% to 10% CMA in chloroform) to provide 1.57 g of 5-[(1,3-dioxo-1,3-dihydro-2H-isoindol-2-yl)methyl]-1-methyl-1H-pyrazole-3-carbonitrile as an off-white solid.

Part F

5-[(1,3-Dioxo-1,3-dihydro-2H-isoindol-2-yl)methyl]-1-methyl-1H-pyrazole-3-carbonitrile (1.57 g, 5.90 mmol) was brominated using a modified version of the method described in Part F of Examples 1-4. In the reaction, 1.4 equivalents of bromine were used instead of 1.1 equivalents. After the reaction was stirred for two days, additional potassium acetate (1.31 g) and bromine (0.211 mL) were added, and the reaction was stirred for five more days. After the addition of sodium hydrogensulfate, most of the acetic acid was removed under reduced pressure, and 2 M aqueous sodium carbonate was added. A solid formed and was isolated by filtration, washed with water, and dried on the vacuum filter funnel to provide 1.85 g of 4-bromo-5-[(1,3-dioxo-1,3-dihydro-2H-isoindol-2-yl)methyl]-1-methyl-1H-pyrazole-3-carbonitrile as a white solid.

Part G

The method described in Part F of Example 23 was followed using 4-bromo-5-[(1,3-dioxo-1,3-dihydro-2H-isoindol-2-yl)methyl]-1-methyl-1H-pyrazole-3-carbonitrile (1.85 g, 5.36 mmol) as the starting material with the modification that dichloromethane (25 mL) was used as the solvent for the reaction with di-tert-butyl dicarbonate (1.75 g, 8.00 mmol); this reaction was stirred overnight and filtered to remove a solid. The filtrate was concentrated under reduced pressure and purified by IFC to provide 1.438 g of tert-butyl (4-bromo-3-cyano-1-methyl-1H-pyrazol-5-yl)methylcarbamate as a white solid.

Part H

A modification of the method described in Example 1283 was used to couple tert-butyl (4-bromo-3-cyano-1-methyl- 1H-pyrazol-5-yl)methylcarbamate (1.43 g, 4.53 mmol) with 2-aminophenylboronic acid hydrochloride (1.57 g, 9.06 mmol). The reaction was completed in 70 minutes. tert-Butyl methyl ether was used instead of chloroform in the work-up procedure. The coupling product was purified by IFC (silica cartridge, eluting with 40% to 60% ethyl acetate in hexane). The reaction with hydrogen chloride was heated at reflux for 24 hours. Diethyl ether (50 mL) was added after the reaction cooled to room temperature. A precipitate was present and was isolated by filtration and dried on the vacuum filter funnel for three hours to provide 1.13 g of 1-(aminomethyl)-2-methyl-2H-pyrazolo[3,4-c]quinolin-4-amine hydrochloride as a white solid, mp>250° C.

MS (APCI) m/z 228 (M+H)$^+$;

Anal. Calcd for $C_{12}H_{13}N_5O.2HCl.0.20H_2O$: C, 47.44; H, 5.11; N, 23.06. Found: C, 47.80; H, 4.90; N, 22.68.

Example 1290

1-(4-Amino-2-propyl-2H-pyrazolo[3,4-c]quinolin-1-yl)-2-methylpropan-2-ol

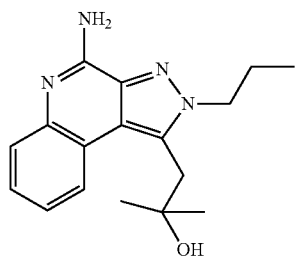 [SMILES: CCCn1nc2c(N)nc3ccccc3c2c1CC(C)(C)O]

Part A

The method described in Part A of Example 1258 was followed on a 0.215 mmol scale using propylhydrazine (35.3 g, 0.215 mmol) instead of butylhydrazine oxalate. After propylhydrazine was added, the reaction was stirred for one hour. The chromatographic purification was carried out on silica gel (eluting with 40% to 50% ethyl acetate in hexane) to provide 15 g of ethyl 5-(2-hydroxy-2-methylpropyl)-1-propyl-1H-pyrazole-3-carboxylate as a brown oil.

Part B

The methods described in Parts D and E of Example 60 were used to convert ethyl 5-(2-hydroxy-2-methylpropyl)-1-propyl-1H-pyrazole-3-carboxylate (14.4 g, 56.6 mmol) to 10 g of 5-(2-hydroxy-2-methylpropyl)-1-propyl-1H-pyrazole-3-carboxamide as an off-white powder. After the saponification in Part D, the product was obtained as an oil after extraction of the acidified solution with dichloromethane.

Part C

A modification of the method described in Part C of Example 1253 was used to treat 5-(2-hydroxy-2-methylpropyl)-1-propyl-1H-pyrazole-3-carboxamide (9.5 g, 42.2 mmol) with trifluoroacetic anhydride (10.6 g, 50.6 mmol) in the presence of triethylamine (12.8 g, 127 mmol). After the reaction was stirred for one hour, additional trifluoroacetic anhydride (3 mL) was added to drive the reaction to completion. The resulting product was brominated according to the method described in Part F of Examples 1-4 to provide 2-(4-bromo-1-butyl-3-cyano-1H-pyrazol-5-yl)-1,1-dimethylethyl trifluoroacetate as a brown oil.

Part D

A modification of the method described in Part C of Example 1258 was used to treat the trifluoroacetate from Part C with potassium carbonate. Chloroform was used in the work-up procedure, and the final product was purified by column chromatography on silica gel (eluting with 30% ethyl acetate in hexane) to provide 5.5 g of 4-bromo-5-(2-hydroxy-2-methylpropyl)-1-propyl-1H-pyrazole-3-carbonitrile.

Part E

The methods described in Parts H and I of Example 60 were followed using 5-(2-hydroxy-2-methylpropyl)-1-propyl-1H-pyrazole-3-carbonitrile (2.75 g, 9.61 mmol) as the starting material with the following modifications. Chloroform was used instead of dichloromethane in the extraction at the end of Part I. Following purification by column chromatography, the product was recrystallized from ethyl acetate. The crystals were isolated by filtration, washed with ethyl acetate, and dried under vacuum at 65° C. for four hours to yield 1.2 g of 1-(4-amino-2-propyl-2H-pyrazolo[3,4-c]quinolin-1-yl)-2-methylpropan-2-ol as off-white crystals, mp 188-190° C.

MS (APCI) m/z 299 (M+H)$^+$;

Anal. Calcd for $C_{17}H_{22}N_4O$: C, 68.43; H, 7.43; N, 18.78. Found: C, 68.16; H, 7.34; N, 18.67.

Example 1291

1-(4-Amino-2-propyl-6,7,8,9-tetrahydro-2H-pyrazolo[3,4-c]quinolin-1-yl)-2-methylpropan-2-ol

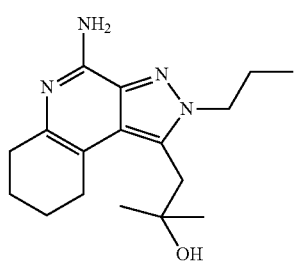 [SMILES: CCCn1nc2c(N)nc3c(c2c1CC(C)(C)O)CCCC3]

A modification of the method described in Example 61 was followed using 1-(4-amino-2-propyl-2H-pyrazolo[3,4-c]quinolin-1-yl)-2-methylpropan-2-ol (0.65 g, 2.18 mmol) as the starting material. The hydrogenation was repeated after the product obtained after chromatographic purification of the first reaction mixture (silica gel, eluting with 5% methanol in dichloromethane) yielded mostly starting material. The product obtained after the second hydrogenation (0.27 g) was recrystallized from ethyl acetate (5 mL) to provide 1-(4-amino-2-propyl-6,7,8,9-tetrahydro-2H-pyrazolo[3,4-c]quinolin-1-yl)-2-methylpropan-2-ol as white crystals, mp 143-145° C.

MS (ESI) m/z 303 (M+H)$^+$;

Anal. Calcd for $C_{17}H_{26}N_4O$: C, 67.52; H, 8.67; N, 18.53. Found: C, 67.21; H, 8.85; N, 18.58.

Example 1292

1-{2-Methyl-2-[2-(methylsulfonyl)ethoxy]propyl}-2-propyl-2H-pyrazolo[3,4-c]quinolin-4-amine

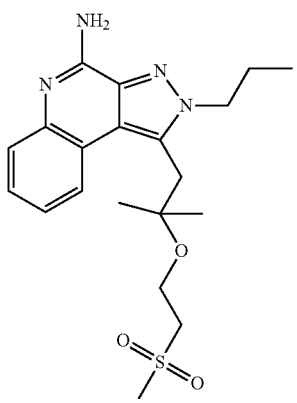 [SMILES: CCCn1nc2c(N)nc3ccccc3c2c1CC(C)(C)OCCS(C)(=O)=O]

Part A

A solution of 4-bromo-5-(2-hydroxy-2-methylpropyl)-1-propyl-1H-pyrazole-3-carbonitrile (2.7 g, 9.43 mmol) in THF (38 mL) was purged with nitrogen, and sodium hydride (37 mg of a 60% dispersion in mineral oil) was added. The reaction was stirred for five minutes, and methyl vinyl sulfone (2.0 g, 19 mmol) was added. The reaction was stirred at room temperature for 18 hours, and additional sodium hydride (0.11 g) was added. The reaction was stirred for one hour, and additional sodium hydride (0.07 g) was added. The reaction was stirred for one hour, and a few drops of water were added. The mixture was concentrated under reduced pressure, and the residue was purified by column chromatography on silica gel (eluting with 50% to 60% ethyl acetate in hexane) to provide 2 g of mixture of 4-bromo-5-{2-methyl-2-[2-(methylsulfonyl)ethoxy]propyl}-1-propyl-1H-pyrazole-3-carbonitrile and methyl vinyl sulfone.

Part B

The methods described in Parts H and I of Example 60 were followed using the material from Part A as the starting material with the following modifications. Chloroform was used instead of dichloromethane in the extraction at the end of Part I. Following purification by column chromatography, the product was recrystallized from acetonitrile. The crystals were isolated by filtration, washed with acetonitrile, and dried under vacuum at 65° C. for four hours to yield 0.6 g of 1-{2-methyl-2-[2-(methylsulfonyl)ethoxy]propyl}-2-propyl-2H-pyrazolo[3,4-c]quinolin-4-amine as a white powder, mp 197-200° C.

MS (APCI) m/z 405 (M+H)$^+$;

Anal. Calcd for $C_{20}H_{28}N_4O_3S$: C, 59.38; H, 6.98; N, 13.85. Found: C, 59.07; H, 6.68; N, 13.78.

Example 1293

2-Ethyl-1-(2-methyl-2-{[2-(methylsulfonyl)ethyl]amino}propyl)-2H-pyrazolo[3,4-c]quinolin-4-amine

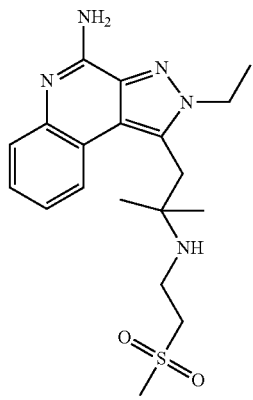 [SMILES: CCn1nc2c(N)nc3ccccc3c2c1CC(C)(C)NCCS(C)(=O)=O]

Part A

Hydrogen chloride (21 mL of a 3.6 M solution in ethanol) was added to a solution of tert-butyl 2-(4-bromo-3-cyano-1-ethyl-1H-pyrazol-5-yl)-1,1-dimethylethylcarbamate (5.6 g, 15 mmol), prepared in Example 1244, in ethanol (75 mL), and the reaction was stirred at room temperature for two days and concentrated under reduced pressure. The residue was suspended in water (50 mL), and aqueous sodium hydroxide (50% w/w) was added to adjust the mixture to pH 12. The basic mixture was extracted with dichloromethane (2×50 mL), and the combined extracts were dried over sodium sulfate, filtered, and concentrated under reduced pressure to provide 4.1 g of 5-(2-amino-2-methylpropyl)-4-bromo-1-ethyl-1H-pyrazole-3-carbonitrile as a colorless oil.

Part B

A solution of 5-(2-amino-2-methylpropyl)-4-bromo-1-ethyl-1H-pyrazole-3-carbonitrile (4.1 g, 15.1 mmol) and methyl vinyl sulfone (3.2 g, 30.2 mmol) in toluene (30 mL) was heated at reflux for 15 hours, allowed to cool to room temperature, and concentrated under reduced pressure. The crude product was purified twice by column chromatography on silica gel (eluting first with 5% methanol in dichloromethane and secondly with ethyl acetate) to provide 2.75 g of 4-bromo-1-ethyl-5-(2-methyl-2-{[2-(methylsulfonyl)ethyl]amino}propyl)-1H-pyrazole-3-carbonitrile as a colorless oil.

Part C

The methods described in Parts F and G of Example 1255 were followed using 4-bromo-1-ethyl-5-(2-methyl-2-{[2-(methylsulfonyl)ethyl]amino}propyl)-1H-pyrazole-3-carbonitrile (2.75 g, 7.29 mmol) as the starting material with the following modifications. The reaction with hydrogen chloride was stirred overnight at room temperature and then heated at reflux for eight hours. Following the work-up procedure, a brown oil was isolated and was purified by column chromatography on silica gel (eluting with 5% methanol in dichloromethane) followed by recrystallization from butyl acetate (10 mL). The crystals were isolated by filtration, washed with butyl acetate, and dried under vacuum at 65° C. for 14 hours to yield 0.8 g of 2-ethyl-1-(2-methyl-2-{[2-(methylsulfonyl)ethyl]amino}propyl)-2H-pyrazolo[3,4-c]quinolin-4-amine as a white powder, mp 155-157° C.

MS (APCI) m/z 405 (M+H)+;

Anal. Calcd for $C_{19}H_{27}N_5O_2S$: C, 58.59; H, 6.99; N, 17.98. Found: C, 58.41; H, 7.00; N, 18.13.

Example 1294

1-[2-Methyl-2-(methylsulfonyl)propyl]-2-propyl-2H-pyrazolo[3,4-c]quinolin-4-amine

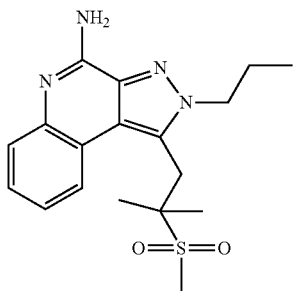 [SMILES: CCCn1nc2c(N)nc3ccccc3c2c1CC(C)(C)S(C)(=O)=O]

Part A

The method described in Part B of Example 60 was followed using 4-methyl-4-(methylthio)pentan-2-one (10.0 g, 68.4 mmol) instead of 4-(propylthio)butan-2-one and propylhydrazine (11.2 g, 68.4 mmol) instead of butylhydrazine with the modification that the reaction with sodium tert-butoxide (6.6 g, 68 mmol) was stirred for one hour. Propylhydrazine was added at room temperature. Following chromatographic purification, 10.6 g of ethyl 5-[2-methyl-2-(methylthio)propyl]-1-propyl-1H-pyrazole-3-carboxylate were obtained and was treated with mCPBA (15 g of 60% pure material) according to the method of Part C of Example 60 to provide 9.4 g of ethyl 5-[2-methyl-2-(methyl sulfonyl)propyl]-1-propyl-1H-pyrazole-3-carboxylate.

Part B

A pressure vessel containing ethyl 5-[2-methyl-2-(methylsulfonyl)propyl]-1-propyl-1H-pyrazole-3-carboxylate (9.4 g, 29.7 mmol) and ammonia (50 mL of a 7 N solution in methanol), and the vessel was sealed and heated at 150° C. for 41 hours and allowed to cool to room temperature. The volatiles were removed under reduced pressure to provide 8.5 g of 5-[2-methyl-2-(methylsulfonyl)propyl]-1-propyl-1H-pyrazole-3-carboxamide as a brown oil.

Part C

A modification of the method described in Part C of Example 1253 was used to treat 5-[2-methyl-2-(methylsulfonyl)propyl]-1-propyl-1H-pyrazole-3-carboxamide (8.5 g, 29.7 mmol) with trifluoroacetic anhydride (7.5 g, 35.6 mmol) in the presence of triethylamine (9 g, 90 mmol). After the reaction was stirred for one hour, additional trifluoroacetic anhydride (2.5 mL) was added to drive the reaction to completion. The resulting product was brominated according to the method described in Part F of Examples 1-4 to provide 4-bromo-5-[2-methyl-2-(methylsulfonyl)propyl]-1-propyl-1H-pyrazole-3-carbonitrile as a colorless oil.

Part D

The methods described in Parts F and G of Example 1255 were followed using 4-bromo-5-[2-methyl-2-(methylsulfonyl)propyl]-1-propyl-1H-pyrazole-3-carbonitrile (5.8 g, 17 mmol) as the starting material with the following modifications. Following the work-up procedure, an oil was isolated and was purified by column chromatography on silica gel (eluting with 5% methanol in dichloromethane) followed by recrystallization from ethanol (32 mL). The crystals were isolated by filtration, washed with ethanol, and dried under vacuum at 65° C. for 17 hours to yield 1.1 g of 1-[2-methyl-2-(methylsulfonyl)propyl]-2-propyl-2H-pyrazolo[3,4-c]quinolin-4-amine as a white powder, mp 202-204° C.

MS (APCI) m/z 361 (M+H)+;

Anal. Calcd for $C_{18}H_{24}N_4O_2S$: C, 59.97; H, 6.71; N, 15.54. Found: C, 60.07; H, 6.38; N, 15.52.

Example 1295

1-[2-Methyl-2-(methylsulfonyl)propyl]-2-propyl-6,7,8,9-tetrahydro-2H-pyrazolo[3,4-c]quinolin-4-amine

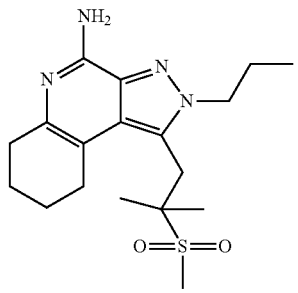 [SMILES: CCCn1nc2c(N)nc3c(c2c1CC(C)(C)S(C)(=O)=O)CCCC3]

A modification of the method described in Example 61 was followed using 1-[2-methyl-2-(methylsulfonyl)propyl]-2-propyl-2H-pyrazolo[3,4-c]quinolin-4-amine (0.45 g, 1.25 mmol) as the starting material. The crude product (0.4 g) was purified by column chromatography on silica gel (eluting with 5% methanol in dichloromethane) followed by recrystallization from ethanol (6 mL). The crystals were isolated by filtration, washed with ethanol, and dried under vacuum at 65° C. for four hours to yield 0.1 g of 1-[2-methyl-2-(methylsulfonyl)propyl]-2-propyl-6,7,8,9-tetrahydro-2H-pyrazolo[3,4-c]quinolin-4-amine as white crystals, mp 209-211° C.

Anal. Calcd for $C_{18}H_{28}N_4O_2S$: C, 59.31; H, 7.74; N, 15.37. Found: C, 59.17; H, 7.51; N, 15.65.

Examples 1296-1297

A mixture of 2-tert-butoxycarbonylamino-3-pyridylboronic acid (prepared as described in Parts A and B of Example 15, 2.0 equivalents) in 1-propanol (20 mL) and 1 M aqueous HCl (15 mL) was heated at 80° C. for 90 minutes. The reaction was allowed to cool to room temperature and solid sodium carbonate (1.5 equivalents) was added with stirring. A 4-bromo-1,5-disubstitued-1H-pyrazole-3-carbonitrile (3.3-3.5 g, 14 mmol, 1 equivalent) shown in the table below, bis(2-diphenylphosphinophenyl)ether (0.05 equivalent), and palladium (II) acetate (0.05 equivalent) were added. The reaction and work-up procedures were carried out as described in Examples 52 through 55. The crude product was purified by chromatography on a HORIZON HPFC system (silica gel, gradient elution using 0-40% CMA in chloroform) followed by recrystallization from the solvent shown in the table below. Crystals were isolated, washed with cold solvent, and dried overnight at 60° C. in a vacuum oven to provide the product.

Example 1296

1-(4-Amino-2-ethyl-2H-pyrazolo[3,4-c][1,8]naphthyridin-1-yl)-2-methylpropan-2-ol was isolated as white needles, mp 283-286° C.

Anal. calcd for $C_{15}H_{19}N_5O \cdot 0.4H_2O$: C, 61.60; H, 6.82; N, 23.94. Found: C, 61.77; H, 6.75; N, 23.96.

Example 1297

1-(4-Amino-2-propyl-2H-pyrazolo[3,4-c][1,8]naphthyridin-1-yl)-2-methylpropan-2-ol was isolated as white needles, mp 252-255° C.

Anal. calcd for $C_{16}H_{21}N_5O$: C, 64.19; H, 7.07; N, 23.39. Found: C, 63.88; II, 7.23; N, 23.25.

Examples 1296-1297

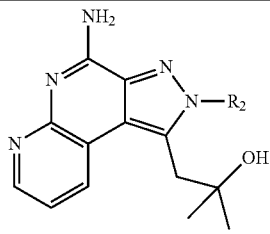

| Example | Starting Material | Recrystallization solvent | $R_2$ |
|---|---|---|---|
| 1296 | 4-Bromo-1-ethyl-5-(2-hydroxy-2-methylpropyl)-1H-pyrazole-3-carbonitrile (Example 62 Parts A-F) | acetonitrile | —$CH_2CH_3$ |
| 1297 | 4-Bromo-5-ethyl-1-propyl-1H-pyrazole-3-carbonitrile (Example 1290 Parts A-D) | 2-propanol | —$CH_2CH_2CH_3$ |

Examples 1298-1300

A mixture of 2-tert-butoxycarbonylamino-3-pyridylboronic acid (prepared as described in Parts A and B of Example 15, 2.0 equivalents) and 1 M aqueous was heated at 80° C. for 45 minutes. The reaction was allowed to cool to room temperature and solid sodium carbonate (3.3 equivalents) was added with stirring. A 4-bromo-1,5-disubstitued-1H-pyrazole-3-carbonitrile (1 equivalent) shown in the table below, DME, and dichlorobis(triphenylphosphine)palladium(II) (0.05 equivalent) were added. The reaction and work-up procedures were carried out as described in Examples 52 through 55. The crude product was purified by chromatography on a HORIZON HPFC system (silica gel, gradient elution using CMA in chloroform) followed by recrystallization from the solvent indicated below. Crystals were isolated, washed with cold solvent, and dried overnight at 60° C. in a vacuum oven to provide the product.

Example 1298

Recrystallization was carried out with acetonitrile to provide 1-(4-amino-2-butyl-2H-pyrazolo[3,4-c][1,8]naphthyridin-1-yl)-2-methylpropan-2-ol as white needles, mp 232-235° C.

Anal. calcd for $C_{17}H_{23}N_5O$: C, 65.15; H, 7.40; N, 22.35. Found: C, 64.97; H, 7.59; N, 22.63.

Example 1299

Recrystallization was carried out with propyl acetate to provide 3-(4-amino-2-propyl-2H-pyrazolo[3,4-c][1,8]naphthyridin-1-yl)-2,2-dimethylpropanenitrile as white needles, mp 249-252° C.

Anal. calcd for $C_{17}H_{20}N_6$: C, 66.21; H, 6.54; N, 27.25. Found: C, 66.15; H, 6.43; N, 27.41.

Example 1300

Recrystallization was carried out with acetonitrile to provide 1-[4-amino-2-(2-methoxyethyl)-2H-pyrazolo[3,4-c][1,8]naphthyridin-1-yl]-2-methylpropan-2-ol as light yellow needles, mp 233-236° C.

Anal. calcd for $C_{16}H_{21}N_5O_2$: C, 60.94; H, 6.71; N, 22.21. Found: C, 60.64; H, 6.72; N, 22.20.

Examples 1298-1300

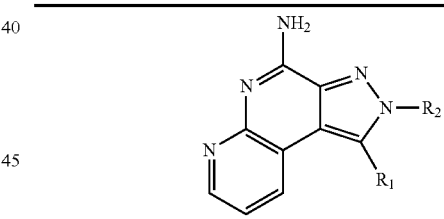

| Example | Starting Material | $R_1$ | $R_2$ |
|---|---|---|---|
| 1298 | 4-Bromo-1-butyl-5-(2-hydroxy-2-methylpropyl)-1H-pyrazole-3-carbonitrile (Example 1258 Parts A-D) | —$CH_2C(CH_3)_2OH$ | —$CH_2CH_2CH_2CH_3$ |
| 1299 | 4-Bromo-5-(2-cyano-2-methylpropyl)-1-propyl-1H-pyrazole-3-carbonitrile (Example 1285 Parts A-C) | —$CH_2C(CH_3)_2CN$ | —$CH_2CH_2CH_3$ |
| 1300 | 4-Bromo-5-(2-hydroxy-2-methylpropyl)-1-(2-methoxyethyl)-1H-pyrazole-3-carbonitrile (Example 1260 Parts A-D) | —$CH_2C(CH_3)_2OH$ | —$CH_2CH_2OCH_3$ |

Example 1301

3-(4-Amino-2-propyl-2H-pyrazolo[3,4-c][1,8]naphthyridin-1-yl)-2,2-dimethylpropanamide

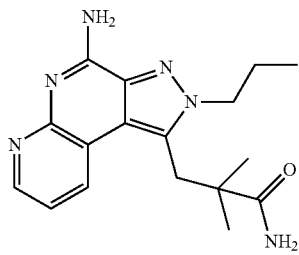 [SMILES: CCCn1nc2c(N)nc3ncccc3c2c1CC(C)(C)C(N)=O]

Hydrogen peroxide (0.8 mL of 30%) was added to a suspension of 3-(4-amino-2-propyl-2H-pyrazolo[3,4-c][1,8]naphthyridin-1-yl)-2,2-dimethylpropanenitrile (0.54 g, 1.75 mmol) in 6 N aqueous sodium hydroxide. The reaction and work-up procedures described in Example 1288 were followed with the modification that the reaction was heated for 5.5 hours. Following chromatographic purification (eluting with 0% to 55% CMA in chloroform) and drying under high vacuum, 0.16 g of 3-(4-amino-2-propyl-2H-pyrazolo[3,4-c][1,8]naphthyridin-1-yl)-2,2-dimethylpropanamide was obtained as a white solid, mp 254-257° C.

Anal. calcd for $C_{17}H_{22}N_6O \cdot 0.1H_2O$: C, 62.21; H, 6.82; N, 25.61. Found: C, 62.01; H, 7.09; N, 25.54.

Example 1302

3-[4-Amino-2-(2-methoxyethyl)-2H-pyrazolo[3,4-c]-1,8-naphthyridin-1-yl]-2,2-dimethylpropanamide

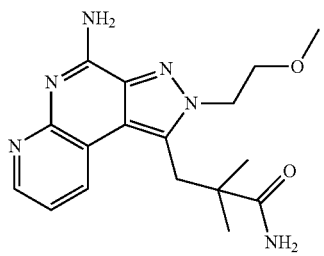 [SMILES: COCCn1nc2c(N)nc3ncccc3c2c1CC(C)(C)C(N)=O]

The method of Examples 1298-1300 and the method of Example 1301 were used to convert 4-bromo-5-(2-cyano-2-methylpropyl)-1-(2-methoxyethyl)-1H-pyrazole-3-carbonitrile to 3-[4-amino-2-(2-methoxyethyl)-2H-pyrazolo[3,4-c]-1,8-naphthyridin-1-yl]-2,2-dimethylpropanamide.
Following chromatographic purification the product was recrystallized from acetonitrile to provide 3-[4-amino-2-(2-methoxyethyl)-2H-pyrazolo[3,4-c]-1,8-naphthyridin-1-yl]-2,2-dimethylpropanamide as a white solid, mp 254-257° C. $^1$H NMR (500 MHz, d$_6$-DMSO) δ 8.50 (dd, J=7.9, 1.9, 1H), 8.46 (dd, J=4.4, 1.6, 1H), 7.14 (dd, J=7.9, 4.4, 1H), 7.15-7.00 (m, 4H), 4.56 (t, J=4.4, 2H), 3.77 (t, J=5.10, 2H), 3.50 (s, 2H), 3.18 (s, 3H), 1.12 (s, 6H); $^{13}$C NMR (125 MHz, d$_6$-DMSO) δ 178.3, 154.9, 153.0, 147.1, 136.9, 135.5, 130.5, 117.7, 116.5, 114.3, 71.0, 58.3, 50.0, 43.9, 33.6, 24.8; HRMS (EI) calcd for $C_{17}H_{22}N_6O_2$ 343.1882. found 343.1886.

Example 1303

4-(4-Amino-2-propyl-2H-pyrazolo[3,4-c]quinolin-1-yl)-N,N-dimethylbutane-1-sulfonamide

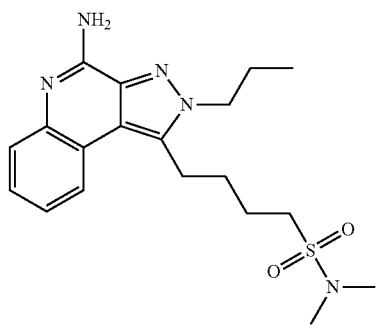 [SMILES: CCCn1nc2c(N)nc3ccccc3c2c1CCCCS(=O)(=O)N(C)C]

Part A

Potassium thioacetate (595 mg, 5.20 mmol) was added to a solution of 1-(4-chlorobutyl)-2-propyl-2H-pyrazolo[3,4-c]quinolin-4-amine (prepared as described in Example 46) (1.50 g, 4.73 mmol) in DMF (24 mL) at ambient temperature. The reaction mixture was stirred for 24 hours and became a light yellow and cloudy mixture. The reaction mixture was concentrated under reduced pressure, diluted with methylene chloride (200 mL), and washed with water (75 mL), and the resulting layers were separated. The aqueous layer was extracted with methylene chloride (50 mL). The combined organic layers were dried over magnesium sulfate and concentrated under reduced pressure to yield 1.92 g of a tan material.

Part B

The material from part A (1.92 g) was dissolved in methanol (47 mL) and degassed with nitrogen for several minutes at ambient temperature. Sodium methoxide in methanol solution (1.20 mL, 25 wt % in MeOH) was added to the reaction mixture, followed by degassing with nitrogen. After 1 hour, 7M HCl (0.9 mL) was added to the reaction mixture and stirred for a few minutes. The reaction mixture was concentrated under reduced pressure, diluted with methylene chloride (80 mL), washed with water (75 mL), and the resulting layers were separated. The aqueous layer was extracted with methylene chloride (50 mL). The combined organic layers were dried over magnesium sulfate and concentrated under reduced pressure to yield 1.37 g of 4-(4-amino-2-propyl-2H-pyrazolo[3,4-c]quinolin-1-yl)butane-1-thiol as a light yellow solid.

Part C

Water (0.2 mL) was added to a suspension of 4-(4-amino-2-propyl-2H-pyrazolo[3,4-c]quinolin-1-yl)butane-1-thiol (1.37 g, 4.36 mmol) in dichloromethane (22 mL) maintained at 0° C. In a separate container, trichloroisocyanuric acid (1.11 g, 4.80 mmol) and benzyltrimethylammonium chloride (2.75 g, 14.8 mmol) were added at ambient temperature to dichloromethane (22 mL), stirred for 45 minutes, and the resulting solution was added dropwise to the reaction mixture containing 4-(4-amino-2-propyl-2H-pyrazolo[3,4-c]quinolin-1-yl)butane-1-thiol over 2 minutes. After 25 minutes, dimethylamine hydrochloride (1.55 g, 13.1 mmol) was added to the reaction mixture. Potassium carbonate (6M, 44 mL) was added to the reaction mixture with vigorous stirring over 2 minutes at ambient temperature. The reaction mixture was stirred for 2 hours and potassium carbonate (6M, 0.5 mL) was added and the mixture was maintained for an additional hour. The reaction mixture was diluted with methylene chloride (250 mL), washed with water (200 mL, pH 10), and the resulting layers were separated. The organic layer was dried over magnesium sulfate and concentrated under reduced pressure to provide 1.13 g of a tan foam. The resulting material was purified by column chromatography on a HORIZON HPFC system (eluting with methanol and ethyl acetate) to provide 460 mg of a white foam. The material was dissolved and triturated from acetonitrile, and dried under reduced pressure to yield 146 mg of 4-(4-amino-2-propyl-2H-pyrazolo[3,4-c]quinolin-1-yl)-N,N-dimethylbutane-1-sulfonamide as a white solid, mp 144-146° C.

MS (EI) m/z 390 (M+H)$^+$;

Anal. calcd for $C_{19}H_{27}N_5O_2S$: C, 58.59; H, 6.99; N, 17.98. Found: C, 58.53; H, 7.13; N, 18.04.

Example 1304

4-(4-Amino-2-propyl-2H-pyrazolo[3,4-c]quinolin-1-yl)-N-methylbutane-1-sulfonamide

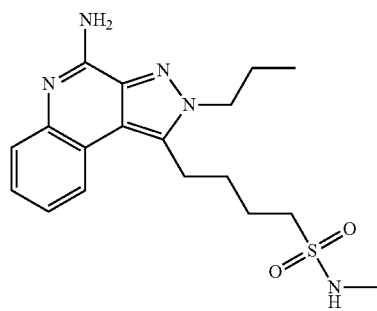 [SMILES: CCCn1nc2c(N)nc3ccccc3c2c1CCCCS(=O)(=O)NC]

Water (0.10 mL) was added to a suspension of 4-(4-amino-2-propyl-2H-pyrazolo[3,4-c]quinolin-1-yl)butane-1-thiol (1.37 g, 4.36 mmol) (prepared as described in Part B of Example 1303) in dichloromethane (24 mL) maintained at 0° C. In a separate container, trichloroisocyanuric acid (600 mg, 2.58 mmol) and benzyltrimethylammonium chloride (1.48 g, 8.0 mmol) were added at ambient temperature to dichloromethane (12 mL), stirred for 45 minutes, and the resulting solution was added dropwise to the reaction mixture containing 4-(4-amino-2-propyl-2H-pyrazolo[3,4-c]quinolin-1-yl)butane-1-thiol over 2 minutes. After 30 minutes, methylamine hydrochloride (475 mg, 7.0 mmol) was added to the reaction mixture. Potassium carbonate (6M, 1.6 mL) was added to the reaction mixture with vigorous stirring over 2.5 hours at ambient temperature. The reaction mixture was diluted with methylene chloride (300 mL), washed with water (300 mL), and the resulting layers were separated. The aqueous layer was extracted with dichloromethane (2×300 mL) and the combined organic layers were dried over magnesium sulfate and concentrated under reduced pressure to provide 0.65 g of foam. The resulting material was purified by column chromatography on a HORIZON HPFC system (eluting with CMA:chloroform ranging in ratios from 0:100 to 20:80) to provide 190 mg of material. The material was recrystallized from isopropanol, dried in a vacuum oven, recrystallized from acetonitrile and dried in a vacuum oven to yield 88 mg of 4-(4-amino-2-propyl-2H-pyrazolo[3,4-c]quinolin-1-yl)-N-methylbutane-1-sulfonamide as a light yellow solid, mp 166-169° C. MS (EI) m/z 376 (M+H)$^+$;

Anal. calcd for $C_{18}H_{25}N_5O_2S \cdot 0.02\ CH_3CN$: C, 57.58; H, 6.71; N, 18.68. Found: C, 57.49; H, 6.85; N, 19.01.

Example 1305

4-(4-Amino-2-propyl-2H-pyrazolo[3,4-c]quinolin-1-yl)butane-1-sulfonamide

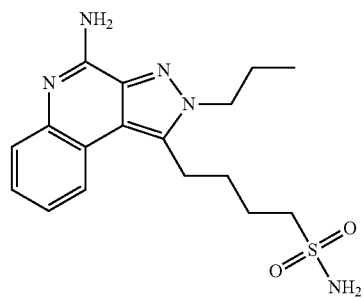 [SMILES: CCCn1nc2c(N)nc3ccccc3c2c1CCCCS(N)(=O)=O]

Part A

A suspension of 4-(4-amino-2-propyl-2H-pyrazolo[3,4-c]quinolin-1-yl)butane-1-thiol (1.37 g, 4.36 mmol) (prepared as described in Part B of Example 1303) in dichloromethane (24 mL) was maintained at 0° C. In a separate container, trichloroisocyanuric acid (632 g, 2.72 mol) and benzyltrimethylammonium chloride (1.56 g, 8.4 mmol) were added at ambient temperature to dichloromethane (12 mL), stirred for 45 minutes, and the resulting solution was added dropwise to the reaction mixture containing 4-(4-amino-2-propyl-2H-pyrazolo[3,4-c]quinolin-1-yl)butane-1-thiol over 2 minutes. Water (0.09 mL) was then added to the red solution. After about 1 hour, 4-methoxybenzylamine (2.10 mL, 16.0 mmol) was added to the reaction mixture, which was maintained for 15 hours at ambient temperature. The reaction mixture was diluted with methylene chloride (225 mL) and water (300 mL), and the resulting layers were separated. The aqueous layer was extracted with dichloromethane (3×100 mL) and the combined organic layers were washed with water (100 mL), dried over magnesium sulfate, and concentrated under reduced pressure to provide 1.8 g of material. The resulting material was suspended in chloroform (20 mL) and filtered. The filtrate was purified by column chromatography on a HORIZON HPFC system (eluting with CMA:chloroform ranging in ratios from 0:100 to 15:85) to provide 420 mg of 4-(4-amino-2-propyl-2H-pyrazolo[3,4-c]quinolin-1-yl)-N-(4-methoxybenzyl)-butane-1-sulfonamide.

Part B

Anisole (108 µL, 1.0 mmol) was added to a solution of 4-(4-amino-2-propyl-2H-pyrazolo[3,4-c]quinolin-1-yl)-N-(4-methoxybenzyl)-butane-1-sulfonamide (400 mg, 0.83 mmol) in trifluoroacetic acid (8 mL) at ambient temperature and stirred for 3.5 hours. The reaction mixture was concentrated under reduced pressure, dissolved in dichloromethane, washed with saturated aqueous sodium bicarbonate, and the layers were separated. The organic layer was diluted with methanol (5-7 mL), dried over magnesium sulfate, and concentrated under reduced pressure to afford 420 mg of material. The material was triturated with ethyl acetate (12 mL) to afford 234 mg of material. The material was then triturated with hot ethyl acetate, recrystallized from methanol (10 mL) and dried in a vacuum oven to provide 155 mg of colorless crystals. The material was adsorbed onto silica gel and purified by column chromatography on a HORIZON HPFC system (eluting with CMA:chloroform ranging in ratios from 0:100 to 30:70) and dried in a vacuum oven to yield 128 mg of 4-(4-amino-2-propyl-2H-pyrazolo[3,4-c]quinolin-1-yl)butane-1-sulfonamide as a white solid, mp 211-213° C.

MS (EI) m/z 362 (M+H)+;

Anal. calcd for $C_{17}H_{23}N_5O_2S$: C, 56.49; H, 6.41; N, 19.37. Found: C, 56.48; H, 6.56; N, 19.40.

Example 1306

(1E,Z)-4-(4-Amino-2-propyl-2H-pyrazolo[3,4-c]quinolin-1-yl)butanal oxime

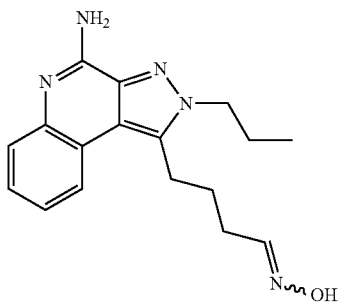 [SMILES: CCCn1nc2c(N)nc3ccccc3c2c1CCCC=NO]

Part A

Hydroxylamine hydrochloride (1.9 g, 27.4 mmol) was added to a solution of di(tert-butyl) 1-(4-oxobutyl)-2-propyl-2H-pyrazolo[3,4-c]quinolin-4-ylimidodicarbonate (12.39 g, 24.95 mmol) (prepared as described in Parts A through D of Example 57) in ethanol (300 mL) and water (200 mL). A 50% w/w solution of aqueous sodium hydroxide (3 mL) was added to the reaction mixture and stirred for 30 minutes. The reaction mixture was partitioned between water and dichloromethane and the phases were separated. The aqueous phase was extracted with dichloromethane and the combined organic phases were washed with water, washed with brine, dried over sodium sulfate, filtered, and concentrated under reduced pressure to afford 11.2 g of a dark yellow solid. The material was purified via column chromatography over silica gel eluting with hexane and ethyl acetate. The material was then triturated with ether to obtain 5.9 g of a white powder and used as is for subsequent reactions.

Part B

6 N Hydrochloric acid solution (4 mL) was added to the material obtained from Part A (0.75 g, 1.466 mmol) and stirred at ambient temperature for 3.5 hours. The reaction mixture was concentrated under reduced pressure and partitioned between 1 N potassium hydroxide solution and dichloromethane. The organic layer was washed with water, washed with brine, dried over potassium carbonate, filtered, and concentrated to afford 0.4458 g of amber oil. The material was purified via column chromatography over silica gel (60 g) eluting with CMA:chloroform in a 10:90 ratio to provide 0.1405 g of material. The material was triturated with ether, filtered, and dried at 70° C. for 18 hours to yield 0.0771 g of (1E,Z)-4-(4-amino-2-propyl-2H-pyrazolo[3,4-c]quinolin-1-yl)butanal oxime as a white powder, mp 211-213° C.

MS (APCI) m/z 312 (M+H)+;

Anal. calcd for $C_{17}H_{21}N_5O$: C, 65.57; H, 6.80; N, 22.49. Found: C, 65.12; H, 7.08; N, 22.36.

Example 1307

1-[3-(5-Phenylisoxazol-3-yl)propyl]-2-propyl-2H-pyrazolo[3,4-c]quinolin-4-amine

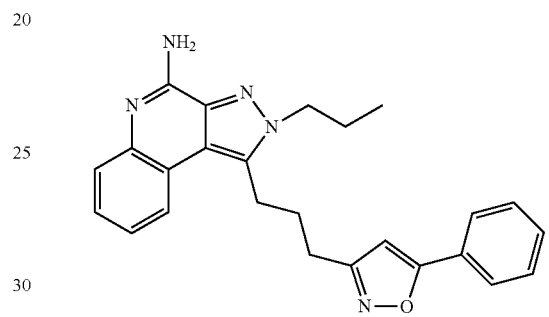

Part A

N-Chlorosuccinimide (0.33 g, 2.47 mmol) was added to a solution of the material from Part A of Example 1306 (1.15 g, 2.25 mmol) in DMF and heated to 50° C. for 2.5 hours. Phenylacetylene (0.5 mL, 4.50 mmol) and anhydrous triethylamine (0.8 mL, 5.62 mmol) were then added to the reaction mixture and heated for an additional hour. The reaction mixture was concentrated under reduced pressure, dissolved in ethyl acetate, washed with water, washed with brine, dried over magnesium sulfate, filtered, and concentrated under reduced pressure. The material was purified via column chromatography over silica gel eluting with hexane and ethyl acetate and concentrated under reduced pressure to yield 0.70 g of material and used as is for subsequent reactions.

Part B

6 M Hydrochloric acid solution in ethanol (20 mL) was added to the material obtained from Part A (0.70 g, 1.144 mmol) and stirred at ambient temperature for 1 hour, heated to 50° C. for 6 hours and maintained overnight at ambient temperature. The reaction mixture was concentrated under reduced pressure. Water was added to the residue and the pH of the water was adjusted to 14 with dropwise addition of 50% sodium hydroxide solution. Material precipitated out of the solution and was filtered and collected. The precipitate was triturated with ether and dried under reduced pressure at 80° C. for 22 hours to yield 0.3982 g of 1-[3-(5-phenylisoxazol-3-yl)propyl]-2-propyl-2H-pyrazolo[3,4-c]quinolin-4-amine as a white powder, mp 172-173° C.

MS (APCI) m/z 412 (M+H)+;

Anal. calcd for $C_{25}H_{25}N_5O \cdot 0.3H_2O$: C, 72.02; H, 6.19; N, 16.80. Found: C, 71.83; H, 6.42; N, 16.81.

Example 1308

1-[3-(5-Butylisoxazol-3-yl)propyl]-2-propyl-2H-pyrazolo[3,4-c]quinolin-4-amine

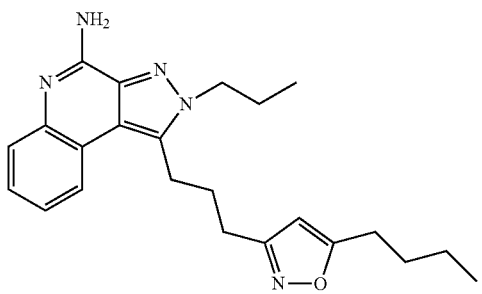 [SMILES: CCCCc1cc(CCCc2c3c(nn2CCC)c(N)nc2ccccc23)no1]

Part A

N-Chlorosuccinimide (0.38 g, 2.82 mmol) was added to a solution of the material from Part A of Example 1306 (1.31 g, 2.56 mmol) in DMF and heated to 50° C. for 2 hours. 1-Hexyne (0.6 mL, 5.12 mmol) and anhydrous triethylamine (0.9 mL, 6.40 mmol) were then added to the reaction mixture and heated for an additional hour. The reaction mixture was diluted with water (200 mL) and extracted with ethyl acetate several times. The combined organic layers were washed with water, washed with brine, dried over magnesium sulfate, filtered, and concentrated under reduced pressure. The material was purified via column chromatography over silica gel (60 g) eluting with hexane and ethyl acetate and concentrated under reduced pressure to afford 0.44 g of material and used as is for subsequent reactions.

Part B

6 M Hydrochloric acid solution in ethanol (20 mL) was added to the material obtained from Part A (0.44 g, 0.7435 mmol) and stirred at 25° C. for 16 hours. The reaction mixture was concentrated under reduced pressure. Water was added to the residue and the pH of the water was adjusted to 14 with dropwise addition of 50% sodium hydroxide solution and stirred for 1 hour at ambient temperature. Material precipitated out of the solution and was filtered and collected. The precipitate was dried under reduced pressure at 85° C. for 18 hours to yield 0.2852 g of 1-[3-(5-butylisoxazol-3-yl)propyl]-2-propyl-2H-pyrazolo[3,4-c]quinolin-4-amine as a tan powder, mp 132-133° C. MS (APCI) m/z 392 (M+H)+;

Anal. calcd for $C_{22}H_{29}N_5O \cdot 0.3H_2O$: C, 69.60; H, 7.52; N, 17.64. Found: C, 69.52; H, 7.22; N, 17.74.

Example 1309

2-Propyl-1-[3-(5-pyridin-3-ylisoxazol-3-yl)propyl]-2H-pyrazolo[3,4-c]quinolin-4-amine

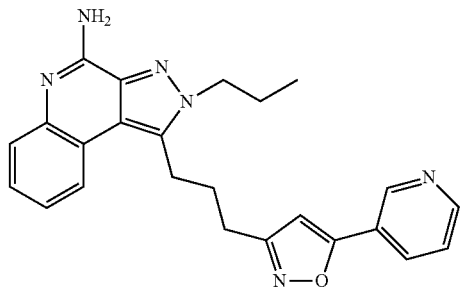 [SMILES: CCCn1nc2c(N)nc3ccccc3c2c1CCCc1cc(-c2cccnc2)on1]

Part A

N-Chlorosuccinimide (0.33 g, 2.47 mmol) was added to a solution of the material from Part A of Example 1305 (1.15 g, 2.25 mmol) in DMF and heated to 50° C. for 1.7 hours. 3-Ethynylpyridine (0.46 g, 4.50 mmol) and anhydrous triethylamine (0.8 mL, 5.62 mmol) were then added to the reaction mixture and heated for an additional hour. The reaction mixture was concentrated under reduced pressure, diluted with dichloromethane, washed sequentially with potassium carbonate solution, water, and brine, dried over sodium sulfate, filtered, and concentrated under reduced pressure. The material was purified via column chromatography over silica gel (60 g) eluting with hexane and ethyl acetate and concentrated under reduced pressure to afford 0.77 g of material and used as is for subsequent reactions.

Part B

6 M Hydrochloric acid solution in ethanol (20 mL) was added to the material obtained from Part A (0.77 g, 1.257 mmol) and stirred at 50° C. for 1.7 hours. The reaction mixture was concentrated under reduced pressure. Water was added to the residue and the pH of the water was adjusted to 14 with dropwise addition of 50% sodium hydroxide solution and stirred for 45 minutes at ambient temperature. Material precipitated out of the solution and was filtered and collected. The precipitate was triturated with ether, then purified via column chromatography over silica gel (60 g eluting with CMA in chloroform in a ratio ranging from 1:99 to 10:90) to yield 0.1638 g of 2-propyl-1-[3-(5-pyridin-3-ylisoxazol-3-yl)propyl]-2H-pyrazolo[3,4-c]quinolin-4-amine as a white crystalline solid, mp 196-198° C.

MS (APCI) m/z 413 (M+H)+;

Anal. calcd for $C_{24}H_{24}N_6O \cdot 0.5CH_4O$: C, 68.75; H, 6.01; N, 19.64. Found: C, 68.58; H, 6.11; N, 19.97.

Example 1310

(1E,Z)-4-(4-Amino-2-propyl-2H-pyrazolo[3,4-c]quinolin-1-yl)butanal O-methyloxime

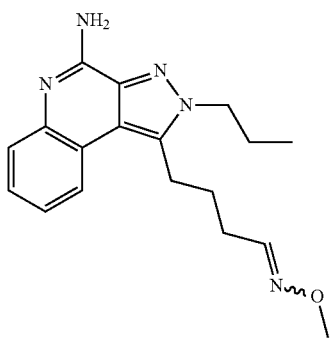 [SMILES: CCCn1nc2c(N)nc3ccccc3c2c1CCCC=NOC]

Part A

O-Methyl hydroxylamine hydrochloride (0.18 g, 2.10 mmol) was added to a solution of di(tert-butyl) 1-(4-oxobutyl)-2-propyl-2H-pyrazolo[3,4-c]quinolin-4-ylimidodicarbonate (0.9462 g, 1.90 mmol) (prepared as described in Parts A through D of Example 57) in ethanol (6 mL) and water (4 mL). A 50% w/w solution of aqueous sodium hydroxide (1 mL) was added to the reaction mixture and stirred for 30 minutes. The reaction mixture was partitioned between water and dichloromethane and the phases were separated. The organic phase was washed with brine, dried over sodium sulfate, filtered, and concentrated under reduced pressure to afford 0.84 g of a dark amber solid. The material was used as is for subsequent reactions.

Part B

6 N Hydrochloric acid solution in ethanol (10 mL) was added to the material obtained from Part A (0.84 g, 1.59 mmol) and stirred at ambient temperature for 4 hours, 50° C. for 1.5 hours, and ambient temperature for 18 hours. The reaction mixture was diluted with water and the pH was adjusted to 14 with dropwise addition of 50% sodium hydroxide solution and material oiled out of solution. The aqueous layer was extracted with dichloromethane and the combined organic layers were washed with water, washed with brine, dried over sodium sulfate, filtered, and concentrated to afford 0.450 g of an amber oil. The material was purified via column chromatography over silica gel (40 g) eluting with 1% CMA in chloroform and recrystallized for hexane/ethyl acetate. The material was further purified via column chromatography over silica gel (40 g) eluting with 1% methanol in ethyl acetate and recrystallized for hexane/ethyl acetate to provide 0.032 g of (1E,Z)-4-(4-amino-2-propyl-2H-pyrazolo[3,4-c]quinolin-1-yl)butanal O-methyloxime as a white crystalline solid, mp 117-119° C.;

MS (APCI) m/z 326 (M+H)$^+$;

Anal. calcd for $C_{18}H_{23}N_5O$: C, 66.44; H, 7.12; N, 21.52. Found: C, 66.57; H, 7.40; N, 21.43.

Example 1311

1-[3-(1-Benzyl-2,5-dihydro-1H-pyrrol-3-yl)propyl]-2-propyl-2H-pyrazolo[3,4-c]quinolin-4-amine

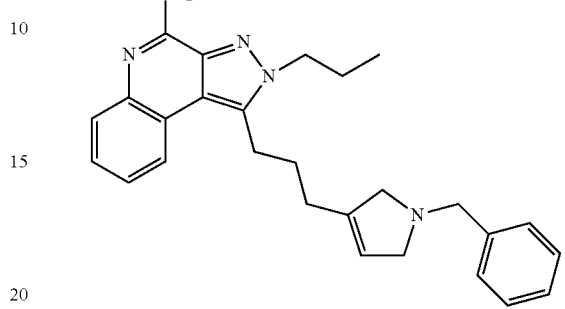

Part A

Benzylamine (51.5 g, 480 mmol) was added to (chloromethyl)trimethylsilane (19.64 g, 160 mmol) and heated at 200° C. for 2 hours. The reaction mixture was diluted with 1 N sodium hydroxide solution and ether and the organic layer was dried over magnesium sulfate and concentrated under reduced pressure. The residue was distilled under reduced pressure to afford 23.00 g of N-benzyl-N-trimethylsilanylmethyl-amine.

Part B

1 N Hydrochloric acid solution (119 mL) was added to N-benzyl-N-trimethylsilanylmethyl-amine (23.00 g, 119 mmol) and white precipitate formed. Tetrahydrofuran (650 mL), potassium cyanide (9.3 g, 143 mmol), and aqueous formaldehyde solution (37 wt. %, 12 mL, 155 mmol) were added to the reaction mixture and stirred at ambient temperature for 15 hours. The mixture was extracted with ether and separated and the combined organic layers were washed with water, dried over magnesium sulfate, and concentrated sequentially under reduced pressure and high vacuum at ambient temperature to afford 27.80 g of (N-Benzyl-N-trimethylsilanylmethyl-amino)acetonitrile.

Part C

Di(tert-butyl) 1-pent-4-ynyl-2-propyl-2H-pyrazolo[3,4-c]quinolin-4-ylimidodicarbonate (prepared as described in Parts A-E of Example 57) (6.40 g, 13.0 mmol), silver fluoride (3.6 g, 28.6 mmol), and acetonitrile (30 mL) were added sequentially to a solution of (N-Benzyl-N-trimethylsilanylmethyl-amino)acetonitrile (6.6 g, 28.6 mmol) in acetonitrile (50 mL) and stirred at ambient temperature in the dark for 22 hours. The reaction mixture was filtered through a bed of activated carbon and CELITE filter agent rinsed with dichloromethane to obtain 9.43 g of a yellow oil. The material was purified via column chromatography over silica gel (40 g) eluting with ethyl acetate to provide 4.7 g of product as a light amber solid and used as is in subsequent reactions.

Part D

6 N Hydrochloric acid in ethanol (75 mL, 75.1 mmol) was added to the material prepared in part C (4.7 g, 7.51 mmol) and stirred at ambient temperature for 14 hours. The reaction mixture was concentrated under reduced pressure and diluted with water and the pH was adjusted to 14 with dropwise addition of 50% sodium hydroxide solution. The aqueous layer was extracted with dichloromethane and the combined organic layers were washed sequentially with water and brine, dried over sodium sulfate, filtered, and concentrated to afford 3.12 g of white solid. The material was purified via recrystallization from isopropanol to obtain 0.5868 g of 1-[3-(1-benzyl-2,5-dihydro-1H-pyrrol-3-yl)propyl]-2-propyl-2H-pyrazolo[3,4-c]quinolin-4-amine as a white powder, mp 150-152° C.

Anal. calcd for $C_{27}H_{31}N_5$: C, 76.20; H, 7.34; N, 16.46. Found: C, 75.95; H, 7.40; N, 16.45.

Example 1312

1-[3-(1-Benzyl-1H-pyrrol-3-yl)propyl]-2-propyl-2H-pyrazolo[3,4-c]quinolin-4-amine

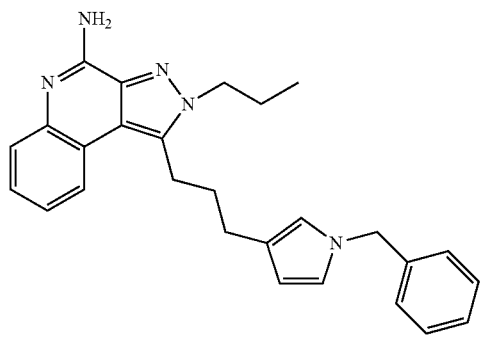 [SMILES: CCCn1nc2c(N)nc3ccccc3c2c1CCCc1ccn(Cc2ccccc2)c1]

2,3-Dichloro-5,6-dicyano-p-benzoquinone (1.13 g, 4.98 mmol) was added to a mixture of 1-[3-(1-benzyl-2,5-dihydro-1H-pyrrol-3-yl)propyl]-2-propyl-2H-pyrazolo[3,4-c]quinolin-4-amine (prepared as described in Example 1311) (2.12 g, 4.98 mmol) in toluene (60 mL) stirred and heated to 70° C. for 2.5 hours. The reaction mixture was cooled to ambient temperature, diluted with dichloromethane, and washed with potassium carbonate solution and the phases were separated. The aqueous layers were washed with chloroform and the combined organic layers were washed sequentially with water and brine, dried over sodium sulfate, and filtered. The dried organic mixture was filtered through a bed of activated carbon with CELITE filter agent and rinsed with hot chloroform and concentrated under reduced pressure to provide 0.556 g of brown oil. The material was purified via column chromatography over silica gel (40 g) eluting with 2-10% CMA in chloroform, recrystallized from isopropanol, and dried under reduced pressure over 1 week to afford 0.2674 g of 1-[3-(1-benzyl-1H-pyrrol-3-yl)propyl]-2-propyl-2H-pyrazolo[3,4-c]quinolin-4-amine as a brown crystalline solid, mp 138-140° C.

MS (APCI) m/z 424 (M+H)$^+$;

Anal. calcd for $C_{27}H_{29}N_5$: C, 76.56; H, 6.90; N, 16.53. Found: C, 76.34; H, 6.83; N, 16.41.

Example 1313

2-Propyl-1-[3-(1H-pyrrol-3-yl)propyl]-2H-pyrazolo[3,4-c]quinolin-4-amine

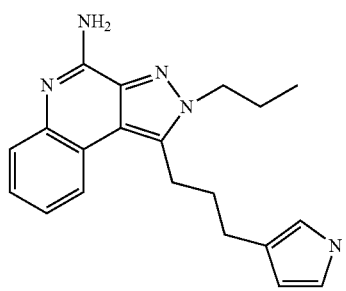 [SMILES: CCCn1nc2c(N)nc3ccccc3c2c1CCCc1cc[nH]c1]

Part A

1-[3-(1-Benzyl-2,5-dihydro-1H-pyrrol-3-yl)propyl]-2-propyl-2H-pyrazolo[3,4-c]quinolin-4-amine (prepared as described in Example 1311) (0.475 g, 1.117 mmol) was added to dioxane (10 mL) and heated at 70° C. open to the atmosphere for 21 hours. The reaction mixture was concentrated under reduced pressure, dried under high vacuum for 18 hours, triturated with ether, and filtered to afford 0.3916 g of material used as is in subsequent reactions.

Part B

Sodium metal (0.058 mg) was dissolved in a solution of liquid ammonia at −78° C. for several minutes and the solution became a dark blue color. The material from Part A (0.3916 g, 0.924 mmol) was added to the reaction mixture as a solution in THF (5 mL), and the mixture became a dark red color within minutes. After 5 minutes and 15 minutes, additional sodium metal (0.015 g and 0.023 g, respectively) was added to the reaction mixture and maintained at −78° C. for 1 hour as a light red solution. Solid ammonium chloride was added to the reaction mixture and the reaction mixture was warmed to ambient temperature. The resulting slurry was diluted with dichloromethane, washed sequentially with water and brine, dried over magnesium sulfate, filtered, and concentrated and dried under reduced pressure to afford 0.32 g of a yellow oil. The material was purified via column chromatography over silica gel (10 g) eluting with 2-5% CMA in chloroform, and concentrated under reduced pressure for 1 week to yield 0.1103 g of 2-propyl-1-[3-(1H-pyrrol-3-yl)propyl]-2H-pyrazolo[3,4-c]quinolin-4-amine as a tan powder, mp 173-174° C.

MS (APCI) m/z 334 (M+H)$^+$;

Anal. calcd for $C_{20}H_{23}N_5 \cdot 0.5H_2O$: C, 70.15; H, 7.06; N, 20.45. Found: C, 69.90; H, 6.95; N, 20.13.

Example 1314

1-[3-(3-Isopropylisoxazol-5-yl)propyl]-2-propyl-6,7,8,9-tetrahydro-2H-pyrazolo[3,4-c]quinolin-4-amine

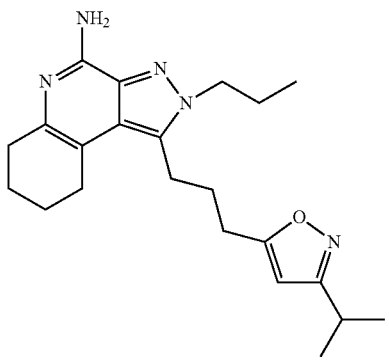 [SMILES: CCCn1nc2c(N)nc3c(c2c1CCCc1cc(C(C)C)no1)CCCC3]

Part A

Isobutyraldehyde (3 mL, 33.0 mmol) and aqueous sodium hydroxide solution (50% w/w, 1.5 mL) were added sequentially to a solution of hydroxylamine hydrochloride (2.52 g, 36.3 mmol) in ethanol (40 mL) and water (80 mL) and stirred at ambient temperature for 17 hours. The pH of the solution was adjusted to 12 with 5 mL of 1 N sodium hydroxide solution and extracted with dichloromethane. The combined organic portions were washed sequentially with water and brine, dried over sodium sulfate, filtered, and concentrated under reduced pressure and high vacuum to obtain 1.863 g of 2-methyl-propionaldehyde oxime.

Part B

N-Chlorosuccinimide (2.85 g, 21.4 mmol) was added in one portion to 2-methyl-propionaldehyde oxime (1.863 g, 21.4 mmol) in DMF contained in a reaction vessel cooled with an ice bath. After 10 minutes, the ice bath was removed, and the mixture was allowed to warm to ambient temperature. The solution was added to a solution of the alkyne prepared in Parts A through F of Example 614 (3.74 g, 7.53 mmol) in DMF (40 mL) cooled by an ice bath. After 1 minute, triethylamine was added to the solution which precipitated. After a couple of minutes, the reaction was heated to 50° C. for 4.7 hours, followed by stirring at ambient temperature for 3 days. The reaction was diluted with dichloromethane, washed with 1 N potassium hydroxide, dried over sodium sulfate, filtered, and purified via column chromatography on silica gel (450 g eluting with 30-40% ethyl acetate in hexane) to afford 1.84 g of material as an amber oil.

Part C

6 M Hydrochloric acid solution in ethanol (10 mL) was added to the material obtained from Part B (1.84 g, 3.16 mmol) and stirred at 60° C. for 2.5 hours. The reaction mixture pH was adjusted to 14 with dropwise addition of 1 N potassium hydroxide solution and concentrated under reduced pressure. The residue was extracted with dichloromethane and the combined organic layers were washed sequentially with water and brine, dried over magnesium sulfate, filtered, and concentrated to afford a white solid. The material was triturated with ether, filtered, and dried to yield 0.9737 g of 1-[3-(3-isopropylisoxazol-5-yl)propyl]-2-propyl-6,7,8,9-tetrahydro-2H-pyrazolo[3,4-c]quinolin-4-amine as a white powder, mp 147.0-149° C.

Anal. calcd for $C_{22}H_{31}N_5O \cdot 0.05CH_2Cl_2$: C, 68.65; H, 8.13; N, 18.15. Found: C, 68.47; H, 8.31; N, 18.19.

Example 1315

N-[2-(4-Amino-2-methyl-6,7,8,9-tetrahydro-2H-pyrazolo[3,4-c]quinolin-1-yl)ethyl]-N'-isopropylurea

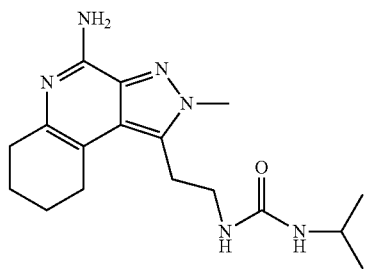 [SMILES: CC(C)NC(=O)NCCc1c2c3c(nc(N)c2nn1C)CCCC3]

Triethylamine (2.84 mL, 20.4 mmol) was added to a suspension of 1-(2-aminoethyl)-2-methyl-6,7,8,9-tetrahydro-2H-pyrazolo[3,4-c]quinolin-4-amine (prepared as described in Example 50) (1.0 g, 4.08 mmol) in dichloromethane (50 mL) and cooled to 4° C. Isopropyl isocyanate (0.44 mL, 4.48 mmol) was added dropwise to the reaction mixture and maintained at ambient temperature for 16 hours. The reaction mixture was diluted with chloroform (50 mL) and the precipitate was collected by filtration, washed with water, and dried under reduced pressure to afford N-[2-(4-amino-2-methyl-6,7,8,9-tetrahydro-2H-pyrazolo[3,4-c]quinolin-1-yl)ethyl]-N'-isopropylurea as tan needles, mp 237-238° C.

MS (APCI) m/z 331.24 (M+H)$^+$;

Anal. calcd for $C_{17}H_{26}N_6O \cdot 0.06CHCl_3$: C, 60.70; H, 7.78; N, 24.89. Found: C, 60.34; H, 8.36; N, 24.64.

Example 1316

N-[2-(4-Amino-2-methyl-6,7,8,9-tetrahydro-2H-pyrazolo[3,4-c]quinolin-1-yl)ethyl]morpholine-4-carboxamide

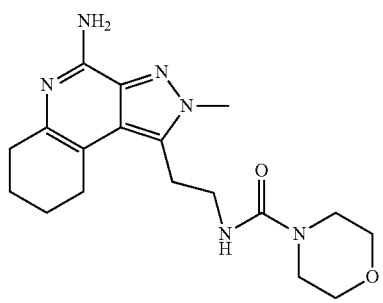 [SMILES: Cn1nc2c(N)nc3c(c2c1CCNC(=O)N1CCOCC1)CCCC3]

Triethylamine (2.84 mL, 20.4 mmol) was added to a suspension of 1-(2-aminoethyl)-2-methyl-6,7,8,9-tetrahydro- 2H-pyrazolo[3,4-c]quinolin-4-amine (prepared as described in Example 50) (1.0 g, 4.08 mmol) in dichloromethane (50 mL) and cooled to 4° C. 4-Morpholinecarbonyl chloride (0.61 g, 4.08 mmol) was added in dichloromethane (5 mL) dropwise over 5 minutes to the reaction mixture and maintained at ambient temperature for 16 hours. The reaction mixture was diluted with dichloromethane (50 mL) and washed sequentially with water (50 mL), 4% sodium bicarbonate (2×50 mL), water (50 mL), and brine (50 mL). The combined organic layers were concentrated under reduced pressure and the residue was purified via column chromatography on silica gel (80 g, eluting with mixtures of chloroform and CMA). The material was crystallized from acetonitrile to provide N-[2-(4-amino-2-methyl-6,7,8,9-tetrahydro-2H-pyrazolo[3,4-c]quinolin-1-yl)ethyl]morpholine-4-carboxamide as orange needles, mp 187-188° C.

MS (APCI) m/z 359.21 (M+H)+;

Anal. calcd for $C_{18}H_{26}N_6O_2$: C, 60.32; H, 7.31; N, 23.45. Found: C, 60.10; H, 7.34; N, 23.68.

Example 1317

N-(1-Isobutyl-2-methyl-2H-pyrazolo[3,4-c]quinolin-4-yl)acetamide

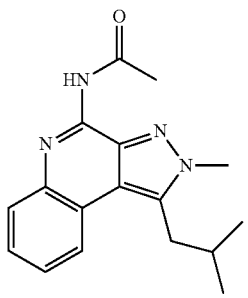 [SMILES: CC(=O)Nc1nc2ccccc2c2c(CC(C)C)n(C)nc12]

Triethylamine (0.49 mL, 3.53 mmol) was added to a suspension of 2-methyl-1-(2-methylpropyl)-2H-pyrazolo[3,4-c]quinolin-4-amine (prepared as described in Example 3) (0.75 g, 2.95 mmol) in dichloromethane (30 mL) and cooled to 4° C. Acetyl chloride (0.255 g, 3.24 mmol) was added in dichloromethane (5 mL) dropwise over 5 minutes to the reaction mixture and maintained at ambient temperature for 16 hours. The reaction mixture was diluted with dichloromethane (25 mL) and washed sequentially with water (25 mL), 4% sodium bicarbonate (2×25 mL), water (25 mL), and brine (25 mL). The combined organic layers were concentrated under reduced pressure and the residue was purified via column chromatography on silica gel (80 g, eluting with 0-20% CMA/chloroform), concentrated under reduced pressure, and recrystallized from diethyl ether to yield 0.49 g of N-(1-isobutyl-2-methyl-2H-pyrazolo[3,4-c]quinolin-4-yl)acetamide as white crystals, mp 130-131° C.

MS (APCI) m/z 297.16 (M+H)+;

Anal. calcd for $C_{17}H_{20}N_4O$: C, 68.90; H, 6.80; N, 18.90. Found: C, 68.96; H, 6.64; N, 19.14.

Example 1318

Ethyl 1-isobutyl-2-methyl-2H-pyrazolo[3,4-c]quinolin-4-ylcarbamate

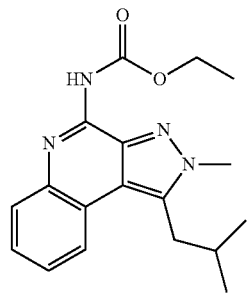 [SMILES: CCOC(=O)Nc1nc2ccccc2c2c(CC(C)C)n(C)nc12]

Triethylamine (0.49 mL, 3.53 mmol) was added to a suspension of 2-methyl-1-(2-methylpropyl)-2H-pyrazolo[3,4-c]quinolin-4-amine (prepared as described in Example 3) (0.75 g, 2.95 mmol) in dichloromethane (30 mL) and cooled to 4° C. Ethyl chloroformate (0.352 g, 3.24 mmol) was added in dichloromethane (5 mL) dropwise over 5 minutes to the reaction mixture and maintained at ambient temperature for 16 hours. The reaction mixture was diluted with dichloromethane (25 mL) and washed sequentially with water (25 mL), 4% sodium bicarbonate (2×25 mL), water (25 mL), and brine (25 mL). The combined organic layers were concentrated under reduced pressure and the residue was purified via column chromatography on silica gel (80 g, eluting with 0-10% CMA/chloroform), concentrated under reduced pressure, and recrystallized from diethyl ether to afford 0.45 g of ethyl 1-isobutyl-2-methyl-2H-pyrazolo[3,4-c]quinolin-4-ylcarbamate as white crystals, mp 120-121° C.

MS (APCI) m/z 327.18 (M+H)+;

Anal. calcd for $C_{18}H_{22}N_4O_2$: C, 66.24; H, 6.79; N, 17.16. Found: C, 66.32; H, 6.62; N, 17.48.

Example 1319

Ethyl 2-methyl-1-{2-[(methylsulfonyl)amino]ethyl}-6,7,8,9-tetrahydro-2H-pyrazolo[3,4-c]quinolin-4-ylcarbamate

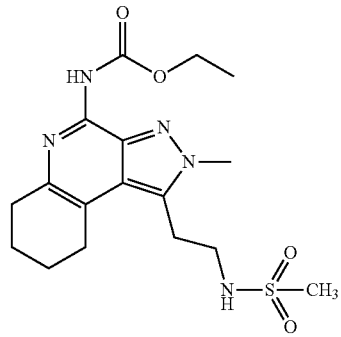 [SMILES: CCOC(=O)Nc1nc2c(c3c(CCNS(C)(=O)=O)n(C)nc13)CCCC2]

Triethylamine (0.044 g, 0.4 mmol) was added to a suspension of the amine of Example 128 (0.07 g, 0.2 mmol) in dichloromethane (5 mL) and cooled to 4° C. Ethyl chloroformate (0.024 g, 0.2 mmol) was added in dichloromethane (1 mL) dropwise over 5 minutes to the reaction mixture and maintained at ambient temperature for 2 hours. The reaction mixture was diluted with dichloromethane (5 mL) and washed sequentially with water (5 mL), 4% sodium bicarbonate (2×5 mL), water (5 mL), and brine (5 mL). The combined organic layers were concentrated under reduced pressure and the residue was purified via column chromatography on silica gel (80 g, eluting with 5-30% CMA/chloroform), concentrated under reduced pressure, and recrystallized from acetonitrile to yield 0.044 g of ethyl 2-methyl-1-{2-[(methylsulfonyl)amino]ethyl}-6,7,8,9-tetrahydro-2H-pyrazolo[3,4-c]quinolin-4-ylcarbamate as a white solid, mp 214-215° C.

$^1$H-NMR (300 MHz, DMSO) δ 9.41 (br s, 1H), 7.29 (br s, 1H), 4.11-4.05 (m, 5H), 3.27-3.21 (m, 4H), 2.99 (br s, 2H), 2.87 (s, 3H), 2.72 (br s, 2H), 1.81 (br s, 4H), 1.21 (t, J=7.1 Hz, 3H).

MS (APCI) m/z 396.16 (M+H)$^+$.

Example 1320

7-(Benzyloxy)-2-ethyl-2H-pyrazolo[3,4-c]quinolin-4-amine

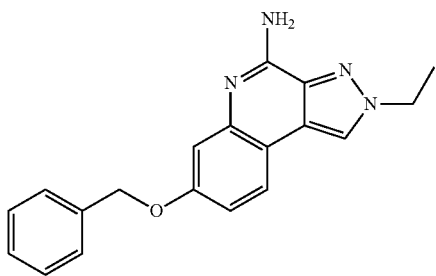 [SMILES: CCn1cc2c(n1)c(N)nc1cc(OCc3ccccc3)ccc12]

Part A

Pyridine (1.30 mL, 16.12 mmol) was added to a suspension of 6-benzyloxyindole (3.0 g, 13.44 mmol) in diethylether (20 mL) cooled to 4° C. Chloroethyl oxalate (2.02 g, 14.78 mmol) was added in diethylether (7 mL) dropwise over 5 minutes to the reaction mixture and maintained at ambient temperature for 20 hours. The reaction mixture was diluted with diethylether (30 mL) and the yellow precipitate was collected via filtration and washed with diethylether. The solid was suspended in water (20 mL), stirred for 10 minutes, and the solid was harvested by filtration and dried to provide 3.5 g of 6-benzyloxy-1H-indol-3-yl)-oxo-acetic acid ethyl ester as a yellow solid.

Part B

Acetyl chloride (1.49 mL, 21.02 mmol), acetic acid (6M, 1.75 mL), and ethylhydrazine oxalate (3.2 g, 21.02 mmol) were sequentially added to a suspension of 6-benzyloxy-1H-indol-3-yl)-oxo-acetic acid ethyl ester (3.4 g, 10.51 mmol) in ethanol (53 mL) and heated at reflux temperature overnight. The reaction mixture was cooled to ambient temperature and the insoluble material was removed via filtration. The filtrate was concentrated under reduced pressure, purified via column chromatography on silica gel (80 g, eluting with 0-10% CMA/chloroform), concentrated under reduced pressure, and recrystallized from acetonitrile to yield 1.34 g of 7-benzyloxy-2-ethyl-2,5-dihydro-pyrazolo[3,4-c]quinolin-4-one as a brown solid, mp 240-241° C.

Part C

Phosphorous oxychloride (15 mL) was added to 7-benzyloxy-2-ethyl-2,5-dihydro-pyrazolo[3,4-c]quinolin-4-one (1.20 g, 3.76 mmol) and heated at 100° C. for 1 hour. The reaction mixture was cooled to ambient temperature and the poured onto crushed ice while stirring. 6 N Sodium hydroxide solution was added to the suspension at 4° C. and the solid was harvested by filtration and dried to afford 1.23 g of 7-benzyloxy-4-chloro-2-ethyl-2H-pyrazolo[3,4-c]quinoline as a yellow solid, mp 155-157° C.

Part D

A mixture of 7-benzyloxy-4-chloro-2-ethyl-2H-pyrazolo[3,4-c]quinoline (1.20 g, 3.55 mmol) and 7 N ammonia in methanol (25 mL) was heated in a pressure vessel at 150° C. for 24 hours. The reaction mixture was concentrated under reduced pressure, purified via column chromatography on silica gel (eluting with 0-35% CMA/chloroform), concentrated under reduced pressure, and crystallized from acetonitrile to yield 0.93 g of 7-(benzyloxy)-2-ethyl-2H-pyrazolo[3,4-c]quinolin-4-amine as a tan solid, mp 229-230° C.

MS (APCI) m/z 319.13 (M+H)$^+$;

Anal. calcd for $C_{19}H_{18}N_4O \cdot 0.1HCl$: C, 70.87; H, 5.67; N, 17.40. Found: C, 70.66; H, 5.92; N, 17.57.

Example 1321

4-Amino-2-ethyl-2H-pyrazolo[3,4-c]quinolin-7-ol

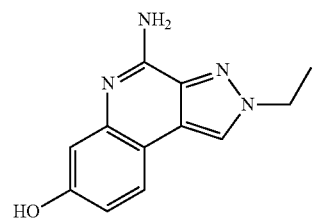 [SMILES: CCn1cc2c(n1)c(N)nc1cc(O)ccc12]

A suspension of 7-benzyloxy-2-ethyl-2H-pyrazolo[3,4-c]quinolin-4-ylamine (prepared as described in Example 1320) (0.80 g, 2.51 mmol) in ethanol (80 mL) and methanol (20 mL) and palladium on carbon (10% palladium w/w on carbon) (0.4 g,) were combined in a pressure vessel and placed under hydrogen pressure ((50 psi (3.4×10$^5$ Pa)) for 24 hours. The reaction mixture was diluted with DMF (50 mL), filtered through CELITE filter agent, and the filtrate was concentrated under reduced pressure. The residue was purified via column chromatography on silica gel (eluting with 20-50% CMA/chloroform), concentrated under reduced pressure, and crystallized from acetonitrile to yield 0.31 g of 4-amino-2-ethyl-2H-pyrazolo[3,4-c]quinolin-7-ol as a light-yellow solid, mp 214-215° C.

MS (APCI) m/z 229.10 (M+H)$^+$;

Anal. calcd for $C_{12}H_{12}N_4O$: C, 63.15; H, 5.30; N, 24.55. Found: C, 62.91; H, 4.99; N, 24.65.

Example 1322

5-(4-Amino-2-propyl-2H-pyrazolo[3,4-c]quinolin-1-yl)-N-hydroxypentanamidine

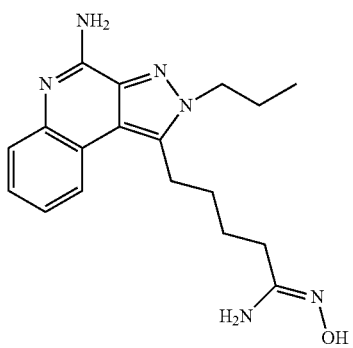 [SMILES: CCCn1nc2c(N)nc3ccccc3c2c1CCCC/C(N)=N/O]

Part A

Potassium cyanide (247 mg, 3.79 mmol) and sodium iodide (142 mg, 0.95 mmol) were added sequentially to a solution of 1-(4-chlorobutyl)-2-propyl-2H-pyrazolo[3,4-c]quinolin-4-amine (prepared as described in Example 46) (1.0 g, 3.16 mmol) in DMF (15 mL) and heated to reflux for 6 hours. The reaction mixture was stirred for 24 hours and became a light yellow and cloudy mixture. The reaction mixture was diluted with dichloromethane, and washed with saturated aqueous sodium bicarbonate (75 mL), and the resulting layers were separated. The aqueous layer was extracted with dichloromethane. The combined organic layers were washed with brine, dried over magnesium sulfate, filtered, and concentrated under reduced pressure to yield 971 mg of white solid.

Part B

Hydroxylamine hydrochloride (413 mg, 5.95 mmol) and potassium carbonate (549 mg, 3.97 mmol) were added to a solution of the material from Part A (610 mg, 1.98 mmol) in ethanol (20 mL) and stirred overnight. The reaction mixture was concentrated under reduced pressure, diluted with dichloromethane, and washed with saturated aqueous sodium bicarbonate, and the resulting layers were separated. The aqueous layer was extracted with dichloromethane. The combined organic layers were washed with brine, dried over magnesium sulfate, filtered, concentrated under reduced pressure, and recrystallized from acetonitrile to yield 200 mg of 5-(4-amino-2-propyl-2H-pyrazolo[3,4-c]quinolin-1-yl)-N-hydroxypentanamidine as a white crystalline solid, mp 222-224° C. $^1$H NMR (300 MHz, CDCl$_3$) δ 8.70 (s, 1H), 7.90 (d, J=8.4 Hz, 1H), 7.48 (d, J=8.2 Hz, 1H), 7.32 (dd, J=6.8, 8.1 Hz, 1H), 7.22 (dd, J=6.3, 7.5 Hz, 1H), 6.62 (s, 2H), 5.34 (s, 2H), 4.34 (dd, J=6.8, 7.5 Hz, 2H), 3.23 (br s, 2H), 2.04 (br s, 2H), 1.92 (m, 2H), 1.69 (m, 4H), 0.92 (t, J=7.6 Hz, 3H); MS (APCI) m/z 341 (M+H$^+$); Anal. calcd for C$_{18}$H$_{24}$N$_6$O (with 0.3 eq. H$_2$O): C, 62.52; H, 7.17; N, 24.30. Found: C, 62.23; H, 6.89; N, 24.50.

Exemplary Compounds

Certain exemplary compounds, including some of those described above in the Examples, have the following Formula (IIIa, IIIb, IVa, VIIa, VIIa, VIIIa, or IXa) and the following R$_1$, and R$_2$ substituents, wherein each line of the table represents a specific compound.

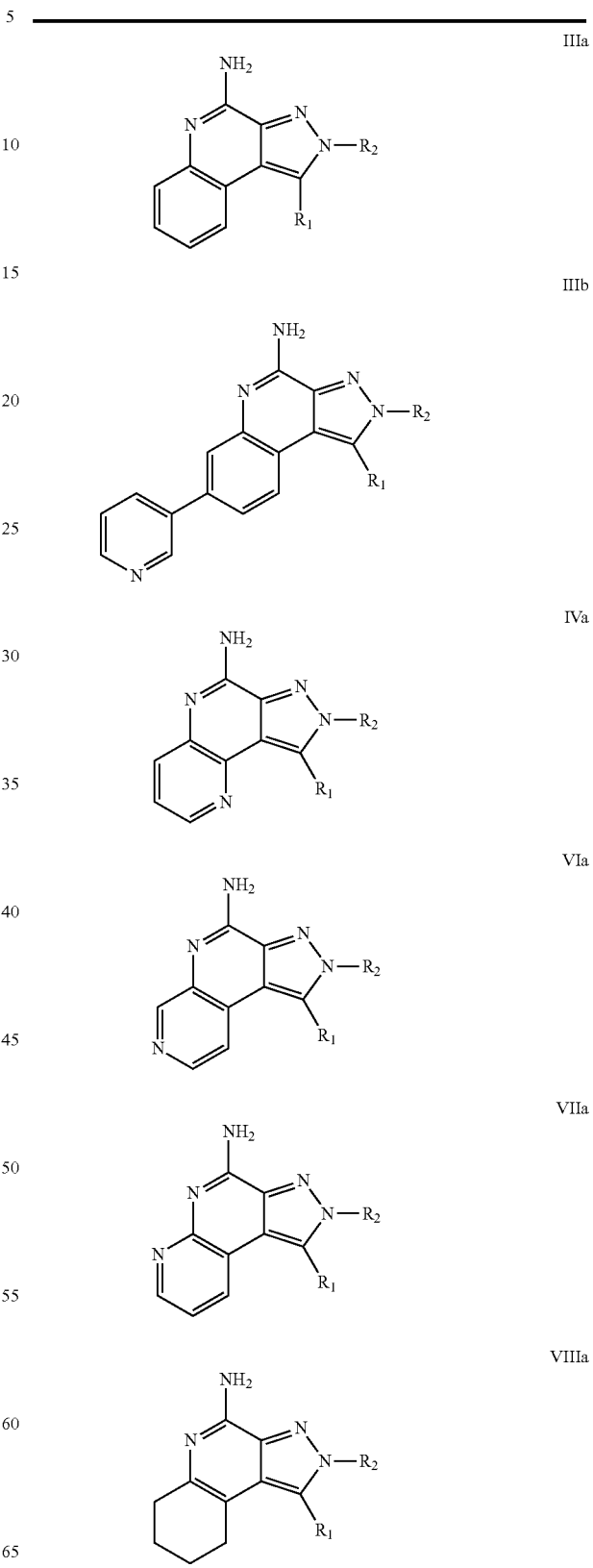

IXa

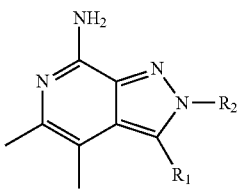

| R₁ | R₂ |
|---|---|
| methyl | hydrogen |
| methyl | methyl |
| methyl | ethyl |
| methyl | n-propyl |
| methyl | n-butyl |
| methyl | benzyl |
| methyl | 2-methoxyethyl |
| methyl | 2-hydroxyethyl |
| ethyl | hydrogen |
| ethyl | methyl |
| ethyl | ethyl |
| ethyl | n-propyl |
| ethyl | n-butyl |
| ethyl | benzyl |
| ethyl | 2-methoxyethyl |
| ethyl | 2-hydroxyethyl |
| 2-methylpropyl | hydrogen |
| 2-methylpropyl | methyl |
| 2-methylpropyl | ethyl |
| 2-methylpropyl | n-propyl |
| 2-methylpropyl | n-butyl |
| 2-methylpropyl | benzyl |
| 2-methylpropyl | 2-methoxyethyl |
| 2-methylpropyl | 2-hydroxyethyl |
| 2-methanesulfonylethyl | hydrogen |
| 2-methanesulfonylethyl | methyl |
| 2-methanesulfonylethyl | ethyl |
| 2-methanesulfonylethyl | n-propyl |
| 2-methanesulfonylethyl | n-butyl |
| 2-methanesulfonylethyl | benzyl |
| 2-methanesulfonylethyl | 2-methoxyethyl |
| 2-methanesulfonylethyl | 2-hydroxyethyl |
| 4-methanesulfonylaminobutyl | hydrogen |
| 4-methanesulfonylaminobutyl | methyl |
| 4-methanesulfonylaminobutyl | ethyl |
| 4-methanesulfonylaminobutyl | n-propyl |
| 4-methanesulfonylaminobutyl | n-butyl |
| 4-methanesulfonylaminobutyl | benzyl |
| 4-methanesulfonylaminobutyl | 2-methoxyethyl |
| 4-methanesulfonylaminobutyl | 2-hydroxyethyl |
| 2-(2-propanesulfonylamino)ethyl | hydrogen |
| 2-(2-propanesulfonylamino)ethyl | methyl |
| 2-(2-propanesulfonylamino)ethyl | ethyl |
| 2-(2-propanesulfonylamino)ethyl | n-propyl |
| 2-(2-propanesulfonylamino)ethyl | n-butyl |
| 2-(2-propanesulfonylamino)ethyl | benzyl |
| 2-(2-propanesulfonylamino)ethyl | 2-methoxyethyl |
| 2-(2-propanesulfonylamino)ethyl | 2-hydroxyethyl |
| 2-(benzenesulfonylamino)ethyl | hydrogen |
| 2-(benzenesulfonylamino)ethyl | methyl |
| 2-(benzenesulfonylamino)ethyl | ethyl |
| 2-(benzenesulfonylamino)ethyl | n-propyl |
| 2-(benzenesulfonylamino)ethyl | n-butyl |
| 2-(benzenesulfonylamino)ethyl | benzyl |
| 2-(benzenesulfonylamino)ethyl | 2-methoxyethyl |
| 2-(benzenesulfonylamino)ethyl | 2-hydroxyethyl |
| 2-(dimethylaminosulfonylamino)ethyl | hydrogen |
| 2-(dimethylaminosulfonylamino)ethyl | methyl |
| 2-(dimethylaminosulfonylamino)ethyl | ethyl |
| 2-(dimethylaminosulfonylamino)ethyl | n-propyl |
| 2-(dimethylaminosulfonylamino)ethyl | n-butyl |
| 2-(dimethylaminosulfonylamino)ethyl | benzyl |
| 2-(dimethylaminosulfonylamino)ethyl | 2-methoxyethyl |
| 2-(dimethylaminosulfonylamino)ethyl | 2-hydroxyethyl |
| 4-hydroxybutyl | hydrogen |
| 4-hydroxybutyl | methyl |
| 4-hydroxybutyl | ethyl |
| 4-hydroxybutyl | n-propyl |
| 4-hydroxybutyl | n-butyl |
| 4-hydroxybutyl | benzyl |
| 4-hydroxybutyl | 2-methoxyethyl |
| 4-hydroxybutyl | 2-hydroxyethyl |
| 2-aminoethyl | hydrogen |
| 2-aminoethyl | methyl |
| 2-aminoethyl | ethyl |
| 2-aminoethyl | n-propyl |
| 2-aminoethyl | n-butyl |
| 2-aminoethyl | benzyl |
| 2-aminoethyl | 2-methoxyethyl |
| 2-aminoethyl | 2-hydroxyethyl |
| 2-(cyclopropanecarbonylamino)ethyl | hydrogen |
| 2-(cyclopropanecarbonylamino)ethyl | methyl |
| 2-(cyclopropanecarbonylamino)ethyl | ethyl |
| 2-(cyclopropanecarbonylamino)ethyl | n-propyl |
| 2-(cyclopropanecarbonylamino)ethyl | n-butyl |
| 2-(cyclopropanecarbonylamino)ethyl | benzyl |
| 2-(cyclopropanecarbonylamino)ethyl | 2-methoxyethyl |
| 2-(cyclopropanecarbonylamino)ethyl | 2-hydroxyethyl |
| 2-(benzoylamino)ethyl | hydrogen |
| 2-(benzoylamino)ethyl | methyl |
| 2-(benzoylamino)ethyl | ethyl |
| 2-(benzoylamino)ethyl | n-propyl |
| 2-(benzoylamino)ethyl | n-butyl |
| 2-(benzoylamino)ethyl | benzyl |
| 2-(benzoylamino)ethyl | 2-methoxyethyl |
| 2-(benzoylamino)ethyl | 2-hydroxyethyl |
| 2-(benzoylamino)-2-methylpropyl | hydrogen |
| 2-(benzoylamino)-2-methylpropyl | methyl |
| 2-(benzoylamino)-2-methylpropyl | ethyl |
| 2-(benzoylamino)-2-methylpropyl | n-propyl |
| 2-(benzoylamino)-2-methylpropyl | n-butyl |
| 2-(benzoylamino)-2-methylpropyl | benzyl |
| 2-(benzoylamino)-2-methylpropyl | 2-methoxyethyl |
| 2-(benzoylamino)-2-methylpropyl | 2-hydroxyethyl |
| 2-(pyridine-3-carbonylamino)ethyl | hydrogen |
| 2-(pyridine-3-carbonylamino)ethyl | methyl |
| 2-(pyridine-3-carbonylamino)ethyl | ethyl |
| 2-(pyridine-3-carbonylamino)ethyl | n-propyl |
| 2-(pyridine-3-carbonylamino)ethyl | n-butyl |
| 2-(pyridine-3-carbonylamino)ethyl | benzyl |
| 2-(pyridine-3-carbonylamino)ethyl | 2-methoxyethyl |
| 2-(pyridine-3-carbonylamino)ethyl | 2-hydroxyethyl |
| 2-(2-propanecarbonylamino)ethyl | hydrogen |
| 2-(2-propanecarbonylamino)ethyl | methyl |
| 2-(2-propanecarbonylamino)ethyl | ethyl |
| 2-(2-propanecarbonylamino)ethyl | n-propyl |
| 2-(2-propanecarbonylamino)ethyl | n-butyl |
| 2-(2-propanecarbonylamino)ethyl | benzyl |
| 2-(2-propanecarbonylamino)ethyl | 2-methoxyethyl |
| 2-(2-propanecarbonylamino)ethyl | 2-hydroxyethyl |
| 4-(1,3-dioxo-1,3-dihydroisoindol-2-yl)butyl | hydrogen |
| 4-(1,3-dioxo-1,3-dihydroisoindol-2-yl)butyl | methyl |
| 4-(1,3-dioxo-1,3-dihydroisoindol-2-yl)butyl | ethyl |
| 4-(1,3-dioxo-1,3-dihydroisoindol-2-yl)butyl | n-propyl |
| 4-(1,3-dioxo-1,3-dihydroisoindol-2-yl)butyl | n-butyl |
| 4-(1,3-dioxo-1,3-dihydroisoindol-2-yl)butyl | benzyl |
| 4-(1,3-dioxo-1,3-dihydroisoindol-2-yl)butyl | 2-methoxyethyl |
| 4-(1,3-dioxo-1,3-dihydroisoindol-2-yl)butyl | 2-hydroxyethyl |
| 2-(3-phenylureido)ethyl | hydrogen |
| 2-(3-phenylureido)ethyl | methyl |
| 2-(3-phenylureido)ethyl | ethyl |
| 2-(3-phenylureido)ethyl | n-propyl |
| 2-(3-phenylureido)ethyl | n-butyl |
| 2-(3-phenylureido)ethyl | benzyl |
| 2-(3-phenylureido)ethyl | 2-methoxyethyl |
| 2-(3-phenylureido)ethyl | 2-hydroxyethyl |
| 2-(3-pyridinylureido)ethyl | hydrogen |
| 2-(3-pyridinylureido)ethyl | methyl |
| 2-(3-pyridinylureido)ethyl | ethyl |
| 2-(3-pyridinylureido)ethyl | n-propyl |
| 2-(3-pyridinylureido)ethyl | n-butyl |
| 2-(3-pyridinylureido)ethyl | benzyl |
| 2-(3-pyridinylureido)ethyl | 2-methoxyethyl |
| 2-(3-pyridinylureido)ethyl | 2-hydroxyethyl |
| 2-[3,3-(dimethyl)ureido]ethyl | hydrogen |

| | |
|---|---|
| 2-[3,3-(dimethyl)ureido]ethyl | methyl |
| 2-[3,3-(dimethyl)ureido]ethyl | ethyl |
| 2-[3,3-(dimethyl)ureido]ethyl | n-propyl |
| 2-[3,3-(dimethyl)ureido]ethyl | n-butyl |
| 2-[3,3-(dimethyl)ureido]ethyl | benzyl |
| 2-[3,3-(dimethyl)ureido]ethyl | 2-methoxyethyl |
| 2-[3,3-(dimethyl)ureido]ethyl | 2-hydroxyethyl |

Certain exemplary compounds, including some of those described above in the Examples, have the following Formula (IIIa, IIIb, IVa, VIIa, VIIa, VIIIa, or IXa) and the following $R_1$, and $R_2$ substituents, wherein each line of the table represents a specific compound.

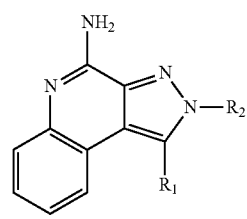

IIIa

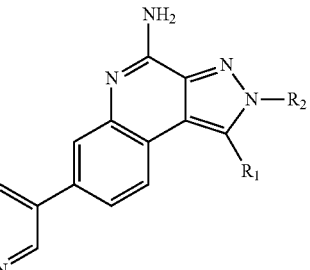

IIIb

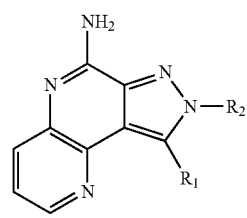

IVa

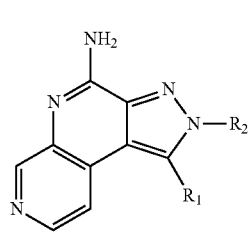

VIa

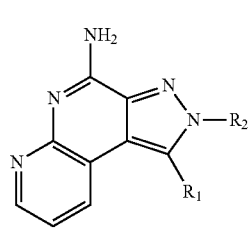

VIIa

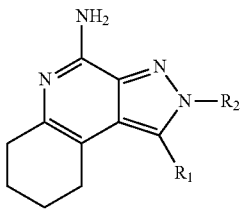

VIIIa

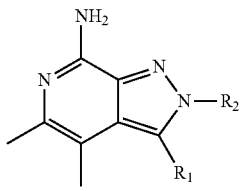

IXa

| $R_1$ | $R_2$ |
|---|---|
| 2-(propylsulfonyl)ethyl | hydrogen |
| 2-(propylsulfonyl)ethyl | methyl |
| 2-(propylsulfonyl)ethyl | ethyl |
| 2-(propylsulfonyl)ethyl | n-propyl |
| 2-(propylsulfonyl)ethyl | n-butyl |
| 2-(propylsulfonyl)ethyl | benzyl |
| 2-(propylsulfonyl)ethyl | 2-methoxyethyl |
| 2-(propylsulfonyl)ethyl | 2-hydroxyethyl |
| 2-hydroxy-2-methylpropyl | hydrogen |
| 2-hydroxy-2-methylpropyl | methyl |
| 2-hydroxy-2-methylpropyl | ethyl |
| 2-hydroxy-2-methylpropyl | n-propyl |
| 2-hydroxy-2-methylpropyl | n-butyl |
| 2-hydroxy-2-methylpropyl | benzyl |
| 2-hydroxy-2-methylpropyl | 2-methoxyethyl |
| 2-hydroxy-2-methylpropyl | 2-hydroxyethyl |
| 2,2-dimethylpropyl | hydrogen |
| 2,2-dimethylpropyl | methyl |
| 2,2-dimethylpropyl | ethyl |
| 2,2-dimethylpropyl | n-propyl |
| 2,2-dimethylpropyl | n-butyl |
| 2,2-dimethylpropyl | benzyl |
| 2,2-dimethylpropyl | 2-methoxyethyl |
| 2,2-dimethylpropyl | 2-hydroxyethyl |
| 2-phenylethyl | hydrogen |
| 2-phenylethyl | methyl |
| 2-phenylethyl | ethyl |
| 2-phenylethyl | n-propyl |
| 2-phenylethyl | n-butyl |
| 2-phenylethyl | benzyl |
| 2-phenylethyl | 2-methoxyethyl |
| 2-phenylethyl | 2-hydroxyethyl |
| 2-[(cyclohexylcarbonyl)amino]-2-methylpropyl | hydrogen |
| 2-[(cyclohexylcarbonyl)amino]-2-methylpropyl | methyl |
| 2-[(cyclohexylcarbonyl)amino]-2-methylpropyl | ethyl |
| 2-[(cyclohexylcarbonyl)amino]-2-methylpropyl | n-propyl |
| 2-[(cyclohexylcarbonyl)amino]-2-methylpropyl | n-butyl |
| 2-[(cyclohexylcarbonyl)amino]-2-methylpropyl | benzyl |
| 2-[(cyclohexylcarbonyl)amino]-2-methylpropyl | 2-methoxyethyl |
| 2-[(cyclohexylcarbonyl)amino]-2-methylpropyl | 2-hydroxyethyl |
| 2-methyl-2-[(methylsulfonyl)amino]propyl | hydrogen |
| 2-methyl-2-[(methylsulfonyl)amino]propyl | methyl |
| 2-methyl-2-[(methylsulfonyl)amino]propyl | ethyl |
| 2-methyl-2-[(methylsulfonyl)amino]propyl | n-propyl |
| 2-methyl-2-[(methylsulfonyl)amino]propyl | n-butyl |
| 2-methyl-2-[(methylsulfonyl)amino]propyl | benzyl |
| 2-methyl-2-[(methylsulfonyl)amino]propyl | 2-methoxyethyl |
| 2-methyl-2-[(methylsulfonyl)amino]propyl | 2-hydroxyethyl |
| 2-(isobutyrylamino)-2-methylpropyl | hydrogen |
| 2-(isobutyrylamino)-2-methylpropyl | methyl |
| 2-(isobutyrylamino)-2-methylpropyl | ethyl |
| 2-(isobutyrylamino)-2-methylpropyl | n-propyl |
| 2-(isobutyrylamino)-2-methylpropyl | n-butyl |
| 2-(isobutyrylamino)-2-methylpropyl | benzyl |
| 2-(isobutyrylamino)-2-methylpropyl | 2-methoxyethyl |

-continued

| | |
|---|---|
| 2-(isobutyrylamino)-2-methylpropyl | 2-hydroxyethyl |
| 2-methyl-2-[(pyridin-3-ylcarbonyl)amino]propyl | hydrogen |
| 2-methyl-2-[(pyridin-3-ylcarbonyl)amino]propyl | methyl |
| 2-methyl-2-[(pyridin-3-ylcarbonyl)amino]propyl | ethyl |
| 2-methyl-2-[(pyridin-3-ylcarbonyl)amino]propyl | n-propyl |
| 2-methyl-2-[(pyridin-3-ylcarbonyl)amino]propyl | n-butyl |
| 2-methyl-2-[(pyridin-3-ylcarbonyl)amino]propyl | benzyl |
| 2-methyl-2-[(pyridin-3-ylcarbonyl)amino]propyl | 2-methoxyethyl |
| 2-methyl-2-[(pyridin-3-ylcarbonyl)amino]propyl | 2-hydroxyethyl |
| 2-{[(isopropylamino)carbonyl]amino}-2-methylpropyl | hydrogen |
| 2-{[(isopropylamino)carbonyl]amino}-2-methylpropyl | methyl |
| 2-{[(isopropylamino)carbonyl]amino}-2-methylpropyl | ethyl |
| 2-{[(isopropylamino)carbonyl]amino}-2-methylpropyl | n-propyl |
| 2-{[(isopropylamino)carbonyl]amino}-2-methylpropyl | n-butyl |
| 2-{[(isopropylamino)carbonyl]amino}-2-methylpropyl | benzyl |
| 2-{[(isopropylamino)carbonyl]amino}-2-methylpropyl | 2-methoxyethyl |
| 2-{[(isopropylamino)carbonyl]amino}-2-methylpropyl | 2-hydroxyethyl |
| 2-(acetylamino)-2-methylpropyl | hydrogen |
| 2-(acetylamino)-2-methylpropyl | methyl |
| 2-(acetylamino)-2-methylpropyl | ethyl |
| 2-(acetylamino)-2-methylpropyl | n-propyl |
| 2-(acetylamino)-2-methylpropyl | n-butyl |
| 2-(acetylamino)-2-methylpropyl | benzyl |
| 2-(acetylamino)-2-methylpropyl | 2-methoxyethyl |
| 2-(acetylamino)-2-methylpropyl | 2-hydroxyethyl |
| 4-(4-pyridin-2-ylpiperazin-1-yl)butyl | hydrogen |
| 4-(4-pyridin-2-ylpiperazin-1-yl)butyl | methyl |
| 4-(4-pyridin-2-ylpiperazin-1-yl)butyl | ethyl |
| 4-(4-pyridin-2-ylpiperazin-1-yl)butyl | n-propyl |
| 4-(4-pyridin-2-ylpiperazin-1-yl)butyl | n-butyl |
| 4-(4-pyridin-2-ylpiperazin-1-yl)butyl | benzyl |
| 4-(4-pyridin-2-ylpiperazin-1-yl)butyl | 2-methoxyethyl |
| 4-(4-pyridin-2-ylpiperazin-1-yl)butyl | 2-hydroxyethyl |
| 3-(3-pyridin-3-ylisoxazol-5-yl)propyl | hydrogen |
| 3-(3-pyridin-3-ylisoxazol-5-yl)propyl | methyl |
| 3-(3-pyridin-3-ylisoxazol-5-yl)propyl | ethyl |
| 3-(3-pyridin-3-ylisoxazol-5-yl)propyl | n-propyl |
| 3-(3-pyridin-3-ylisoxazol-5-yl)propyl | n-butyl |
| 3-(3-pyridin-3-ylisoxazol-5-yl)propyl | benzyl |
| 3-(3-pyridin-3-ylisoxazol-5-yl)propyl | 2-methoxyethyl |
| 3-(3-pyridin-3-ylisoxazol-5-yl)propyl | 2-hydroxyethyl |

Certain exemplary compounds, including some of those described above in the Examples, have the following Formula (IIIc, IIIb, IVa, VIIa, VIIa, VIIIa, or IXa) and the following $R_1$, and $R_2$ substituents, wherein each line of the table represents a specific compound.

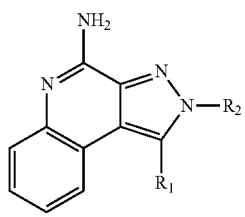

IIIa

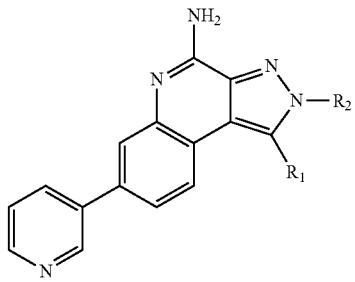

IIIb

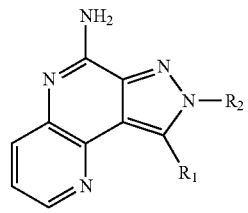

IVa

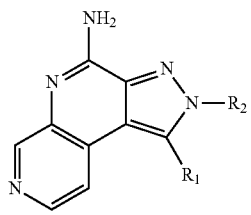

VIa

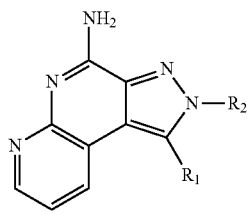

VIIa

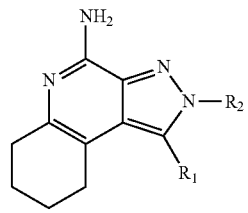

VIIIa

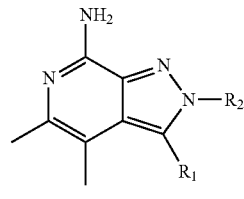

IXa

| $R_1$ | $R_2$ |
|---|---|
| n-butyl | hydrogen |
| n-butyl | methyl |
| n-butyl | ethyl |
| n-butyl | n-propyl |
| n-butyl | n-butyl |
| n-butyl | benzyl |
| n-butyl | 2-methoxyethyl |
| n-butyl | 2-hydroxyethyl |
| 4-aminobutyl | hydrogen |
| 4-aminobutyl | methyl |
| 4-aminobutyl | ethyl |
| 4-aminobutyl | n-propyl |
| 4-aminobutyl | n-butyl |
| 4-aminobutyl | benzyl |
| 4-aminobutyl | 2-methoxyethyl |
| 4-aminobutyl | 2-hydroxyethyl |
| 2-amino-2-methylpropyl | hydrogen |
| 2-amino-2-methylpropyl | methyl |
| 2-amino-2-methylpropyl | ethyl |

| | |
|---|---|
| 2-amino-2-methylpropyl | n-propyl |
| 2-amino-2-methylpropyl | n-butyl |
| 2-amino-2-methylpropyl | benzyl |
| 2-amino-2-methylpropyl | 2-methoxyethyl |
| 2-amino-2-methylpropyl | 2-hydroxyethyl |
| 4-acetoxybutyl | hydrogen |
| 4-acetoxybutyl | methyl |
| 4-acetoxybutyl | ethyl |
| 4-acetoxybutyl | n-propyl |
| 4-acetoxybutyl | n-butyl |
| 4-acetoxybutyl | benzyl |
| 4-acetoxybutyl | 2-methoxyethyl |
| 4-acetoxybutyl | 2-hydroxyethyl |
| 4-(methylsulfonyl)butyl | hydrogen |
| 4-(methylsulfonyl)butyl | methyl |
| 4-(methylsulfonyl)butyl | ethyl |
| 4-(methylsulfonyl)butyl | n-propyl |
| 4-(methylsulfonyl)butyl | n-butyl |
| 4-(methylsulfonyl)butyl | benzyl |
| 4-(methylsulfonyl)butyl | 2-methoxyethyl |
| 4-(methylsulfonyl)butyl | 2-hydroxyethyl |
| 3-(phenylsulfonyl)propyl | hydrogen |
| 3-(phenylsulfonyl)propyl | methyl |
| 3-(phenylsulfonyl)propyl | ethyl |
| 3-(phenylsulfonyl)propyl | n-propyl |
| 3-(phenylsulfonyl)propyl | n-butyl |
| 3-(phenylsulfonyl)propyl | benzyl |
| 3-(phenylsulfonyl)propyl | 2-methoxyethyl |
| 3-(phenylsulfonyl)propyl | 2-hydroxyethyl |
| 2-methyl-2-[2-(methylsulfonyl)ethoxy]propyl | hydrogen |
| 2-methyl-2-[2-(methylsulfonyl)ethoxy]propyl | methyl |
| 2-methyl-2-[2-(methylsulfonyl)ethoxy]propyl | ethyl |
| 2-methyl-2-[2-(methylsulfonyl)ethoxy]propyl | n-propyl |
| 2-methyl-2-[2-(methylsulfonyl)ethoxy]propyl | n-butyl |
| 2-methyl-2-[2-(methylsulfonyl)ethoxy]propyl | benzyl |
| 2-methyl-2-[2-(methylsulfonyl)ethoxy]propyl | 2-methoxyethyl |
| 2-methyl-2-[2-(methylsulfonyl)ethoxy]propyl | 2-hydroxyethyl |
| 4-(aminosulfonyl)butyl | hydrogen |
| 4-(aminosulfonyl)butyl | methyl |
| 4-(aminosulfonyl)butyl | ethyl |
| 4-(aminosulfonyl)butyl | n-propyl |
| 4-(aminosulfonyl)butyl | n-butyl |
| 4-(aminosulfonyl)butyl | benzyl |
| 4-(aminosulfonyl)butyl | 2-methoxyethyl |
| 4-(aminosulfonyl)butyl | 2-hydroxyethyl |
| 4-[(methylamino)sulfonyl]butyl | hydrogen |
| 4-[(methylamino)sulfonyl]butyl | methyl |
| 4-[(methylamino)sulfonyl]butyl | ethyl |
| 4-[(methylamino)sulfonyl]butyl | n-propyl |
| 4-[(methylamino)sulfonyl]butyl | n-butyl |
| 4-[(methylamino)sulfonyl]butyl | benzyl |
| 4-[(methylamino)sulfonyl]butyl | 2-methoxyethyl |
| 4-[(methylamino)sulfonyl]butyl | 2-hydroxyethyl |
| 4-[(dimethylamino)sulfonyl]butyl | hydrogen |
| 4-[(dimethylamino)sulfonyl]butyl | methyl |
| 4-[(dimethylamino)sulfonyl]butyl | ethyl |
| 4-[(dimethylamino)sulfonyl]butyl | n-propyl |
| 4-[(dimethylamino)sulfonyl]butyl | n-butyl |
| 4-[(dimethylamino)sulfonyl]butyl | benzyl |
| 4-[(dimethylamino)sulfonyl]butyl | 2-methoxyethyl |
| 4-[(dimethylamino)sulfonyl]butyl | 2-hydroxyethyl |
| 2-[(cyclopropylcarbonyl)amino]-2-methylpropyl | hydrogen |
| 2-[(cyclopropylcarbonyl)amino]-2-methylpropyl | methyl |
| 2-[(cyclopropylcarbonyl)amino]-2-methylpropyl | ethyl |
| 2-[(cyclopropylcarbonyl)amino]-2-methylpropyl | n-propyl |
| 2-[(cyclopropylcarbonyl)amino]-2-methylpropyl | n-butyl |
| 2-[(cyclopropylcarbonyl)amino]-2-methylpropyl | benzyl |
| 2-[(cyclopropylcarbonyl)amino]-2-methylpropyl | 2-methoxyethyl |
| 2-[(cyclopropylcarbonyl)amino]-2-methylpropyl | 2-hydroxyethyl |
| 2-methyl-2-(propionylamino)propyl | hydrogen |
| 2-methyl-2-(propionylamino)propyl | methyl |
| 2-methyl-2-(propionylamino)propyl | ethyl |
| 2-methyl-2-(propionylamino)propyl | n-propyl |
| 2-methyl-2-(propionylamino)propyl | n-butyl |
| 2-methyl-2-(propionylamino)propyl | benzyl |
| 2-methyl-2-(propionylamino)propyl | 2-methoxyethyl |
| 2-methyl-2-(propionylamino)propyl | 2-hydroxyethyl |
| 2-[(4-fluorobenzoyl)amino]-2-methylpropyl | hydrogen |
| 2-[(4-fluorobenzoyl)amino]-2-methylpropyl | methyl |
| 2-[(4-fluorobenzoyl)amino]-2-methylpropyl | ethyl |
| 2-[(4-fluorobenzoyl)amino]-2-methylpropyl | n-propyl |
| 2-[(4-fluorobenzoyl)amino]-2-methylpropyl | n-butyl |
| 2-[(4-fluorobenzoyl)amino]-2-methylpropyl | benzyl |
| 2-[(4-fluorobenzoyl)amino]-2-methylpropyl | 2-methoxyethyl |
| 2-[(4-fluorobenzoyl)amino]-2-methylpropyl | 2-hydroxyethyl |
| 2-[(3,4-difluorobenzoyl)amino]-2-methylpropyl | hydrogen |
| 2-[(3,4-difluorobenzoyl)amino]-2-methylpropyl | methyl |
| 2-[(3,4-difluorobenzoyl)amino]-2-methylpropyl | ethyl |
| 2-[(3,4-difluorobenzoyl)amino]-2-methylpropyl | n-propyl |
| 2-[(3,4-difluorobenzoyl)amino]-2-methylpropyl | n-butyl |
| 2-[(3,4-difluorobenzoyl)amino]-2-methylpropyl | benzyl |
| 2-[(3,4-difluorobenzoyl)amino]-2-methylpropyl | 2-methoxyethyl |
| 2-[(3,4-difluorobenzoyl)amino]-2-methylpropyl | 2-hydroxyethyl |
| 2-methyl-2-[(pyridin-4-ylcarbonyl)amino]propyl | hydrogen |
| 2-methyl-2-[(pyridin-4-ylcarbonyl)amino]propyl | methyl |
| 2-methyl-2-[(pyridin-4-ylcarbonyl)amino]propyl | ethyl |
| 2-methyl-2-[(pyridin-4-ylcarbonyl)amino]propyl | n-propyl |
| 2-methyl-2-[(pyridin-4-ylcarbonyl)amino]propyl | n-butyl |
| 2-methyl-2-[(pyridin-4-ylcarbonyl)amino]propyl | benzyl |
| 2-methyl-2-[(pyridin-4-ylcarbonyl)amino]propyl | 2-methoxyethyl |
| 2-methyl-2-[(pyridin-4-ylcarbonyl)amino]propyl | 2-hydroxyethyl |
| 3-(3-methylisoxazol-5-yl)propyl | hydrogen |
| 3-(3-methylisoxazol-5-yl)propyl | methyl |
| 3-(3-methylisoxazol-5-yl)propyl | ethyl |
| 3-(3-methylisoxazol-5-yl)propyl | n-propyl |
| 3-(3-methylisoxazol-5-yl)propyl | n-butyl |
| 3-(3-methylisoxazol-5-yl)propyl | benzyl |
| 3-(3-methylisoxazol-5-yl)propyl | 2-methoxyethyl |
| 3-(3-methylisoxazol-5-yl)propyl | 2-hydroxyethyl |
| 3-(3-isopropylisoxazol-5-yl)propyl | hydrogen |
| 3-(3-isopropylisoxazol-5-yl)propyl | methyl |
| 3-(3-isopropylisoxazol-5-yl)propyl | ethyl |
| 3-(3-isopropylisoxazol-5-yl)propyl | n-propyl |
| 3-(3-isopropylisoxazol-5-yl)propyl | n-butyl |
| 3-(3-isopropylisoxazol-5-yl)propyl | benzyl |
| 3-(3-isopropylisoxazol-5-yl)propyl | 2-methoxyethyl |
| 3-(3-isopropylisoxazol-5-yl)propyl | 2-hydroxyethyl |
| 3-(3-phenylisoxazol-5-yl)propyl | hydrogen |
| 3-(3-phenylisoxazol-5-yl)propyl | methyl |
| 3-(3-phenylisoxazol-5-yl)propyl | ethyl |
| 3-(3-phenylisoxazol-5-yl)propyl | n-propyl |
| 3-(3-phenylisoxazol-5-yl)propyl | n-butyl |
| 3-(3-phenylisoxazol-5-yl)propyl | benzyl |
| 3-(3-phenylisoxazol-5-yl)propyl | 2-methoxyethyl |
| 3-(3-phenylisoxazol-5-yl)propyl | 2-hydroxyethyl |
| 4-(3,5,5-trimethyl-1,2,4-oxadiazol-4(5H)-yl)butyl | hydrogen |
| 4-(3,5,5-trimethyl-1,2,4-oxadiazol-4(5H)-yl)butyl | methyl |
| 4-(3,5,5-trimethyl-1,2,4-oxadiazol-4(5H)-yl)butyl | ethyl |
| 4-(3,5,5-trimethyl-1,2,4-oxadiazol-4(5H)-yl)butyl | n-propyl |
| 4-(3,5,5-trimethyl-1,2,4-oxadiazol-4(5H)-yl)butyl | n-butyl |
| 4-(3,5,5-trimethyl-1,2,4-oxadiazol-4(5H)-yl)butyl | benzyl |
| 4-(3,5,5-trimethyl-1,2,4-oxadiazol-4(5H)-yl)butyl | 2-methoxyethyl |
| 4-(3,5,5-trimethyl-1,2,4-oxadiazol-4(5H)-yl)butyl | 2-hydroxyethyl |
| 4-(3-methyl-1-oxa-2,4-diazaspiro[4.4]non-2-en-4-yl)butyl | hydrogen |
| 4-(3-methyl-1-oxa-2,4-diazaspiro[4.4]non-2-en-4-yl)butyl | methyl |
| 4-(3-methyl-1-oxa-2,4-diazaspiro[4.4]non-2-en-4-yl)butyl | ethyl |
| 4-(3-methyl-1-oxa-2,4-diazaspiro[4.4]non-2-en-4-yl)butyl | n-propyl |
| 4-(3-methyl-1-oxa-2,4-diazaspiro[4.4]non-2-en-4-yl)butyl | n-butyl |
| 4-(3-methyl-1-oxa-2,4-diazaspiro[4.4]non-2-en-4-yl)butyl | benzyl |
| 4-(3-methyl-1-oxa-2,4-diazaspiro[4.4]non-2-en-4-yl)butyl | 2-methoxyethyl |
| 4-(3-methyl-1-oxa-2,4-diazaspiro[4.4]non-2-en-4-yl)butyl | 2-hydroxyethyl |
| pent-4-ynyl | hydrogen |
| pent-4-ynyl | methyl |
| pent-4-ynyl | ethyl |
| pent-4-ynyl | n-propyl |
| pent-4-ynyl | n-butyl |
| pent-4-ynyl | benzyl |
| pent-4-ynyl | 2-methoxyethyl |
| pent-4-ynyl | 2-hydroxyethyl |

Certain exemplary compounds, including some of those described above in the Examples, have the following Formula (IIIa, IIIb, IVa, VIIa, VIIa, VIIIa, or IXa) and the following $R_1$, and $R_2$ substituents, wherein each line of the table represents a specific compound.

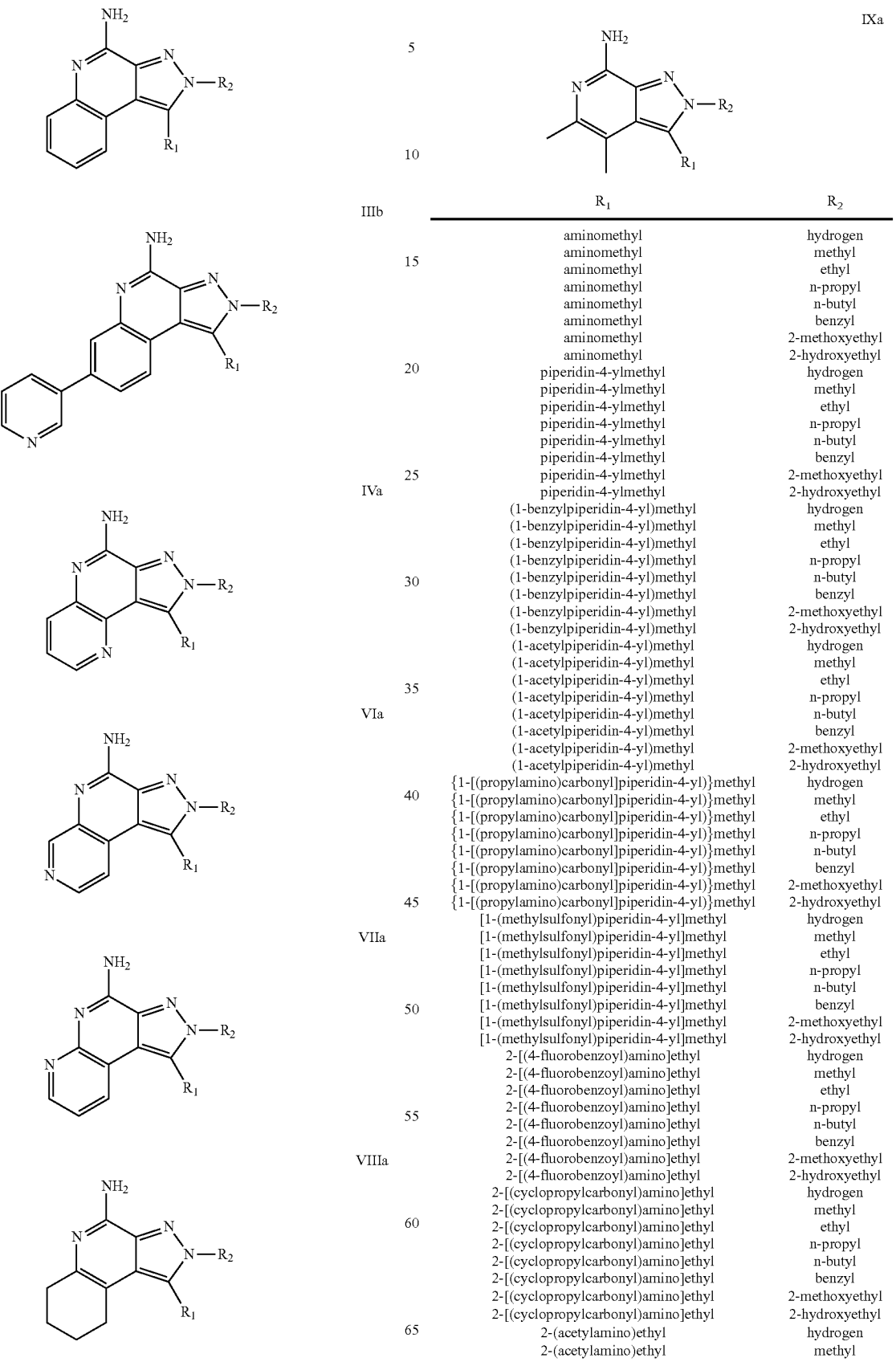

| R₁ | R₂ |
|---|---|
| aminomethyl | hydrogen |
| aminomethyl | methyl |
| aminomethyl | ethyl |
| aminomethyl | n-propyl |
| aminomethyl | n-butyl |
| aminomethyl | benzyl |
| aminomethyl | 2-methoxyethyl |
| aminomethyl | 2-hydroxyethyl |
| piperidin-4-ylmethyl | hydrogen |
| piperidin-4-ylmethyl | methyl |
| piperidin-4-ylmethyl | ethyl |
| piperidin-4-ylmethyl | n-propyl |
| piperidin-4-ylmethyl | n-butyl |
| piperidin-4-ylmethyl | benzyl |
| piperidin-4-ylmethyl | 2-methoxyethyl |
| piperidin-4-ylmethyl | 2-hydroxyethyl |
| (1-benzylpiperidin-4-yl)methyl | hydrogen |
| (1-benzylpiperidin-4-yl)methyl | methyl |
| (1-benzylpiperidin-4-yl)methyl | ethyl |
| (1-benzylpiperidin-4-yl)methyl | n-propyl |
| (1-benzylpiperidin-4-yl)methyl | n-butyl |
| (1-benzylpiperidin-4-yl)methyl | benzyl |
| (1-benzylpiperidin-4-yl)methyl | 2-methoxyethyl |
| (1-benzylpiperidin-4-yl)methyl | 2-hydroxyethyl |
| (1-acetylpiperidin-4-yl)methyl | hydrogen |
| (1-acetylpiperidin-4-yl)methyl | methyl |
| (1-acetylpiperidin-4-yl)methyl | ethyl |
| (1-acetylpiperidin-4-yl)methyl | n-propyl |
| (1-acetylpiperidin-4-yl)methyl | n-butyl |
| (1-acetylpiperidin-4-yl)methyl | benzyl |
| (1-acetylpiperidin-4-yl)methyl | 2-methoxyethyl |
| (1-acetylpiperidin-4-yl)methyl | 2-hydroxyethyl |
| {1-[(propylamino)carbonyl]piperidin-4-yl}methyl | hydrogen |
| {1-[(propylamino)carbonyl]piperidin-4-yl}methyl | methyl |
| {1-[(propylamino)carbonyl]piperidin-4-yl}methyl | ethyl |
| {1-[(propylamino)carbonyl]piperidin-4-yl}methyl | n-propyl |
| {1-[(propylamino)carbonyl]piperidin-4-yl}methyl | n-butyl |
| {1-[(propylamino)carbonyl]piperidin-4-yl}methyl | benzyl |
| {1-[(propylamino)carbonyl]piperidin-4-yl}methyl | 2-methoxyethyl |
| {1-[(propylamino)carbonyl]piperidin-4-yl}methyl | 2-hydroxyethyl |
| [1-(methylsulfonyl)piperidin-4-yl]methyl | hydrogen |
| [1-(methylsulfonyl)piperidin-4-yl]methyl | methyl |
| [1-(methylsulfonyl)piperidin-4-yl]methyl | ethyl |
| [1-(methylsulfonyl)piperidin-4-yl]methyl | n-propyl |
| [1-(methylsulfonyl)piperidin-4-yl]methyl | n-butyl |
| [1-(methylsulfonyl)piperidin-4-yl]methyl | benzyl |
| [1-(methylsulfonyl)piperidin-4-yl]methyl | 2-methoxyethyl |
| [1-(methylsulfonyl)piperidin-4-yl]methyl | 2-hydroxyethyl |
| 2-[(4-fluorobenzoyl)amino]ethyl | hydrogen |
| 2-[(4-fluorobenzoyl)amino]ethyl | methyl |
| 2-[(4-fluorobenzoyl)amino]ethyl | ethyl |
| 2-[(4-fluorobenzoyl)amino]ethyl | n-propyl |
| 2-[(4-fluorobenzoyl)amino]ethyl | n-butyl |
| 2-[(4-fluorobenzoyl)amino]ethyl | benzyl |
| 2-[(4-fluorobenzoyl)amino]ethyl | 2-methoxyethyl |
| 2-[(4-fluorobenzoyl)amino]ethyl | 2-hydroxyethyl |
| 2-[(cyclopropylcarbonyl)amino]ethyl | hydrogen |
| 2-[(cyclopropylcarbonyl)amino]ethyl | methyl |
| 2-[(cyclopropylcarbonyl)amino]ethyl | ethyl |
| 2-[(cyclopropylcarbonyl)amino]ethyl | n-propyl |
| 2-[(cyclopropylcarbonyl)amino]ethyl | n-butyl |
| 2-[(cyclopropylcarbonyl)amino]ethyl | benzyl |
| 2-[(cyclopropylcarbonyl)amino]ethyl | 2-methoxyethyl |
| 2-[(cyclopropylcarbonyl)amino]ethyl | 2-hydroxyethyl |
| 2-(acetylamino)ethyl | hydrogen |
| 2-(acetylamino)ethyl | methyl |

| | |
|---|---|
| 2-(acetylamino)ethyl | ethyl |
| 2-(acetylamino)ethyl | n-propyl |
| 2-(acetylamino)ethyl | n-butyl |
| 2-(acetylamino)ethyl | benzyl |
| 2-(acetylamino)ethyl | 2-methoxyethyl |
| 2-(acetylamino)ethyl | 2-hydroxyethyl |
| 2-(propionylamino)ethyl | hydrogen |
| 2-(propionylamino)ethyl | methyl |
| 2-(propionylamino)ethyl | ethyl |
| 2-(propionylamino)ethyl | n-propyl |
| 2-(propionylamino)ethyl | n-butyl |
| 2-(propionylamino)ethyl | benzyl |
| 2-(propionylamino)ethyl | 2-methoxyethyl |
| 2-(propionylamino)ethyl | 2-hydroxyethyl |
| 2-[(methylsulfonyl)amino]ethyl | hydrogen |
| 2-[(methylsulfonyl)amino]ethyl | methyl |
| 2-[(methylsulfonyl)amino]ethyl | ethyl |
| 2-[(methylsulfonyl)amino]ethyl | n-propyl |
| 2-[(methylsulfonyl)amino]ethyl | n-butyl |
| 2-[(methylsulfonyl)amino]ethyl | benzyl |
| 2-[(methylsulfonyl)amino]ethyl | 2-methoxyethyl |
| 2-[(methylsulfonyl)amino]ethyl | 2-hydroxyethyl |
| 2-(1,1-dioxidoisothiazolidin-2-yl)ethyl | hydrogen |
| 2-(1,1-dioxidoisothiazolidin-2-yl)ethyl | methyl |
| 2-(1,1-dioxidoisothiazolidin-2-yl)ethyl | ethyl |
| 2-(1,1-dioxidoisothiazolidin-2-yl)ethyl | n-propyl |
| 2-(1,1-dioxidoisothiazolidin-2-yl)ethyl | n-butyl |
| 2-(1,1-dioxidoisothiazolidin-2-yl)ethyl | benzyl |
| 2-(1,1-dioxidoisothiazolidin-2-yl)ethyl | 2-methoxyethyl |
| 2-(1,1-dioxidoisothiazolidin-2-yl)ethyl | 2-hydroxyethyl |
| 2-{[(ethylamino)carbonyl]amino}ethyl | hydrogen |
| 2-{[(ethylamino)carbonyl]amino}ethyl | methyl |
| 2-{[(ethylamino)carbonyl]amino}ethyl | ethyl |
| 2-{[(ethylamino)carbonyl]amino}ethyl | n-propyl |
| 2-{[(ethylamino)carbonyl]amino}ethyl | n-butyl |
| 2-{[(ethylamino)carbonyl]amino}ethyl | benzyl |
| 2-{[(ethylamino)carbonyl]amino}ethyl | 2-methoxyethyl |
| 2-{[(ethylamino)carbonyl]amino}ethyl | 2-hydroxyethyl |
| 2-({[(3,4-difluorophenyl)amino]carbonyl}amino)ethyl | hydrogen |
| 2-({[(3,4-difluorophenyl)amino]carbonyl}amino)ethyl | methyl |
| 2-({[(3,4-difluorophenyl)amino]carbonyl}amino)ethyl | ethyl |
| 2-({[(3,4-difluorophenyl)amino]carbonyl}amino)ethyl | n-propyl |
| 2-({[(3,4-difluorophenyl)amino]carbonyl}amino)ethyl | n-butyl |
| 2-({[(3,4-difluorophenyl)amino]carbonyl}amino)ethyl | benzyl |
| 2-({[(3,4-difluorophenyl)amino]carbonyl}amino)ethyl | 2-methoxyethyl |
| 2-({[(3,4-difluorophenyl)amino]carbonyl}amino)ethyl | 2-hydroxyethyl |
| 2-({[(4-fluorophenyl)amino]carbonyl}amino)ethyl | hydrogen |
| 2-({[(4-fluorophenyl)amino]carbonyl}amino)ethyl | methyl |
| 2-({[(4-fluorophenyl)amino]carbonyl}amino)ethyl | ethyl |
| 2-({[(4-fluorophenyl)amino]carbonyl}amino)ethyl | n-propyl |
| 2-({[(4-fluorophenyl)amino]carbonyl}amino)ethyl | n-butyl |
| 2-({[(4-fluorophenyl)amino]carbonyl}amino)ethyl | benzyl |
| 2-({[(4-fluorophenyl)amino]carbonyl}amino)ethyl | 2-methoxyethyl |
| 2-({[(4-fluorophenyl)amino]carbonyl}amino)ethyl | 2-hydroxyethyl |
| 2-{[(isopropylamino)carbonyl]amino}ethyl | hydrogen |
| 2-{[(isopropylamino)carbonyl]amino}ethyl | methyl |
| 2-{[(isopropylamino)carbonyl]amino}ethyl | ethyl |
| 2-{[(isopropylamino)carbonyl]amino}ethyl | n-propyl |
| 2-{[(isopropylamino)carbonyl]amino}ethyl | n-butyl |
| 2-{[(isopropylamino)carbonyl]amino}ethyl | benzyl |
| 2-{[(isopropylamino)carbonyl]amino}ethyl | 2-methoxyethyl |
| 2-{[(isopropylamino)carbonyl]amino}ethyl | 2-hydroxyethyl |
| 2-[(ethoxycarbonyl)amino]ethyl | hydrogen |
| 2-[(ethoxycarbonyl)amino]ethyl | methyl |
| 2-[(ethoxycarbonyl)amino]ethyl | ethyl |
| 2-[(ethoxycarbonyl)amino]ethyl | n-propyl |
| 2-[(ethoxycarbonyl)amino]ethyl | n-butyl |
| 2-[(ethoxycarbonyl)amino]ethyl | benzyl |
| 2-[(ethoxycarbonyl)amino]ethyl | 2-methoxyethyl |
| 2-[(ethoxycarbonyl)amino]ethyl | 2-hydroxyethyl |
| 2-[(morpholin-4-ylcarbonyl)amino]ethyl | hydrogen |
| 2-[(morpholin-4-ylcarbonyl)amino]ethyl | methyl |
| 2-[(morpholin-4-ylcarbonyl)amino]ethyl | ethyl |
| 2-[(morpholin-4-ylcarbonyl)amino]ethyl | n-propyl |
| 2-[(morpholin-4-ylcarbonyl)amino]ethyl | n-butyl |
| 2-[(morpholin-4-ylcarbonyl)amino]ethyl | benzyl |
| 2-[(morpholin-4-ylcarbonyl)amino]ethyl | 2-methoxyethyl |
| 2-[(morpholin-4-ylcarbonyl)amino]ethyl | 2-hydroxyethyl |
| hydroxymethyl | hydrogen |
| hydroxymethyl | methyl |
| hydroxymethyl | ethyl |
| hydroxymethyl | n-propyl |
| hydroxymethyl | n-butyl |
| hydroxymethyl | benzyl |
| hydroxymethyl | 2-methoxyethyl |
| hydroxymethyl | 2-hydroxyethyl |
| 2-methyl-2-(methylsulfonyl)propyl | hydrogen |
| 2-methyl-2-(methylsulfonyl)propyl | methyl |
| 2-methyl-2-(methylsulfonyl)propyl | ethyl |
| 2-methyl-2-(methylsulfonyl)propyl | n-propyl |
| 2-methyl-2-(methylsulfonyl)propyl | n-butyl |
| 2-methyl-2-(methylsulfonyl)propyl | benzyl |
| 2-methyl-2-(methylsulfonyl)propyl | 2-methoxyethyl |
| 2-methyl-2-(methylsulfonyl)propyl | 2-hydroxyethyl |
| 2-methyl-2-{[2-(methylsulfonyl)ethyl]amino}propyl | hydrogen |
| 2-methyl-2-{[2-(methylsulfonyl)ethyl]amino}propyl | methyl |
| 2-methyl-2-{[2-(methylsulfonyl)ethyl]amino}propyl | ethyl |
| 2-methyl-2-{[2-(methylsulfonyl)ethyl]amino}propyl | n-propyl |
| 2-methyl-2-{[2-(methylsulfonyl)ethyl]amino}propyl | n-butyl |
| 2-methyl-2-{[2-(methylsulfonyl)ethyl]amino}propyl | benzyl |
| 2-methyl-2-{[2-(methylsulfonyl)ethyl]amino}propyl | 2-methoxyethyl |
| 2-methyl-2-{[2-(methylsulfonyl)ethyl]amino}propyl | 2-hydroxyethyl |
| 3-[(methylsulfonyl)amino]propyl | hydrogen |
| 3-[(methylsulfonyl)amino]propyl | methyl |
| 3-[(methylsulfonyl)amino]propyl | ethyl |
| 3-[(methylsulfonyl)amino]propyl | n-propyl |
| 3-[(methylsulfonyl)amino]propyl | n-butyl |
| 3-[(methylsulfonyl)amino]propyl | benzyl |
| 3-[(methylsulfonyl)amino]propyl | 2-methoxyethyl |
| 3-[(methylsulfonyl)amino]propyl | 2-hydroxyethyl |
| 2-cyano-2-methylpropyl | hydrogen |
| 2-cyano-2-methylpropyl | methyl |
| 2-cyano-2-methylpropyl | ethyl |
| 2-cyano-2-methylpropyl | n-propyl |
| 2-cyano-2-methylpropyl | n-butyl |
| 2-cyano-2-methylpropyl | benzyl |
| 2-cyano-2-methylpropyl | 2-methoxyethyl |
| 2-cyano-2-methylpropyl | 2-hydroxyethyl |
| 3-(5-butylisoxazol-3-yl)propyl | hydrogen |
| 3-(5-butylisoxazol-3-yl)propyl | methyl |
| 3-(5-butylisoxazol-3-yl)propyl | ethyl |
| 3-(5-butylisoxazol-3-yl)propyl | n-propyl |
| 3-(5-butylisoxazol-3-yl)propyl | n-butyl |
| 3-(5-butylisoxazol-3-yl)propyl | benzyl |
| 3-(5-butylisoxazol-3-yl)propyl | 2-methoxyethyl |
| 3-(5-butylisoxazol-3-yl)propyl | 2-hydroxyethyl |
| 3-(5-phenylisoxazol-3-yl)propyl | hydrogen |
| 3-(5-phenylisoxazol-3-yl)propyl | methyl |
| 3-(5-phenylisoxazol-3-yl)propyl | ethyl |
| 3-(5-phenylisoxazol-3-yl)propyl | n-propyl |
| 3-(5-phenylisoxazol-3-yl)propyl | n-butyl |
| 3-(5-phenylisoxazol-3-yl)propyl | benzyl |
| 3-(5-phenylisoxazol-3-yl)propyl | 2-methoxyethyl |
| 3-(5-phenylisoxazol-3-yl)propyl | 2-hydroxyethyl |
| 3-(5-pyridin-3-ylisoxazol-3-yl)propyl | hydrogen |
| 3-(5-pyridin-3-ylisoxazol-3-yl)propyl | methyl |
| 3-(5-pyridin-3-ylisoxazol-3-yl)propyl | ethyl |
| 3-(5-pyridin-3-ylisoxazol-3-yl)propyl | n-propyl |
| 3-(5-pyridin-3-ylisoxazol-3-yl)propyl | n-butyl |
| 3-(5-pyridin-3-ylisoxazol-3-yl)propyl | benzyl |
| 3-(5-pyridin-3-ylisoxazol-3-yl)propyl | 2-methoxyethyl |
| 3-(5-pyridin-3-ylisoxazol-3-yl)propyl | 2-hydroxyethyl |
| 4-(hydroxyimino)butyl | hydrogen |
| 4-(hydroxyimino)butyl | methyl |
| 4-(hydroxyimino)butyl | ethyl |
| 4-(hydroxyimino)butyl | n-propyl |
| 4-(hydroxyimino)butyl | n-butyl |
| 4-(hydroxyimino)butyl | benzyl |
| 4-(hydroxyimino)butyl | 2-methoxyethyl |
| 4-(hydroxyimino)butyl | 2-hydroxyethyl |
| 4-(methoxyimino)butyl | hydrogen |
| 4-(methoxyimino)butyl | methyl |
| 4-(methoxyimino)butyl | ethyl |
| 4-(methoxyimino)butyl | n-propyl |
| 4-(methoxyimino)butyl | n-butyl |
| 4-(methoxyimino)butyl | benzyl |
| 4-(methoxyimino)butyl | 2-methoxyethyl |
| 4-(methoxyimino)butyl | 2-hydroxyethyl |

-continued

| | |
|---|---|
| 5-amino-5-(hydroxyimino)pentyl | hydrogen |
| 5-amino-5-(hydroxyimino)pentyl | methyl |
| 5-amino-5-(hydroxyimino)pentyl | ethyl |
| 5-amino-5-(hydroxyimino)pentyl | n-propyl |
| 5-amino-5-(hydroxyimino)pentyl | n-butyl |
| 5-amino-5-(hydroxyimino)pentyl | benzyl |
| 5-amino-5-(hydroxyimino)pentyl | 2-methoxyethyl |
| 5-amino-5-(hydroxyimino)pentyl | 2-hydroxyethyl |
| 3-(1H-pyrrol-3-yl)propyl | hydrogen |
| 3-(1H-pyrrol-3-yl)propyl | methyl |
| 3-(1H-pyrrol-3-yl)propyl | ethyl |
| 3-(1H-pyrrol-3-yl)propyl | n-propyl |
| 3-(1H-pyrrol-3-yl)propyl | n-butyl |
| 3-(1H-pyrrol-3-yl)propyl | benzyl |
| 3-(1H-pyrrol-3-yl)propyl | 2-methoxyethyl |
| 3-(1H-pyrrol-3-yl)propyl | 2-hydroxyethyl |
| 3-(1-benzyl-1H-pyrrol-3-yl)propyl | hydrogen |
| 3-(1-benzyl-1H-pyrrol-3-yl)propyl | methyl |
| 3-(1-benzyl-1H-pyrrol-3-yl)propyl | ethyl |
| 3-(1-benzyl-1H-pyrrol-3-yl)propyl | n-propyl |
| 3-(1-benzyl-1H-pyrrol-3-yl)propyl | n-butyl |
| 3-(1-benzyl-1H-pyrrol-3-yl)propyl | benzyl |
| 3-(1-benzyl-1H-pyrrol-3-yl)propyl | 2-methoxyethyl |
| 3-(1-benzyl-1H-pyrrol-3-yl)propyl | 2-hydroxyethyl |
| 3-(1-benzyl-2,5-dihydro-1H-pyrrol-3-yl)propyl | hydrogen |
| 3-(1-benzyl-2,5-dihydro-1H-pyrrol-3-yl)propyl | methyl |
| 3-(1-benzyl-2,5-dihydro-1H-pyrrol-3-yl)propyl | ethyl |
| 3-(1-benzyl-2,5-dihydro-1H-pyrrol-3-yl)propyl | n-propyl |
| 3-(1-benzyl-2,5-dihydro-1H-pyrrol-3-yl)propyl | n-butyl |
| 3-(1-benzyl-2,5-dihydro-1H-pyrrol-3-yl)propyl | benzyl |
| 3-(1-benzyl-2,5-dihydro-1H-pyrrol-3-yl)propyl | 2-methoxyethyl |
| 3-(1-benzyl-2,5-dihydro-1H-pyrrol-3-yl)propyl | 2-hydroxyethyl |

Compounds of the invention have been found to modulate cytokine biosynthesis by inducing the production of interferon α and/or tumor necrosis factor α when tested using the method described below.

CYTOKINE INDUCTION IN HUMAN CELLS

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (molar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

Certain compounds of the invention may modulate cytokine biosynthesis by inhibiting production of tumor necrosis factor α (TNF-α) when tested using the method described below.

TNF-α INHIBITION IN MOUSE CELLS

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EG_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4\times10^5$ cells/mL in RPMI with 10% FBS. Cell suspension (250 µl) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$, concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:
1. A compound of formula (II):

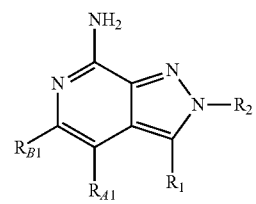

II wherein:
when taken together, $R_{A1}$ and $R_{B1}$ form a fused aryl ring or form a fused heteroaryl ring containing one heteroatom selected from the group consisting of N and S, wherein the aryl or heteroaryl ring is unsubstituted or substituted by one or more R groups;
R is selected from the group consisting of:
  halogen,
  hydroxy,
  alkyl,
  alkenyl,
  haloalkyl,
  alkoxy,
  alkylthio, and
  —N($R_9$)$_2$;
$R_1$ is selected from the group consisting of:
  —$R_4$,
  —X—$R_4$,
  —X—Y—$R_4$,
  —X—Y—X—Y—$R_4$, and
  —X—$R_5$;
$R_2$ is selected from the group consisting of:
  hydrogen,
  alkyl,
  hydroxyalkylenyl,
  alkoxyalkylenyl, and
  —$X^2$—$Y^2$—$R_4^2$;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

$X^2$ is alkylene that is optionally terminated by arylene or heterocyclylene;

Y is selected from the group consisting of:
- —O—,
- —S(O)$_{0-2}$-,
- —S(O)$_2$—N(R$_8$)—,
- —C(R$_6$)—,
- —C(R$_6$)—O—,
- —O—C(R$_6$)—,
- —O—C(O)—O—,
- —N(R$_8$)-Q-,
- —C(R$_6$)—N(R$_8$)—,
- —O—C(R$_6$)—N(R$_8$)—,
- —C(R$_6$)—N(OR$_9$)—,
- —O—N(R$_8$)-Q-,
- —O—N=C(R$_4$)—,
- —C(=N—O—R$_8$)—,
- —C(=N—O—R$_8$)—NH—,
- —CH(—N(—O—R$_8$)-Q-R$_4$)—,

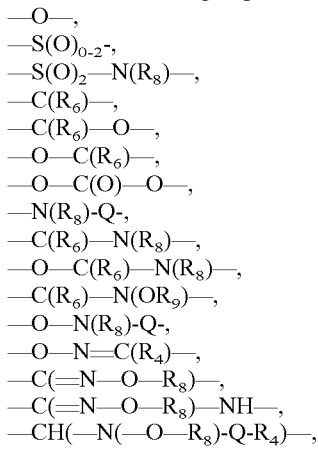

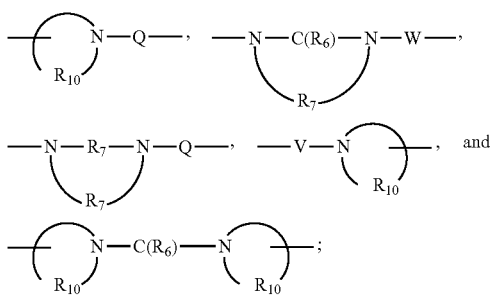

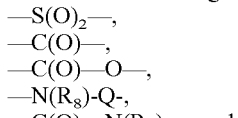

$Y^2$ is selected from the group consisting of:
- —S(O)$_2$—,
- —C(O)—,
- —C(O)—O—,
- —N(R$_8$)-Q-,
- —C(O)—N(R$_8$)—, and

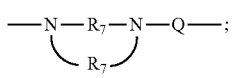

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_4^2$ is selected from the group consisting of hydrogen, alkyl, aryl, arylalkylenyl, aryloxyalkylenyl, heterocyclyl, and heteroaryl, wherein the alkyl, aryl, aryloxyalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, cyano, aryl, aryloxy, heteroaryl, heterocyclyl, and in the case of heterocyclyl, oxo;

R$_5$ is selected from the group consisting of

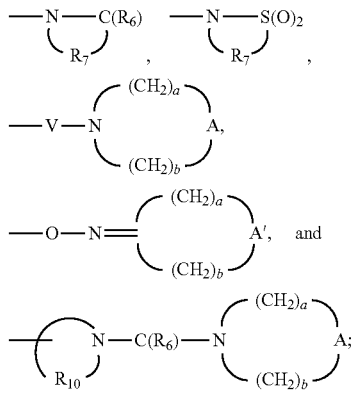

R$_6$ is selected from the group consisting of =O and =S;

R$_7$ is C$_{2-7}$ alkylene;

R$_8$ is selected from the group consisting of hydrogen, alkyl, alkoxyalkylenyl, hydroxyalkylenyl, arylalkylenyl, and heteroarylalkylenyl;

R$_9$ is selected from the group consisting of hydrogen and alkyl;

R$_{10}$ is C$_{3-8}$ alkylene;

A is selected from the group consisting of —O—, —C(O)—, —S(O)$_{0-2}$-, and —N(R$_4$)—;

A' is selected from the group consisting of —O—, —S(O)$_{0-2}$-, —N(-Q-R$_4$)—, and —CH$_2$—;

Q is selected from the group consisting of a bond, —C(R$_6$)—, —C(R$_6$)—C(R$_6$)—, —S(O)$_{2-5}$-C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

2. The compound or salt of claim 1, wherein R$_{A1}$ and R$_{B1}$ form a fused benzene ring which is unsubstituted.

3. The compound or salt of claim 1, wherein R$_{A1}$ and R$_{B1}$ form a fused pyridine ring which is unsubstituted or substituted by one or more R groups.

4. The compound or salt of claim 1, wherein R$_1$ is selected from the group consisting of:
- —R$_4$,
- —X—R$_4$,
- X—Y—R$_4$,
- —X—Y—X$^1$—Y$^1$—R$_4$, and
- —X—R$_5$; wherein —X is alkylene that is optionally interrupted or terminated by heterocyclylene and optionally interrupted by one —O— group;

Y is selected from the group consisting of:
- —O—,
- —S(O)$_2$—,
- —S(O)$_2$—N(R$_8$)—,
- —C(O)—,

—C(O)—O—,
—O—C(O)—,
—N(R$_8$)-Q-,
—C(O)—N(R$_8$)—,

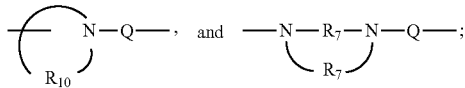

$X^1$ is selected from the group consisting of alkylene and arylene;
$Y^1$ is selected from the group consisting of:
—S—,
—C(O)—,
—C(O)—O—,
—C(O)—N(R$_8$)—,
—S(O)$_2$—N(R$_8$)—, and
—N(R$_8$)—C(O)—;
R$_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo;
R$_5$ is selected from the group consisting of:

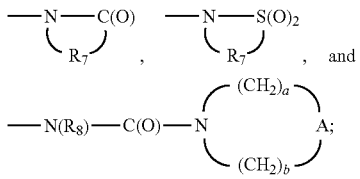

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_{10}$ is C$_{3-8}$ alkylene;
A is selected from the group consisting of —O—, —C(O)—, and —N(R$_4$)—;
Q is selected from the group consisting of a bond, —C(R$_6$)—, —S(O)$_2$—, —C(R$_6$)—N(R$_8$)—W—, —S(O)$_2$—N(R$_8$)—, —C(O)—O—, and —C(O)—S—;
W is selected from the group consisting of a bond and —C(O)—; and
a and b are independently integers from 1 to 6 with the proviso that a+b is ≤7.

5. The compound or salt of claim 4, wherein R$_1$ is selected from the group consisting of hydrogen, C$_{1-5}$ alkyl, C$_{2-5}$ alkynyl, arylC$_{1-4}$ alkylenyl, cycloalkylC$_{1-4}$ alkylenyl, C$_{1-4}$ alkyl-S(O)$_2$—C$_{1-4}$ alkylenyl, aryl-S(O)$_2$—C$_{1-4}$ alkylenyl, C$_{1-4}$ alkyl-S(O)$_2$—C$_{1-4}$ alkylenyl-O—C$_{1-4}$ alkylenyl, C$_{1-4}$ alkyl-S(O)$_2$—C$_{1-4}$ alkylenyl-NH—C$_{1-4}$ alkylenyl, C$_{1-4}$ alkyl-S(O)$_2$—NH—C$_{1-4}$ alkylenyl, hydroxyC$_{1-4}$ alkylenyl, haloC$_{1-4}$ alkylenyl, aminoC$_{1-4}$ alkylenyl, cyanoC$_{1-4}$ alkylenyl, hydroxyiminoC$_{2-5}$ alkylenyl, C$_{1-4}$ alkoxyiminoC$_{2-5}$ alkylenyl, amino(hydroxyimino)C$_{2-5}$ alkylenyl, NH$_2$—C(O)—C$_{1-4}$ alkylenyl, C$_{1-4}$ alkyl-C(O)—C$_{1-4}$ alkylenyl, C$_{1-4}$ alkyl-C(O)—O—C$_{1-4}$ alkylenyl, C$_{1-6}$ alkyl-C(O)—NH—C$_{1-4}$ alkylenyl, C$_{1-6}$ alkyl-O—C(O)—NH—C$_{1-4}$ alkylenyl, aryl-C(O)—NH—C$_{1-4}$ alkylenyl and aryl-NH—C(O)—NH—C$_{1-4}$ alkylenyl, wherein aryl is unsubstituted or substituted with one or two halogen groups, heteroaryl-C(O)—NH—C$_{1-4}$ alkylenyl, di(C$_{1-4}$alkyl)amino-S(O)$_2$—NH—C$_{1-4}$alkylenyl, aryl-S(O)$_2$—NH—C$_{1-4}$ alkylenyl, heteroaryl-NH—C(S)—NH—C$_{1-4}$ alkylenyl, di(C$_{1-4}$ alkyl)amino-C(O)—NH—C$_{1-4}$ alkylenyl, C$_{1-4}$ alkylamino-C(O)—NH—C$_{1-4}$ alkylenyl, di(C$_{1-4}$ alkyl)amino-S(O)$_2$—C$_{1-4}$alkylenyl, C$_{1-4}$ alkylamino-S(O)$_2$—C$_{1-4}$ alkylenyl, amino-S(O)$_2$—C$_{1-4}$ alkylenyl, heteroarylC$_{1-4}$ alkylenyl wherein heteroaryl is unsubstituted or substituted by a substituent selected from the group consisting of aryl, arylalkylenyl, heteroaryl, and alkyl, and heterocyclylC$_{1-4}$ alkylenyl and heterocyclyl-C(O)—NH—C$_{1-4}$ alkylenyl wherein heterocyclyl is unsubstituted or substituted by one or two substituents selected from the group consisting of arylalkylenyl, heteroaryl, alkylcarbonyl, alkylsulfonyl, alkylaminocarbonyl, and oxo.

6. The compound or salt of claim 1, wherein $Y^2$ is selected from the group consisting of:
—C(O)—O—,
—N(H)—C(O)—,
—N(H)—S(O)$_2$—,
—N(H)—C(R$_6$)—N(H)—,
—N(H)—S(O)$_2$—N(H)—,
—C(O)—N(H)—, and

—N—R$_7$—N—C(O)—;
        R$_7$ and
$R_4^2$ is selected from the group consisting of hydrogen, alkyl, aryl, and heteroaryl, wherein the aryl groups can be unsubstituted or substituted by one or more substituents independently selected from the group consisting of alkyl, alkoxy, hydroxyalkyl, haloalkyl, haloalkoxy, halogen, nitro, hydroxy, and cyano.

7. The compound or salt of claim 1, wherein R$_2$ is selected from the group consisting of hydrogen, C$_{1-5}$ alkyl, C$_{1-4}$ alkoxyC$_{1-4}$ alkylenyl, and hydroxyC$_{1-4}$ alkylenyl.

8. A pharmaceutical composition comprising a therapeutically effective amount of the compound or salt of claim 1 in combination with a pharmaceutically acceptable carrier.

9. A compound of formula (III):

III

[Structure of formula III with NH$_2$, N, N—R$_2$, R$_1$, (R)$_n$, (R$_3$)$_m$ substituents]

wherein:
R is selected from the group consisting of:
halogen,
hydroxy,
alkyl,
alkenyl,
haloalkyl, alkoxy,
alkylthio, and
—N(R$_9$)$_2$;

R$_1$ is selected from the group consisting of:
—R$_4$,
—X—R$_4$,
—X—Y—R$_4$,
—X—Y—X—Y—R$_4$, and
—X—R$_5$;

R$_2$ is selected from the group consisting of:
hydrogen,
alkyl,
hydroxyalkylenyl,
alkoxyalkylenyl, and
—X$^2$—Y$^2$—R$_4^2$;

R$_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;

n is 0 to 4;
m is 0;
X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
X$^2$ is alkylene that is optionally terminated by arylene or heterocyclylene;
Y is selected from the group consisting of:
—O—,
—S(O)$_{0-2}$-,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—C(=N—O—R$_8$)—NH—,
—CH(—N(—O—R$_8$)-Q-R$_4$)—,

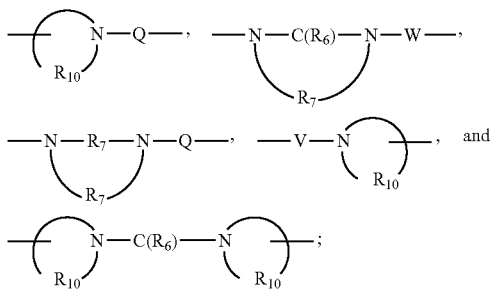

Y$^2$ is selected from the group consisting of:
—S(O)$_2$—,
—C(O)—,
—C(O)—O—,
—N(R$_8$)-Q-,
—C(O)—N(R$_8$)—, and

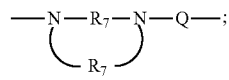

Z is a bond or —O—;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_4^2$ is selected from the group consisting of hydrogen, alkyl, aryl, arylalkylenyl, aryloxyalkylenyl, heterocyclyl, and heteroaryl, wherein the alkyl, aryl, aryloxyalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, cyano, aryl, aryloxy, heteroaryl, heterocyclyl, and in the case of heterocyclyl, oxo;
R$_5$ is selected from the group consisting of

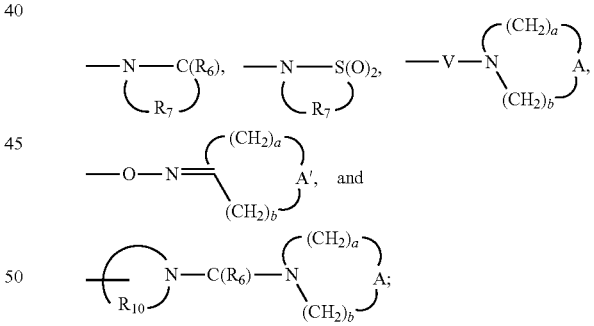

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$-, and —N(R$_4$)—;
A' is selected from the group consisting of —O—, —S(O)$_{0-2}$-, —N(-Q-R$_4$)—, and —CH$_2$—;
Q is selected from the group consisting of a bond, —C(R$_6$)—, —C(R$_6$)—C(R$_6$)—, —S(O)$_{2-5}$—C(R$_6$)—

—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

10. The compound or salt of claim 9, wherein R$_1$ is selected from the group consisting of:
—R$_4$,
—X—R$_4$,
—X—Y—R$_4$,
—X—Y—X$^1$—Y$^1$—R$_4$, and
—X—R$_5$; wherein X is alkylene that is optionally interrupted or terminated by heterocyclylene and optionally interrupted by one —O— group;

Y is selected from the group consisting of:
—O—,
—S(O)$_2$—,
—S(O)$_2$—N(R$_8$)—,
—C(O)—,
—C(O)—O—,
—O—C(O)—,
—N(R$_8$)-Q-,
—C(O)—N(R$_8$)—,

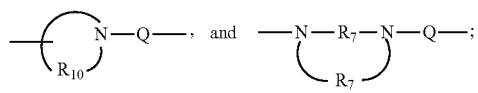

X$^1$ is selected from the group consisting of alkylene and arylene;

Y$^1$ is selected from the group consisting of:
—S—,
—C(O)—,
—C(O)—O—,
—C(O)—N(R$_8$)—,
—S(O)$_2$—N(R$_8$)—, and
—N(R$_8$)—C(O)—;

R$_4$ is selected from the group consisting of hydrogen, alkyl, aryl, heterocyclyl, heteroaryl, heteroarylalkylenyl, alkynyl, arylalkylenyl, and arylalkenylenyl, wherein the alkyl, aryl, arylalkylenyl, heterocyclyl, heteroaryl, and heteroarylalkylenyl groups can be unsubstituted or substituted by one or more substituents independently selected from the group consisting of alkyl, alkoxy, haloalkyl, haloalkoxy, halogen, hydroxy, cyano, aryl, aryloxy, heteroaryl, heterocyclyl, amino, dialkylamino, and in the case of alkyl and heterocyclyl, oxo;

R$_5$ is selected from the group consisting of:

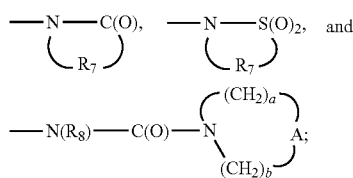

R$_6$ is selected from the group consisting of =O and =S;
R$_7$ is C$_{2-7}$ alkylene;

R$_5$ is selected from the group consisting of hydrogen, alkyl, alkoxyalkylenyl, hydroxyalkylenyl, arylalkylenyl, and heteroarylalkylenyl;

R$_{10}$ is C$_{3-8}$ alkylene;

A is selected from the group consisting of —O—, —C(O)—, and —N(R$_4$)—;

Q is selected from the group consisting of a bond, —C(R$_6$)—, —S(O)$_2$—, —C(R$_6$)—N(R$_8$)—W—, —S(O)$_2$—N(R$_8$)—, —C(O)—O—, and —C(O)—S—;

W is selected from the group consisting of a bond and —C(O)—; and a and b are independently integers from 1 to 6 with the proviso that a+b is ≤7.

11. The compound or salt of claim 10, wherein R$_1$ is selected from the group consisting of hydrogen, C$_{1-5}$ alkyl, C$_{2-5}$ alkynyl, arylC$_{1-4}$ alkylenyl, cycloalkylC$_{1-4}$ alkylenyl, C$_{1-4}$ alkyl-S(O)$_2$—C$_{1-4}$ alkylenyl, aryl-S(O)$_2$—C$_{1-4}$ alkylenyl, C$_{1-4}$ alkyl-S(O)$_2$—C$_{1-4}$ alkylenyl-O—C$_{1-4}$ alkylenyl, C$_{1-4}$ alkyl-S(O)$_2$—C$_{1-4}$ alkylenyl-NH—C$_{1-4}$ alkylenyl, C$_{1-4}$ alkyl-S(O)$_2$—NH—C$_{1-4}$ alkylenyl, hydroxyC$_{1-4}$ alkylenyl, haloC$_{1-4}$ alkylenyl, aminoC$_{1-4}$ alkylenyl, cyanoC$_{1-4}$ alkylenyl, hydroxyiminoC$_{2-5}$ alkylenyl, C$_{1-4}$ alkoxyiminoC$_{2-5}$ alkylenyl, amino(hydroxyimino)C$_{2-5}$ alkylenyl, NH$_2$—C(O)—C$_{1-4}$ alkylenyl, C$_{1-4}$ alkyl-C(O)—C$_{1-4}$ alkylenyl, C$_{1-4}$ alkyl-C(O)—O—C$_{1-4}$ alkylenyl, C$_{1-6}$ alkyl-C(O)—NH—C$_{1-4}$ alkylenyl, C$_{1-6}$ alkyl-O—C(O)—NH—C$_{1-4}$ alkylenyl, aryl-C(O)—NH—C$_{1-4}$ alkylenyl and aryl-NH—C(O)—NH—C$_{1-4}$ alkylenyl, wherein aryl is unsubstituted or substituted with one or two halogen groups, heteroaryl-C(O)—NH—C$_{1-4}$ alkylenyl, di(C$_{1-4}$ alkyl)amino-S(O)$_2$—NH—C$_{1-4}$ alkylenyl, aryl-S(O)$_2$—NH—C$_{1-4}$ alkylenyl, heteroaryl-NH—C(S)—NH—C$_{1-4}$ alkylenyl, di(C$_{1-4}$ alkyl)amino-C(O)—NH—C$_{1-4}$ alkylenyl, C$_{1-4}$ alkylamino-C(O)—NH—C$_{1-4}$ alkylenyl, di(C$_{1-4}$ alkyl)amino-S(O)$_2$—C$_{1-4}$ alkylenyl, C$_{1-4}$ alkylamino-S(O)$_2$—C$_{1-4}$ alkylenyl, amino-S(O)$_2$—C$_{1-4}$ alkylenyl, heteroarylC$_{1-4}$ alkylenyl wherein heteroaryl is unsubstituted or substituted by a substituent selected from the group consisting of aryl, arylalkylenyl, heteroaryl, and alkyl, and heterocyclylC$_{1-4}$ alkylenyl and heterocyclyl-C(O)—NH—C$_{1-4}$ alkylenyl wherein heterocyclyl is unsubstituted or substituted by one or two substituents selected from the group consisting of arylalkylenyl, heteroaryl, alkylcarbonyl, alkylsulfonyl, alkylaminocarbonyl, and oxo.

12. The compound or salt of claim 11, wherein R$_1$ is selected from the group consisting of hydrogen, methyl, ethyl, propyl, 2-methylpropyl, 2,2-dimethylpropyl, butyl, pent-4-ynyl, 2-phenylethyl, hydroxymethyl, 2-hydroxy-2-methylpropyl, 4-hydroxybutyl, 2-amino-2-methylpropyl, aminomethyl, 2-aminoethyl, 4-aminobutyl, 2-cyano-2-methylpropyl, 3-amino-2,2-dimethyl-3-oxopropyl, 2,2-dimethyl-4-oxopentyl, 2-methanesulfonylethyl, 2-methyl-2-(methylsulfonyl)propyl, 2-(propylsulfonyl)ethyl, 4-(methylsulfonyl)butyl, 3-(phenylsulfonyl)propyl, 2-methyl-2-[2-(methylsulfonyl)ethoxy]propyl, 2-methyl-2-{[2-(methylsulfonyl)ethyl]amino}propyl, 4-acetoxybutyl, 2-[(methylsulfonyl)amino]ethyl, 3-[(methylsulfonyl)amino]propyl, 4-methanesulfonylaminobutyl, 2-methyl-2-Rmethylsulfonyl)aminopropyl, 2-(2-propanesulfonylamino)ethyl, 2-(benzenesulfonylamino)ethyl, 2-(dimethylaminosulfonylamino)ethyl, 4-(aminosulfonyl)butyl, 4-[(methylamino)sulfonyl]butyl, 4-[(dimethylamino)sulfonyl]butyl, 2-[(cyclohexylcarbonyl)amino]-2-methylpropyl, 2-[(cyclopropylcarbonyl)amino]ethyl, 2-[(cyclopropylcarbonyl)amino]-2-methylpropyl, 2-(acetylamino)ethyl, 2-(propionylamino)ethyl, 2-(isobutyrylamino)-2-methylpropyl, 2-methyl-2-(propionylamino)propyl, 2-methyl-2-[(pyridin-3-ylcarbonyl)amino]propyl, 2-methyl-2-[(pyridin-4-ylcarbonyl)amino]propyl, 2-(acetylamino)-2-methylpropyl, 2-(benzoylamino)ethyl, 2-(benzoylamino)-2-methylpropyl, 2-[(4-fluorobenzoyl)amino]ethyl, 2-[(4-fluorobenzoyl)amino]-2-methylpropyl, 2-[(3,4-difluorobenzoyl)amino]-2-methylpropyl, 2-[(pyridin-3-ylcarbonyl)amino]ethyl, 2-(isobutyrylamino)ethyl, 2-{[(ethylamino)carbonyl]amino}ethyl, 2-{[(isopropylamino)carbonyl]amino]-2-methylpropyl, 2-{[(isopropylamino)carbonyl]amino}ethyl, 2-[(morpholin-4-ylcarbonyl)amino]ethyl, 4-[(morpholin-4-ylcarbonyl)amino]butyl, 2-[(ethoxycarbonyl)amino]ethyl, piperidin-4-ylmethyl, (1-benzylpiperidin-4-yl)methyl, (1-acetylpiperidin-4-yl)methyl, 1-[(propylamino)carbonyl]piperidin-4-yl}methyl, [1-(methylsulfonyl)piperidin-4-yl]methyl, 2-(1,1-dioxidoisothiazolidin-2-yl)ethyl, 3-(1H-pyrrol-3-yl)propyl, 3-(1-benzyl-1H-pyrrol-3-yl)propyl, 3-(1-benzyl-2,5-dihydro-1H-pyrrol-3-yl)propyl, 4-(4-pyridin-2-ylpiperazin-1-yl)butyl, 3-(3-methylisoxazol-5-yl)propyl, 3-(5-butylisoxazol-3-yl)propyl, 3-(3-isopropylisoxazol-5-yl)propyl, 3-(3-phenylisoxazol-5-yl)propyl, 3-(5-phenylisoxazol-3-yl)propyl, 3-(3-pyridin-3-ylisoxazol-5-yl)propyl, 3-(5-pyridin-3-ylisoxazol-3-yl)propyl, 4-(3,5,5-trimethyl-1,2,4-oxadiazol-4(5H)-yl)butyl, 4-(3-methyl-1-oxa-2,4-diazaspiro[4.4]non-2-en-4-yl)butyl, 2-{[(pyridin-3-ylamino)carbonothioyl]amino} ethyl, 2-{[(dimethylamino)carbonyl]amino}ethyl, 2-{[(phenylamino)carbonyl]amino}ethyl, 2-({[(3,4-difluorophenyl)amino]carbonyl}amino)ethyl, 2-({[(4-fluorophenyl)amino]carbonyl}amino)ethyl, 4-(hydroxyimino)butyl, 4-(methoxyimino)butyl, and 5-amino-5-(hydroxyimino)pentyl.

13. The compound or salt of claim 9, wherein $R_2$ is selected from the group consisting of hydrogen, alkyl, alkoxyalkylenyl, and hydroxyalkylenyl.

14. The compound or salt of claim 9, wherein R is selected from the group consisting of hydroxy, halogen, and alkoxy, m is 0, and n is 1.

15. The compound or salt of claim 9, wherein $R_1$ is selected from the group consisting of methyl, ethyl, propyl, butyl, 2-methylpropyl, 2,2-dimethylpropyl, 2-hydroxy-2-methylpropyl, 2-(propylsulfonyl)ethyl, 2-methanesulfonylethyl, 2-methyl-2-[(methylsulfonyl)amino]propyl, 2-[(cyclohexylcarbonyl)amino]-2-methylpropyl, 2-{[(isopropylamino)carbonyl]amino}ethyl, 4-[(morpholin-4-ylcarbonyl)amino]butyl, 2-(benzoylamino)ethyl, 3-amino-2,2-dimethyl-3-oxopropyl, 2,2-dimethyl-4-oxopentyl, and 4-methanesulfonylaminobutyl; and $R_2$ is selected from the group consisting of methyl, ethyl, propyl, butyl, 2-methoxyethyl, and 2-hydroxyethyl.

16. A pharmaceutical composition comprising a therapeutically effective amount of a compound or salt of claim 9 in combination with a pharmaceutically acceptable carrier.

17. The compound or salt of claim 1, wherein $R_2$ is selected from the group consisting of hydrogen, alkyl, alkoxyalkylenyl, and hydroxyalkylenyl.

* * * * *